(12) United States Patent
Oegema et al.

(10) Patent No.: US 11,612,604 B2
(45) Date of Patent: Mar. 28, 2023

(54) METHODS OF TREATING CANCER WITH PLK4 INHIBITORS

(71) Applicant: LUDWIG INSTITUTE FOR CANCER RESEARCH LTD, Zurich (CH)

(72) Inventors: Karen Oegema, La Jolla, CA (US); Andrew Shiau, La Jolla, CA (US); Arshad Desai, La Jolla, CA (US); Franz Meitinger, La Jolla, CA (US); Robert Davis, La Jolla, CA (US)

(73) Assignee: Ludwig Institute for Cancer Research Ltd, Zurich (CH)

( * ) Notice: Subject to any disclaimer, the term of this patent is extended or adjusted under 35 U.S.C. 154(b) by 180 days.

(21) Appl. No.: 16/769,458

(22) PCT Filed: Dec. 6, 2018

(86) PCT No.: PCT/US2018/064243
§ 371 (c)(1),
(2) Date: Jun. 3, 2020

(87) PCT Pub. No.: WO2019/113311
PCT Pub. Date: Jun. 13, 2019

(65) Prior Publication Data
US 2020/0383990 A1 Dec. 10, 2020

Related U.S. Application Data

(60) Provisional application No. 62/650,957, filed on Mar. 30, 2018, provisional application No. 62/595,498, filed on Dec. 6, 2017.

(51) Int. Cl.
*A61K 31/5377* (2006.01)
*A61P 35/00* (2006.01)
*A61K 31/506* (2006.01)
*A61K 31/55* (2006.01)

(52) U.S. Cl.
CPC ........ *A61K 31/5377* (2013.01); *A61K 31/506* (2013.01); *A61K 31/55* (2013.01); *A61P 35/00* (2018.01)

(58) Field of Classification Search
CPC .................... A61K 31/5377; A61K 31/506
See application file for complete search history.

(56) References Cited

U.S. PATENT DOCUMENTS

2003/0004161 A1  1/2003  Bebbington et al.

FOREIGN PATENT DOCUMENTS

| CA | 2982890 A1 | 10/2016 |
| WO | WO-2012/121662 A1 | 9/2012 |
| WO | WO-2016/166604 A1 | 10/2016 |

OTHER PUBLICATIONS

Wong et al., Science (2015), 348(6239), pp. 1155-1160.*
Coelho et al., Open Biology (2015), 5:150209, 15 pages.*
Bebbington, D. et al. (Jul. 1, 2009, e-published May 3, 2009). "The discovery of the potent aurora inhibitor MK-0457 (VX-680)," *Bioorg Med Chem Lett* 19(13):3586-3592.
Extended European Search Report dated Dec. 3, 2021, for EP Patent Application No. 18886861.6, 25 pages.
Fiskus, W. et al. (Sep. 2012, e-published Jul. 24, 2012). "Co-treatment with vorinostat synergistically enhances activity of Aurora kinase inhibitor against human breast cancer cells," *Breast Cancer Res Treat* 135(2):433-444.
Giles, F.J. et al. (Jan. 2013). "MK-0457, an Aurora kinase and BCR-ABL inhibitor, is active in patients with BCR-ABL T315I leukemia," *Leukemia* 27(1):113-117.
Ham, J. et al. (Feb. 8, 2016). "Exploitation of the Apoptosis-Primed State of MYCN-Amplified Neuroblastoma to Develop a Potent and Specific Targeted Therapy Combination," *Cancer Cell* 29(2): 159-172.
Jiang, J. et al. (Feb. 2016, e-published Sep. 22, 2015). "TRIM37 promoted the growth and migration of the pancreatic cancer cells," *Tumour Biol* 37(2):2629-2634.
Meitinger, F. et al. (2018). "Abstract 4130: TRIM37 expression levels dictate susceptibility to centrosome removal, supporting Plk4 inhibition as a potential new strategy for targeting neuroblastoma," Cancer Research, Proceedings: AACR Annual Meeting Apr. 14-18, 2018, Chicago, IL, located at <https://cancerres.aacrjournals.org/content/78/13_supplement/4130>, 4 pages.
Meitinger, F. et al. (Sep. 2020, e-published Sep. 9, 2020). "TRIM37 controls cancer-specific vulnerability to PLK4 inhibition," *Nature* 585(7825):440-446.
Michaelis, M. et al. (Sep. 30, 2014). "Aurora kinases as targets in drug-resistant neuroblastoma cells," *PLoS One* 9(9):e108758.
Okabe, S. et al. (Nov. 2010, e-published Jun. 20, 2010). "Efficacy of MK-0457 and in combination with vorinostat against Philadelphia chromosome positive acute lymphoblastic leukemia cells," *Ann Hematol* 89(11):1081-1087.
Partial Supplementary European Search Report dated Aug. 4, 2021, for EP Patent Application No. 18886861.6, 25 pages.
Pirker, C. et al. (Dec. 2010). "Response of experimental malignant melanoma models to the pan-Aurora kinase inhibitor VE-465," *Exp Dermatol* 19(12):1040-1047.
Schubbert, S. et al. (Dec. 1, 2014, e-published Oct. 6, 2014). "Targeting the MYC and PI3K pathways eliminates leukemia-initiating cells in T-cell acute lymphoblastic leukemia," *Cancer Res* 74(23):7048-7059.
Tavanti, E. et al. (Nov. 12, 2013, e-published Oct. 15, 2013). "Preclinical validation of Aurora kinases-targeting drugs in osteosarcoma," *Br J Cancer* 109(10):2607-2618.
Winter, G.E. et al. (Oct. 2011, e-published Jul. 18, 2011). "An integrated chemical biology approach identifies specific vulnerability of Ewing's sarcoma to combined inhibition of Aurora kinases A and B," *Mol Cancer Ther* 10(10):1846-1856.
Yao, R. et al. (Jan. 2014, e-published Oct. 29, 2013). "VX680 suppresses the growth of HepG2 cells and enhances the chemosensitivity to cisplatin," *Oncol Lett* 7(1):121-124.

(Continued)

*Primary Examiner* — Brian J Davis
(74) *Attorney, Agent, or Firm* — Mintz, Levin, Cohn, Ferris, Glovsky and Popeo, P.C.

(57) ABSTRACT

Provided herein, inter alia, are compounds and methods for inhibiting PLK4 and for treating cancer in a subject in need thereof.

20 Claims, 12 Drawing Sheets

(56) References Cited

OTHER PUBLICATIONS

Yoshida, K. et al. (Dec. 15, 2011, e-published Sep. 29, 2011). "Vincristine potentiates the anti-proliferative effect of an aurora kinase inhibitor, VE-465, in myeloid leukemia cells," *Biochem Pharmacol* 82(12):1884-1890.

Engstrom, P.F. et al. (Apr. 15, 1982). "Combination chemotherapy of advanced colorectal cancer utilizing 5-fluorouracil, semustine, dacarbazine, vincristine, and hydroxyurea: a phase III trial by the Eastern Cooperative Oncology Group (EST: 4275)," *Cancer* 49(8):1555-1560.

Hu, C.E. et al. (Mar. 2017, e-published Jan. 16, 2017). "TRIM37 promotes epithelial-mesenchymal transition in colorectal cancer," *Mol Med Rep* 15(3):1057-1062.

International Search Report dated Feb. 27, 2019, for PCT Application No. PCT/US2018/064243, filed Dec. 6, 2018, 3 pages.

Kidd, M. et al. (Feb. 2006). "Q RT-PCR detection of chromogranin A: a new standard in the identification of neuroendocrine tumor disease," *Annals of Surgery* 243(2):273-280.

Marsella, J.M. et al. (Sep. 1997). "Susceptibility of p53-deficient mice to induction of mesothelioma by crocidolite asbestos fibers," *Environmental Health Perspectives* 105 Suppl 5(Suppl 5):1069-1072.

Recchia, F. et al. (May 2007, e-published Sep. 6, 2006). "Phase II study of interleukin-2 and 13-cis-retinoic acid as maintenance therapy in metastatic colorectal cancer," *Cancer Immunol Immunother* 56(5):699-708.

Ries, L. et al. "Cancer Incidence and Survival among Children and Adolescents: United States SEER Program 1975-1995," located at https://seer.cancer.gov/archive/publications/childhood/childhood-monograph.pdf, retrieved on Jan. 22, 2018, 65 pages.

Soda, M. et al. (Aug. 2, 2007, e-published Jul. 11, 2007). "Identification of the transforming EML4-ALK fusion gene in non-small-cell lung cancer," *Nature* 448(7153):561-566.

Sotlar, K. et al. (Mar. 2001). "Human papillomavirus type 16-associated primary squamous cell carcinoma of the rectum," *Gastroenterology* 120(4):988-994.

Written Opinion dated Feb. 27, 2019, for PCT Application No. PCT/US2018/064243, filed Dec. 6, 2018, 23 pages.

\* cited by examiner

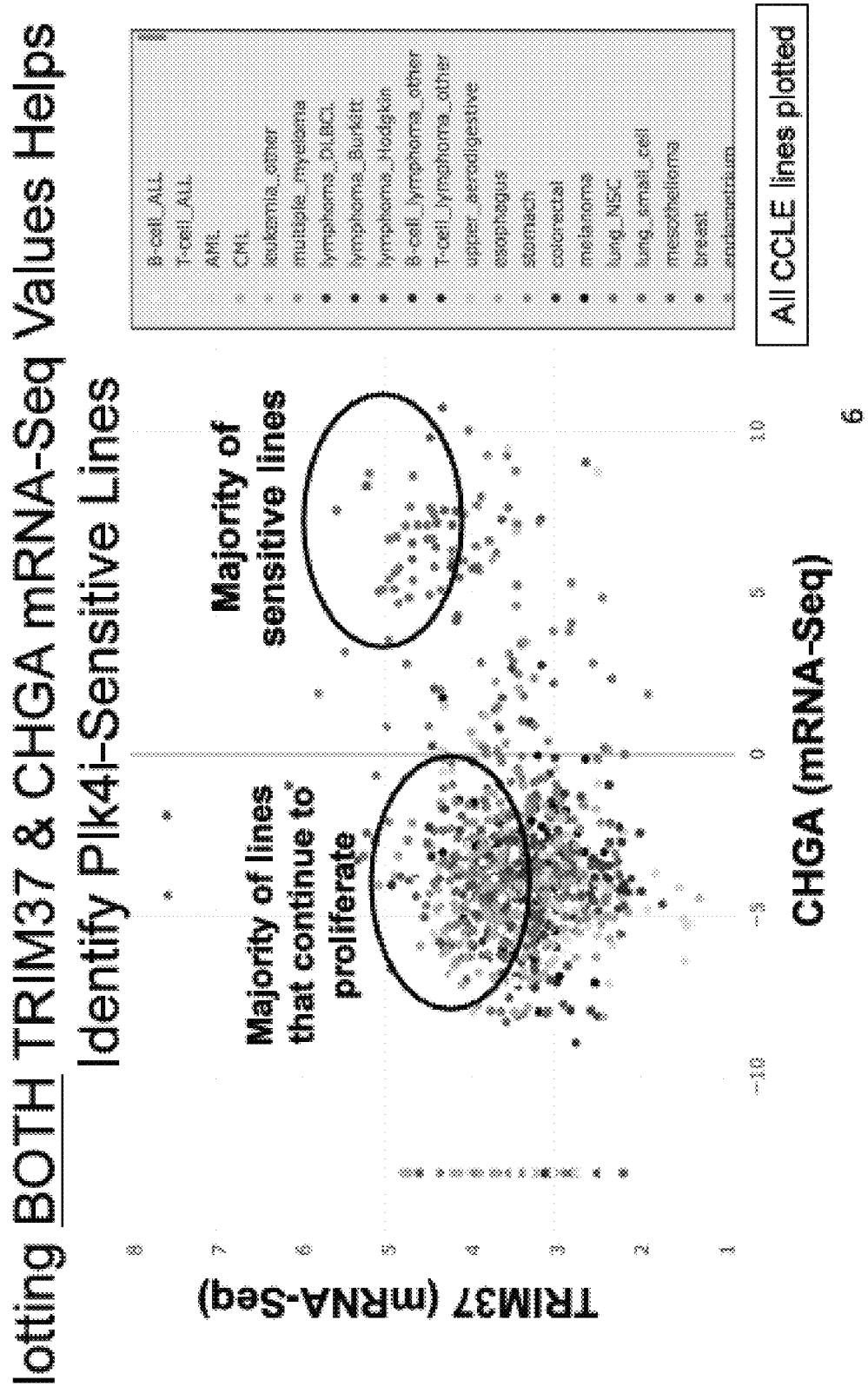

METHODS OF TREATING CANCER WITH PLK4 INHIBITORS

CROSS-REFERENCE TO RELATED APPLICATIONS

This application is a § 371 US National Phase of International Application No. PCT/US2018/064243 filed Dec. 6, 2018, which claims priority to U.S. Application No. 62/650,957 filed Mar. 30, 2018, and to U.S. Application No. 62/595,498 filed Dec. 6, 2017, the disclosures of which are incorporated by reference herein in their entirety.

STATEMENT AS TO RIGHTS TO INVENTIONS MADE UNDER FEDERALLY SPONSORED RESEARCH AND DEVELOPMENT

This invention was made with the government support under Grant No. R01 GM074207, awarded by the National Institutes of Health. The government has certain rights in the invention.

BACKGROUND

Centrioles play a role in cytokinesis. Centrioles are small cellular organelles whose distinguishing feature is an outer wall made up of a 9-fold symmetric array of stabilized microtubules. Centrioles have two critical functions in cells: (i) they template the formation of microtubule-based projections called cilia, and (2) they direct the assembly of pericentriolar material that nucleates and anchors microtubules to form centrosomes (Conduit et al., Nat Rev Mol Cell Biol. 16:611-624 (2015); Wong et al., Science. 348:1155-1160 (2014)). Centrosomes catalyze microtubule assembly to accelerate formation of the mitotic spindle that segregates the chromosomes during cell division and to ensure its bipolarity. Centriole duplication is tightly controlled to ensure that mitotic cells have precisely two centrosomes. Centrioles duplicate in S-phase, when a single daughter centriole forms adjacent to each mother centriole (Banterle et al., Annu. Rev. Cell. Dev. Biol., 33:23-49 (2017); Fu et al., Cold Spring Harb Perspect Biol. 7:a015800 (2015); Zitouni et al., Nat Rev Mol Cell Biol. 15:433-452 (2014)). Centriole duplication is controlled by the mitotic kinase PLK4 (Banterle et al.; Wong et al.; Zitouni et al.).

Polo-like kinase (PLK4) is one regulator of centriole biogenesis. PLK4 overexpression may trigger centriole over duplication which can lead to cancer. PLK4 shares active site homology with other kinases, including Aurora kinases. To analyze the effect of centrosome removal in normal and cancer cells, centrinone, a potent specific PLK4 inhibitor was developed (Wong et al.) Centrinone treatment blocks centriole duplication, leading to progressive depelion of centrosomes as cells divide. Many cell lines with cancer-associated mutations (which frequently target the p53 circuit) continue to proliferate, albeit at reduced rates, following centrinone-mediated centrosome removal. However, RPE1 cells and 3 tested primary cell cultures with an intact p53 pathway were found to stabilize p53 and arrest in G1 following centrinone-induced centrosome loss (Wong et al.). A more detailed analysis revealed that centrosome removal led to p53 stabilization because it triggered the mitotic duration sensor (Fong et al., Elife. 5 (2016); Lambrus et al., J Cell Biol. 214:143-153 (2016); Meitinger et al., J Cell Biol. 214:155-166 (2016)). Prior work showed that cells monitor the amount of time they spend in mitosis and, if the mother cell spends too long in mitosis, p53 is stabilized in the resulting daughter cells (Uetake et al., Curr Biol. 20:1666-1671 (2010)). For example, in RPE1 cells mitosis (nuclear envelope breakdown to anaphase onset) normally takes 25 minutes, if this interval is greater than 100 minutes, the daughter cells exhibit a p53-dependent arrest (Uetake et al.). Centrosome removal increases the amount of time that it takes to assemble as spindle and complete mitosis and is thought to stabilize p53 because it triggers the mitotic duration sensor (Fong et al.; Lambrus et al.; Meitinger et al.).

Thus, the response of cells to centrosome removal via small molecule-mediated PLK4 inhibition was expected to depend on: (1) how well the cells can assemble a spindle that can accomplish chromosome segregation in the absence of centrosomes and, (2) if the cells are p53 positive, whether they can assemble a spindle fast enough to avoid activating the mitotic duration sensor. Genome-wide CRISPR/Cas9-based screens identified three genes whose inhibition allows RPE1 cells, which are p53 positive, to proliferate in the absence of centrosomes. Two, USP28 and 53BP1, were proteins whose loss inactivates the mitotic duration sensor (Fong et al.; Lambrus et al.; Meitinger et al.). The third protein whose knockdown facilitates proliferation in the absence of centrosomes is TRIM37 (Fong et al.; Meitinger et al.), an E3 ubiquitin ligase of the TRIpartite Motif (TRIM) protein family (Kallijarvi et al., Exp Cell Res. 308:146-155 (2005)). Instead of disrupting the function of the mitotic duration sensor that detects the defects present when centrosomes are removed, knocking out TRIM37 made spindle assembly in the absence of centrosomes faster and more robust (Meitinger et al.). The TRIM37 knockout appeared to exert its effect by promoting the assembly of ectopic foci containing centrosomal components that are able to nucleate microtubules and promote spindle formation (Meitinger et al.), thereby reducing mitotic duration in cells that lack centrosomes.

Prior data has shown that removing TRIM37 makes cells more robust to centrosome removal by accelerating spindle assembly (Meitinger et al., 2016). The gene expression data across cancer cell lines in the Cancer Cell Line Encyclopedia (Barretina et al., Nature. 483:603-607 (2012)) suggested that neuroblastoma cells have high levels of TRIM37 gene expression. In addition, many neuroblastoma cell lines are p53 positive (Kwiatkowski et al., Nature. 511:616-620 (2014)).

There is a need in the art for selective kinase inhibitors for PLK4. Described herein are solutions to these and other problems in the art.

BRIEF SUMMARY

Provided herein are methods of treating cancer in a subject in need thereof by administering to the subject an effective amount of a PLK4 inhibitor to treat the cancer; wherein the subject has an elevated level of TRIM37, an elevated level of Chromogranin A, and/or an elevated level of Synaptophysin. In embodiments, the elevated level of TRIM37, Chromogranin A, and/or Synaptophysin are compared to a control. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the cancer is a cancer tumor. In embodiments, the cancer is a pediatric cancer. In embodiments, the pediatric cancer is a rhabdoid tumor, a neuroblastoma, an acute lymphoblastic leukemia tumor, or a brain and central nervous system tumor. In embodiments, the cancer is a neural crest-derived cancer. In embodiments, the neural crest-derived tumor is a small cell lung cancer, a melanoma, or a breast cancer. In embodiments, the cancer is neuroblastoma. In embodiments, the cancer is acute myeloid leukemia, prostate cancer, glioma, mesothelioma, osteosarcoma, breast cancer, Ewing's sarcoma, soft tissue cancer, or T cell lymphoma. In embodiments, the cancer is a rhabdoid tumor, basal cell carcinoma, small cell lung cancer, endometrial cancer, non-small cell lung cancer, ovarian cancer, thyroid cancer, kidney cancer, Hodgkin's lymphoma, stomach cancer, liver cancer, Burkitt lymphoma, giant cell tumor of bone, medulloblastoma, a urinary tract cancer, meningioma, bile duct cancer, melanoma, esophageal cancer, upper aerodigestive cancer, colorectal cancer, chondrosarcoma, multiple myeloma, B cell lymphoma, leukemia, diffuse large B cell lymphoma, or chronic myeloid leukemia. In embodiments, the cancer is a p53 positive cancer, including a wild type p53 positive cancer or a mutant p53 positive cancer. In embodiments, the methods further comprising administering a chemotherapeutic agent, radiation therapy, or a combination thereof.

Provided herein are methods of treating a p53 positive cancer in a subject in need thereof, the method comprising administering to the subject an effective amount of a PLK4 inhibitor to treat the p53 positive cancer. In embodiments, the p53 positive cancer is a wild type p53 positive cancer. In embodiments, the p53 positive cancer is a mutant p53 positive cancer. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the p53 positive cancer is a pediatric cancer. In embodiments, the pediatric cancer is a rhabdoid tumor, a neuroblastoma, an acute lymphoblastic leukemia tumor, or a brain and central nervous system tumor. In embodiments, the p53 positive cancer is a neural crest-derived cancer. In embodiments, the neural crest-derived tumor is a small cell lung cancer, a melanoma, or a breast cancer. In embodiments, the p53 positive cancer is neuroblastoma. In embodiments, the methods further comprising administering a chemotherapeutic agent, radiation therapy, or a combination thereof.

Provided herein are methods of treating a wild type p53 positive pediatric cancer in a subject in need thereof, the method comprising administering to the subject an effective amount of a PLK4 inhibitor to treat the wild type p53 positive pediatric cancer. In embodiments, the disclosure provides methods of treating a wild-type p53 positive pediatric cancer in a subject in need thereof by administering to the subject an effective amount of a PLK4 inhibitor to treat the wild-type p53 positive pediatric cancer; wherein the subject has an elevated level of TRIM37, an elevated level of Chromogranin A, and/or an elevated level of Synaptophysin, when compared to a control. In embodiments, the disclosure provides methods of treating a mutant p53 positive pediatric cancer in a subject in need thereof by administering to the subject an effective amount of a PLK4 inhibitor to treat the mutant p53 positive pediatric cancer; wherein the subject has an elevated level of TRIM37, an elevated level of Chromogranin A, and/or an elevated level of Synaptophysin, when compared to a control. In embodiments, the pediatric cancer is a rhabdoid tumor, a neuroblastoma, an acute lymphoblastic leukemia tumor, or a brain and central nervous system tumor. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the methods further comprising administering a chemotherapeutic agent, radiation therapy, or a combination thereof.

Provided herein are methods of treating a wild type p53 positive, neural crest-derived cancer in a subject in need thereof, the method comprising administering to the subject an effective amount of a PLK4 inhibitor to treat the wild type p53 positive, neural crest-derived cancer. In embodiments, the disclosure provides methods of treating a wild type p53 positive, neural crest-derived cancer in a subject in need thereof by administering to the subject an effective amount of a PLK4 inhibitor to treat the wild type p53 positive, neural crest-derived cancer; wherein the subject has an elevated level of TRIM37, an elevated level of Chromogranin A, and/or an elevated level of Synaptophysin, when compared to a control. In embodiments, the disclosure provides methods of treating a mutant p53 positive, neural crest-derived cancer in a subject in need thereof by administering to the subject an effective amount of a PLK4 inhibitor to treat the mutant p53 positive, neural crest-derived cancer; wherein the subject has an elevated level of TRIM37, an elevated level of Chromogranin A, and/or an elevated level of Synaptophysin, when compared to a control. In embodiments, the neural crest-derived tumor is a small cell lung cancer, a melanoma, or a breast cancer. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the methods further comprising administering a chemotherapeutic agent, radiation therapy, or a combination thereof.

Provided herein are methods of treating a wild-type p53 positive cancer in a subject in need thereof, the method comprising administering to the subject an effective amount of a PLK4 inhibitor to treat the wild-type p53 positive cancer; wherein the subject has an elevated level of TRIM37, an elevated level of Chromogranin A, and/or an elevated level of Synaptophysin, when compared to a control. In embodiments, the disclosure provides methods of treating a mutant p53 positive cancer in a subject in need thereof by administering to the subject an effective amount of a PLK4 inhibitor to treat the mutant p53 positive cancer; wherein the subject has an elevated level of TRIM37, an elevated level of Chromogranin A, and/or an elevated level of Synaptophysin, when compared to a control. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the methods further comprising administering a chemotherapeutic agent, radiation therapy, or a combination thereof.

Provided herein are methods of treating a wild type p53 positive neuroblastoma in a subject in need thereof, the method comprising administering to the subject an effective amount of a PLK4 inhibitor to treat the wild type p53 positive neuroblastoma; wherein the subject has an elevated level of TRIM37, an elevated level of Chromogranin A, and/or an elevated level of Synaptophysin, when compared to a control. In embodiments, the disclosure provides methods of treating a mutant p53 positive neuroblastoma in a subject in need thereof, the method comprising administering to the subject an effective amount of a PLK4 inhibitor to treat the mutant p53 positive neuroblastoma; wherein the subject has an elevated level of TRIM37, an elevated level of Chromogranin A, and/or an elevated level of Synaptophysin, when compared to a control. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the methods further comprising administering a chemotherapeutic agent, radiation therapy, or a combination thereof.

Provided herein are methods of treating cancer in a subject in need thereof by: (i) measuring a TRIM37 level, a Chromogranin A level, and/or a Synaptophysin level, in a biological sample obtained from the subject; and (ii) administering an effective amount of a PLK4 inhibitor to the subject to treat the cancer. In embodiments, the subject has an elevated level of TRIM37, Chromogranin A level, and/or a Synaptophysin. In embodiments, the subject has an elevated level of TRIM37, Chromogranin A level, and/or a Synaptophysin compared to a control. In embodiments, the biological sample is a tumor sample, such as a resected tumor sample, a tumor biopsy sample, a primary tumor sample, a resected primary tumor sample, a primary tumor biopsy sample, a metastatic tumor sample, a resected metastatic tumor sample, or a metastatic tumor biopsy sample. In embodiments, the biological sample is a blood sample, such as a peripheral blood sample. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the cancer is a cancer tumor. In embodiments, the cancer is a pediatric cancer. In embodiments, the pediatric cancer is a rhabdoid tumor, a neuroblastoma, an acute lymphoblastic leukemia tumor, or a brain and central nervous system tumor. In embodiments, the cancer is a neural crest-derived cancer. In embodiments, the neural crest-derived tumor is a small cell lung cancer, a melanoma, or a breast cancer. In embodiments, the cancer is neuroblastoma. In embodiments, the cancer is acute myeloid leukemia, prostate cancer, glioma, mesothelioma, osteosarcoma, breast cancer, Ewing's sarcoma, soft tissue cancer, or T cell lymphoma. In embodiments, the cancer is a rhabdoid tumor, basal cell carcinoma, small cell lung cancer, endometrial cancer, non-small cell lung cancer, ovarian cancer, thyroid cancer, kidney cancer, Hodgkin's lymphoma, stomach cancer, liver cancer, Burkitt lymphoma, giant cell tumor of bone, medulloblastoma, a urinary tract cancer, meningioma, bile duct cancer, melanoma, esophageal cancer, upper aerodigestive cancer, colorectal cancer, chondrosarcoma, multiple myeloma, B cell lymphoma, leukemia, diffuse large B cell lymphoma, or chronic myeloid leukemia. In embodiments, the cancer is a p53 positive cancer, including a wild type p53 positive cancer or a mutant p53 positive cancer. In embodiments, the methods further comprising administering a chemotherapeutic agent, radiation therapy, or a combination thereof.

Provided herein are methods to identify a subject responsive to a PLK4 inhibitor by: (i) obtaining a biological sample from the subject; and (ii) measuring a TRIM37 level, a Chromogranin A level, and/or a Synaptophysin level, in the biological sample; wherein if the TRIM37 level, the Chromogranin A level, and/or the Synaptophysin level, is elevated, then the subject is identified as responsive to the PLK4 inhibitor. In embodiments, the TRIM37 level, the Chromogranin A level, and/or the Synaptophysin level, is elevated when compared to a control. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the biological sample is a tumor sample, such as a resected tumor sample, a tumor biopsy sample, a primary tumor sample, a resected primary tumor sample, a primary tumor biopsy sample, a metastatic tumor sample, a resected metastatic tumor sample, or a metastatic tumor biopsy sample. In embodiments, the biological sample is a blood sample, such as a peripheral blood sample.

Provided herein are methods of selecting a subject for treatment with a PLK4 inhibitor by: (i) obtaining a biological sample from the subject; and (ii) measuring a TRIM37 level, a Chromogranin A level, and/or a Synaptophysin level, in the biological sample; wherein if the TRIM37 level, the Chromogranin A level, and/or the Synaptophysin level, is elevated, then the subject is selected for treatment with the PLK4 inhibitor. In embodiments, the TRIM37 level, the Chromogranin A level, and/or the Synaptophysin level, is elevated when compared to a control. In embodiments, the PLK4 inhibitor is a compound of Formula (I), (Ia), (Ia1), (Ia2), (Ia3), (Ia4), (Ia5), (Ia6), (Ia7), (Ia8), (Ia9a), (Ia9c), (Ia9d), (Ia9f), (Ib), (Ib1), (Ib2), (Ib3), (Ib4), (Ib5), (Ib6), (Ib7), (IC), (I), (II), or (III). In embodiments, the PLK4 inhibitor is a compound set forth in Table 1. In embodiments, the PLK4 inhibitor is a compound set forth in Table 2. In embodiments, the biological sample is a tumor sample, such as a resected tumor sample, a tumor biopsy sample, a primary tumor sample, a resected primary tumor sample, a primary tumor biopsy sample, a metastatic tumor sample, a resected metastatic tumor sample, or a metastatic tumor biopsy sample. In embodiments, the biological sample is a blood sample, such as a peripheral blood sample.

BRIEF DESCRIPTION OF THE DRAWINGS

FIG. 1A provides graphs showing the results of passaging assays for the indicated cancer cell lines that monitor cell proliferation after the addition of DMSO (vehicle; black; upper line with sharp peaks and valleys or circle in upper right hand corner) or 150 nM centrinone (lower line) at day 0. The second graph in each pair shows a rescaled version of centrinone-treated curve. Cell lines in which the number of cells decreased to zero within 12 days following centrinone addition were considered sensitive to PLK4 inhibition (marked with the filled circles in the upper right hand corner), whereas cell lines that continued to proliferate were considered 'Not Sensitive' (marked with the empty circles in the upper right hand corner). FIG. 1B provides graphs showing the results of passaging assays for CHP134 cells and CHP134 cells in which both endogenous PLK4 alleles have been engineered to express a G95L mutant PLK4 protein. Growth is shown after the addition of DMSO (vehicle; black; upper line) or 150 nM centrinone (lower line) at day 0. FIG. 1C provides a graph plotting the percentage of apoptotic cells for each cancer cell line after treatment for four cell cycle durations with 150 nm centrinone, 500 nm centrinone B or DMSO (wherein control is left; centrinone is center; centrinone B is right).

FIG. 2A shows the CHP134 neuroblastoma cell line has 4 copies of the TRIM37 gene. After CRISPR targeting, CHP134 clones with varying TRIM37 copy numbers were isolated and the levels of TRIM37 protein were measured by quantitative western blotting. Alpha-tubulin was used as a blotting control. Clones with TRIM37 levels between 12 and 64% of the levels in the WT cell line were isolated. FIGS. 2B and 2C show analysis of mitosis by live cell filming in the CHP134 clones after 3 cell cycles in 150 nM centrinone and the duration of mitosis and rate of anaphase failure were measured for each clone. Graphs plot mean mitotic duration (FIG. 2B) and the percentage of cells exhibiting anaphase failure (FIG. 2C) versus measured TRIM37 protein level. FIG. 2D presents data in which cellular proliferation was assessed for each of the CHP134 clones by performing an ATPlite assay after 5 days in 125 nM centrinone. Results are expressed as the percent of the value for the equivalent DMSO-treated control and are plotted versus measured TRIM37 protein level. Note that WT CHP134 cells exhibited a loss in proliferation comparable to that of the two highest mutant clones. Thus, for centrinone-treated CHP134 cells, mitotic success and cell viability both decreased as TRIM37 levels increased.

FIG. 3A is a graph plotting TRIM37 copy number versus expression level for breast cancer cell lines (data from the CCLE database; (Barretina et al., 2012)). FIG. 3B are graphs showing the results of passaging assays for the indicated cancer cell lines that monitor cell proliferation after the addition of DMSO (vehicle; black) or 150 nM centrinone (grey) at day 0. The right graph in each pair shows the centrinone-treated curve without the control. Cell lines in which the number of cells decreased to zero following centrinone addition were considered 'Sensitive' to PLK4 inhibition (marked with the filled circles in the upper right hand corner, whereas cell lines that continued to proliferate were considered 'Not Sensitive' (marked with the empty circles in the upper right hand corner). The two cell lines with amplification of the TRIM37 locus (BT474 and MCF7) were highly sensitive to centrosome removal, whereas MDA-MB-231, which has not amplified the TRIM37 locus was not.

FIG. 4A provides a graph shows relative p53 activity across the indicated panel of cell lines. The circles are color-coded to indicate which cell lines are p53 positive (p53+, CHP212, BT-16, HepG2, BT-12, RPE1, CHP134, MR32, SH—SY5Y, SK-N—SH) and negative (p53−, A673, HeLa, SK-ES-1, SK-N-F1). FIG. 4B provides a graph shows the relative amount of TRIM37 protein in each of the indicated cancer cell lines as measured by quantitative western blotting. The circles are color coded to indicate which cell lines are p53+(BT-16, BT-12, HepG2, RPE1, SK-N—SH, SK-ES-1, SH—SY5Y, IMR32, CHP212, CHP134) and p53− (A673, HeLa, SK-N-F1) and which are sensitive (SK-N—SH, SH—SY5Y, IMR32, CHP212, SK-N-F1, CHP134) and not sensitive (BT-16, A673, BT-12, HepG2, HeLa, RPE, SK-ES-1) to PLK4 inhibition based on the data in FIG. 2. FIG. 4C is a graph shows the correlation between measured levels of TRIM37 mRNA (from the CCLE database; (Barretina et al., 2012)) and measured protein amount.

FIG. 5A and FIG. 5B are graphs plotting the distribution of mitotic phenotypes (FIG. 5A) and mitotic duration (FIG. 5B) for the indicated cell lines after growth for three cell cycle durations in DMSO or centrinone. Graph in FIG. 5B is a 5-95% box-and-whiskers plot. FIG. 5C provides an analysis of the mitotic duration sensor in the indicated cell lines. Vertical bars represent individual daughter cells. Bar height shows the time the mother cell spent in mitosis, and bar color indicates whether the daughter cell divided (grey), arrested, or died (black). Black dashed lines mark the mitotic duration threshold for each cell line. The majority of daughter cells whose mothers spent longer than the threshold in mitosis exhibit p53-dependent cell death or arrest.

FIG. 6A provides graphs plotting the distribution of mitotic phenotypes (left panel) and the mitotic duration (right panel) after growth for three cell cycle durations in DMSO or centrinone for control CHP134 cells and CHP134 cells in which TRIM37 was deleted (TRIM37Δ), p53 was inhibited (TP53-sh), or both. Right graph is a 5-95% box-and-whiskers plot. FIG. 6B provides graphs plotting the results of passaging assays that monitor the proliferation of wild-type and mutant CHP134 cell lines after addition of DMSO (vehicle) or centrinone at day 0.

FIG. 7A provides immunofluorescence images of wild-type RPE1, RPE1 TRIM37Δ and RPE1 TRIM37Δ cells stably expressing wild-type TRIM37 or a ligase-inactive mutant TRIM37-C18R from the UbC-promoter. Cells were stained for DNA (blue) and with antibodies to the centrosomal protein Cep192 (green). Bar, 10 μm. FIG. 7B provides graphs plotting the percentage of cells that have ectopic Cep192 foci around the centrosome as shown in FIG. 7A. FIG. 7C provides an immunoblot showing the expression level of TRIM37 from the wild-type and C18R transgenes compared to the amount of endogenous TRIM37 in the control RPE1 and RPE1 TRIM37Δ cell lines. FIG. 7D provides a graph plotting mitotic duration for RPE1, RPE1 TRIM37Δ and RPE1 TRIM37Δ cells stably expressing wild-type and ligase-inactive mutant (C18R) TRIM37 from the UbC-promoter after three cell cycle durations in DMSO or centrinone. Graph is a 5-95% box-and-whiskers plot.

FIG. 8 shows a plot of CHGA versus TRIM37 mRNA—Seq values for a number of cancer cell lines. Higher TRIM37 and CHGA values indicate sensitivity to a PLK4 inhibitor. PLK4i sensitivity was measured similarly to experiments in FIG. 3B above.

DETAILED DESCRIPTION

Figure 1A:
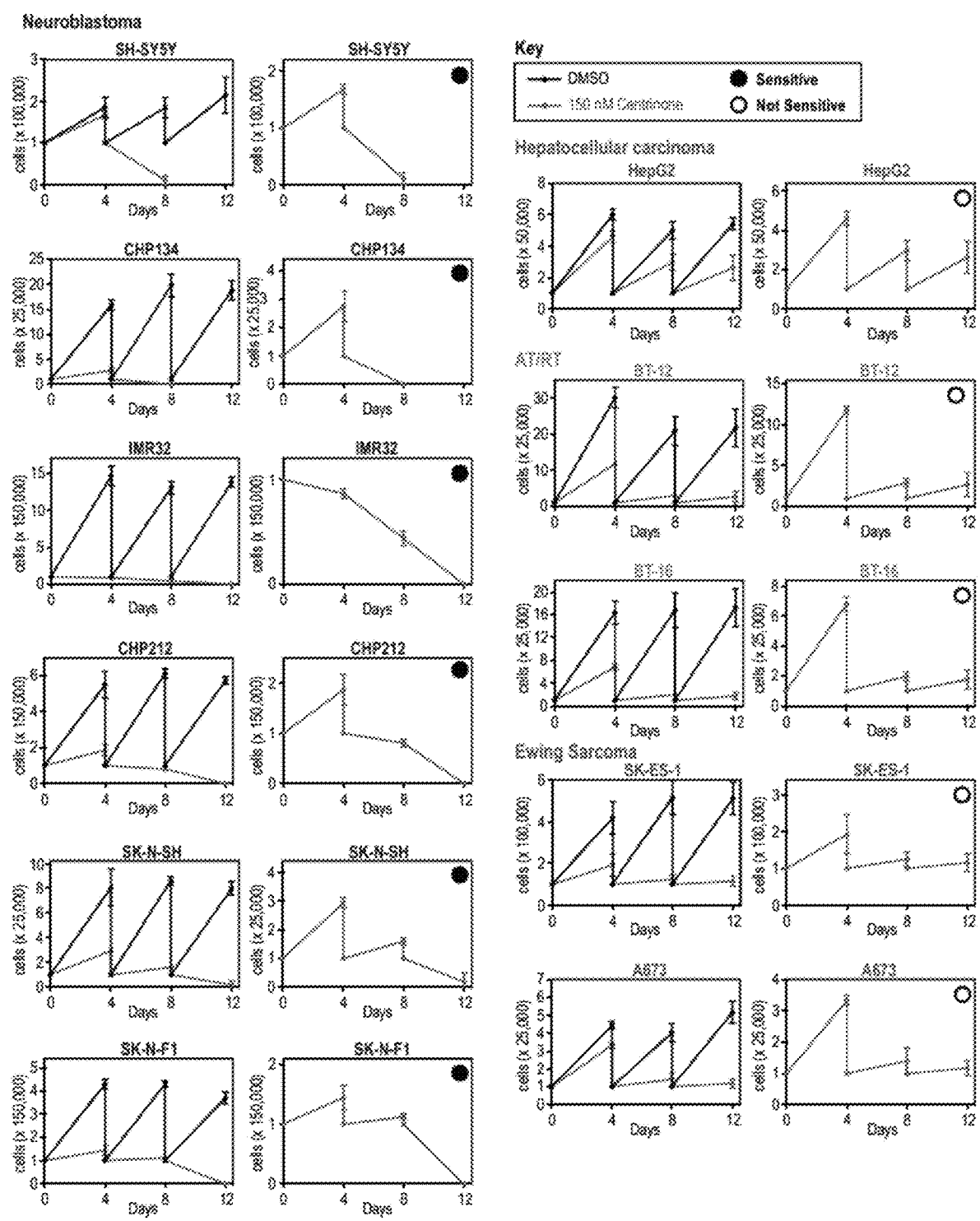
FIGS. 1A-1C show sensitivity of cancer cell lines to PLK4 inhibition.

The abbreviations used herein have their conventional meaning within the chemical and biological arts. The chemical structures and formulae set forth herein are constructed according to the standard rules of chemical valency known in the chemical arts.

"PLK4" is used according to its common, ordinary meaning and refers to proteins of the same or similar names and functional fragments and homologs thereof. The term includes recombinant or naturally occurring forms of PLK4 (e.g. Polo-like Kinase 4; GI No: 160113150), or variants thereof that maintain PLK4 activity (e.g. within at least 30%, 40%, 50%, 60%, 70%, 80%, 90%, 95%, or 100% activity compared to PLK4).

The term "inhibitor," "inhibition," "inhibit," "inhibiting," and the like, in reference to a protein-inhibitor interaction, means negatively affecting (e.g. decreasing) the activity or function of the protein relative to the activity or function of the protein in the absence of the inhibitor. Inhibition may refer to negatively affecting (e.g. decreasing) the concentration or level of the protein relative to the concentration or level of the protein in the absence of the inhibitor. Inhibition may refer reduction of a disease or symptoms of disease. Inhibition may refer to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"PLK4 inhibitor" refers to a compound that selectively inhibits PLK4. In embodiments, PLK4 inhibitors cause depletion of centrioles, disruption in mitosis, induction of apoptosis, prevention of cell division, and inhibition of proliferation of PLK4-overexpressing tumor cells. Exemplary PLK4 inhibitors include compounds of Formula (I), Formula (Ia), Formula (Ia1), Formula (Ia2), Formula (Ia3), Formula (Ia4), Formula (Ia5), Formula (Ia6), Formula (Ia1), Formula (Ia.), Formula (Ia9a), Formula (Ia9b), Formula (Ia9c), Formula (Ia9d), Formula (Ia9f), Formula (Ib), Formula (Ib1), Formula (Ib2), Formula (Ib3), Formula (Ib4), Formula (Ib5), Formula (Ib6), Formula (Ib7), Formula (IC), Formula (II), and Formula (III). Other Exemplary PLK4 inhibitors include the compounds in Table 1 and Table 2.

"Selective" or "selectively" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"TRIM37" as referred to herein includes any of the recombinant or naturally-occurring forms of the E3 ubiquitin ligase of the TRIpartite Motif (TRIM) protein family Tripartite Motif Containing 37 (TRIM37) or variants or homologs thereof that maintain TRIM37 activity (e.g. within at least 50%, 80%, 90%, 95%, 96%, 97%, 98%, 99% or 100% activity compared to TRIM37). In aspects, the variants or homologs have at least 90%, 95%, 96%, 97%, 98%, 99% or 100% nucleic acid sequence identity across the whole sequence or a portion of the sequence (e.g. a 50, 100, 150 or 200 continuous nucleotide portion) compared to a naturally occurring TRIM37 gene or mRNA. In embodiments, the TRIM37 gene is substantially identical to the gene identified by the UniProtKB Reference Number TRI37_HUMAN,) 94972 or a variant or homolog having substantial identity thereto. In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TRIM37 protein. In embodiments, the TRIM37 protein is substantially identical to the protein identified by the UniProtKB Reference Number 094972-TRI37_HUMAN or a variant or homolog having substantial identity thereto. In embodiments, the TRIM37 is a mutant TRIM37. In embodiments, the TRIM37 is TRIM37A.

"TRIM37 levels" as referred to herein is the level of TRIM37 expressed by a tumor. The TRIM37 levels can be measured by genes, mRNA, or proteins in a biological sample.

"An elevated level of TRIM37" as referred to herein is an elevated level of TRIM37 genes on a tumor or an elevated level of TRIM37 expressed (e.g., mRNA, proteins) by a tumor in a subject when compared to a control. TRIM37 levels can be measured from biological samples, such as a tumor sample (e.g., resected, biopsy) or a blood sample (e.g., peripheral blood), obtained from a subject. A tumor can be a primary tumor or a metastasis. A tumor as provided herein is a cellular mass including cancer cells and non-cancer cells. The non-cancer cells forming part of a tumor may be stromal cells, and immune cells (e.g., T cells, dendritic cells, B cells, macrophages). Thus, the elevated level of TRIM37 is expressed by a non-cancer cell (e.g., a stromal cell) or a cancer cell (e.g., a malignant T cell).

TRIM37 levels can be detected at either the protein or the gene expression level. TRIM37 protein can for example be quantified by immunoblotting, immunohistochemistry (TIC) or flow cytometry with an antibody that detects TRIM37. TRIM37 gene expression can, for example, be quantified by multiple platforms such as reverse transcription polymerase chain reaction (rtPCR), Nanostring, RNA sequencing (RNA—Seq), also called whole transcriptome shotgun sequencing (WTSS), or in situ hybridization. TRIM37 gene copy number variation (CNV) (particularly gene amplification) can, for example, be quantified by array comparative genomic hybridization (array CGH), fluorescent in situ hybridization (FISH), genomic sequencing or quantitative polymerase chain reaction (qPCR). There is a range of TRIM37 expression across and within tumor types that shows concordance when measured with either immunoblotting, rtPCR and/or RNA—Seq. There is a range of TRIM37 expression across and within tumor types that shows concordance when measured with either IHC, Nanostring and/or by in situ hybridization. One skilled in the art will understand the importance of selecting a threshold of TRIM37 expression that constitutes elevated levels. Controls are also valuable for determining the significance of data. For example, if values for a given parameter are widely variant in controls, variation in test samples will not be considered as significant. In some examples of the disclosed methods, when the expression level of TRIM37 is assessed, the level is compared with a control expression level of TRIM37. By control expression level is meant the expression level of TRIM37 from a sample or subject lacking cancer, a sample or subject at a selected stage of cancer or cancer state, or in the absence of a particular variable such as a therapeutic agent. Alternatively, the control level comprises a known amount of TRIM37. Such a known amount correlates with an average level of subjects lacking cancer, at a selected stage of cancer or cancer state, or in the absence of a particular variable such as a therapeutic agent. A control level also includes the expression level of TRIM37 from one or more selected samples or subjects as described herein. For example, a control level includes an assessment of the expression level of TRIM37 in a sample from a subject that does not have cancer, is at a selected stage of cancer or cancer state, or has not received treatment for cancer. Another exemplary control level includes an assessment of the expression level of TRIM37 in samples taken from multiple subjects that do not have cancer, are at a selected stage of cancer, or have not received treatment for cancer. In some embodiments, a threshold for elevated TRIM37 may be above the median expression level of a group of control samples. In some embodiments it may be above the first or third quartile of TRIM37 expression in a group of control samples. In some embodiments it may be above the $10^{th}$, $20^{th}$, $30^{th}$, $40^{th}$, $60^{th}$, $70^{th}$, $80^{th}$ or $90^{th}$ percentile of TRIM37 expression for a group of control samples. When the control level includes the expression level of TRIM37 in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

In embodiments, a control level is the TRIM37 expression level calculated from a biological sample from a subject with cancer prior to treatment. In embodiments, the elevated level of TRIM37 is calculated by determining the percentage of cells a biological sample that are positive for TRIM37. The cells may be tumor cells, tumor infiltrating cells, stromal cells, vasculature cells, or a composite thereof. In embodiments, the cells are tumor cells. In embodiments, the percentage of cells that are positive for TRIM37 may be greater than 1%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 90%, or greater than 95%. In aspects, the percentage of cells that are positive for TRIM37 is 1% or more. In aspects, the percentage of cells that are positive for TRIM37 is 2% or more. In aspects, the percentage of cells that are positive for TRIM37 is 3% or more. In aspects, the percentage of cells that are positive for TRIM37 is 4% or more. In aspects, the percentage of cells that are positive for TRIM37 is 5% or more. In aspects, the percentage of cells that are positive for TRIM37 is 6% or more. In aspects, the percentage of cells that are positive for TRIM37 is 7% or more. In aspects, the percentage of cells that are positive for TRIM37 is 8% or more. In aspects, the percentage of cells that are positive for TRIM37 is 9% or more. In aspects, the percentage of cells that are positive for TRIM37 is 10% or more. In aspects, the percentage of cells that are positive for TRIM37 is 11% or more. In aspects, the percentage of cells that are positive for TRIM37 is 12% or more. In aspects, the percentage of cells that are positive for TRIM37 is 13% or more. In aspects, the percentage of cells that are positive for TRIM37 is 14% or more. In aspects, the percentage of cells that are positive for TRIM37 is 15% or more. In aspects, the percentage of cells that are positive for TRIM37 is 16% or more. In aspects, the percentage of cells that are positive for TRIM37 is 17% or more. In aspects, the percentage of cells that are positive for TRIM37 is 18% or more. In aspects, the percentage of cells that are positive for TRIM37 is 19% or more. In aspects, the percentage of cells that are positive for TRIM37 is 20% or more. In aspects, the percentage of cells that are positive for TRIM37 is 21% or more. In aspects, the percentage of cells that are positive for TRIM37 is 22% or more. In aspects, the percentage of cells that are positive for TRIM37 is 23% or more. In aspects, the percentage of cells that are positive for TRIM37 is 24% or more. In aspects, the percentage of cells that are positive for TRIM37 is 25% or more. In aspects, the percentage of cells that are positive for TRIM37 is 26% or more. In aspects, the percentage of cells that are positive for TRIM37 is 27% or more. In aspects, the percentage of cells that are positive for TRIM37 is 28% or more. In aspects, the percentage of cells that are positive for TRIM37 is 29% or more. In aspects, the percentage of cells that are positive for TRIM37 is 30% or more. In aspects, the percentage of cells that are positive for TRIM37 is 31% or more. In aspects, the percentage of cells that are positive for TRIM37 is 32% or more. In aspects, the percentage of cells that are positive for TRIM37 is 33% or more. In aspects, the percentage of cells that are positive for TRIM37 is 34% or more. In aspects, the percentage of cells that are positive for TRIM37 is 35% or more. In aspects, the percentage of cells that are positive for TRIM37 is 36% or more. In aspects, the percentage of cells that are positive for TRIM37 is 37% or more. In aspects, the percentage of cells that are positive for TRIM37 is 38% or more. In aspects, the percentage of cells that are positive for TRIM37 is 39% or more. In aspects, the percentage of cells that are positive for TRIM37 is 40% or more. In aspects, the percentage of cells that are positive for TRIM37 is 41% or more. In aspects, the percentage of cells that are positive for TRIM37 is 42% or more. In aspects, the percentage of cells that are positive for TRIM37 is 43% or more. In aspects, the percentage of cells that are positive for TRIM37 is 44% or more. In aspects, the percentage of cells that are positive for TRIM37 is 45% or more. In aspects, the percentage of cells that are positive for TRIM37 is 46% or more. In aspects, the percentage of cells that are positive for TRIM37 is 47% or more. In aspects, the percentage of cells that are positive for TRIM37 is 48% or more. In aspects, the percentage of cells that are positive for TRIM37 is 49% or more. In aspects, the percentage of cells that are positive for TRIM37 is 50% or more. In aspects, the percentage of cells that are positive for TRIM37 is 51% or more. In aspects, the percentage of cells that are positive for TRIM37 is 52% or more. In aspects, the percentage of cells that are positive for TRIM37 is 53% or more. In aspects, the percentage of cells that are positive for TRIM37 is 54% or more. In aspects, the percentage of cells that are positive for TRIM37 is 55% or more. In aspects, the percentage of cells that are positive for TRIM37 is 56% or more. In aspects, the percentage of cells that are positive for TRIM37 is 57% or more. In aspects, the percentage of cells that are positive for TRIM37 is 58% or more. In aspects, the percentage of cells that are positive for TRIM37 is 59% or more. In aspects, the percentage of cells that are positive for TRIM37 is 60% or more. In aspects, the percentage of cells that are positive for TRIM37 is 61% or more. In aspects, the percentage of cells that are positive for TRIM37 is 62% or more. In aspects, the percentage of cells that are positive for TRIM37 is 63% or more. In aspects, the percentage of cells that are positive for TRIM37 is 64% or more. In aspects, the percentage of cells that are positive for TRIM37 is 65% or more. In aspects, the percentage of cells that are positive for TRIM37 is 66% or more. In aspects, the percentage of cells that are positive for TRIM37 is 67% or more. In aspects, the percentage of cells that are positive for TRIM37 is 68% or more. In aspects, the percentage of cells that are positive for TRIM37 is 69% or more. In aspects, the percentage of cells that are positive for TRIM37 is 70% or more. In aspects, the percentage of cells that are positive for TRIM37 is 71% or more. In aspects, the percentage of cells that are positive for TRIM37 is 72% or more. In aspects, the percentage of cells that are positive for TRIM37 is 73% or more. In aspects, the percentage of cells that are positive for TRIM37 is 74% or more. In aspects, the percentage of cells that are positive for TRIM37 is 75% or more. In aspects, the percentage of cells that are positive for TRIM37 is 76% or more. In aspects, the percentage of cells that are positive for TRIM37 is 77% or more. In aspects, the percentage of cells that are positive for TRIM37 is 78% or more. In aspects, the percentage of cells that are positive for TRIM37 is 79% or more. In aspects, the percentage of cells that are positive for TRIM37 is 80% or more. In aspects, the percentage of cells that are positive for TRIM37 is 81% or more. In aspects, the percentage of cells that are positive for TRIM37 is 82% or more. In aspects, the percentage of cells that are positive for TRIM37 is 83% or more. In aspects, the percentage of cells that are positive for TRIM37 is 84% or more. In aspects, the percentage of cells that are positive for TRIM37 is 85% or more. In aspects, the percentage of cells that are positive for TRIM37 is 86% or more. In aspects, the percentage of cells that are positive for TRIM37 is 87% or more. In aspects, the percentage of cells that are positive for TRIM37 is 88% or more. In aspects, the percentage of cells that are positive for TRIM37 is 89% or more. In aspects, the percentage of cells that are positive for TRIM37 is 90% or more. In aspects, the percentage of cells that are positive for TRIM37 is 91% or more. In aspects, the percentage of cells that are positive for TRIM37 is 92% or more. In aspects, the percentage of cells that are positive for TRIM37 is 93% or more. In aspects, the percentage of cells that are positive for TRIM37 is 94% or more. In aspects, the percentage of cells that are positive for TRIM37 is 95% or more. In aspects, the percentage of cells that are positive for TRIM37 is 96% or more. In aspects, the percentage of cells that are positive for TRIM37 is 97% or more. In aspects, the percentage of cells that are positive for TRIM37 is 98% or more. In aspects, the percentage of cells that are positive for TRIM37 is 99% or more.

In embodiments, TRIM37 gene expression is used to assay for elevated TRIM37. For example, quantitative rtPCR, Nanostring, and in situ hybridization are platforms to quantitate gene expression. For Nanostring, RNA is extracted from tumor samples and a known quantity of RNA is placed on the Nanostring machine for gene expression detection using gene specific probes. The number of counts of TRIM37 within a sample is determined and normalized to a set of "housekeeping" genes. The term "levels of the TRIM37 gene" and variations thereof can be used interchangeably with the term "copies of the TRIM37 gene." The term "measuring the level of the TRIM37 gene" and variations thereof can be used interchangeably with the term "measuring copies of the TRIM37 gene."

"Chromogranin A" or "CHGA" as referred to herein includes any recombinant or naturally-occurring form of parathyroid secretory protein 1 (including homologs, isoforms, and functional fragments thereof) that maintain Chromogranin A activity (e.g. within at least 30%, 40%, 50%, 60%, 70%, 80%, 90%, 95%, or 100% activity compared to wild type Chromogranin A). In embodiments, the Chromogranin A protein encoded by the CHGA gene has the amino acid sequence set forth in or corresponding to Entrez 1113, UniProt P10645, or RefSeq (protein) XP_011534672.1. In embodiments, the CHGA gene has the nucleic acid sequence set forth in RefSeq (mRNA) XM_011536370.1. In embodiments, the amino acid sequence or nucleic acid sequence is the sequence known at the time of filing of the present application. In embodiments, the Chromogranin A is a human Chromogranin A. In aspects, the variants or homologs have at least 90%, 95%, 96%, 97%, 98%, 99% or 100% nucleic acid sequence identity across the whole sequence or a portion of the sequence (e.g. a 50, 100, 150 or 200 continuous nucleotide portion) compared to a naturally occurring Chromogranin A gene or mRNA. In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Chromogranin A protein.

"Chromogranin A levels" as referred to herein is the level of Chromogranin A expressed by a tumor. The Chromogranin A levels can be measured by genes, mRNA, or proteins in a biological sample.

"An elevated level of Chromogranin A" as referred to herein is an elevated level of Chromogranin A genes on a tumor or an elevated level of Chromogranin A expressed (e.g., mRNA, proteins) by a tumor in a subject when compared to a control. Chromogranin A levels can be measured from biological samples, such as a tumor sample (e.g., resected, biopsy) or a blood sample (e.g., peripheral blood), obtained from a subject. A tumor can be a primary tumor or a metastasis. A tumor as provided herein is a cellular mass including cancer cells and non-cancer cells. The non-cancer cells forming part of a tumor may be stromal cells, and immune cells (e.g., T cells, dendritic cells, B cells, macrophages). Thus, the elevated level of Chromogranin A may be expressed by a non-cancer cell (e.g., a stromal cell) or a cancer cell (e.g., a malignant T cell).

Chromogranin A levels can be detected at either the protein or gene expression level. Chromogranin A protein can be quantified by immunohistochemistry (IHC) or flow cytometry with an antibody that detects Chromogranin A. Chromogranin A gene expression can be quantified by multiple platforms such as real-time polymerase chain reaction (rtPCR), Nanostring, or in situ hybridization. There is a range of Chromogranin A expression across and within tumor types that shows concordance when measured with either IHC or by Nanostring. One skilled in the art will understand the importance of selecting a threshold of Chromogranin A expression that constitutes elevated levels. Controls are also valuable for determining the significance of data. For example, if values for a given parameter are widely variant in controls, variation in test samples will not be considered as significant. In some examples of the disclosed methods, when the expression level of Chromogranin A is assessed, the level is compared with a control expression level of Chromogranin A. By control expression level is meant the expression level of Chromogranin A from a sample or subject lacking cancer, a sample or subject at a selected stage of cancer or cancer state, or in the absence of a particular variable such as a therapeutic agent. Alternatively, the control level comprises a known amount of Chromogranin A. Such a known amount correlates with an average level of subjects lacking cancer, at a selected stage of cancer or cancer state, or in the absence of a particular variable such as a therapeutic agent. A control level also includes the expression level of Chromogranin A from one or more selected samples or subjects as described herein. For example, a control level includes an assessment of the expression level of Chromogranin A in a sample from a subject that does not have cancer, is at a selected stage of cancer or cancer state, or has not received treatment for cancer. Another exemplary control level includes an assessment of the expression level of Chromogranin A in samples taken from multiple subjects that do not have cancer, are at a selected stage of cancer, or have not received treatment for cancer. In some embodiments, a threshold for elevated Chromogranin A may be above the median expression level of a group of control samples. In some embodiments it may be above the first or third quartile of Chromogranin A expression in a group of control samples. In some embodiments it may be above the $10^{th}$, $20^{th}$, $30^{th}$, $40^{th}$, $60^{th}$, $70^{th}$, $80^{th}$ or $90^{th}$ percentile of Chromogranin A expression for a group of control samples. When the control level includes the expression level of Chromogranin A in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

In embodiments, the elevated level of Chromogranin A is calculated by determining the percentage of cells a biological sample that are positive for Chromogranin A. The cells may be tumor cells, tumor infiltrating cells, stromal cells, vasculature cells, or a composite thereof. In embodiments, the cells are tumor cells. In embodiments, the percentage of cells that are positive for Chromogranin A may be greater than 1%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 90%, or greater than 95%. In aspects, the percentage of cells that are positive for Chromogranin A is 1% or more. In aspects, the percentage of cells that are positive for Chromogranin A is 2% or more. In aspects, the percentage of cells that are positive for Chromogranin A is 3% or more. In aspects, the percentage of cells that are positive for Chromogranin A is 4% or more. In aspects, the percentage of cells that are positive for Chromogranin A is 5% or more. In aspects, the percentage of cells that are positive for Chromogranin A is 6% or more. In aspects, the percentage of cells that are positive for Chromogranin A is 7% or more. In aspects, the percentage of cells that are positive for Chromogranin A is 8% or more. In aspects, the percentage of cells that are positive for Chromogranin A is 9% or more. In aspects, the percentage of cells that are positive for Chromogranin A is 10% or more. In aspects, the percentage of cells that are positive for Chromogranin A is 11% or more. In aspects, the percentage of cells that are positive for Chromogranin A is 12% or more. In aspects, the percentage of cells that are positive for Chromogranin A is 13% or more. In aspects, the percentage of cells that are positive for Chromogranin A is 14% or more. In aspects, the percentage of cells that are positive for Chromogranin A is 15% or more. In aspects, the percentage of cells that are positive for Chromogranin A is 16% or more. In aspects, the percentage of cells that are positive for Chromogranin A is 17% or more. In aspects, the percentage of cells that are positive for Chromogranin A is 18% or more. In aspects, the percentage of cells that are positive for Chromogranin A is 19% or more. In aspects, the percentage of cells that are positive for Chromogranin A is 20% or more. In aspects, the percentage of cells that are positive for Chromogranin A is 21% or more. In aspects, the percentage of cells that are positive for Chromogranin A is 22% or more. In aspects, the percentage of cells that are positive for Chromogranin A is 23% or more. In aspects, the percentage of cells that are positive for Chromogranin A is 24% or more. In aspects, the percentage of cells that are positive for Chromogranin A is 25% or more. In aspects, the percentage of cells that are positive for Chromogranin A is 26% or more. In aspects, the percentage of cells that are positive for Chromogranin A is 27% or more. In aspects, the percentage of cells that are positive for Chromogranin A is 28% or more. In aspects, the percentage of cells that are positive for Chromogranin A is 29% or more. In aspects, the percentage of cells that are positive for Chromogranin A is 30% or more. In aspects, the percentage of cells that are positive for Chromogranin A is 31% or more. In aspects, the percentage of cells that are positive for Chromogranin A is 32% or more. In aspects, the percentage of cells that are positive for Chromogranin A is 33% or more. In aspects, the percentage of cells that are positive for Chromogranin A is 34% or more. In aspects, the percentage of cells that are positive for Chromogranin A is 35% or more. In aspects, the percentage of cells that are positive for Chromogranin A is 36% or more. In aspects, the percentage of cells that are positive for Chromogranin A is 37% or more. In aspects, the percentage of cells that are positive for Chromogranin A is 38% or more. In aspects, the percentage of cells that are positive for Chromogranin A is 39% or more. In aspects, the percentage of cells that are positive for Chromogranin A is 40% or more. In aspects, the percentage of cells that are positive for Chromogranin A is 41% or more. In aspects, the percentage of cells that are positive for Chromogranin A is 42% or more. In aspects, the percentage of cells that are positive for Chromogranin A is 43% or more. In aspects, the percentage of cells that are positive for Chromogranin A is 44% or more. In aspects, the percentage of cells that are positive for Chromogranin A is 45% or more. In aspects, the percentage of cells that are positive for Chromogranin A is 46% or more. In aspects, the percentage of cells that are positive for Chromogranin A is 47% or more. In aspects, the percentage of cells that are positive for Chromogranin A is 48% or more. In aspects, the percentage of cells that are positive for Chromogranin A is 49% or more. In aspects, the percentage of cells that are positive for Chromogranin A is 50% or more. In aspects, the percentage of cells that are positive for Chromogranin A is 51% or more. In aspects, the percentage of cells that are positive for Chromogranin A is 52% or more. In aspects, the percentage of cells that are positive for Chromogranin A is 53% or more. In aspects, the percentage of cells that are positive for Chromogranin A is 54% or more. In aspects, the percentage of cells that are positive for Chromogranin A is 55% or more. In aspects, the percentage of cells that are positive for Chromogranin A is 56% or more. In aspects, the percentage of cells that are positive for Chromogranin A is 57% or more. In aspects, the percentage of cells that are positive for Chromogranin A is 58% or more. In aspects, the percentage of cells that are positive for Chromogranin A is 59% or more. In aspects, the percentage of cells that are positive for Chromogranin A is 60% or more. In aspects, the percentage of cells that are positive for Chromogranin A is 61% or more. In aspects, the percentage of cells that are positive for Chromogranin A is 62% or more. In aspects, the percentage of cells that are positive for Chromogranin A is 63% or more. In aspects, the percentage of cells that are positive for Chromogranin A is 64% or more. In aspects, the percentage of cells that are positive for Chromogranin A is 65% or more. In aspects, the percentage of cells that are positive for Chromogranin A is 66% or more. In aspects, the percentage of cells that are positive for Chromogranin A is 67% or more. In aspects, the percentage of cells that are positive for Chromogranin A is 68% or more.

In aspects, the percentage of cells that are positive for Chromogranin A is 69% or more. In aspects, the percentage of cells that are positive for Chromogranin A is 70% or more. In aspects, the percentage of cells that are positive for Chromogranin A is 71% or more. In aspects, the percentage of cells that are positive for Chromogranin A is 72% or more. In aspects, the percentage of cells that are positive for Chromogranin A is 73% or more. In aspects, the percentage of cells that are positive for Chromogranin A is 74% or more. In aspects, the percentage of cells that are positive for Chromogranin A is 75% or more. In aspects, the percentage of cells that are positive for Chromogranin A is 76% or more. In aspects, the percentage of cells that are positive for Chromogranin A is 77% or more. In aspects, the percentage of cells that are positive for Chromogranin A is 78% or more. In aspects, the percentage of cells that are positive for Chromogranin A is 79% or more. In aspects, the percentage of cells that are positive for Chromogranin A is 80% or more. In aspects, the percentage of cells that are positive for Chromogranin A is 81% or more. In aspects, the percentage of cells that are positive for Chromogranin A is 82% or more. In aspects, the percentage of cells that are positive for Chromogranin A is 83% or more. In aspects, the percentage of cells that are positive for Chromogranin A is 84% or more. In aspects, the percentage of cells that are positive for Chromogranin A is 85% or more. In aspects, the percentage of cells that are positive for Chromogranin A is 86% or more. In aspects, the percentage of cells that are positive for Chromogranin A is 87% or more. In aspects, the percentage of cells that are positive for Chromogranin A is 88% or more. In aspects, the percentage of cells that are positive for Chromogranin A is 89% or more. In aspects, the percentage of cells that are positive for Chromogranin A is 90% or more. In aspects, the percentage of cells that are positive for Chromogranin A is 91% or more. In aspects, the percentage of cells that are positive for Chromogranin A is 92% or more. In aspects, the percentage of cells that are positive for Chromogranin A is 93% or more. In aspects, the percentage of cells that are positive for Chromogranin A is 94% or more. In aspects, the percentage of cells that are positive for Chromogranin A is 95% or more. In aspects, the percentage of cells that are positive for Chromogranin A is 96% or more. In aspects, the percentage of cells that are positive for Chromogranin A is 97% or more. In aspects, the percentage of cells that are positive for Chromogranin A is 98% or more. In aspects, the percentage of cells that are positive for Chromogranin A is 99% or more.

In embodiments, Chromogranin A gene expression is used to assay for elevated Chromogranin A. For example, quantitative rtPCR, Nanostring, and in situ hybridization are platforms to quantitate gene expression. For Nanostring, RNA is extracted from tumor samples and a known quantity of RNA is placed on the Nanostring machine for gene expression detection using gene specific probes. The number of counts of Chromogranin A within a sample is determined and normalized to a set of "housekeeping" genes.

"Synaptophysin" or "SYP" as referred to herein includes any recombinant or naturally-occurring form of major synaptic vesicle protein p38 (including homologs, isoforms, and functional fragments thereof) that maintain Synaptophysin activity (e.g. within at least 30%, 40%, 50%, 60%, 70%, 80%, 90%, 95%, or 100% activity compared to wild type Synaptophysin). In embodiments, the Synaptophysin protein encoded by the SYP gene has the amino acid sequence set forth in or corresponding to Entrez 6855, UniProt P08247, or RefSeq (protein) NP_003170.1. In embodiments, the amino acid sequence or nucleic acid sequence is the sequence known at the time of filing of the present application. In embodiments, the Synaptophysin is a human Synaptophysin. In aspects, the variants or homologs have at least 90%, 95%, 96%, 97%, 98%, 99% or 100% nucleic acid sequence identity across the whole sequence or a portion of the sequence (e.g. a 50, 100, 150 or 200 continuous nucleotide portion) compared to a naturally occurring Synaptophysin gene or mRNA. In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Synaptophysin protein.

"Synaptophysin levels" as referred to herein is the level of Synaptophysin expressed by a tumor. The Synaptophysin levels can be measured by genes, mRNA, or proteins in a biological sample.

"An elevated level of Synaptophysin" as referred to herein is an elevated level of Synaptophysin genes on a tumor or an elevated level of Synaptophysin expressed (e.g., mRNA, proteins) by a tumor in a subject when compared to a control. Synaptophysin levels can be measured from biological samples, such as a tumor sample (e.g., resected, biopsy) or a blood sample (e.g., peripheral blood), obtained from a subject. A tumor can be a primary tumor or a metastasis. A tumor as provided herein is a cellular mass including cancer cells and non-cancer cells. The non-cancer cells forming part of a tumor may be stromal cells, and immune cells (e.g., T cells, dendritic cells, B cells, macrophages). Thus, the elevated level of Synaptophysin may be expressed by a non-cancer cell (e.g., a stromal cell) or a cancer cell (e.g., a malignant T cell).

Synaptophysin levels can be detected at either the protein or gene expression level. Synaptophysin protein can be quantified by immunohistochemistry (IHC) or flow cytometry with an antibody that detects Synaptophysin. Synaptophysin gene expression can be quantified by multiple platforms such as real-time polymerase chain reaction (rtPCR), Nanostring, or in situ hybridization. There is a range of Synaptophysin expression across and within tumor types that shows concordance when measured with either IHC or by Nanostring. One skilled in the art will understand the importance of selecting a threshold of Synaptophysin expression that constitutes elevated levels. Controls are also valuable for determining the significance of data. For example, if values for a given parameter are widely variant in controls, variation in test samples will not be considered as significant. In some examples of the disclosed methods, when the expression level of Synaptophysin is assessed, the level is compared with a control expression level of Synaptophysin. By control expression level is meant the expression level of Synaptophysin from a sample or subject lacking cancer, a sample or subject at a selected stage of cancer or cancer state, or in the absence of a particular variable such as a therapeutic agent. Alternatively, the control level comprises a known amount of Synaptophysin. Such a known amount correlates with an average level of subjects lacking cancer, at a selected stage of cancer or cancer state, or in the absence of a particular variable such as a therapeutic agent. A control level also includes the expression level of Synaptophysin from one or more selected samples or subjects as described herein. For example, a control level includes an assessment of the expression level of Synaptophysin in a sample from a subject that does not have cancer, is at a selected stage of cancer or cancer state, or has not received treatment for cancer. Another exemplary control level includes an assessment of the expression level of Synaptophysin in samples taken from multiple subjects that do not have cancer, are at a selected stage of cancer, or have not received treatment for cancer. In some embodiments, a threshold for elevated Synaptophysin may be above the median expression level of a group of control samples. In some embodiments it may be above the first or third quartile of Synaptophysin expression in a group of control samples. In some embodiments it may be above the $10^{th}$, $20^{th}$, $30^{th}$, $40^{th}$, $60^{th}$, $70^{th}$, $80^{th}$ or $90^{th}$ percentile of Synaptophysin expression for a group of control samples. When the control level includes the expression level of Synaptophysin in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

In embodiments, the elevated level of Synaptophysin is calculated by determining the percentage of cells in a biological sample that are positive for Synaptophysin. The cells may be tumor cells, tumor infiltrating cells, stromal cells, vasculature cells, or a composite thereof. In embodiments, the cells are tumor cells. In embodiments, the percentage of cells that are positive for Synaptophysin may be greater than 1%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 90%, or greater than 95%. In aspects, the percentage of cells that are positive for Synaptophysin is 1% or more. In aspects, the percentage of cells that are positive for Synaptophysin is 2% or more. In aspects, the percentage of cells that are positive for Synaptophysin is 3% or more. In aspects, the percentage of cells that are positive for Synaptophysin is 4% or more. In aspects, the percentage of cells that are positive for Synaptophysin is 5% or more. In aspects, the percentage of cells that are positive for Synaptophysin is 6% or more. In aspects, the percentage of cells that are positive for Synaptophysin is 7% or more. In aspects, the percentage of cells that are positive for Synaptophysin is 8% or more. In aspects, the percentage of cells that are positive for Synaptophysin is 9% or more. In aspects, the percentage of cells that are positive for Synaptophysin is 10% or more. In aspects, the percentage of cells that are positive for Synaptophysin is 11% or more. In aspects, the percentage of cells that are positive for Synaptophysin is 12% or more. In aspects, the percentage of cells that are positive for Synaptophysin is 13% or more. In aspects, the percentage of cells that are positive for Synaptophysin is 14% or more. In aspects, the percentage of cells that are positive for Synaptophysin is 15% or more. In aspects, the percentage of cells that are positive for Synaptophysin is 16% or more. In aspects, the percentage of cells that are positive for Synaptophysin is 17% or more. In aspects, the percentage of cells that are positive for Synaptophysin is 18% or more. In aspects, the percentage of cells that are positive for Synaptophysin is 19% or more. In aspects, the percentage of cells that are positive for Synaptophysin is 20% or more. In aspects, the percentage of cells that are positive for Synaptophysin is 21% or more. In aspects, the percentage of cells that are positive for Synaptophysin is 22% or more. In aspects, the percentage of cells that are positive for Synaptophysin is 23% or more. In aspects, the percentage of cells that are positive for Synaptophysin is 24% or more. In aspects, the percentage of cells that are positive for Synaptophysin is 25% or more. In aspects, the percentage of cells that are positive for Synaptophysin is 26% or more. In aspects, the percentage of cells that are positive for Synaptophysin is 27% or more. In aspects, the percentage of cells that are positive for Synaptophysin is 28% or more. In aspects, the percentage of cells that are positive for Synaptophysin is 29% or more. In aspects, the percentage of cells that are positive for Synaptophysin is 30% or more. In aspects, the percentage of cells that are positive for Synaptophysin is 31% or more. In aspects, the percentage of cells that are positive for Synaptophysin is 32% or more. In aspects, the percentage of cells that are positive for Synaptophysin is 33% or more. In aspects, the percentage of cells that are positive for Synaptophysin is 34% or more. In aspects, the percentage of cells that are positive for Synaptophysin is 35% or more. In aspects, the percentage of cells that are positive for Synaptophysin is 36% or more. In aspects, the percentage of cells that are positive for Synaptophysin is 37% or more. In aspects, the percentage of cells that are positive for Synaptophysin is 38% or more. In aspects, the percentage of cells that are positive for Synaptophysin is 39% or more. In aspects, the percentage of cells that are positive for Synaptophysin is 40% or more. In aspects, the percentage of cells that are positive for Synaptophysin is 41% or more. In aspects, the percentage of cells that are positive for Synaptophysin is 42% or more. In aspects, the percentage of cells that are positive for Synaptophysin is 43% or more. In aspects, the percentage of cells that are positive for Synaptophysin is 44% or more. In aspects, the percentage of cells that are positive for Synaptophysin is 45% or more. In aspects, the percentage of cells that are positive for Synaptophysin is 46% or more. In aspects, the percentage of cells that are positive for Synaptophysin is 47% or more. In aspects, the percentage of cells that are positive for Synaptophysin is 48% or more. In aspects, the percentage of cells that are positive for Synaptophysin is 49% or more. In aspects, the percentage of cells that are positive for Synaptophysin is 50% or more. In aspects, the percentage of cells that are positive for Synaptophysin is 51% or more. In aspects, the percentage of cells that are positive for Synaptophysin is 52% or more. In aspects, the percentage of cells that are positive for Synaptophysin is 53% or more. In aspects, the percentage of cells that are positive for Synaptophysin is 54% or more. In aspects, the percentage of cells that are positive for Synaptophysin is 55% or more. In aspects, the percentage of cells that are positive for Synaptophysin is 56% or more. In aspects, the percentage of cells that are positive for Synaptophysin is 57% or more. In aspects, the percentage of cells that are positive for Synaptophysin is 58% or more. In aspects, the percentage of cells that are positive for Synaptophysin is 59% or more. In aspects, the percentage of cells that are positive for Synaptophysin is 60% or more. In aspects, the percentage of cells that are positive for Synaptophysin is 61% or more. In aspects, the percentage of cells that are positive for Synaptophysin is 62% or more. In aspects, the percentage of cells that are positive for Synaptophysin is 63% or more. In aspects, the percentage of cells that are positive for Synaptophysin is 64% or more. In aspects, the percentage of cells that are positive for Synaptophysin is 65% or more. In aspects, the percentage of cells that are positive for Synaptophysin is 66% or more. In aspects, the percentage of cells that are positive for Synaptophysin is 67% or more. In aspects, the percentage of cells that are positive for Synaptophysin is 68% or more. In aspects, the percentage of cells that are positive for Synaptophysin is 69% or more. In aspects, the percentage of cells that are positive for Synaptophysin is 70% or more. In aspects, the percentage of cells that are positive for Synaptophysin is 71% or more. In aspects, the percentage of cells that are positive for Synaptophysin is 72% or more. In aspects, the percentage of cells that are positive for Synaptophysin is 73% or more. In aspects, the percentage of cells that are positive for Synaptophysin is 74% or more. In aspects, the percentage of cells that are positive for Synaptophysin is 75% or more. In aspects, the percentage of cells that are positive for Synaptophysin is 76% or more. In aspects, the percentage of cells that are positive for Synaptophysin is 77% or more. In aspects, the percentage of cells that are positive for Synaptophysin is 78% or more. In aspects, the percentage of cells that are positive for Synaptophysin is 79% or more. In aspects, the percentage of cells that are positive for Synaptophysin is 80% or more. In aspects, the percentage of cells that are positive for Synaptophysin is 81% or more. In aspects, the percentage of cells that are positive for Synaptophysin is 82% or more. In aspects, the percentage of cells that are positive for Synaptophysin is 83% or more. In aspects, the percentage of cells that are positive for Synaptophysin is 84% or more. In aspects, the percentage of cells that are positive for Synaptophysin is 85% or more. In aspects, the percentage of cells that are positive for Synaptophysin is 86% or more. In aspects, the percentage of cells that are positive for Synaptophysin is 87% or more. In aspects, the percentage of cells that are positive for Synaptophysin is 88% or more. In aspects, the percentage of cells that are positive for Synaptophysin is 89% or more. In aspects, the percentage of cells that are positive for Synaptophysin is 90% or more. In aspects, the percentage of cells that are positive for Synaptophysin is 91% or more. In aspects, the percentage of cells that are positive for Synaptophysin is 92% or more. In aspects, the percentage of cells that are positive for Synaptophysin is 93% or more. In aspects, the percentage of cells that are positive for Synaptophysin is 94% or more. In aspects, the percentage of cells that are positive for Synaptophysin is 95% or more. In aspects, the percentage of cells that are positive for Synaptophysin is 96% or more. In aspects, the percentage of cells that are positive for Synaptophysin is 97% or more. In aspects, the percentage of cells that are positive for Synaptophysin is 98% or more. In aspects, the percentage of cells that are positive for Synaptophysin is 99% or more.

In embodiments, Synaptophysin gene expression is used to assay for elevated Synaptophysin. For example, quantitative rtPCR, Nanostring, and in situ hybridization are platforms to quantitate gene expression. For Nanostring, RNA is extracted from tumor samples and a known quantity of RNA is placed on the Nanostring machine for gene expression detection using gene specific probes. The number of counts of Synaptophysin within a sample is determined and normalized to a set of "housekeeping" genes.

The phrase "a TRIM37 level, a Chromogranin A level, and/or a Synaptophysin level" refers to the following: (i) a TRIM37 level; (ii) a Chromogranin A level; (iii) a Synaptophysin level; (iv) a TRIM37 level and a Chromogranin A level; (v) a TRIM37 level and a Synaptophysin level; (vi) a Chromogranin A level and a Synaptophysin level; or (vii) a TRIM37 level, a Chromogranin A level, and a Synaptophysin level. In embodiments, "a TRIM37 level, a Chromogranin A level, and/or a Synaptophysin level" is (i). In embodiments, "a TRIM37 level, a Chromogranin A level, and/or a Synaptophysin level" is (ii). In embodiments, "a TRIM37 level, a Chromogranin A level, and/or a Synaptophysin level" is (iii). In embodiments, "a TRIM37 level, a Chromogranin A level, and/or a Synaptophysin level" is (iv). In embodiments, "a TRIM37 level, a Chromogranin A level, and/or a Synaptophysin level" is (v). In embodiments, "a TRIM37 level, a Chromogranin A level, and/or a Synaptophysin level" is (vi). In embodiments, "a TRIM37 level, a Chromogranin A level, and/or a Synaptophysin level" is (vii).

The phrase "an elevated level of TRIM37, Chromogranin A, and/or Synaptophysin" and the phrase "an elevated level of TRIM37, an elevated level of Chromogranin A, and/or an elevated level of Synaptophysin" refer to the following: (i) an elevated level of TRIM37; (ii) an elevated level of Chromogranin A; (iii) an elevated level of Synaptophysin; (iv) an elevated level of TRIM37 and an elevated level of Chromogranin A; (v) an elevated level of TRIM37 and an elevated level of Synaptophysin; (vi) an elevated level of Chromogranin A and an elevated level of Synaptophysin; or (vii) an elevated level of TRIM37, an elevated level of Chromogranin A, and an elevated level of Synaptophysin. In embodiments, "an elevated level of TRIM37, an elevated level of Chromogranin A, and/or an elevated level of Synaptophysin" is (i). In embodiments, "an elevated level of TRIM37, an elevated level of Chromogranin A, and/or an elevated level of Synaptophysin" is (ii). In embodiments, "an elevated level of TRIM37, an elevated level of Chromogranin A, and/or an elevated level of Synaptophysin" is (iii). In embodiments, "an elevated level of TRIM37, an elevated level of Chromogranin A, and/or an elevated level of Synaptophysin" is (iv). In embodiments, "an elevated level of TRIM37, an elevated level of Chromogranin A, and/or an elevated level of Synaptophysin" is (v). In embodiments, "an elevated level of TRIM37, an elevated level of Chromogranin A, and/or an elevated level of Synaptophysin" is (vi). In embodiments, "an elevated level of TRIM37, an elevated level of Chromogranin A, and/or an elevated level of Synaptophysin" is (vii).

"Subject responsive to a PLK4 inhibitor" refers to a subject that responds to treatment when administered a PLK4 inhibitor. "Responsive" and "responds" indicate that: (i) a cancerous tumor does not grow in size or volume over time; (ii) a cancerous tumor decreases in size or volume over time; (iii) a cancerous tumor does not metastasize; or (iv) a combination of two or more of the foregoing. In embodiments, a subject responsive to a PLK4 inhibitor shows a decrease (i.e., reduction) in tumor size or volume after treatment compared to baseline or a control. In embodiments, a subject responsive to a PLK4 inhibitor shows at least a 5% reduction in tumor size or volume after treatment compared to baseline or a control. In embodiments, a subject responsive to a PLK4 inhibitor shows at least a 10% reduction in tumor size or volume after treatment compared to baseline or a control. In embodiments, a subject responsive to a PLK4 inhibitor shows at least a 15% reduction in tumor size or volume after treatment compared to baseline or a control. In embodiments, a subject responsive to a PLK4 inhibitor shows at least a 20% reduction in tumor size or volume after treatment compared to baseline or a control. In embodiments, a subject responsive to a PLK4 inhibitor shows at least a 25% reduction in tumor size or volume after treatment compared to baseline or a control. In embodiments, a subject responsive to a PLK4 inhibitor shows at least a 30% reduction in tumor size or volume after treatment compared to baseline or a control. In embodiments, a subject responsive to a PLK4 inhibitor shows at least a 35% reduction in tumor size or volume after treatment compared to baseline or a control. In embodiments, a subject responsive to a PLK4 inhibitor shows at least a 40% reduction in tumor size or volume after treatment compared to baseline or a control. In embodiments, a subject responsive to a PLK4 inhibitor shows at least a 45% reduction in tumor size or volume after treatment compared to baseline or a control. In embodiments, a subject responsive to a PLK4 inhibitor shows at least a 50% reduction in tumor size or volume after treatment compared to baseline or a control. In embodiments, a subject responsive to a PLK4 inhibitor shows at least a 60% reduction in tumor size or volume after treatment compared to baseline or a control.

"Biological sample" refers to any biological sample taken from a subject. Biological samples include blood, plasma, serum, tumors, tissue, cells, and the like. In embodiments, the biological sample is a blood sample. In embodiments, the biological sample is a peripheral blood sample. In embodiments, the biological sample is a tumor sample. In embodiments, the biological sample is a primary tumor sample. In embodiments, the biological sample is a metastatic tumor sample. In embodiments, the biological sample is a resected tumor sample. In embodiments, the biological sample is a tumor biopsy sample. In embodiments, the biological sample is a resected tumor sample from a primary tumor. In embodiments, the biological sample is a resected tumor sample from a metastisic tumor. In embodiments, the biological sample is a tumor biopsy sample from a primary tumor. In embodiments, the biological sample is a tumor biopsy sample from a metastisic tumor. Biological samples can be taken from a subject by methods known in the art, and can be analyzed by methods known in the art.

A "control" sample or value refers to a sample that serves as a reference, usually a known reference, for comparison to a test sample. For example, a test sample can be taken from a patient suspected of having a given disease (cancer) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In embodiments, a control is a negative control. In embodiments, such as some embodiments relating to detecting the level of expression or infiltration, a control comprises the average amount of expression (e.g., protein or mRNA) of infiltration (e.g., number or percentage of cells in a population of cells) in a population of subjects (e.g., with cancer) or in a healthy or general population. In embodiments, the control comprises an average amount (e.g. percentage or number of infiltrating cells or amount of expression) in a population in which the number of subjects (n) is 5 or more, 6 or more, 7 or more, 8 or more, 9 or more, 10 or more, 25 of more, 50 or more, 100 or more, 1000 or more, 5000 or more, or 10000 or more. In embodiments, the control is a standard control. ne of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

A "p53 protein" or "p53" as referred to herein includes any of the recombinant or naturally-occurring forms of cellular tumor antigen p53 (p53) or variants or homologs thereof that maintain p53 activity (e.g. within at least 50%, 80%, 90%, 95%, 96%, 97%, 98%, 99% or 100% activity compared to p53). In aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring p53.

The term "wild type p53" or "wild type p53 protein" refers to a p53 protein that is substantially identical to the protein identified by the UniProt reference number P04637 or a variant or homolog having substantial identity thereto. In embodiments, the p53 protein is a wild type p53 protein.

The term "mutant protein" as used herein refers to a protein having aberrant biological activity compared to a non-mutant protein (e.g., a non-mutant p53 protein may be a protein identified by UniProt reference number P04637). A mutant protein may have increased or decreased biological activity or the mutant protein may have no detectable biological activity compared to the corresponding non-mutant protein (e.g. a non-mutant p53 protein identified by UniProt reference number P04637). A mutant protein may have biological activity distinct from the non-mutant protein (e.g. a non-mutant p53 protein identified by UniProt reference number P04637). Mutant proteins are encoded by DNA sequences (e.g., genes) including base pair insertions, deletions, or substitutions that are absent in the corresponding non-mutant protein and that result in the modulation (e.g., increased, decreased, loss of function, gain of function) of biological activity compared to the non-mutant protein.

The term "p53 mutant" or "p53 mutant protein" refers to a p53 protein with aberrant biological activity compared to a non-mutant (wild type) p53 protein (e.g., the p53 protein identified by UniProt reference number P04637). The mutant p53 protein as referred to herein fails to act as a suppressor of cell division and may exist at elevated intracellular levels compared to a non-mutant p53 protein. Mutations in the p53 gene (e.g., the human p53 gene identified by Ensebl reference number ENSG00000141510) have been found to correlate with aggressive disease characteristics and metastasis.

"p53 positive" or "p53+" as used herein refers to a cancer, tumor, or cell that expresses a p53 protein. "Wild type p53 positive" refers to a cancer, tumor, or cell that expresses a wild type p53 protein. "Mutant p53 positive" refers to a cancer, tumor, or cell that expresses a mutant p53 protein. In embodiments, a cancer is identified as p53 positive when there is a positive test result of a biological sample by immunohistochemical (IHC) analysis. In embodiments, a cancer is identified as p53 positive when at least 1% of the cells from a biological sample test positive by IHC. In embodiments, a cancer is identified as p53 positive when at least 2% of the cells from a biological sample test positive by IHC analysis. In embodiments, a cancer is identified as p53 positive when at least 3% of the cells from a biological sample test positive by IHC analysis. In embodiments, a cancer is identified as p53 positive when at least 4% of the cells from a biological sample test positive by IHC analysis. In embodiments, a cancer is identified as p53 positive when at least 5% of the cells from a biological sample test positive by IHC analysis. In embodiments, a cancer is identified as p53 positive when at least 6% of the cells from a biological sample test positive by IHC analysis. In embodiments, a cancer is identified as p53 positive when at least 7% of the cells from a biological sample test positive by IHC analysis. In embodiments, a cancer is identified as p53 positive when at least 8% of the cells from a biological sample test positive by IHC analysis. In embodiments, a cancer is identified as p53 positive when at least 9% of the cells from a biological sample test positive by IHC analysis. In embodiments, a cancer is identified as p53 positive when at least 10% of the cells from a biological sample test positive by IHC analysis. In embodiments, a cancer is identified as p53 positive when at least 11% of the cells from a biological sample test positive by IHC analysis. In embodiments, a cancer is identified as p53 positive when at least 12% of the cells from a biological sample test positive by IHC analysis. In embodiments, a cancer is identified as p53 positive when at least 13% of the cells from a biological sample test positive by IHC analysis. In embodiments, a cancer is identified as p53 positive when at least 14% of the cells from a biological sample test positive by IHC analysis. In embodiments, a cancer is identified as p53 positive when at least 15% of the cells from a biological sample test positive by IHC analysis. In embodiments, a cancer is identified as p53 positive when at least 16% of the cells from a biological sample test positive by IHC analysis. In embodiments, a cancer is identified as p53 positive when at least 17% of the cells from a biological sample test positive by IHC analysis. In embodiments, a cancer is identified as p53 positive when at least 18% of the cells from a biological sample test positive by IHC analysis. In embodiments, a cancer is identified as p53 positive when at least 19% of the cells from a biological sample test positive by IHC analysis. In embodiments, a cancer is identified as p53 positive when at least 20% of the cells from a biological sample test positive by IHC analysis. In embodiments, a cancer is identified as p53 positive when at least 21% of the cells from a biological sample test positive by IHC analysis. In embodiments, a cancer is identified as p53 positive when at least 22% of the cells from a biological sample test positive by IHC analysis. In embodiments, a cancer is identified as p53 positive when at least 23% of the cells from a biological sample test positive by IHC analysis. In embodiments, a cancer is identified as p53 positive when at least 24% of the cells from a biological sample test positive by IHC analysis. In embodiments, a cancer is identified as p53 positive when at least 25% of the cells test positive by IHC analysis. In embodiments, a cancer is identified as p53 positive when at least 26% of the cells test positive by IHC analysis. In embodiments, a cancer is identified as p53 positive when at least 27% of the cells test positive by IHC analysis. In embodiments, a cancer is identified as p53 positive when at least 28% of the cells test positive by IHC analysis. In embodiments, a cancer is identified as p53 positive when at least 29% of the cells test positive by IHC analysis. In embodiments, a cancer is identified as p53 positive when at least 30% of the cells test positive by IHC analysis. In embodiments, a cancer is identified as p53 positive when at least 31% of the cells test positive by IHC analysis. In embodiments, a cancer is identified as p53 positive when at least 32% of the cells test positive by IHC analysis. In embodiments, a cancer is identified as p53 positive when at least 33% of the cells test positive by IHC analysis. In embodiments, a cancer is identified as p53 positive when at least 34% of the cells test positive by IHC analysis. In embodiments, a cancer is identified as p53 positive when at least 35% of the cells test positive by IHC analysis. In embodiments, a cancer is identified as p53 positive when at least 36% of the cells test positive by IHC analysis. In embodiments, a cancer is identified as p53 positive when at least 37% of the cells test positive by IHC analysis. In embodiments, a cancer is identified as p53 positive when at least 38% of the cells test positive by IHC analysis. In embodiments, a cancer is identified as p53 positive when at least 39% of the cells test positive by IHC analysis. In embodiments, a cancer is identified as p53 positive when at least 40% of the cells test positive by IHC analysis. In embodiments, a cancer is identified as p53 positive when at least 41% of the cells test positive by IHC analysis. In embodiments, a cancer is identified as p53 positive when at least 42% of the cells test positive by IHC analysis. In embodiments, a cancer is identified as p53 positive when at least 43% of the cells test positive by IHC analysis. In embodiments, a cancer is identified as p53 positive when at least 44% of the cells test positive by IHC analysis. In embodiments, a cancer is identified as p53 positive when at least 45% of the cells test positive by IHC analysis. In embodiments, a cancer is identified as p53 positive when at least 46% of the cells test positive by IHC analysis. In embodiments, a cancer is identified as p53 positive when at least 47% of the cells test positive by IHC analysis. In embodiments, a cancer is identified as p53 positive when at least 48% of the cells test positive by IHC analysis. In embodiments, a cancer is identified as p53 positive when at least 49% of the cells test positive by IHC analysis. In embodiments, a cancer is identified as p53 positive when at least 50% of the cells test positive by IHC analysis. In embodiments, a cancer is identified as p53 positive when at least 51% of the cells test positive by IHC analysis. In embodiments, a cancer is identified as p53 positive when at least 52% of the cells test positive by IHC analysis. In embodiments, a cancer is identified as p53 positive when at least 53% of the cells test positive by IHC analysis. In embodiments, a cancer is identified as p53 positive when at least 54% of the cells test positive by IHC analysis. In embodiments, a cancer is identified as p53 positive when at least 55% of the cells test positive by IHC analysis. In embodiments, a cancer is identified as p53 positive when at least 56% of the cells test positive by IHC analysis. In embodiments, a cancer is identified as p53 positive when at least 57% of the cells test positive by IHC analysis. In embodiments, a cancer is identified as p53 positive when at least 58% of the cells test positive by IHC analysis. In embodiments, a cancer is identified as p53 positive when at least 59% of the cells test positive by IHC analysis. In embodiments, a cancer is identified as p53 positive when at least 60% of the cells test positive by IHC analysis. In embodiments, a cancer is identified as p53 positive when at least 61% of the cells test positive by IHC analysis. In embodiments, a cancer is identified as p53 positive when at least 62% of the cells test positive by IHC analysis. In embodiments, a cancer is identified as p53 positive when at least 63% of the cells test positive by IHC analysis. In embodiments, a cancer is identified as p53 positive when at least 64% of the cells test positive by IHC analysis. In embodiments, a cancer is identified as p53 positive when at least 65% of the cells test positive by IHC analysis. In embodiments, a cancer is identified as p53 positive when at least 66% of the cells test positive by IHC analysis. In embodiments, a cancer is identified as p53 positive when at least 67% of the cells test positive by IHC analysis. In embodiments, a cancer is identified as p53 positive when at least 68% of the cells test positive by IHC analysis. In embodiments, a cancer is identified as p53 positive when at least 69% of the cells test positive by IHC analysis. In embodiments, a cancer is identified as p53 positive when at least 70% of the cells test positive by IHC analysis. In embodiments, a cancer is identified as p53 positive when at least 71% of the cells test positive by IHC analysis. In embodiments, a cancer is identified as p53 positive when at least 72% of the cells test positive by IHC analysis. In embodiments, a cancer is identified as p53 positive when at least 73% of the cells test positive by IHC analysis. In embodiments, a cancer is identified as p53 positive when at least 74% of the cells test positive by IHC analysis. In embodiments, a cancer is identified as p53 positive when at least 75% of the cells test positive by IHC analysis. In embodiments, a cancer is identified as p53 positive when at least 76% of the cells test positive by IHC analysis. In embodiments, a cancer is identified as p53 positive when at least 77% of the cells test positive by IHC analysis. In embodiments, a cancer is identified as p53 positive when at least 78% of the cells test positive by IHC analysis. In embodiments, a cancer is identified as p53 positive when at least 79% of the cells test positive by IHC analysis. In embodiments, a cancer is identified as p53 positive when at least 80% of the cells test positive by IHC analysis. In embodiments, a cancer is identified as p53 positive when at least 81% of the cells test positive by IHC analysis. In embodiments, a cancer is identified as p53 positive when at least 82% of the cells test positive by IHC analysis. In embodiments, a cancer is identified as p53 positive when at least 83% of the cells test positive by IHC analysis. In embodiments, a cancer is identified as p53 positive when at least 84% of the cells test positive by IHC analysis. In embodiments, a cancer is identified as p53 positive when at least 85% of the cells test positive by IHC analysis. In embodiments, a cancer is identified as p53 positive when at least 86% of the cells test positive by IHC analysis. In embodiments, a cancer is identified as p53 positive when at least 87% of the cells test positive by IHC analysis. In embodiments, a cancer is identified as p53 positive when at least 88% of the cells test positive by IHC analysis. In embodiments, a cancer is identified as p53 positive when at least 89% of the cells test positive by IHC analysis. In embodiments, a cancer is identified as p53 positive when at least 90% of the cells test positive by IHC analysis. In embodiments, a cancer is identified as p53 positive when at least 91% of the cells test positive by IHC analysis. In embodiments, a cancer is identified as p53 positive when at least 92% of the cells test positive by IHC analysis. In embodiments, a cancer is identified as p53 positive when at least 93% of the cells test positive by IHC analysis. In embodiments, a cancer is identified as p53 positive when at least 94% of the cells test positive by IHC analysis. In embodiments, a cancer is identified as p53 positive when at least 95% of the cells test positive by IHC analysis. In embodiments, a cancer is identified as p53 positive when at least 96% of the cells test positive by IHC analysis. In embodiments, a cancer is identified as p53 positive when at least 97% of the cells test positive by IHC analysis. In embodiments, a cancer is identified as p53 positive when at least 98% of the cells test positive by IHC analysis. In embodiments, a cancer is identified as p53 positive when at least 99% of the cells test positive by IHC analysis. In embodiments, a cancer is identified as p53 positive when about 1% to about 100% of the cells test positive by IHC analysis. In embodiments, a cancer is identified as p53 positive when about 5% to about 100% of the cells test positive by IHC analysis. In embodiments, a cancer is identified as p53 positive when about 10% to about 100% of the cells test positive by IHC analysis. In embodiments, a cancer is identified as p53 positive when about 25% to about 100% of the cells test positive by IHC analysis. In embodiments, a cancer is identified as p53 positive when about 50% to about 100% of the cells test positive by IHC analysis. In embodiments, a cancer is identified as p53 positive when about 55% to about 100% of the cells test positive by IHC analysis. In embodiments, a cancer is identified as p53 positive when about 60% to about 100% of the cells test positive by IHC analysis. In embodiments, a cancer is identified as p53 positive when about 65% to about 100% of the cells test positive by IHC analysis. In embodiments, a cancer is identified as p53 positive when about 70% to about 100% of the cells test positive by IHC analysis. In embodiments, a cancer is identified as p53 positive when about 75% to about 100% of the cells test positive by IHC analysis. In embodiments, a cancer is identified as p53 positive when about 80% to about 100% of the cells test positive by IHC analysis.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g. selected from the group consisting of O, N, P, Si, and S, and wherein the nitrogen and sulfur atoms may optionally be oxidized, and the nitrogen heteroatom may optionally be quaternized). The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. The ring-forming substituents may be attached to adjacent members of the base structure. For example, two ring-forming substituents attached to adjacent members of a cyclic base structure create a fused ring structure. The ring-forming substituents may be attached to a single member of the base structure. For example, two ring-forming substituents attached to a single member of a cyclic base structure create a spirocyclic structure. The ring-forming substituents may be attached to non-adjacent members of the base structure.

Two of the substituents on adjacent atoms of the aryl or heteroaryl ring may optionally form a ring of the formula -T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

Each substituted group described in the compounds herein may be substituted with at least one substituent group. More specifically, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein may be substituted with at least one substituent group. At least one or all of these groups may be substituted with at least one size-limited substituent group. At least one or all of these groups may be substituted with at least one lower substituent group.

Each substituted or unsubstituted alkyl may be a substituted or unsubstituted $C_1$-$C_{20}$ alkyl, each substituted or unsubstituted heteroalkyl may be a substituted or unsubstituted 2 to 20 membered heteroalkyl, each substituted or unsubstituted cycloalkyl may be a substituted or unsubstituted $C_3$-$C_8$ cycloalkyl, and/or each substituted or unsubstituted heterocycloalkyl may be a substituted or unsubstituted 3 to 8 membered heterocycloalkyl. Each substituted or unsubstituted alkylene may be a substituted or unsubstituted $C_1$-$C_{20}$ alkylene, each substituted or unsubstituted heteroalkylene may be a substituted or unsubstituted 2 to 20 membered heteroalkylene, each substituted or unsubstituted cycloalkylene may be a substituted or unsubstituted $C_3$-$C_8$ cycloalkylene, and/or each substituted or unsubstituted heterocycloalkylene may be a substituted or unsubstituted 3 to 8 membered heterocycloalkylene.

Each substituted or unsubstituted alkyl may be a substituted or unsubstituted $C_1$-$C_8$ alkyl, each substituted or unsubstituted heteroalkyl may be a substituted or unsubstituted 2 to 8 membered heteroalkyl, each substituted or unsubstituted cycloalkyl may be a substituted or unsubstituted $C_3$-$C_7$ cycloalkyl, and/or each substituted or unsubstituted heterocycloalkyl may be a substituted or unsubstituted 3 to 7 membered heterocycloalkyl. Each substituted or unsubstituted alkylene may be a substituted or unsubstituted $C_1$-$C_8$ alkylene, each substituted or unsubstituted heteroalkylene may be a substituted or unsubstituted 2 to 8 membered heteroalkylene, each substituted or unsubstituted cycloalkylene may be a substituted or unsubstituted $C_3$-$C_7$ cycloalkylene, and/or each substituted or unsubstituted heterocycloalkylene may be a substituted or unsubstituted 3 to 7 membered heterocycloalkylene.

Certain compounds herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the compounds described herein. The compounds described herein do not include those which are known in art to be too unstable to synthesize and/or isolate. The compounds described herein also are meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds described herein may exist in tautomeric forms, and that all such tautomeric forms of the compounds may be considered within the scope of the compounds described herein.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the compounds described herein.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the compounds described herein.

The compounds described herein may also contain unnatural proportions of atomic isotopes at one or more of the atoms that constitute such compounds. For example, the compounds may be radiolabeled with radioactive isotopes, such as for example tritium (3H), iodine-125 ($^{125}$I), or carbon-14 ($^{14}$C). All isotopic variations of the compounds described herein, whether radioactive or not, are encompassed within the scope of the compounds described herein.

The symbol "  " or "-" denotes the point of attachment of a chemical moiety to the remainder of a molecule or chemical formula.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{133.2}$, $R^{13.3}$, $R^{13.4}$, etc., wherein each of $R^{13.1}$, $R^{13.2}$, $R^{13.3C}$, $R^{13.4}$, etc. is defined within the scope of the definition of $R^{13}$ and optionally differently.

Description of compounds described herein is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Tozasertib" is the compound having PubChem CID 5494449, and is also known as VX-680 and MK-0457.

The term "pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Compounds described herein may contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound could differ from the various salt forms in certain physical properties, such as solubility in polar solvents.

In addition to salt forms, the compounds described herein may be provided in a prodrug form. Prodrugs of the compounds described herein include those compounds that readily undergo chemical or enzymatic changes under physiological conditions to provide the compounds described herein. Additionally, prodrugs can be converted to the compounds described herein by chemical or biochemical methods in an ex vivo environment. For example, prodrugs can be slowly converted to the compounds described herein when placed in a transdermal patch reservoir with a suitable enzyme or chemical reagent.

Certain compounds described herein can exist in unsolvated forms as well as solvated forms, including hydrated forms. In general, the solvated forms are equivalent to unsolvated forms and are encompassed within the scope of the compounds described herein. Certain compounds described herein may exist in multiple crystalline or amorphous forms.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment of symptoms can be based on objective or subjective parameters; including the results of a physical examination, neuropsychiatric exams, and/or a psychiatric evaluation.

As used herein "treating a cancer tumor" means preventing an increase in size or volume of the cancer tumor. In embodiments, the cancer tumor is a solid tumor. In embodiments, treating a cancer tumor includes decreasing the size of volume of a cancer tumor. In embodiments, treating a cancer tumor includes eliminating the cancer tumor altogether. In embodiments, a cancer tumor is eliminated when it is not detectable by an imaging test such as magnetic resonance imaging (MRI), a positron emission tomography (PET) scan, X-ray computed tomography (CT), ultrasound, or single-photon emission computed tomography (SPECT). In embodiments, treating a cancer tumor further comprises reducing or preventing metastasis of the cancer tumor.

An "effective amount" is an amount sufficient to accomplish a stated purpose (e.g. achieve the effect for which it is administered, treat a disease, reduce enzyme activity, or reduce one or more symptoms of a disease or condition). An example of an "effective amount" is an amount sufficient to contribute to the treatment, prevention, or reduction of a symptom or symptoms of a disease, which herein is referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (e.g., Lieberman, Pharmaceutical Dosage Forms (vols. 1-3, 1992); Lloyd, The Art, Science and Technology of Pharmaceutical Compounding (1999); Pickar, Dosage Calculations (1999); Remington: The Science and Practice of Pharmacy, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the compounds described herein should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Pharmaceutically acceptable excipient" and "pharmaceutically acceptable carrier" refer to a substance that aids the administration of an active agent to and absorption by a subject and can be included in the compositions of the compounds described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. Pharmaceutically acceptable excipients are described in the Handbook of Pharmaceutical Excipients, $8^{th}$ Edition, published by the Pharmaceutical Press (2017), and the United States Food and Drug Administration Inactive Ingredient Database (July 2017), the disclosures of which are incorporated by reference herein in their entirety. One of skill in the art will recognize that other pharmaceutical excipients are useful in combination with the compounds described herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route compatible with the selected compound preparation, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The pharmaceutical compositions described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). The formulations of the compositions of the compounds described herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the compounds described herein into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions can also be delivered as nanoparticles.

Pharmaceutical compositions may include compositions wherein the active ingredient (e.g. compounds described herein) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The compounds and complexes described herein can be used in combination with one another, with other active drugs known to be useful in treating a disease (e.g. anti-cancer agents) or with adjunctive agents that may not be effective alone, but may contribute to the efficacy of the active agent.

By "co-administer" it is meant that a composition described herein is administered at the same time, just prior to, or just after the administration of one or more additional therapies, for example an anti-cancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anti-cancer agents).

Co-administration includes administering one active agent (e.g. a compound described herein) within 0.5, 1, 2, 4, 6, 8, 10, 12, 16, 20, or 24 hours of a second active agent (e.g. anti-cancer agents). Co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. The active agents can be formulated separately. The active and/or adjunctive agents may be linked or conjugated to one another. The compounds described herein may be combined with treatments for cancer such as chemotherapy or radiation therapy.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In embodiments, a patient is a human. In embodiments, a patient is a human adult. In embodiments a patient is a human child.

"Child" refers to a human from the age of birth to 19 years. In embodiments, "child" refers to a human from the age of birth to 14 years.

"Disease" or "condition" refer to a state of being or health status of a patient or subject capable of being treated with the compounds or methods provided herein. Disease as used herein may refer to cancer.

As used herein, the term "cancer" refers to all types of cancer, neoplasm, malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "neural crest cell" refers to a temporary group of cells unique to vertebrates that arise from the embryonic ectoderm cell layer, and in turn give rise to a diverse cell lineage including, but not limited to, melanocytes, craniofacial cartilage and bone, smooth muscle, peripheral and enteric neurons, the adrenal medulla, and glia.

The term "neural crest-derived cancer" as used herein refers to tumors derived from the neural crest. Exemplary neural crest-derived cancers include small cell lung cancer, melanoma, breast cancer, medullary thyroid carcinoma, pheochromocytoma, and neuroblastoma. In aspects of the disclosure, the neural crest-derived tumor is a small cell lung cancer, a melanoma, or a breast cancer.

The term "pediatric cancer" or "childhood cancer" as used herein refers to any cancer occurring in a subject between birth and 19 years of age. In embodiments, "pediatric cancer" refers to cancers occurring in a subject between birth and 14 years of age. Exemplary pediatric cancers include acute lymphoblastic leukemia tumors, soft tissue sarcomas (e.g., rhabdomyosarcoma), rhabdoid tumors, neuroblastoma, kidney tumors, lymphoma, and brain and central nervous system tumors (e.g., astrocytoma, brain stem glioma, ependymoma, germ cell tumor, medulloblastoma). In aspects of the disclosure, the pediatric cancer is a rhabdoid tumor, a neuroblastoma, an acute lymphoblastic leukemia tumor, or a brain and central nervous system tumor.

"Radiation therapy" is used in accordance with its plain and ordinary meaning and refers to the use of ionizing radiation to kill or inhibit the growth or proliferation of cancer cells. Exemplary forms of radiation therapy include external beam radiation therapy, contact x-ray brachytherapy, sealed source radiotherapy, systemic radioisotope therapy, intraoperative radiotherapy, and deep inspiration breath-hold therapy. Systemic radioisotope therapy includes the delivery of radioisotopes (e.g., metaiodobenzylguanidine, iodine-131, lutetium-177, yttrium-90, strontium-89, samarium lexidronam) through infusion, injection, or ingestion. In embodiments, a radioisotope can be conjugated to an antibody (e.g., ZEVALIN®, BEXXAR®).

"Differentiation therapy" refers to a cancer treatment in which compounds change the phenotype of cancer cells into normal cells. Exemplary compounds include retinoids (e.g., 13-cis-retinoic acid, all-trans-retinoic acid).

"Tubulin binding drugs" as used herein refers to compounds that target the mitotic spindle, and not the DNA, of cancer cells. Tubulin binding drugs include tubulin depolymerization inhibitors (e.g., paclitaxtel, epothilone, docetaxel, discodermolide) and tubulin polymerization inhibitors. Tubuling depolymerization inhibitors bind to the taxan site of tubulin. Tubulin polymerization inhibitors can bind to the vinca domain of tubulin. Such vinca domain-binding inhibitors include vinblastine, vincristine, vinorelbine, vinfluine, dolastatins, halichondrins, hemiasterlins, cryptophysin 52. Other tubulin polymerization inhibitors can bind to the colchicine domain of tubulin. Such colchine domain-binding inhibitors include colchine, combrestatin, 2-methoxyestradiol, and methoxy benzenesulfonamide.

"Anti-cancer agent" or "chemotherapeutic agent" is used in accordance with its plain and ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. An anti-cancer agent may be an agent approved by the FDA or similar regulatory agency of a country other than the USA, for treating cancer. The methods described herein may further comprise administering a therapeutically effective amount of an anti-cancer or chemotherapeutic agent.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate;

phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L—Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1

(Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstiIbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

PLK4 Inhibitors

In embodiments, the PLK4 inhibitor is a compound of Formula (I) or a pharmaceutically acceptable salt thereof. In embodiments, the compound of Formula (I) is a compound of Formula (Ia), a compound of Formula (Ib), a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), or a pharmaceutically acceptable salt of any one of the foregoing.

In embodiments, the compound of Formula (Ia) is a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), or a compound of Formula (Ia9f).

In embodiments, the compound of Formula (Ib) is a compound of Formula (Ib1), a compound of Formula (Ib2), a compound of Formula (Ib3), a compound of Formula (Ib4), a compound of Formula (Ib5), a compound of Formula (Ib6), or a compound of Formula (Ib7).

In embodiments, the PLK4 inhibitor is a compound of Formula (Ia) or a pharmaceutically acceptable salt thereof:

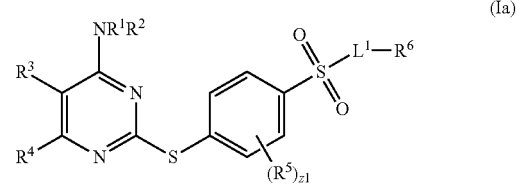

(Ia)

wherein the substituents are defined herein. In embodiments, the PLK4 inhibitor is a compound of Formula (Ib) or a pharmaceutically acceptable salt thereof:

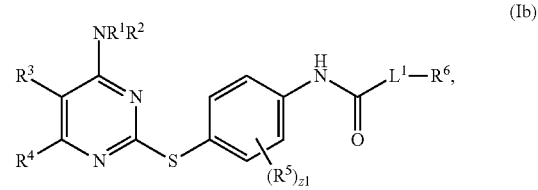

(Ib)

wherein the substituents are defined herein.

$L^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{2B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —N—ONR$^{4A}$R$^{4B}$, ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^3$ and R$^4$ are optionally combined to form a substituted or unsubstituted cycloalkyl (e.g. R$^{3C}$-substituted or unsubstituted cycloalkyl), substituted or unsubstituted heterocycloalkyl (e.g. R$^{3C}$-substituted or unsubstituted heterocycloalkyl), substituted or unsubstituted aryl (e.g. R$^{3C}$-substituted or unsubstituted aryl), or substituted or unsubstituted heteroaryl (e.g. R$^{3C}$-substituted or unsubstituted heteroaryl). R$^5$ is independently hydrogen, halogen, —N$_3$, —CF$_3$, —CCl$_3$, —CBr$_3$, —CI$_3$, —CN, —COR$^{5A}$, —OR$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, —C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n5, and n6 are independently 1 or 2. The symbol z1 is 1, 2, 3, or 4. R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$, and R$^{13}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the compound of Formula (Ib) is not tozasertib. In embodiments of Formula (Ib), R$^4$ is not a para-methyl piperidinyl. In embodiments of Formula (Ib), R$^4$ is not a para-ethyl piperidinyl. In embodiments of Formula (Ib), R$^4$ is not a para-propyl piperidinyl. In embodiments of Formula (Ib), R$^4$ is not a piperidinyl substituted with a methyl. In embodiments of Formula (Ib), R$^4$ is not a piperidinyl substituted with a ethyl. In embodiments of Formula (Ib), R$^4$ is not a piperidinyl substituted with a propyl. In embodiments of Formula (Ib), R$^4$ is not a piperidinyl substituted with an unsubstituted alkyl at the para position. In embodiments of Formula (Ib), R$^4$ is not a piperidinyl substituted with an unsubstituted alkyl. In embodiments of Formula (Ib), R$^4$ is not a piperidinyl substituted with a substituted or unsubstituted alkyl. In embodiments of Formula (Ib), R$^4$ is not a substituted or unsubstituted piperidinyl. In embodiments of Formula (Ib), R$^4$ is not a substituted heterocycloalkyl. In embodiments of Formula (Ib), R$^4$ is not a substituted or unsubstituted heterocycloalkyl. In embodiments of Formula (Ia), R$^4$ is not a para-methyl piperidinyl. In embodiments of Formula (Ib), R$^4$ is not a para-ethyl piperidinyl. In embodiments of Formula (Ib), R$^4$ is not a para-propyl piperidinyl. In embodiments of Formula (Ib) Formula (Ib), R$^4$ is not a piperidinyl substituted with a methyl. In embodiments of Formula (Ib), R$^4$ is not a piperidinyl substituted with a ethyl. In embodiments of Formula (Ib), R$^4$ is not a piperidinyl substituted with a propyl. In embodiments of Formula (Ia), R$^4$ is not a piperidinyl substituted with an unsubstituted alkyl at the para position. In embodiments of Formula (Ia), R$^4$ is not a piperidinyl substituted with an unsubstituted alkyl. In embodiments of Formula (Ia), R$^4$ is not a piperidinyl substituted with a substituted or unsubstituted alkyl. In embodiments of Formula (Ia), R$^4$ is not a substituted or unsubstituted piperidinyl. In embodiments of Formula (Ia), R$^4$ is not a substituted heterocycloalkyl. In embodiments of Formula (Ia), R$^4$ is not a substituted or unsubstituted heterocycloalkyl. In embodiments, the provisos set forth in the embodiments of the paragraph apply only when -L$^1$-R$^6$ is cyclopropyl. The embodiments in this paragraph are equally applicable to all other appropriate formulae set forth herein.

In embodiments of the compound of Formula (Ib), -L$^1$-R$^6$ is not cyclopropyl. In embodiments of Formula (Ia), -L$^1$-R$^6$ is not cyclopropyl. In embodiments of Formula (Ib), -L$^1$-R$^6$ is not cyclopropyl when R$^4$ is piperidinyl. In embodiments of Formula (Ib), -L$^1$-R$^6$ is not cyclopropyl when R$^4$ is piperidinyl substituted with substituted or unsubstituted alkyl. In embodiments of Formula (Ib), -L$^1$-R$^6$ is not cyclopropyl when R$^4$ is piperidinyl substituted with unsubstituted alkyl. In embodiments of Formula (Ib), -L$^1$-R$^6$ is not cyclopropyl when R$^4$ is piperidinyl substituted with methyl, ethyl or propyl. In embodiments of Formula (Ib), -L$^1$-R$^6$ is not cyclopropyl when R$^4$ is piperidinyl substituted with para methyl, para ethyl or para propyl. In embodiments of Formula (Ia), -L$^1$-R$^6$ is not cyclopropyl when R$^4$ is piperidinyl. In embodiments of Formula (Ia), -L$^1$-R$^6$ is not cyclopropyl when R$^4$ is piperidinyl substituted with substituted or unsubstituted alkyl. In embodiments of Formula (Ia), -L$^1$-R$^6$ is not cyclopropyl when R$^4$ is piperidinyl substituted with unsubstituted alkyl. In embodiments of Formula (Ia), -L$^1$-R$^6$ is not cyclopropyl when R$^4$ is piperidinyl substituted with methyl, ethyl or propyl. In embodiments of Formula (Ia), -L$^1$-R$^6$ is not cyclopropyl when R$^4$ is piperidinyl substituted with para methyl, para ethyl or para propyl. The embodiments in this paragraph are equally applicable to all other appropriate formulae set forth herein.

In embodiments, R$^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, or —C(O)NR$^{1A}$R$^{1B}$. In aspects, R$^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, or —C(O)NR$^{1A}$R$^{1B}$ where R$^{1A}$ and R$^{1B}$ are independently hydrogen, oxo, halogen, —$CF_3$, —OH, —$NH_2$, —COOH, —$CONH_2$, substituted or unsubstituted alkyl, or substituted or unsubstituted aryl. In aspects, $R^1$ is hydrogen. In aspects, $R^1$ is hydrogen or substituted or unsubstituted alkyl.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be substituted or unsubstituted alkyl. $R^1$ may be substituted alkyl. $R^1$ may be unsubstituted alkyl. $R^1$ may be substituted or unsubstituted $C_1$-$C_{20}$ alkyl. $R^1$ may be substituted $C_1$-$C_{20}$ alkyl. $R^1$ may be unsubstituted $C_1$-$C_{20}$ alkyl. $R^1$ may be substituted or unsubstituted $C_1$-$C_{10}$ alkyl. $R^1$ may be substituted $C_1$-$C_{10}$ alkyl. $R^1$ may be unsubstituted $C_1$-$C_{10}$ alkyl. $R^1$ may be substituted or unsubstituted $C_1$-$C_5$ alkyl. $R^1$ may be unsubstituted $C_1$-$C_5$ alkyl. $R^1$ may be substituted $C_1$-$C_5$ alkyl. $R^1$ may be methyl, substituted or unsubstituted ethyl, or substituted or unsubstituted propyl. $R^1$ may be methyl. $R^1$ may be ethyl.

$R^1$ may be $R^{1C}$-substituted or unsubstituted alkyl. $R^1$ may be $R^{1C}$-substituted alkyl. $R^1$ may be $R^{1C}$-substituted or unsubstituted $C_1$-$C_{20}$ alkyl. $R^1$ may be $R^{1C}$-substituted $C_1$-$C_{20}$ alkyl. $R^1$ may be $R^{1C}$-substituted or unsubstituted $C_1$-$C_{10}$ alkyl. $R^1$ may be $R^{1C}$-substituted $C_1$-$C_{10}$ alkyl. $R^1$ may be $R^{1C}$-substituted or unsubstituted $C_1$-$C_5$ alkyl. $R^1$ may be $R^{1C}$-substituted $C_1$-$C_5$ alkyl. $R^1$ may be methyl, $R^{1C}$-substituted or unsubstituted ethyl, or $R^{1C}$-substituted or unsubstituted propyl.

$R^1$ may be substituted or unsubstituted heteroalkyl. $R^1$ may be substituted heteroalkyl. $R^1$ may be unsubstituted heteroalkyl. $R^1$ may be substituted or unsubstituted 2 to 20 membered heteroalkyl. $R^1$ may be substituted 2 to 20 membered heteroalkyl. $R^1$ may be substituted or unsubstituted 2 to 10 membered heteroalkyl. $R^1$ may be substituted 2 to 10 membered heteroalkyl. $R^1$ may be substituted or unsubstituted 2 to 6 membered heteroalkyl. $R^1$ may be substituted 2 to 6 membered heteroalkyl.

$R^1$ may be $R^{1C}$-substituted or unsubstituted heteroalkyl. $R^1$ may be $R^{1C}$-substituted heteroalkyl. $R^1$ may be $R^{1C}$-substituted or unsubstituted 2 to 20 membered heteroalkyl. $R^1$ may be $R^{1C}$-substituted 2 to 20 membered heteroalkyl. $R^1$ may be $R^{1C}$-substituted or unsubstituted 2 to 10 membered heteroalkyl. $R^1$ may be $R^{1C}$-substituted 2 to 10 membered heteroalkyl. $R^1$ may be $R^{1C}$-substituted or unsubstituted 2 to 6 membered heteroalkyl. $R^1$ may be $R^{1C}$-substituted 2 to 6 membered heteroalkyl.

$R^1$ may be substituted or unsubstituted cycloalkyl. $R^1$ may be substituted cycloalkyl. $R^1$ may be unsubstituted cycloalkyl. $R^1$ may be substituted or unsubstituted 3 to 20 membered cycloalkyl. $R^1$ may be substituted 3 to 20 membered cycloalkyl. $R^1$ may be substituted or unsubstituted 3 to 10 membered cycloalkyl. $R^1$ may be substituted 3 to 10 membered cycloalkyl. $R^1$ may be substituted or unsubstituted 3 to 6 membered cycloalkyl. $R^1$ may be substituted 3 to 6 membered cycloalkyl.

$R^1$ may be $R^{1C}$-substituted or unsubstituted cycloalkyl. $R^1$ may be $R^{1C}$-substituted cycloalkyl. $R^1$ may be $R^{1C}$-substituted or unsubstituted 3 to 20 membered cycloalkyl. $R^1$ may be $R^{1C}$-substituted 3 to 20 membered cycloalkyl. $R^1$ may be $R^{1C}$-substituted or unsubstituted 3 to 10 membered cycloalkyl. $R^1$ may be $R^{1C}$-substituted 3 to 10 membered cycloalkyl. $R^1$ may be $R^{1C}$-substituted or unsubstituted 3 to 6 membered cycloalkyl. $R^1$ may be $R^{1C}$-substituted 3 to 6 membered cycloalkyl.

$R^1$ may be substituted or unsubstituted heterocycloalkyl. $R^1$ may be substituted heterocycloalkyl. $R^1$ may be unsubstituted heterocycloalkyl. $R^1$ may be substituted or unsubstituted 3 to 20 membered heterocycloalkyl. $R^1$ may be substituted 3 to 20 membered heterocycloalkyl. $R^1$ may be substituted or unsubstituted 3 to 10 membered heterocycloalkyl. $R^1$ may be substituted 3 to 10 membered heterocycloalkyl. $R^1$ may be substituted or unsubstituted 3 to 6 membered heterocycloalkyl. $R^1$ may be substituted 3 to 6 membered heterocycloalkyl.

$R^1$ may be $R^{1C}$-substituted or unsubstituted heterocycloalkyl. $R^1$ may be $R^{1C}$-substituted heterocycloalkyl. $R^1$ may be $R^{1C}$-substituted or unsubstituted 3 to 20 membered heterocycloalkyl. $R^1$ may be $R^{1C}$-substituted 3 to 20 membered heterocycloalkyl. $R^1$ may be $R^{1C}$-substituted or unsubstituted 3 to 10 membered heterocycloalkyl. $R^1$ may be $R^{1C}$-substituted 3 to 10 membered heterocycloalkyl. $R^1$ may be $R^{1C}$-substituted or unsubstituted 3 to 6 membered heterocycloalkyl. $R^1$ may be $R^{1C}$-substituted 3 to 6 membered heterocycloalkyl.

$R^1$ may be substituted or unsubstituted aryl. $R^1$ may be substituted aryl. $R^1$ may be unsubstituted aryl. $R^1$ may be substituted or unsubstituted 5 to 20 membered aryl. $R^1$ may be substituted 5 to 20 membered aryl. $R^1$ may be substituted or unsubstituted 5 to 8 membered aryl (e.g. phenyl). $R^1$ may be substituted 5 to 8 membered aryl. $R^1$ may be substituted or unsubstituted 5 or 6 membered aryl. $R^1$ may be substituted 5 or 6 membered aryl.

$R^1$ may be $R^{1C}$-substituted or unsubstituted aryl. $R^1$ may be $R^{1C}$-substituted aryl. $R^1$ may be $R^{1C}$-substituted or unsubstituted 5 to 20 membered aryl. $R^1$ may be $R^{1C}$-substituted 5 to 20 membered aryl. $R^1$ may be $R^{1C}$-substituted or unsubstituted 5 to 8 membered aryl. $R^1$ may be $R^{1C}$-substituted 5 to 8 membered aryl. $R^1$ may be $R^{1C}$-substituted or unsubstituted 5 or 6 membered aryl. $R^1$ may be $R^{1C}$-substituted 5 or 6 membered aryl (e.g. phenyl).

$R^1$ may be substituted or unsubstituted heteroaryl. $R^1$ may be substituted heteroaryl. $R^1$ may be unsubstituted heteroaryl. $R^1$ may be substituted or unsubstituted 5 to 20 membered heteroaryl. $R^1$ may be substituted 5 to 20 membered heteroaryl. $R^1$ may be substituted or unsubstituted 5 to 8 membered heteroaryl. $R^1$ may be substituted 5 to 8 membered heteroaryl. $R^1$ may be substituted or unsubstituted 5 or 6 membered heteroaryl. $R^1$ may be substituted 5 or 6 membered heteroaryl.

$R^1$ may be $R^{1C}$-substituted or unsubstituted heteroaryl. $R^1$ may be $R^{1C}$-substituted heteroaryl. $R^1$ may be $R^{1C}$-substituted or unsubstituted 5 to 20 membered heteroaryl. $R^1$ may be $R^{1C}$-substituted 5 to 20 membered heteroaryl. $R^1$ may be $R^{1C}$-substituted or unsubstituted 5 to 8 membered heteroaryl. $R^1$ may be $R^{1C}$-substituted 5 to 8 membered heteroaryl. $R^1$ may be $R^{1C}$-substituted or unsubstituted 5 or 6 membered heteroaryl. $R^1$ may be $R^{1C}$-substituted 5 or 6 membered heteroaryl.

$R^{1A}$ may independently be hydrogen, halogen, oxo, $N_3$, —$CF_3$, —$CCl_3$, —$CBr_3$, —$CI_3$, —CN, —$OR^{1D}$, —$COR^{1D}$, —$NR^{1D}R^{1E}$, —$COOR^{1D}$, —$CONR^{1D}R^{1E}$, —$NO_2$, —$SR^{1D}$, —$S(O)_2R^{1D}$, —$S(O)_3R^{1D}$, —$S(O)_4R^{1D}$, —$S(O)_2NR^{1D}R^{1E}$, —$NHNR^{1D}R^{1E}$, —$ONR^{1D}R^{1E}$, —$NHC(O)NHNR^{1D}R^{1E}$, —$NHC(O)NR^{1D}R^{1E}$, —$NHS(O)_2R^{1D}$, —$NHC(O)R^{1D}$, —NHC(O)—$OR^{1D}$, —$NHOR^{1D}$, —$OCF_3$, —$OCHF_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl.

$R^{1C}$ is independently halogen, oxo, $N_3$, —$CF_3$, —$CCl_3$, —$CBr_3$, —$CI_3$, —CN, —OH, —$COR^{1D}$, —$NH_2$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{1C}$ may independently be halogen, oxo, $N_3$, —$CF_3$, —$CCl_3$, —$CBr_3$, —$CI_3$, —CN, —OH, —COH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{1B}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{1D}$ and $R^{1E}$ are independently hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted heteroalkyl, unsubstituted cycloalkyl, unsubstituted heterocycloalkyl, unsubstituted aryl, or unsubstituted heteroaryl.

$R^2$ may be hydrogen, halogen, —$N_3$, —$CF_3$, —$CCl_3$, —$CBr_3$, —$CI_3$, —CN, —$COR^{2A}$, —$OR^{2A}$, —$NR^{2A}R^{2B}$, —$C(O)OR^{2A}$, or —$C(O)NR^{2A}R^{2B}$. $R^2$ may be hydrogen, halogen, —$N_3$, —$CF_3$, —$CCl_3$, —$CBr_3$, —$CI_3$, —CN, —$COR^{2A}$, —$OR^{2A}$, —$NR^{2A}R^{2B}$, —$C(O)OR^{2A}$, or —$C(O)NR^{2A}R^{2B}$ where $R^{2A}$ and $R^{2B}$ are independently hydrogen, oxo, halogen, —$CF_3$, —OH, —$NH_2$, —COOH, —$CONH_2$, substituted or unsubstituted cycloalkyl, substituted or unsubstituted heterocycloalkyl, substituted or unsubstituted aryl, or substituted or unsubstituted heteroaryl.

$R^2$ may be substituted or unsubstituted cycloalkyl, substituted or unsubstituted heterocycloalkyl, substituted or unsubstituted aryl, or substituted or unsubstituted heteroaryl. $R^2$ may be $R^{2A}$-substituted or unsubstituted cycloalkyl, $R^{2A}$-substituted or unsubstituted heterocycloalkyl, $R^{2A}$-substituted or unsubstituted aryl, or $R^{2A}$-substituted or unsubstituted heteroaryl. $R^2$ may be substituted or unsubstituted heterocycloalkyl, substituted or unsubstituted aryl, or substituted or unsubstituted heteroaryl. $R^2$ may be $R^{2A}$-substituted or unsubstituted heterocycloalkyl, $R^{2A}$-substituted or unsubstituted aryl, or $R^{2A}$-substituted or unsubstituted heteroaryl.

$R^2$ may be $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl. In embodiments, $R^2$ is substituted with an alkyl, heteroalkyl, cycloalkyl, heterocycloalkyl, aryl or heteroaryl, wherein the alkyl, heteroalkyl, cycloalkyl, heterocycloalkyl, aryl or heteroaryl is substituted with a substituent selected from —$N_3$, —$CF_3$, —$CCl_3$, —$CBr_3$, —$CI_3$, —CN, —OH, —$NH_2$, —C(O)OH, —$C(O)NH_2$, —$NO_2$, —SH, substituted or unsubstituted alkyl, and substituted or unsubstituted heteroalkyl.

$R^2$ may be substituted or unsubstituted alkyl. $R^2$ may be substituted alkyl. $R^2$ may be unsubstituted alkyl. $R^2$ may be substituted or unsubstituted $C_1$-$C_{20}$ alkyl. $R^2$ may be substituted $C_1$-$C_{20}$ alkyl. $R^2$ may be unsubstituted $C_1$-$C_{20}$ alkyl. $R^2$ may be substituted or unsubstituted $C_1$-$C_{10}$ alkyl. $R^2$ may be substituted $C_1$-$C_{10}$ alkyl. $R^2$ may be unsubstituted $C_1$-$C_{10}$ alkyl. $R^2$ may be substituted or unsubstituted $C_1$-$C_5$ alkyl. $R^2$ may be unsubstituted $C_1$-$C_5$ alkyl. $R^2$ may be substituted $C_1$-$C_5$ alkyl. $R^2$ may be methyl, substituted or unsubstituted ethyl, or substituted or unsubstituted propyl. $R^2$ may be methyl. $R^2$ may be ethyl.

$R^2$ may be $R^{2C}$-substituted or unsubstituted alkyl. $R^2$ may be $R^2$-substituted alkyl. $R^2$ may be $R^{2C}$-substituted or unsubstituted $C_1$-$C_{20}$ alkyl. $R^2$ may be $R^{2C}$-substituted $C_1$-$C_{20}$ alkyl. $R^2$ may be $R^{2C}$-substituted or unsubstituted $C_1$-$C_{10}$ alkyl. $R^2$ may be $R^{2C}$-substituted $C_1$-$C_{10}$ alkyl. $R^2$ may be $R^{2C}$-substituted or unsubstituted $C_1$-$C_5$ alkyl. $R^2$ may be $R^2$-substituted $C_1$-$C_5$ alkyl. $R^2$ may be methyl, $R^{2C}$-substituted or unsubstituted ethyl, or $R^{2C}$-substituted or unsubstituted propyl.

$R^2$ may be substituted or unsubstituted heteroalkyl. $R^2$ may be substituted heteroalkyl. $R^2$ may be unsubstituted heteroalkyl. $R^2$ may be substituted or unsubstituted 2 to 20 membered heteroalkyl. $R^2$ may be substituted 2 to 20 membered heteroalkyl. $R^2$ may be unsubstituted 2 to 20 membered heteroalkyl. $R^2$ may be substituted or unsubstituted 2 to 10 membered heteroalkyl. $R^2$ may be substituted 2 to 10 membered heteroalkyl. $R^2$ may be unsubstituted 2 to 10 membered heteroalkyl. $R^2$ may be substituted or unsubstituted 2 to 6 membered heteroalkyl. $R^2$ may be substituted 2 to 6 membered heteroalkyl. $R^2$ may be unsubstituted 2 to 6 membered heteroalkyl.

$R^2$ may be $R^{2C}$-substituted or unsubstituted heteroalkyl. $R^2$ may be $R^{2C}$-substituted heteroalkyl. $R^2$ may be $R^{2C}$-substituted or unsubstituted 2 to 20 membered heteroalkyl. $R^2$ may be $R^{2C}$-substituted 2 to 20 membered heteroalkyl. $R^2$ may be $R^{2C}$-substituted or unsubstituted 2 to 10 membered heteroalkyl. $R^2$ may be $R^{2C}$-substituted 2 to 10 membered heteroalkyl. $R^2$ may be $R^{2C}$-substituted or unsubstituted 2 to 6 membered heteroalkyl. $R^2$ may be $R^{2C}$-substituted 2 to 6 membered heteroalkyl.

$R^2$ may be substituted or unsubstituted cycloalkyl. $R^2$ may be substituted cycloalkyl. $R^2$ may be unsubstituted cycloalkyl. $R^2$ may be substituted or unsubstituted 3 to 20 membered cycloalkyl. $R^2$ may be substituted 3 to 20 membered cycloalkyl. $R^2$ may be unsubstituted 3 to 20 membered cycloalkyl. $R^2$ may be substituted or unsubstituted 3 to 10 membered cycloalkyl. $R^2$ may be substituted 3 to 10 membered cycloalkyl. $R^2$ may be unsubstituted 3 to 10 membered cycloalkyl. $R^2$ may be unsubstituted 3 to 6 membered cycloalkyl. $R^2$ may be substituted 3 to 6 membered cycloalkyl.

$R^2$ may be $R^{2C}$-substituted or unsubstituted cycloalkyl. $R^2$ may be $R^{2C}$-substituted cycloalkyl. $R^2$ may be $R^{2C}$-substituted or unsubstituted 3 to 20 membered cycloalkyl. $R^2$ may be $R^{2C}$-substituted 3 to 20 membered cycloalkyl. $R^2$ may be $R^{2C}$-substituted or unsubstituted 3 to 10 membered cycloalkyl. $R^2$ may be $R^{2C}$-substituted 3 to 10 membered cycloalkyl. $R^2$ may be $R^{2C}$-substituted or unsubstituted 3 to 6 membered cycloalkyl. $R^2$ may be $R^{2C}$-substituted 3 to 6 membered cycloalkyl.

$R^2$ may be substituted or unsubstituted heterocycloalkyl. $R^2$ may be substituted heterocycloalkyl. $R^2$ may be unsubstituted heterocycloalkyl. $R^2$ may be substituted or unsubstituted 3 to 20 membered heterocycloalkyl. $R^2$ may be substituted 3 to 20 membered heterocycloalkyl. $R^2$ may be unsubstituted 3 to 20 membered heterocycloalkyl. $R^2$ may be substituted or unsubstituted 3 to 10 membered heterocycloalkyl. $R^2$ may be substituted 3 to 10 membered heterocycloalkyl. $R^2$ may be unsubstituted 3 to 10 membered heterocycloalkyl. $R^2$ may be substituted or unsubstituted 3 to 6 membered heterocycloalkyl. $R^2$ may be substituted 3 to 6 membered heterocycloalkyl. $R^2$ may be unsubstituted 3 to 6 membered heterocycloalkyl.

$R^2$ may be $R^{2C}$-substituted or unsubstituted heterocycloalkyl. $R^2$ may be $R^{2C}$-substituted heterocycloalkyl. $R^2$ may be $R^{2C}$-substituted or unsubstituted 3 to 20 membered heterocycloalkyl. $R^2$ may be $R^{2C}$-substituted 3 to 20 membered heterocycloalkyl. $R^2$ may be $R^{2C}$-substituted or unsubstituted 3 to 10 membered heterocycloalkyl. $R^2$ may be $R^{2C}$-substituted 3 to 10 membered heterocycloalkyl. $R^2$ may be $R^{2C}$-substituted or unsubstituted 3 to 6 membered heterocycloalkyl. $R^2$ may be $R^{2C}$-substituted 3 to 6 membered heterocycloalkyl.

$R^2$ may be substituted or unsubstituted aryl. $R^2$ may be substituted aryl. $R^2$ may be unsubstituted aryl. $R^2$ may be substituted or unsubstituted 5 to 20 membered aryl. $R^2$ may be substituted 5 to 20 membered aryl. $R^2$ may be unsubstituted 5 to 20 membered aryl. $R^2$ may be substituted or unsubstituted 5 to 8 membered aryl (e.g. phenyl). $R^2$ may be substituted 5 to 8 membered aryl. $R^2$ may be substituted or unsubstituted 5 or 6 membered aryl. $R^2$ may be unsubstituted 5 to 8 membered aryl (e.g. phenyl). $R^2$ may be substituted 5 or 6 membered aryl. $R^2$ may be unsubstituted 5 or 6 membered aryl.

$R^2$ may be $R^{2C}$-substituted or unsubstituted aryl. $R^2$ may be $R^{2C}$-substituted aryl. $R^2$ may be $R^{2C}$-substituted or unsubstituted 5 to 20 membered aryl. $R^2$ may be $R^{2C}$-substituted 5 to 20 membered aryl. $R^2$ may be $R^{2C}$-substituted or unsubstituted 5 to 8 membered aryl. $R^2$ may be $R^{2C}$-substituted 5 to 8 membered aryl. $R^2$ may be $R^{2C}$-substituted or unsubstituted 5 or 6 membered aryl. $R^2$ may be $R^{2C}$-substituted 5 or 6 membered aryl (e.g. phenyl).

$R^2$ may be substituted or unsubstituted heteroaryl. $R^2$ may be substituted heteroaryl. $R^2$ may be unsubstituted heteroaryl. $R^2$ may be substituted or unsubstituted 5 to 20 membered heteroaryl. $R^2$ may be substituted 5 to 20 membered heteroaryl. $R^2$ may be unsubstituted 5 to 20 membered heteroaryl. $R^2$ may be substituted or unsubstituted 5 to 8 membered heteroaryl. $R^2$ may be substituted 5 to 8 membered heteroaryl. $R^2$ may be unsubstituted 5 to 8 membered heteroaryl. $R^2$ may be substituted or unsubstituted 5 or 6 membered heteroaryl. $R^2$ may be substituted 5 or 6 membered heteroaryl. $R^2$ may be unsubstituted 5 or 6 membered heteroaryl.

$R^2$ may be $R^{2C}$-substituted or unsubstituted heteroaryl. $R^2$ may be $R^2$-substituted heteroaryl. $R^2$ may be $R^{2C}$-substituted or unsubstituted 5 to 20 membered heteroaryl. $R^2$ may be $R^{2C}$-substituted 5 to 20 membered heteroaryl. $R^2$ may be $R^{2C}$-substituted or unsubstituted 5 to 8 membered heteroaryl. $R^2$ may be $R^{2C}$-substituted 5 to 8 membered heteroaryl. $R^2$ may be $R^{2C}$-substituted or unsubstituted 5 or 6 membered heteroaryl. $R^2$ may be $R^{2C}$-substituted 5 or 6 membered heteroaryl.

$R^{2A}$ may independently be hydrogen, halogen, oxo, $N_3$, —$CF_3$, —$CCl_3$, —$CBr_3$, —$CI_3$, —CN, —OH, —$COR^{2C}$, —$NH_2$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl. $R^{2A}$ may independently be substituted or unsubstituted $C_1$-$C_5$ alkyl. $R^{2A}$ may independently be methyl.

$R^{2C}$ is independently hydrogen, halogen, oxo, $N_3$, —$CF_3$, —$CCl_3$, —$CBr_3$, —$CI_3$, —CN, —$OR^{2D}$, —$COR^{2D}$, —$NR^{2D}R^{2E}$, —$COOR^{2D}$, —$CONR^{2D}R^{2E}$, —$NO_2$, —SH, —$S(O)_2R^{2D}$, —$S(O)_3R^{2D}$, —$S(O)_4R^{2D}$, —$S(O)_2NR^{2D}R^{2E}$, —$NHNR^{2D}R^{2E}$, —$ONR^{2D}R^{2E}$, —$NHC(O)NHNR^{2D}R^{2E}$, —$NHC(O)NR^{2D}R^{2E}$, —$NHS(O)_2R^{2D}$, —$NHC(O)R^{2D}$, —$NHC(O)$—$OR^{2D}$, —$NHOR^{2D}$, —$OCF_3$, —$OCHF_2$, $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl, or $R^{2D}$-substituted or unsubstituted heteroaryl.

$R^{2C}$ may independently be hydrogen, halogen, oxo, $N_3$, —$CF_3$, —$CCl_3$, —$CBr_3$, —$CI_3$, —CN, —OH, —$COR^{2D}$, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl, or $R^{2D}$-substituted or unsubstituted heteroaryl.

$R^{2C}$ may independently be hydrogen, halogen, oxo, $N_3$, —$CF_3$, —$CCl_3$, —$CBr_3$, —$CI_3$, —CN, —OH, —COH, —$NH_2$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{2D}$-substituted or unsubstituted alkyl, $R^{2D}$-substituted or unsubstituted heteroalkyl, $R^{2D}$-substituted or unsubstituted cycloalkyl, $R^{2D}$-substituted or unsubstituted heterocycloalkyl, $R^{2D}$-substituted or unsubstituted aryl, or $R^{2D}$-substituted or unsubstituted heteroaryl.

$R^{2B}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{2D}$ and $R^{2E}$ are independently hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted heteroalkyl, unsubstituted cycloalkyl, unsubstituted heterocycloalkyl, unsubstituted aryl, or unsubstituted heteroaryl.

$R^2$ may be $R^{2A}$-substituted or unsubstituted heteroaryl where $R^{2A}$ is —$N_3$, —$CF_3$, —$CCl_3$, —$CBr_3$, —$CI_3$, —CN, —OH, —$NH_2$, —C(O)OH, —C(O)$NH_2$, —$NO_2$, —SH, substituted or unsubstituted alkyl, substituted or unsubstituted heteroalkyl. $R^2$ may be $R^{2A}$-substituted or unsubstituted heteroaryl where $R^{2A}$ is —$CF_3$, —CN, —OH, —$NH_2$, —C(O)OH, —C(O)$NH_2$, —$NO_2$, or substituted or unsubstituted alkyl. $R^{2A}$ may be substituted or unsubstituted $C_1$-$C_5$ alkyl. $R^{2A}$ may be methyl.

$R^2$ may be substituted or unsubstituted furanyl, substituted or unsubstituted pyrroyl, substituted or unsubstituted thiophenyl, substituted or unsubstituted imidazoyl, substituted or unsubstituted pyrazolyl, substituted or unsubstituted oxazoyl, substituted or unsubstituted isoxazolyl, substituted or unsubstituted thiazolyl, substituted or unsubstituted pyridinyl, substituted or unsubstituted pyrazinyl, substituted or unsubstituted pyrimidinyl, or substituted or unsubstituted pyridazinyl. $R^2$ may be substituted or unsubstituted furanyl. $R^2$ may be substituted or unsubstituted pyrroyl. $R^2$ may be substituted or unsubstituted thiophenyl. $R^2$ may be substituted or unsubstituted imidazoyl. $R^2$ may be substituted or unsubstituted pyrazolyl. $R^2$ may be substituted or unsubstituted oxazoyl. $R^2$ may be substituted or unsubstituted isoxazolyl. $R^2$ may be substituted or unsubstituted thiazolyl. $R^2$ may be substituted or unsubstituted pyridinyl. $R^2$ may be substituted or unsubstituted pyrazinyl. $R^2$ may be substituted or unsubstituted pyrimidinyl. $R^2$ may be substituted or unsubstituted pyridazinyl.

$R^2$ may be $R^{2A}$-substituted or unsubstituted furanyl, substituted or unsubstituted pyrroyl, substituted or unsubstituted thiophenyl, substituted or unsubstituted imidazoyl, substituted or unsubstituted pyrazolyl, substituted or unsubstituted oxazoyl, substituted or unsubstituted isoxazolyl, substituted or unsubstituted thiazolyl, substituted or unsubstituted pyridinyl, substituted or unsubstituted pyrazinyl, substituted or unsubstituted pyrimidinyl, or substituted or unsubstituted pyridazinyl. $R^2$ may be $R^{2A}$-substituted or unsubstituted furanyl. $R^2$ may be $R^{2A}$-substituted or unsubstituted pyrrolyl. $R^2$ may be $R^{2A}$-substituted or unsubstituted thiophenyl. $R^2$ may be $R^{2A}$-substituted or unsubstituted imidazoyl. $R^2$ may be $R^{2A}$-substituted or unsubstituted pyrazolyl. $R^2$ may be $R^{2A}$-substituted or unsubstituted pyrazolyl where $R^{2A}$ is —$N_3$, —$CF_3$, —$CCl_3$, —$CBr_3$, —$CI_3$, —CN, —OH, —$NH_2$, —C(O)OH, —C(O)$NH_2$, —$NO_2$, —SH, substituted or unsubstituted alkyl, or substituted or unsubstituted heteroalkyl. $R^2$ may be $R^{2A}$-substituted or unsubstituted oxazoyl. $R^2$ may be $R^{2A}$-substituted or unsubstituted isoxazolyl. $R^2$ may be $R^{2A}$-substituted or unsubstituted thiazolyl. $R^2$ may be $R^{2A}$-substituted or unsubstituted pyridinyl. $R^2$ may be $R^{2A}$-substituted or unsubstituted pyrazinyl. $R^2$ may be $R^{2A}$-substituted or unsubstituted pyrimidinyl. $R^2$ may be $R^{2A}$-substituted or unsubstituted pyridazinyl. $R^2$ may be 5-methyl-1H-pyrazolyl.

$R^3$ may be hydrogen, halogen, —$N_3$, —$CF_3$, —$CCl_3$, —$CBr_3$, —$CI_3$, —CN, —$COR^{3A}$, —$OR^{3A}$, —$NR^{3A}R^{3B}$, —C(O)$OR^{3A}$, —C(O)$NR^{3A}R^{3B}$, —$NO_2$, —$SR^{3A}$, —S(O)$_{n3}R^{3A}$, —S(O)$_{n3}OR^{3A}$, —S(O)$_{n3}NR^{3A}R^{3B}$, —$NHNR^{3A}R^{3B}$, —$ONR^{3A}R^{3B}$, —NHC(O)$NHNR^{3A}R^{3B}$, substituted or unsubstituted alkyl, or optionally combined with $R^4$ to form a substituted or unsubstituted cycloalkyl where $R^{3A}$ and $R^{3B}$ are independently hydrogen, oxo, halogen, —$CF_3$, —OH, —$NH_2$, —COOH, —$CONH_2$, substituted or unsubstituted alkyl, or substituted or unsubstituted aryl.

$R^3$ may be hydrogen, halogen, —$OR^{3A}$, or substituted or unsubstituted alkyl, where $R^{3A}$ is as defined herein. $R^3$ may be hydrogen, halogen, —$OR^{3A}$, or $R^{3C}$-substituted or unsubstituted alkyl, where $R^{3A}$ and $R^{3C}$ are as defined herein. $R^3$ may be hydrogen, halogen, —$OR^{3A}$, or substituted or unsubstituted alkyl where $R^{3A}$ is substituted or unsubstituted alkyl. $R^3$ may be hydrogen, halogen, —$OR^{3A}$, or $R^{3C}$-substituted or unsubstituted alkyl where $R^{3A}$ is substituted or unsubstituted alkyl and $R^{3C}$ is as defined herein. $R^3$ may be hydrogen, halogen, —$OR^{3A}$, or substituted or unsubstituted alkyl where $R^{3A}$ is $R^{3C}$-substituted or unsubstituted alkyl. $R^3$ may be hydrogen, halogen, —$OR^{3A}$, or $R^{3C}$-substituted or unsubstituted alkyl where $R^{3A}$ is $R^{3C}$-substituted or unsubstituted alkyl and $R^{3C}$ is as defined herein.

$R^3$ may be —Cl, —I, or —Br. $R^3$ may be —Cl. $R^3$ may be —Br. $R^3$ may be —I. $R^3$ may be —F. $R^3$ may be —$OR^{3A}$, where $R^{3A}$ is as defined herein. $R^3$ may be —$OR^{3A}$ where $R^{3A}$ is substituted or unsubstituted alkyl. $R^3$ may be —$OR^{3A}$ where $R^{3A}$ is substituted or unsubstituted $C_1$-$C_5$ alkyl. $R^3$ may be —$OR^{3A}$ where $R^{3A}$ is $R^{3C}$-substituted or unsubstituted $C_1$-$C_5$ alkyl. $R^3$ may be —$OCH_3$. $R^3$ may be —$OCH_2CH_3$. $R^3$ may be —$OR^{3A}$ where $R^{3A}$ is substituted or unsubstituted $C_5$-$C_6$ aryl.

$R^3$ may be substituted or unsubstituted alkyl. $R^3$ may be substituted alkyl. $R^3$ may be unsubstituted alkyl. $R^3$ may be substituted or unsubstituted $C_1$-$C_{20}$ alkyl. $R^3$ may be substituted $C_1$-$C_{20}$ alkyl. $R^3$ may be unsubstituted $C_1$-$C_{20}$ alkyl. $R^3$ may be substituted or unsubstituted $C_1$-$C_{10}$ alkyl. $R^3$ may be substituted $C_1$-$C_{10}$ alkyl. $R^3$ may be unsubstituted $C_1$-$C_{10}$ alkyl. $R^3$ may be substituted or unsubstituted $C_1$-$C_5$ alkyl. $R^3$ may be unsubstituted $C_1$-$C_5$ alkyl. $R^3$ may be substituted $C_1$-$C_5$ alkyl. $R^3$ may be methyl, substituted or unsubstituted ethyl, or substituted or unsubstituted propyl. $R^3$ may be methyl. $R^3$ may be ethyl.

$R^3$ may be $R^{3C}$-substituted or unsubstituted alkyl. $R^3$ may be $R^3$-substituted alkyl. $R^3$ may be $R^{3C}$-substituted or unsubstituted $C_1$-$C_{20}$ alkyl. $R^3$ may be $R^3$-substituted $C_1$-$C_{20}$ alkyl. $R^3$ may be $R^{3C}$-substituted or unsubstituted $C_1$-$C_{10}$ alkyl. $R^3$ may be $R^3$-substituted $C_1$-$C_{10}$ alkyl. $R^3$ may be $R^{3C}$-substituted or unsubstituted $C_1$-$C_5$ alkyl. $R^3$ may be $R^3$-substituted $C_1$-$C_5$ alkyl. $R^3$ may be methyl, $R^{3C}$-substituted or unsubstituted ethyl, or $R^{3C}$-substituted or unsubstituted propyl.

$R^3$ may be substituted or unsubstituted heteroalkyl. $R^3$ may be substituted heteroalkyl. $R^3$ may be unsubstituted heteroalkyl. $R^3$ may be substituted or unsubstituted 2 to 20 membered heteroalkyl. $R^3$ may be substituted 2 to 20 membered heteroalkyl. $R^3$ may be substituted 2 to 20 membered heteroalkyl. $R^3$ may be substituted or unsubstituted 2 to 10 membered heteroalkyl. $R^3$ may be substituted 2 to 10 membered heteroalkyl. $R^3$ may be substituted 2 to 10 membered heteroalkyl. $R^3$ may be substituted or unsubstituted 2 to 6 membered heteroalkyl. $R^3$ may be substituted 2 to 6 membered heteroalkyl. $R^3$ may be unsubstituted 2 to 6 membered heteroalkyl.

$R^3$ may be $R^{3C}$-substituted or unsubstituted heteroalkyl. $R^3$ may be $R^3$-substituted heteroalkyl. $R^3$ may be $R^{3C}$-substituted or unsubstituted 2 to 20 membered heteroalkyl. $R^3$ may be $R^{3C}$-substituted 2 to 20 membered heteroalkyl. $R^3$ may be $R^{3C}$-substituted or unsubstituted 2 to 10 membered heteroalkyl. $R^3$ may be $R^{3C}$-substituted 2 to 10 membered heteroalkyl. $R^3$ may be $R^{3C}$-substituted or unsubstituted 2 to 6 membered heteroalkyl. $R^3$ may be $R^{3C}$-substituted 2 to 6 membered heteroalkyl.

$R^3$ may be substituted or unsubstituted cycloalkyl. $R^3$ may be substituted cycloalkyl. $R^3$ may be unsubstituted cycloalkyl. $R^3$ may be substituted or unsubstituted 3 to 20 membered cycloalkyl. $R^3$ may be substituted 3 to 20 membered cycloalkyl. $R^3$ may be unsubstituted 3 to 20 membered cycloalkyl. $R^3$ may be substituted or unsubstituted 3 to 10 membered cycloalkyl. $R^3$ may be substituted 3 to 10 membered cycloalkyl. $R^3$ may be substituted or unsubstituted 3 to 10 membered cycloalkyl. $R^3$ may be unsubstituted 3 to 6 membered cycloalkyl. $R^3$ may be substituted 3 to 6 membered cycloalkyl.

$R^3$ may be $R^{3C}$-substituted or unsubstituted cycloalkyl. $R^3$ may be $R^3$-substituted cycloalkyl. $R^3$ may be $R^{3C}$-substituted or unsubstituted 3 to 20 membered cycloalkyl. $R^3$ may be $R^{3C}$-substituted 3 to 20 membered cycloalkyl. $R^3$ may be $R^{3C}$-substituted or unsubstituted 3 to 10 membered cycloalkyl. $R^3$ may be $R^{3C}$-substituted 3 to 10 membered cycloalkyl. $R^3$ may be $R^{3C}$-substituted or unsubstituted 3 to 6 membered cycloalkyl. $R^3$ may be $R^{3C}$-substituted 3 to 6 membered cycloalkyl.

$R^3$ may be substituted or unsubstituted heterocycloalkyl. $R^3$ may be substituted heterocycloalkyl. $R^3$ may be unsubstituted heterocycloalkyl. $R^3$ may be substituted or unsubstituted 3 to 20 membered heterocycloalkyl. $R^3$ may be substituted 3 to 20 membered heterocycloalkyl. $R^3$ may be unsubstituted 3 to 20 membered heterocycloalkyl. $R^3$ may be substituted or unsubstituted 3 to 10 membered heterocycloalkyl. $R^3$ may be substituted 3 to 10 membered heterocycloalkyl. $R^3$ may be unsubstituted 3 to 10 membered heterocycloalkyl. $R^3$ may be substituted or unsubstituted 3 to 6 membered heterocycloalkyl. $R^3$ may be substituted 3 to 6 membered heterocycloalkyl. $R^3$ may be unsubstituted 3 to 6 membered heterocycloalkyl.

$R^3$ may be $R^{3C}$-substituted or unsubstituted heterocycloalkyl. $R^3$ may be $R^{3C}$-substituted heterocycloalkyl. $R^3$ may be $R^{3C}$-substituted or unsubstituted 3 to 20 membered heterocycloalkyl. $R^3$ may be $R^{3C}$-substituted 3 to 20 membered heterocycloalkyl. $R^3$ may be $R^{3C}$-substituted or unsubstituted 3 to 10 membered heterocycloalkyl. $R^3$ may be $R^{3C}$-substituted 3 to 10 membered heterocycloalkyl. $R^3$ may be $R^{3C}$-substituted or unsubstituted 3 to 6 membered heterocycloalkyl. $R^3$ may be $R^{3C}$-substituted 3 to 6 membered heterocycloalkyl.

$R^3$ may be substituted or unsubstituted aryl. $R^3$ may be substituted aryl. $R^3$ may be unsubstituted aryl. $R^3$ may be substituted or unsubstituted 5 to 20 membered aryl. $R^3$ may be substituted 5 to 20 membered aryl. $R^3$ may be unsubstituted 5 to 20 membered aryl. $R^3$ may be substituted or unsubstituted 5 to 8 membered aryl (e.g. phenyl). $R^3$ may be substituted 5 to 8 membered aryl. $R^3$ may be substituted or unsubstituted 5 or 6 membered aryl. $R^3$ may be unsubstituted 5 to 8 membered aryl (e.g. phenyl). $R^3$ may be substituted 5 or 6 membered aryl. $R^3$ may be unsubstituted 5 or 6 membered aryl.

$R^3$ may be $R^{3C}$-substituted or unsubstituted aryl. $R^3$ may be $R^3$-substituted aryl. $R^3$ may be $R^{3C}$-substituted or unsubstituted 5 to 20 membered aryl. $R^3$ may be $R^{3C}$-substituted 5 to 20 membered aryl. $R^3$ may be $R^{3C}$-substituted or unsubstituted 5 to 8 membered aryl. $R^3$ may be $R^{3C}$-substituted 5 to 8 membered aryl. $R^3$ may be $R^{3C}$-substituted or unsubstituted 5 or 6 membered aryl. $R^3$ may be $R^{3C}$-substituted 5 or 6 membered aryl (e.g. phenyl).

$R^3$ may be substituted or unsubstituted heteroaryl. $R^3$ may be substituted heteroaryl. $R^3$ may be unsubstituted heteroaryl. $R^3$ may be substituted or unsubstituted 5 to 20 membered heteroaryl. $R^3$ may be substituted 5 to 20 membered heteroaryl. $R^3$ may be unsubstituted 5 to 20 membered heteroaryl. $R^3$ may be substituted or unsubstituted 5 to 8 membered heteroaryl. $R^3$ may be substituted 5 to 8 membered heteroaryl. $R^3$ may be unsubstituted 5 to 8 membered heteroaryl. $R^3$ may be substituted or unsubstituted 5 or 6 membered heteroaryl. $R^3$ may be substituted 5 or 6 membered heteroaryl. $R^3$ may be unsubstituted 5 or 6 membered heteroaryl.

$R^3$ may be $R^{3C}$-substituted or unsubstituted heteroaryl. $R^3$ may be $R^3$-substituted heteroaryl. $R^3$ may be $R^{3C}$-substituted or unsubstituted 5 to 20 membered heteroaryl. $R^3$ may be $R^{3C}$-substituted 5 to 20 membered heteroaryl. $R^3$ may be $R^{3C}$-substituted or unsubstituted 5 to 8 membered heteroaryl. $R^3$ may be $R^{3C}$-substituted 5 to 8 membered heteroaryl. $R^3$ may be $R^{3C}$-substituted or unsubstituted 5 or 6 membered heteroaryl. $R^3$ may be $R^{3C}$-substituted 5 or 6 membered heteroaryl.

$R^{3A}$ may independently be hydrogen, halogen, oxo, $N_3$, $-CF_3$, $-CCl_3$, $-CBr_3$, $-CI_3$, $-CN$, $-COR^{3C}$, $-OH$, $-NH_2$, $-COOH$, $-CONH_2$, $-NO_2$, $-SH$, $-S(O)_2C$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{3C}$-substituted or unsubstituted alkyl, $R^{3C}$-substituted or unsubstituted heteroalkyl, $R^{3C}$-substituted or unsubstituted cycloalkyl, $R^{3C}$-substituted or unsubstituted heterocycloalkyl, $R^{3C}$-substituted or unsubstituted aryl, or $R^{3C}$-substituted or unsubstituted heteroaryl.

$R^{3C}$ is independently hydrogen, halogen, oxo, $N_3$, $-CF_3$, $-CCl_3$, $-CBr_3$, $-CI_3$, $-CN$, $-COR^{3D}$, $-OR^{3D}$, $-NR^{3D}R^{3E}$, $-COOR^{3D}$, $-CONR^{3D}R^{3E}$, $-NO_2$, $-SR^{3D}$, $-S(O)_2R^{3D}$, $-S(O)_3R^{3D}$, $-S(O)_4R^{3D}$, $-S(O)_2NR^{3D}R^{3E}$, $-NHNR^{3D}R^{3E}$, $-ONR^{3D}R^{3E}$, $-NHC(O)NHNR^{3D}R^{3E}$, $-NHC(O)NR^{3D}R^{3E}$, $-NHS(O)_2R^{3D}$, $-NHC(O)R^{3D}$, $-NHC(O)-OR^{3D}$, $-NHOR^{3D}$, $-OCF_3$, $-OCHF_2$, $R^{3D}$-substituted or unsubstituted alkyl, $R^{3D}$-substituted or unsubstituted heteroalkyl, $R^{3D}$-substituted or unsubstituted cycloalkyl, $R^{3D}$-substituted or unsubstituted heterocycloalkyl, $R^{3D}$-substituted or unsubstituted aryl, or $R^{3D}$-substituted or unsubstituted heteroaryl.

$R^{3C}$ may independently be hydrogen, halogen, oxo, $N_3$, $-CF_3$, $-CCl_3$, $-CBr_3$, $-CI_3$, $-CN$, $-COR^{3D}$, $-OH$, $-NH_2$, $-COOH$, $-CONH_2$, $-NO_2$, $-SH$, $-S(O)_2C$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{3D}$-substituted or unsubstituted alkyl, $R^{3D}$-substituted or unsubstituted heteroalkyl, $R^{3D}$-substituted or unsubstituted cycloalkyl, $R^{3D}$-substituted or unsubstituted heterocycloalkyl, $R^{3D}$-substituted or unsubstituted aryl, or $R^{3D}$-substituted or unsubstituted heteroaryl.

$R^{3B}$ may independently be hydrogen, halogen, oxo, $N_3$, $-CF_3$, $-CCl_3$, $-CBr_3$, $-CI_3$, $-CN$, $-OH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{3D}$ is independently hydrogen, halogen, oxo, $N_3$, $-CF_3$, $-CCl_3$, $-CBr_3$, $-CI_3$, $-CN$, $-OH$, $-COR^{3F}$, $-NH_2$, $-COH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{3F}$-substituted or unsubstituted heteroalkyl, $R^{3F}$-substituted or unsubstituted cycloalkyl, $R^{3F}$-substituted or unsubstituted heterocycloalkyl, $R^{3F}$-substituted or unsubstituted aryl, or $R^{3F}$-substituted or unsubstituted heteroaryl.

$R^{3D}$ may independently be hydrogen, halogen, oxo, $N_3$, $-CF_3$, $-CCl_3$, $-CBr_3$, $-CI_3$, $-CN$, $-OH$, $-COH$, $-NH_2$, $-COOH$, $-CONH_2$, $-COH$, $-COCH_3$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted heteroalkyl, unsubstituted cycloalkyl, unsubstituted heterocycloalkyl, unsubstituted aryl, or unsubstituted heteroaryl.

$R^{3E}$ and $R^{3F}$ are independently hydrogen, halogen, oxo, $N_3$, $-CF_3$, $-CCl_3$, $-CBr_3$, $-CI_3$, $-CN$, $-OH$, $-NH_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^3$ and R$^4$ may together form a substituted or unsubstituted cycloalkyl. R$^3$ and R$^4$ may together form a R$^{3C}$-substituted or unsubstituted cycloalkyl. R$^3$ and R$^4$ may together form an unsubstituted cycloalkyl. R$^3$ and R$^4$ may together form an unsubstituted C$_3$-C$_6$ cycloalkyl. R$^3$ and R$^4$ may together form an unsubstituted saturated C$_3$-C$_6$ cycloalkyl. R$^3$ and R$^4$ may together form an C$_3$-C$_6$ unsubstituted unsaturated cycloalkyl. R$^3$ and R$^4$ may together form an R$^{3C}$-substituted saturated C$_3$-C$_6$ cycloalkyl where R$^{3C}$ is as defined herein. R$^{3C}$ may be halogen, —COR$^{3D}$, unsubstituted C$_1$-C$_5$ alkyl, substituted or unsubstituted cycloalkyl, or substituted or unsubstituted heterocycloalkyl. R$^{3C}$ may be methyl, unsubstituted ethyl, or unsubstituted propyl. R$^{3C}$ may be substituted or unsubstituted C$_3$-C$_6$ cycloalkyl. R$^{3C}$ may be unsubstituted C$_3$-C$_6$ cycloalkyl. R$^{3C}$ may be substituted C$_3$-C$_6$ cycloalkyl. R$^{3C}$ may be R$^{3D}$-substituted cycloalkyl, where R$^{3D}$ is as defined herein. R$^{3C}$ may be substituted or unsubstituted C$_3$-C$_6$ heterocycloalkyl. R$^{3C}$ may be unsubstituted C$_3$-C$_6$ heterocycloalkyl. R$^{3C}$ may be substituted C$_3$-C$_6$ heterocycloalkyl. R$^{3C}$ may be R$^{3D}$-substituted heterocycloalkyl, where R$^{3D}$ is as defined herein. R$^{3D}$ may be —COR$^{3E}$, substituted or unsubstituted alkyl or substituted or unsubstituted heterocycloalkyl.

R$^4$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ may be substituted or unsubstituted cycloalkyl, substituted or unsubstituted heterocycloalkyl, substituted or unsubstituted aryl, or substituted or unsubstituted heteroaryl.

R$^4$ may be substituted or unsubstituted alkyl. R$^4$ may be substituted alkyl. R$^4$ may be unsubstituted alkyl. R$^4$ may be substituted or unsubstituted C$_1$-C$_{20}$ alkyl. R$^4$ may be substituted C$_1$-C$_{20}$ alkyl. R$^4$ may be unsubstituted C$_1$-C$_{20}$ alkyl. R$^4$ may be substituted or unsubstituted C$_1$-C$_{10}$ alkyl. R$^4$ may be substituted C$_1$-C$_{10}$ alkyl. R$^4$ may be unsubstituted C$_1$-C$_{10}$ alkyl. R$^4$ may be substituted or unsubstituted C$_1$-C$_5$ alkyl. R$^4$ may be substituted C$_1$-C$_5$ alkyl. R$^4$ may be unsubstituted C$_1$-C$_5$ alkyl. R$^4$ may be methyl, substituted or unsubstituted ethyl, or substituted or unsubstituted propyl.

R$^4$ may be R$^{40}$-substituted or unsubstituted alkyl. R$^4$ may be R$^{40}$-substituted alkyl. R$^4$ may be R$^{40}$-substituted or unsubstituted C$_1$-C$_{20}$ alkyl. R$^4$ may be R$^{40}$-substituted C$_1$-C$_{20}$ alkyl. R$^4$ may be R$^{40}$-substituted or unsubstituted C$_1$-C$_{10}$ alkyl. R$^4$ may be R$^{40}$-substituted C$_1$-C$_{10}$ alkyl. R$^4$ may be R$^{40}$-substituted or unsubstituted C$_1$-C$_5$ alkyl. R$^4$ may be R$^{40}$-substituted C$_1$-C$_5$ alkyl. R$^4$ may be methyl, R$^{40}$-substituted or unsubstituted ethyl, or R$^{40}$-substituted or unsubstituted propyl.

R$^4$ may be substituted or unsubstituted heteroalkyl. R$^4$ may be substituted heteroalkyl. R$^4$ may be unsubstituted heteroalkyl. R$^4$ may be substituted or unsubstituted 2 to 20 membered heteroalkyl. R$^4$ may be substituted 2 to 20 membered heteroalkyl. R$^4$ may be unsubstituted 2 to 20 membered heteroalkyl. R$^4$ may be substituted or unsubstituted 2 to 10 membered heteroalkyl. R$^4$ may be substituted 2 to 10 membered heteroalkyl. R$^4$ may be unsubstituted 2 to 10 membered heteroalkyl. R$^4$ may be substituted or unsubstituted 2 to 6 membered heteroalkyl. R$^4$ may be substituted 2 to 6 membered heteroalkyl. R$^4$ may be unsubstituted 2 to 6 membered heteroalkyl.

R$^4$ may be R$^{40}$-substituted or unsubstituted heteroalkyl. R$^4$ may be R$^{40}$-substituted heteroalkyl. R$^4$ may be R$^{40}$-substituted or unsubstituted 2 to 20 membered heteroalkyl. R$^4$ may be R$^{40}$-substituted 2 to 20 membered heteroalkyl. R$^4$ may be R$^{40}$-substituted or unsubstituted 2 to 10 membered heteroalkyl. R$^4$ may be R$^{40}$-substituted 2 to 10 membered heteroalkyl. R$^4$ may be R$^{40}$-substituted or unsubstituted 2 to 6 membered heteroalkyl. R$^4$ may be R$^{40}$-substituted 2 to 6 membered heteroalkyl.

R$^4$ may be substituted or unsubstituted cycloalkyl. R$^4$ may be substituted cycloalkyl. R$^4$ may be unsubstituted cycloalkyl. R$^4$ may be substituted or unsubstituted 3 to 20 membered cycloalkyl. R$^4$ may be substituted 3 to 20 membered cycloalkyl. R$^4$ may be unsubstituted 3 to 20 membered cycloalkyl. R$^4$ may be substituted or unsubstituted 3 to 10 membered cycloalkyl. R$^4$ may be substituted 3 to 10 membered cycloalkyl. R$^4$ may be unsubstituted 3 to 10 membered cycloalkyl. R$^4$ may be substituted or unsubstituted 3 to 6 membered cycloalkyl. R$^4$ may be substituted 3 to 6 membered cycloalkyl. R$^4$ may be unsubstituted 3 to 6 membered cycloalkyl.

R$^4$ may be R$^{40}$-substituted or unsubstituted cycloalkyl. R$^4$ may be R$^{40}$-substituted cycloalkyl. R$^4$ may be R$^{40}$-substituted or unsubstituted 3 to 20 membered cycloalkyl. R$^4$ may be R$^{40}$-substituted 3 to 20 membered cycloalkyl. R$^4$ may be R$^{40}$-substituted or unsubstituted 3 to 10 membered cycloalkyl. R$^4$ may be R$^{40}$-substituted 3 to 10 membered cycloalkyl. R$^4$ may be R$^{40}$-substituted or unsubstituted 3 to 6 membered cycloalkyl. R$^4$ may be R$^{40}$-substituted 3 to 6 membered cycloalkyl.

R$^4$ may be substituted or unsubstituted heterocycloalkyl. R$^4$ may be substituted heterocycloalkyl. R$^4$ may be unsubstituted heterocycloalkyl. R$^4$ may be substituted or unsubstituted 3 to 20 membered heterocycloalkyl. R$^4$ may be substituted 3 to 20 membered heterocycloalkyl. R$^4$ may be unsubstituted 3 to 20 membered heterocycloalkyl. R$^4$ may be substituted or unsubstituted 3 to 10 membered heterocycloalkyl. R$^4$ may be substituted 3 to 10 membered heterocycloalkyl. R$^4$ may be unsubstituted 3 to 10 membered heterocycloalkyl. R$^4$ may be substituted or unsubstituted 3 to 6 membered heterocycloalkyl. R$^4$ may be substituted 3 to 6 membered heterocycloalkyl. R$^4$ may be unsubstituted 3 to 6 membered heterocycloalkyl.

R$^4$ may be R$^{40}$-substituted or unsubstituted heterocycloalkyl. R$^4$ may be R$^{40}$-substituted heterocycloalkyl. R$^4$ may be R$^{40}$-substituted or unsubstituted 3 to 20 membered heterocycloalkyl. R$^4$ may be R$^{40}$-substituted 3 to 20 membered heterocycloalkyl. R$^4$ may be R$^{40}$-substituted or unsubstituted 3 to 10 membered heterocycloalkyl. R$^4$ may be R$^{40}$-substituted 3 to 10 membered heterocycloalkyl. R$^4$ may be R$^{40}$-substituted or unsubstituted 3 to 6 membered heterocycloalkyl. R$^4$ may be R$^{40}$-substituted 3 to 6 membered heterocycloalkyl.

R$^4$ may be substituted or unsubstituted aryl. R$^4$ may be substituted aryl. R$^4$ may be unsubstituted aryl. R$^4$ may be substituted or unsubstituted 5 to 20 membered aryl. R$^4$ may be substituted 5 to 20 membered aryl. R$^4$ may be unsubstituted 5 to 20 membered aryl. R$^4$ may be substituted or unsubstituted 5 to 8 membered aryl. R$^4$ may be substituted 5 to 8 membered aryl. R$^4$ may be unsubstituted 5 to 8 membered aryl. R$^4$ may be substituted or unsubstituted 5 or 6 membered aryl. R$^4$ may be substituted 5 or 6 membered aryl (e.g. phenyl). R$^4$ may be unsubstituted 5 or 6 membered aryl.

$R^4$ may be $R^{40}$-substituted or unsubstituted aryl. $R^4$ may be $R^{40}$-substituted aryl. $R^4$ may be $R^{40}$-substituted or unsubstituted 5 to 20 membered aryl. $R^4$ may be $R^{40}$-substituted 5 to 20 membered aryl. $R^4$ may be $R^{40}$-substituted or unsubstituted 5 to 8 membered aryl. $R^4$ may be $R^{40}$-substituted 5 to 8 membered aryl. $R^4$ may be $R^{40}$-substituted or unsubstituted 5 or 6 membered aryl. $R^4$ may be $R^{40}$-substituted 5 or 6 membered aryl (e.g. phenyl).

$R^4$ may be substituted or unsubstituted aryl. $R^4$ may be substituted heteroaryl. $R^4$ may be unsubstituted heteroaryl. $R^4$ may be substituted or unsubstituted 5 to 20 membered heteroaryl. $R^4$ may be substituted 5 to 20 membered aryl. $R^4$ may be unsubstituted 5 to 20 membered heteroaryl. $R^4$ may be substituted or unsubstituted 5 to 8 membered heteroaryl. $R^4$ may be substituted 5 to 8 membered heteroaryl. $R^4$ may be unsubstituted 5 to 8 membered heteroaryl. $R^4$ may be substituted or unsubstituted 5 or 6 membered heteroaryl. $R^4$ may be substituted 5 or 6 membered heteroaryl. $R^4$ may be unsubstituted 5 or 6 membered heteroaryl.

$R^4$ may be $R^{40}$-substituted or unsubstituted heteroaryl. $R^4$ may be $R^{40}$-substituted heteroaryl. $R^4$ may be $R^{40}$-substituted or unsubstituted 5 to 20 membered heteroaryl. $R^4$ may be $R^{40}$-substituted 5 to 20 membered heteroaryl. $R^4$ may be $R^{40}$-substituted or unsubstituted 5 to 8 membered heteroaryl. $R^4$ may be $R^{40}$-substituted 5 to 8 membered heteroaryl. $R^4$ may be $R^{40}$-substituted or unsubstituted 5 or 6 membered heteroaryl. $R^4$ may be $R^{40}$-substituted 5 or 6 membered heteroaryl.

$R^4$ may be $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. $R^4$ may be $R^{40}$-substituted or unsubstituted cycloalkyl. $R^4$ may be $R^{40}$-substituted or unsubstituted aryl. $R^4$ may be $R^{40}$-substituted or unsubstituted heteroaryl.

$R^4$ may be $R^{40}$-substituted or unsubstituted heterocycloalkyl. $R^4$ may be substituted or unsubstituted 5 to 8 membered heterocycloalkyl. $R^4$ may be $R^{40}$-substituted or unsubstituted 5 to 8 membered heterocycloalkyl. $R^4$ may be substituted or unsubstituted 5 to 8 membered heterocycloalkyl having at least one ring nitrogen. $R^4$ may be $R^4$-substituted or unsubstituted 5 to 8 membered heterocycloalkyl having at least one ring nitrogen.

$R^4$ may be substituted or unsubstituted piperidinyl, substituted or unsubstituted piperazinyl, substituted or unsubstituted morpholino, or substituted or unsubstituted pyrrolidinyl. $R^4$ may be substituted or unsubstituted piperidinyl. $R^4$ may be substituted or unsubstituted piperazinyl. $R^4$ may be substituted or unsubstituted morpholino. $R^4$ may be substituted or unsubstituted pyrrolidinyl.

$R^4$ may be $R^{40}$-substituted or unsubstituted piperidinyl, $R^{40}$-substituted or unsubstituted piperazinyl, $R^{40}$-substituted or unsubstituted morpholino, or $R^{40}$-substituted or unsubstituted pyrrolidinyl. $R^4$ may be $R^{40}$-substituted or unsubstituted piperidinyl. $R^4$ may be $R^{40}$-substituted or unsubstituted piperazinyl. $R^4$ may be $R^{40}$-substituted or unsubstituted morpholino. $R^4$ may be $R^{40}$-substituted or unsubstituted pyrrolidinyl.

$R^{40}$ is independently oxo, halogen, —$N_3$, —$CF_3$, —$CCl_3$, —$CBr_3$, —$CI_3$, —CN, —$COR^{40A}$, —$OR^{40A}$, —$NR^{40A}R^{40B}$, —$C(O)OR^{40A}$, —$C(O)NR^{40A}R^{40B}$, —$NO_2$, —$SR^{40A}$, —$S(O)_2R^{40A}$, —$S(O)_2OR^{40A}$, —$S(O)_2NR^{40A}R^{40B}$, —$NHNR^{40A}R^{40B}$, —$ONR^{40A}R^{40B}$, —$NHC(O)NHNR^{40A}R^{40B}$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl.

$R^{40}$ may independently be oxo, halogen, —$N_3$, —$CF_3$, —$CCl_3$, —$CBr_3$, —$CI_3$, —CN, —$COR^{40A}$, —$OR^{40A}$, —$NR^{40A}R^{40B}$, —$C(O)OR^{40A}$, —$C(O)NR^{40A}R^{40B}$, —$NO_2$, —$SR^{40A}$, —$S(O)_2R^{40A}$, —$S(O)_2OR^{40A}$, —$S(O)_2NR^{40A}R^{40B}$, —$NHNR^{40A}R^{40B}$, —$ONR^{40A}R^{40B}$, —$NHC(O)NHNR^{40A}R^{40B}$, unsubstituted alkyl, unsubstituted heteroalkyl, unsubstituted cycloalkyl, unsubstituted heterocycloalkyl, unsubstituted aryl, or unsubstituted heteroaryl.

$R^{40}$ may independently be oxo, halogen, —$N_3$, —$CF_3$, —$CCl_3$, —$CBr_3$, —$CI_3$, —CN, —OH, —$NH_2$, —C(O)OH, —$C(O)NH_2$, —COH, —$COCH_3$, —$NO_2$, —SH, —$S(O)_2H$, —$S(O)_2OH$, —$S(O)_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{40A}$ is independently hydrogen, oxo, halogen, —$N_3$, —$CF_3$, —$CCl_3$, —$CBr_3$, —$CI_3$, —CN, —$OR^{41}$, —$NR^{41}R^{40C}$, —$COR^{41}$, —$COOR^{41}$, —$CONR^{41}R^{40C}$, —$NO_2$, —$SR^{41}$, —$S(O)_2R^{41}$, —$S(O)_3R^{41}$, —$S(O)_2NR^{41}R^{40C}$, $S(O)_4R^{41}$, —$NHNR^{41}R^{40C}$, $ONR^{41}R^{40C}$, —$NHC(O)NHNR^{41}R^{40C}$, —$NHC(O)NR^{41}R^{40C}$, —$NHS(O)_2R^{41}$, —$NHC(O)R^{41}$, —$NHC(O)$—$OR^{41}$, —$NHOR^{41}$, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{40A}$ may independently be hydrogen, oxo, halogen, —$N_3$, —$CF_3$, —$CCl_3$, —$CBr_3$, —$CI_3$, —CN, —OH, —$NH_2$, —$COR^{41}$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{40A}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{41}$ is independently hydrogen, halogen, —$N_3$, —$CF_3$, —$CCl_3$, —$CBr_3$, —$CI_3$, —CN, —$COR^{41A}$, —$OR^{41A}$, —$NR^{41A}R^{41B}$, —$C(O)OR^{41A}$, —$C(O)NR^{41A}R^{41B}$, —$NO_2$, —$SR^{41A}$, —$S(O)_2R^{41A}$, —$S(O)_2OR^{41A}$, —$S(O)_2NR^{41A}R^{41B}$, —$NR^{41A}R^{41B}$, —$ONR^{41A}R^{41B}$, —$NHC(O)NHNR^{41A}R^{41B}$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

$R^{41}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{42}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

$R^{42}$ may independently be oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

$R^{43}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

$R^{41A}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{41C}$-substituted or unsubstituted heteroalkyl, $R^{41C}$-substituted or unsubstituted cycloalkyl, $R^{41C}$-substituted or unsubstituted heterocycloalkyl, $R^{41C}$-substituted or unsubstituted aryl, or $R^{41C}$-substituted or unsubstituted heteroaryl.

$R^{41C}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{41D}$-substituted or unsubstituted alkyl, $R^{41D}$-substituted or unsubstituted heteroalkyl, $R^{41D}$-substituted or unsubstituted cycloalkyl, $R^{41D}$-substituted or unsubstituted heterocycloalkyl, $R^{41D}$-substituted or unsubstituted aryl, or $R^{41D}$-substituted or unsubstituted heteroaryl.

$R^{41B}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{41E}$-substituted or unsubstituted alkyl, $R^{41E}$-substituted or unsubstituted heteroalkyl, $R^{41E}$-substituted or unsubstituted cycloalkyl, $R^{41E}$-substituted or unsubstituted heterocycloalkyl, $R^{41E}$-substituted or unsubstituted aryl, or $R^{41E}$-substituted or unsubstituted heteroaryl.

$R^{41E}$ is independently oxo, halogen, —N$_3$, —CF$_3$, —CCl$_3$, —CBr$_3$, —CI$_3$, —CN, —OH, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{41F}$-substituted or unsubstituted alkyl, $R^{41F}$-substituted or unsubstituted heteroalkyl, $R^{41F}$-substituted or unsubstituted cycloalkyl, $R^{41F}$-substituted or unsubstituted heterocycloalkyl, $R^{41F}$-substituted or unsubstituted aryl, or $R^{41F}$-substituted or unsubstituted heteroaryl.

$R^{40B}$ is independently hydrogen, oxo, halogen, —N$_3$, —CF$_3$, —CCl$_3$, —CBr$_3$, —CI$_3$, —CN, —OR$^{45}$, —NR$^{45}$R$^{40D}$, —COR$^{45}$, —COOR$^{45}$, —CONR$^{45}$R$^{40D}$, —NO$_2$, —SR$^{45}$, —S(O)R$^{45}$, —S(O)$_3$R$^{45}$, —S(O)$_4$R$^{45}$, —S(O)$_2$NR$^{45}$R$^{40D}$, —NHNR$^{45}$R$^{40D}$, —ONR$^{45}$R$^{40D}$, —NHC(O)NHNR$^{45}$R$^{40D}$, —NHC(O)NR$^{45}$R$^{40D}$, —NHS(O)$_2$R$^{45}$, —NHC(O)R$^{45}$, —NHC(O)—OR$^{45}$, —NHOR$^{45}$, —OCF$_3$, —OCHF$_2$, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

$R^{40B}$ may independently be hydrogen, oxo, halogen, —N$_3$, —CF$_3$, —CCl$_3$, —CBr$_3$, —CI$_3$, —CN, —OH, —NH$_2$, —COR$^{45}$, —COOH, —CONH$_2$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

$R^{40B}$ may independently be hydrogen, oxo, halogen, —N$_3$, —CF$_3$, —CCl$_3$, —CBr$_3$, —CI$_3$, —CN, —OH, —NH$_2$, —COOH, —COH, —COCH$_3$, —CONH$_2$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

$R^{45}$ is independently hydrogen, halogen, oxo, —N$_3$, —CF$_3$, —CCl$_3$, —CBr$_3$, —CI$_3$, —CN, —COR$^{45A}$, —OR$^{45A}$, —NR$^{45A}$R$^{45B}$, —C(O)OR$^{45A}$, —C(O)NR$^{45A}$R$^{45B}$, —NO$_2$, —SR$^{45A}$, —S(O)$_2$R$^{45A}$, —S(O)$_2$OR$^{45A}$, —S(O)$_2$NR$^{45A}$R$^{45B}$, —NHNR$^{45A}$R$^{45B}$, —ONR$^{45A}$R$^{45B}$, —NHC(O)NHNR$^{45A}$R$^{45B}$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

$R^{45A}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{45C}$-substituted or unsubstituted heteroalkyl, $R^{45C}$-substituted or unsubstituted cycloalkyl, $R^{45C}$-substituted or unsubstituted heterocycloalkyl, $R^{45C}$-substituted or unsubstituted aryl, or $R^{45C}$-substituted or unsubstituted heteroaryl.

$R^{45C}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{45D}$-substituted or unsubstituted alkyl, $R^{45D}$-substituted or unsubstituted heteroalkyl, $R^{45D}$-substituted or unsubstituted cycloalkyl, $R^{45D}$-substituted or unsubstituted heterocycloalkyl, $R^{45D}$-substituted or unsubstituted aryl, or $R^{45D}$-substituted or unsubstituted heteroaryl.

$R^{45B}$ is independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{45E}$-substituted or unsubstituted alkyl, $R^{45E}$-substituted or unsubstituted heteroalkyl, $R^{45E}$-substituted or unsubstituted cycloalkyl, $R^{45E}$-substituted or unsubstituted heterocycloalkyl, $R^{45E}$-substituted or unsubstituted aryl, or $R^{45E}$-substituted or unsubstituted heteroaryl.

$R^{45E}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{45F}$-substituted or unsubstituted alkyl, $R^{45F}$-substituted or unsubstituted heteroalkyl, $R^{45F}$-substituted or unsubstituted cycloalkyl, $R^{45F}$-substituted or unsubstituted heterocycloalkyl, $R^{45F}$-substituted or unsubstituted aryl, or $R^{45F}$-substituted or unsubstituted heteroaryl.

$R^{46}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{47}$-substituted or unsubstituted alkyl, $R^{47}$-substituted or unsubstituted heteroalkyl, $R^{47}$-substituted or unsubstituted cycloalkyl, $R^{47}$-substituted or unsubstituted heterocycloalkyl, $R^{47}$-substituted or unsubstituted aryl, or $R^{47}$-substituted or unsubstituted heteroaryl.

$R^{40C}$, $R^{40D}$, $R^{41D}$, $R^{41F}$, and $R^{45D}$ are independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

$R^{45F}$, $R^{44}$, and $R^{47}$ are independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl $R^4$ may be —NR$^{4A}$R$^{4B}$. $R^{4A}$ and $R^{4B}$ are as defined herein. $R^{4A}$ may be hydrogen, $R^{41}$-substituted or unsubstituted alkyl, or $R^{41}$-substituted or unsubstituted heteroalkyl, where $R^{41}$ is as defined herein. $R^{4A}$ may be hydrogen, $R^{41}$-substituted or unsubstituted alkyl, or $R^{41}$-substituted or unsubstituted heteroalkyl, where $R^{41}$ is hydrogen, halogen, —CF$_3$, —OR$^{41A}$, —NR$^{41A}$R$^{41B}$, $R^{42}$-substituted or unsubstituted alkyl, $R^{42}$-substituted or unsubstituted heteroalkyl, or $R^{42}$-substituted or unsubstituted aryl. $R^{44}$ may be hydrogen, $R^{41}$-substituted or unsubstituted alkyl, or $R^{41}$-substituted or unsubstituted heteroalkyl, where $R^{41}$ is hydrogen, halogen, —CF$_3$, —OR$^{41A}$, —NR$^{41A}$R$^{41B}$, $R^{42}$-substituted or unsubstituted alkyl, $R^{42}$-substituted or unsubstituted heteroalkyl, or $R^{42}$-substituted or unsubstituted aryl, $R^{41A}$ and $R^{41B}$ are independently hydrogen or unsubstituted C$_1$-C$_5$ alkyl, and $R^{42}$ is as described herein.

$R^{4B}$ may be hydrogen, $R^{45}$-substituted or unsubstituted alkyl, or $R^{45}$-substituted or unsubstituted heteroalkyl, where $R^{45}$ is as defined herein. $R^{4B}$ may be hydrogen, $R^{45}$-substituted or unsubstituted alkyl, or $R^{45}$-substituted or unsubstituted heteroalkyl, where $R^{45}$ is hydrogen, halogen, CF$_3$, —OR$^{45A}$, —NR$^{45A}$R$^{45B}$, $R^{46}$-substituted or unsubstituted alkyl, $R^{46}$-substituted or unsubstituted heteroalkyl, or $R^{46}$-substituted or unsubstituted aryl. $R^{4B}$ may be hydrogen, $R^{45}$-substituted or unsubstituted alkyl, or $R^{45}$-substituted or unsubstituted heteroalkyl, where $R^{45}$ is hydrogen, halogen, CF$_3$, —OR$^{45A}$, —NR$^{45A}$R$^{45B}$, $R^{46}$-substituted or unsubstituted alkyl, $R^{46}$-substituted or unsubstituted heteroalkyl, or $R^{46}$-substituted or unsubstituted aryl, $R^{45A}$ and $R^{45B}$ are independently hydrogen or unsubstituted C$_1$-C$_5$ alkyl and $R^{46}$ is as defined herein.

$R^{44}$ may independently be hydrogen, oxo, halogen, —N$_3$, —CF$_3$, —CCl$_3$, —CBr$_3$, —CI$_3$, —CN, —OR$^{41}$, —NR$^{41}$R$^{40C}$, —COR$^{41}$, —COOR$^{41}$, —CONR$^{41}$R$^{40C}$, —NO$_2$, —SR$^{41}$, —S(O)$_2$R$^{41}$, —S(O)$_3$R$^{41}$, —S(O)$_4$R$^{41}$, —NHNR$^{41}$R$^{40C}$, ONR$^{41}$R$^{40C}$, —NHC(O)NHNR$^{41}$R$^{40C}$, —NHC(O)NR$^{41}$R$^{40C}$, —NHS(O)$_2$R$^{41}$, —NHC(O)R$^{41}$, —NHC(O)—OR$^{41}$, —NHOR$^{41}$, —OCF$_3$, —OCHF$_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{44}$ may independently be hydrogen, oxo, halogen, —N$_3$, —CF$_3$, —CCl$_3$, —CBr$_3$, —CI$_3$, —CN, —OH, —NH$_2$, —COR$^{41}$, —COOH, —CONH$_2$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{44}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{4B}$ may independently be hydrogen, oxo, halogen, —N$_3$, —CF$_3$, —CCl$_3$, —CBr$_3$, —CI$_3$, —CN, —OR$^{45}$, —NR$^{45}$R$^{4D}$, —COR$^{45}$, —COOR$^{45}$, —CONR$^{45}$R$^{40D}$, —NO$_2$, —SR$^{45}$, —S(O)$_2$R$^{45}$, —S(O)$_3$R$^{45}$, —S(O)$_4$R$^{45}$, —S(O)$_2$NR$^{45}$R$^{40D}$, —NHNR$^{45}$R$^{40D}$, —ONR$^{45}$R$^{40D}$, —NHC(O)NHNR$^{45}$R$^{40D}$, —NHC(O)NR$^{45}$R$^{40D}$, —NHS(O)$_2$R$^{45}$, —NHC(O)R$^{45}$, —NHC(O)—OR$^{45}$, —NHOR$^{45}$, —OCF$_3$, —OCHF$_2$, $R^{45}$-substituted or unsubstituted heteroalkyl, $R^{45}$-substituted or unsubstituted cycloalkyl, $R^{45}$- substituted or unsubstituted heterocycloalkyl, $R^{45}$-substituted or unsubstituted aryl, or $R^{45}$-substituted or unsubstituted heteroaryl.

$R^{4B}$ may independently be oxo, halogen, —$CF_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

In embodiments, the PLK4 inhibitor is the compound of Formula (Ia1) or a pharmaceutically acceptable salt thereof:

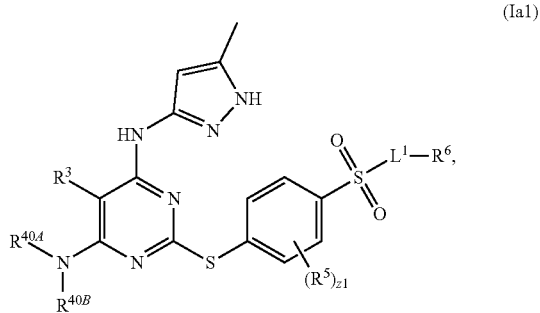

(Ia1)

where $L^1$, z1, $R^3$, $R^5$, $R^6$, $R^{40A}$, and $R^{40B}$ are as described herein.

In embodiments, the PLK4 inhibitor is the compound of Formula (Ib1) or a pharmaceutically acceptable salt thereof:

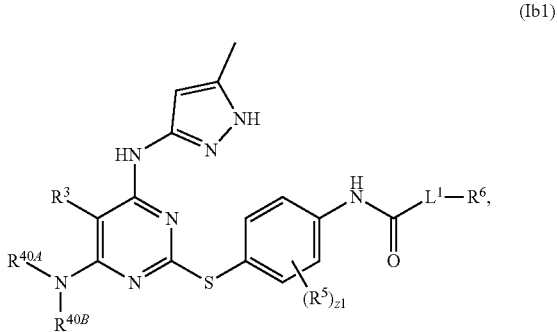

(Ib1)

where $L^1$, z1, $R^3$, $R^5$, $R^6$, $R^{40A}$, and $R^{40B}$ are as described herein.

$R^5$ may independently be hydrogen, halogen, —$N_3$, —$CF_3$, —$CCl_3$, —$CBr_3$, —$CI_3$, —CN, —$COR^{5A}$, —$OR^{5A}$, —$NR^{5A}R^{5B}$, —$C(O)OR^{5A}$, —$C(O)NR^{5A}R^{5B}$, —$NO_2$, —$SR^{5A}$, —$S(O)_{n5}R^{5A}$, —$S(O)_{n5}OR^{5A}$, —$S(O)_{n5}NR^{5A}R^{5B}$, —$NHNR^{5A}R^{5B}$, —$ONR^{5A}R^{5B}$ or —$NHC(O)NHNR^{5A}R^{5B}$. $R^5$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ may be hydrogen or halogen. $R^5$ may be hydrogen or —Cl, —I, or —Br. $R^5$ may be hydrogen or —Cl or —F. $R^5$ may be hydrogen. $R^5$ may be —Cl. $R^5$ may be —I. $R^5$ may be —Br. $R^5$ may be —F. The symbol z1 may be 1, 2, or 3. The symbol z1 may be 1 or 2. $R^5$ may be hydrogen or —Cl or —F where the symbol z1 is 1 or 2.

$R^5$ may be substituted or unsubstituted alkyl. $R^5$ may be substituted alkyl. $R^5$ may be unsubstituted alkyl. $R^5$ may be substituted or unsubstituted $C_1$-$C_{20}$ alkyl. $R^5$ may be substituted $C_1$-$C_{20}$ alkyl. $R^5$ may be unsubstituted $C_1$-$C_{20}$ alkyl. $R^5$ may be substituted or unsubstituted $C_1$-$C_{10}$ alkyl. $R^5$ may be substituted $C_1$-$C_{10}$ alkyl. $R^5$ may be unsubstituted $C_1$-$C_{10}$ alkyl. $R^5$ may be substituted or unsubstituted $C_1$-$C_5$ alkyl. $R^5$ may be unsubstituted $C_1$-$C_5$ alkyl. $R^5$ may be substituted $C_1$-$C_5$ alkyl. $R^5$ may be methyl, substituted or unsubstituted ethyl, or substituted or unsubstituted propyl. $R^5$ may be methyl. $R^5$ may be ethyl.

$R^5$ may be $R^{5C}$-substituted or unsubstituted alkyl. $R^5$ may be $R^{5C}$-substituted alkyl. $R^5$ may be $R^{5C}$-substituted or unsubstituted $C_1$-$C_{20}$ alkyl. $R^5$ may be $R^{5C}$-substituted $C_1$-$C_{20}$ alkyl. $R^5$ may be $R^{5C}$-substituted or unsubstituted $C_1$-$C_{10}$ alkyl. $R^5$ may be $R^{5C}$-substituted $C_1$-$C_{10}$ alkyl. $R^5$ may be $R^{5C}$-substituted or unsubstituted $C_1$-$C_5$ alkyl. $R^5$ may be $R^{5C}$-substituted $C_1$-$C_5$ alkyl. $R^5$ may be methyl, $R^{5C}$-substituted or unsubstituted ethyl, or $R^{5C}$-substituted or unsubstituted propyl.

$R^5$ may be substituted or unsubstituted heteroalkyl. $R^5$ may be substituted heteroalkyl. $R^5$ may be unsubstituted heteroalkyl. $R^5$ may be substituted or unsubstituted 2 to 20 membered heteroalkyl. $R^5$ may be substituted 2 to 20 membered heteroalkyl. $R^5$ may be substituted or unsubstituted 2 to 10 membered heteroalkyl. $R^5$ may be substituted 2 to 10 membered heteroalkyl. $R^5$ may be substituted or unsubstituted 2 to 6 membered heteroalkyl. $R^5$ may be substituted 2 to 6 membered heteroalkyl.

$R^5$ may be $R^{5C}$-substituted or unsubstituted heteroalkyl. $R^5$ may be $R^{5C}$-substituted heteroalkyl. $R^5$ may be $R^{5C}$-substituted or unsubstituted 2 to 20 membered heteroalkyl. $R^5$ may be $R^{5C}$-substituted 2 to 20 membered heteroalkyl. $R^5$ may be $R^{5C}$-substituted or unsubstituted 2 to 10 membered heteroalkyl. $R^5$ may be $R^{5C}$-substituted 2 to 10 membered heteroalkyl. $R^5$ may be $R^{5C}$-substituted or unsubstituted 2 to 6 membered heteroalkyl. $R^5$ may be $R^{5C}$-substituted 2 to 6 membered heteroalkyl.

$R^5$ may be substituted or unsubstituted cycloalkyl. $R^5$ may be substituted cycloalkyl. $R^5$ may be unsubstituted cycloalkyl. $R^5$ may be substituted or unsubstituted 3 to 20 membered cycloalkyl. $R^5$ may be substituted 3 to 20 membered cycloalkyl. $R^5$ may be substituted or unsubstituted 3 to 10 membered cycloalkyl. $R^5$ may be substituted 3 to 10 membered cycloalkyl. $R^5$ may be substituted or unsubstituted 3 to 6 membered cycloalkyl. $R^5$ may be substituted 3 to 6 membered cycloalkyl.

$R^5$ may be $R^{5C}$-substituted or unsubstituted cycloalkyl. $R^5$ may be $R^{5C}$-substituted cycloalkyl. $R^5$ may be $R^{5C}$-substituted or unsubstituted 3 to 20 membered cycloalkyl. $R^5$ may be $R^{5C}$-substituted 3 to 20 membered cycloalkyl. $R^5$ may be $R^{5C}$-substituted or unsubstituted 3 to 10 membered cycloalkyl. $R^5$ may be $R^{5C}$-substituted 3 to 10 membered cycloalkyl. $R^5$ may be $R^{5C}$-substituted or unsubstituted 3 to 6 membered cycloalkyl. $R^5$ may be $R^{5C}$-substituted 3 to 6 membered cycloalkyl.

$R^5$ may be substituted or unsubstituted heterocycloalkyl. $R^5$ may be substituted heterocycloalkyl. $R^5$ may be unsubstituted heterocycloalkyl. $R^5$ may be substituted or unsubstituted 3 to 20 membered heterocycloalkyl. $R^5$ may be substituted 3 to 20 membered heterocycloalkyl. $R^5$ may be substituted or unsubstituted 3 to 10 membered heterocycloalkyl. $R^5$ may be substituted 3 to 10 membered heterocycloalkyl. $R^5$ may be substituted or unsubstituted 3 to 6 membered heterocycloalkyl. $R^5$ may be substituted 3 to 6 membered heterocycloalkyl.

$R^5$ may be $R^{5C}$-substituted or unsubstituted heterocycloalkyl. $R^5$ may be $R^{5C}$-substituted heterocycloalkyl. $R^5$ may be $R^{5C}$-substituted or unsubstituted 3 to 20 membered heterocycloalkyl. $R^5$ may be $R^{5C}$-substituted 3 to 20 membered heterocycloalkyl. $R^5$ may be $R^{5C}$-substituted or unsubstituted 3 to 10 membered heterocycloalkyl. $R^5$ may be $R^{5C}$-substituted 3 to 10 membered heterocycloalkyl. $R^5$ may be $R^{5C}$-substituted or unsubstituted 3 to 6 membered heterocycloalkyl. $R^5$ may be $R^{5C}$-substituted 3 to 6 membered heterocycloalkyl.

$R^5$ may be substituted or unsubstituted aryl. $R^5$ may be substituted aryl. $R^5$ may be unsubstituted aryl. $R^5$ may be substituted or unsubstituted 5 to 20 membered aryl. $R^5$ may be substituted 5 to 20 membered aryl. $R^5$ may be substituted or unsubstituted 5 to 8 membered aryl (e.g. phenyl). $R^5$ may be substituted 5 to 8 membered aryl. $R^5$ may be substituted or unsubstituted 5 or 6 membered aryl. $R^5$ may be substituted 5 or 6 membered aryl.

$R^5$ may be $R^{5C}$-substituted or unsubstituted aryl. $R^5$ may be $R^5$-substituted aryl. $R^5$ may be $R^{5C}$-substituted or unsubstituted 5 to 20 membered aryl. $R^5$ may be $R^{5C}$-substituted 5 to 20 membered aryl. $R^5$ may be $R^{5C}$-substituted or unsubstituted 5 to 8 membered aryl. $R^5$ may be $R^{5C}$-substituted 5 to 8 membered aryl. $R^5$ may be $R^{5C}$-substituted or unsubstituted 5 or 6 membered aryl. $R^5$ may be $R^{5C}$-substituted 5 or 6 membered aryl (e.g. phenyl).

$R^5$ may be substituted or unsubstituted heteroaryl. $R^5$ may be substituted heteroaryl. $R^5$ may be unsubstituted heteroaryl. $R^5$ may be substituted or unsubstituted 5 to 20 membered heteroaryl. $R^5$ may be substituted 5 to 20 membered heteroaryl. $R^5$ may be substituted or unsubstituted 5 to 8 membered heteroaryl. $R^5$ may be substituted 5 to 8 membered heteroaryl. $R^5$ may be substituted or unsubstituted 5 or 6 membered heteroaryl. $R^5$ may be substituted 5 or 6 membered heteroaryl.

$R^5$ may be $R^{5C}$-substituted or unsubstituted heteroaryl. $R^5$ may be $R^5$-substituted heteroaryl. $R^5$ may be $R^{5C}$-substituted or unsubstituted 5 to 20 membered heteroaryl. $R^5$ may be $R^{5C}$-substituted 5 to 20 membered heteroaryl. $R^5$ may be $R^{5C}$-substituted or unsubstituted 5 to 8 membered heteroaryl. $R^5$ may be $R^{5C}$-substituted 5 to 8 membered heteroaryl. $R^5$ may be $R^{5C}$-substituted or unsubstituted 5 or 6 membered heteroaryl. $R^5$ may be $R^{5C}$-substituted 5 or 6 membered heteroaryl.

$R^{5A}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{5C}$-substituted or unsubstituted alkyl, $R^5$-substituted or unsubstituted heteroalkyl, $R^{5C}$-substituted or unsubstituted cycloalkyl, $R^{5C}$-substituted or unsubstituted heterocycloalkyl, $R^{5C}$-substituted or unsubstituted aryl, or $R^{5C}$-substituted or unsubstituted heteroaryl.

$R^{5C}$ is independently halogen, oxo, $N_3$, —$CF_3$, —$CCl_3$, —$CBr_3$, —$CI_3$, —CN, —OH, —$COR^{5D}$, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{5D}$-substituted or unsubstituted alkyl, $R^{5D}$-substituted or unsubstituted heteroalkyl, $R^{5D}$-substituted or unsubstituted cycloalkyl, $R^{5D}$-substituted or unsubstituted heterocycloalkyl, $R^{5D}$-substituted or unsubstituted aryl, or $R^{5D}$-substituted or unsubstituted heteroaryl.

$R^{5B}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{5D}$ is independently halogen, oxo, $N_3$, —$CF_3$, —$CCl_3$, —$CBr_3$, —$CI_3$, —CN, —OH, —$COR^{5E}$, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl.

$R^{5E}$ is independently halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^6$ may be hydrogen, —$NH_2$, —$CF_3$, —$NR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ may be hydrogen, —$CF_3$, —$NR^{6A}R^{6B}$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^6$ may be substituted or unsubstituted cycloalkyl, substituted or unsubstituted heterocycloalkyl, substituted or unsubstituted aryl, or substituted or unsubstituted heteroaryl.

$R^6$ may be substituted or unsubstituted alkyl. $R^6$ may be substituted alkyl. $R^6$ may be unsubstituted alkyl. $R^6$ may be substituted or unsubstituted $C_1$-$C_{20}$ alkyl. $R^6$ may be substituted $C_1$-$C_{20}$ alkyl. $R^6$ may be unsubstituted $C_1$-$C_{20}$ alkyl. $R^6$ may be substituted or unsubstituted $C_1$-$C_{10}$ alkyl. $R^6$ may be substituted $C_1$-$C_{10}$ alkyl. $R^6$ may be unsubstituted $C_1$-$C_{10}$ alkyl. $R^6$ may be substituted or unsubstituted $C_1$-$C_5$ alkyl. $R^6$ may be substituted $C_1$-$C_5$ alkyl. $R^6$ may be unsubstituted $C_1$-$C_5$ alkyl. $R^6$ may be methyl, substituted or unsubstituted ethyl, or substituted or unsubstituted propyl. $R^6$ may be hydrogen, methyl, ethyl or propyl. $R^6$ may be hydrogen. $R^6$ may be methyl.

$R^6$ may be $R^{60}$-substituted or unsubstituted alkyl. $R^6$ may be $R^{60}$-substituted alkyl. $R^6$ may be $R^{60}$-substituted or unsubstituted $C_1$-$C_{20}$ alkyl. $R^6$ may be $R^{60}$-substituted $C_1$-$C_{20}$ alkyl. $R^6$ may be $R^{60}$-substituted or unsubstituted $C_1$-$C_{10}$ alkyl. $R^6$ may be $R^{60}$-substituted $C_1$-$C_{10}$ alkyl. $R^6$ may be $R^{60}$-substituted or unsubstituted $C_1$-$C_5$ alkyl. $R^6$ may be $R^{60}$-substituted $C_1$-$C_5$ alkyl. $R^6$ may be methyl, $R^{60}$-substituted or unsubstituted ethyl, or $R^{60}$-substituted or unsubstituted propyl.

$R^6$ may be substituted or unsubstituted heteroalkyl. $R^6$ may be substituted heteroalkyl. $R^6$ may be unsubstituted heteroalkyl. $R^6$ may be substituted or unsubstituted 2 to 20 membered heteroalkyl. $R^6$ may be substituted 2 to 20 membered heteroalkyl. $R^6$ may be unsubstituted 2 to 20 membered heteroalkyl. $R^6$ may be substituted or unsubstituted 2 to 10 membered heteroalkyl. $R^6$ may be substituted 2 to 10 membered heteroalkyl. $R^6$ may be unsubstituted 2 to 10 membered heteroalkyl. $R^6$ may be substituted or unsubstituted 2 to 6 membered heteroalkyl. $R^6$ may be substituted 2 to 6 membered heteroalkyl. $R^6$ may be unsubstituted 2 to 6 membered heteroalkyl.

$R^6$ may be $R^{60}$-substituted or unsubstituted heteroalkyl. $R^6$ may be $R^{60}$-substituted heteroalkyl. $R^6$ may be $R^{60}$-substituted or unsubstituted 2 to 20 membered heteroalkyl. $R^6$ may be $R^{60}$-substituted 2 to 20 membered heteroalkyl. $R^6$ may be $R^{60}$-substituted or unsubstituted 2 to 10 membered heteroalkyl. $R^6$ may be $R^{60}$-substituted 2 to 10 membered heteroalkyl. $R^6$ may be $R^{60}$-substituted or unsubstituted 2 to 6 membered heteroalkyl. $R^6$ may be $R^{60}$-substituted 2 to 6 membered heteroalkyl.

$R^6$ may be substituted or unsubstituted cycloalkyl. $R^6$ may be substituted cycloalkyl. $R^6$ may be unsubstituted cycloalkyl. $R^6$ may be substituted or unsubstituted 3 to 20 membered cycloalkyl. $R^6$ may be substituted 3 to 20 membered cycloalkyl. $R^6$ may be unsubstituted 3 to 20 membered cycloalkyl. $R^6$ may be substituted or unsubstituted 3 to 10 membered cycloalkyl. $R^6$ may be substituted 3 to 10 membered cycloalkyl. $R^6$ may be unsubstituted 3 to 10 membered cycloalkyl. $R^6$ may be substituted or unsubstituted 3 to 6 membered cycloalkyl. $R^6$ may be substituted 3 to 6 membered cycloalkyl. $R^6$ may be unsubstituted 3 to 6 membered cycloalkyl.

$R^6$ may be $R^{60}$-substituted or unsubstituted cycloalkyl. $R^6$ may be $R^{60}$-substituted cycloalkyl. $R^6$ may be $R^{60}$-substituted or unsubstituted 3 to 20 membered cycloalkyl. $R^6$ may be $R^{60}$-substituted 3 to 20 membered cycloalkyl. $R^6$ may be $R^{60}$-substituted or unsubstituted 3 to 10 membered cycloalkyl. $R^6$ may be $R^{60}$-substituted 3 to 10 membered cycloalkyl. $R^6$ may be $R^{60}$-substituted or unsubstituted 3 to 6 membered cycloalkyl. $R^6$ may be $R^{60}$-substituted 3 to 6 membered cycloalkyl.

$R^6$ may be substituted or unsubstituted heterocycloalkyl. $R^6$ may be substituted heterocycloalkyl. $R^6$ may be unsubstituted heterocycloalkyl. $R^6$ may be substituted or unsubstituted 3 to 20 membered heterocycloalkyl. $R^6$ may be substituted 3 to 20 membered heterocycloalkyl. $R^6$ may be unsubstituted 3 to 20 membered heterocycloalkyl. $R^6$ may be substituted or unsubstituted 3 to 10 membered heterocycloalkyl. $R^6$ may be substituted 3 to 10 membered heterocycloalkyl. $R^6$ may be unsubstituted 3 to 10 membered heterocycloalkyl. $R^6$ may be substituted or unsubstituted 3 to 6 membered heterocycloalkyl. $R^6$ may be substituted 3 to 6 membered heterocycloalkyl. $R^6$ may be unsubstituted 3 to 6 membered heterocycloalkyl.

$R^6$ may be $R^{60}$-substituted or unsubstituted heterocycloalkyl. $R^6$ may be $R^{60}$-substituted heterocycloalkyl. $R^6$ may be $R^{60}$-substituted or unsubstituted 3 to 20 membered heterocycloalkyl. $R^6$ may be $R^{60}$-substituted 3 to 20 membered heterocycloalkyl. $R^6$ may be $R^{60}$-substituted or unsubstituted 3 to 10 membered heterocycloalkyl. $R^6$ may be $R^{60}$-substituted 3 to 10 membered heterocycloalkyl. $R^6$ may be $R^{60}$-substituted or unsubstituted 3 to 6 membered heterocycloalkyl. $R^6$ may be $R^{60}$-substituted 3 to 6 membered heterocycloalkyl.

$R^6$ may be substituted or unsubstituted aryl. $R^6$ may be substituted aryl. $R^6$ may be unsubstituted aryl. $R^6$ may be substituted or unsubstituted 5 to 20 membered aryl. $R^6$ may be substituted 5 to 20 membered aryl. $R^6$ may be unsubstituted 5 to 20 membered aryl. $R^6$ may be substituted or unsubstituted 5 to 8 membered aryl. $R^6$ may be substituted 5 to 8 membered aryl. $R^6$ may be unsubstituted 5 to 8 membered aryl. $R^6$ may be substituted or unsubstituted 5 or 6 membered aryl. $R^6$ may be substituted 5 or 6 membered aryl (e.g. phenyl). $R^6$ may be unsubstituted 5 or 6 membered aryl (e.g. phenyl).

$R^6$ may be $R^{60}$-substituted or unsubstituted aryl. $R^6$ may be $R^{60}$-substituted aryl. $R^6$ may be $R^{60}$-substituted or unsubstituted 5 to 20 membered aryl. $R^6$ may be $R^{60}$-substituted 5 to 20 membered aryl. $R^6$ may be $R^{60}$-substituted or unsubstituted 5 to 8 membered aryl. $R^6$ may be $R^{60}$-substituted 5 to 8 membered aryl. $R^6$ may be $R^{60}$-substituted or unsubstituted 5 or 6 membered aryl. $R^6$ may be $R^{60}$-substituted 5 or 6 membered aryl (e.g. phenyl).

$R^6$ may be substituted or unsubstituted heteroaryl. $R^6$ may be substituted heteroaryl. $R^6$ may be unsubstituted heteroaryl. $R^6$ may be substituted or unsubstituted 5 to 20 membered heteroaryl. $R^6$ may be substituted 5 to 20 membered heteroaryl. $R^6$ may be unsubstituted 5 to 20 membered heteroaryl. $R^6$ may be substituted or unsubstituted 5 to 8 membered heteroaryl. $R^6$ may be substituted 5 to 8 membered heteroaryl. $R^6$ may be unsubstituted 5 to 8 membered heteroaryl. $R^6$ may be substituted or unsubstituted 5 or 6 membered heteroaryl. $R^6$ may be substituted 5 or 6 membered heteroaryl. $R^6$ may be unsubstituted 5 or 6 membered heteroaryl.

$R^6$ may be $R^{60}$-substituted or unsubstituted heteroaryl. $R^6$ may be $R^{60}$-substituted heteroaryl. $R^6$ may be $R^{60}$-substituted or unsubstituted 5 to 20 membered heteroaryl. $R^6$ may be $R^{60}$-substituted 5 to 20 membered heteroaryl. $R^6$ may be $R^{60}$-substituted or unsubstituted 5 to 8 membered heteroaryl. $R^6$ may be $R^{60}$-substituted 5 to 8 membered heteroaryl. $R^6$ may be $R^{60}$-substituted or unsubstituted 5 or 6 membered heteroaryl. $R^6$ may be $R^{60}$-substituted 5 or 6 membered heteroaryl.

$R^6$ may be $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^6$ may be $R^{60}$-substituted or unsubstituted $C_3$ cycloalkyl. $R^6$ may be unsubstituted $C_3$ cycloalkyl. $R^6$ may be $R^{60}$-substituted or unsubstituted $C_4$ cycloalkyl. $R^6$ may be unsubstituted $C_4$ cycloalkyl. $R^6$ may be $R^{60}$-substituted or unsubstituted C5 cycloalkyl. $R^6$ may be unsubstituted $C_5$ cycloalkyl. $R^6$ may be $R^{60}$-substituted or unsubstituted saturated $C_3$ cycloalkyl. $R^6$ may be unsubstituted saturated $C_3$ cycloalkyl. $R^6$ may be $R^{60}$-substituted or unsubstituted saturated $C_4$ cycloalkyl. $R^6$ may be $R^{60}$-substituted or unsubstituted saturated $C_5$ cycloalkyl. $R^6$ may be unsubstituted saturated $C_5$ cycloalkyl.

$R^6$ may $R^{60}$-substituted or unsubstituted aryl where $R^{60}$ is as defined herein, $R^{60A}$ is hydrogen, halogen, $-NO_2$, $-CF_3$, $-CN$, $-COR^{61}$, $R^{61}$-substituted or unsubstituted alkyl, $R^{61}$-substituted or unsubstituted heteroalkyl, or $R^{61}$-substituted or unsubstituted aryl, where $R^{61}$ is as defined herein and $R^{60B}$ is hydrogen, halogen, or unsubstituted alkyl.

$R^6$ may be $R^{60}$-substituted or unsubstituted heteroaryl where $R^{60}$ is halogen, $-CF_3$, $-NR^{60A}R^{60B}$, $-NO_2$, $-OR^{60A}$, $COOR^{60A}$, $-COR^{61}$, $R^{61}$-substituted or unsubstituted alkyl, $R^{61}$-substituted or unsubstituted heteroalkyl, or $R^{61}$-substituted or unsubstituted aryl, where $R^{61}$ is $-NR^{61A}R^{61B}$, and $R^{60A}$, $R^{60B}$, $R^{61A}$, and $R^{61B}$ are independently hydrogen or unsubstituted $C_1$-$C_5$ unsubstituted alkyl.

$R^6$ may be substituted or unsubstituted thiophenyl, substituted or unsubstituted thiazolyl, substituted or unsubstituted imidazolyl, or substituted or unsubstituted oxazolyl.

$R^6$ may be substituted or unsubstituted thiophenyl. $R^6$ may be substituted or unsubstituted thiazolyl. $R^6$ may be substituted or unsubstituted imidazolyl. $R^6$ may be substituted or unsubstituted oxazolyl.

$R^6$ may be $R^{60}$-substituted or unsubstituted thiophenyl, $R^{60}$-substituted or unsubstituted thiazolyl, $R^{60}$-substituted or unsubstituted imidazolyl, or $R^{60}$-substituted or unsubstituted oxazolyl. $R^6$ may be $R^{60}$-substituted or unsubstituted thiophenyl. $R^6$ may be $R^{60}$-substituted or unsubstituted thiazolyl. $R^6$ may be $R^{60}$-substituted or unsubstituted imidazolyl. $R^6$ may be $R^{60}$-substituted or unsubstituted oxazolyl.

$R^{60}$ is independently hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —$C(O)OR^{60A}$, —$C(O)NR^{60A}R^{60B}$, —$NO_2$, —$SR^{60A}$, —$S(O)_2H$, —$S(O)_2OH$, —$S(O)_2NH_2$, —$NHNH_2$, —$ONH_2$, —$NHC(O)NHNR^{60A}R^{60B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

$R^{60}$ may independently be oxo, halogen, —$N_3$, —$CF_3$, —$CCl_3$, —$CBr_3$, —$CI_3$, —CN, —COH, —$COCH_3$, —OH, —$NH_2$, —C(O)OH, —$C(O)NH_2$, —$NO_2$, —SH, —$S(O)_2H$, —$S(O)_2OH$, —$S(O)_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{60A}$ is independently hydrogen, oxo, halogen, —$N_3$, —$CF_3$, —$CCl_3$, —$CBr_3$, —$CI_3$, —CN, —$OR^{61}$, —$NR^{61}R^{60C}$, —$COOR^{61}$, —$CONR^{61}R^{60C}$, —$COR^{61}$, —$NO_2$, —$SR^{61}$, —$S(O)_2R^{61}$, —$S(O)_3R^{61}$, —$S(O)_4R^{61}$, —$S(O)_2NR^{61}R^{60C}$, —$NHNR^{61}R^{60C}$, —$ONR^{61}R^{60C}$, —$NHC(O)NHNR^{61}R^{60C}$, —$NHC(O)NR^{61}R^{60C}$, —$NHS(O)_2R^{61}$, —$NHC(O)R^{61}$, —NHC(O)—$OR^{61}$, —$NHOR^{61}$, —$OCF_3$, —$OCHF_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

$R^{60A}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —$COR^{61}$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

$R^{60A}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. $R^{60A}$ may independently be hydrogen or unsubstituted $C_1$-$C_5$ alkyl. $R^{60A}$ may independently be hydrogen. $R^{60A}$ may independently be methyl or unsubstituted ethyl. $R^{60A}$ may independently be methyl.

$R^{61}$ is independently hydrogen, halogen, —$N_3$, —$CF_3$, —$CCl_3$, —$CBr_3$, —$CI_3$, —CN, —$COR^{61A}$, —$OR^{61A}$, —$NR^{61A}R^{61B}$, —$C(O)OR^{61A}$, —$C(O)NR^{61A}R^{61B}$, —$NO_2$, —$SR^{61A}$, —$S(O)_2R^{61A}$, —$S(O)_2OR^{61A}$, —$S(O)_2NR^{61A}R^{61B}$, —$NHNR^{61A}R^{61B}$, —$ONR^{61A}R^{61B}$, —NHC(O)$NHNR^{61A}R^{61B}$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{61}$ is independently hydrogen, halogen, —$N_3$, —$CF_3$, —$CCl_3$, —$CBr_3$, —$CI_3$, —CN, —$COR^{61A}$, —$OR^{61A}$, —$NR^{61A}R^{61B}$, —$C(O)OR^{61A}$, —$C(O)NR^{61A}R^{61B}$, —$NO_2$, —$SR^{61A}$, —$S(O)_2H$, —$S(O)_2OH$, —$S(O)_2NH_2$, —$NHNH_2$, —$ONH_2$, —NHC(O)$NHNR^{61A}R^{61B}$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{61}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{62}$ is independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

$R^{62}$ may independently be oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{63}$ is independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl.

$R^{61A}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, $R^{61C}$-substituted or unsubstituted heteroalkyl, $R^{61C}$-substituted or unsubstituted cycloalkyl, $R^{61C}$-substituted or unsubstituted heterocycloalkyl, $R^{61C}$-substituted or unsubstituted aryl, or $R^{61C}$-substituted or unsubstituted heteroaryl. $R^{61A}$ may independently be hydrogen or unsubstituted $C_1$-$C_5$ alkyl. $R^{61A}$ may independently be hydrogen. $R^{61A}$ may independently be methyl or unsubstituted ethyl. $R^{61A}$ may independently be methyl.

$R^{61C}$ is independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{61D}$-substituted or unsubstituted alkyl, $R^{61D}$-substituted or unsubstituted heteroalkyl, $R^{61D}$-substituted or unsubstituted cycloalkyl, $R^{61D}$-substituted or unsubstituted heterocycloalkyl, $R^{61D}$-substituted or unsubstituted aryl, or $R^{61D}$-substituted or unsubstituted heteroaryl.

$R^{61B}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{61E}$-substituted or unsubstituted alkyl, $R^{61E}$-substituted or unsubstituted heteroalkyl, $R^{61E}$-substituted or unsubstituted cycloalkyl, $R^{61E}$-substituted or unsubstituted heterocycloalkyl, $R^{61E}$-substituted or unsubstituted aryl, or $R^{61E}$-substituted or unsubstituted heteroaryl. $R^{61B}$ may independently be hydrogen or unsubstituted $C_1$-$C_5$ alkyl. $R^{61B}$ may independently be hydrogen. $R^{61B}$ may independently be methyl or unsubstituted ethyl. $R^{61B}$ may independently be methyl.

$R^{61E}$ is independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{61F}$-substituted or unsubstituted alkyl, $R^{61F}$-substituted or unsubstituted heteroalkyl, $R^{61F}$-substituted or unsubstituted cycloalkyl, $R^{61F}$-substituted or unsubstituted heterocycloalkyl, $R^{61F}$-substituted or unsubstituted aryl, or $R^{61F}$-substituted or unsubstituted heteroaryl.

$R^{60B}$ is independently hydrogen, oxo, halogen, —$N_3$, —$CF_3$, —$CCl_3$, —$CBr_3$, —$CI_3$, —CN, —$OR^{65}$, —$NR^{65}R^{60D}$, $COOR^{65}$, $CONR^{65}R^{60D}$, —$COR^{65}$, —$NO_2$, —SH, —$S(O)_2R^{65}$, —$S(O)_3R^{65}$, —$S(O)_4R^{65}$, —$S(O)_2NR^{65}R^{60D}$, —$NHNR^{65}R^{60D}$, —$ONR^{65}R^{60D}$, —$NHC(O)NHNR^{65}R^{60D}$, —$NHC(O)NR^{65}R^{60D}$, —NHS$(O)_2R^{65}$, —$NHC(O)R^{65}$, —$NHC(O)$—$OR^{65}$, —$NHOR^{65}$, —$OCF_3$, —$OCHF_2$, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl. $R^{60B}$ may independently be hydrogen or unsubstituted $C_1$-$C_5$ alkyl. $R^{60B}$ may independently be hydrogen. $R^{60B}$ may independently be methyl or unsubstituted ethyl. $R^{60B}$ may independently be methyl.

$R^{60B}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —$COR^{65}$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl. $R^{60B}$ may independently be hydrogen or unsubstituted $C_1$-$C_5$ alkyl. $R^{60B}$ may independently be hydrogen. $R^{60B}$ may independently be methyl or unsubstituted ethyl. $R^{60B}$ may independently be methyl.

$R^{60B}$ may independently be hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{65}$ is independently hydrogen, halogen, oxo, —$N_3$, —$CF_3$, —$CCl_3$, —$CBr_3$, —$CI_3$, —CN, —$COR^{65A}$, —$OR^{65A}$, —$NR^{65A}R^{65B}$, —$C(O)OR^{65A}$, $C(O)NR^{65A}R^{65B}$, —$NO_2$, —$SR^{65A}$, —$S(O)_2H$, —$S(O)_2OH$, —$S(O)_2NH_2$, —$NHNH_2$, —$ONH_2$, —$NHC(O)NHNR^{65A}R^{65B}$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl.

$R^{65A}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{65C}$-substituted or unsubstituted heteroalkyl, $R^{65C}$-substituted or unsubstituted cycloalkyl, $R^{65C}$-substituted or unsubstituted heterocycloalkyl, $R^{65C}$-substituted or unsubstituted aryl, or $R^{65C}$-substituted or unsubstituted heteroaryl. $R^{65A}$ may independently be hydrogen or unsubstituted $C_1$-$C_5$ alkyl. $R^{65A}$ may independently be hydrogen. $R^{65A}$ may independently be methyl or unsubstituted ethyl. $R^{65A}$ may independently be methyl.

$R^{65C}$ is independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{65D}$-substituted or unsubstituted alkyl, $R^{65D}$-substituted or unsubstituted heteroalkyl, $R^{65D}$-substituted or unsubstituted cycloalkyl, $R^{65D}$-substituted or unsubstituted heterocycloalkyl, $R^{65D}$-substituted or unsubstituted aryl, or $R^{65D}$-substituted or unsubstituted heteroaryl.

$R^{65B}$ is independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, $R^{65E}$-substituted or unsubstituted alkyl, $R^{65E}$-substituted or unsubstituted heteroalkyl, $R^{65E}$-substituted or unsubstituted cycloalkyl, $R^{65E}$-substituted or unsubstituted heterocycloalkyl, $R^{65E}$-substituted or unsubstituted aryl, or $R^{65E}$-substituted or unsubstituted heteroaryl. $R^{65B}$ may independently be hydrogen or unsubstituted $C_1$-$C_5$ alkyl. $R^{65B}$ may independently be hydrogen. $R^{65B}$ may independently be methyl or unsubstituted ethyl. $R^{65B}$ may independently be methyl.

$R^{65E}$ is independently oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —OCF$_3$, —OCHF$_2$, R$^{65F}$-substituted or unsubstituted alkyl, R$^{65F}$-substituted or unsubstituted heteroalkyl, R$^{65F}$-substituted or unsubstituted cycloalkyl, R$^{65F}$-substituted or unsubstituted heterocycloalkyl, R$^{65F}$-substituted or unsubstituted aryl, or R$^{65F}$-substituted or unsubstituted heteroaryl.

R$^{66}$ is independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{67}$-substituted or unsubstituted alkyl, R$^{67}$-substituted or unsubstituted heteroalkyl, R$^{67}$-substituted or unsubstituted cycloalkyl, R$^{67}$-substituted or unsubstituted heterocycloalkyl, R$^{67}$-substituted or unsubstituted aryl, or R$^{67}$-substituted or unsubstituted heteroaryl.

R$^{60C}$, R$^{60D}$, R$^{61D}$, R$^{61F}$, R$^{65D}$, R$^{65F}$, R$^{64}$, and R$^{67}$ are independently oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

R$^{64}$ may independently be hydrogen, oxo, halogen, —N$_3$, —CF$_3$, —CCl$_3$, —CBr$_3$, —CI$_3$, —CN, —OR$^{61}$, —NR$^{61}$R$^{60C}$, —COOR$^{61}$, —CONR$^{61}$R$^{60C}$, —COR$^{61}$, —NO$_2$, —SR$^{61}$, —S(O)$_2$R$^{61}$, —S(O)$_3$R$^{61}$, —S(O)$_4$R$^{61}$, —S(O)$_2$NR$^{61}$R$^{60C}$, —NHNR$^{61}$R$^{60C}$, —ONR$^{61}$R$^{60C}$, —NHC(O)NHNR$^{61}$R$^{60C}$, —NHC(O)NR$^{61}$R$^{60C}$, —NHS(O)$_2$R$^{61}$, —NHC(O)R$^{61}$, —NHC(O)—OR$^{61}$, —NHOR$^{61}$, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

R$^{64}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

R$^{6B}$ may independently be hydrogen, oxo, halogen, —N$_3$, —CF$_3$, —CCl$_3$, —CBr$_3$, —CI$_3$, —CN, —OR$^{65}$, —NR$^{65}$R$^{60D}$, COOR$^{65}$, CONR$^{65}$R$^{60D}$, —COR$^{65}$, —NO$_2$, —SH, —S(O)$_2$R$^{65}$, —S(O)$_3$R$^{65}$, —S(O)$_4$R$^{65}$, —S(O)$_2$NR$^{65}$R$^{60D}$, —NHNR$^{65}$R$^{60D}$, —ONR$^{65}$R$^{60D}$, —NHC(O)NHNR$^{65}$R$^{60D}$, —NHC(O)NR$^{65}$R$^{60D}$, —NHS(O)$_2$R$^{65}$, —NHC(O)R$^{65}$, —NHC(O)—OR$^{65}$, —NHOR$^{65}$, —OCF$_3$, —OCHF$_2$, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl.

R$^{6B}$ may independently be oxo, halogen, —CF$_3$, —CN, —OH, —NH$_2$, —COOH, —CONH$_2$, —NO$_2$, —SH, —S(O)$_2$Cl, —S(O)$_3$H, —COH, —COCH$_3$, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{65}$-substituted or unsubstituted alkyl, R$^{65}$-substituted or unsubstituted heteroalkyl, R$^{65}$-substituted or unsubstituted cycloalkyl, R$^{65}$-substituted or unsubstituted heterocycloalkyl, R$^{65}$-substituted or unsubstituted aryl, or R$^{65}$-substituted or unsubstituted heteroaryl.

In embodiments, the compound of Formula (Ia) is:

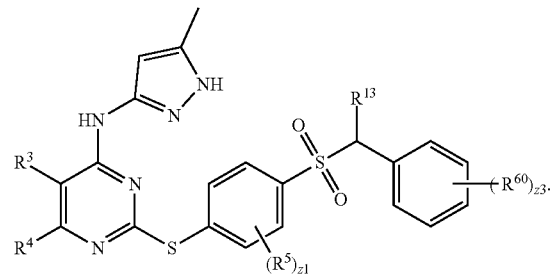

Wherein R$^3$, R$^4$, R$^5$, z1, R$^{13}$, and R$^{60}$ are as described herein. The symbol z3 is an integer of 0, 1, 2, 3, 4, or 5. The symbol z3 may be 1, 2, or 3. The symbol z3 may be 1. The symbol z3 may be 2. The symbol z3 may be 3.

R$^{60}$ may independently be hydrogen, halogen, —N$_3$, —CF$_3$, —CCl$_3$, —CBr$_3$, —CI$_3$, —CN, —COR$^{61}$, —OR$^{60A}$, —NR$^{60A}$R$^{60B}$, —C(O)OR$^{60A}$, —C(O)NR$^{60A}$R$^{60B}$, —NO$_2$, —SR$^{60A}$, —S(O)$_2$H, —S(O)$_2$OH, —S(O)$_2$NH$_2$, —NHNH$_2$, —ONH$_2$, —NHC(O)NHNR$^{60A}$R$^{60B}$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl. R$^{60A}$ may independently be hydrogen, halogen, —NO$_2$, —CF$_3$, —CN, —COR$^{61}$, R$^{61}$-substituted or unsubstituted alkyl, R$^{61}$-substituted or unsubstituted heteroalkyl, or R$^{61}$-substituted or unsubstituted aryl. R$^{61}$ may independently be hydrogen, halogen, —N$_3$, —CF$_3$, —CCl$_3$, —CBr$_3$, —CI$_3$, —CN, —COR$^{61A}$, —OR$^{61A}$, —NR$^{61A}$R$^{61B}$, —C(O)OR$^{61A}$, —C(O)NR$^{61A}$R$^{61B}$, —NO$_2$, —SR$^{61A}$, —S(O)$_2$H, —S(O)$_2$OH, —S(O)$_2$NH$_2$, —NHNH$_2$, —ONH$_2$, —NHC(O)NHNR$^{61A}$R$^{61B}$, R$^{62}$-substituted or unsubstituted alkyl, R$^{62}$-substituted or unsubstituted heteroalkyl, R$^{62}$-substituted or unsubstituted cycloalkyl, R$^{62}$-substituted or unsubstituted heterocycloalkyl, R$^{62}$-substituted or unsubstituted aryl, or R$^{62}$-substituted or unsubstituted heteroaryl. R$^{62}$ may independently be hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. R$^{60B}$ may independently be hydrogen halogen, or unsubstituted alkyl.

In embodiments, the compound of Formula (Ia) is:

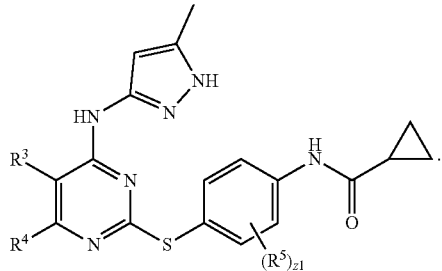

In embodiments, the compound of Formula (Ia) is:

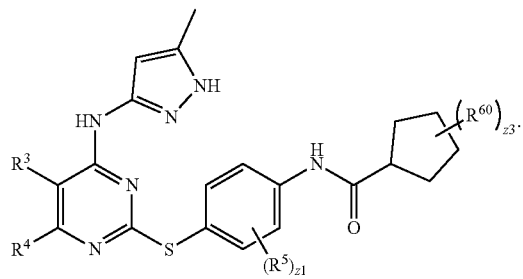

Wherein $R^3$, $R^4$, $R^5$, z1, z3, and $R^{60}$ are as described herein. $R^{60}$ are independently hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —C(O)$OR^{60A}$, —C(O)$NR^{60A}R^{60B}$, —$NO_2$, —$SR^{60A}$, —S(O)$_2$H, —S(O)$_2$OH, —S(O)$_2NH_2$, —$NHNH_2$, —$ONH_2$, —NHC(O)$NHNR^{60A}R^{60B}$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. $R^{60A}$ may independently be hydrogen, halogen, —$NO_2$, —$CF_3$, —CN, —$COR^{61}$, $R^{61}$-substituted or unsubstituted alkyl, $R^{61}$-substituted or unsubstituted heteroalkyl, or $R^{61}$-substituted or unsubstituted aryl; $R^{61}$ is independently hydrogen, halogen, or unsubstituted alkyl. $R^{60B}$ may independently be hydrogen halogen, or unsubstituted alkyl.

In embodiments, the PLK4 inhibitor is the compound of Formula: (Ia2) or a pharmaceutically acceptable salt thereof:

(Ia2)

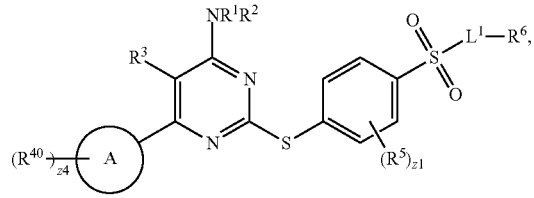

where $L^1$, z1, $R^1$, $R^2$, $R^5$, $R^6$, and $R^{40}$ are as described herein. The symbol z4 is an integer of 0, 1, 2, 3, 4, 5, 6, or 7. Ring A is cycloalkyl or heterocycloalkyl. In embodiments, the compound of Formula (Ia2) is:

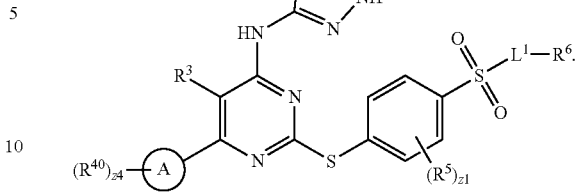

In embodiments, the PLK4 inhibitor is the compound of Formula (Ia3) or a pharmaceutically acceptable salt thereof:

(Ia3)

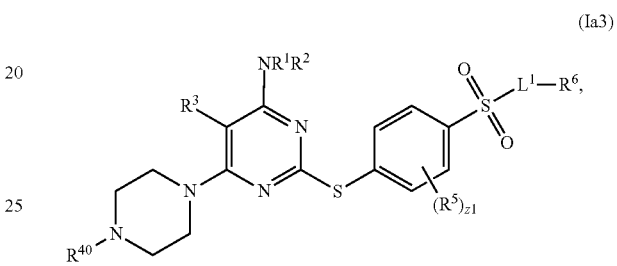

where $L^1$, z1, $R^1$, $R^2$, $R^5$, $R^6$, and $R^{40}$ are as described herein. In embodiments, the compound of Formula (Ia3) is:

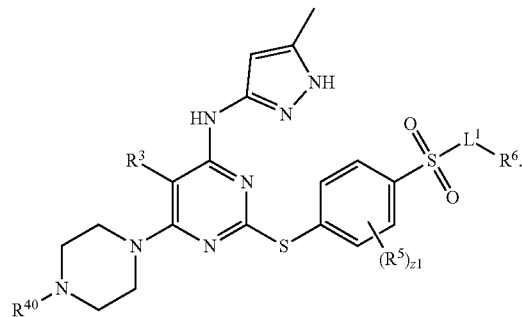

In embodiments, the PLK4 inhibitor is the compound of Formula (Ia4) or a pharmaceutically acceptable salt thereof:

(Ia4)

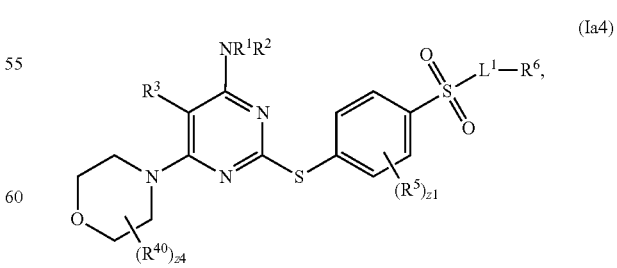

where $L^1$, z1, $R^1$, $R^2$, $R^5$, $R^6$, and $R^{40}$ are as described herein and the symbol z4 is an integer of 0, 1, 2, 3, or 4. In embodiments, the compound of Formula (Ia4) is:

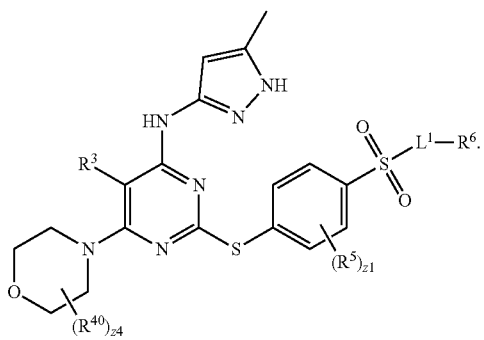

In embodiments, the PLK4 inhibitor is the compound of Formula (Ia5) or a pharmaceutically acceptable salt thereof:

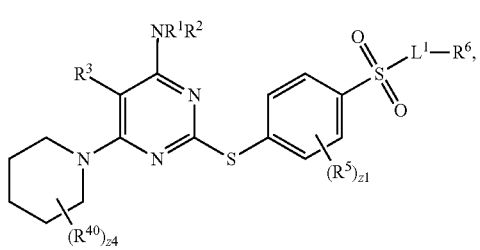

(Ia5)

where $L^1$, z1, z4, $R^1$, $R^2$, $R^5$, $R^6$, and $R^{40}$ are as described herein. In embodiments, the compound of Formula (Ia5) is:

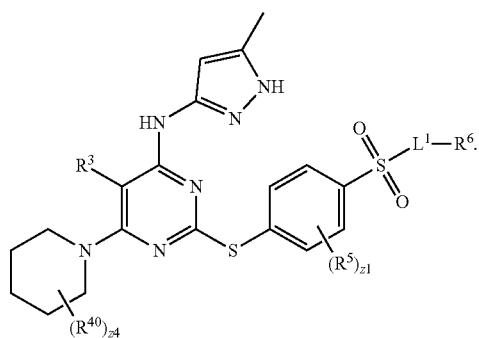

In embodiments, the PLK4 inhibitor is the compound of Formula (Ia6) or a pharmaceutically acceptable salt thereof:

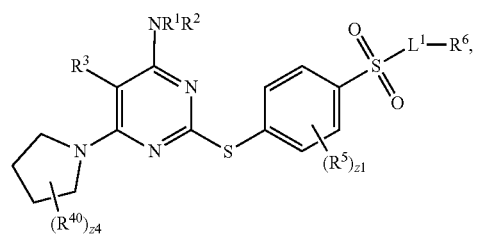

(Ia6)

where $L^1$, z1, $R^1$, $R^2$, $R^5$, $R^6$, and $R^{40}$ are as described herein and the symbol z4 is an integer of 0, 1, 2, 3, or 4. In embodiments, the compound of Formula (Ia6) is:

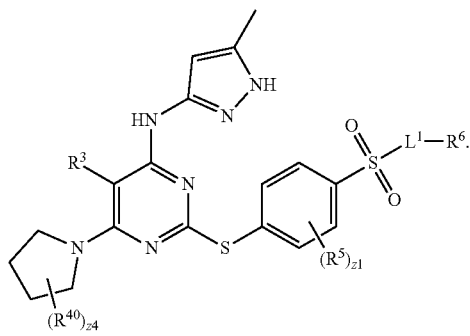

In embodiments, the PLK4 inhibitor is the compound of Formula (Ib2) or a pharmaceutically acceptable salt thereof:

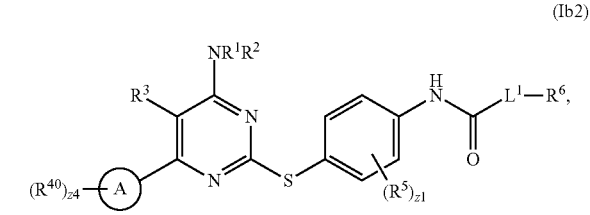

(Ib2)

where $L^1$, z1, z4, $R^1$, $R^2$, $R^5$, $R^6$, and $R^{40}$ are as described herein and the compound is not tozasertib. Ring A is cycloalkyl or heterocycloalkyl. In embodiments, the compound of Formula (Ib2) is:

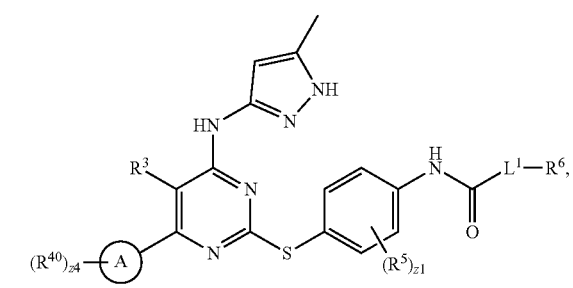

In embodiments, the compound of Formula (Ib2) is not tozasertib.

In embodiments, the PLK4 inhibitor is the compound of Formula (Ib3) or a pharmaceutically acceptable salt thereof:

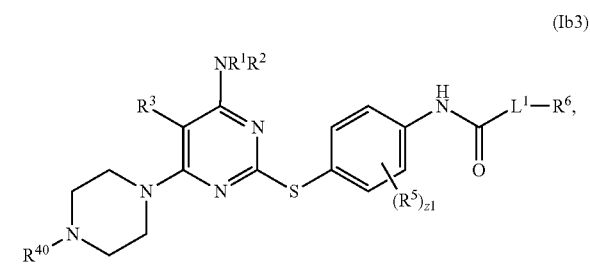

(Ib3)

where $L^1$, z1, $R^1$, $R^2$, $R^5$, $R^6$, and $R^{40}$ are as described herein. In embodiments, the compound of Formula (Ib3) is:

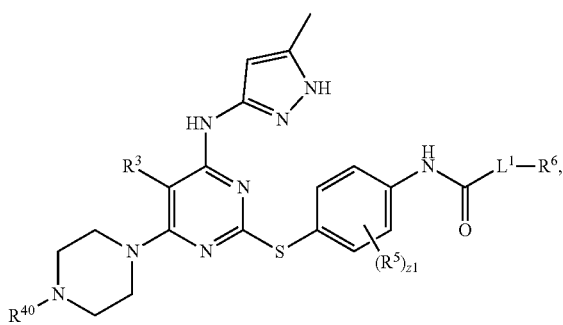

In embodiments, the compound of Formula (Ib3) is not tozasertib.

In embodiments, the PLK4 inhibitor is the compound of Formula (Ib4) or a pharmaceutically acceptable salt thereof:

(Ib4)

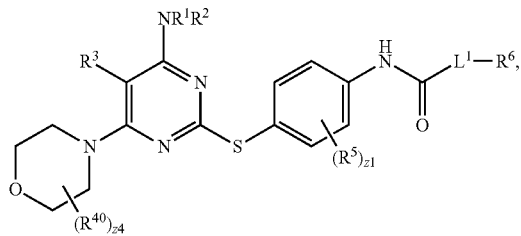

where $L^1$, z1, $R^1$, $R^2$, $R^5$, $R^6$, and $R^{40}$ are as described herein and the symbol z4 is an integer of 0, 1, 2, 3, or 4. In embodiments, the compound of Formula (Ib4) is:

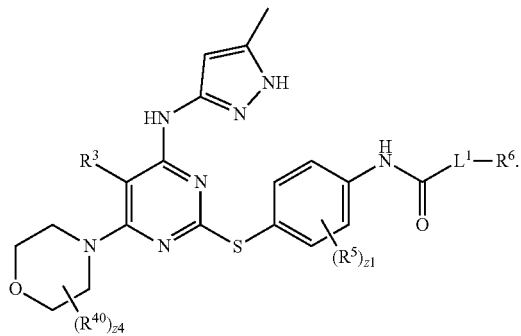

In embodiments, the PLK4 inhibitor is the compound of Formula (Ib5) or a pharmaceutically acceptable salt thereof:

(Ib5)

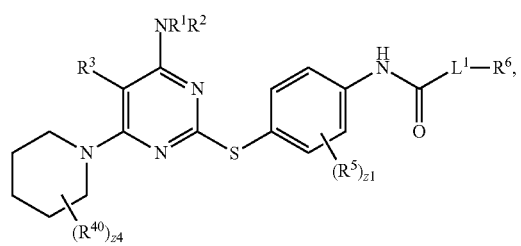

where $L^1$, z1, $R^1$, $R^2$, $R^5$, $R^6$, and $R^{40}$ are as described herein and the symbol z4 is an integer of 0, 1, 2, 3, 4, or 5. In embodiments, the compound of Formula (Ib5) is:

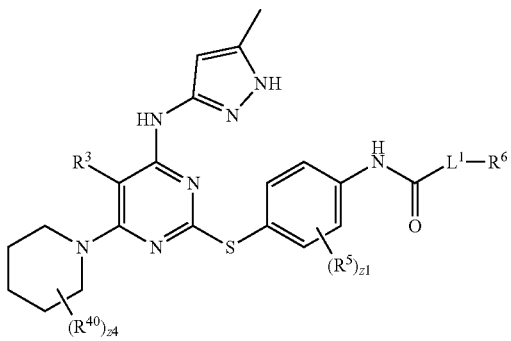

In embodiments, the PLK4 inhibitor is the compound of Formula (Ib6) or a pharmaceutically acceptable salt thereof:

(Ib6)

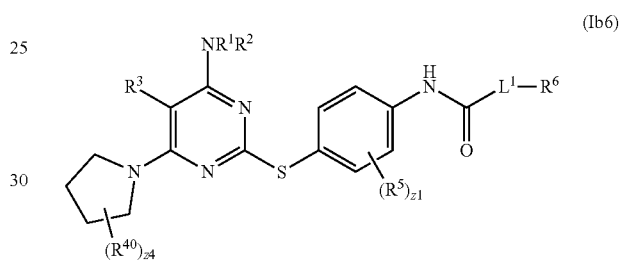

where $L^1$, z1, $R^1$, $R^2$, $R^5$, $R^6$, and $R^{40}$ are as described herein and the symbol z4 is an integer of 0, 1, 2, 3, or 4. In embodiments, the compound of Formula (Ib6) is:

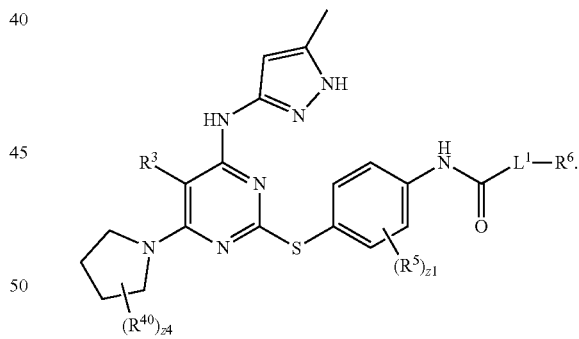

Further to any of Formulae (Ia) or (Ib), or embodiments thereof, $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—. $L^1$ may be a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^1$ may be a bond, substituted or unsubstituted alkylene, or substituted or unsubstituted heteroalkylene. $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, or substituted or unsubstituted heteroalkylene. $L^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, or substituted or unsubstituted heteroalkylene where R$^{13}$ is hydrogen or substituted or unsubstituted alkyl. L$^1$ may be a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, R$^{13}$-substituted or unsubstituted alkylene, or R$^{13}$-substituted or unsubstituted heteroalkylene where R$^{13}$ is hydrogen or substituted or unsubstituted alkyl. R$^{13}$ may be unsubstituted alkyl.

L$^1$ may be a bond or substituted or unsubstituted alkylene. L$^1$ may be a bond or R$^{13}$-substituted or unsubstituted alkylene. L$^1$ may be a bond or R$^{13}$-substituted or unsubstituted alkylene where R$^{13}$ is hydrogen or substituted or unsubstituted alkyl. L$^1$ may be a bond or substituted or unsubstituted C$_1$-C$_5$ alkylene. L$^1$ may be a bond or R$^{13}$-substituted or unsubstituted C$_1$-C$_5$ alkylene. L$^1$ may be a bond or R$^{13}$-substituted or unsubstituted C$_1$-C$_5$ alkylene where R$^{13}$ is hydrogen or substituted or unsubstituted C$_1$-C$_5$ alkyl. L$^1$ may be R$^{13}$-substituted or unsubstituted alkylene where R$^{13}$ is hydrogen, halogen, or substituted or unsubstituted alkyl. In embodiments, L$^1$ may be unsubstituted alkylene. In embodiments, L$^1$ may be unsubstituted methylene. In embodiments, L$^1$ may be R$^{13}$-substituted methylene. In embodiments, L$^1$ may be methylene substituted with one R$^{13}$-substituent. In embodiments, the R$^{13}$-substituent may be halogen. In embodiments, L$^1$ may be methylene substituted with one fluoro substituent. In embodiments, L$^1$ may be methylene independently substituted with two R$^{13}$-substituents. In embodiments, L$^1$ may be methylene independently substituted with halogen substituents. In embodiments, the R$^{13}$-substituent may be alkyl. In embodiments, L$^1$ may be methylene mono substituted with substituted or unsubstituted alkyl. In embodiments, L$^1$ may be methylene disubstituted with substituted or unsubstituted alkyl. In embodiments, the two independent R$^{13}$-substitutents combine to form a substituted or unsubstituted cycloalkyl, or a substituted or unsubstituted heterocycloalkyl. In embodiments, L$^1$ may be methylene singly substituted with halogen or unsubstituted alkyl. In embodiments, L$^1$ may be methylene independently disubstituted with halogen or unsubstituted alkyl. In embodiments, L$^1$ may be methylene singly substituted with halogen or substituted alkyl. In embodiments, L$^1$ may be methylene independently disubstituted with halogen or substituted alkyl.

R$^{13}$ may independently be hydrogen, halogen, oxo, N$_3$, —CF$_3$, —CCl$_3$, —CBr$_3$, —CI$_3$, —CN, —OH, —COH, —NH$_2$, —COOH, —CONH$_2$, —NO$_2$, —SH, —S(O)$_2$C, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, R$^{13A}$-substituted or unsubstituted heteroalkyl, R$^{13A}$-substituted or unsubstituted cycloalkyl, R$^{13A}$-substituted or unsubstituted heterocycloalkyl, R$^{13A}$-substituted or unsubstituted aryl, or R$^{13A}$-substituted or unsubstituted heteroaryl.

R$^{13A}$ is independently halogen, oxo, N$_3$, —CF$_3$, —CCl$_3$, —CBr$_3$, —CI$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, where L$^1$ is a substituted or unsubstituted cycloalkylene or heterocycloalkylene, a single carbon of the cycloalkylene or heterocycloalkylene is connected (bonded) to both the sulfonyl moiety and R$^6$. For example, in some embodiments, L$^1$ is:

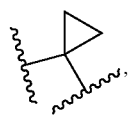

wherein "⌇" denotes the point of attachment to the sulfonyl moiety and R$^6$.

In embodiments, L$^1$ may be substituted or unsubstituted C$_1$-C$_5$ cycloalkylene. In embodiments, L$^1$ may be substituted or unsubstituted cyclopropylene. In embodiments, L$^1$ may be substituted or unsubstituted cyclobutylene. In embodiments, L$^1$ may be substituted or unsubstituted cyclopentylene. In embodiments, L may be unsubstituted cyclopropylene. In embodiments, L$^1$ may be unsubstituted cyclobutylene. In embodiments, L$^1$ may be unsubstituted cyclopentylene. In embodiments, L may be C$_1$-C$_5$ cycloalkylene substituted with halogen, or substituted or unsubstituted alkyl.

In embodiments, the PLK4 inhibitor is the compound of Formula (Ib7) or a pharmaceutically acceptable salt thereof:

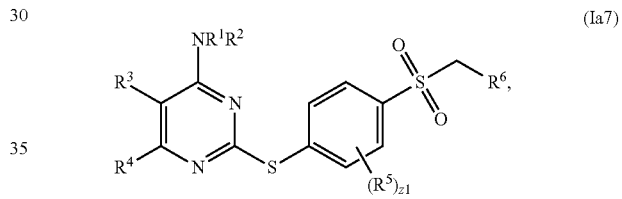

where z1, R$^1$, R$^2$, R$^3$, R$^4$, R$^5$, and R$^6$ are as described herein. In embodiments, the compound of Formula (Ia7) is:

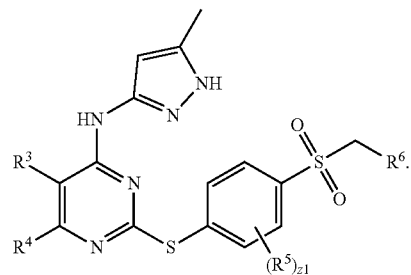

In embodiments, the PLK4 inhibitor is the compound of Formula (Ib8) or a pharmaceutically acceptable salt thereof:

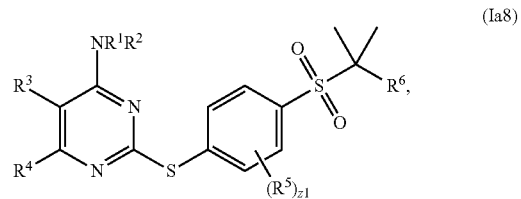

where z1, $R^1$, $R^2$, $R^3$, $R^4$, $R^5$, and $R^6$ are as described herein.
In embodiments, the compound of Formula (Ia8) is:

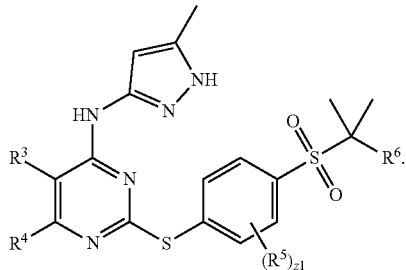

In embodiments, the PLK4 inhibitor is the compound of Formula (Ia9a) or a pharmaceutically acceptable salt thereof.

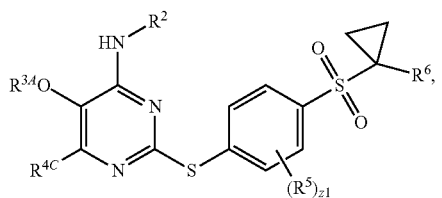

wherein $R^{3A}$ is substituted or unsubstituted alkyl, and $R^{4C}$ is substituted or unsubstituted heterocycloalkyl.

In embodiments, $R^2$ is substituted or unsubstituted heteroaryl. In embodiments, $R^2$ is unsubstituted heteroaryl. In embodiments, $R^2$ is substituted heteroaryl. In embodiments, $R^2$ is $R^{2C}$-substituted heteroaryl, wherein $R^{2C}$ is as defined herein. $R^2$ may be $R^{2C}$-substituted or unsubstituted 5 to 20 membered heteroaryl. $R^2$ may be $R^{2C}$-substituted 5 to 20 membered heteroaryl. $R^2$ may be $R^{2C}$-substituted or unsubstituted 5 to 8 membered heteroaryl. $R^2$ may be $R^{2C}$-substituted 5 to 8 membered heteroaryl. $R^2$ may be $R^{2C}$-substituted or unsubstituted 5 or 6 membered heteroaryl. $R^2$ may be $R^{2C}$-substituted 5 or 6 membered heteroaryl.

In embodiments, $R^2$ is substituted or unsubstituted pyrazolyl. In embodiments, $R^2$ is unsubstituted pyrazolyl. In embodiments, $R^2$ is substituted pyrazolyl. In embodiments, $R^2$ is pyrazolyl substituted with substituted or unsubstituted alkyl. In embodiments, $R^2$ is pyrazolyl substituted with unsubstituted alkyl. In embodiments, $R^2$ is pyrazolyl substituted with unsubstituted lower alkyl. In embodiments, $R^2$ is pyrazolyl substituted methyl, ethyl or propyl. In embodiments, $R^2$ is methyl substituted pyrazolyl.

In embodiments, $R^2$ is $R^{2C}$-substituted pyrazolyl. In embodiments, $R^2$ is $R^{2C}$-substituted pyrazolyl, wherein $R^{2C}$ is substituted or unsubstituted alkyl. In embodiments, $R^2$ is $R^{2C}$-substituted pyrazolyl, wherein $R^{2C}$ is unsubstituted alkyl. In embodiments, $R^2$ is $R^{2C}$-substituted pyrazolyl, wherein $R^{2C}$ is unsubstituted lower alkyl. In embodiments, $R^2$ is $R^{2C}$-substituted pyrazolyl, wherein $R^{2C}$ is unsubstituted methyl, ethyl or propyl. In embodiments, $R^2$ is $R^{2C}$-substituted pyrazolyl, wherein $R^{2C}$ is unsubstituted methyl.

In embodiments, the PLK4 inhibitor is the compound of Formula (Ia9b) or a pharmaceutically acceptable salt thereof:

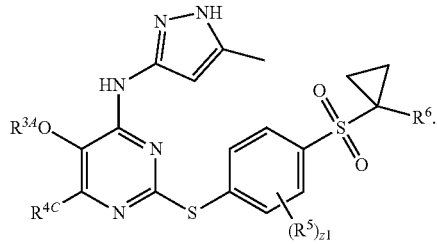

Further to any of Formulae (Ia9a)-(Ia9b), in embodiments $R^{3A}$ is substituted or unsubstituted alkyl. In embodiments $R^{3A}$ is unsubstituted alkyl. In embodiments, $R^{3A}$ is unsubstituted lower alkyl. In embodiments, $R^{3A}$ is methyl, ethyl or propyl. In embodiments, $R^{3A}$ is methyl. In embodiments, $R^{3A}$ is $R^{3C}$-substituted or unsubstituted alkyl, wherein $R^{3C}$ is as defined herein.

In embodiments, the PLK4 inhibitor is the compound of Formula (Ia9c) or a pharmaceutically acceptable salt thereof:

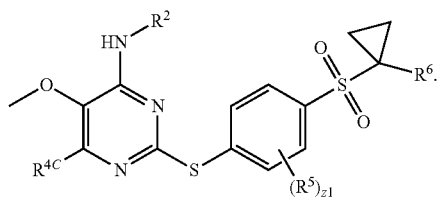

In embodiments, $R^{4C}$ is substituted or unsubstituted heterocycloalkyl. In embodiments, $R^{4C}$ is unsubstituted heterocycloalkyl. In embodiments, $R^{4C}$ is substituted heterocycloalkyl. In embodiments, $R^{3C}$ is $R^{40}$-substituted heterocycloalkyl, wherein $R^{40}$ is as defined herein.

In embodiments, the PLK4 inhibitor is the compound of Formula (Ia9d) or a pharmaceutically acceptable salt thereof:

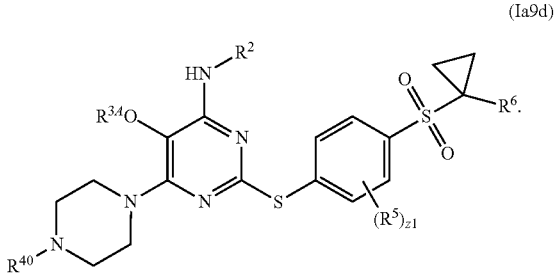

In formula (Ia9d), $R^{40}$ may be substituted or unsubstituted alkyl or substituted or unsubstituted heteroalkyl (e.g. —$CH_2C(O)N(CH_3)_2$).

Further to any of Formulae (Ia9a)-(Ia9d), in embodiments $R^5$ and z1 are as defined herein. In embodiments, $R^5$ is halogen, and z1 is 1. In embodiments, $R^5$ is fluoro.

Further to any of Formulae (Ia9a)-(Ia9d), in embodiments $R^6$ is substituted or unsubstituted aryl. In embodiments, $R^6$ is unsubstituted aryl. $R^6$ is aryl independently substituted one or more times with halogen or —$NO_2$.

In embodiments, the PLK4 inhibitor is the compound of Formula (Ia9f) or a pharmaceutically acceptable salt thereof:

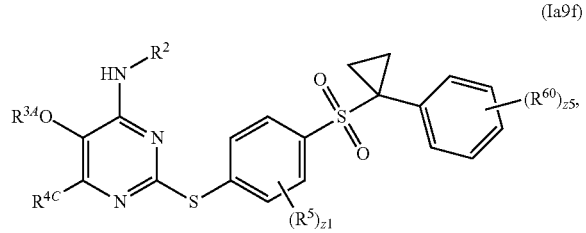

(Ia9f)

wherein $R^{60}$ and z5 are as defined herein. In embodiments, $R^{60}$ is halogen or —$NO_2$, and z5 is 1 or 2. In embodiments, z5 is 1. In embodiments, z5 is 2.

In embodiments, the PLK4 inhibitor is the compound of Formula (Ib7) or a pharmaceutically acceptable salt thereof:

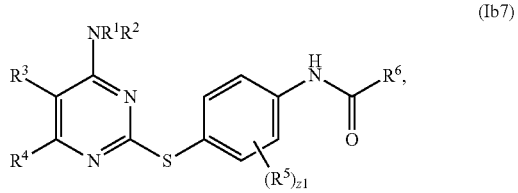

(Ib7)

wherein z1, $R^1$, $R^2$, $R^3$, $R^4$, $R^5$, and $R^6$ are as described herein. In embodiments, the compound of Formula (Ib7) is:

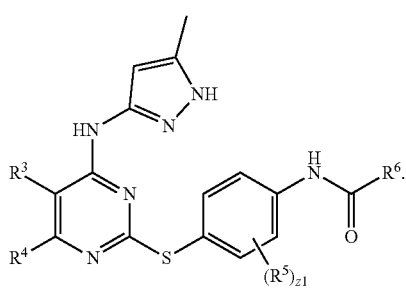

In embodiments, the compound of Formula (Ib7) is not tozasertib.

In embodiments, the PLK4 inhibitor is the compound of Formula (IC) or a pharmaceutically acceptable salt thereof:

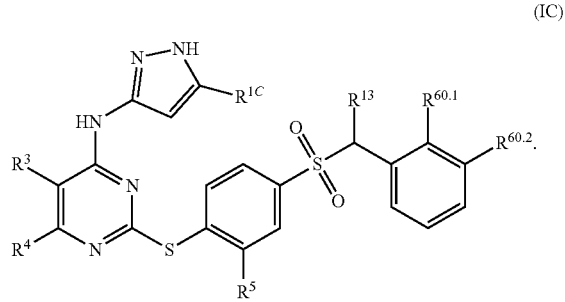

(IC)

In Formula (IC), $R^3$, $R^4$, $R^{1C}$, $R^5$ and $R^{13}$ are as defined herein, including all embodiments thereof. $R^{60.1}$ and $R^{60.2}$ are independently as defined for $R^{60}$. In embodiments, $R^{60.1}$ and $R^{60.2}$ are different. In embodiments, $R^{13}$ is hydrogen. In embodiments, $R^3$ is methoxy (—O—$CH_3$). In embodiments, $R^5$ is halogen (e.g. F). In embodiments, $R^{1C}$ is substituted or unsubstituted alkyl (e.g. methyl). In embodiments, $R^{60.1}$ is halogen (e.g. F). In embodiments, $R^{60.2}$ is nitro (—$NO_2$). In embodiments, $R^4$ is substituted or unsubstituted heterocycloalkyl (e.g. unsubstituted morphilino or unsubstituted piperidinyl). In embodiments, $R^4$ is substituted or unsubstituted heterocycloalkyl wherein the point of attachment to the remainder of the molecule is a ring nitrogen.

In embodiments, the PLK4 inhibitor is the compound of Formula (II) or a pharmaceutically acceptable salt thereof:

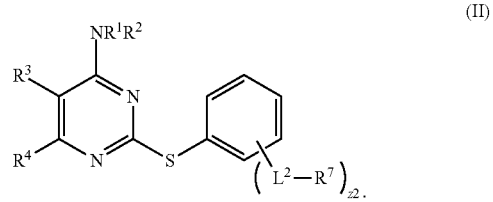

(II)

In a first aspect of formula (II), $L^2$ is independently a bond, —C(O)—, —C(O)O—, —O—, —S—, —$NR^{14}$—, —C(O)$NR^{14}$—, —$NR^{14}$C(O)—, —S(O)—, —S(O)$_2$—, —S(O)$NR^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is independently hydrogen, oxo, halogen, —$N_3$, —$CF_3$, —$CCl_3$, —$CBr_3$, —$CI_3$, —CN, —$COR^{7A}$, —$OR^{7A}$, —$NR^{7A}R^{7B}$, —C(O)$OR^{7A}$, —C(O)$NR^{7A}R^{7B}$, —$NO_2$, —$SR^{7A}$, —S(O)$_{n7}R^{7A}$, —S(O)$_7OR^{7A}$, —S(O)$_{n7}NR^{7A}R^{7B}$, —$NHNR^{7A}R^{7B}$, —$ONR^{7A}R^{7B}$, —NHC(O)$NHNR^{7A}R^{7B}$, -$L^1$-$R^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol n7 is independently 1 or 2. The symbol z2 is 1, 2, 3, 4, or 5. $R^{7A}$, $R^{7B}$, $R^{13}$, and $R^{14}$ are independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The compound is not tozasertib.

$L^1$, $R^1$, $R^2$, and $R^6$ of the compound of formula (II) are as described hereinabove for compounds having formula (I), including all embodiments thereof.

$R^3$ of the compound of formula (II) is as described hereinabove for compounds of formula (I) with the proviso that $R^3$ is not hydrogen. Thus, $R^3$ may be halogen, —$N_3$, —$CF_3$, —$CCl_3$, —$CBr_3$, —$CI_3$, —CN, —$COR^{3A}$, —$OR^{3A}$, —$NR^{3A}R^{3B}$, —C(O)$OR^{3A}$, —C(O)$NR^{3A}R^{3B}$, —$NO_2$, —$SR^{3A}$, —S(O)$_{n3}R^{3A}$, —S(O)$_{n3}OR^{3A}$, —S(O)$_{n3}NR^{3A}R^{3B}$, —$NHNR^{3A}R^{3B}$, —$ONR^{3A}R^{3B}$, —NHC(O)$NHNR^{3A}R^{3B}$, or substituted or unsubstituted alkyl, where $R^{3A}$, $R^{3B}$, and $R^{3C}$ are as described herein. $R^3$ may be halogen, —$N_3$, —$CF_3$, —$CCl_3$, —$CBr_3$, —$CI_3$, —CN, —$COR^{3A}$, —$OR^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NR$^{3A}$R$^{3B}$, —ONR$^{3A}$R$^{3B}$, —NHC(O)NHNR$^{3A}$R$^{3B}$, or substituted or unsubstituted alkyl, where R$^{3A}$, R$^{3B}$, and R$^{3C}$ are independently hydrogen, oxo, halogen, —CF$_3$, —OH, —NH$_2$, —COOH, —CONH$_2$, substituted or unsubstituted alkyl, or substituted or unsubstituted aryl. R$^3$ may be —OCH$_3$. R$^3$ may be —OCH$_3$CH$_3$.

R$^3$ may be halogen, —OR$^{3A}$, or substituted or unsubstituted alkyl. R$^3$ may be halogen, —OR$^{3A}$, or substituted or unsubstituted alkyl where f substituted or unsubstituted alkyl. R$^3$ may be —OR$^{3A}$. R$^3$ may be —OR$^{3A}$ where R$^{3A}$ is substituted or unsubstituted alkyl R$^4$ of the compound of formula (II) is as described hereinabove for compounds of formula (I) with the proviso that R$^4$ is not hydrogen or substituted or unsubstituted alkyl.

The compound of formula (II) may be compound having one of the formulae Ia, Ia1, Ia2, Ia3, Ia4, Ia5, Ia6, Ia7, Ia8, Ib, Ib1, Ib2, Ib3, Ib4, Ib5, Ib6, or Ib7.

R$^7$ may independently be hydrogen, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, or —NHC(O)NHNR$^{7A}$R$^{7B}$. R$^7$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^7$ may be hydrogen or halogen. R$^7$ may be hydrogen or —Cl, —I, or —Br. R$^7$ may be hydrogen or —Cl or —F. R$^7$ may be hydrogen. R$^7$ may be —Cl. R$^7$ may be —I. R$^7$ may be —I. R$^7$ may be —F. The symbol z1 may be 1, 2, or 3. The symbol z1 may be 1 or 2. R$^7$ may be hydrogen or —Cl or —F where the symbol z1 is 1 or 2.

R$^7$ may be substituted or unsubstituted alkyl. R$^7$ may be substituted alkyl. R$^7$ may be unsubstituted alkyl. R$^7$ may be substituted or unsubstituted C$_1$-C$_{20}$ alkyl. R$^7$ may be substituted C$_1$-C$_{20}$ alkyl. R$^7$ may be unsubstituted C$_1$-C$_{20}$ alkyl. R$^7$ may be substituted or unsubstituted C$_1$-C$_{10}$ alkyl. R$^7$ may be substituted C$_1$-C$_{10}$ alkyl. R$^7$ may be unsubstituted C$_1$-C$_{10}$ alkyl. R$^7$ may be substituted or unsubstituted C$_1$-C$_5$ alkyl. R$^7$ may be unsubstituted C$_1$-C$_5$ alkyl. R$^7$ may be substituted C$_1$-C$_5$ alkyl. R$^7$ may be methyl, substituted or unsubstituted ethyl, or substituted or unsubstituted propyl. R$^7$ may be methyl. R$^7$ may be ethyl.

R$^7$ may be R$^{7C}$-substituted or unsubstituted alkyl. R$^7$ may be R$^{7C}$-substituted alkyl. R$^7$ may be R$^{7C}$-substituted or unsubstituted C$_1$-C$_{20}$ alkyl. R$^7$ may be R$^{7C}$-substituted C$_1$-C$_{20}$ alkyl. R$^7$ may be R$^{7C}$-substituted or unsubstituted C$_1$-C$_{10}$ alkyl. R$^7$ may be R$^{7C}$-substituted C$_1$-C$_{10}$ alkyl. R$^7$ may be R$^{7C}$-substituted or unsubstituted C$_1$-C$_5$ alkyl. R$^7$ may be R$^{7C}$-substituted C$_1$-C$_5$ alkyl. R$^7$ may be methyl, R$^{7C}$-substituted or unsubstituted ethyl, or R$^{7C}$-substituted or unsubstituted propyl.

R$^7$ may be substituted or unsubstituted heteroalkyl. R$^7$ may be substituted heteroalkyl. R$^7$ may be unsubstituted heteroalkyl. R$^7$ may be substituted or unsubstituted 2 to 20 membered heteroalkyl. R$^7$ may be substituted 2 to 20 membered heteroalkyl. R$^7$ may be unsubstituted 2 to 10 membered heteroalkyl. R$^7$ may be substituted 2 to 10 membered heteroalkyl. R$^7$ may be substituted or unsubstituted 2 to 6 membered heteroalkyl. R$^7$ may be substituted 2 to 6 membered heteroalkyl.

R$^7$ may be R$^{7C}$-substituted or unsubstituted heteroalkyl. R$^7$ may be R$^{7C}$-substituted heteroalkyl. R$^7$ may be R$^{7C}$-substituted or unsubstituted 2 to 20 membered heteroalkyl. R$^7$ may be R$^{7C}$-substituted 2 to 20 membered heteroalkyl. R$^7$ may be R$^{7C}$-substituted or unsubstituted 2 to 10 membered heteroalkyl. R$^7$ may be R$^{7C}$-substituted 2 to 10 membered heteroalkyl. R$^7$ may be R$^{7C}$-substituted or unsubstituted 2 to 6 membered heteroalkyl. R$^7$ may be R$^{7C}$-substituted 2 to 6 membered heteroalkyl.

R$^7$ may be substituted or unsubstituted cycloalkyl. R$^7$ may be substituted cycloalkyl. R$^7$ may be unsubstituted cycloalkyl. R$^7$ may be substituted or unsubstituted 3 to 20 membered cycloalkyl. R$^7$ may be substituted 3 to 20 membered cycloalkyl. R$^7$ may be substituted or unsubstituted 3 to 10 membered cycloalkyl. R$^7$ may be substituted 3 to 10 membered cycloalkyl. R$^7$ may be substituted or unsubstituted 3 to 6 membered cycloalkyl. R$^7$ may be substituted 3 to 6 membered cycloalkyl.

R$^7$ may be R$^{7C}$-substituted or unsubstituted cycloalkyl. R$^7$ may be R$^{7C}$-substituted cycloalkyl. R$^7$ may be R$^{7C}$-substituted or unsubstituted 3 to 20 membered cycloalkyl. R$^7$ may be R$^{7C}$-substituted 3 to 20 membered cycloalkyl. R$^7$ may be R$^{7C}$-substituted or unsubstituted 3 to 10 membered cycloalkyl. R$^7$ may be R$^{7C}$-substituted 3 to 10 membered cycloalkyl. R$^7$ may be R$^{7C}$-substituted or unsubstituted 3 to 6 membered cycloalkyl. R$^7$ may be R$^{7C}$-substituted 3 to 6 membered cycloalkyl.

R$^7$ may be substituted or unsubstituted heterocycloalkyl. R$^7$ may be substituted heterocycloalkyl. R$^7$ may be unsubstituted heterocycloalkyl. R$^7$ may be substituted or unsubstituted 3 to 20 membered heterocycloalkyl. R$^7$ may be substituted 3 to 20 membered heterocycloalkyl. R$^7$ may be substituted or unsubstituted 3 to 10 membered heterocycloalkyl. R$^7$ may be substituted 3 to 10 membered heterocycloalkyl. R$^7$ may be substituted or unsubstituted 3 to 6 membered heterocycloalkyl. R$^7$ may be substituted 3 to 6 membered heterocycloalkyl.

R$^7$ may be R$^{7C}$-substituted or unsubstituted heterocycloalkyl. R$^7$ may be R$^{7C}$-substituted heterocycloalkyl. R$^7$ may be R$^{7C}$-substituted or unsubstituted 3 to 20 membered heterocycloalkyl. R$^7$ may be R$^{7C}$-substituted 3 to 20 membered heterocycloalkyl. R$^7$ may be R$^{7C}$-substituted or unsubstituted 3 to 10 membered heterocycloalkyl. R$^7$ may be R$^{7C}$-substituted 3 to 10 membered heterocycloalkyl. R$^7$ may be R$^{7C}$-substituted or unsubstituted 3 to 6 membered heterocycloalkyl. R$^7$ may be R$^{7C}$-substituted 3 to 6 membered heterocycloalkyl.

R$^7$ may be substituted or unsubstituted aryl. R$^7$ may be substituted aryl. R$^7$ may be unsubstituted aryl. R$^7$ may be substituted or unsubstituted 5 to 20 membered aryl. R$^7$ may be substituted 5 to 20 membered aryl. R$^7$ may be substituted or unsubstituted 5 to 8 membered aryl (e.g. phenyl). R$^7$ may be substituted 5 to 8 membered aryl. R$^7$ may be substituted or unsubstituted 5 or 6 membered aryl. R$^7$ may be substituted 5 or 6 membered aryl.

R$^7$ may be R$^{7C}$-substituted or unsubstituted aryl. R$^7$ may be R$^{7C}$-substituted aryl. R$^7$ may be R$^{7C}$-substituted or unsubstituted 5 to 20 membered aryl. R$^7$ may be R$^{7C}$-substituted 5 to 20 membered aryl. R$^7$ may be R$^{7C}$-substituted or unsubstituted 5 to 8 membered aryl. R$^7$ may be R$^{7C}$-substituted 5 to 8 membered aryl. R$^7$ may be R$^{7C}$-substituted or unsubstituted 5 or 6 membered aryl. R$^7$ may be R$^{7C}$-substituted 5 or 6 membered aryl (e.g. phenyl).

R$^7$ may be substituted or unsubstituted heteroaryl. R$^7$ may be substituted heteroaryl. R$^7$ may be unsubstituted heteroaryl. R$^7$ may be substituted or unsubstituted 5 to 20 membered heteroaryl. R$^7$ may be substituted 5 to 20 membered heteroaryl. R$^7$ may be substituted 5 to 8 membered heteroaryl. R$^7$ may be substituted 5 to 8 membered heteroaryl. $R^7$ may be substituted or unsubstituted 5 or 6 membered heteroaryl. $R^7$ may be substituted 5 or 6 membered heteroaryl.

$R^7$ may be $R^{7C}$-substituted or unsubstituted heteroaryl. $R^7$ may be $R^{7C}$-substituted heteroaryl. $R^7$ may be $R^{7C}$-substituted or unsubstituted 5 to 20 membered heteroaryl. $R^7$ may be $R^{7C}$-substituted 5 to 20 membered heteroaryl. $R^7$ may be $R^{7C}$-substituted or unsubstituted 5 to 8 membered heteroaryl. $R^7$ may be $R^{7C}$-substituted 5 to 8 membered heteroaryl. $R^7$ may be $R^{7C}$-substituted or unsubstituted 5 or 6 membered heteroaryl. $R^7$ may be $R^{7C}$-substituted 5 or 6 membered heteroaryl.

$R^{7A}$ is independently hydrogen, halogen, oxo, $N_3$, —$CF_3$, —$CCl_3$, —$CBr_3$, —$CI_3$, —CN, —OH, —$NH_2$, —COOH, —$CONH_2$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, $R^{7C}$-substituted or unsubstituted alkyl, $R^{7C}$-substituted or unsubstituted heteroalkyl, $R^{7C}$-substituted or unsubstituted cycloalkyl, $R^{7C}$-substituted or unsubstituted heterocycloalkyl, $R^{7C}$-substituted or unsubstituted aryl, or $R^{7C}$-substituted or unsubstituted heteroaryl.

$R^{7C}$ is independently halogen, oxo, $N_3$, —$CF_3$, —$CCl_3$, —$CBr_3$, —$CI_3$, —CN, —OH, —$COR^{7D}$, —$NR^{7D}R^{7E}$, —$COOR^{7D}$, —$CONR^{7D}R^{7E}$, —$NO_2$, —$SR^{7D}$, —$S(O)_2R^{7D}$, —$S(O)_3R^{7D}$, —$S(O)_4R^{7D}$, —$S(O)_2NR^{7D}R^{7E}$, —$NHNR^{7D}R^{7E}$, —$ONR^{7D}R^{7E}$, —NHC(O)$NHNR^{7D}R^{7E}$, —NHC(O)$NR^{7D}R^{7E}$, —$NHS(O)_2R^{7D}$, —NHC(O)$R^{7D}$, —NHC(O)—$OR^{7D}$, —$NHOR^{7D}$, —$OCF_3$, —$OCHF_2$, $R^{7D}$-substituted or unsubstituted alkyl, $R^{7D}$-substituted or unsubstituted heteroalkyl, $R^{7D}$-substituted or unsubstituted cycloalkyl, $R^{7D}$-substituted or unsubstituted heterocycloalkyl, $R^{7D}$-substituted or unsubstituted aryl, or $R^{7D}$-substituted or unsubstituted heteroaryl.

$R^{7C}$ may independently be halogen, oxo, $N_3$, —$CF_3$, —$CCl_3$, —$CBr_3$, —$CI_3$, —CN, —OH, —$NH_2$, —COOH, —$CONH_2$, —C(O)H, —$COCH_3$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, $R^{7D}$-substituted or unsubstituted alkyl, $R^{7D}$-substituted or unsubstituted heteroalkyl, $R^{7D}$-substituted or unsubstituted cycloalkyl, $R^{7D}$-substituted or unsubstituted heterocycloalkyl, $R^{7D}$-substituted or unsubstituted aryl, or $R^{7D}$-substituted or unsubstituted heteroaryl.

$R^{7B}$ and $R^{7E}$ may independently be hydrogen, halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{7D}$ is independently hydrogen, halogen, oxo, $N_3$, —$CF_3$, —$CCl_3$, —$CBr_3$, —$CI_3$, —CN, —OH, —$COR^{7F}$, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, $R^{7F}$-substituted or unsubstituted heteroalkyl, $R^{7F}$-substituted or unsubstituted cycloalkyl, $R^{7F}$-substituted or unsubstituted heterocycloalkyl, $R^{7F}$-substituted or unsubstituted aryl, or $R^{7F}$-substituted or unsubstituted heteroaryl.

$R^{7F}$ is independently halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^7$ may be -$L^1$-$R^6$, where $L^1$ and $R^6$ are independently as described herein. $R^7$ may be -$L^1$-$R^6$, where $L^1$ and $R^6$ are independently as described herein and $L^2$ is a bond, —$SO_2$, or —NHC(O)—.

$L^2$ may independently be a bond, —C(O)—, —C(O)O—, —O—, —S—, —$NR^{14}$—, —C(O)$NR^{14}$—, —$NR^{14}$C(O)—, —S(O)—, —$S(O)_2$—, —$S(O)NR^{14}$—. $L^2$ may independently be a bond, —$S(O)_2$—, or —$NR^{14}$C(O)—, where $R^{14}$ is hydrogen or unsubstituted $C_1$-$C_5$ alkyl. $L^2$ may independently be a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ may independently be a bond, substituted or unsubstituted alkylene, or substituted or unsubstituted heteroalkylene. $L^2$ may independently be a bond, —C(O)—, —C(O)O—, —O—, —S—, —$NR^{14}$—, —C(O)$NR^{14}$—, —$NR^{14}$C(O)—, —$S(O)_2$—, —$S(O)NR^{14}$—, substituted or unsubstituted alkylene, or substituted or unsubstituted heteroalkylene. $L^2$ may independently be a bond, —C(O)—, —C(O)O—, —O—, —S—, —$NR^{14}$—, —C(O)$NR^{14}$—, —$NR^{14}$C(O)—, —$S(O)_2$—, —$S(O)NR^{14}$—, substituted or unsubstituted alkylene, or substituted or unsubstituted heteroalkylene where $R^{14}$ is hydrogen or substituted or unsubstituted alkyl. $L^2$ may independently be a bond, —C(O)—, —C(O)O—, —O—, —S—, —$NR^{14}$—, —C(O)$NR^{14}$—, —$NR^{14}$C(O)—, —$S(O)_2$—, —$S(O)NR^{14}$—, $R^{14}$-substituted or unsubstituted alkylene, or $R^{14}$-substituted or unsubstituted heteroalkylene where $R^{14}$ is hydrogen or substituted or unsubstituted alkyl. $R^{14}$ may be unsubstituted alkyl.

$L^2$ may independently be a bond or substituted or unsubstituted alkylene. $L^2$ may independently be a bond or $R^{14}$-substituted or unsubstituted alkylene. $L^2$ may independently be a bond or $R^{14}$-substituted or unsubstituted alkylene where $R^{14}$ is hydrogen or substituted or unsubstituted alkyl. $L^2$ may independently be a bond or substituted or unsubstituted $C_1$-$C_5$ alkylene. $L^2$ may independently be a bond or $R^{14}$-substituted or unsubstituted $C_1$-$C_5$ alkylene. $L^2$ may independently be a bond or $R^{14}$-substituted or unsubstituted $C_1$-$C_5$ alkylene where $R^{14}$ is hydrogen or substituted or unsubstituted $C_1$-$C_5$ alkyl. $L^2$ may independently be $R^{14}$-substituted or unsubstituted alkylene where $R^{14}$ is hydrogen, halogen, or substituted or unsubstituted alkyl. $L^2$ may independently be a bond. $L^2$ may independently be bond, —$SO_2$, or —NHC(O)— and $R^7$ may be $L^1$-$R^6$, where $L^1$ and $R^6$ are as described herein.

$R^{14}$ may independently be hydrogen, halogen, oxo, $N_3$, —$CF_3$, —$CCl_3$, —$CBr_3$, —$CI_3$, —CN, —OH, —COH, —$NH_2$, —COOH, —$CONH_2$, —COH, —$COCH_3$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, $R^{14A}$-substituted or unsubstituted heteroalkyl, $R^{14A}$-substituted or unsubstituted cycloalkyl, $R^{14A}$-substituted or unsubstituted heterocycloalkyl, $R^{14A}$-substituted or unsubstituted aryl, or $R^{14A}$-substituted or unsubstituted heteroaryl.

$R^{14A}$ is independently halogen, oxo, $N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2C$, —$S(O)_3H$, —$S(O)_2H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound of Formula (II) is:

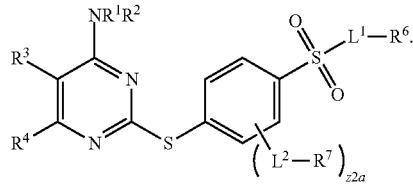

In embodiments, the compound of Formula (II) is:

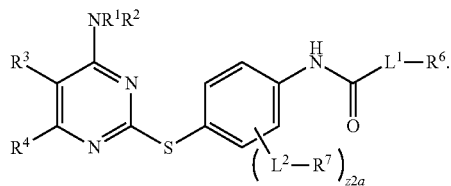

wherein z2a is 0, 1, 2, 3, or 4, and the compound is not tozasertib. z2a may be 0, 1, or 2. z2a may be 0. z2a may be 1. z2a may be 2. z2a may be 3. z2a may be 4.

In a second aspect of formula (II), compounds are provided in which $R^1$, $R^2$, and $R^4$ are as described hereinabove for compounds of formula (I). $L^2$, $R^7$, and z2 are as described hereinabove for first aspect of the compound having formula (II). $R^7$ may be -$L^1$-$R^6$, where $L^1$ and $R^6$ are independently as described herein. The compound is not tozasertib.

$R^3$ of the second aspect of the compound of formula (II) is as described hereinabove for compounds of formula (I) with the proviso that $R^3$ is not hydrogen, halogen, or substituted or unsubstituted alkyl. $R^3$ may be —$N_3$, —$CF_3$, —$CCl_3$, —$CBr_3$, —$CI_3$, —CN, —$COR^{3A}$, —$OR^{3A}$, —$NR^{3A}R^{3B}$, —$C(O)OR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}NR^{3A}R^{3B}$, —$NHNR^{3A}R^{3B}$, —$ONR^{3A}R^{3B}$, —$NHC(O)NHNR^{3A}R^{3B}$, where $R^{3A}$, $R^{3B}$, $R^3$, are as described herein. $R^3$ may be —$N_3$, —$CF_3$, —$CCl_3$, —$CBr_3$, —$CI_3$, —CN, —$COR^{3A}$, —$OR^{3A}$, —$NR^{3A}R^{3B}$, —$C(O)OR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}NR^{3A}R^{3B}$, —$NHNR^{3A}R^{3B}$, —$ONR^{3A}R^{3B}$, —$NHC(O)NHNR^{3A}R^{3B}$, where $R^{3A}$, $R^{3B}$, $R^{3C}$, are independently hydrogen, oxo, halogen, —$CF_3$, —OH, —$NH_2$, —COOH, —$CONH_2$, substituted or unsubstituted alkyl, or substituted or unsubstituted aryl. $R^3$ may be —$OCH_3$.

$R^3$ may be —$OR^{3A}$. $R^3$ may be —$OR^{3A}$ where $R^{3A}$ is substituted or unsubstituted alkyl.

In embodiments, the compound of Formula (II) is:

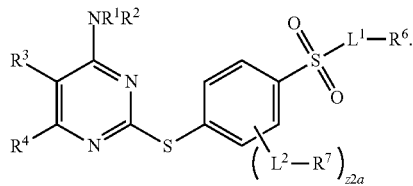

In embodiments, the compound of Formula (II) is:

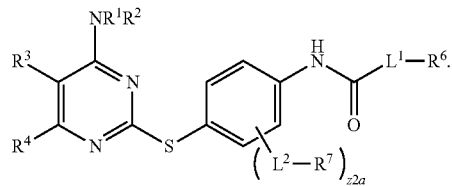

wherein z2a is 0, 1, 2, 3, or 4, and the compound is not tozasertib. z2a may be 0, 1, or 2. z2a may be 0. z2a may be 1. z2a may be 2. z2a may be 3. z2a may be 4.

In embodiments, the PLK4 inhibitor is the compound of Formula (III) or a pharmaceutically acceptable salt thereof.

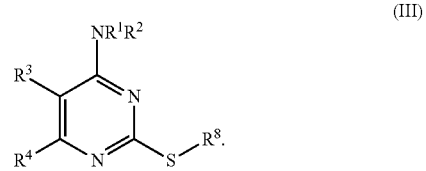

(III)

$R^1$, $R^2$, $R^3$, and $R^4$ are as described hereinabove for formula (I). In embodiments, $R^3$, and $R^4$ are as set forth hereinabove for formula (II) (including the first and second aspects). $R^8$ is unsubstituted $C_1$-$C_5$ alkyl. $R^8$ may be methyl, ethyl, or propyl. $R^8$ may be methyl.

In embodiments, the PLK4 inhibitor is a compound set forth in Table 1. In embodiments, the PLK4 inhibitor is a compound set forth in Table 1 having activity indicated as "XXX." In embodiments, the PLK4 inhibitor is a compound set forth in Table 1 having the formula (I). In embodiments, the PLK4 inhibitor is a compound set forth in Table 1, having the formula (I) and having activity indicated as "XXX." In embodiments, the PLK4 inhibitor is a compound set forth in Table 1, having the formula (I) and having activity indicated as "XX". In embodiments, the PLK4 inhibitor is a compound set forth in Table 1, having the formula (I) and having activity indicated as "X". In embodiments, the PLK4 inhibitor is a compound set forth in Table 1, having the formula (II) (including the first or second aspect). In embodiments, the PLK4 inhibitor is a compound set forth in Table 1, having the formula (II) (including the first or second aspect) and having activity indicated as "XXX". In embodiments, the PLK4 inhibitor is a compound set forth in Table 1, having the formula (II) (including the first or second aspect) and having activity indicated as "XX". In embodiments, the PLK4 inhibitor is a compound set forth in Table 1, having the formula (II) (including the first or second aspect) and having activity indicated as "X". In embodiments, the PLK4 inhibitor is a compound set forth in Table 1, having the formula (III). In embodiments, the PLK4 inhibitor is a compound set forth in Table 1, having the formula (III) and having activity indicated as "XXX". In embodiments, the PLK4 inhibitor is a compound set forth in Table 1, having the formula (III) and having activity indicated as "XX". In embodiments, the PLK4 inhibitor is a compound set forth in Table 1, having the formula (III) and having activity indicated as "X".

In embodiments, the PLK4 inhibitor is centrinone or a pharmaceutically acceptable salt thereof. Centrinone has PubChem CID 91801159.

In embodiments, the PLK4 inhibitor is centrinone B or a pharmaceutically acceptable salt thereof. Centrinone B has PubChem CID 118704753.

In embodiments the compound is not a compound set forth in U.S. Pat. No. 8,455,507, which is herein incorporated by reference in its entirety. In embodiments the compound is not a compound set forth in U.S. Pat. No. 7,531,536 which is herein incorporated by reference in its entirety. In embodiments the compound is not a compound set forth in U.S. Pat. No. 7,951,820 which is herein incorporated by reference in its entirety.

Table 1 exemplifies compounds of Formula (I), (II), and (III). Activity denoted by X indicates the compound has $IC_{50}$ value greater than about 1 µM. Activity denoted by XX indicates the compound has $IC_{50}$ value of about 100 nM to about 1 µM. Activity denoted by XXX indicates compound has $IC_{50}$ value less than about 100 nM. All compounds were confirmed by mass spectroscopy and by $^1$H and $^{13}$C NMR.

TABLE 1

| | Activity |
|---|---|
| 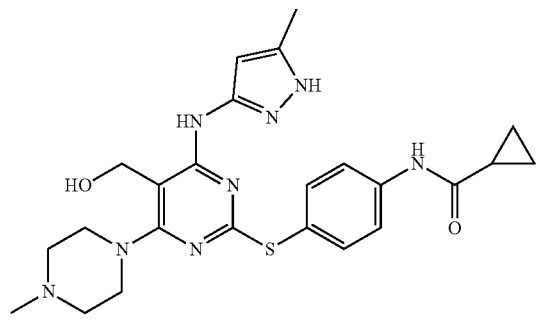 [SMILES: Cc1cc(Nc2nc(Sc3ccc(NC(=O)C4CC4)cc3)nc(N3CCN(C)CC3)c2CO)n[nH]1] | XX |
| 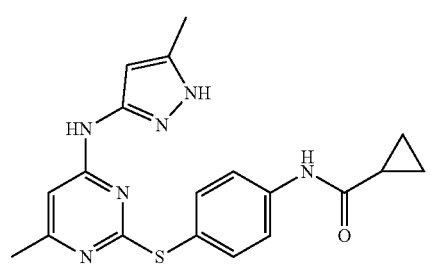 [SMILES: Cc1cc(Nc2cc(C)[nH]n2)nc(Sc2ccc(NC(=O)C3CC3)cc2)n1] | XXX |
| 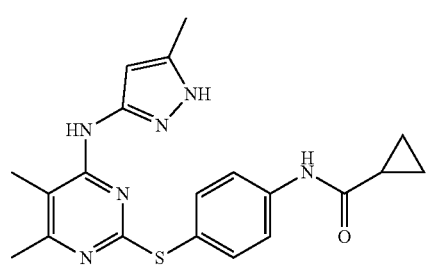 [SMILES: Cc1cc(Nc2nc(Sc3ccc(NC(=O)C4CC4)cc3)nc(C)c2C)n[nH]1] | XXX |
| 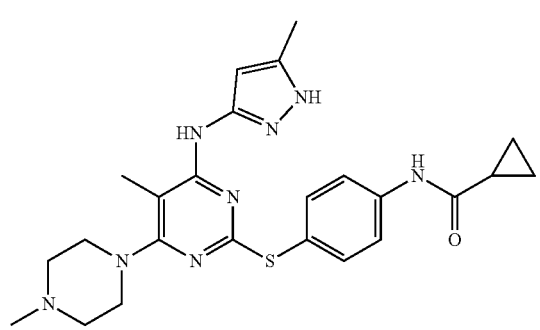 [SMILES: Cc1cc(Nc2nc(Sc3ccc(NC(=O)C4CC4)cc3)nc(N3CCN(C)CC3)c2C)n[nH]1] | XXX |

TABLE 1-continued

| Structure | Activity |
|---|---|
| (structure) | X |
| (structure) | X |
| (structure) | X |
| (structure) | XXX |
| (structure) | XXX |

TABLE 1-continued
| | Activity |
|---|---|
| 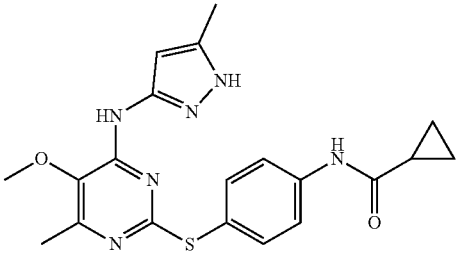 [SMILES: CCc1c(C)nc(Sc2ccc(NC(=O)C3CC3)cc2)nc1Nc1cc(C)[nH]n1] | XXX |
| 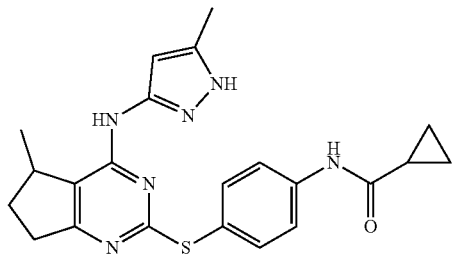 [SMILES: Cc1cc(Nc2nc(Sc3ccc(NC(=O)C4CC4)cc3)nc3c2C(C)CC3)n[nH]1] | XXX |
| 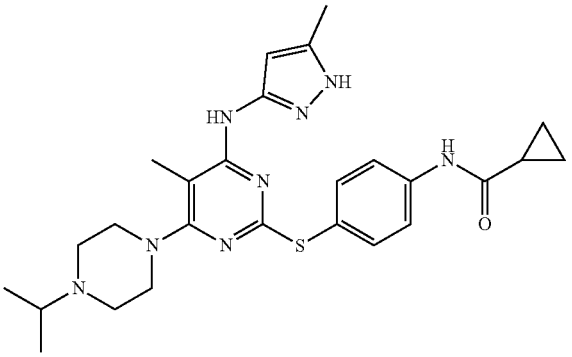 [SMILES: Cc1cc(Nc2nc(Sc3ccc(NC(=O)C4CC4)cc3)nc(N3CCN(C(C)C)CC3)c2C)n[nH]1] | XXX |
| 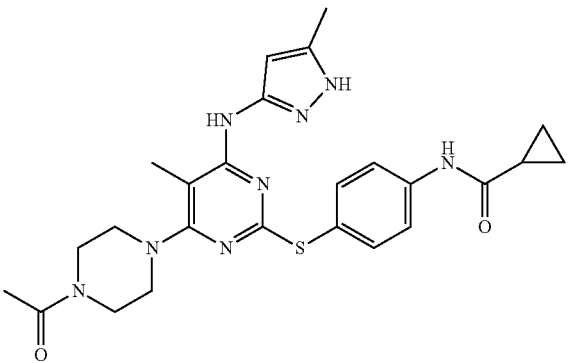 [SMILES: CC(=O)N1CCN(c2nc(Sc3ccc(NC(=O)C4CC4)cc3)nc(Nc3cc(C)[nH]n3)c2C)CC1] | XXX |
| 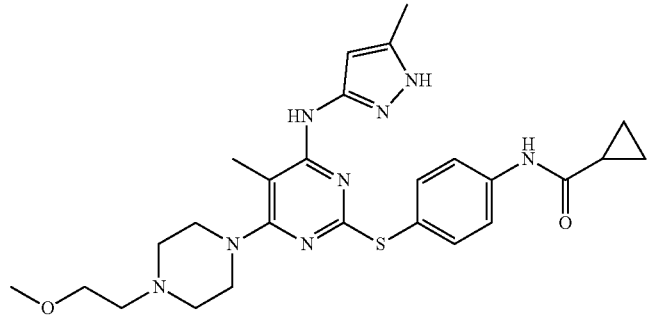 [SMILES: COCCN1CCN(c2nc(Sc3ccc(NC(=O)C4CC4)cc3)nc(Nc3cc(C)[nH]n3)c2C)CC1] | XXX |

TABLE 1-continued
| | Activity |
|---|---|
| 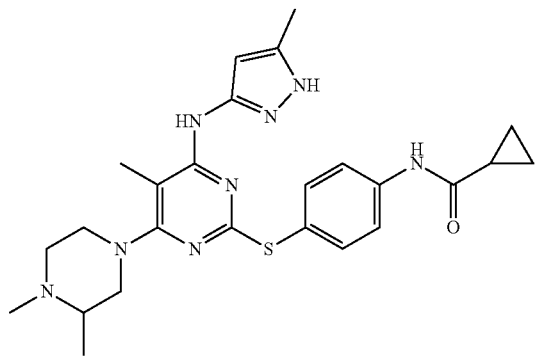 [SMILES: Cc1cc(Nc2nc(Sc3ccc(NC(=O)C4CC4)cc3)nc(N3CCN(C)C(C)C3)c2C)n[nH]1] | XXX |
| 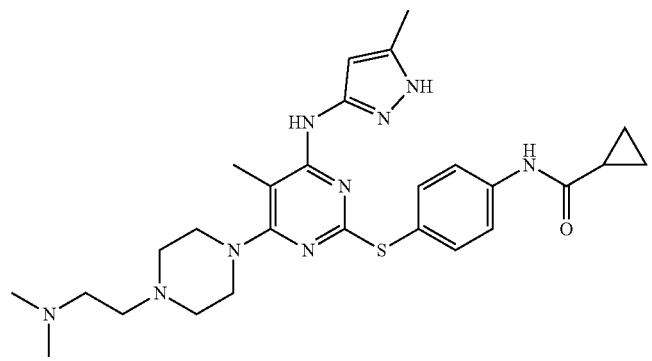 [SMILES: Cc1cc(Nc2nc(Sc3ccc(NC(=O)C4CC4)cc3)nc(N3CCN(CCN(C)C)CC3)c2C)n[nH]1] | XXX |
| 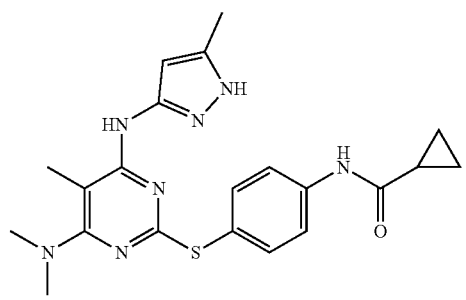 [SMILES: Cc1cc(Nc2nc(Sc3ccc(NC(=O)C4CC4)cc3)nc(N(C)C)c2C)n[nH]1] | XXX |
| 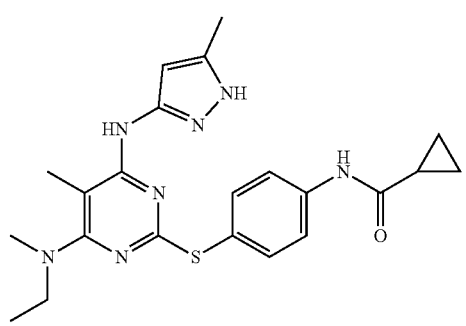 [SMILES: CCN(C)c1nc(Sc2ccc(NC(=O)C3CC3)cc2)nc(Nc2cc(C)[nH]n2)c1C] | XXX |

TABLE 1-continued
| | Activity |
|---|---|
| 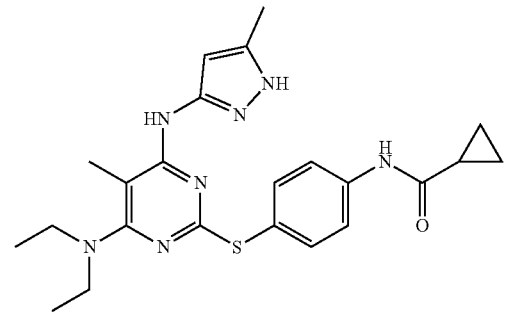 [SMILES: CCN(CC)c1nc(Sc2ccc(NC(=O)C3CC3)cc2)nc(Nc2cc(C)[nH]n2)c1C] | XXX |
| 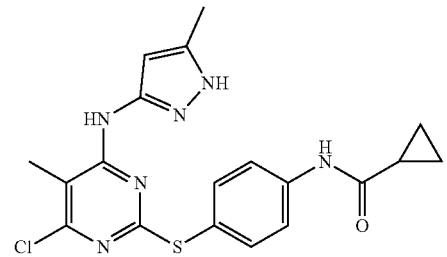 [SMILES: Cc1cc(Nc2nc(Sc3ccc(NC(=O)C4CC4)cc3)nc(Cl)c2C)n[nH]1] | XXX |
| 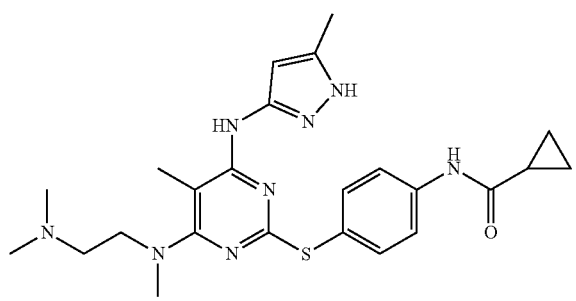 [SMILES: Cc1cc(Nc2nc(Sc3ccc(NC(=O)C4CC4)cc3)nc(N(C)CCN(C)C)c2C)n[nH]1] | XXX |
| 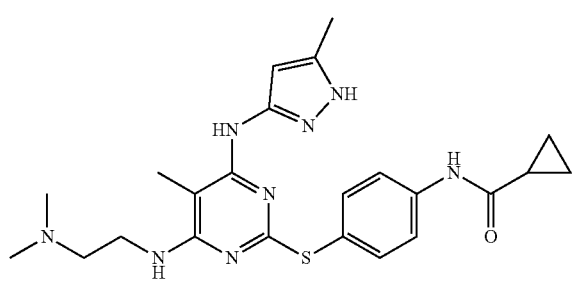 [SMILES: Cc1cc(Nc2nc(Sc3ccc(NC(=O)C4CC4)cc3)nc(NCCN(C)C)c2C)n[nH]1] | XXX |
| 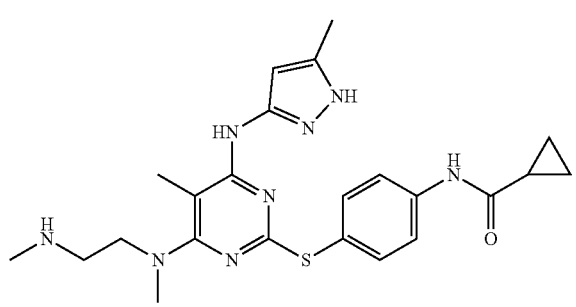 [SMILES: CNCCN(C)c1nc(Sc2ccc(NC(=O)C3CC3)cc2)nc(Nc2cc(C)[nH]n2)c1C] | XXX |

TABLE 1-continued
| | Activity |
|---|---|
| 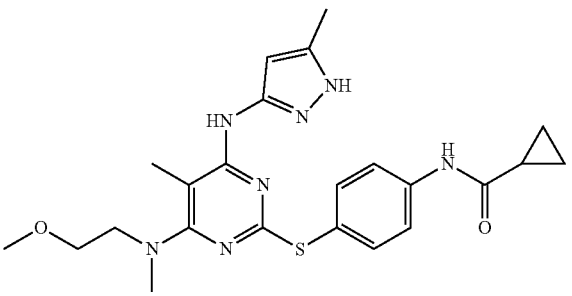 [SMILES: COCCN(C)c1nc(Sc2ccc(NC(=O)C3CC3)cc2)nc(Nc2cc(C)[nH]n2)c1C] | XXX |
| 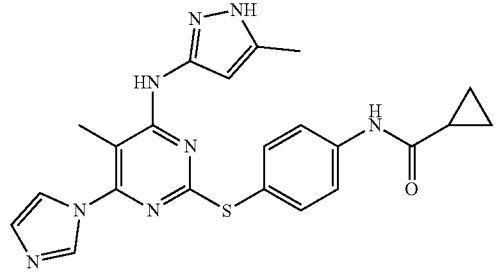 [SMILES: Cc1cc(Nc2nc(Sc3ccc(NC(=O)C4CC4)cc3)nc(-n3ccnc3)c2C)n[nH]1] | XX |
| 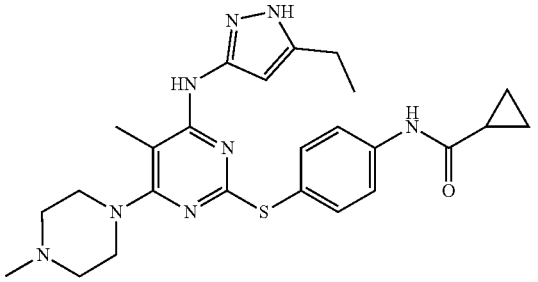 [SMILES: CCc1cc(Nc2nc(Sc3ccc(NC(=O)C4CC4)cc3)nc(N3CCN(C)CC3)c2C)n[nH]1] | X |
| 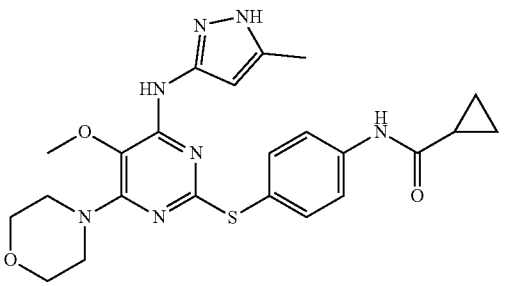 [SMILES: COc1c(Nc2cc(C)[nH]n2)nc(Sc2ccc(NC(=O)C3CC3)cc2)nc1N1CCOCC1] | XXX |
| 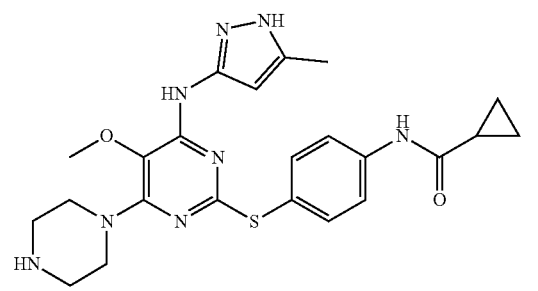 [SMILES: COc1c(Nc2cc(C)[nH]n2)nc(Sc2ccc(NC(=O)C3CC3)cc2)nc1N1CCNCC1] | XXX |

TABLE 1-continued
| | Activity |
|---|---|
| 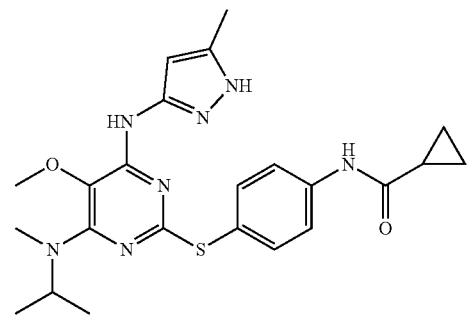 [SMILES: COc1c(Nc2cc(C)[nH]n2)nc(Sc2ccc(NC(=O)C3CC3)cc2)nc1N(C)C(C)C] | XX |
| 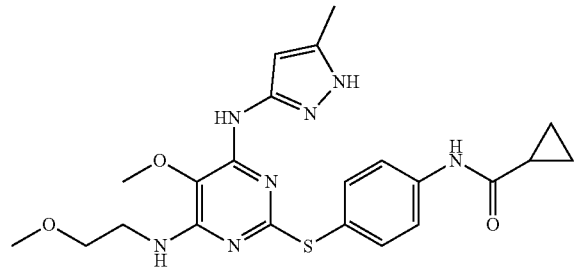 [SMILES: COCCNc1nc(Sc2ccc(NC(=O)C3CC3)cc2)nc(Nc2cc(C)[nH]n2)c1OC] | XXX |
| 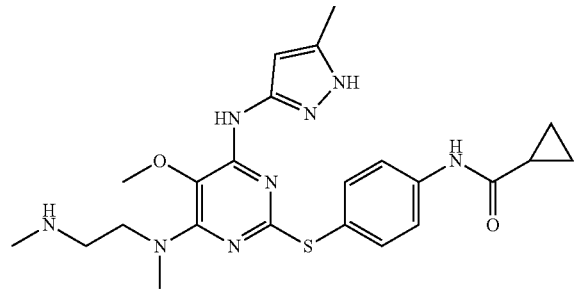 [SMILES: CNCCN(C)c1nc(Sc2ccc(NC(=O)C3CC3)cc2)nc(Nc2cc(C)[nH]n2)c1OC] | XX |
| 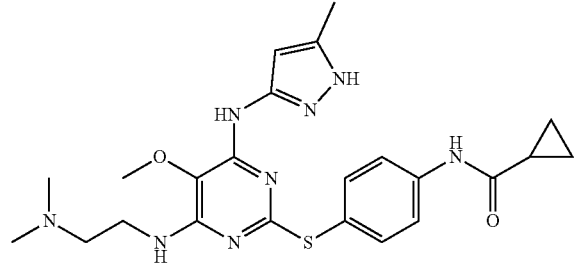 [SMILES: COc1c(NCCN(C)C)nc(Sc2ccc(NC(=O)C3CC3)cc2)nc1Nc1cc(C)[nH]n1] | XX |
| 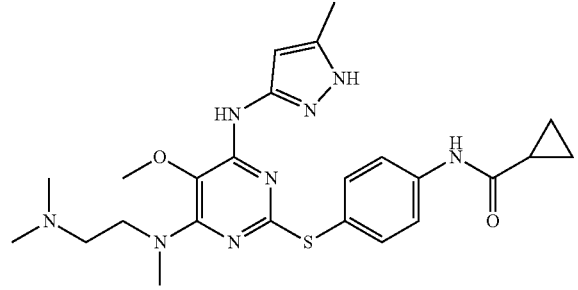 [SMILES: COc1c(Nc2cc(C)[nH]n2)nc(Sc2ccc(NC(=O)C3CC3)cc2)nc1N(C)CCN(C)C] | XX |

TABLE 1-continued
| | Activity |
|---|---|
| 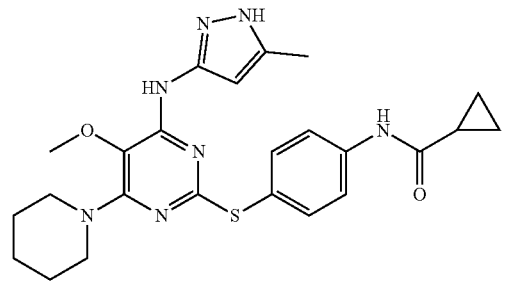 [SMILES: COc1c(Nc2cc(C)[nH]n2)nc(Sc2ccc(NC(=O)C3CC3)cc2)nc1N1CCCCC1] | XXX |
| 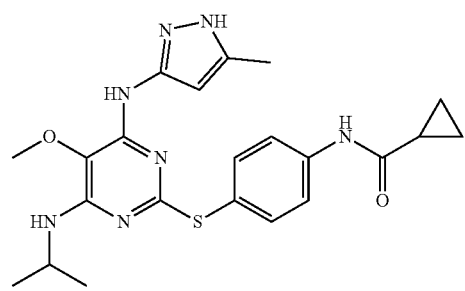 [SMILES: COc1c(Nc2cc(C)[nH]n2)nc(Sc2ccc(NC(=O)C3CC3)cc2)nc1NC(C)C] | XXX |
| 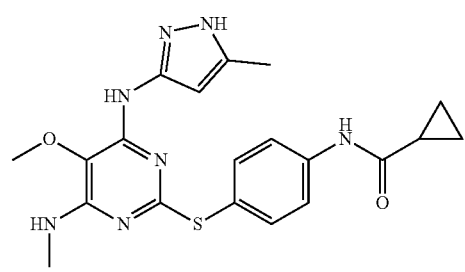 [SMILES: CNc1nc(Sc2ccc(NC(=O)C3CC3)cc2)nc(Nc2cc(C)[nH]n2)c1OC] | XXX |
| 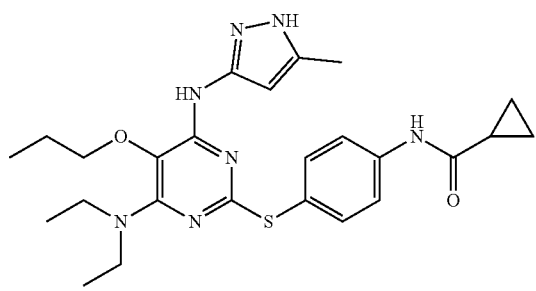 [SMILES: CCCOc1c(Nc2cc(C)[nH]n2)nc(Sc2ccc(NC(=O)C3CC3)cc2)nc1N(CC)CC] | XX |
| 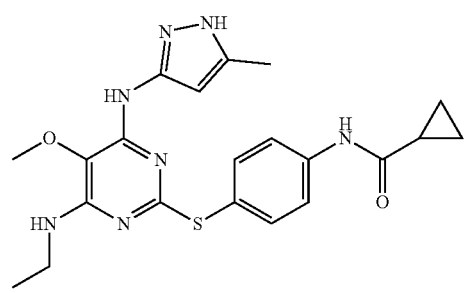 [SMILES: CCNc1nc(Sc2ccc(NC(=O)C3CC3)cc2)nc(Nc2cc(C)[nH]n2)c1OC] | XXX |

TABLE 1-continued
| | Activity |
|---|---|
| 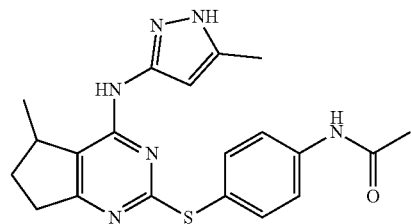 [SMILES: CC(=O)Nc1ccc(Sc2nc3c(c(Nc4cc(C)[nH]n4)n2)C(C)CC3)cc1] | XXX |
| 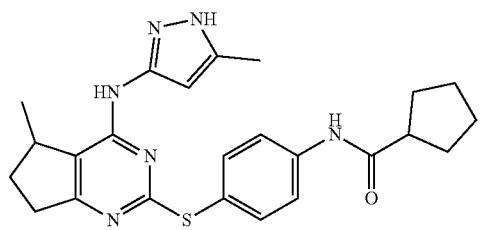 [SMILES: Cc1cc(Nc2nc(Sc3ccc(NC(=O)C4CCCC4)cc3)nc3c2C(C)CC3)n[nH]1] | XXX |
| 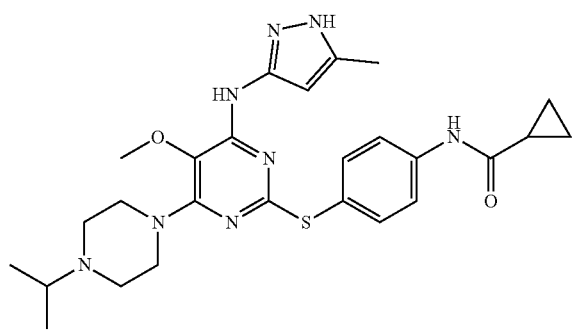 [SMILES: COc1c(Nc2cc(C)[nH]n2)nc(Sc2ccc(NC(=O)C3CC3)cc2)nc1N1CCN(C(C)C)CC1] | XXX |
| 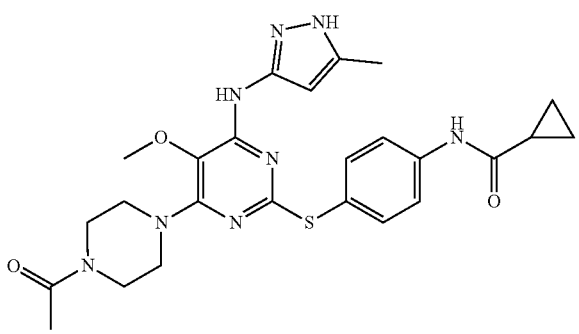 [SMILES: COc1c(Nc2cc(C)[nH]n2)nc(Sc2ccc(NC(=O)C3CC3)cc2)nc1N1CCN(C(C)=O)CC1] | XXX |
| 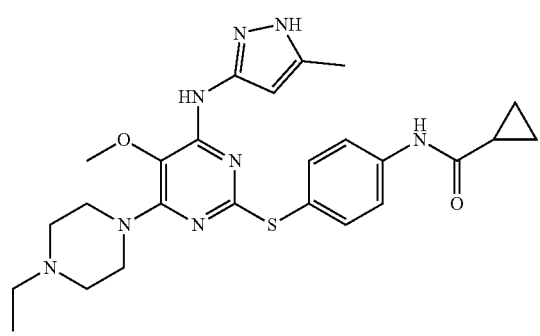 [SMILES: CCN1CCN(c2nc(Sc3ccc(NC(=O)C4CC4)cc3)nc(Nc3cc(C)[nH]n3)c2OC)CC1] | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 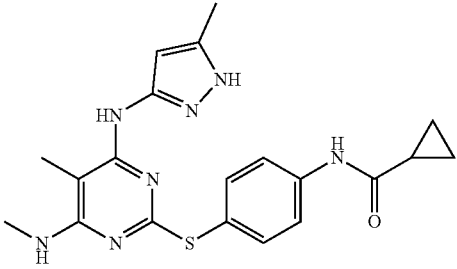 [SMILES: CNc1nc(Sc2ccc(NC(=O)C3CC3)cc2)nc(Nc2cc(C)[nH]n2)c1C] | XXX |
| 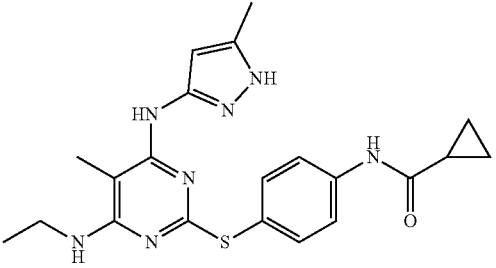 [SMILES: CCNc1nc(Sc2ccc(NC(=O)C3CC3)cc2)nc(Nc2cc(C)[nH]n2)c1C] | XXX |
| 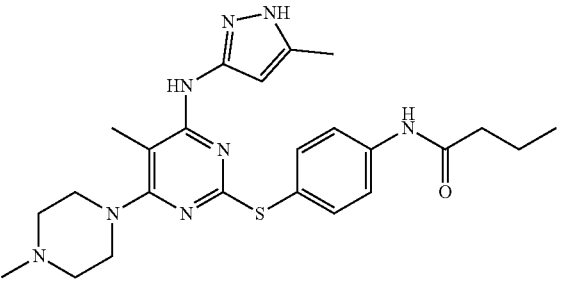 [SMILES: CCCC(=O)Nc1ccc(Sc2nc(Nc3cc(C)[nH]n3)c(C)c(N3CCN(C)CC3)n2)cc1] | XXX |
| 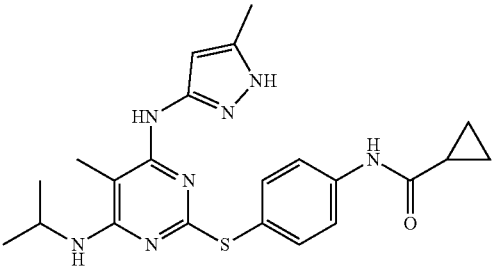 [SMILES: Cc1cc(Nc2nc(Sc3ccc(NC(=O)C4CC4)cc3)nc(NC(C)C)c2C)n[nH]1] | XXX |
| 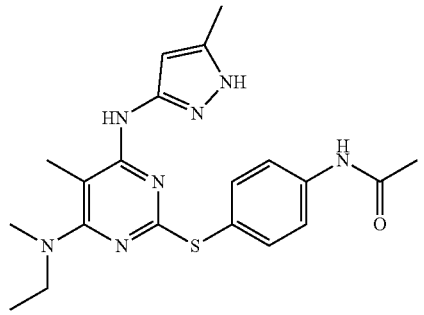 [SMILES: CCN(C)c1nc(Sc2ccc(NC(C)=O)cc2)nc(Nc2cc(C)[nH]n2)c1C] | XXX |

TABLE 1-continued
| | Activity |
|---|---|
| 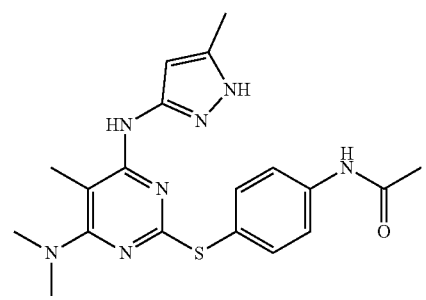 [SMILES: CC(=O)Nc1ccc(Sc2nc(Nc3cc(C)[nH]n3)c(C)c(N(C)C)n2)cc1] | XXX |
| 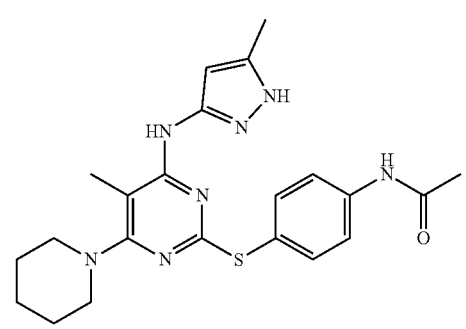 [SMILES: CC(=O)Nc1ccc(Sc2nc(Nc3cc(C)[nH]n3)c(C)c(N3CCCCC3)n2)cc1] | XXX |
| 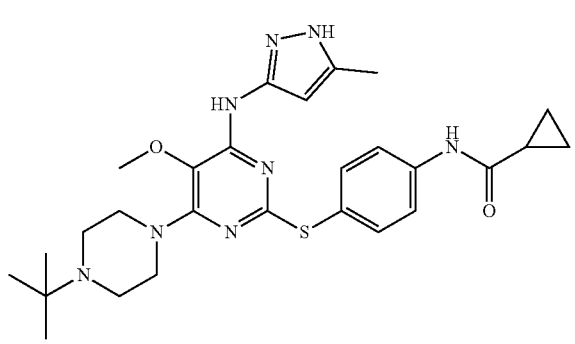 [SMILES: COc1c(Nc2cc(C)[nH]n2)nc(Sc2ccc(NC(=O)C3CC3)cc2)nc1N1CCN(C(C)(C)C)CC1] | X |
| 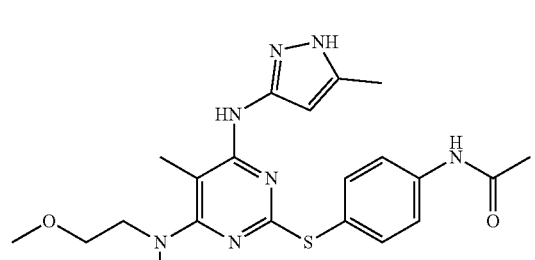 | XXX |
| 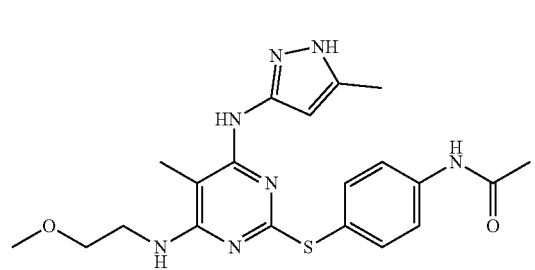 [SMILES: COCCNc1nc(Sc2ccc(NC(C)=O)cc2)nc(Nc2cc(C)[nH]n2)c1C] | XXX |

TABLE 1-continued
| | Activity |
|---|---|
| 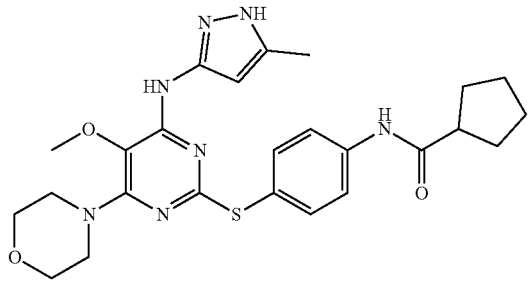 [SMILES: COc1c(Nc2cc(C)[nH]n2)nc(Sc2ccc(NC(=O)C3CCCC3)cc2)nc1N1CCOCC1] | XXX |
| 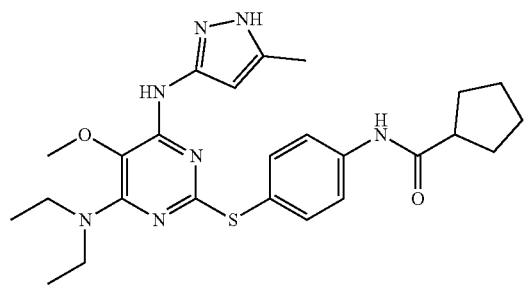 [SMILES: CCN(CC)c1nc(Sc2ccc(NC(=O)C3CCCC3)cc2)nc(Nc2cc(C)[nH]n2)c1OC] | XX |
| 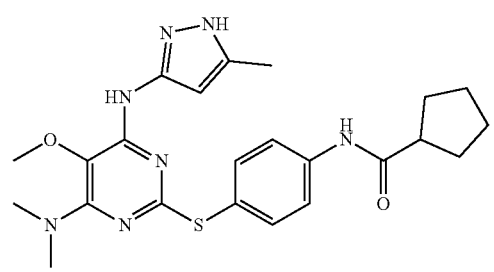 [SMILES: COc1c(Nc2cc(C)[nH]n2)nc(Sc2ccc(NC(=O)C3CCCC3)cc2)nc1N(C)C] | XXX |
| 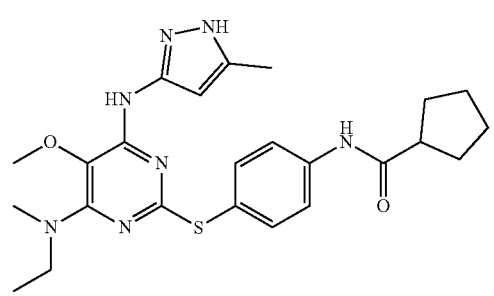 [SMILES: CCN(C)c1nc(Sc2ccc(NC(=O)C3CCCC3)cc2)nc(Nc2cc(C)[nH]n2)c1OC] | XX |
| 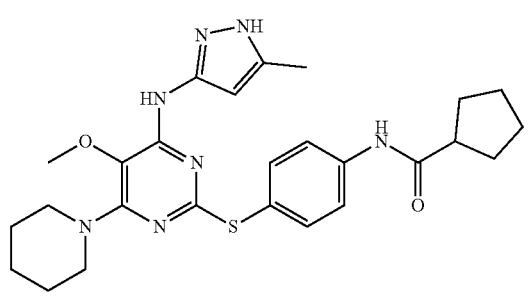 [SMILES: COc1c(Nc2cc(C)[nH]n2)nc(Sc2ccc(NC(=O)C3CCCC3)cc2)nc1N1CCCCC1] | XX |

TABLE 1-continued
| | Activity |
|---|---|
| 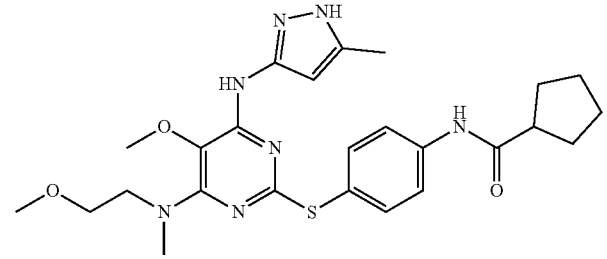 [SMILES: COCCN(C)c1nc(Sc2ccc(NC(=O)C3CCCC3)cc2)nc(Nc2cc(C)[nH]n2)c1OC] | XX |
| 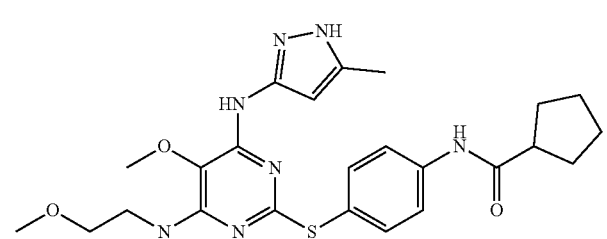 | XXX |
| 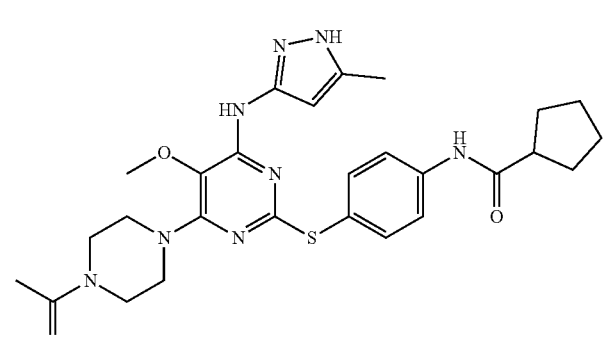 | XXX |
| 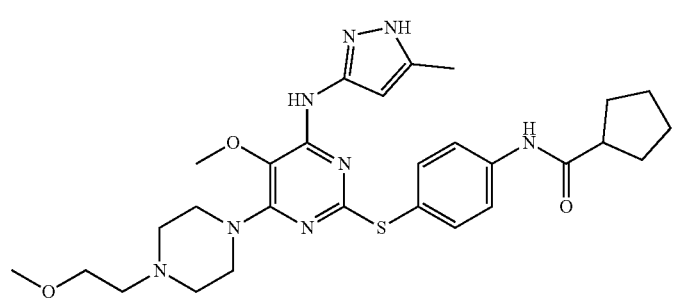 [SMILES: COCCN1CCN(c2nc(Sc3ccc(NC(=O)C4CCCC4)cc3)nc(Nc3cc(C)[nH]n3)c2OC)CC1] | XXX |
| 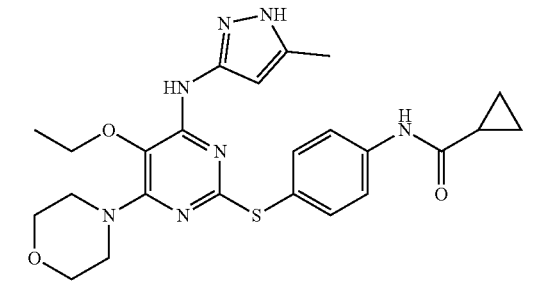 [SMILES: CCOc1c(Nc2cc(C)[nH]n2)nc(Sc2ccc(NC(=O)C3CC3)cc2)nc1N1CCOCC1] | XXX |

TABLE 1-continued

| Structure | Activity |
|---|---|
| (pyrimidine with ethoxy, piperidine, NH-methylpyrazole, S-phenyl-NH-cyclopropanecarboxamide) | XX |
| (pyrimidine with methoxy, 4-methylpiperazine, NH-methylpyrazole, S-phenyl-NH-cyclopentanecarboxamide) | XXX |
| (pyrimidine with methoxy, piperazine, NH-methylpyrazole, S-phenyl-NH-cyclopentanecarboxamide) | XXX |
| (pyrimidine with methoxy, 4-(2-dimethylaminoethyl)piperazine, NH-methylpyrazole, S-phenyl-NH-cyclopentanecarboxamide) | XXX |
| (pyrimidine with ethoxy, piperazine, NH-methylpyrazole, S-phenyl-NH-cyclopropanecarboxamide) | XXX |

TABLE 1-continued

| | Activity |
|---|---|
| [structure: 4-(diethylamino)-5-ethoxy-6-((5-methyl-1H-pyrazol-3-yl)amino)pyrimidin-2-yl thio phenyl cyclopropanecarboxamide] | XXX |
| [structure: 4-(ethyl(methyl)amino)-5-ethoxy-6-((5-methyl-1H-pyrazol-3-yl)amino)pyrimidin-2-yl thio phenyl cyclopropanecarboxamide] | XXX |
| [structure: 4-(dimethylamino)-5-ethoxy-6-((5-methyl-1H-pyrazol-3-yl)amino)pyrimidin-2-yl thio phenyl cyclopropanecarboxamide] | XXX |
| [structure: 5-ethoxy-6-((5-methyl-1H-pyrazol-3-yl)amino)-4-(piperazin-1-yl)pyrimidin-2-yl thio phenyl cyclopropanecarboxamide] | XX |
| [structure: 4-(diethylamino)-5-ethoxy-6-((5-methyl-1H-pyrazol-3-yl)amino)pyrimidin-2-yl thio phenyl cyclopropanecarboxamide variant] | XX |

TABLE 1-continued
| | Activity |
|---|---|
| 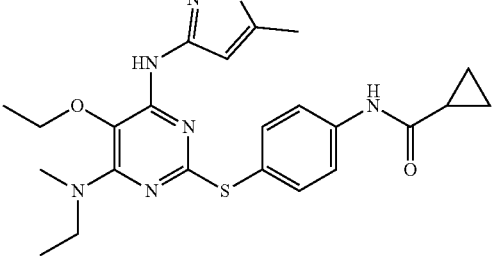 | XX |
| 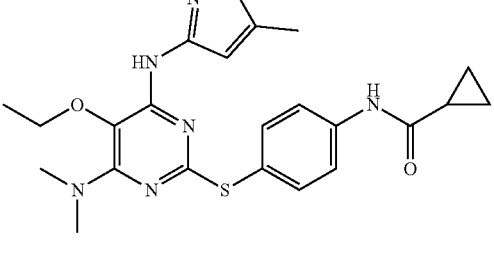 | XX |
| 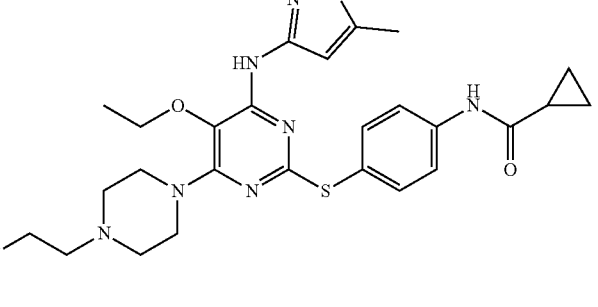 | XX |
| 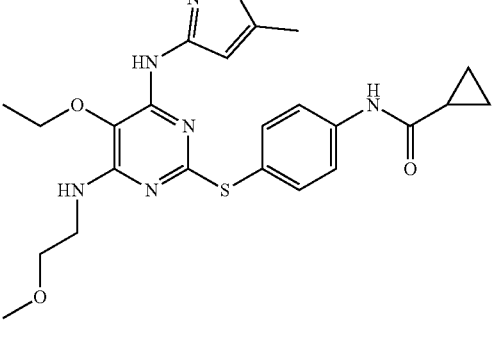 | XX |
| 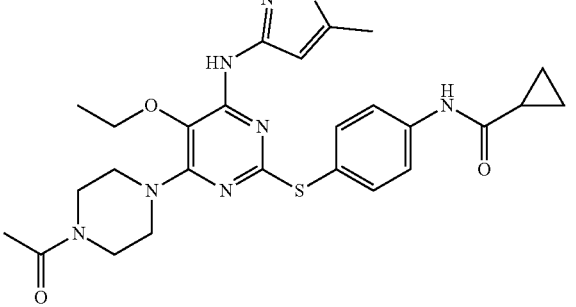 | XX |

TABLE 1-continued
| | Activity |
|---|---|
| 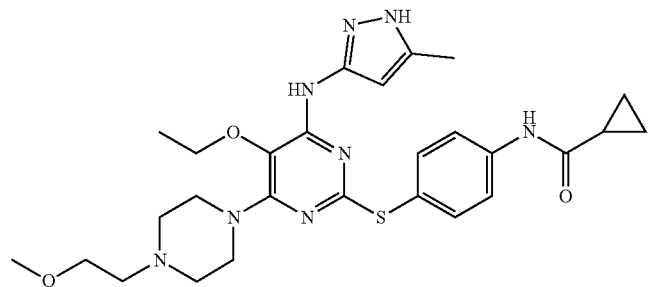 [SMILES: CCOc1c(Nc2cc(C)[nH]n2)nc(Sc2ccc(NC(=O)C3CC3)cc2)nc1N1CCN(CCOC)CC1] | XX |
| 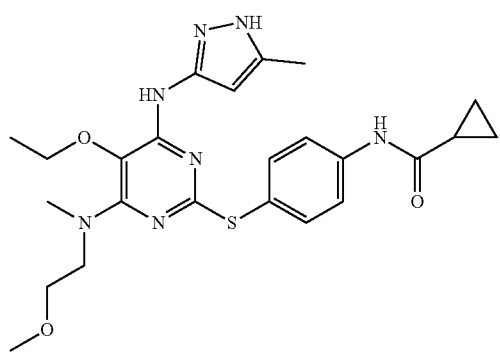 [SMILES: CCOc1c(Nc2cc(C)[nH]n2)nc(Sc2ccc(NC(=O)C3CC3)cc2)nc1N(C)CCOC] | XX |
| 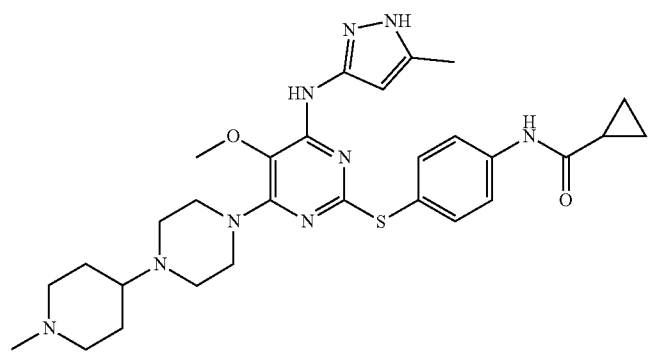 [SMILES: COc1c(Nc2cc(C)[nH]n2)nc(Sc2ccc(NC(=O)C3CC3)cc2)nc1N1CCN(C2CCN(C)CC2)CC1] | XXX |
| 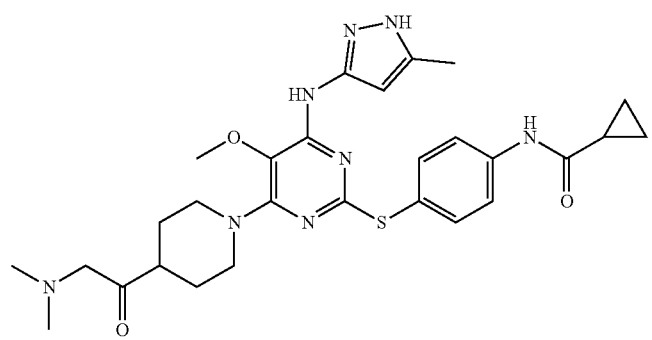 [SMILES: COc1c(Nc2cc(C)[nH]n2)nc(Sc2ccc(NC(=O)C3CC3)cc2)nc1N1CCC(C(=O)CN(C)C)CC1] | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 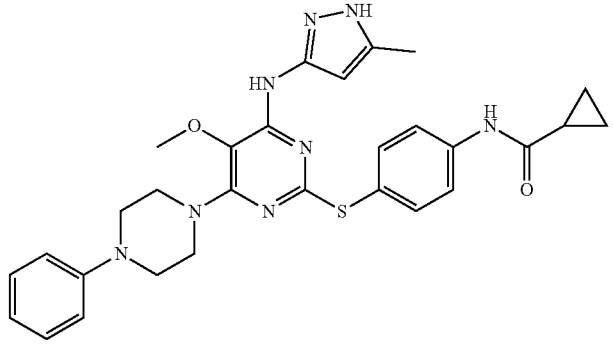 [SMILES: COc1c(Nc2cc(C)[nH]n2)nc(Sc2ccc(NC(=O)C3CC3)cc2)nc1N1CCN(c2ccccc2)CC1] | XX |
| 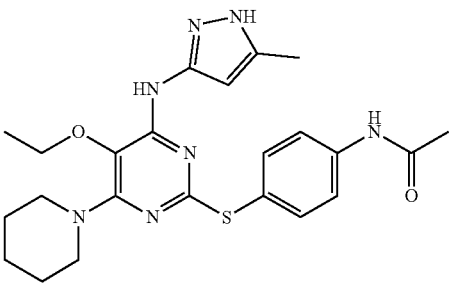 [SMILES: CCOc1c(Nc2cc(C)[nH]n2)nc(Sc2ccc(NC(C)=O)cc2)nc1N1CCCCC1] | XX |
| 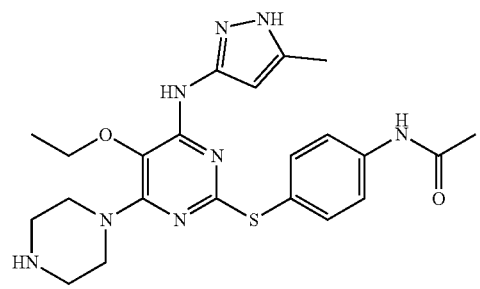 [SMILES: CCOc1c(Nc2cc(C)[nH]n2)nc(Sc2ccc(NC(C)=O)cc2)nc1N1CCNCC1] | XX |
| 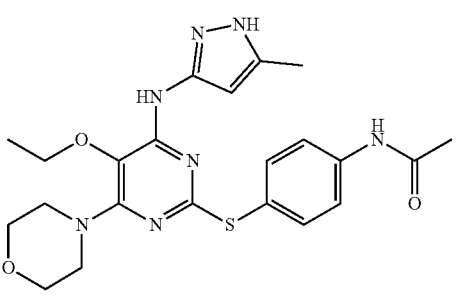 [SMILES: CCOc1c(Nc2cc(C)[nH]n2)nc(Sc2ccc(NC(C)=O)cc2)nc1N1CCOCC1] | XX |
| 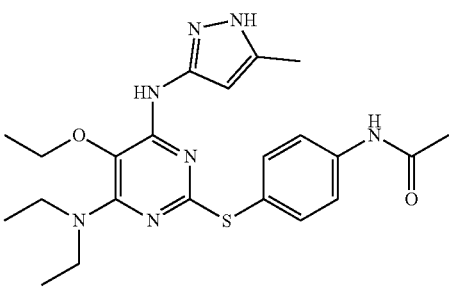 [SMILES: CCOc1c(Nc2cc(C)[nH]n2)nc(Sc2ccc(NC(C)=O)cc2)nc1N(CC)CC] | XX |

TABLE 1-continued

| Structure | Activity |
|---|---|
| (chemical structure) | XX |
| (chemical structure) | XX |
| (chemical structure) | XX |
| (chemical structure) | XX |
| (chemical structure) | XX |

TABLE 1-continued
| | Activity |
|---|---|
| 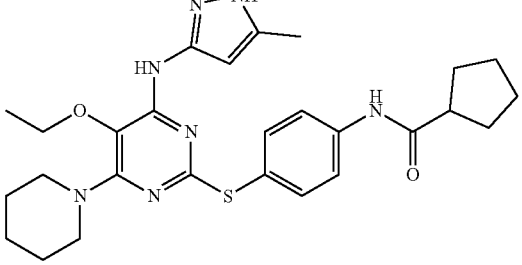 | XX |
| 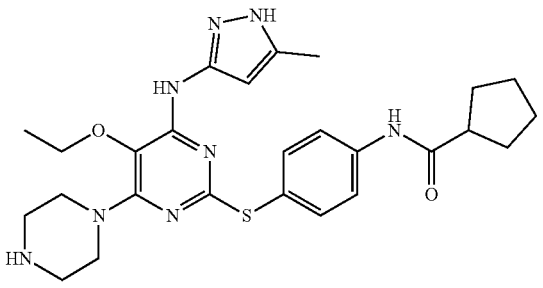 [SMILES: CCOc1c(Nc2cc(C)[nH]n2)nc(Sc2ccc(NC(=O)C3CCCC3)cc2)nc1N1CCNCC1] | XX |
| 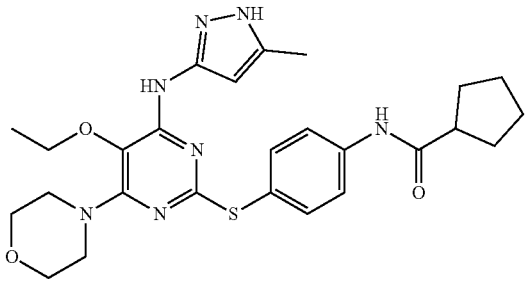 [SMILES: CCOc1c(Nc2cc(C)[nH]n2)nc(Sc2ccc(NC(=O)C3CCCC3)cc2)nc1N1CCOCC1] | XX |
| 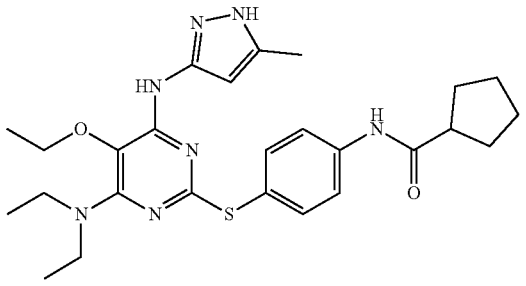 [SMILES: CCOc1c(Nc2cc(C)[nH]n2)nc(Sc2ccc(NC(=O)C3CCCC3)cc2)nc1N(CC)CC] | X |
| 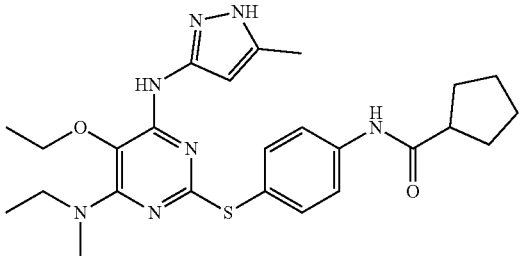 [SMILES: CCOc1c(Nc2cc(C)[nH]n2)nc(Sc2ccc(NC(=O)C3CCCC3)cc2)nc1N(C)CC] | XX |

TABLE 1-continued
| | Activity |
|---|---|
| 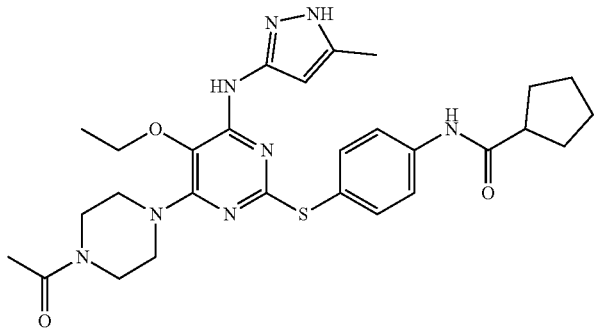 [SMILES: CCOc1c(Nc2cc(C)[nH]n2)nc(Sc2ccc(NC(=O)C3CCCC3)cc2)nc1N1CCN(C(C)=O)CC1] | XX |
| 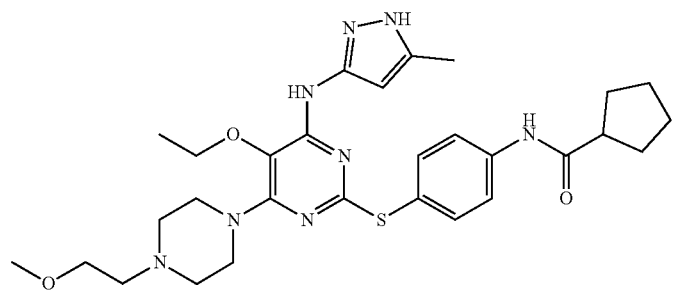 [SMILES: CCOc1c(Nc2cc(C)[nH]n2)nc(Sc2ccc(NC(=O)C3CCCC3)cc2)nc1N1CCN(CCOC)CC1] | XX |
| 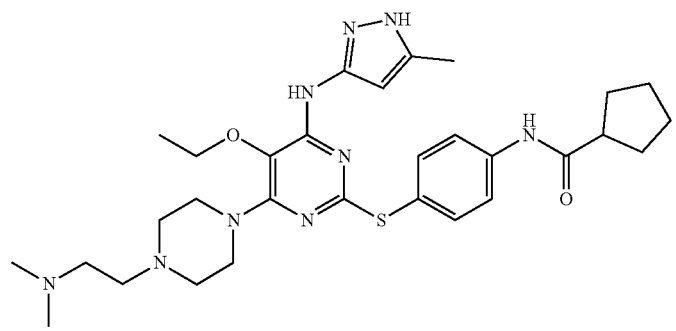 [SMILES: CCOc1c(Nc2cc(C)[nH]n2)nc(Sc2ccc(NC(=O)C3CCCC3)cc2)nc1N1CCN(CCN(C)C)CC1] | XX |
| 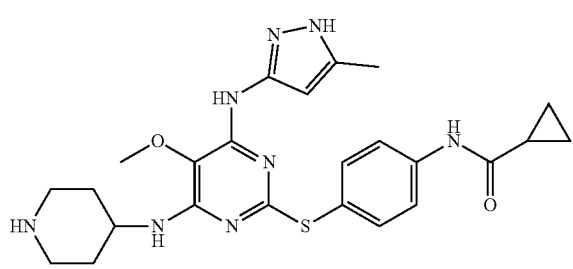 [SMILES: COc1c(Nc2cc(C)[nH]n2)nc(Sc2ccc(NC(=O)C3CC3)cc2)nc1NC1CCNCC1] | XX |
| 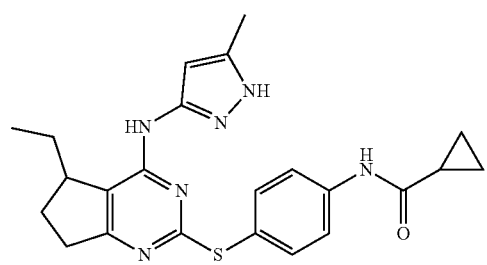 [SMILES: CCC1CCc2nc(Sc3ccc(NC(=O)C4CC4)cc3)nc(Nc3cc(C)[nH]n3)c21] | XXX |

TABLE 1-continued
| | Activity |
|---|---|
| 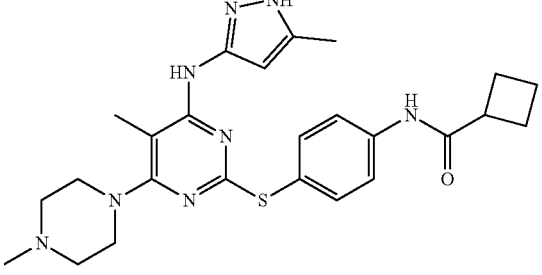 | XXX |
| 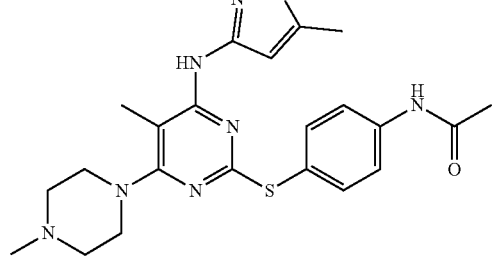 | XXX |
| 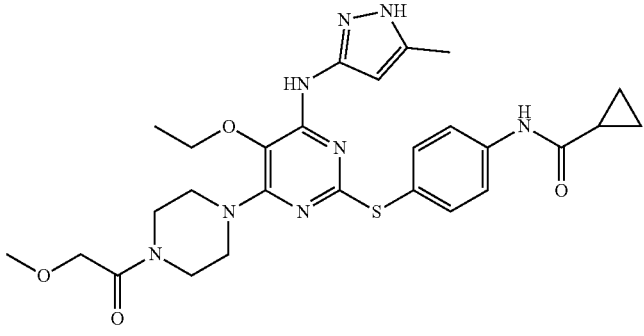 [SMILES: CCOc1c(Nc2cc(C)[nH]n2)nc(Sc2ccc(NC(=O)C3CC3)cc2)nc1N1CCN(C(=O)COC)CC1] | XX |
| 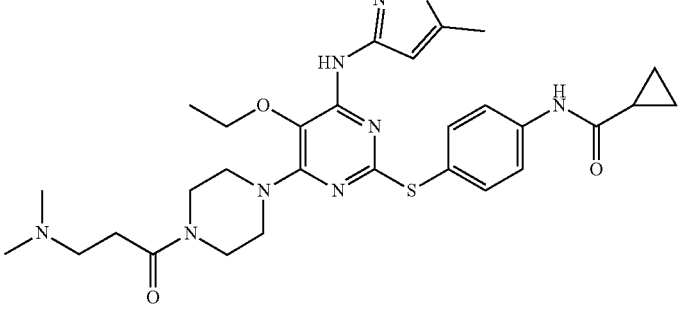 | XX |
| 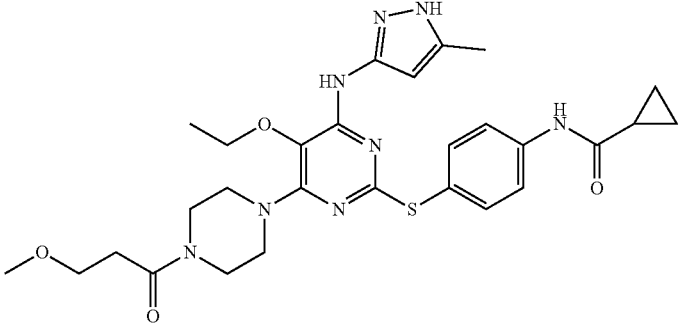 [SMILES: CCOc1c(Nc2cc(C)[nH]n2)nc(Sc2ccc(NC(=O)C3CC3)cc2)nc1N1CCN(C(=O)CCOC)CC1] | XX |

TABLE 1-continued
| | Activity |
|---|---|
| 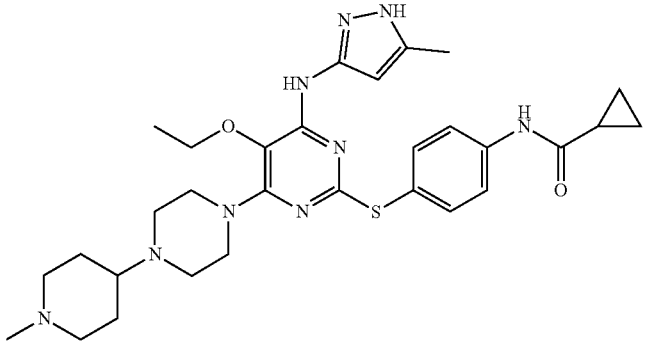 [SMILES: CCOc1c(Nc2cc(C)[nH]n2)nc(Sc2ccc(NC(=O)C3CC3)cc2)nc1N1CCN(C2CCN(C)CC2)CC1] | XX |
| 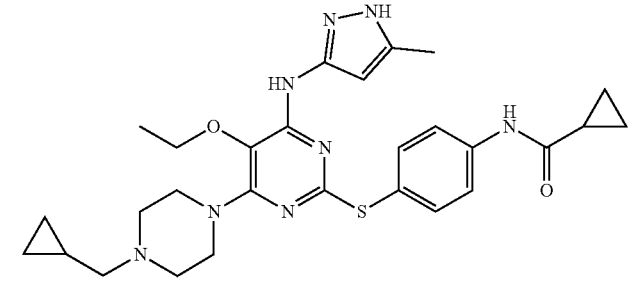 [SMILES: CCOc1c(Nc2cc(C)[nH]n2)nc(Sc2ccc(NC(=O)C3CC3)cc2)nc1N1CCN(CC2CC2)CC1] | XX |
| 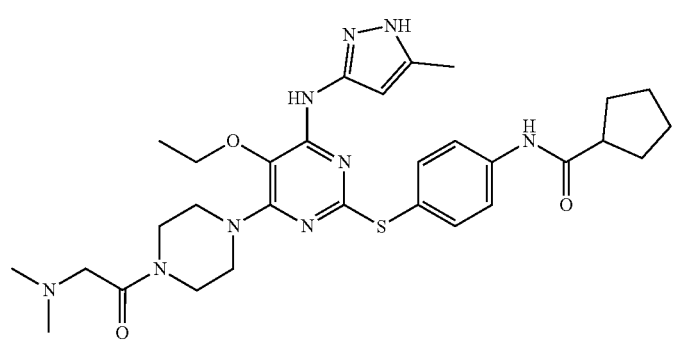 [SMILES: CCOc1c(Nc2cc(C)[nH]n2)nc(Sc2ccc(NC(=O)C3CCCC3)cc2)nc1N1CCN(C(=O)CN(C)C)CC1] | XX |
| 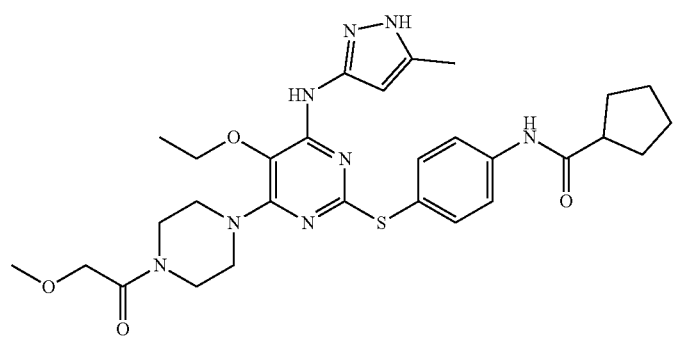 [SMILES: CCOc1c(Nc2cc(C)[nH]n2)nc(Sc2ccc(NC(=O)C3CCCC3)cc2)nc1N1CCN(C(=O)COC)CC1] | XX |

TABLE 1-continued

| Structure | Activity |
|---|---|
| (chemical structure) | XX |
| (chemical structure) | XX |
| (chemical structure) | XX |
| (chemical structure) | XX |
| (chemical structure) | XX |

TABLE 1-continued
| | Activity |
|---|---|
| 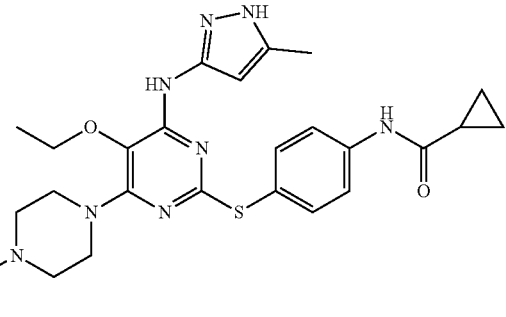 | XX |
| 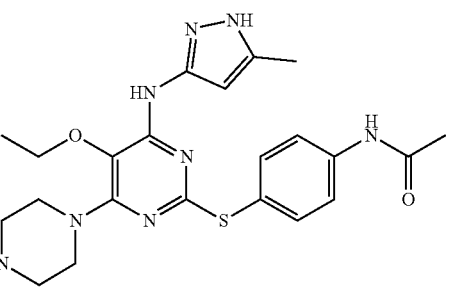 | XX |
| 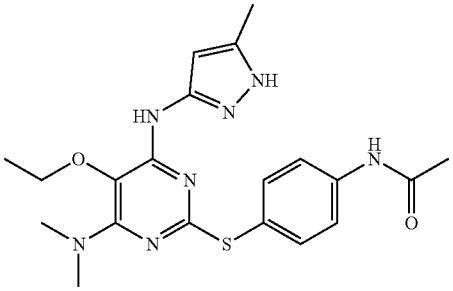 [SMILES: CCOc1c(Nc2cc(C)[nH]n2)nc(Sc2ccc(NC(C)=O)cc2)nc1N(C)C] | XX |
| 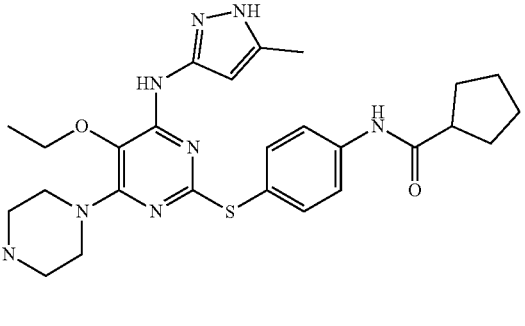 | XX |
| 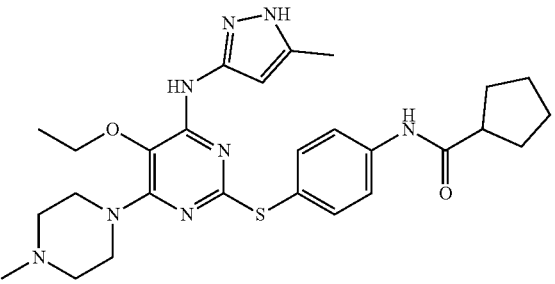 [SMILES: CCOc1c(Nc2cc(C)[nH]n2)nc(Sc2ccc(NC(=O)C3CCCC3)cc2)nc1N1CCN(C)CC1] | XX |

TABLE 1-continued
| | Activity |
|---|---|
| 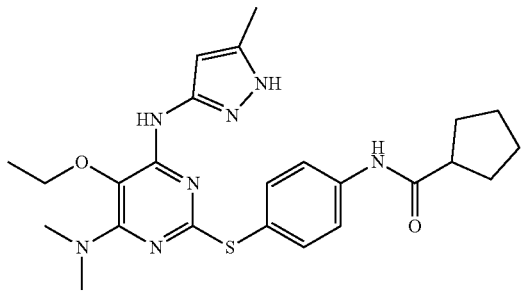 [SMILES: CCOc1c(Nc2cc(C)[nH]n2)nc(Sc2ccc(NC(=O)C3CCCC3)cc2)nc1N(C)C] | XX |
| 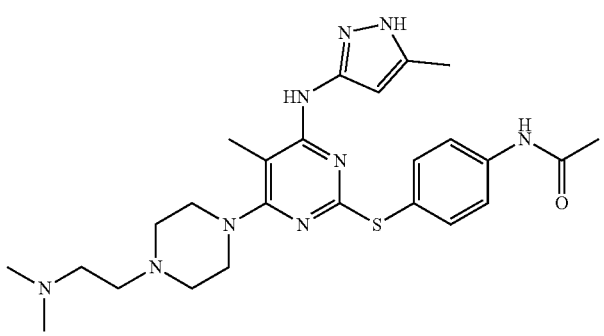 | XXX |
| 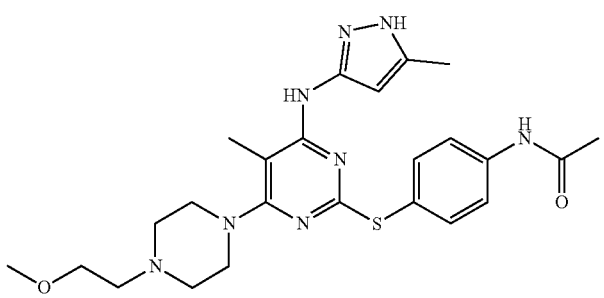 [SMILES: COCCN1CCN(c2nc(Sc3ccc(NC(C)=O)cc3)nc(Nc3cc(C)[nH]n3)c2C)CC1] | XXX |
| 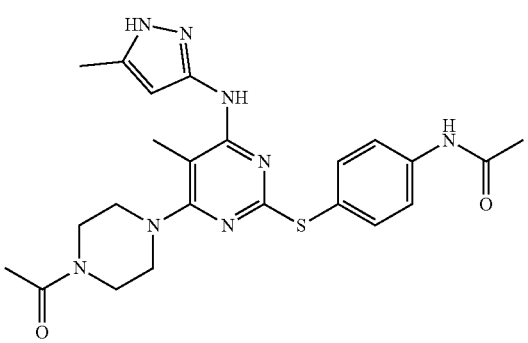 | XXX |
| 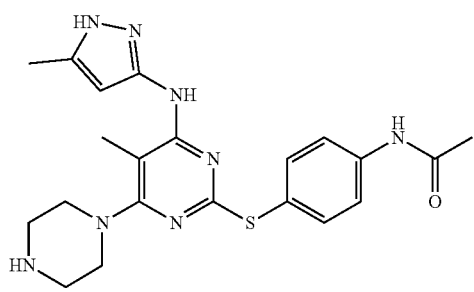 [SMILES: CC(=O)Nc1ccc(Sc2nc(Nc3cc(C)[nH]n3)c(C)c(N3CCNCC3)n2)cc1] | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 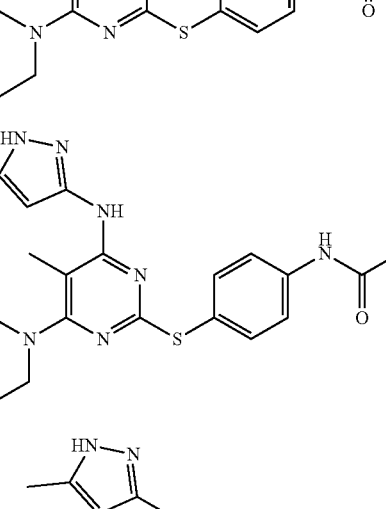 | XXX |
| 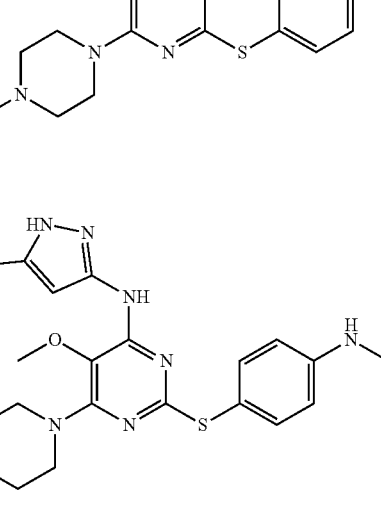 | XXX |
|  | XXX |
|  | XXX |
| 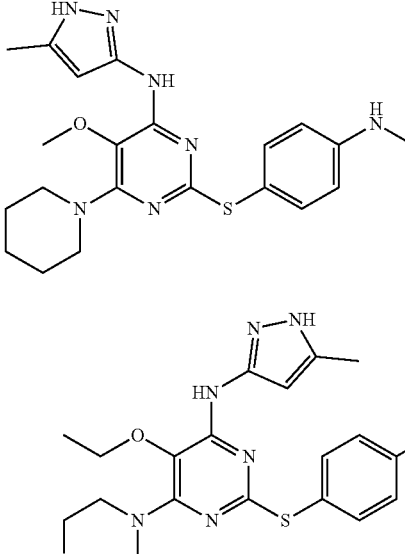 | X |

TABLE 1-continued

| | Activity |
|---|---|
| (structure) | XX |
| (structure) | XXX |
| (structure) | XXX |
| (structure) | XXX |
| (structure) | XXX |

TABLE 1-continued
| | Activity |
|---|---|
| 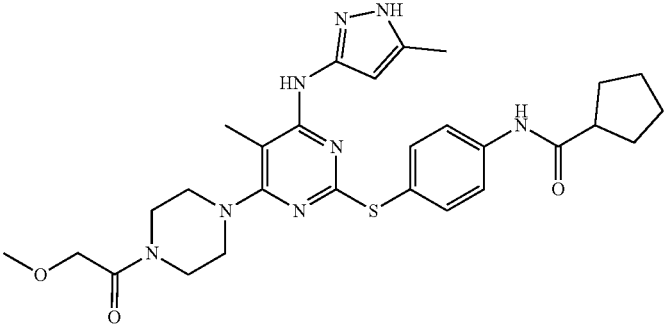 [SMILES: COCC(=O)N1CCN(c2nc(Sc3ccc(NC(=O)C4CCCC4)cc3)nc(Nc3cc(C)[nH]n3)c2C)CC1] | XXX |
| 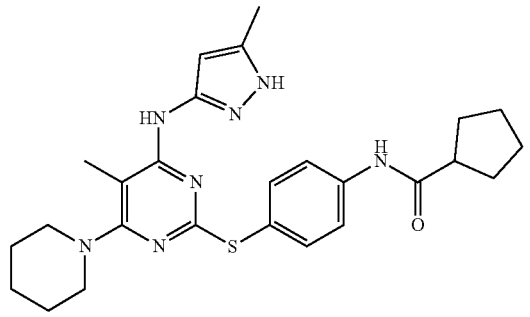 [SMILES: Cc1cc(Nc2nc(Sc3ccc(NC(=O)C4CCCC4)cc3)nc(N3CCCCC3)c2C)n[nH]1] | XXX |
| 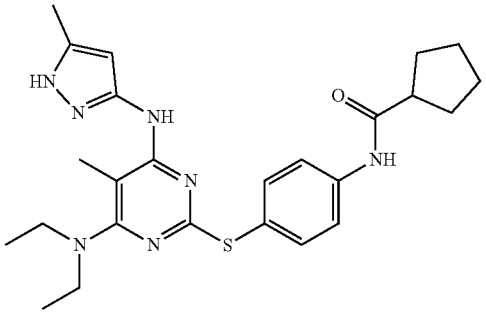 [SMILES: CCN(CC)c1nc(Sc2ccc(NC(=O)C3CCCC3)cc2)nc(Nc2cc(C)[nH]n2)c1C] | XX |
| 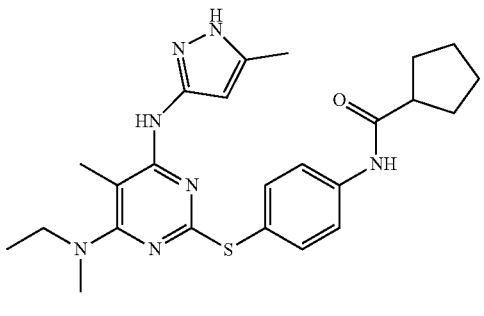 [SMILES: CCN(C)c1nc(Sc2ccc(NC(=O)C3CCCC3)cc2)nc(Nc2cc(C)[nH]n2)c1C] | XXX |
| 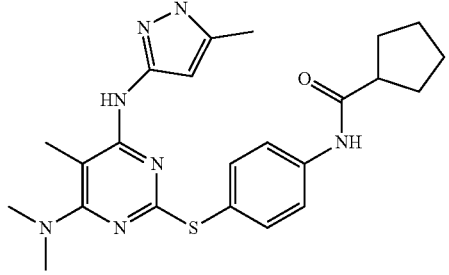 | XXX |

| | Activity |
|---|---|
| 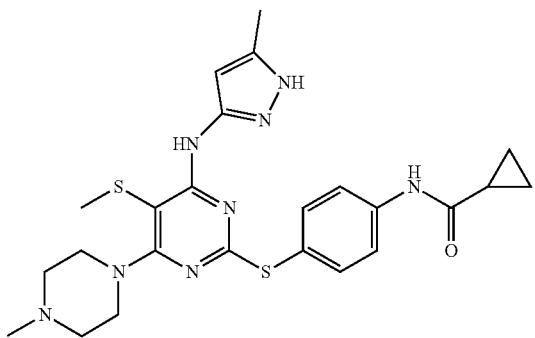 [SMILES: CSc1c(Nc2cc(C)[nH]n2)nc(Sc2ccc(NC(=O)C3CC3)cc2)nc1N1CCN(C)CC1] | XX |
| 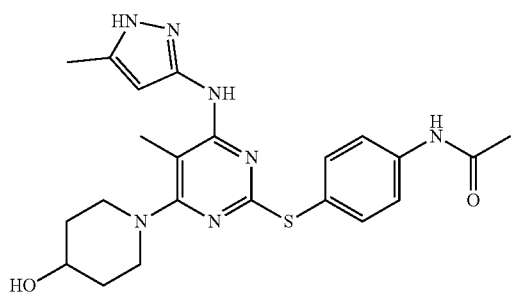 [SMILES: CC(=O)Nc1ccc(Sc2nc(Nc3cc(C)[nH]n3)c(C)c(N3CCC(O)CC3)n2)cc1] | XXX |
| 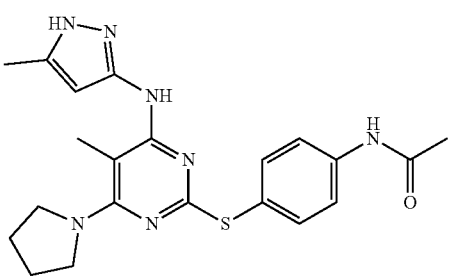 [SMILES: CC(=O)Nc1ccc(Sc2nc(Nc3cc(C)[nH]n3)c(C)c(N3CCCC3)n2)cc1] | XXX |
| 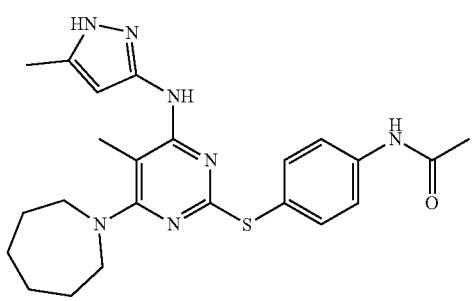 [SMILES: CC(=O)Nc1ccc(Sc2nc(Nc3cc(C)[nH]n3)c(C)c(N3CCCCCC3)n2)cc1] | XXX |
| 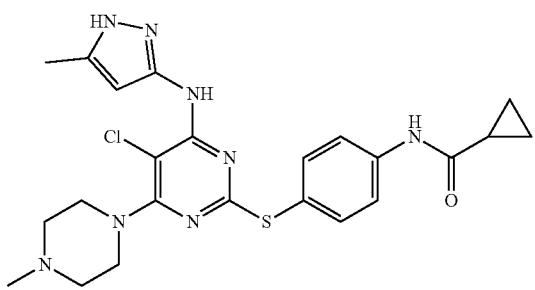 [SMILES: Cc1cc(Nc2nc(Sc3ccc(NC(=O)C4CC4)cc3)nc(N3CCN(C)CC3)c2Cl)n[nH]1] | XX |

TABLE 1-continued
| | Activity |
|---|---|
| 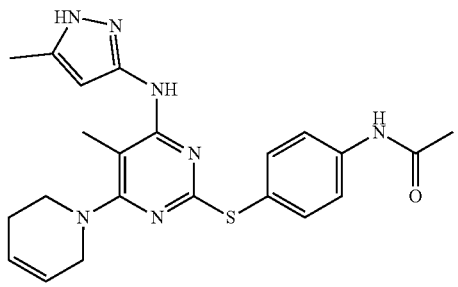 [SMILES: CC(=O)Nc1ccc(Sc2nc(Nc3cc(C)[nH]n3)c(C)c(N3CC=CCC3)n2)cc1] | XXX |
| 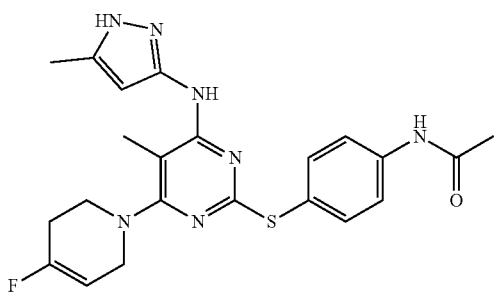 [SMILES: CC(=O)Nc1ccc(Sc2nc(Nc3cc(C)[nH]n3)c(C)c(N3CC=C(F)CC3)n2)cc1] | XXX |
| 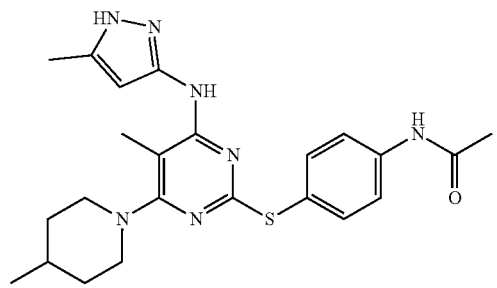 [SMILES: CC(=O)Nc1ccc(Sc2nc(Nc3cc(C)[nH]n3)c(C)c(N3CCC(C)CC3)n2)cc1] | XXX |
| 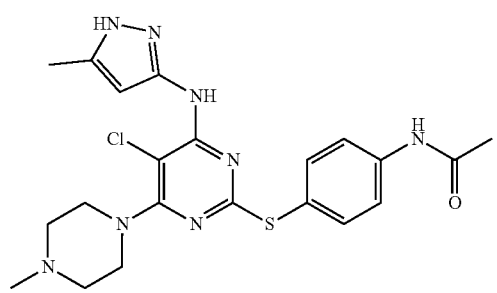 | XXX |
| 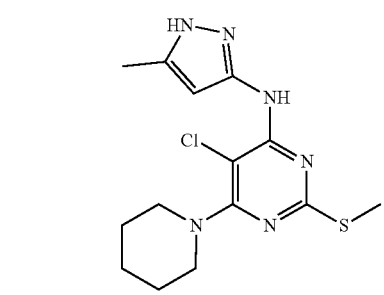 [SMILES: CSc1nc(Nc2cc(C)[nH]n2)c(Cl)c(N2CCCCC2)n1] | XXX |

TABLE 1-continued

| Structure | Activity |
|---|---|
| (pyrazole-NH-pyrimidine with methyl, piperidine, S-phenyl) | XXX |
| (pyrazole-NH-pyrimidine with methyl, piperidine, S-(4-methylphenyl)) | XXX |
| (pyrazole-NH-pyrimidine with methyl, piperidine, S-(4-aminophenyl)) | XXX |
| (pyrazole-NH-pyrimidine with methyl, piperidine, S-phenyl-NH-C(O)-NH-methyl) | XXX |
| (pyrazole-NH-pyrimidine with methyl, piperidine, S-phenyl-NH-C(O)-O-methyl) | XXX |

TABLE 1-continued
| | Activity |
|---|---|
| 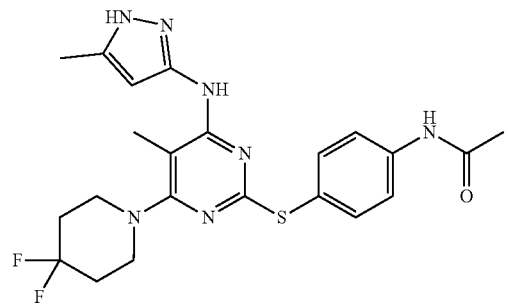 [SMILES: CC(=O)Nc1ccc(Sc2nc(Nc3cc(C)[nH]n3)c(C)c(N3CCC(F)(F)CC3)n2)cc1] | XXX |
| 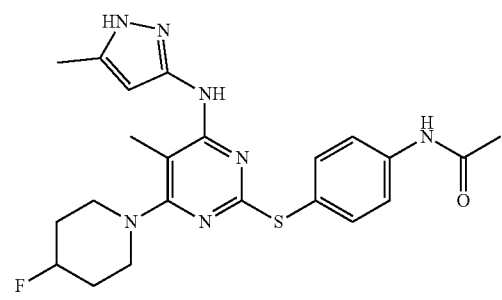 [SMILES: CC(=O)Nc1ccc(Sc2nc(Nc3cc(C)[nH]n3)c(C)c(N3CCC(F)CC3)n2)cc1] | XXX |
| 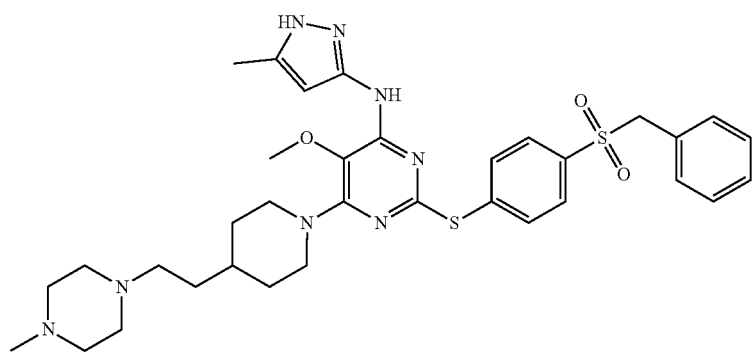 | XXX |
| 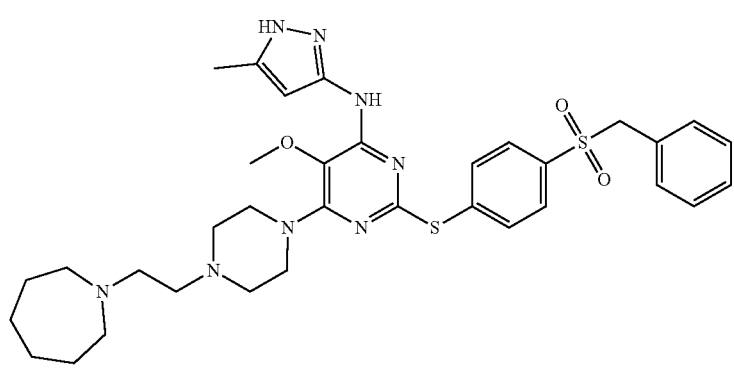 [SMILES: COc1c(Nc2cc(C)[nH]n2)nc(Sc2ccc(S(=O)(=O)Cc3ccccc3)cc2)nc1N1CCN(CCN2CCCCCC2)CC1] | XXX |

TABLE 1-continued
| | Activity |
|---|---|
| 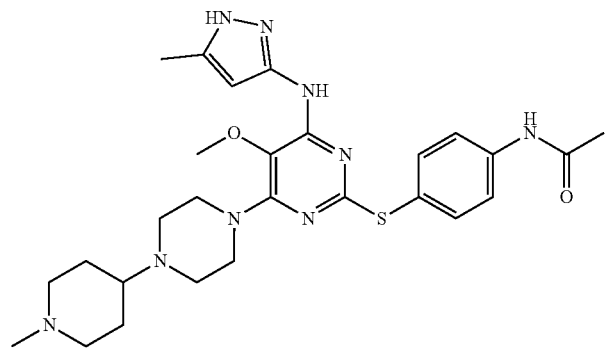 [SMILES: COc1c(Nc2cc(C)[nH]n2)nc(Sc2ccc(NC(C)=O)cc2)nc1N1CCN(C2CCN(C)CC2)CC1] | XXX |
| 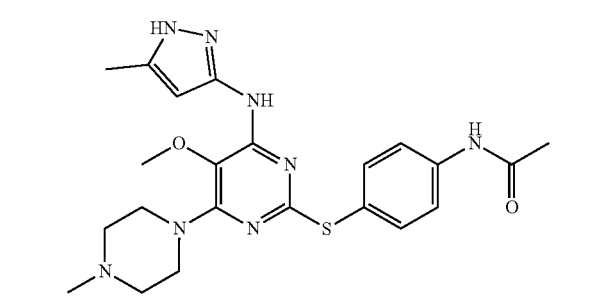 [SMILES: COc1c(Nc2cc(C)[nH]n2)nc(Sc2ccc(NC(C)=O)cc2)nc1N1CCN(C)CC1] | XXX |
| 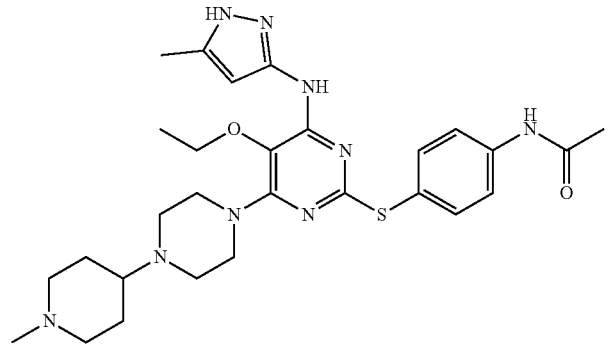 [SMILES: CCOc1c(Nc2cc(C)[nH]n2)nc(Sc2ccc(NC(C)=O)cc2)nc1N1CCN(C2CCN(C)CC2)CC1] | XX |
| 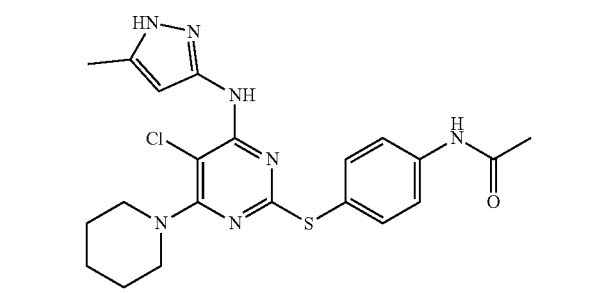 [SMILES: CC(=O)Nc1ccc(Sc2nc(Nc3cc(C)[nH]n3)c(Cl)c(N3CCCCC3)n2)cc1] | XXX |
| 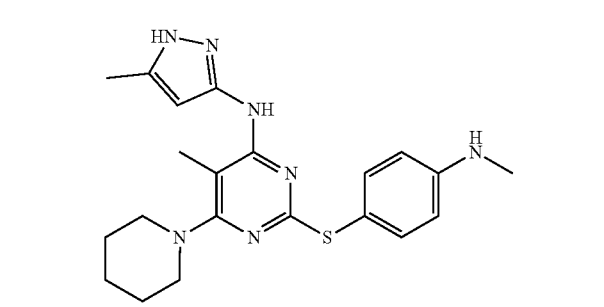 | XXX |

TABLE 1-continued
| | Activity |
|---|---|
| 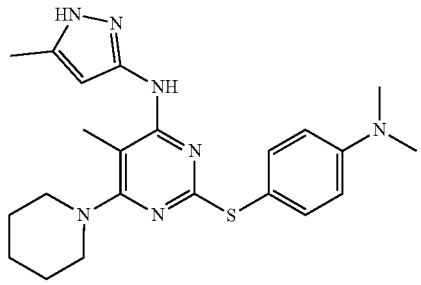 [SMILES: Cc1cc(Nc2nc(Sc3ccc(N(C)C)cc3)nc(N3CCCCC3)c2C)n[nH]1] | XXX |
| 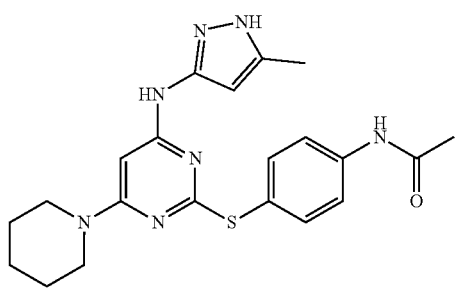 [SMILES: CC(=O)Nc1ccc(Sc2nc(Nc3cc(C)[nH]n3)cc(N3CCCCC3)n2)cc1] | XXX |
| 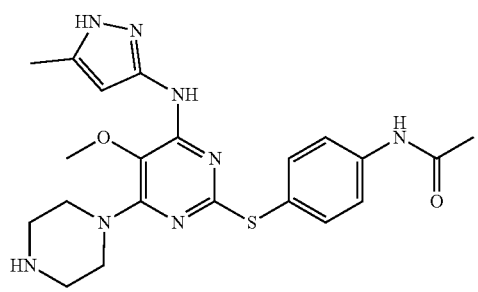 [SMILES: COc1c(Nc2cc(C)[nH]n2)nc(Sc2ccc(NC(C)=O)cc2)nc1N1CCNCC1] | XXX |
| 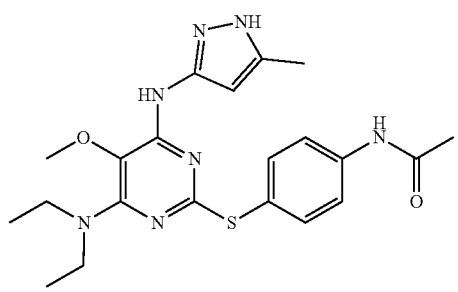 [SMILES: CCN(CC)c1nc(Sc2ccc(NC(C)=O)cc2)nc(Nc2cc(C)[nH]n2)c1OC] | XXX |
| 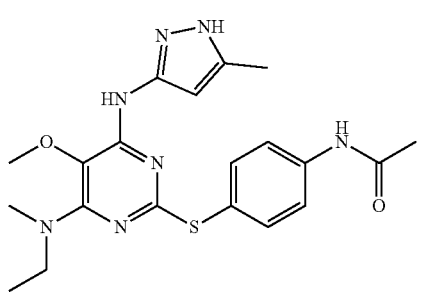 [SMILES: CCN(C)c1nc(Sc2ccc(NC(C)=O)cc2)nc(Nc2cc(C)[nH]n2)c1OC] | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued

| Structure | Activity |
|---|---|
| (chemical structure) | XXX |
| (chemical structure) | XX |
| (chemical structure) | XX |
| (chemical structure) | XXX |
| (chemical structure) | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 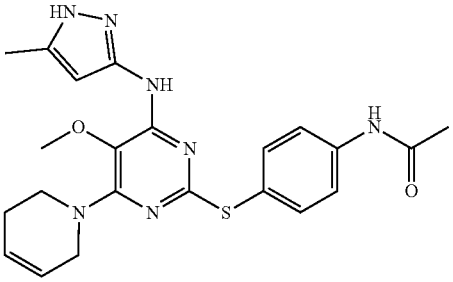 [SMILES: COc1c(Nc2cc(C)[nH]n2)nc(Sc2ccc(NC(C)=O)cc2)nc1N1CC=CCC1] | XXX |
| 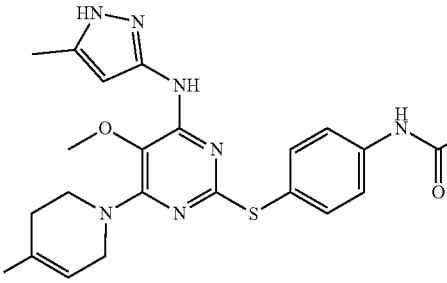 | XXX |
| 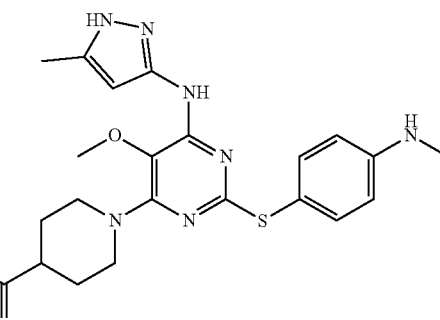 | XXX |
| 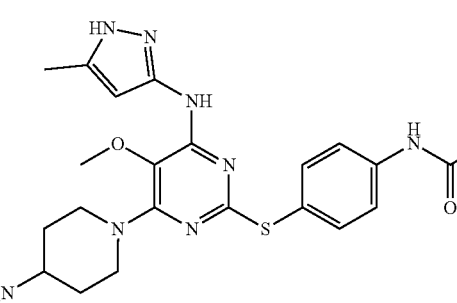 | XXX |
| 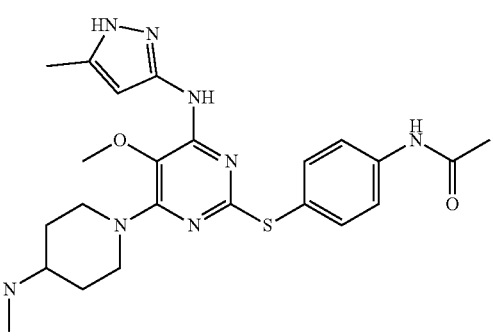 | XXX |

TABLE 1-continued

| Structure | Activity |
|---|---|
| (chemical structure) | XXX |
| (chemical structure) | XX |
| (chemical structure) | XXX |
| (chemical structure) | XXX |
| (chemical structure) | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 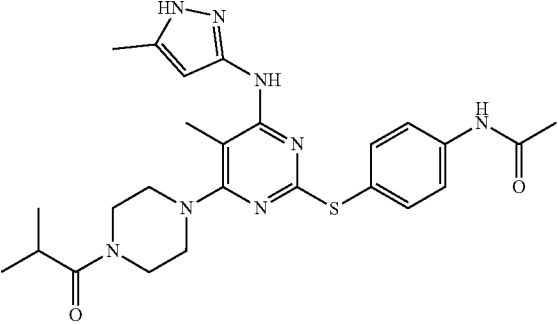 [SMILES: CC(=O)Nc1ccc(Sc2nc(Nc3cc(C)[nH]n3)c(C)c(N3CCN(C(=O)C(C)C)CC3)n2)cc1] | XXX |
| 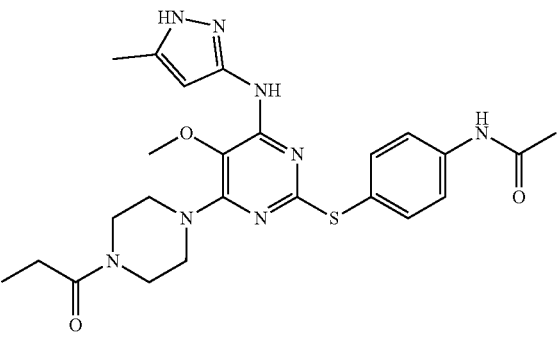 [SMILES: CCC(=O)N1CCN(c2nc(Sc3ccc(NC(C)=O)cc3)nc(Nc3cc(C)[nH]n3)c2OC)CC1] | XXX |
| 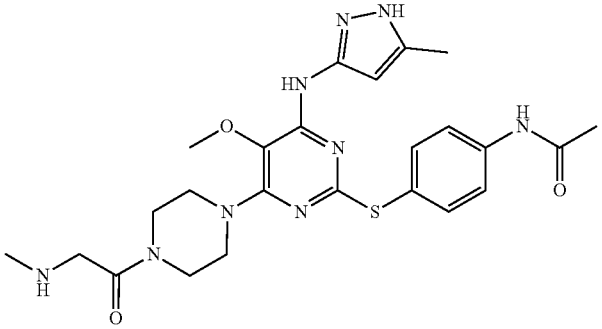 | XXX |
| 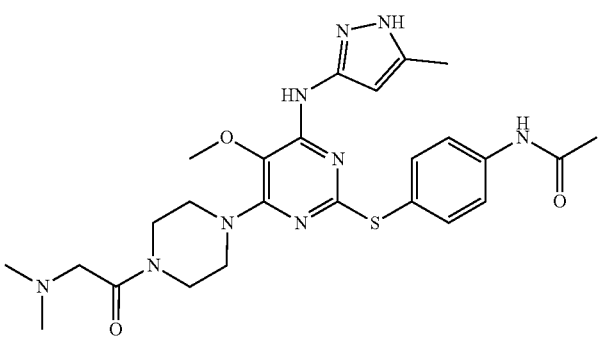 [SMILES: COc1c(Nc2cc(C)[nH]n2)nc(Sc2ccc(NC(C)=O)cc2)nc1N1CCN(C(=O)CN(C)C)CC1] | XXX |

TABLE 1-continued

| Structure | Activity |
|---|---|
| (chemical structure) | xxx |
| (chemical structure) | xxx |
| (chemical structure) | xxx |
| (chemical structure) | xxx |

TABLE 1-continued
| | Activity |
|---|---|
| 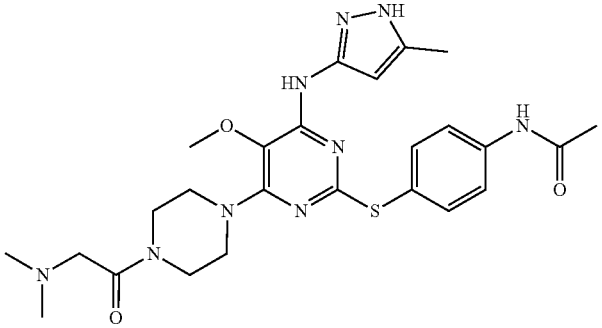 [SMILES: COc1c(Nc2cc(C)[nH]n2)nc(Sc2ccc(NC(C)=O)cc2)nc1N1CCN(C(=O)CN(C)C)CC1] | XXX |
| 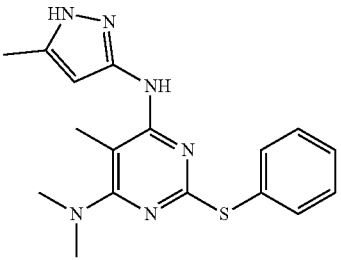 [SMILES: Cc1cc(Nc2nc(Sc3ccccc3)nc(N(C)C)c2C)n[nH]1] | XXX |
| 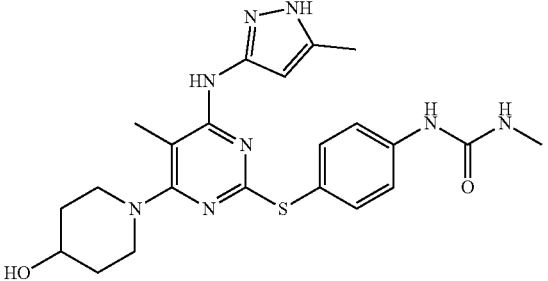 [SMILES: CNC(=O)Nc1ccc(Sc2nc(Nc3cc(C)[nH]n3)c(C)c(N3CCC(O)CC3)n2)cc1] | XXX |
| 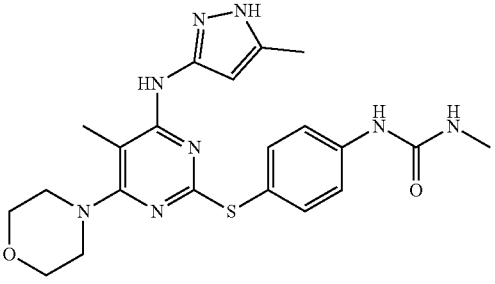 [SMILES: CNC(=O)Nc1ccc(Sc2nc(Nc3cc(C)[nH]n3)c(C)c(N3CCOCC3)n2)cc1] | XXX |
| 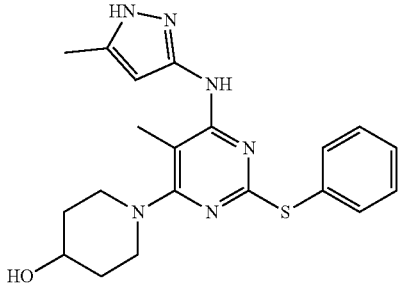 [SMILES: Cc1cc(Nc2nc(Sc3ccccc3)nc(N3CCC(O)CC3)c2C)n[nH]1] | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 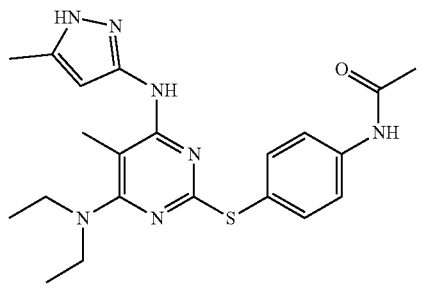 [SMILES: CCN(CC)c1nc(Sc2ccc(NC(C)=O)cc2)nc(Nc2cc(C)[nH]n2)c1C] | XXX |
| 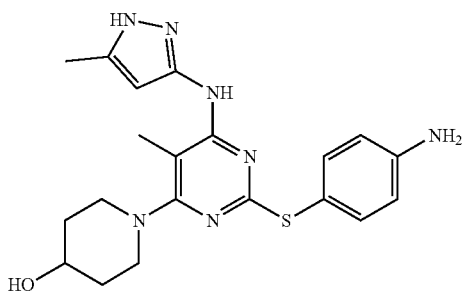 [SMILES: Cc1cc(Nc2nc(Sc3ccc(N)cc3)nc(N3CCC(O)CC3)c2C)n[nH]1] | XXX |
| 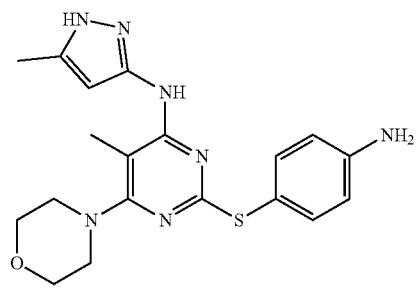 [SMILES: Cc1cc(Nc2nc(Sc3ccc(N)cc3)nc(N3CCOCC3)c2C)n[nH]1] | XXX |
| 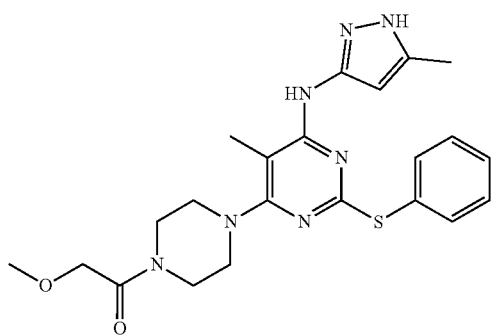 [SMILES: COCC(=O)N1CCN(c2nc(Sc3ccccc3)nc(Nc3cc(C)[nH]n3)c2C)CC1] | XXX |
| 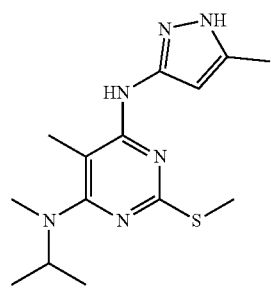 | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 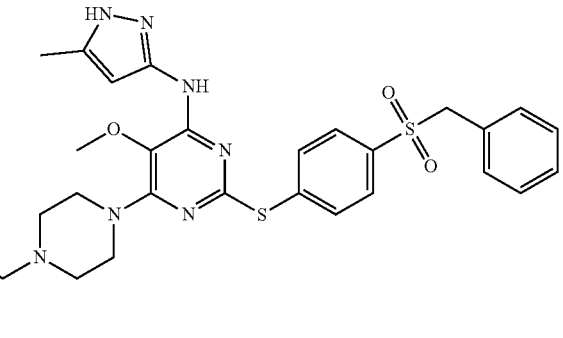 | XXX |
| 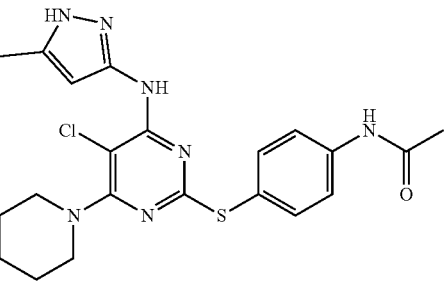 | XXX |
| 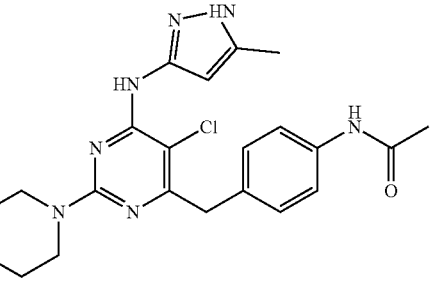 | XXX |
| 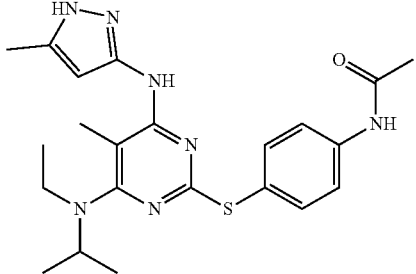 [SMILES: CCN(c1nc(Sc2ccc(NC(C)=O)cc2)nc(Nc2cc(C)[nH]n2)c1C)C(C)C] | XXX |
| 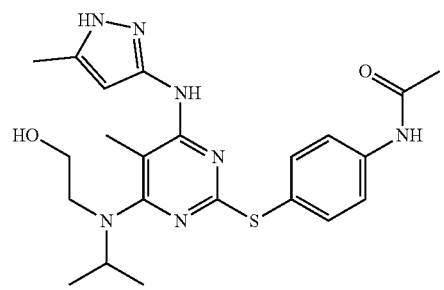 [SMILES: CC(=O)Nc1ccc(Sc2nc(Nc3cc(C)[nH]n3)c(C)c(N(CCO)C(C)C)n2)cc1] | XXX |

TABLE 1-continued
| | Activity |
|---|---|
| 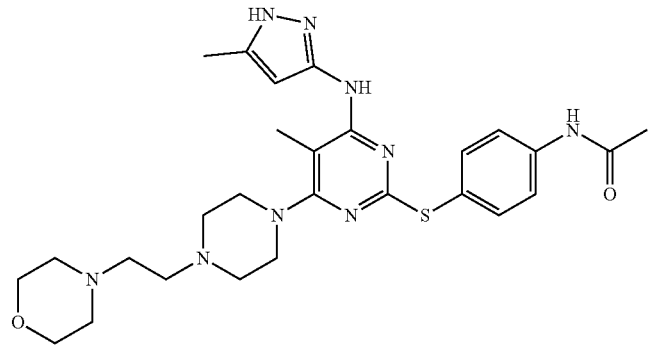 [SMILES: CC(=O)Nc1ccc(Sc2nc(Nc3cc(C)[nH]n3)c(C)c(N3CCN(CCN4CCOCC4)CC3)n2)cc1] | XXX |
| 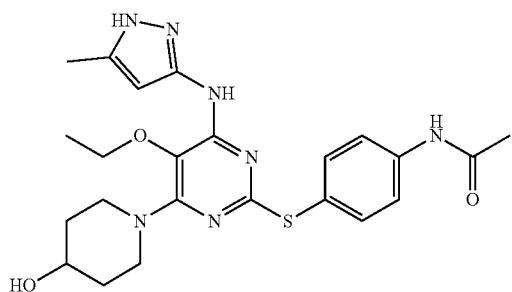 [SMILES: CCOc1c(Nc2cc(C)[nH]n2)nc(Sc2ccc(NC(C)=O)cc2)nc1N1CCC(O)CC1] | XXX |
| 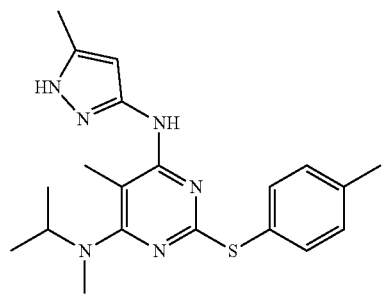 [SMILES: Cc1ccc(Sc2nc(Nc3cc(C)[nH]n3)c(C)c(N(C)C(C)C)n2)cc1] | XXX |
| 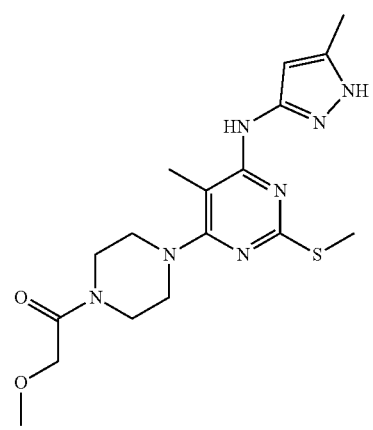 [SMILES: COCC(=O)N1CCN(c2nc(SC)nc(Nc3cc(C)[nH]n3)c2C)CC1] | XXX |

TABLE 1-continued
| | Activity |
|---|---|
| 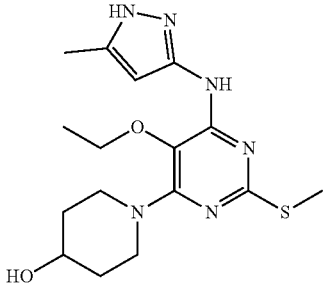 [SMILES: CCOc1c(Nc2cc(C)[nH]n2)nc(SC)nc1N1CCC(O)CC1] | XX |
| 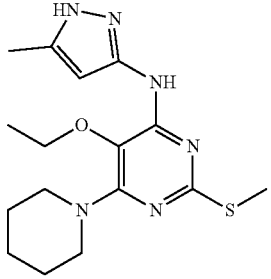 [SMILES: CCOc1c(Nc2cc(C)[nH]n2)nc(SC)nc1N1CCCCC1] | XX |
| 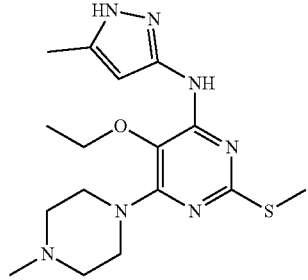 | XX |
| 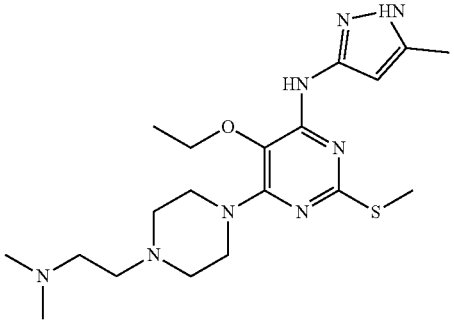 | XX |
| 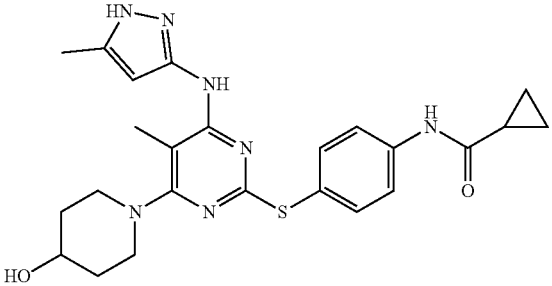 [SMILES: Cc1cc(Nc2nc(Sc3ccc(NC(=O)C4CC4)cc3)nc(N3CCC(O)CC3)c2C)n[nH]1] | XXX |

TABLE 1-continued
| | Activity |
|---|---|
| 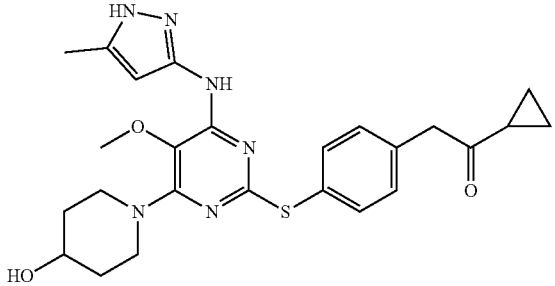 [SMILES: COc1c(Nc2cc(C)[nH]n2)nc(Sc2ccc(CC(=O)C3CC3)cc2)nc1N1CCC(O)CC1] | XXX |
| 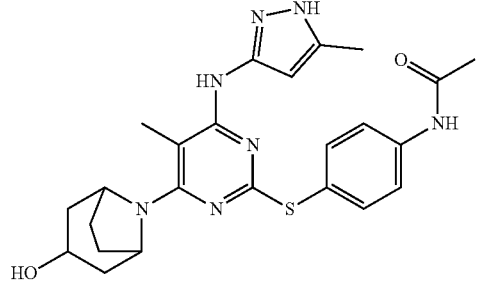 [SMILES: CC(=O)Nc1ccc(Sc2nc(Nc3cc(C)[nH]n3)c(C)c(N3C4CCC3CC(O)C4)n2)cc1] | XXX |
| 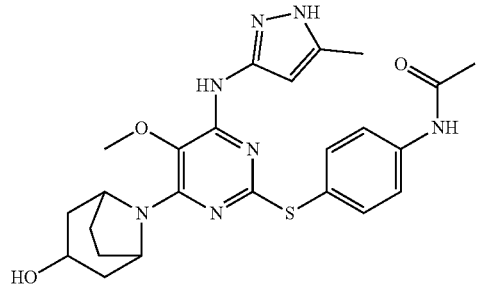 [SMILES: COc1c(Nc2cc(C)[nH]n2)nc(Sc2ccc(NC(C)=O)cc2)nc1N1C2CCC1CC(O)C2] | XXX |
| 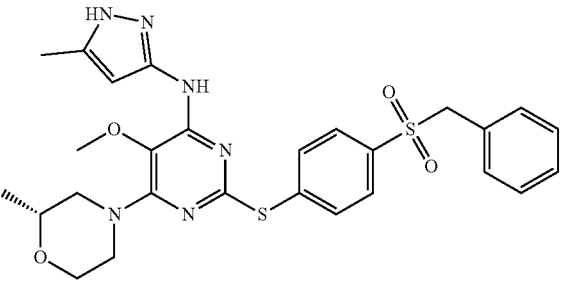 [SMILES: COc1c(Nc2cc(C)[nH]n2)nc(Sc2ccc(S(=O)(=O)Cc3ccccc3)cc2)nc1N1CCO[C@H](C)C1] | XXX |
| 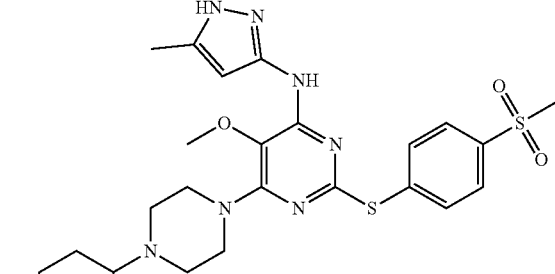 | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 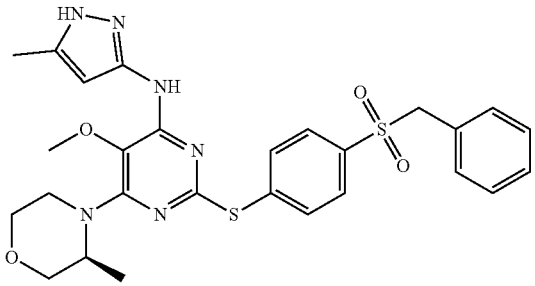 [SMILES: COc1c(Nc2cc(C)[nH]n2)nc(Sc2ccc(S(=O)(=O)Cc3ccccc3)cc2)nc1N1CCOC[C@@H]1C] | XXX |
| 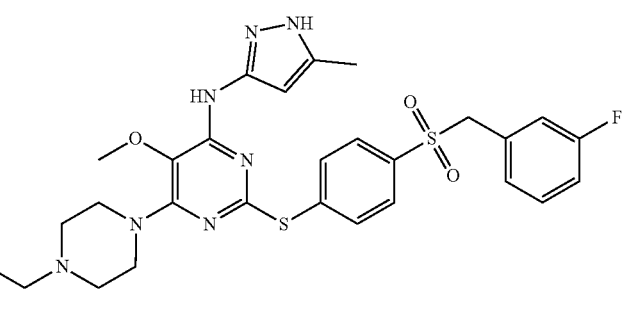 | XXX |
| 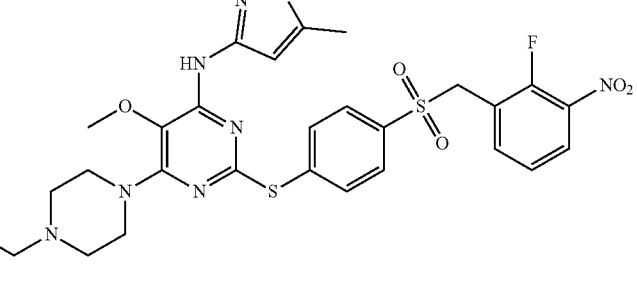 | XXX |
| 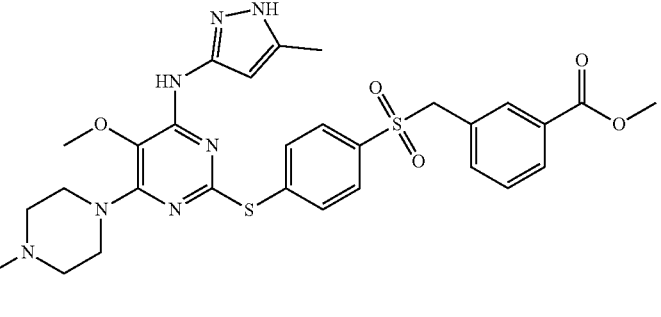 | XXX |
| 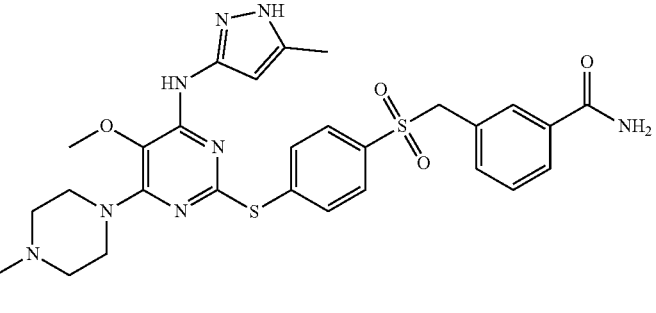 | XXX |

TABLE 1-continued
| | Activity |
|---|---|
| 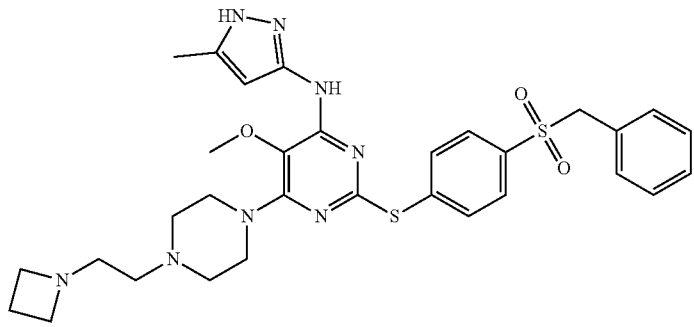 [SMILES: COc1c(Nc2cc(C)[nH]n2)nc(Sc2ccc(S(=O)(=O)Cc3ccccc3)cc2)nc1N1CCN(CCN2CCC2)CC1] | XXX |
| 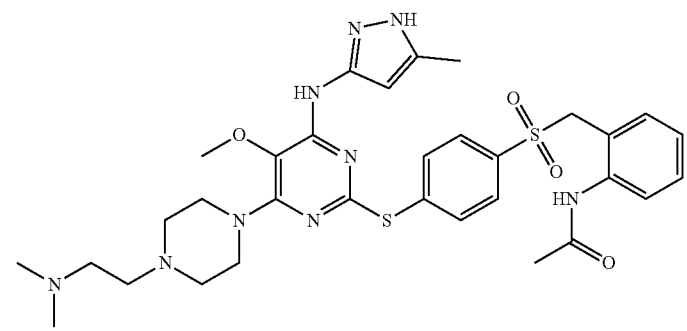 [SMILES: COc1c(Nc2cc(C)[nH]n2)nc(Sc2ccc(S(=O)(=O)Cc3ccccc3NC(C)=O)cc2)nc1N1CCN(CCN(C)C)CC1] | XXX |
| 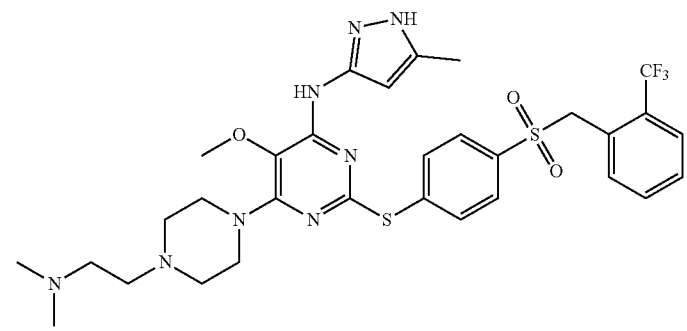 | XXX |
| 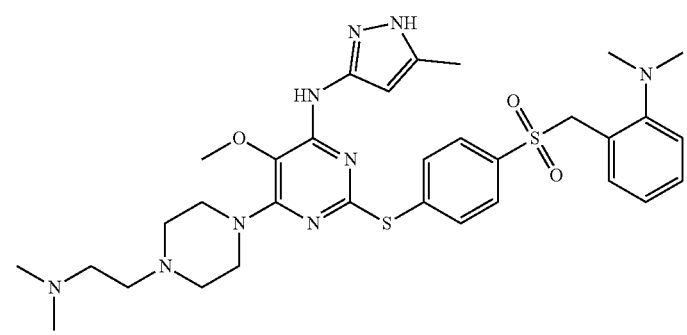 | XXX |

TABLE 1-continued
| | Activity |
|---|---|
| 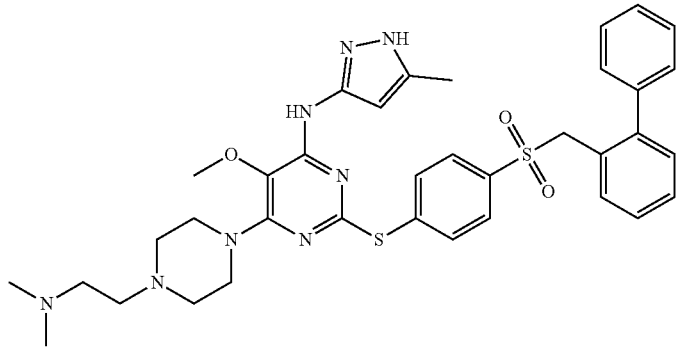 [SMILES: COc1c(Nc2cc(C)[nH]n2)nc(Sc2ccc(S(=O)(=O)Cc3ccccc3-c3ccccc3)cc2)nc1N1CCN(CCN(C)C)CC1] | XXX |
| 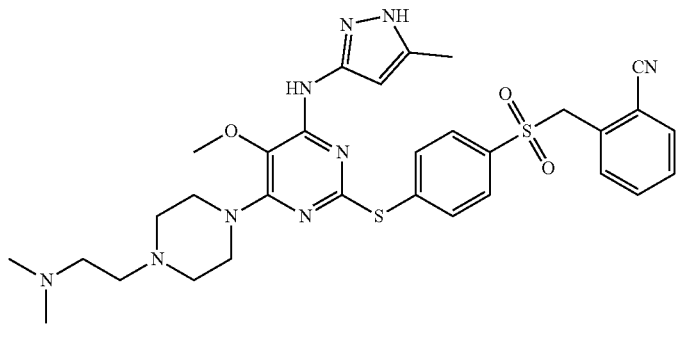 [SMILES: COc1c(Nc2cc(C)[nH]n2)nc(Sc2ccc(S(=O)(=O)Cc3ccccc3C#N)cc2)nc1N1CCN(CCN(C)C)CC1] | XXX |
| 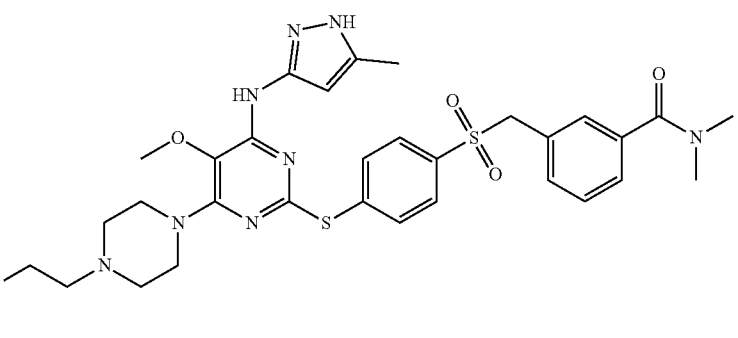 | XXX |
| 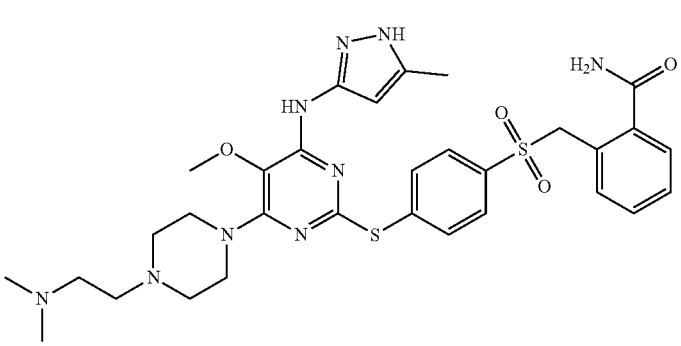 [SMILES: COc1c(Nc2cc(C)[nH]n2)nc(Sc2ccc(S(=O)(=O)Cc3ccccc3C(N)=O)cc2)nc1N1CCN(CCN(C)C)CC1] | XXX |

TABLE 1-continued
| | Activity |
|---|---|
| 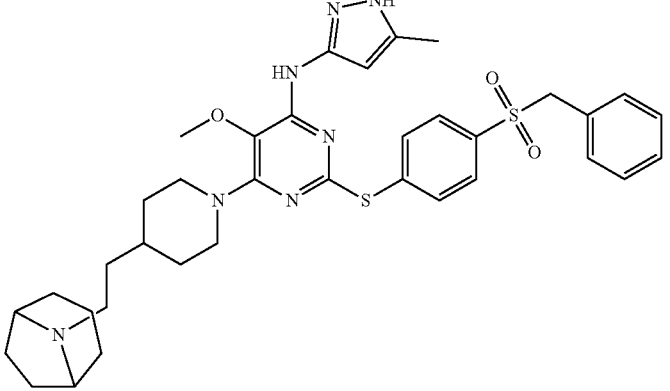 | XXX |
| 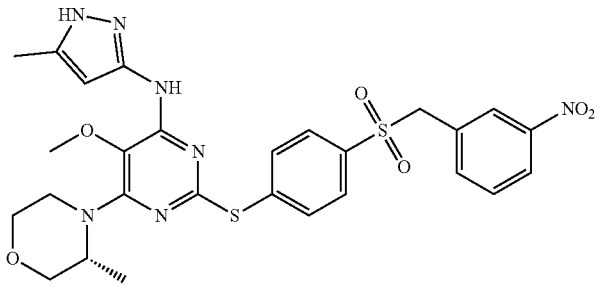 [SMILES: COc1c(Nc2cc(C)[nH]n2)nc(Sc2ccc(S(=O)(=O)Cc3cccc([N+](=O)[O-])c3)cc2)nc1N1CCOC[C@H]1C] | XXX |
| 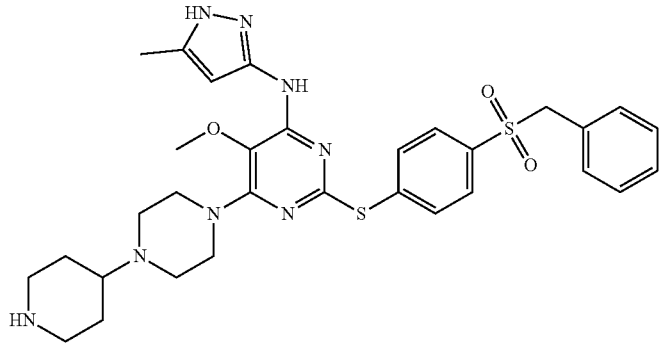 [SMILES: COc1c(Nc2cc(C)[nH]n2)nc(Sc2ccc(S(=O)(=O)Cc3ccccc3)cc2)nc1N1CCN(C2CCNCC2)CC1] | XXX |
| 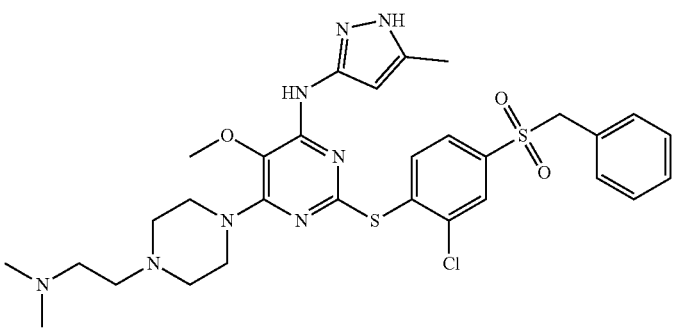 [SMILES: COc1c(Nc2cc(C)[nH]n2)nc(Sc2ccc(S(=O)(=O)Cc3ccccc3)cc2Cl)nc1N1CCN(CCN(C)C)CC1] | XXX |

TABLE 1-continued
| | Activity |
|---|---|
| 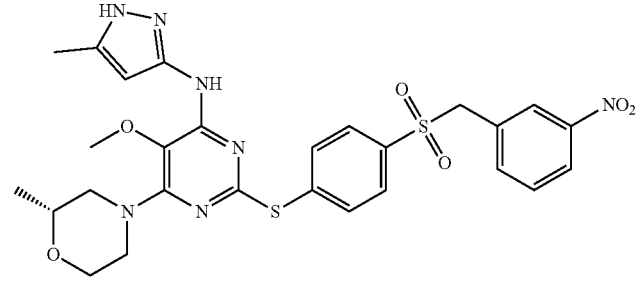 [SMILES: COc1c(Nc2cc(C)[nH]n2)nc(Sc2ccc(S(=O)(=O)Cc3cccc([N+](=O)[O-])c3)cc2)nc1N1CCO[C@H](C)C1] | XXX |
| 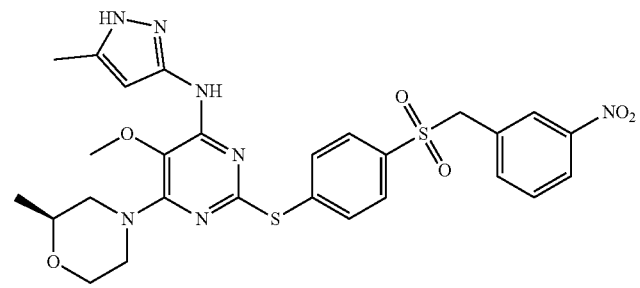 [SMILES: COc1c(Nc2cc(C)[nH]n2)nc(Sc2ccc(S(=O)(=O)Cc3cccc([N+](=O)[O-])c3)cc2)nc1N1CCO[C@@H](C)C1] | XXX |
| 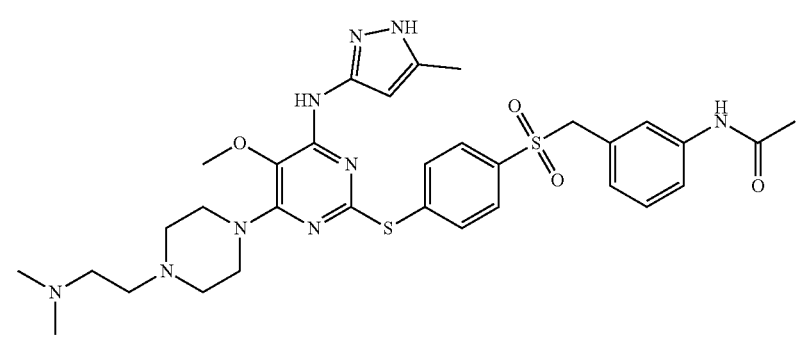 [SMILES: COc1c(Nc2cc(C)[nH]n2)nc(Sc2ccc(S(=O)(=O)Cc3cccc(NC(C)=O)c3)cc2)nc1N1CCN(CCN(C)C)CC1] | XXX |
| 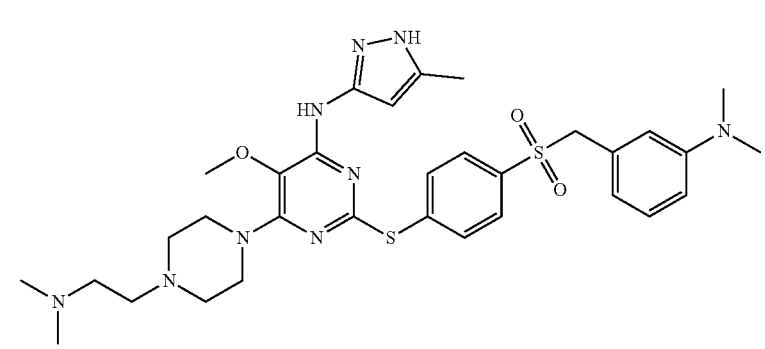 | XXX |
| 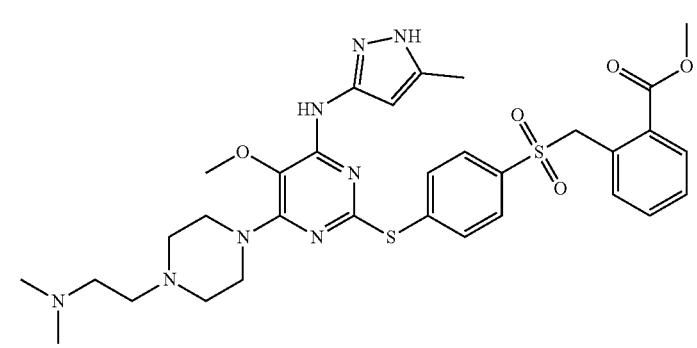 | XXX |

TABLE 1-continued
| Structure | Activity |
|---|---|
| 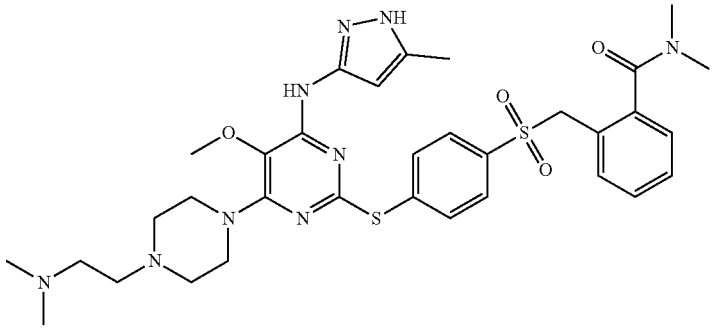 | XXX |
| 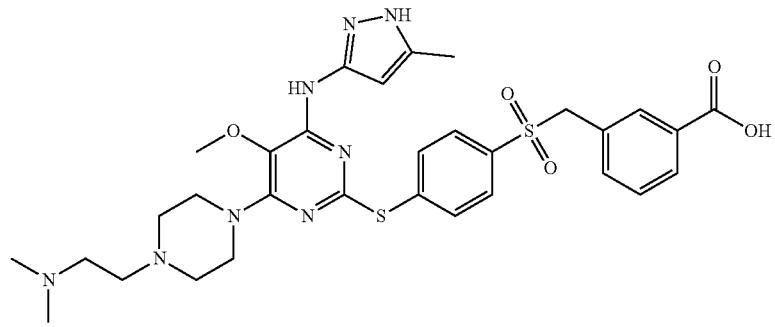 [SMILES: COc1c(Nc2cc(C)[nH]n2)nc(Sc2ccc(S(=O)(=O)Cc3cccc(C(=O)O)c3)cc2)nc1N1CCN(CCN(C)C)CC1] | XXX |
| 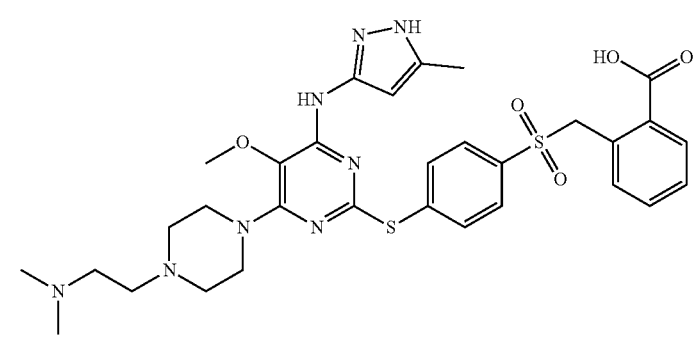 [SMILES: COc1c(Nc2cc(C)[nH]n2)nc(Sc2ccc(S(=O)(=O)Cc3ccccc3C(=O)O)cc2)nc1N1CCN(CCN(C)C)CC1] | XXX |
| 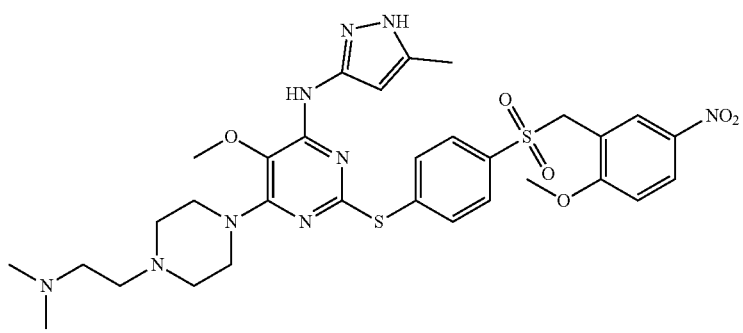 [SMILES: COc1ccc([N+](=O)[O-])cc1CS(=O)(=O)c1ccc(Sc2nc(Nc3cc(C)[nH]n3)c(OC)c(N3CCN(CCN(C)C)CC3)n2)cc1] | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 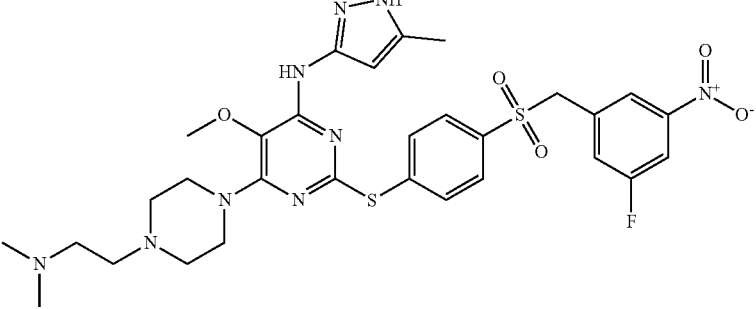 | XXX |
| 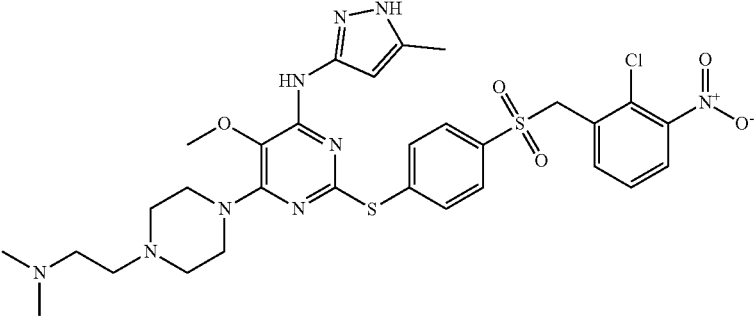 [SMILES: COc1c(Nc2cc(C)[nH]n2)nc(Sc2ccc(S(=O)(=O)Cc3cccc([N+](=O)[O-])c3Cl)cc2)nc1N1CCN(CCN(C)C)CC1] | XXX |
| 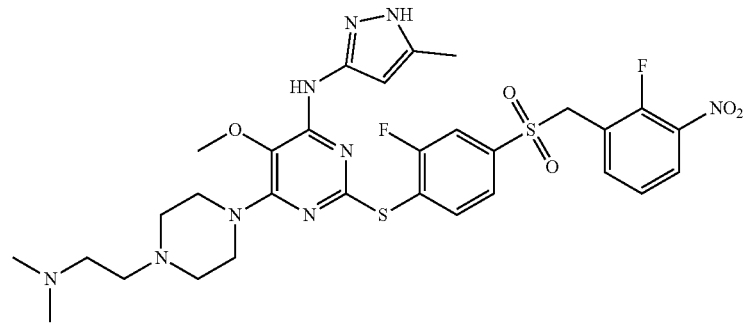 [SMILES: COc1c(Nc2cc(C)[nH]n2)nc(Sc2ccc(S(=O)(=O)Cc3cccc([N+](=O)[O-])c3F)cc2F)nc1N1CCN(CCN(C)C)CC1] | XXX |
| 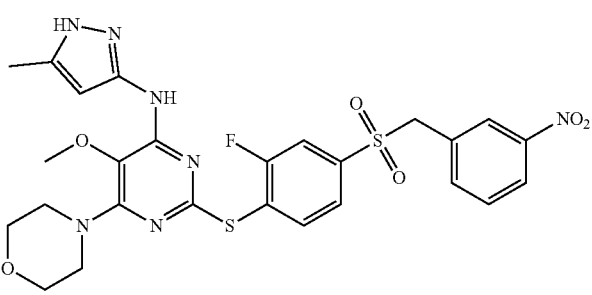 [SMILES: COc1c(Nc2cc(C)[nH]n2)nc(Sc2ccc(S(=O)(=O)Cc3cccc([N+](=O)[O-])c3)cc2F)nc1N1CCOCC1] | XXX |
| 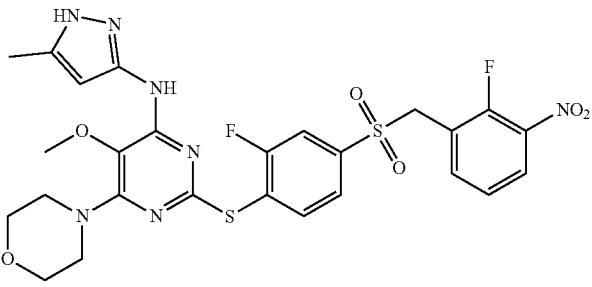 [SMILES: COc1c(Nc2cc(C)[nH]n2)nc(Sc2ccc(S(=O)(=O)Cc3cccc([N+](=O)[O-])c3F)cc2F)nc1N1CCOCC1] | XXX |

TABLE 1-continued
| | Activity |
|---|---|
| 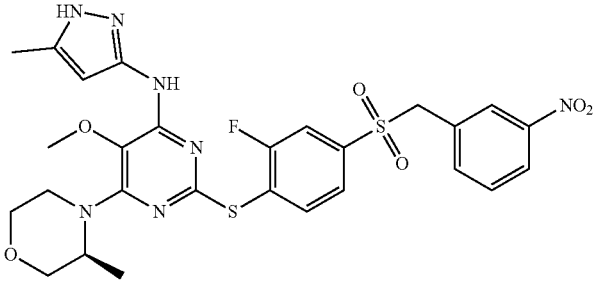 [SMILES: COc1c(Nc2cc(C)[nH]n2)nc(Sc2ccc(S(=O)(=O)Cc3cccc([N+](=O)[O-])c3)cc2F)nc1N1CCOC[C@@H]1C] | XXX |
| 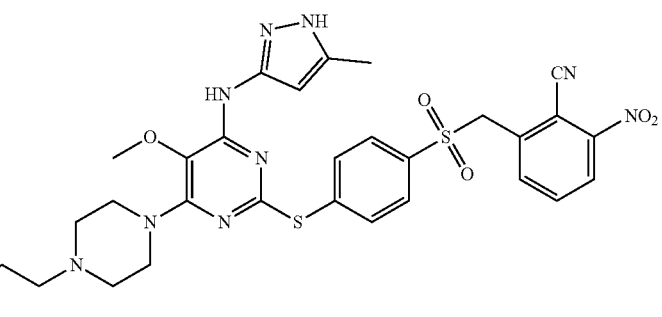 | XXX |
| 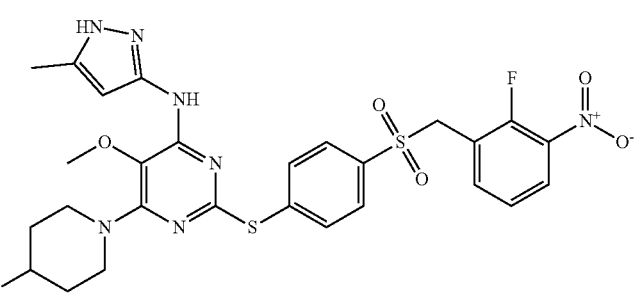 | XXX |
| 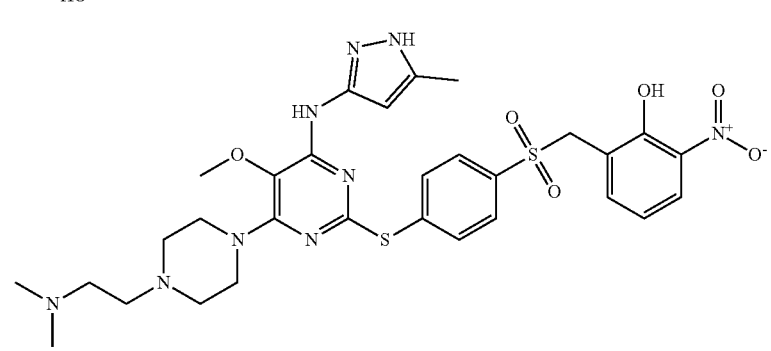 | XXX |
| 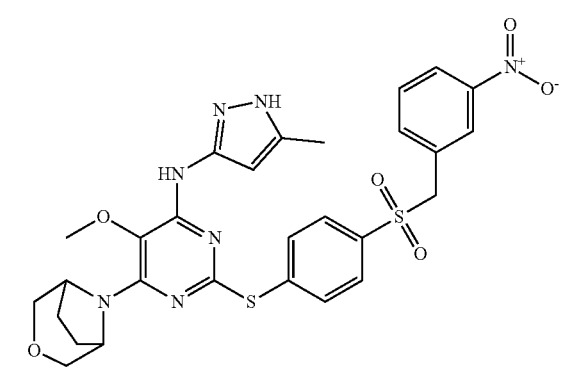 [SMILES: COc1c(Nc2cc(C)[nH]n2)nc(Sc2ccc(S(=O)(=O)Cc3cccc([N+](=O)[O-])c3)cc2)nc1N1C2CCC1COC2] | XXX |

TABLE 1-continued
| | Activity |
|---|---|
| 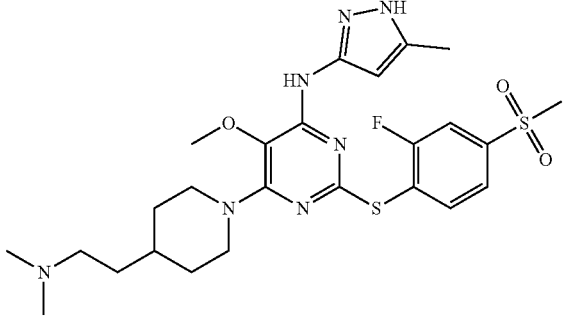 | XXX |
| 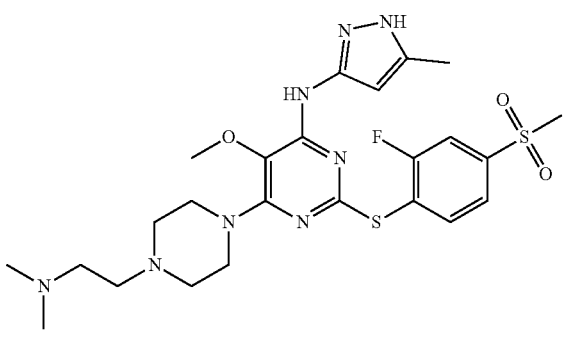 | XXX |
| 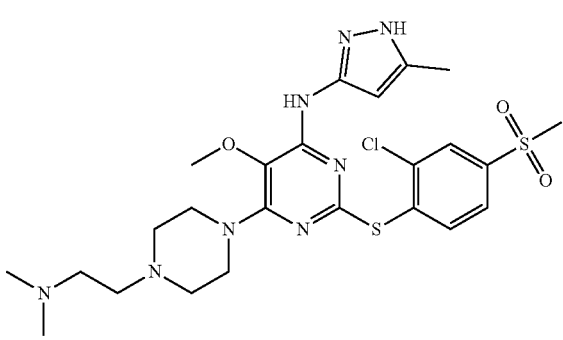 | XXX |
| 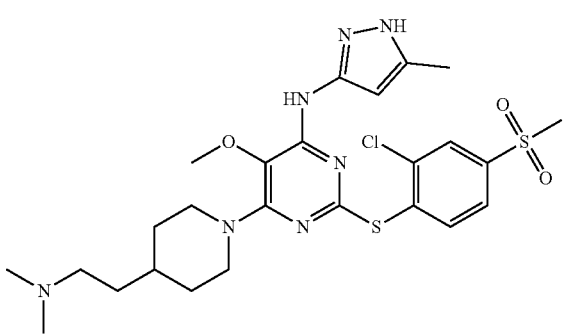 | XXX |

TABLE 1-continued
| | Activity |
|---|---|
| 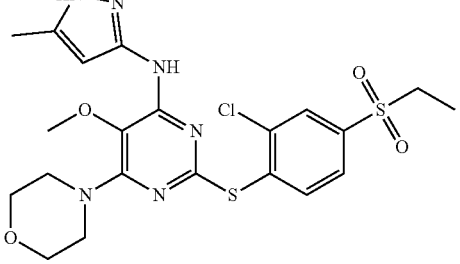 | XXX |
| 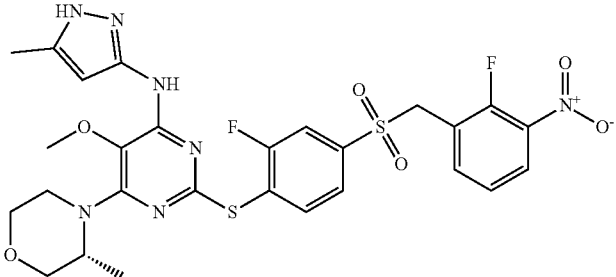 | XXX |
| 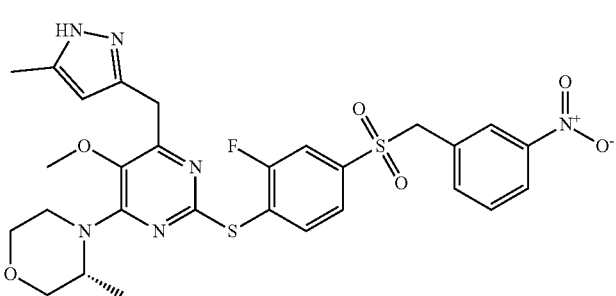 | XXX |
| 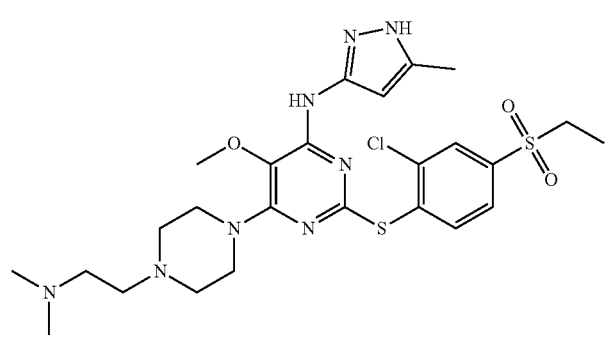 [SMILES: CCS(=O)(=O)c1ccc(Sc2nc(Nc3cc(C)[nH]n3)c(OC)c(N3CCN(CCN(C)C)CC3)n2)c(Cl)c1] | XXX |
| 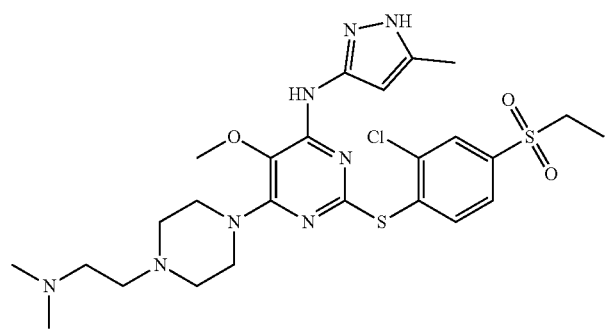 | XXX |

TABLE 1-continued
| | Activity |
|---|---|
| 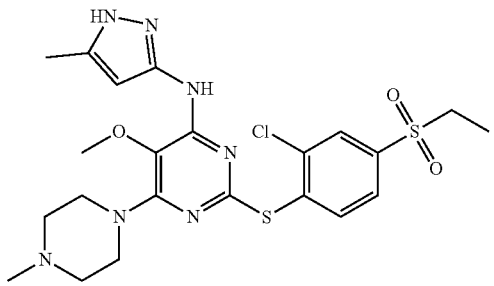 [SMILES: CCS(=O)(=O)c1ccc(Sc2nc(Nc3cc(C)[nH]n3)c(OC)c(N3CCN(C)CC3)n2)c(Cl)c1] | XXX |
| 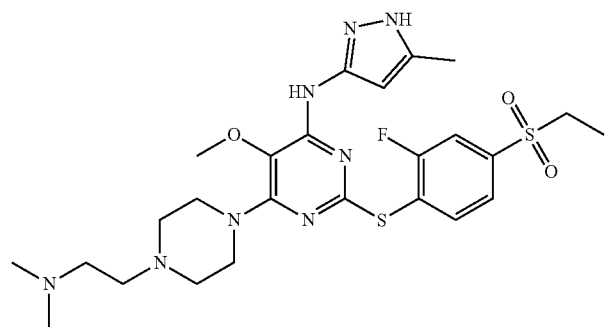 | XXX |
| 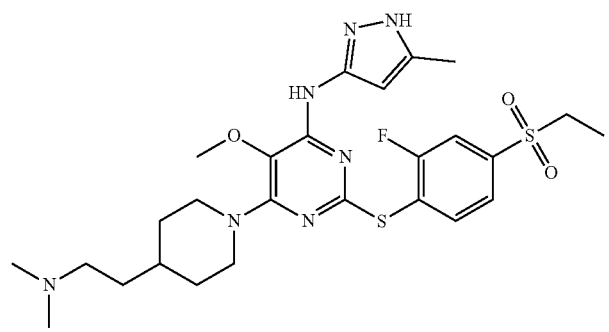 | XXX |
| 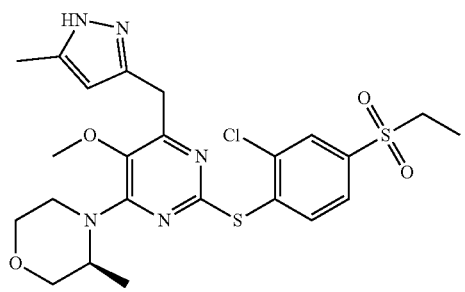 [SMILES: CCS(=O)(=O)c1ccc(Sc2nc(Cc3cc(C)[nH]n3)c(OC)c(N3CCOC[C@@H]3C)n2)c(Cl)c1] | XXX |
| 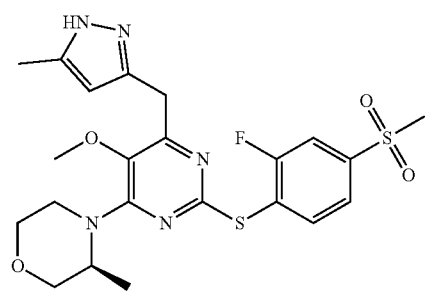 [SMILES: COc1c(Cc2cc(C)[nH]n2)nc(Sc2ccc(S(C)(=O)=O)cc2F)nc1N1CCOC[C@@H]1C] | XXX |

TABLE 1-continued
| | Activity |
|---|---|
| 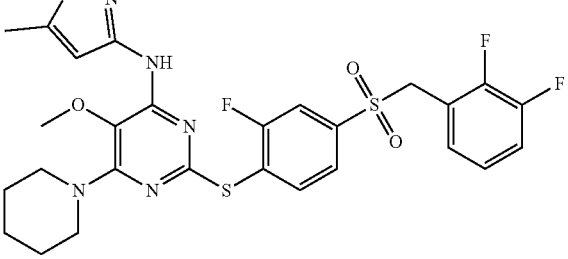 | XXX |
| 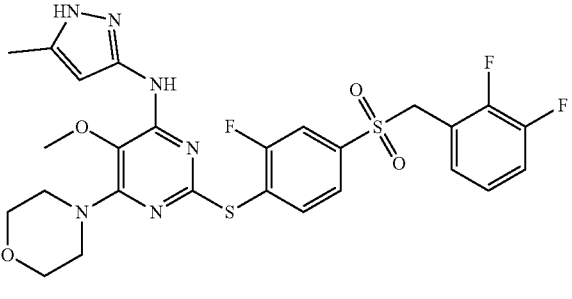 [SMILES: COc1c(Nc2cc(C)[nH]n2)nc(Sc2ccc(S(=O)(=O)Cc3cccc(F)c3F)cc2F)nc1N1CCOCC1] | XXX |
| 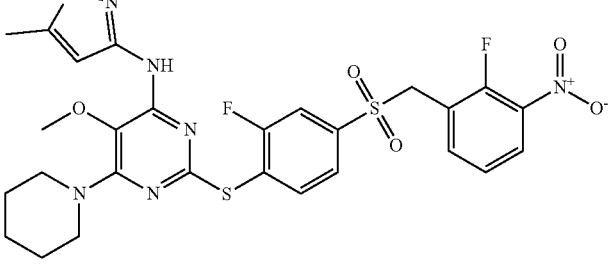 | XXX |
| 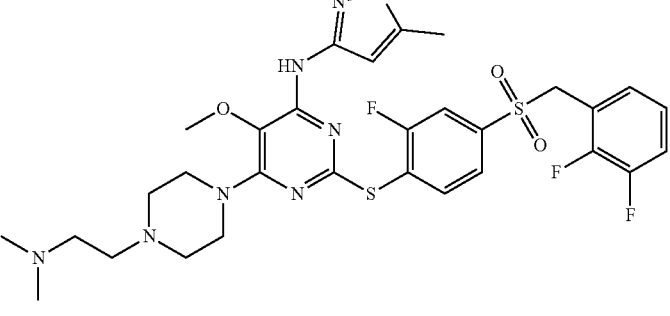 | XXX |
| 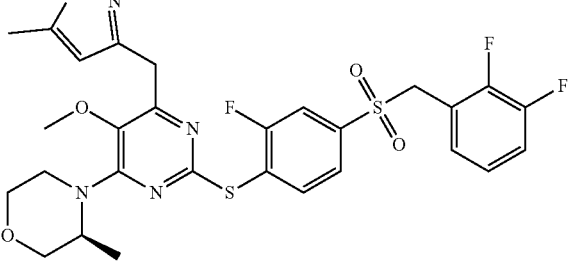 | XXX |

TABLE 1-continued
| | Activity |
|---|---|
| 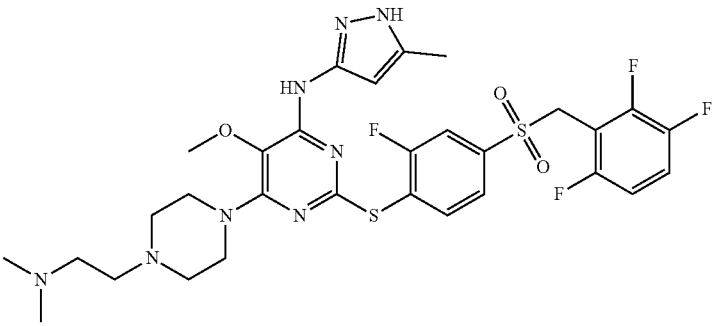 [SMILES: COc1c(Nc2cc(C)[nH]n2)nc(Sc2ccc(S(=O)(=O)Cc3c(F)ccc(F)c3F)cc2F)nc1N1CCN(CCN(C)C)CC1] | XXX |
| 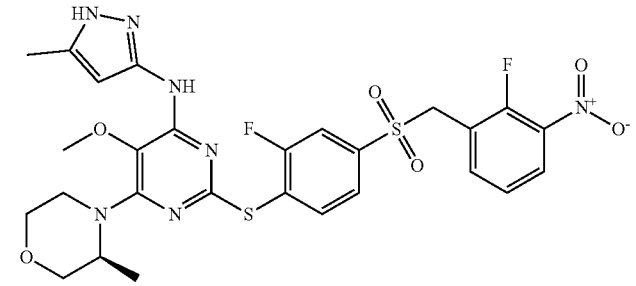 [SMILES: COc1c(Nc2cc(C)[nH]n2)nc(Sc2ccc(S(=O)(=O)Cc3cccc([N+](=O)[O-])c3F)cc2F)nc1N1CCOC[C@@H]1C] | XXX |
| 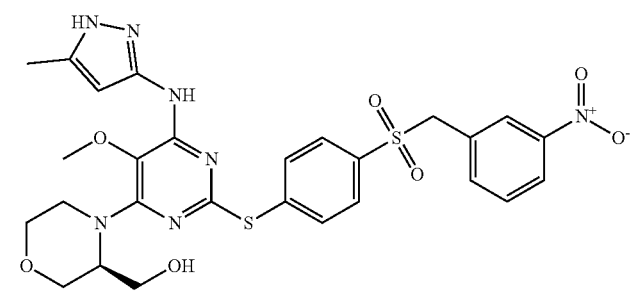 [SMILES: COc1c(Nc2cc(C)[nH]n2)nc(Sc2ccc(S(=O)(=O)Cc3cccc([N+](=O)[O-])c3)cc2)nc1N1CCOC[C@@H]1CO] | XXX |
| 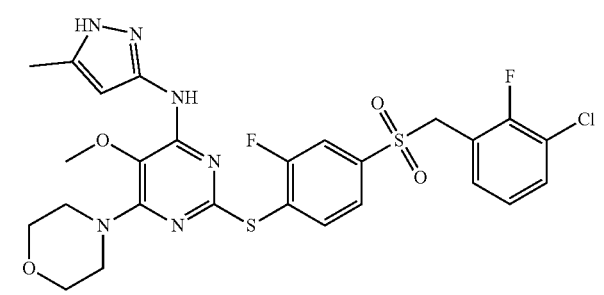 [SMILES: COc1c(Nc2cc(C)[nH]n2)nc(Sc2ccc(S(=O)(=O)Cc3cccc(Cl)c3F)cc2F)nc1N1CCOCC1] | XXX |
| 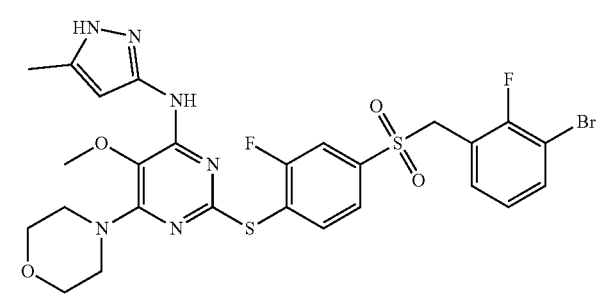 [SMILES: COc1c(Nc2cc(C)[nH]n2)nc(Sc2ccc(S(=O)(=O)Cc3cccc(Br)c3F)cc2F)nc1N1CCOCC1] | XXX |

TABLE 1-continued
| | Activity |
|---|---|
| 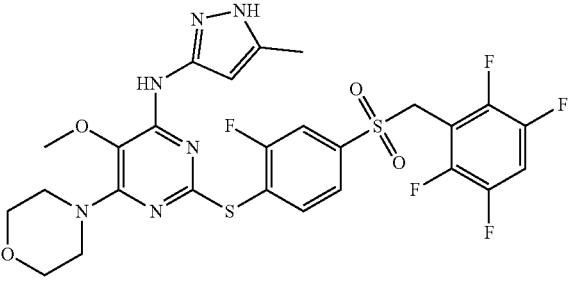 | XXX |
| 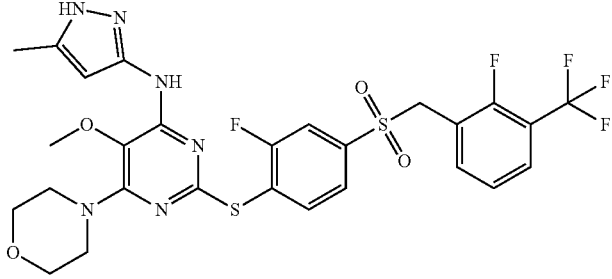 [SMILES: COc1c(Nc2cc(C)[nH]n2)nc(Sc2ccc(S(=O)(=O)Cc3cccc(C(F)(F)F)c3F)cc2F)nc1N1CCOCC1] | XXX |
| 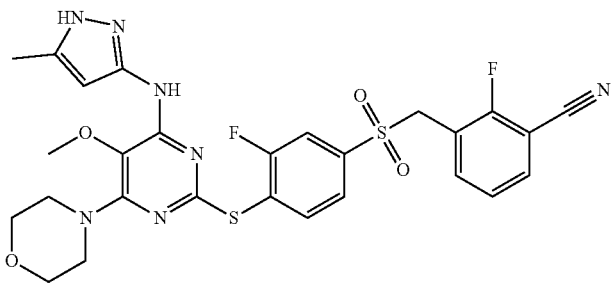 [SMILES: COc1c(Nc2cc(C)[nH]n2)nc(Sc2ccc(S(=O)(=O)Cc3cccc(C#N)c3F)cc2F)nc1N1CCOCC1] | XXX |
| 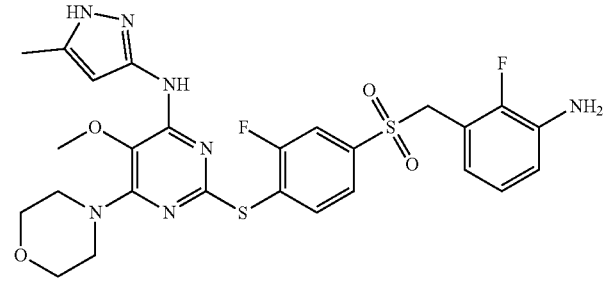 | XXX |
| 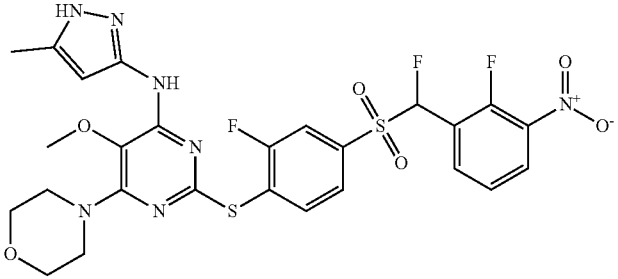 [SMILES: COc1c(Nc2cc(C)[nH]n2)nc(Sc2ccc(S(=O)(=O)C(F)c3cccc([N+](=O)[O-])c3F)cc2F)nc1N1CCOCC1] | XXX |

TABLE 1-continued
| | Activity |
|---|---|
| 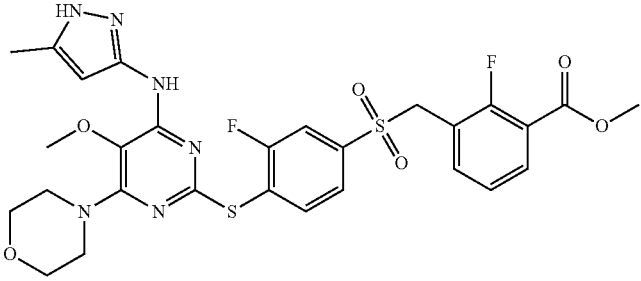 [SMILES: COC(=O)c1cccc(CS(=O)(=O)c2ccc(Sc3nc(Nc4cc(C)[nH]n4)c(OC)c(N4CCOCC4)n3)c(F)c2)c1F] | XXX |
| 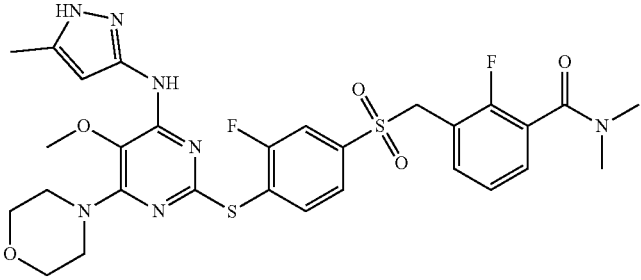 [SMILES: COc1c(Nc2cc(C)[nH]n2)nc(Sc2ccc(S(=O)(=O)Cc3cccc(C(=O)N(C)C)c3F)cc2F)nc1N1CCOCC1] | XXX |
| 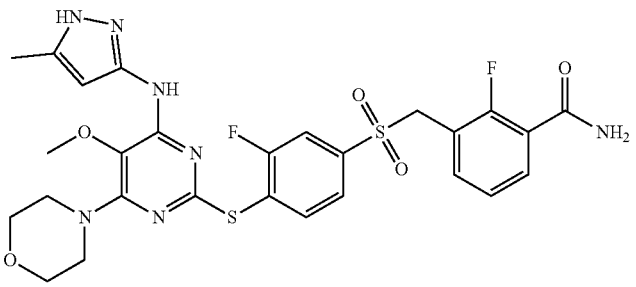 [SMILES: COc1c(Nc2cc(C)[nH]n2)nc(Sc2ccc(S(=O)(=O)Cc3cccc(C(N)=O)c3F)cc2F)nc1N1CCOCC1] | XXX |
| 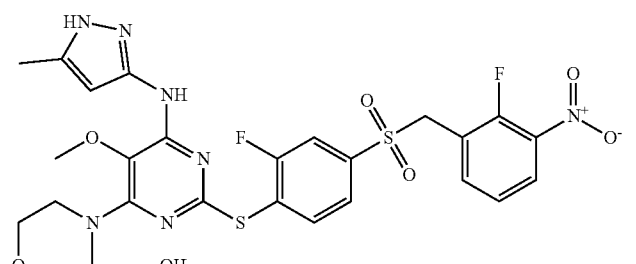 | XXX |
| 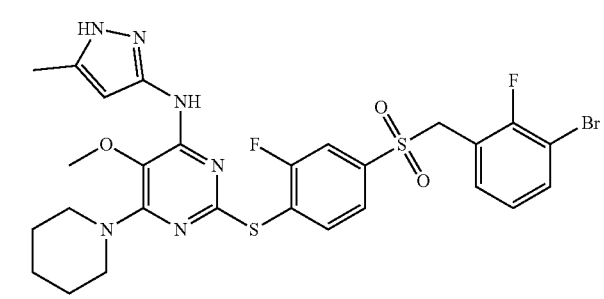 [SMILES: COc1c(Nc2cc(C)[nH]n2)nc(Sc2ccc(S(=O)(=O)Cc3cccc(Br)c3F)cc2F)nc1N1CCCCC1] | XXX |

TABLE 1-continued
| | Activity |
|---|---|
| 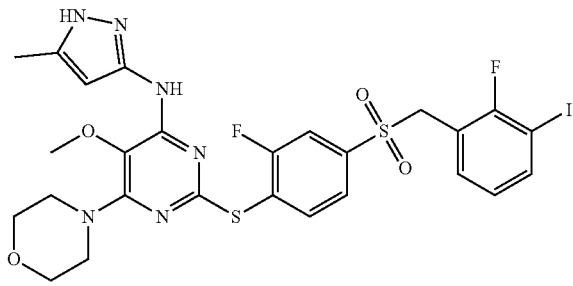 [SMILES: COc1c(Nc2cc(C)[nH]n2)nc(Sc2ccc(S(=O)(=O)Cc3cccc(I)c3F)cc2F)nc1N1CCOCC1] | XXX |
| 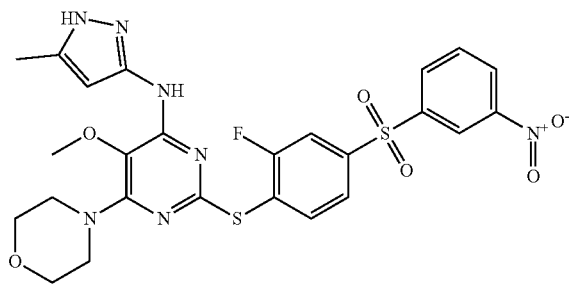 | XXX |
| 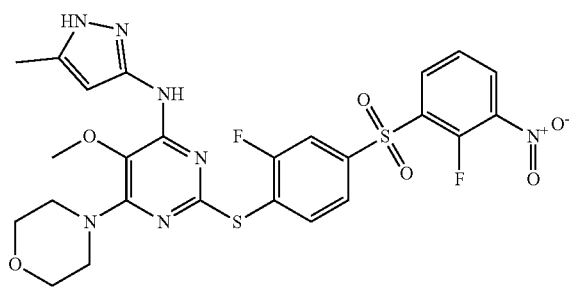 | XXX |
| 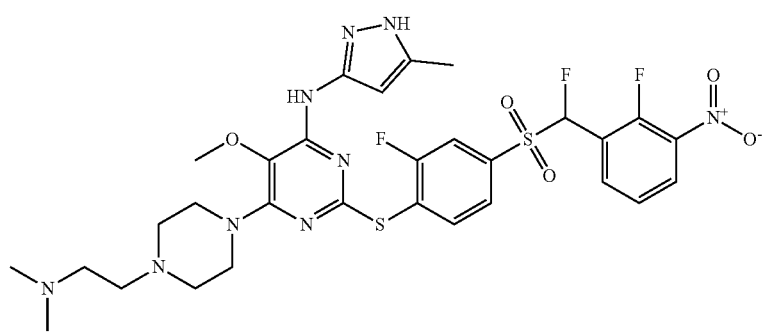 [SMILES: COc1c(Nc2cc(C)[nH]n2)nc(Sc2ccc(S(=O)(=O)C(F)c3cccc([N+](=O)[O-])c3F)cc2F)nc1N1CCN(CCN(C)C)CC1] | XXX |
| 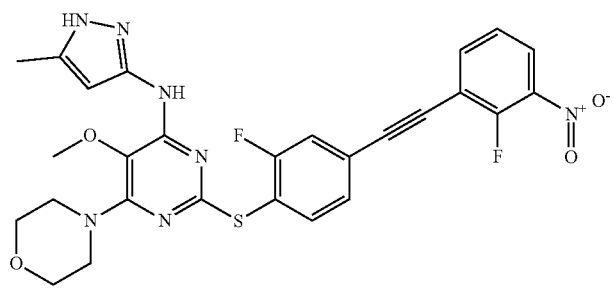 | XXX |

TABLE 1-continued
| | Activity |
|---|---|
| 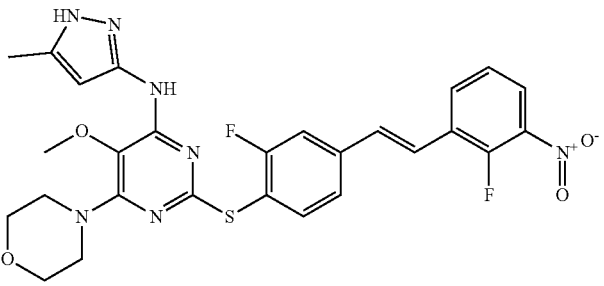 | XXX |
| 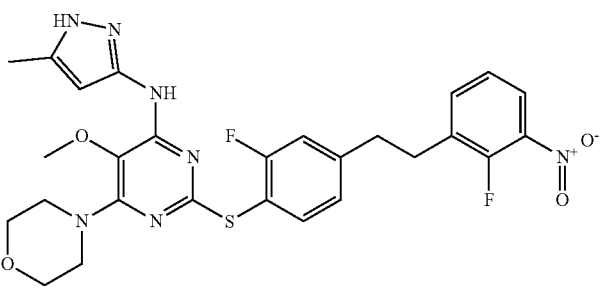 | XXX |
| 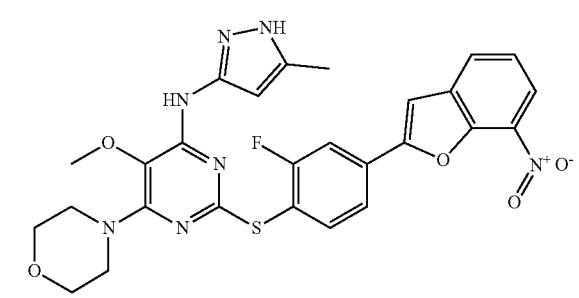 | XX |
| 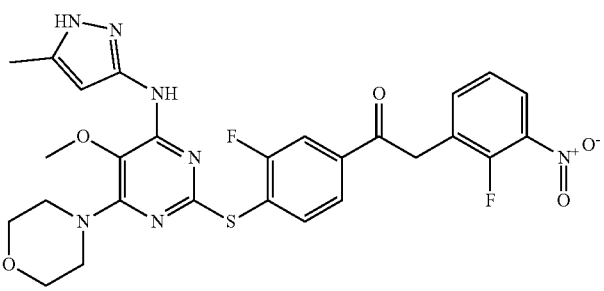 | XXX |
| 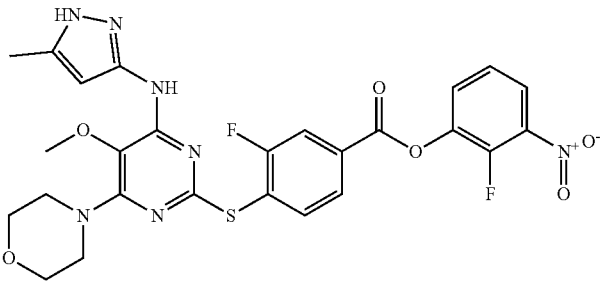 | XXX |

TABLE 1-continued
| | Activity |
|---|---|
| 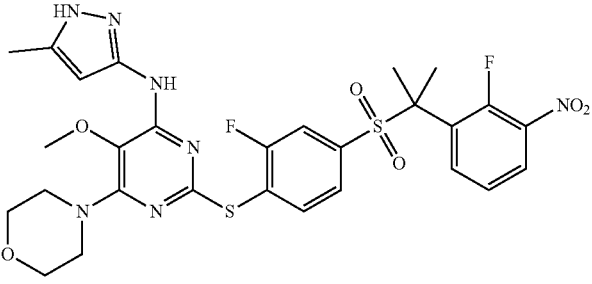 [SMILES: COc1c(Nc2cc(C)[nH]n2)nc(Sc2ccc(S(=O)(=O)C(C)(C)c3cccc([N+](=O)[O-])c3F)cc2F)nc1N1CCOCC1] | XXX |
| 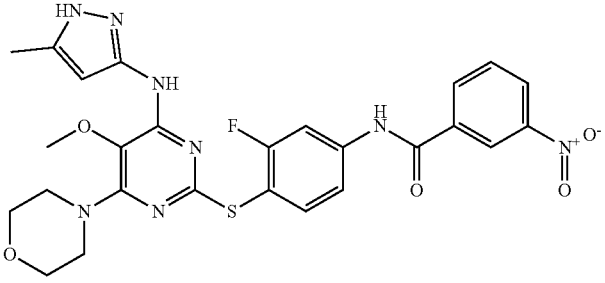 | XX |
| 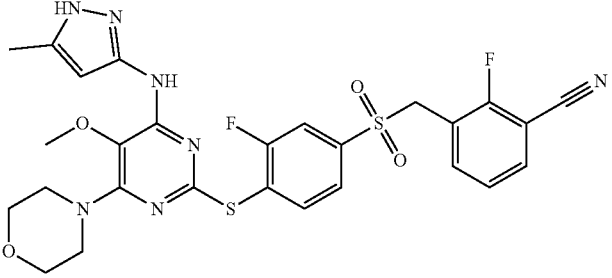 [SMILES: COc1c(Nc2cc(C)[nH]n2)nc(Sc2ccc(S(=O)(=O)Cc3cccc(C#N)c3F)cc2F)nc1N1CCOCC1] | XXX |
| 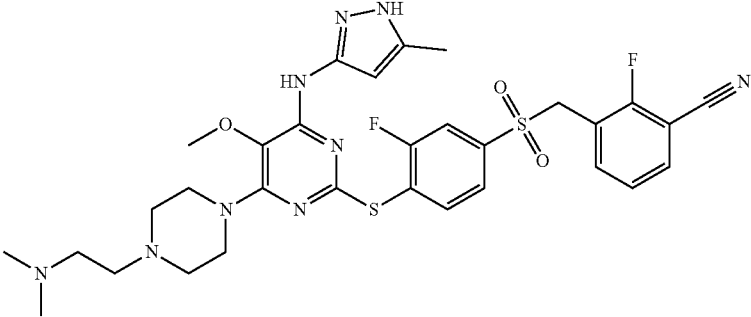 [SMILES: COc1c(Nc2cc(C)[nH]n2)nc(Sc2ccc(S(=O)(=O)Cc3cccc(C#N)c3F)cc2F)nc1N1CCN(CCN(C)C)CC1] | XXX |
| 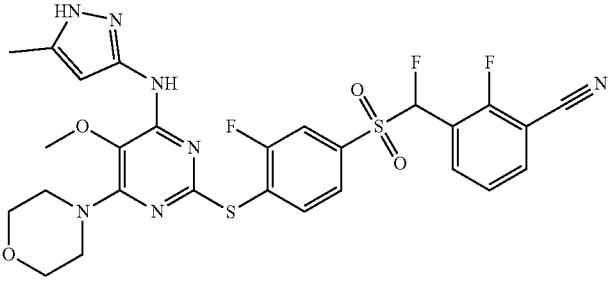 [SMILES: COc1c(Nc2cc(C)[nH]n2)nc(Sc2ccc(S(=O)(=O)C(F)c3cccc(C#N)c3F)cc2F)nc1N1CCOCC1] | XXX |

TABLE 1-continued
| | Activity |
|---|---|
| 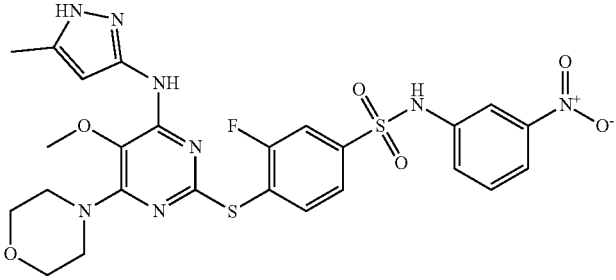 [SMILES: COc1c(Nc2cc(C)[nH]n2)nc(Sc2ccc(S(=O)(=O)Nc3cccc([N+](=O)[O-])c3)cc2F)nc1N1CCOCC1] | XXX |
| 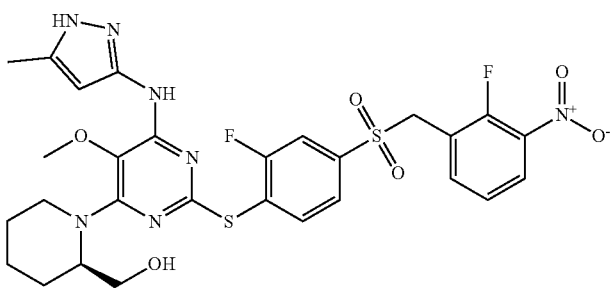 [SMILES: COc1c(Nc2cc(C)[nH]n2)nc(Sc2ccc(S(=O)(=O)Cc3cccc([N+](=O)[O-])c3F)cc2F)nc1N1CCCC[C@@H]1CO] | XXX |
| 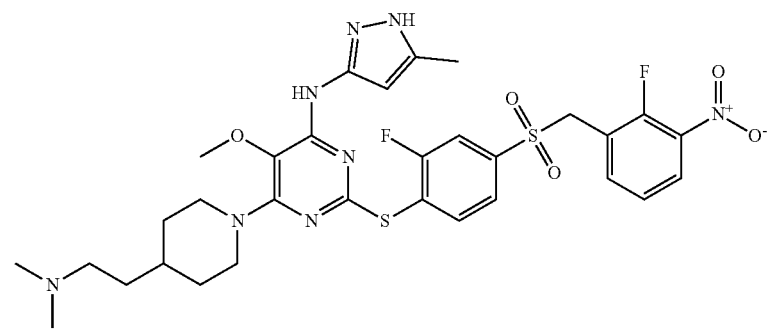 [SMILES: COc1c(Nc2cc(C)[nH]n2)nc(Sc2ccc(S(=O)(=O)Cc3cccc([N+](=O)[O-])c3F)cc2F)nc1N1CCC(CCN(C)C)CC1] | XXX |
| 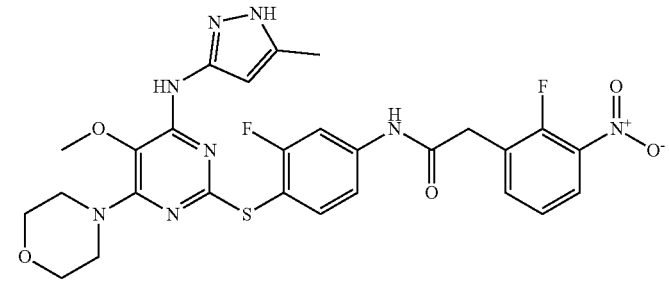 [SMILES: COc1c(Nc2cc(C)[nH]n2)nc(Sc2ccc(NC(=O)Cc3cccc([N+](=O)[O-])c3F)cc2F)nc1N1CCOCC1] | XXX |
| 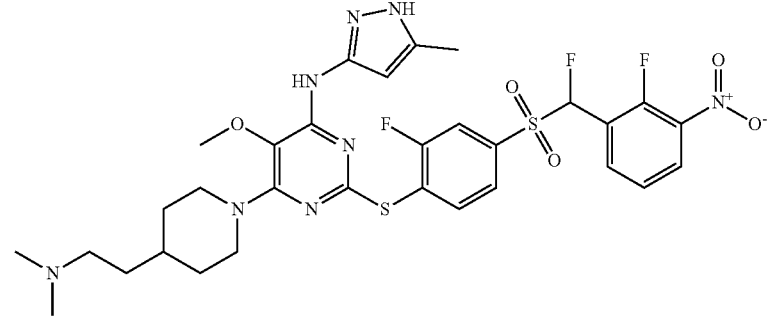 | XXX |

TABLE 1-continued
| | Activity |
|---|---|
| 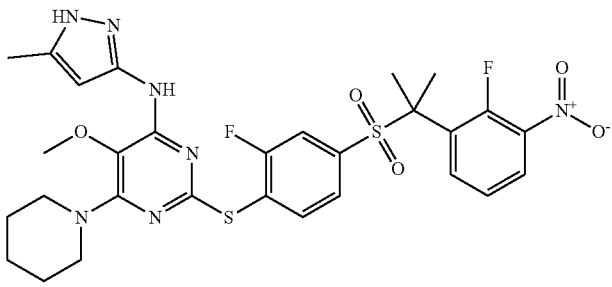 [SMILES: COc1c(Nc2cc(C)[nH]n2)nc(Sc2ccc(S(=O)(=O)C(C)(C)c3cccc([N+](=O)[O-])c3F)cc2F)nc1N1CCCCC1] | XXX |
| 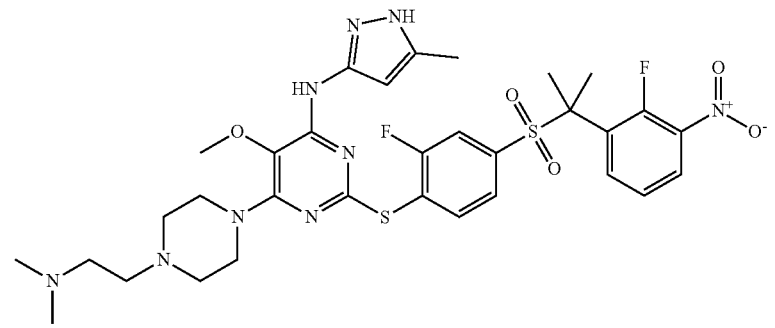 [SMILES: COc1c(Nc2cc(C)[nH]n2)nc(Sc2ccc(S(=O)(=O)C(C)(C)c3cccc([N+](=O)[O-])c3F)cc2F)nc1N1CCN(CCN(C)C)CC1] | XXX |
| 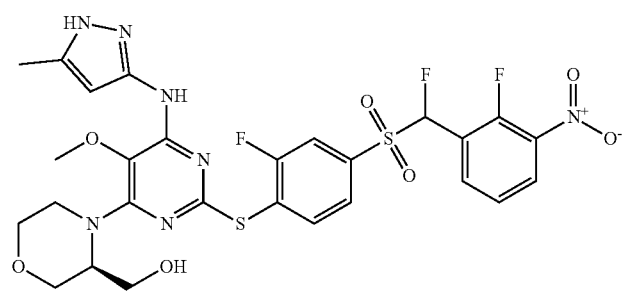 [SMILES: COc1c(Nc2cc(C)[nH]n2)nc(Sc2ccc(S(=O)(=O)C(F)c3cccc([N+](=O)[O-])c3F)cc2F)nc1N1CCOC[C@@H]1CO] | XXX |
| 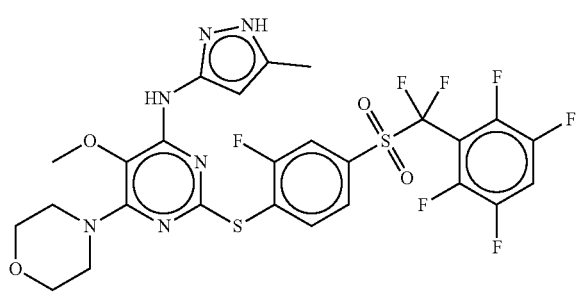 | XXX |
| 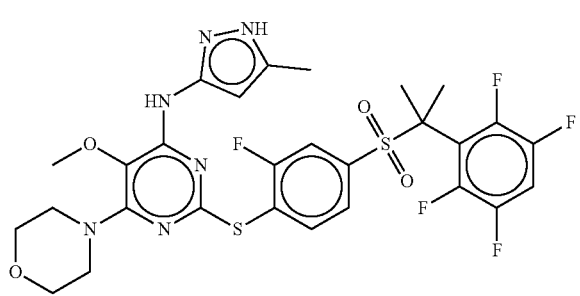 | XXX |

TABLE 1-continued
| | Activity |
|---|---|
| 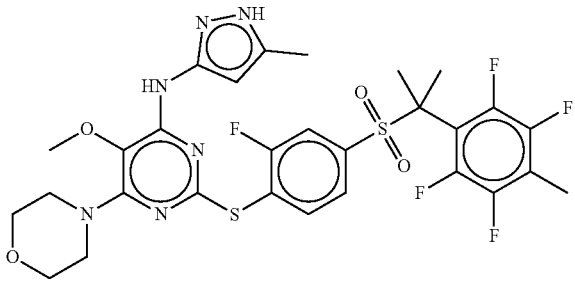 | XXX |
| 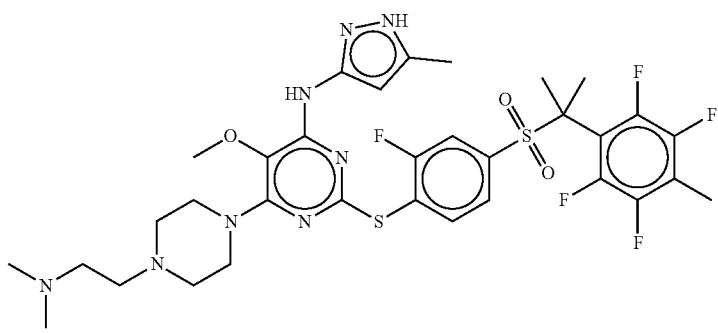 | XXX |
| 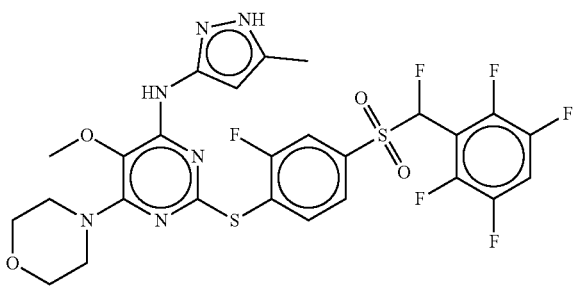 | XXX |
| 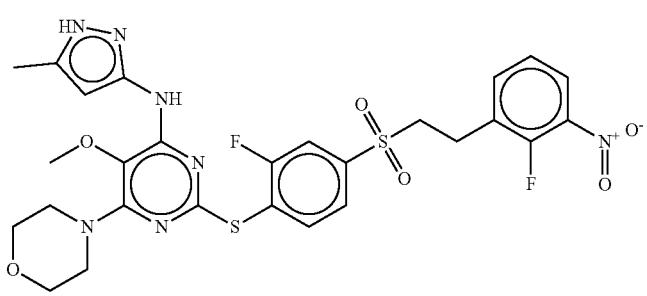 | XXX |
| 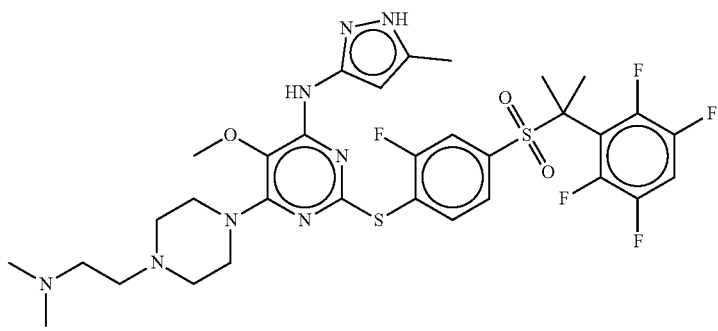 | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 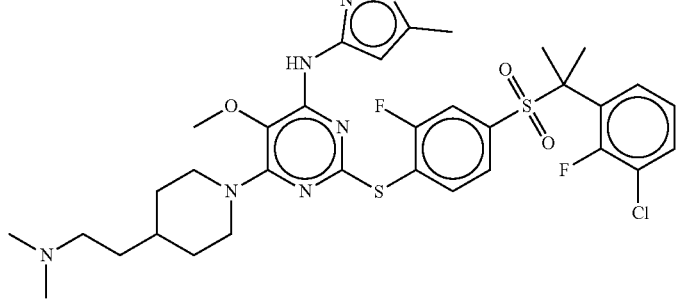 | XXX |
| 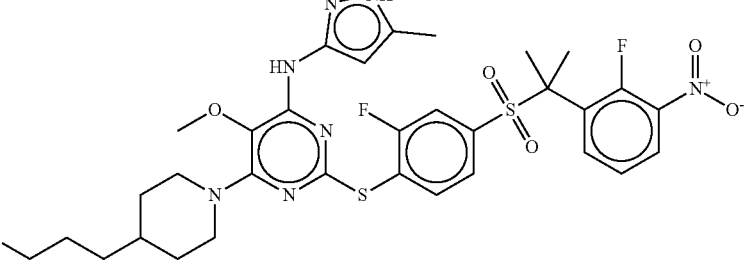 | XXX |
| 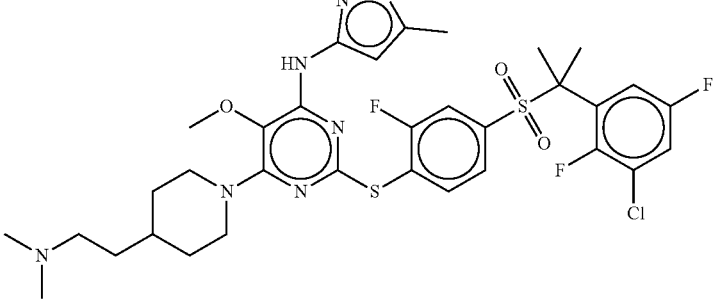 | XXX |
| 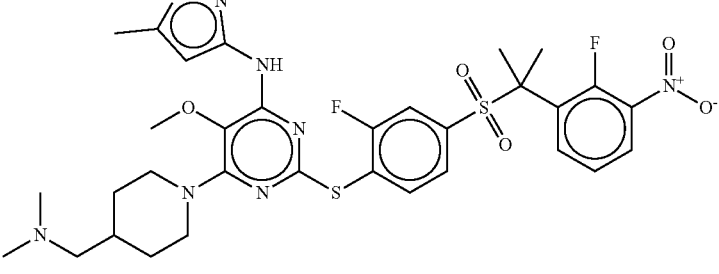 | XXX |
| 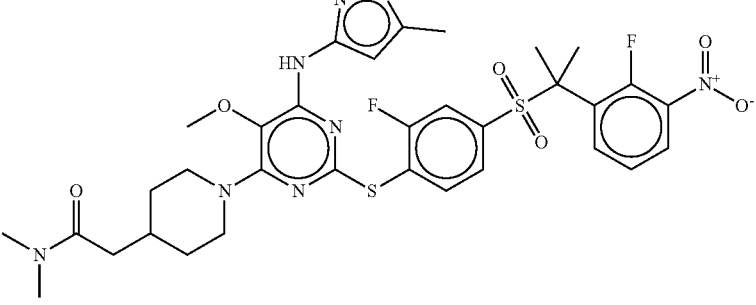 | XXX |

TABLE 1-continued
| | Activity |
|---|---|
| 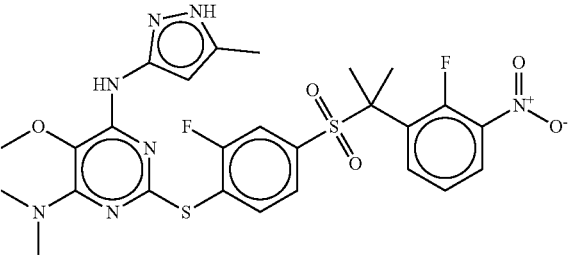 | XXX |
| 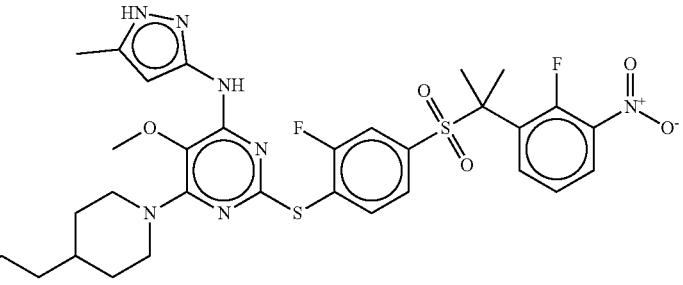 | XXX |
| 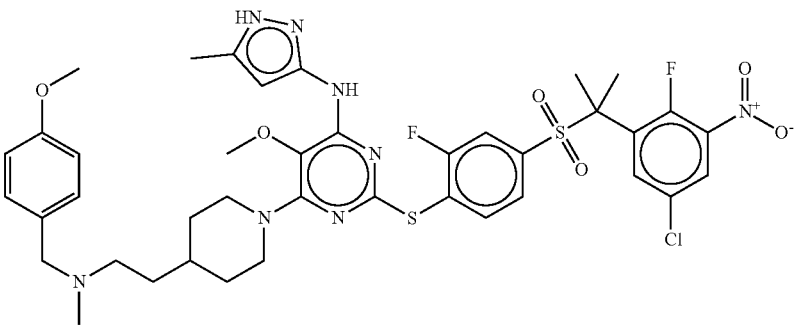 | XXX |
| 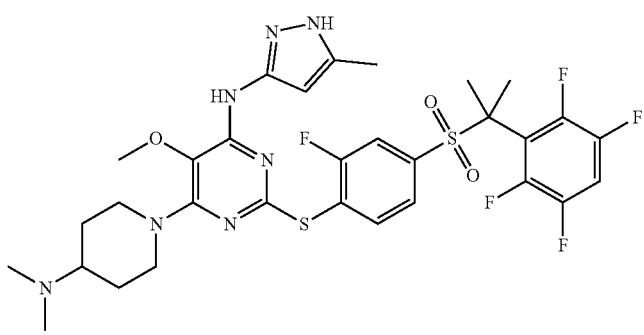 [SMILES: COc1c(Nc2cc(C)[nH]n2)nc(Sc2ccc(S(=O)(=O)C(C)(C)c3c(F)c(F)cc(F)c3F)cc2F)nc1N1CCC(N(C)C)CC1] | XXX |
| 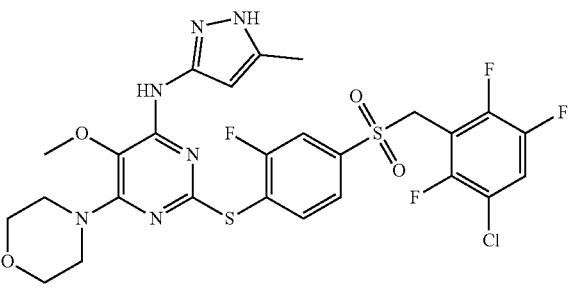 | XXX |

TABLE 1-continued
| | Activity |
|---|---|
| 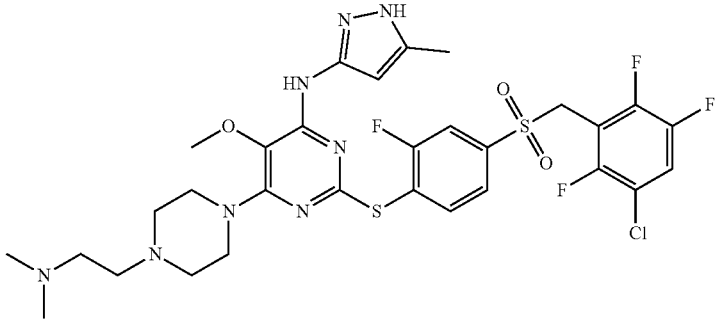 | XXX |
| 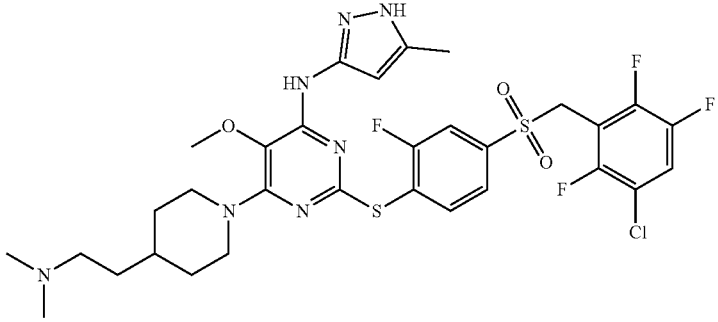 [SMILES: COc1c(Nc2cc(C)[nH]n2)nc(Sc2ccc(S(=O)(=O)Cc3c(F)c(F)cc(Cl)c3F)cc2F)nc1N1CCN(CCN(C)C)CC1] | XXX |
| 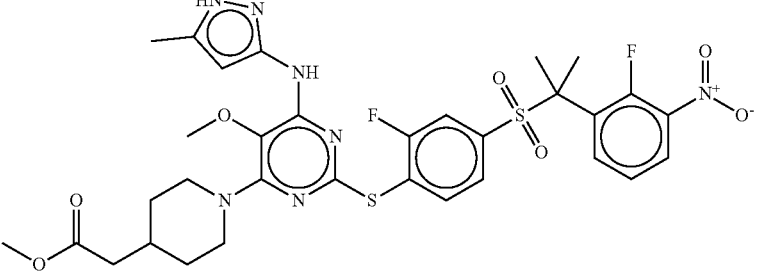 | XXX |
| 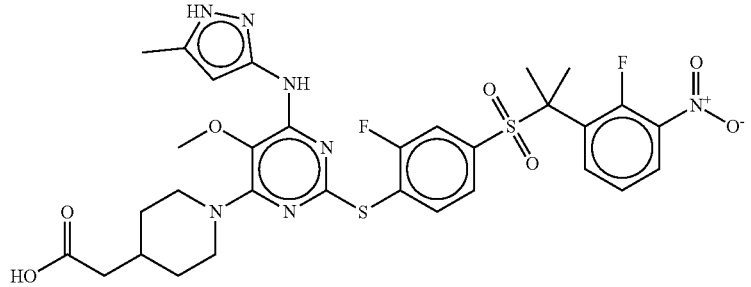 | XXX |
| 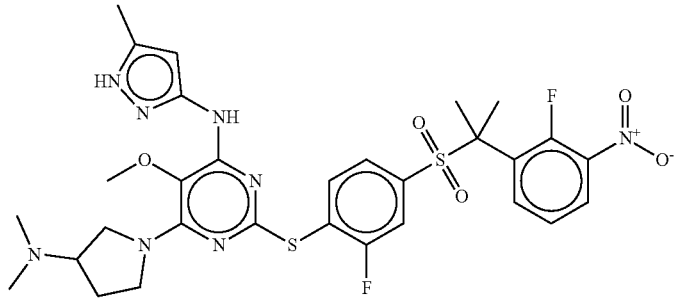 | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 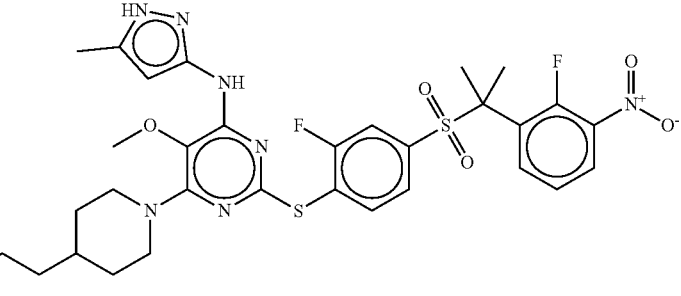 | XXX |
| 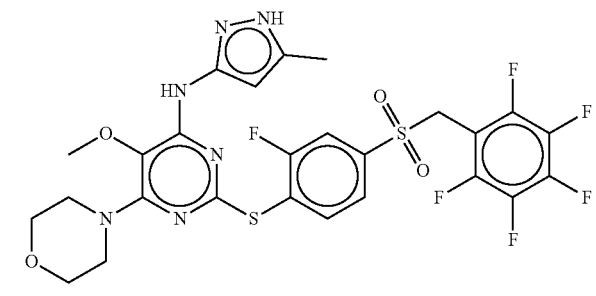 | XXX |
| 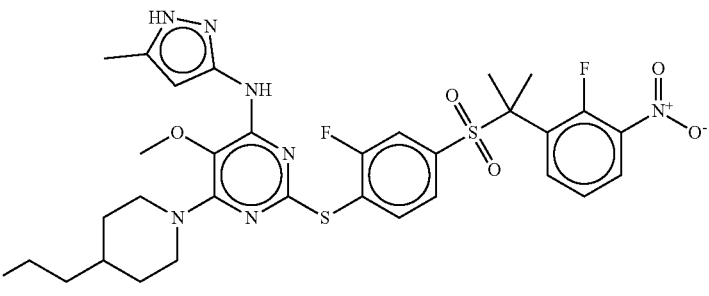 | XXX |
| 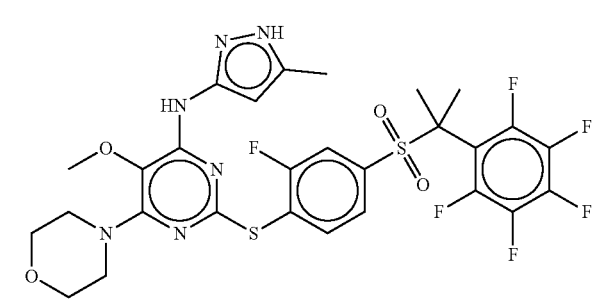 | XXX |
| 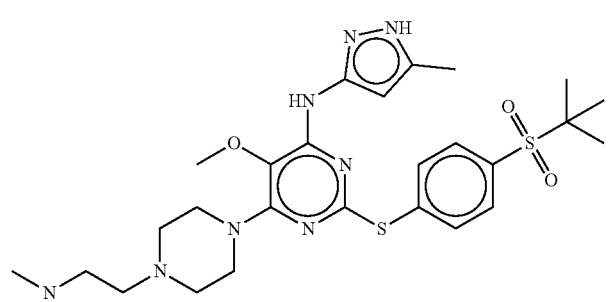 | XXX |

TABLE 1-continued
| | Activity |
|---|---|
| 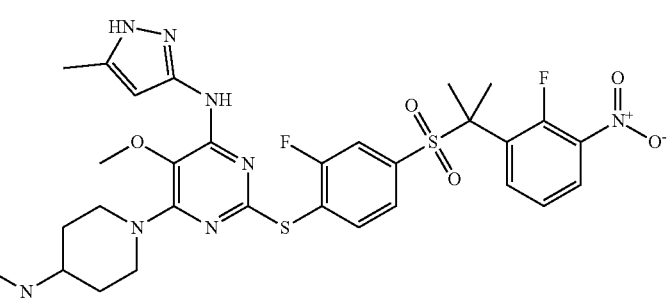 | XXX |
| 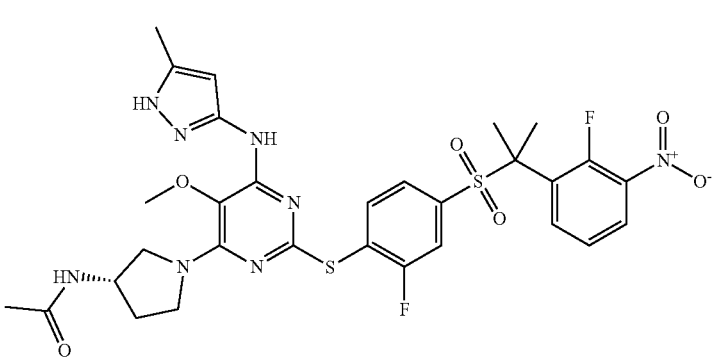 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@H](NC(C)=O)C1] | XXX |
| 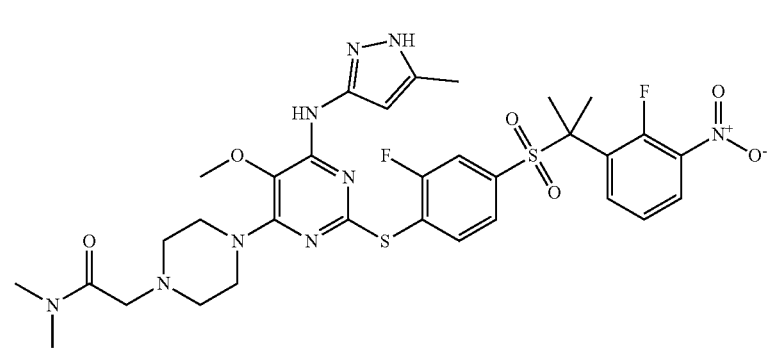 [SMILES: COc1c(Nc2cc(C)[nH]n2)nc(Sc2ccc(S(=O)(=O)C(C)(C)c3cccc([N+](=O)[O-])c3F)cc2F)nc1N1CCN(CC(=O)N(C)C)CC1] | XXX |
| 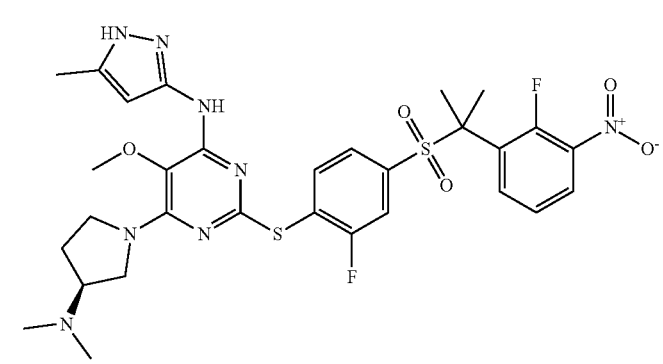 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@H](N(C)C)C1] | XXX |

TABLE 1-continued
| | Activity |
|---|---|
| 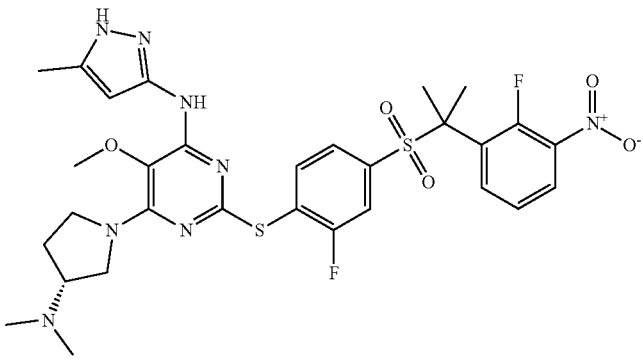 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@@H](N(C)C)C1] | XXX |
| 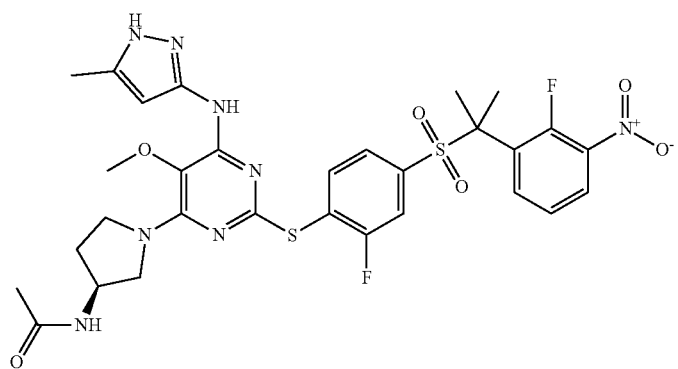 [SMILES: COc1c(Nc2cc(C)[nH]n2)nc(Sc2ccc(S(=O)(=O)C(C)(C)c3cccc([N+](=O)[O-])c3F)cc2F)nc1N1CC[C@H](NC(C)=O)C1] | XXX |
| 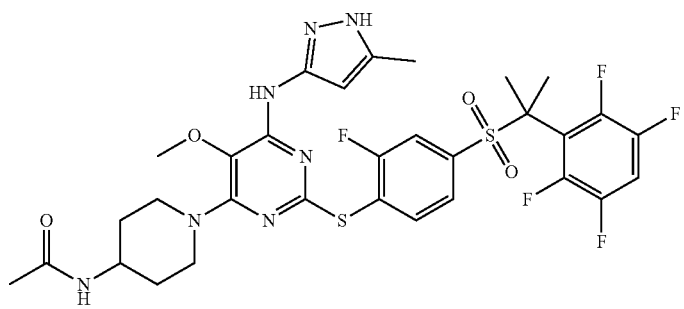 [SMILES: COc1c(Nc2cc(C)[nH]n2)nc(Sc2ccc(S(=O)(=O)C(C)(C)c3c(F)c(F)cc(F)c3F)cc2F)nc1N1CCC(NC(C)=O)CC1] | XXX |
| 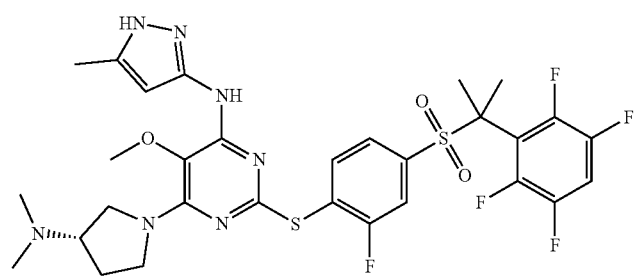 [SMILES: COc1c(Nc2cc(C)[nH]n2)nc(Sc2ccc(S(=O)(=O)C(C)(C)c3c(F)c(F)cc(F)c3F)cc2F)nc1N1CC[C@H](N(C)C)C1] | XXX |

TABLE 1-continued
| | Activity |
|---|---|
| 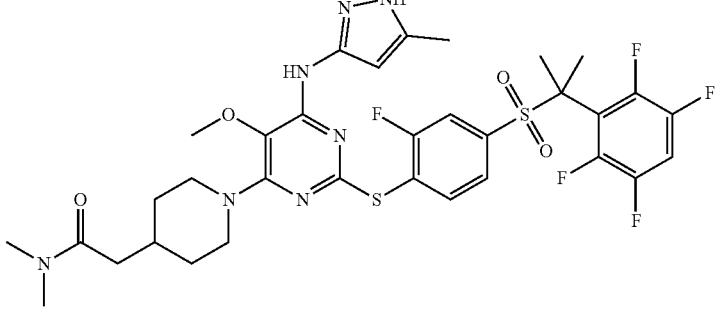 | XXX |
| 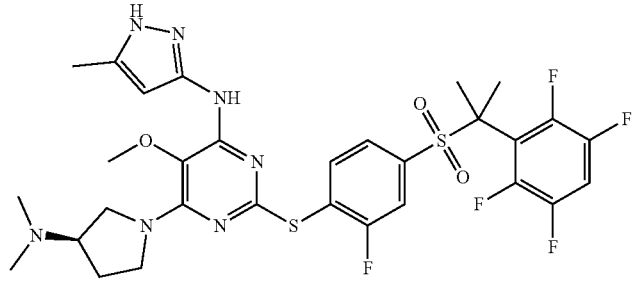 [SMILES: COc1c(Nc2cc(C)[nH]n2)nc(Sc2ccc(S(=O)(=O)C(C)(C)c3c(F)c(F)cc(F)c3F)cc2F)nc1N1CC[C@@H](N(C)C)C1] | XXX |
| 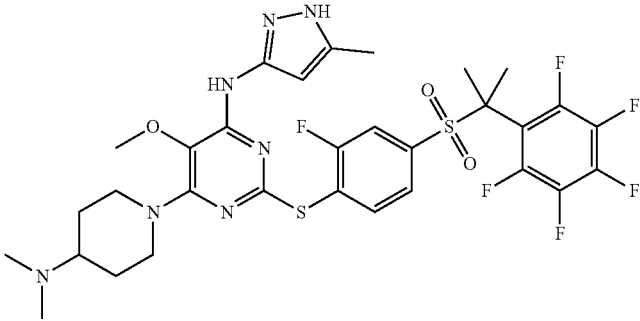 [SMILES: COc1c(Nc2cc(C)[nH]n2)nc(Sc2ccc(S(=O)(=O)C(C)(C)c3c(F)c(F)c(F)c(F)c3F)cc2F)nc1N1CCC(N(C)C)CC1] | XXX |
| 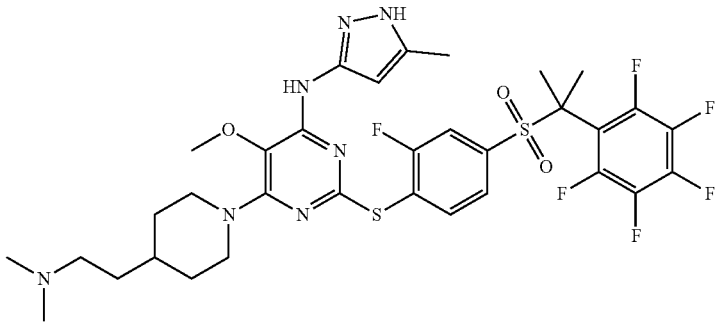 [SMILES: COc1c(Nc2cc(C)[nH]n2)nc(Sc2ccc(S(=O)(=O)C(C)(C)c3c(F)c(F)c(F)c(F)c3F)cc2F)nc1N1CCC(CCN(C)C)CC1] | XXX |
| 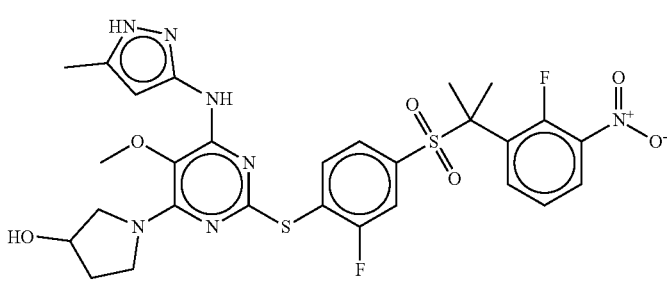 | XXX |

TABLE 1-continued

| | Activity |
|---|---|
| (structure) | XXX |
| (structure) | XXX |
| (structure) | XXX |
| (structure) | XXX |

TABLE 1-continued
| | Activity |
|---|---|
| 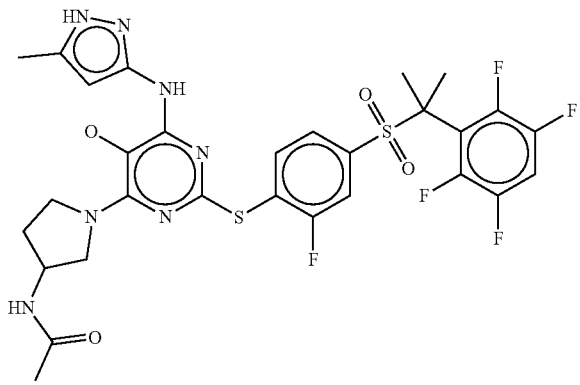 | XXX |
| 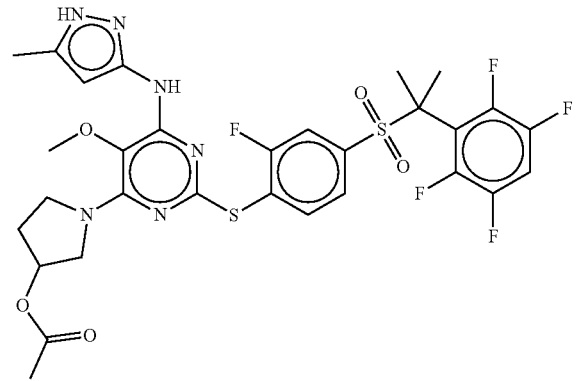 | XXX |
| 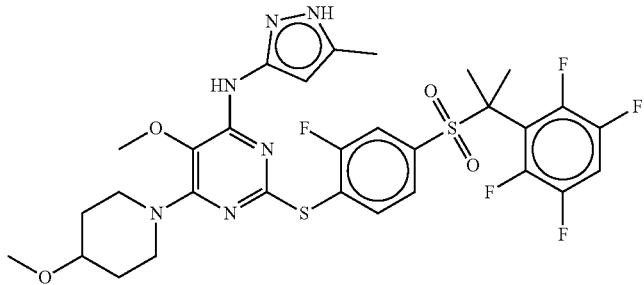 | XXX |
| 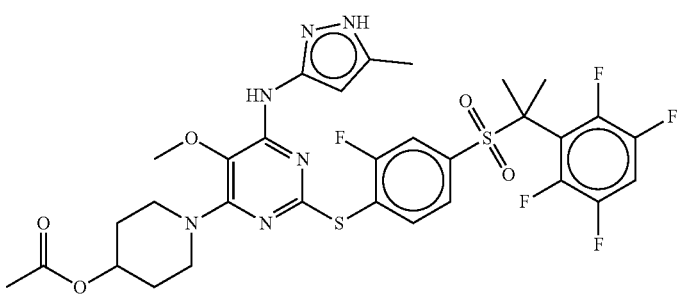 | XXX |

TABLE 1-continued
| | Activity |
|---|---|
| 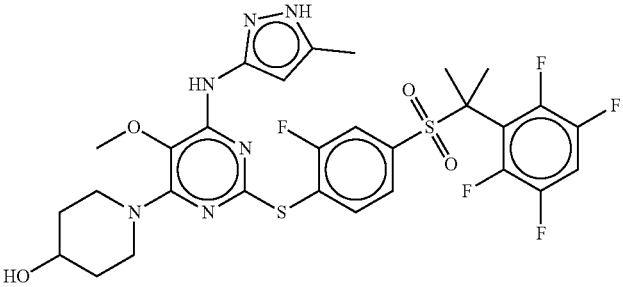 | XXX |
| 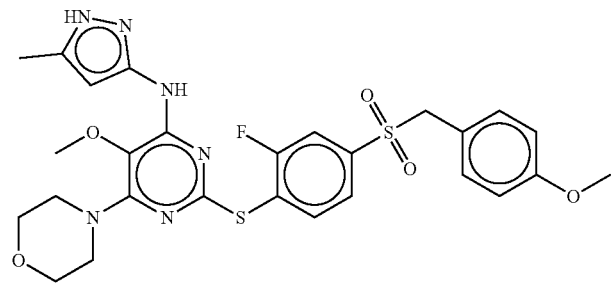 | XXX |
| 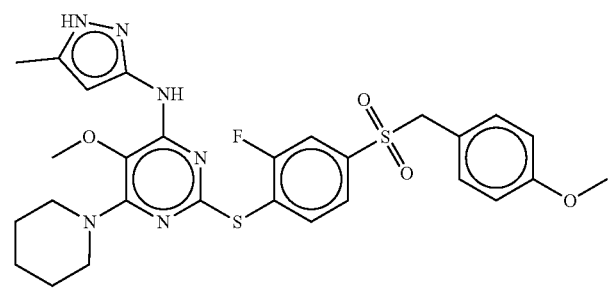 | XXX |
| 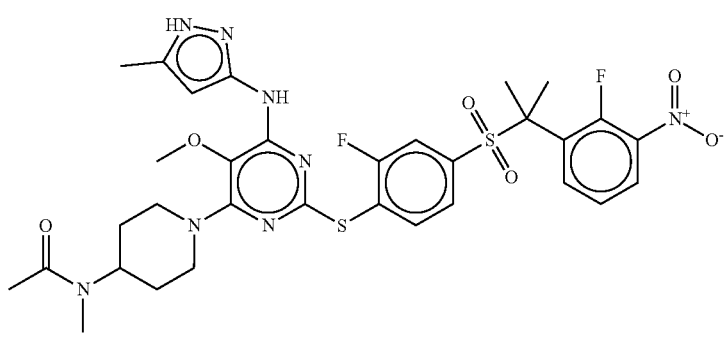 | XXX |
| 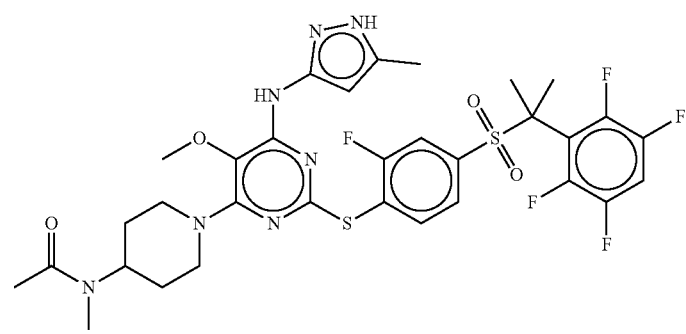 | XXX |

TABLE 1-continued

| Structure | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 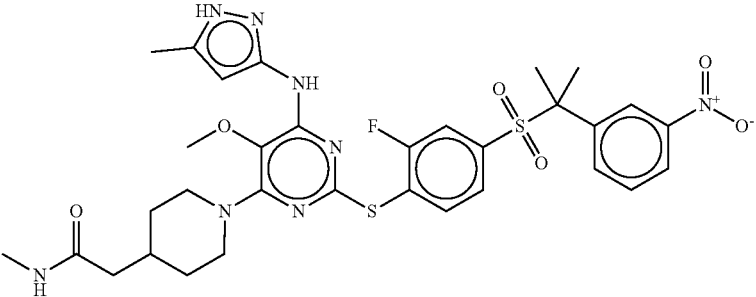 | XXX |
| 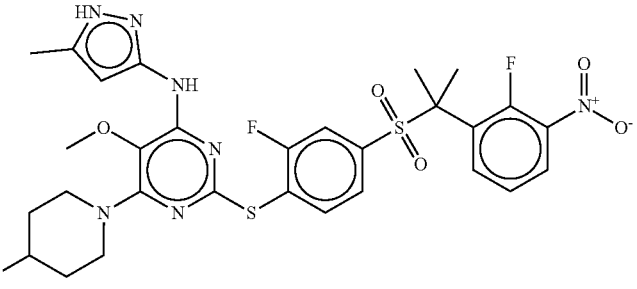 | XXX |
| 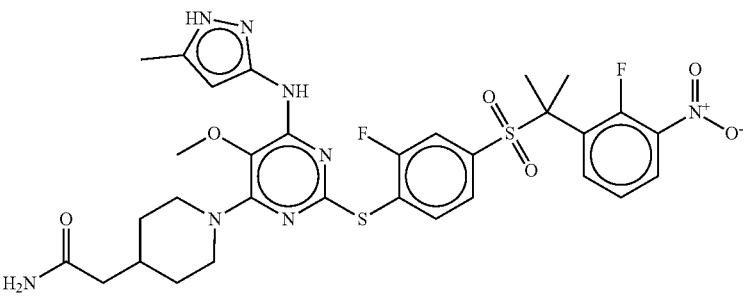 | XXX |
| 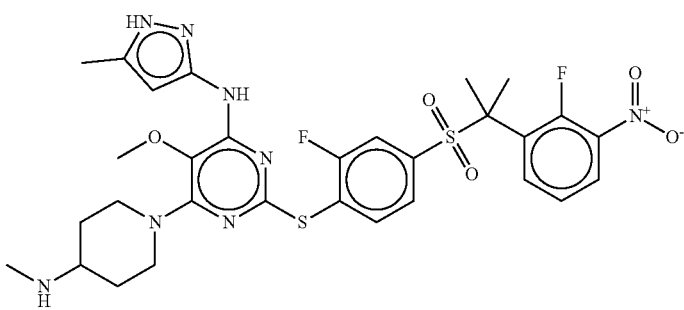 | XXX |
| 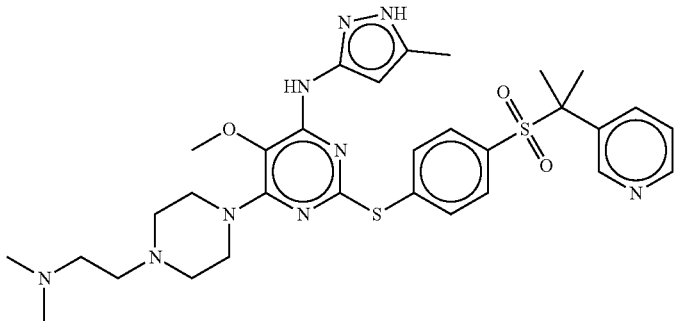 | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 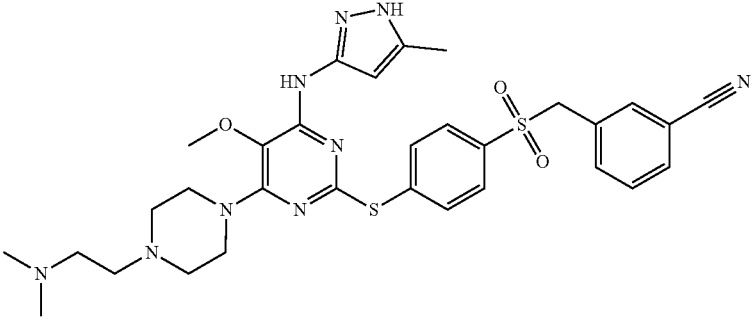 [SMILES: COc1c(Nc2cc(C)[nH]n2)nc(Sc2ccc(S(=O)(=O)Cc3cccc(C#N)c3)cc2)nc1N1CCN(CCN(C)C)CC1] | XXX |
| 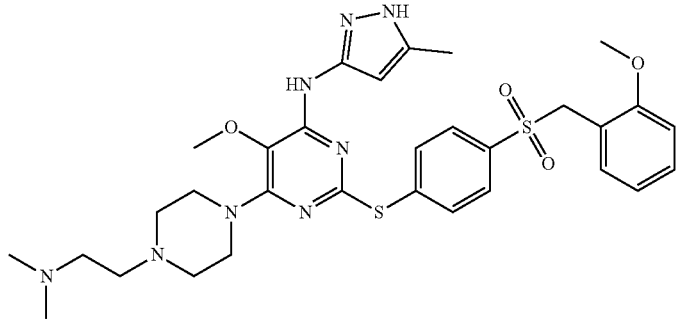 [SMILES: COc1ccccc1CS(=O)(=O)c1ccc(Sc2nc(Nc3cc(C)[nH]n3)c(OC)c(N3CCN(CCN(C)C)CC3)n2)cc1] | XXX |
| 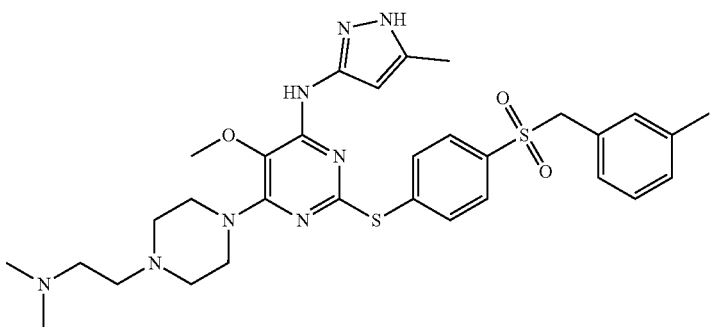 | XXX |
| 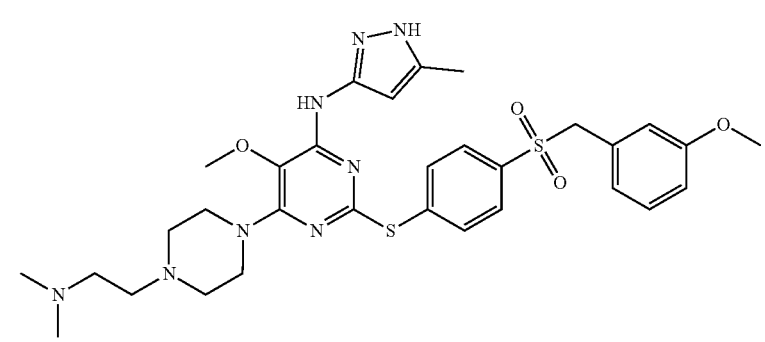 | XXX |

TABLE 1-continued
| | Activity |
|---|---|
| 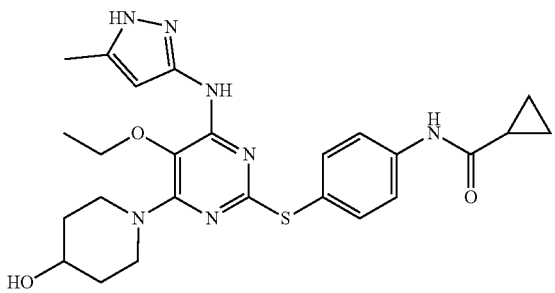 [SMILES: CCOc1c(Nc2cc(C)[nH]n2)nc(Sc2ccc(NC(=O)C3CC3)cc2)nc1N1CCC(O)CC1] | XXX |
| 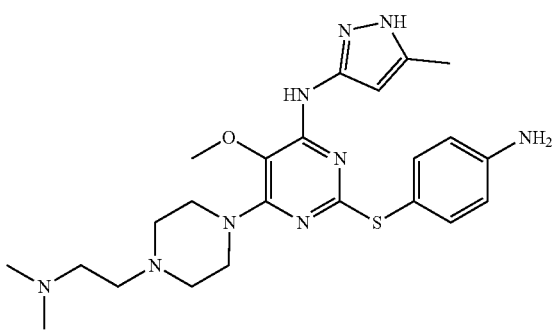 [SMILES: COc1c(Nc2cc(C)[nH]n2)nc(Sc2ccc(N)cc2)nc1N1CCN(CCN(C)C)CC1] | XX |
| 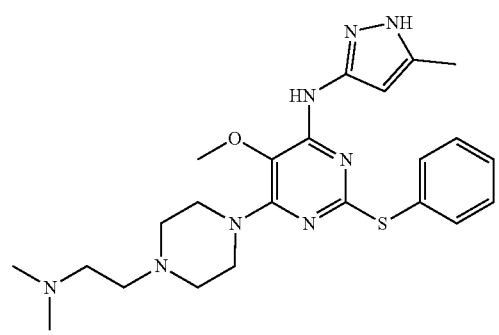 [SMILES: COc1c(Nc2cc(C)[nH]n2)nc(Sc2ccccc2)nc1N1CCN(CCN(C)C)CC1] | XX |
| 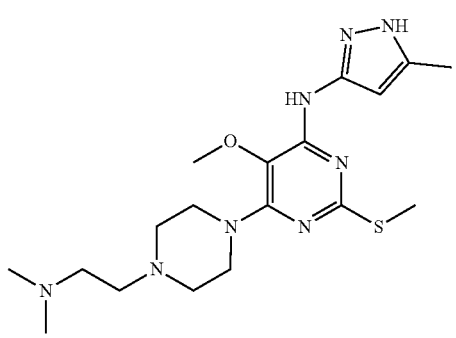 | XX |
| 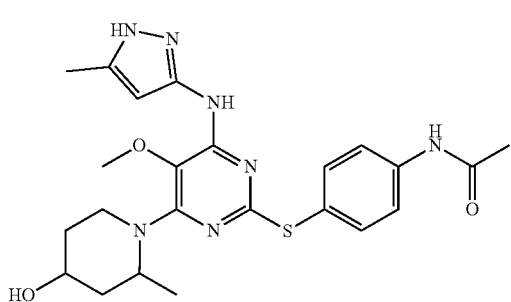 [SMILES: COc1c(Nc2cc(C)[nH]n2)nc(Sc2ccc(NC(C)=O)cc2)nc1N1CCC(O)CC1C] | XXX |

TABLE 1-continued

| | Activity |
|---|---|
| (structure) | XXX |
| (structure) | XXX |
| (structure) | XXX |
| (structure) | XXX |

TABLE 1-continued

| | Activity |
|---|---|
| (structure) | XXX |
| (structure) | XX |
| (structure) | XXX |
| (structure) | XXX |

TABLE 1-continued
| | Activity |
|---|---|
| 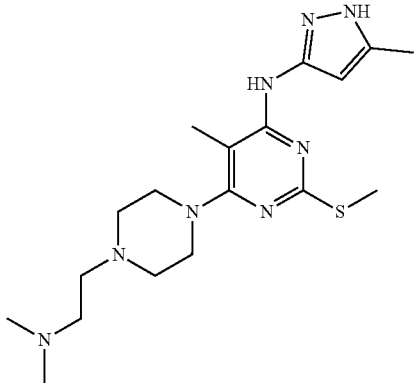 | XXX |
| 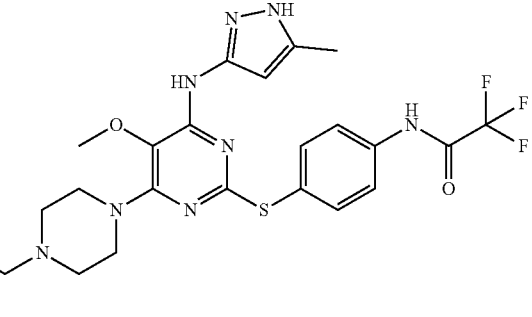 | XXX |
| 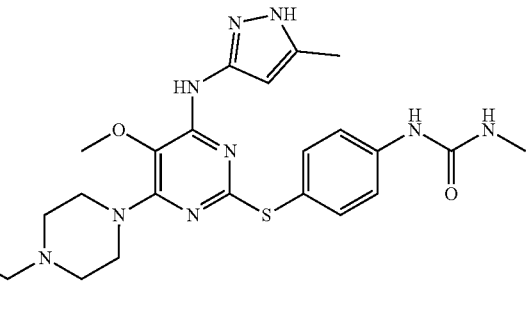 | XXX |
| 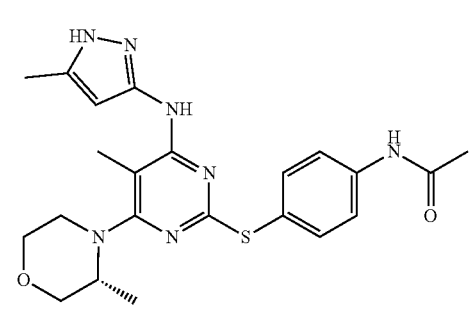 [SMILES: CC(=O)Nc1ccc(Sc2nc(Nc3cc(C)[nH]n3)c(C)c(N3CCOC[C@H]3C)n2)cc1] | XXX |

TABLE 1-continued

| | Activity |
|---|---|
| [structure] | XXX |
| [structure] | XXX |
| [structure] | XXX |
| [structure] | XXX |
| [structure] | XXX |

TABLE 1-continued
| | Activity |
|---|---|
| 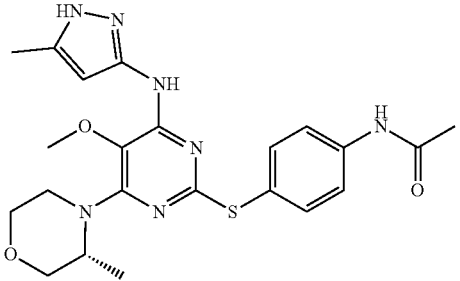 [SMILES: COc1c(Nc2cc(C)[nH]n2)nc(Sc2ccc(NC(C)=O)cc2)nc1N1CCOC[C@H]1C] | XXX |
| 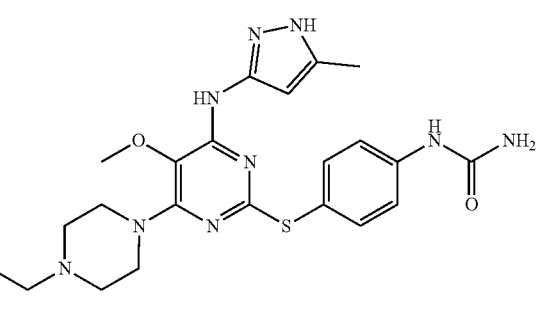 | XXX |
| 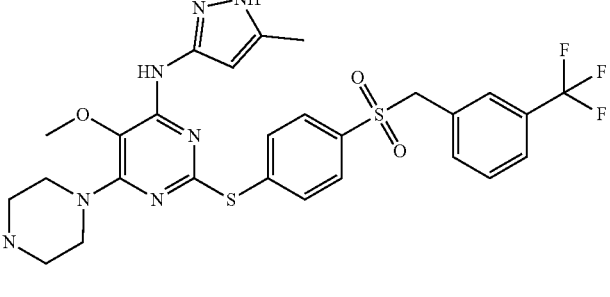 | XXX |
| 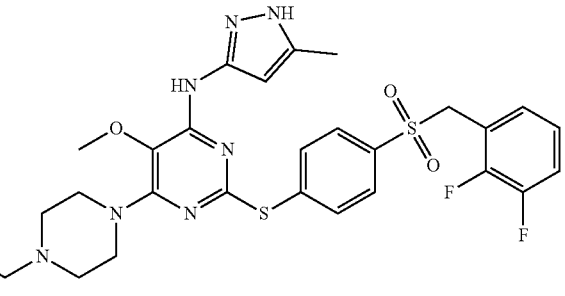 | XXX |
| 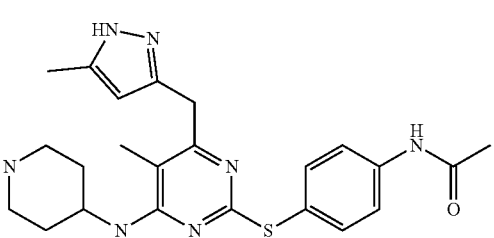 | XXX |

TABLE 1-continued
| | Activity |
|---|---|
| 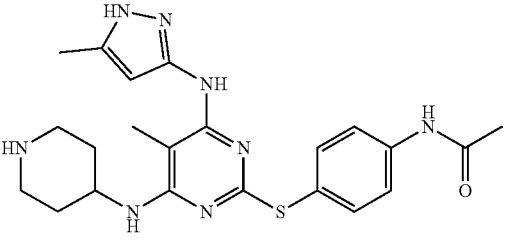 [SMILES: CC(=O)Nc1ccc(Sc2nc(Nc3cc(C)[nH]n3)c(C)c(NC3CCNCC3)n2)cc1] | XXX |
| 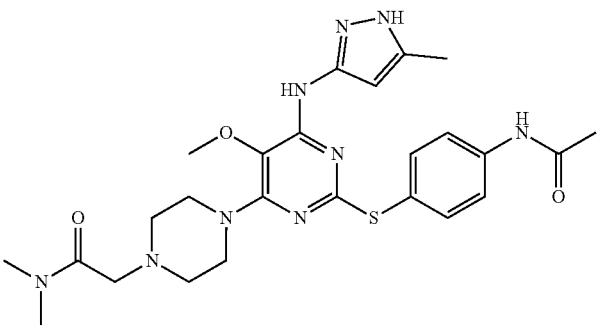 [SMILES: COc1c(Nc2cc(C)[nH]n2)nc(Sc2ccc(NC(C)=O)cc2)nc1N1CCN(CC(=O)N(C)C)CC1] | XXX |
| 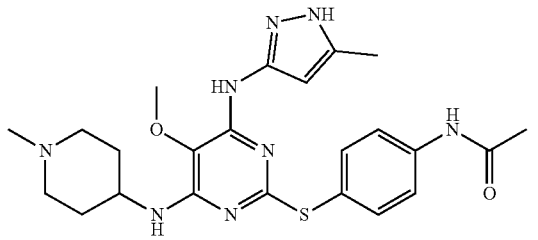 [SMILES: COc1c(Nc2cc(C)[nH]n2)nc(Sc2ccc(NC(C)=O)cc2)nc1NC1CCN(C)CC1] | XXX |
| 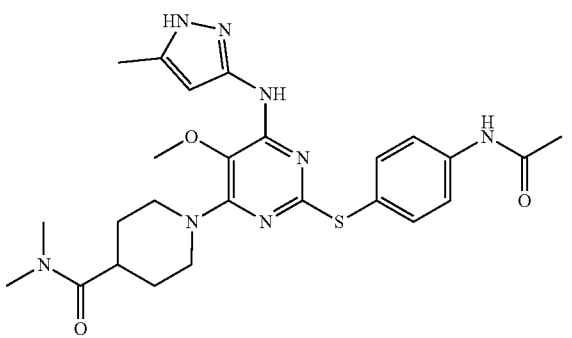 [SMILES: COc1c(Nc2cc(C)[nH]n2)nc(Sc2ccc(NC(C)=O)cc2)nc1N1CCC(C(=O)N(C)C)CC1] | XXX |
| 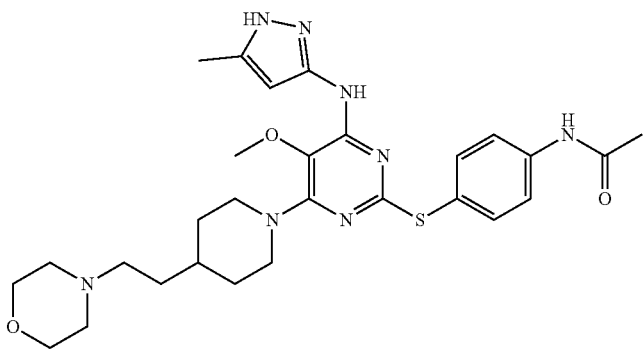 [SMILES: COc1c(Nc2cc(C)[nH]n2)nc(Sc2ccc(NC(C)=O)cc2)nc1N1CCC(CCN2CCOCC2)CC1] | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 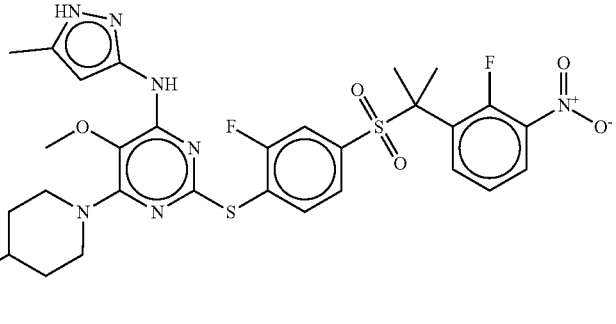 | XXX |
| 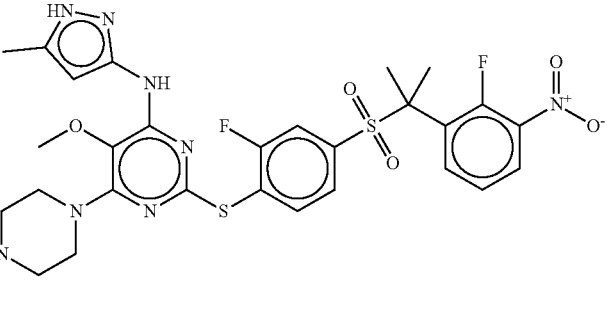 | XXX |
| 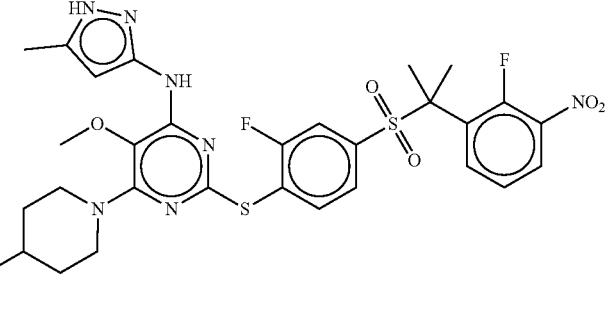 | XXX |
| 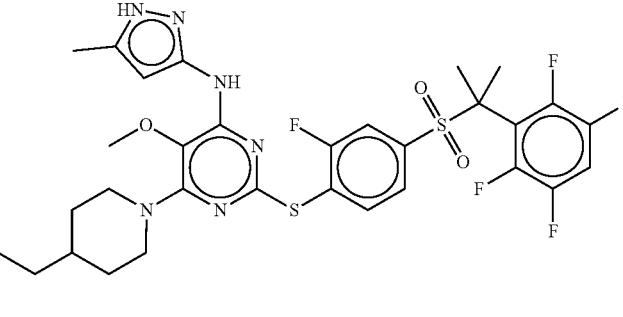 | XXX |
| 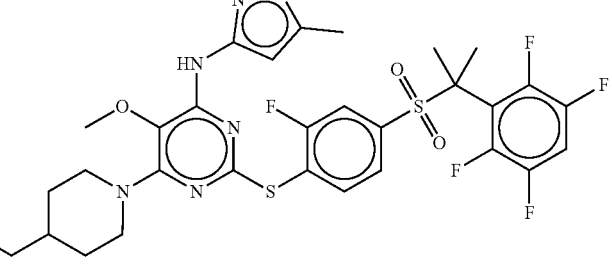 | XXX |

TABLE 1-continued
| | Activity |
|---|---|
| 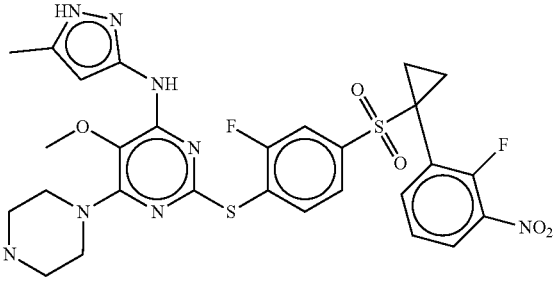 | XXX |
| 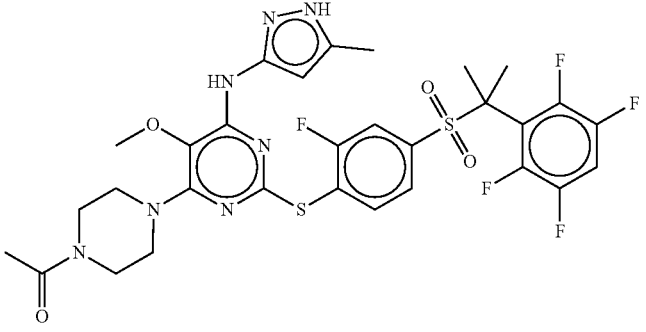 | XXX |
| 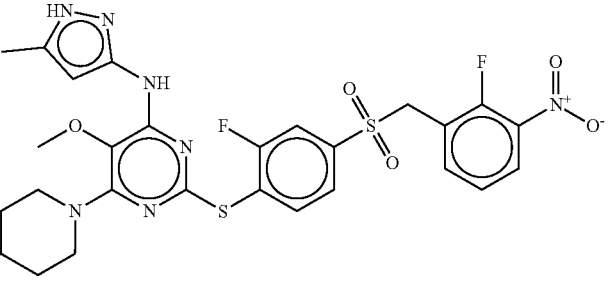 | XXX |
| 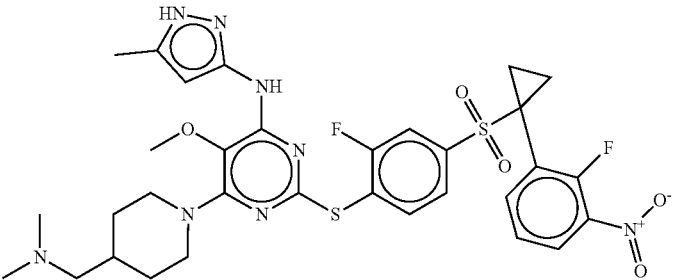 | XXX |
| 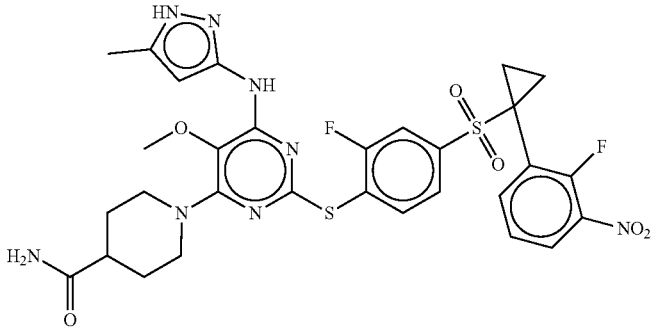 | XXX |

| | Activity |
|---|---|
| 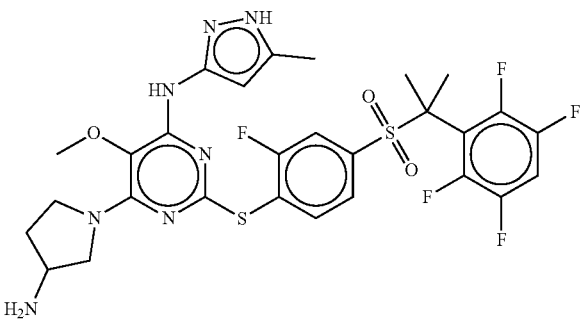 | XXX |
| 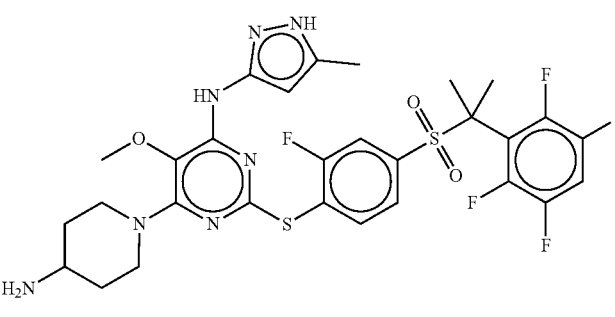 | XXX |
| 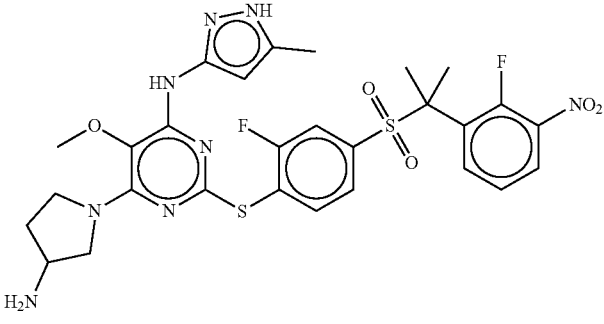 | XXX |
| 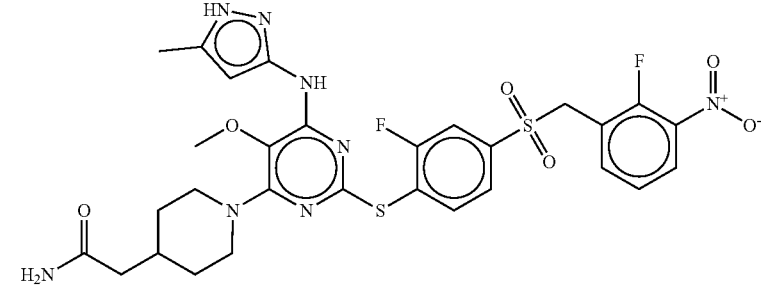 | XXX |
| 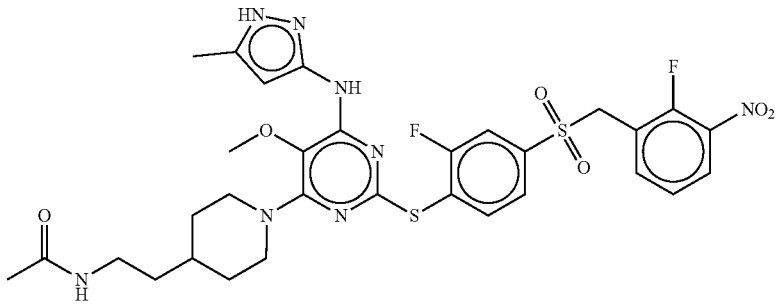 | XXX |

TABLE 1-continued
| | Activity |
|---|---|
| 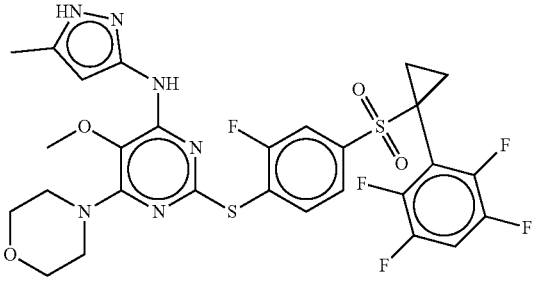 | XXX |
| 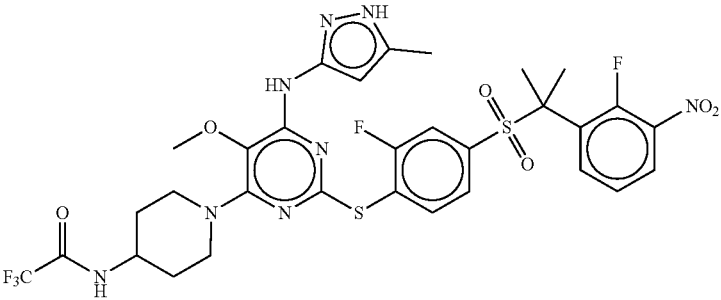 | XXX |
| 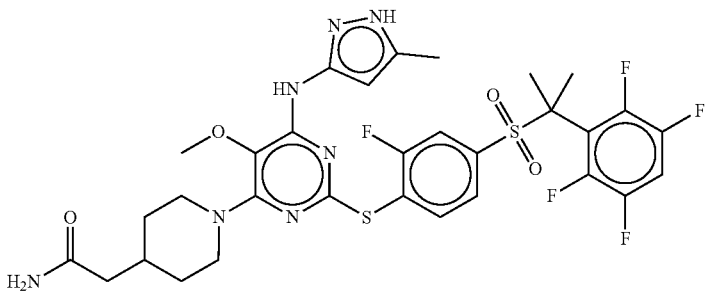 | XXX |
| 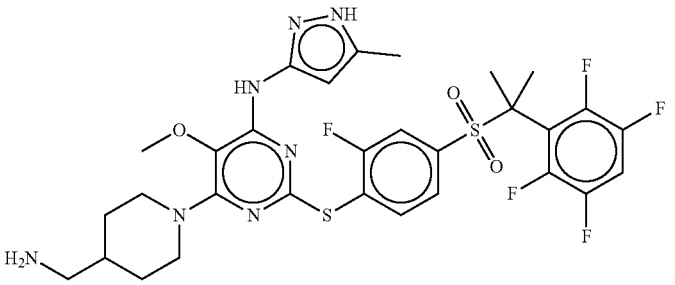 | XXX |
| 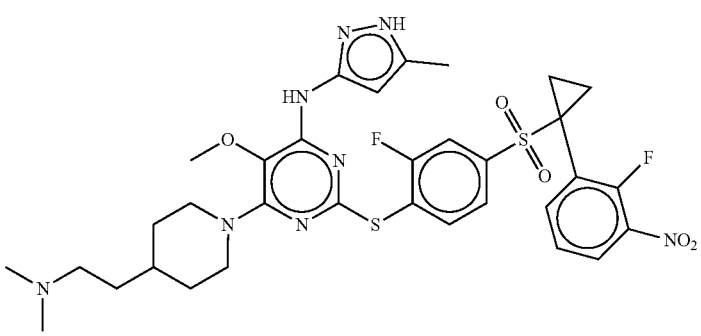 | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 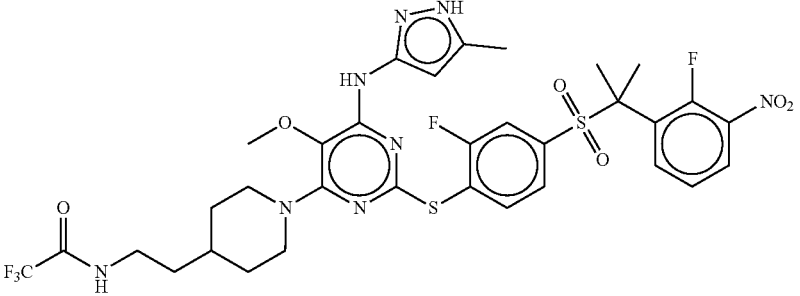 | XXX |
| 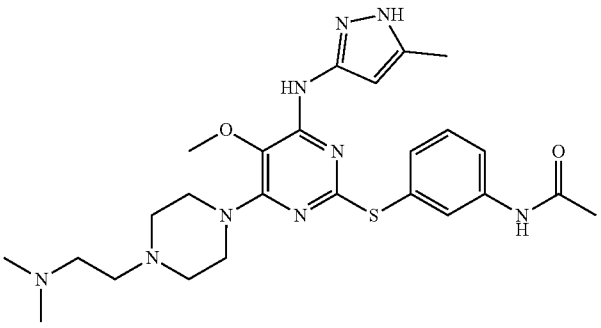 [SMILES: COc1c(Nc2cc(C)[nH]n2)nc(Sc2cccc(NC(C)=O)c2)nc1N1CCN(CCN(C)C)CC1] | XXX |
| 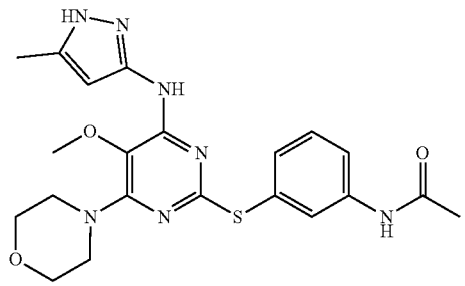 [SMILES: COc1c(Nc2cc(C)[nH]n2)nc(Sc2cccc(NC(C)=O)c2)nc1N1CCOCC1] | XXX |
| 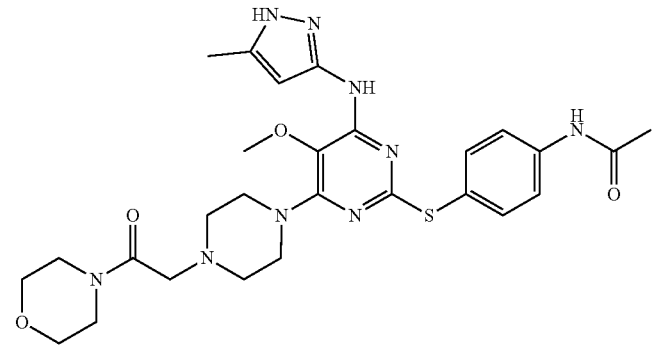 [SMILES: COc1c(Nc2cc(C)[nH]n2)nc(Sc2ccc(NC(C)=O)cc2)nc1N1CCN(CC(=O)N2CCOCC2)CC1] | XXX |

TABLE 1-continued
| | Activity |
|---|---|
| 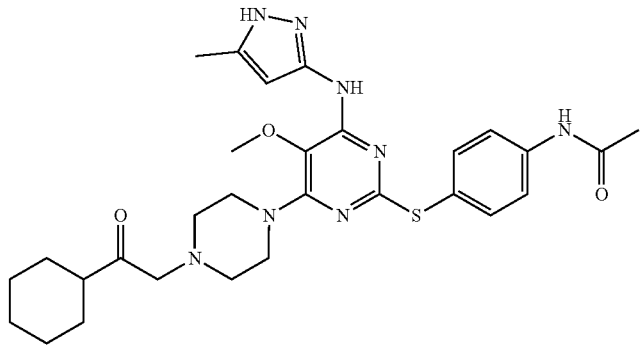 | XXX |
| 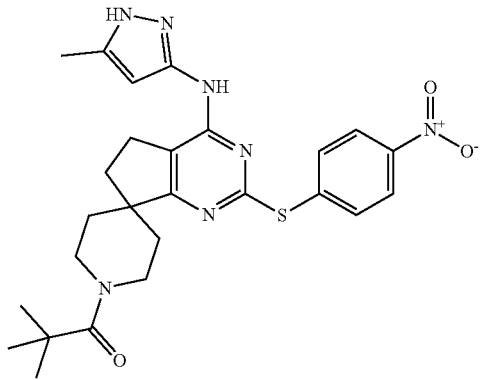 [SMILES: Cc1cc(Nc2nc(Sc3ccc([N+](=O)[O-])cc3)nc3c2CCC32CCN(C(=O)C(C)(C)C)CC2)n[nH]1] | XXX |
| 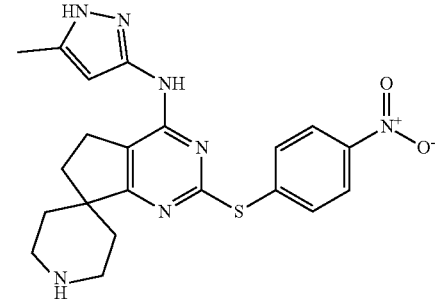 [SMILES: Cc1cc(Nc2nc(Sc3ccc([N+](=O)[O-])cc3)nc3c2CCC32CCNCC2)n[nH]1] | XX |
| 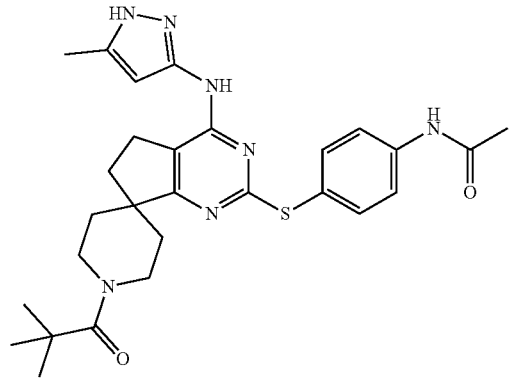 [SMILES: CC(=O)Nc1ccc(Sc2nc(Nc3cc(C)[nH]n3)c3c(n2)C2(CC3)CCN(C(=O)C(C)(C)C)CC2)cc1] | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 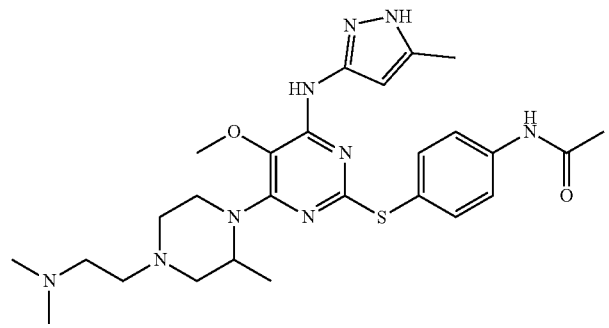 [SMILES: COc1c(Nc2cc(C)[nH]n2)nc(Sc2ccc(NC(C)=O)cc2)nc1N1CCN(CCN(C)C)CC1C] | XXX |
| 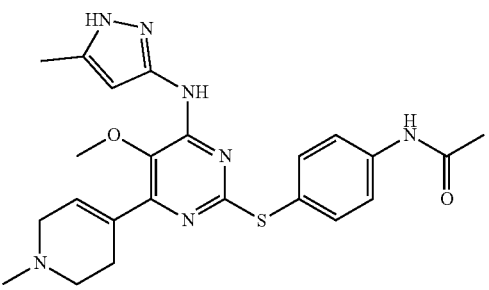 [SMILES: COc1c(Nc2cc(C)[nH]n2)nc(Sc2ccc(NC(C)=O)cc2)nc1C1=CCN(C)CC1] | XXX |
| 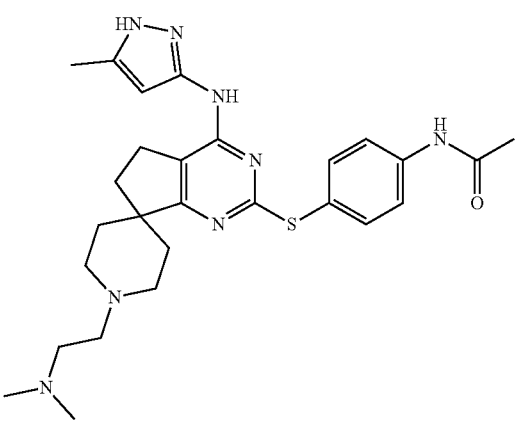 [SMILES: CC(=O)Nc1ccc(Sc2nc(Nc3cc(C)[nH]n3)c3c(n2)C2(CC3)CCN(CCN(C)C)CC2)cc1] | XXX |
| 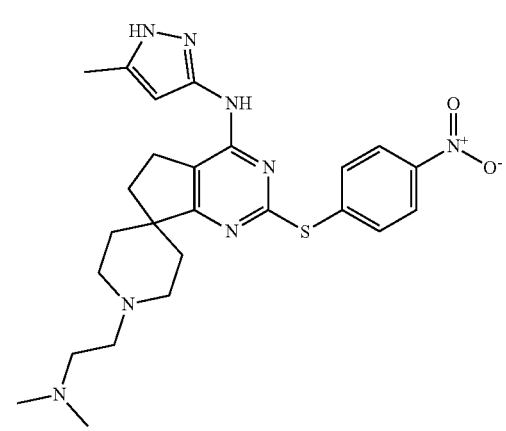 [SMILES: Cc1cc(Nc2nc(Sc3ccc([N+](=O)[O-])cc3)nc3c2CCC32CCN(CCN(C)C)CC2)n[nH]1] | XXX |

TABLE 1-continued
| | Activity |
|---|---|
| 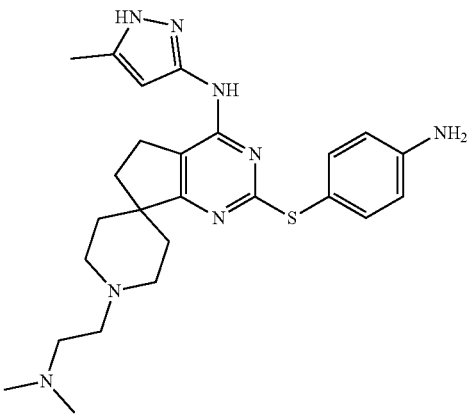 [SMILES: Cc1cc(Nc2nc(Sc3ccc(N)cc3)nc3c2CCC32CCN(CCN(C)C)CC2)n[nH]1] | XXX |
| 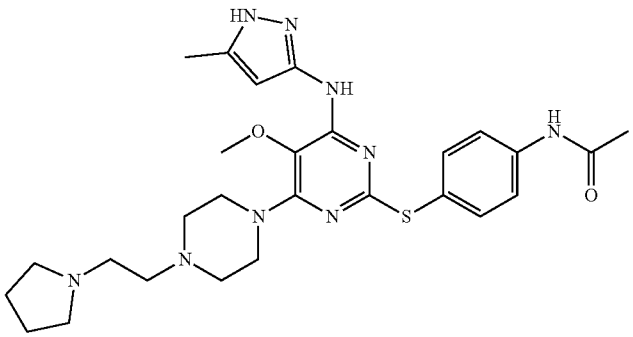 [SMILES: COc1c(Nc2cc(C)[nH]n2)nc(Sc2ccc(NC(C)=O)cc2)nc1N1CCN(CCN2CCCC2)CC1] | XXX |
| 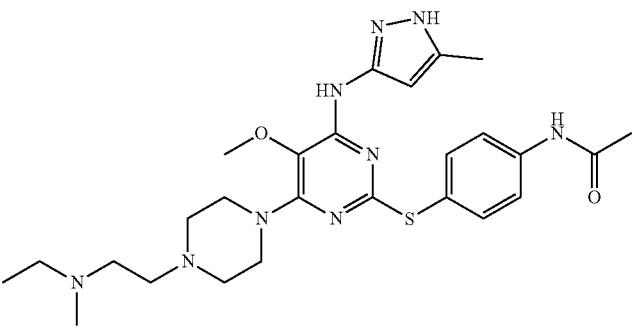 [SMILES: CCN(C)CCN1CCN(c2nc(Sc3ccc(NC(C)=O)cc3)nc(Nc3cc(C)[nH]n3)c2OC)CC1] | XXX |
| 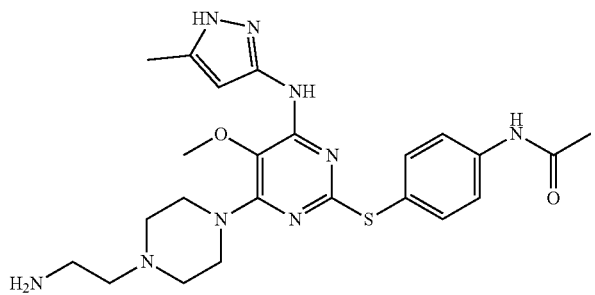 [SMILES: COc1c(Nc2cc(C)[nH]n2)nc(Sc2ccc(NC(C)=O)cc2)nc1N1CCN(CCN)CC1] | XXX |

TABLE 1-continued

| | Activity |
|---|---|
| [structure] | XXX |
| [structure] | XXX |
| [structure] | X |
| [structure] | X |

TABLE 1-continued
| | Activity |
|---|---|
| 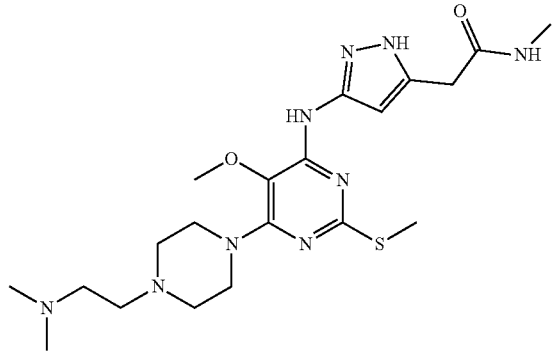 | X |
| 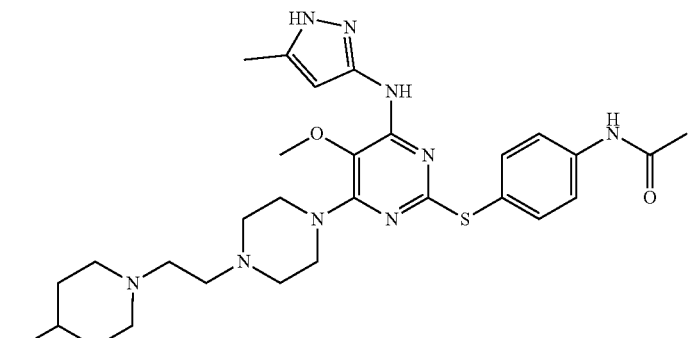 | XX |
| 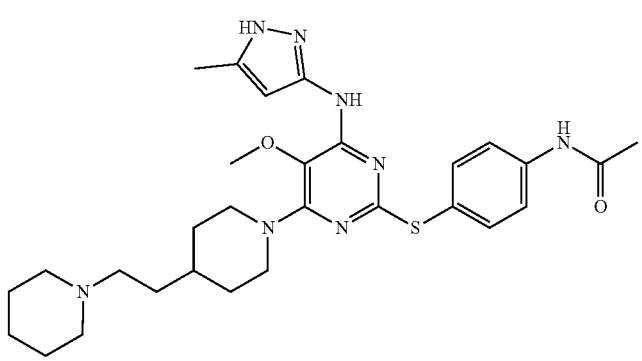 [SMILES: COc1c(Nc2cc(C)[nH]n2)nc(Sc2ccc(NC(C)=O)cc2)nc1N1CCC(CCN2CCCCC2)CC1] | XX |
| 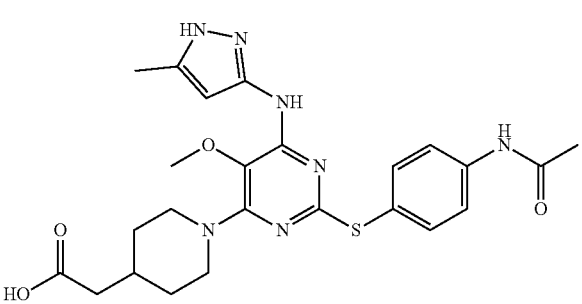 [SMILES: COc1c(Nc2cc(C)[nH]n2)nc(Sc2ccc(NC(C)=O)cc2)nc1N1CCC(CC(=O)O)CC1] | XXX |

TABLE 1-continued
| | Activity |
|---|---|
| 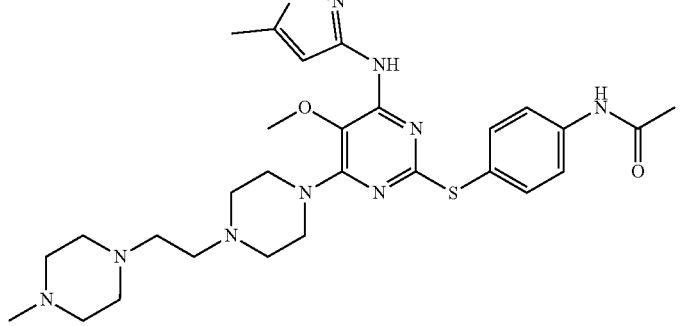 | XXX |
| 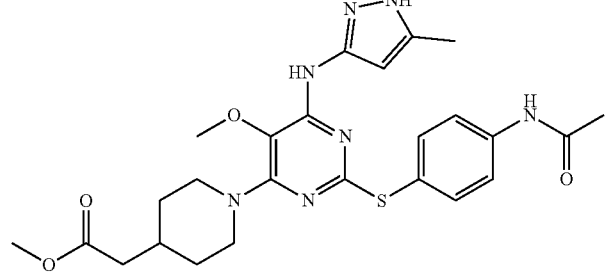 | XXX |
| 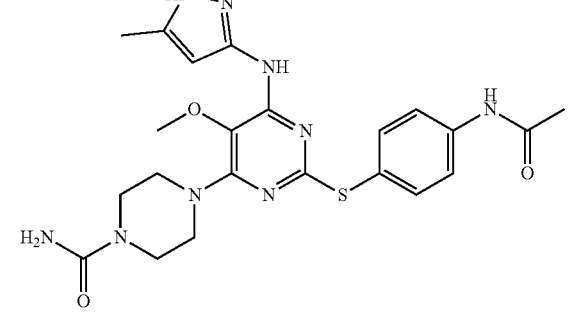 | XXX |
| 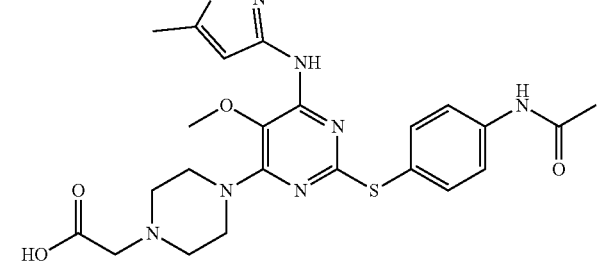 | XXX |
| 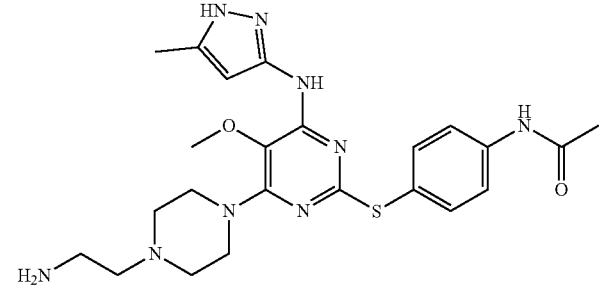 [SMILES: COc1c(Nc2cc(C)[nH]n2)nc(Sc2ccc(NC(C)=O)cc2)nc1N1CCN(CCN)CC1] | XXX |

TABLE 1-continued

| Structure | Activity |
|---|---|
| (chemical structure) | XXX |
| (chemical structure) | XXX |
| (chemical structure) | XXX |
| (chemical structure) | XXX |
| (chemical structure) | XXX |

TABLE 1-continued
| | Activity |
|---|---|
| 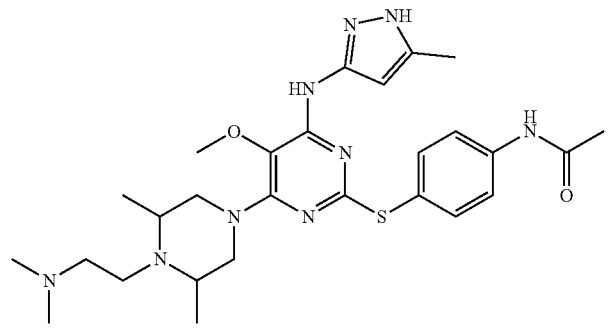 | XXX |
| 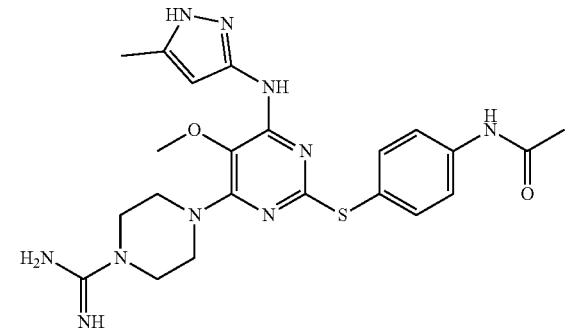 [SMILES: COc1c(Nc2cc(C)[nH]n2)nc(Sc2ccc(NC(C)=O)cc2)nc1N1CCN(C(=N)N)CC1] | XXX |
| 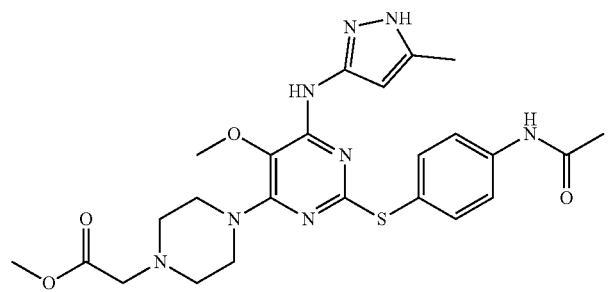 [SMILES: COC(=O)CN1CCN(c2nc(Sc3ccc(NC(C)=O)cc3)nc(Nc3cc(C)[nH]n3)c2OC)CC1] | XXX |
| 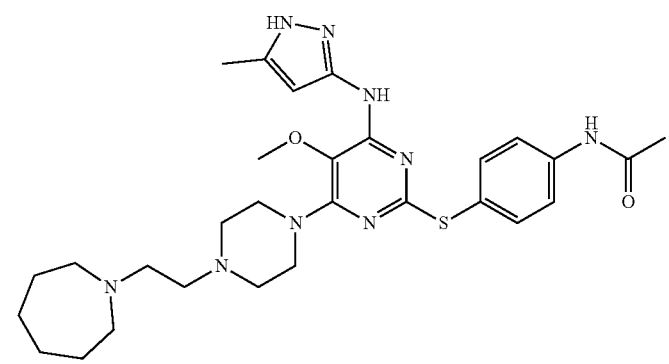 [SMILES: COc1c(Nc2cc(C)[nH]n2)nc(Sc2ccc(NC(C)=O)cc2)nc1N1CCN(CCN2CCCCCC2)CC1] | XXX |

TABLE 1-continued
| | Activity |
|---|---|
| 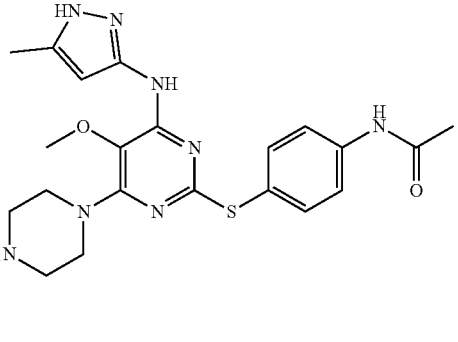 | XXX |
| 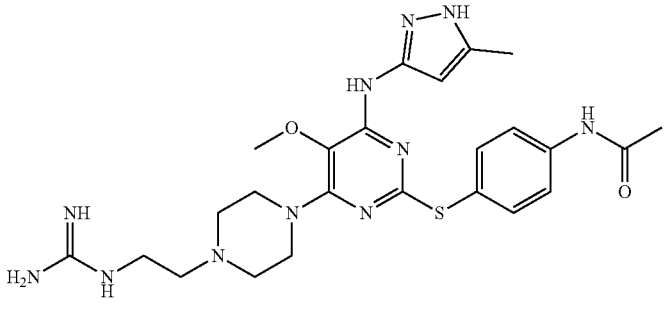 [SMILES: COc1c(Nc2cc(C)[nH]n2)nc(Sc2ccc(NC(C)=O)cc2)nc1N1CCN(CCNC(=N)N)CC1] | XXX |
| 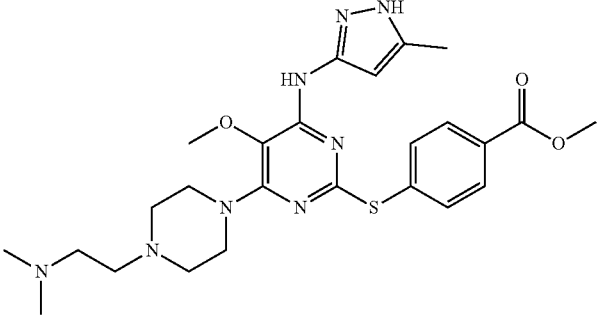 | XXX |
| 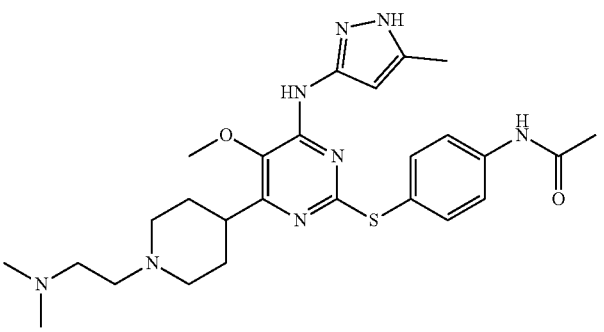 [SMILES: COc1c(Nc2cc(C)[nH]n2)nc(Sc2ccc(NC(C)=O)cc2)nc1C1CCN(CCN(C)C)CC1] | XX |

TABLE 1-continued
| | Activity |
|---|---|
| 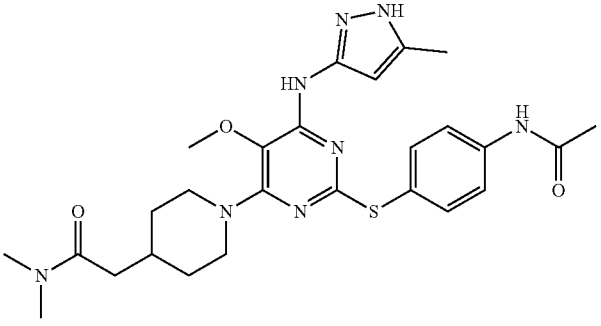 [SMILES: COc1c(Nc2cc(C)[nH]n2)nc(Sc2ccc(NC(C)=O)cc2)nc1N1CCC(CC(=O)N(C)C)CC1] | XXX |
| 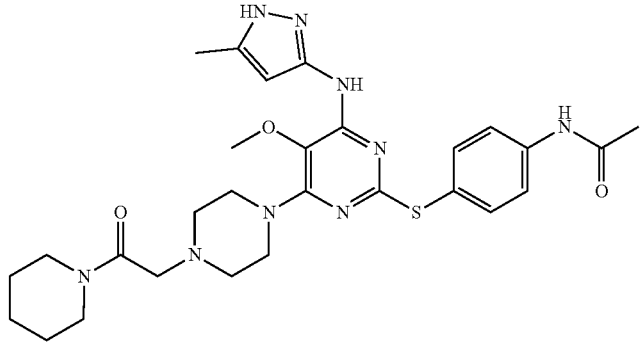 [SMILES: COc1c(Nc2cc(C)[nH]n2)nc(Sc2ccc(NC(C)=O)cc2)nc1N1CCN(CC(=O)N2CCCCC2)CC1] | XXX |
| 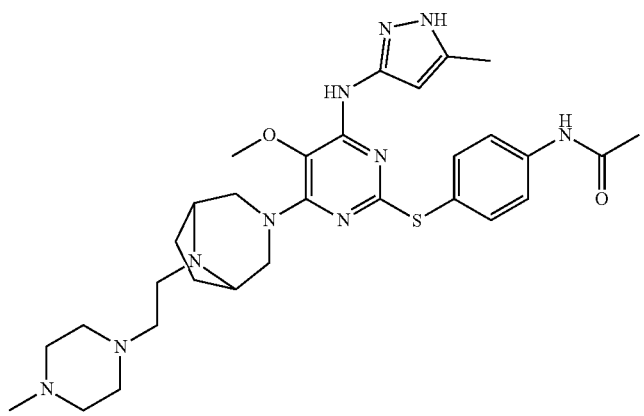 [SMILES: COc1c(Nc2cc(C)[nH]n2)nc(Sc2ccc(NC(C)=O)cc2)nc1N1CC2CCC(C1)N2CCN1CCN(C)CC1] | XXX |
| 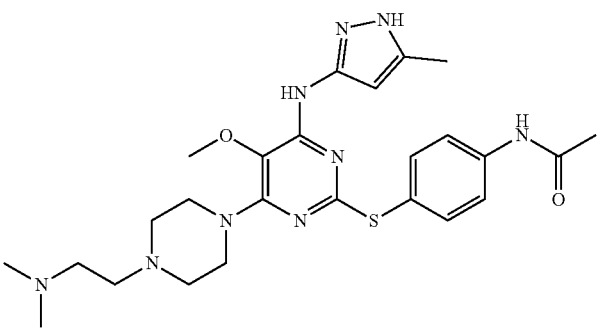 | XXX |

TABLE 1-continued
| | Activity |
|---|---|
| 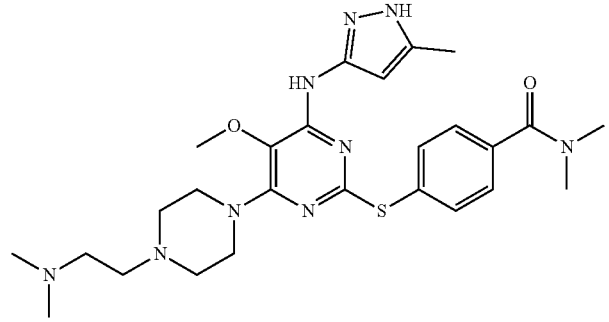 | XXX |
| 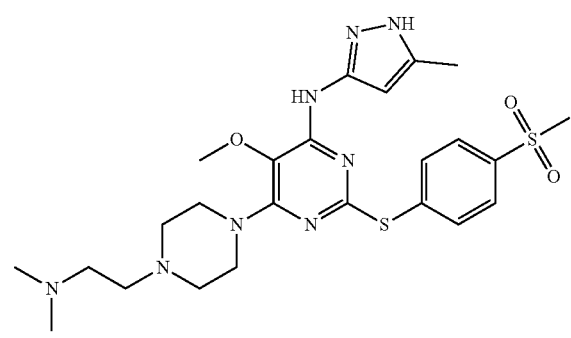 | XXX |
| 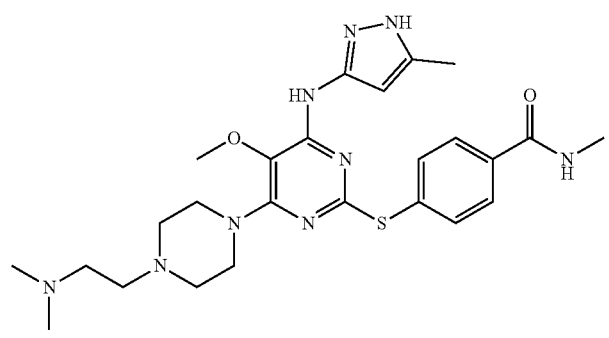 | XXX |
| 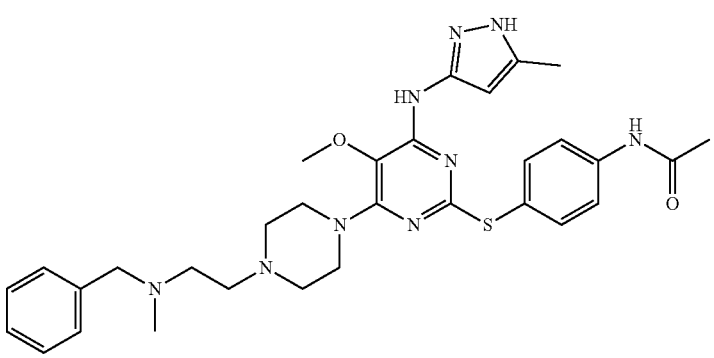 [SMILES: COc1c(Nc2cc(C)[nH]n2)nc(Sc2ccc(NC(C)=O)cc2)nc1N1CCN(CCN(C)Cc2ccccc2)CC1] | XXX |

TABLE 1-continued
| | Activity |
|---|---|
| 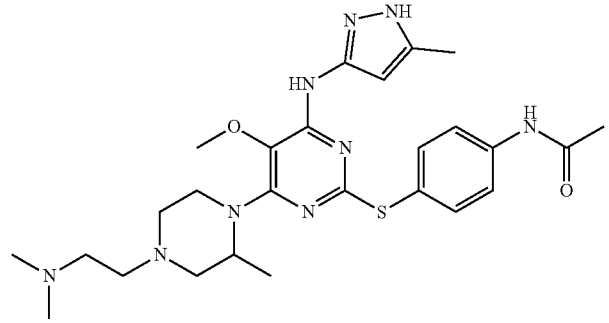 | X |
| 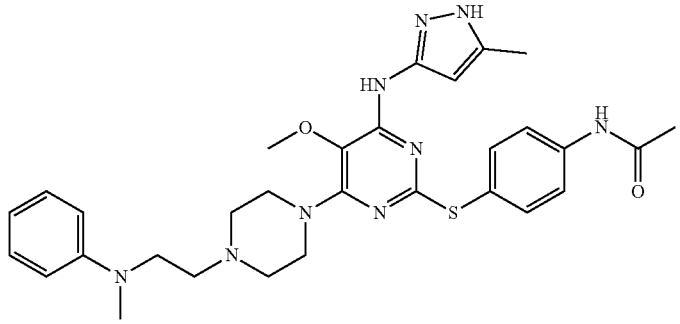 [SMILES: COc1c(Nc2cc(C)[nH]n2)nc(Sc2ccc(NC(C)=O)cc2)nc1N1CCN(CCN(C)c2ccccc2)CC1] | XXX |
| 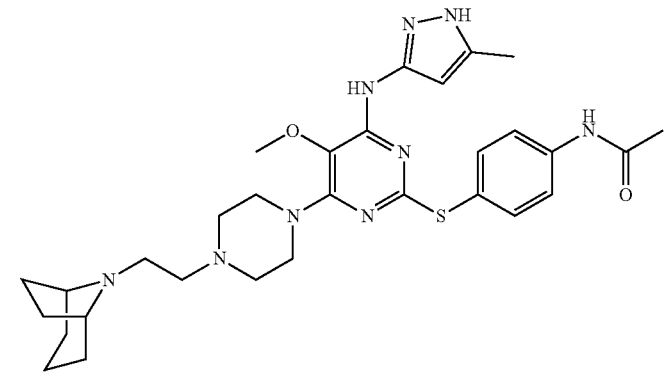 [SMILES: COc1c(Nc2cc(C)[nH]n2)nc(Sc2ccc(NC(C)=O)cc2)nc1N1CCN(CCN2C3CCCC2CC3)CC1] | XXX |
| 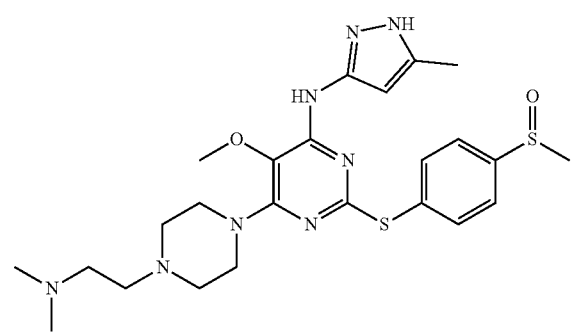 | XXX |

TABLE 1-continued

| Structure | Activity |
|---|---|
| (pyrimidine with methoxy, 3-methylpyrazol-5-ylamino, 4-acetamidophenylthio, and 8-(2-(azocan-1-yl)ethyl)-3,8-diazabicyclo[3.2.1]octan-3-yl substituents) | XXX |
| (pyrimidine with methoxy, 3-methylpyrazol-5-ylamino, 4-acetamidophenylthio, and 4-(2-(methylsulfonyl)ethyl)piperazin-1-yl substituents) | XXX |
| (pyrimidine with methoxy, 3-methylpyrazol-5-ylamino, 4-acetamidophenylthio, and 4-(9-azabicyclo[3.3.1]nonan-3-ylmethyl)piperazin-1-yl substituents) | XXX |
| (pyrimidine with methoxy, 5-methylthiazol-2-ylamino, 4-acetamidophenylthio, and 4-(2-(dimethylamino)ethyl)piperazin-1-yl substituents) | XXX |

TABLE 1-continued
| | Activity |
|---|---|
| 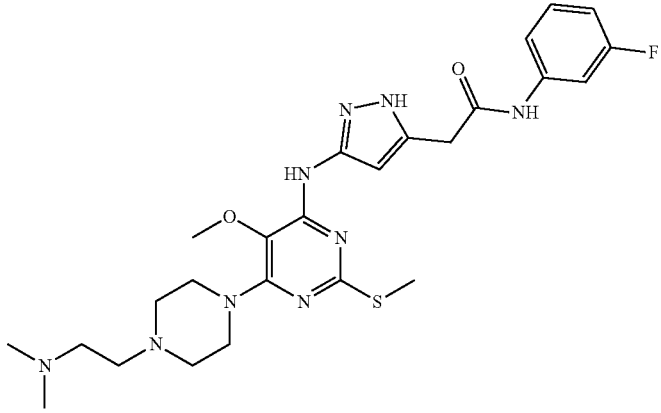 [SMILES: COc1c(Nc2cc(CC(=O)Nc3cccc(F)c3)[nH]n2)nc(SC)nc1N1CCN(CCN(C)C)CC1] | X |
| 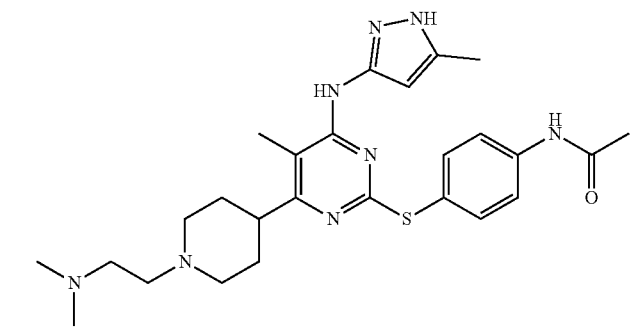 [SMILES: CC(=O)Nc1ccc(Sc2nc(Nc3cc(C)[nH]n3)c(C)c(C3CCN(CCN(C)C)CC3)n2)cc1] | XXX |
| 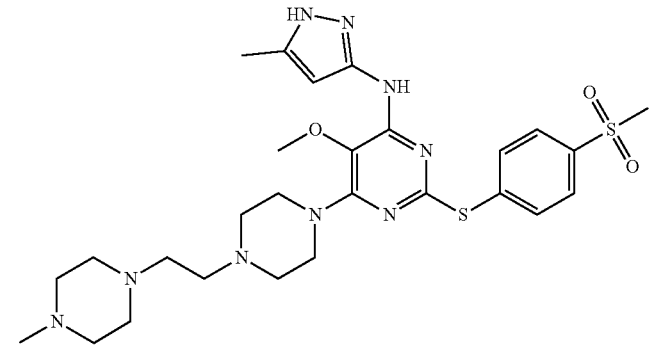 | XXX |
| 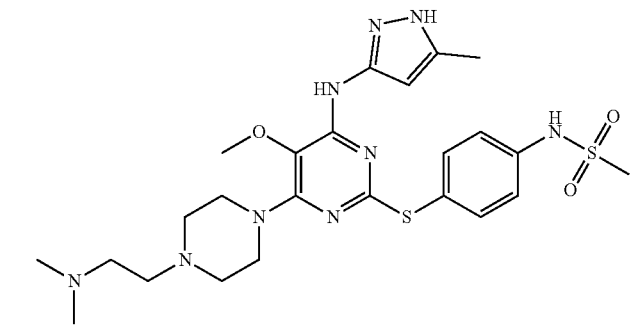 | XXX |

TABLE 1-continued

| Structure | Activity |
|---|---|
| (structure) | XXX |
| (structure) | XXX |
| (structure) | XXX |
| (structure) | XX |

TABLE 1-continued
| | Activity |
|---|---|
| 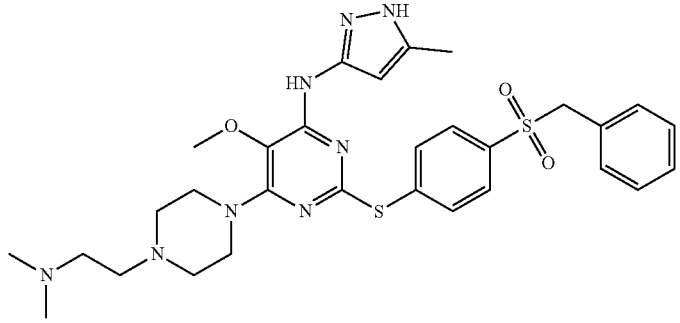 [SMILES: COc1c(Nc2cc(C)[nH]n2)nc(Sc2ccc(S(=O)(=O)Cc3ccccc3)cc2)nc1N1CCN(CCN(C)C)CC1] | XXX |
| 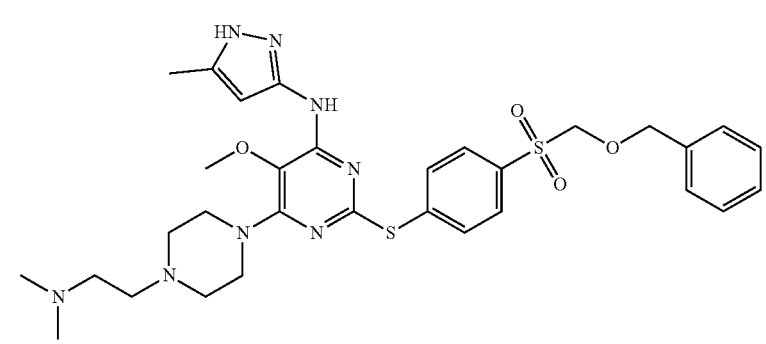 [SMILES: COc1c(Nc2cc(C)[nH]n2)nc(Sc2ccc(S(=O)(=O)COCc3ccccc3)cc2)nc1N1CCN(CCN(C)C)CC1] | XXX |
| 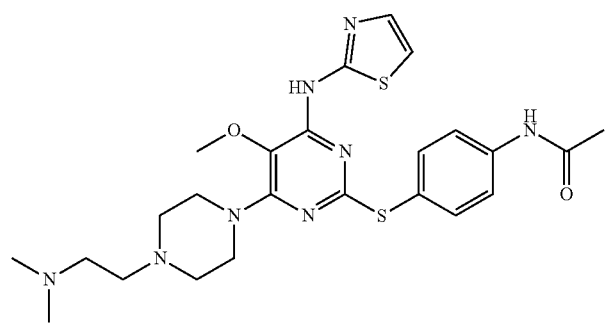 [SMILES: COc1c(Nc2nccs2)nc(Sc2ccc(NC(C)=O)cc2)nc1N1CCN(CCN(C)C)CC1] | XX |
| 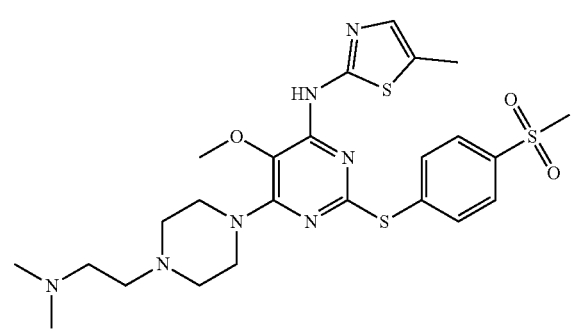 | XXX |

TABLE 1-continued
| | Activity |
|---|---|
| 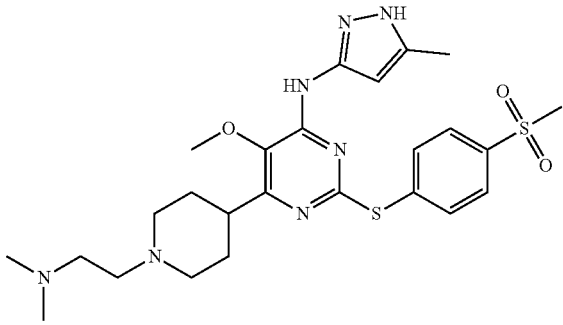 | XX |
| 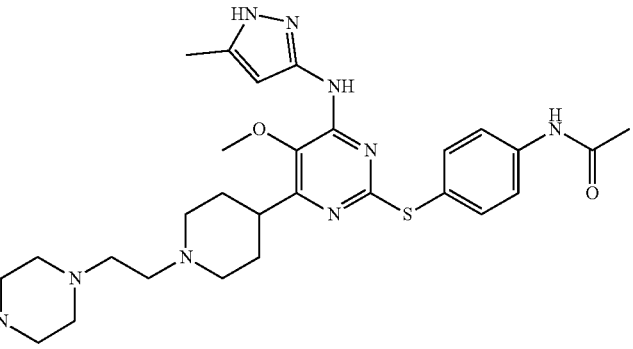 | XX |
| 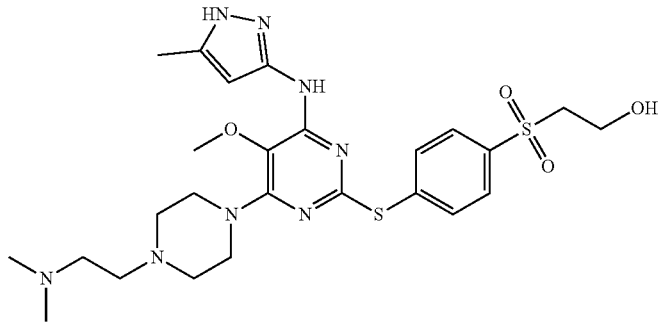 [SMILES: COc1c(Nc2cc(C)[nH]n2)nc(Sc2ccc(S(=O)(=O)CCO)cc2)nc1N1CCN(CCN(C)C)CC1] | XXX |
| 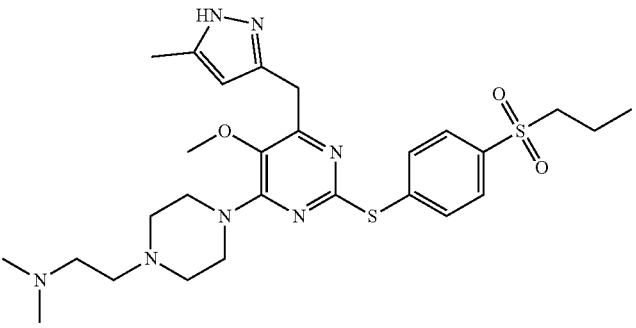 [SMILES: CCCS(=O)(=O)c1ccc(Sc2nc(Cc3cc(C)[nH]n3)c(OC)c(N3CCN(CCN(C)C)CC3)n2)cc1] | XXX |

TABLE 1-continued
| | Activity |
|---|---|
| 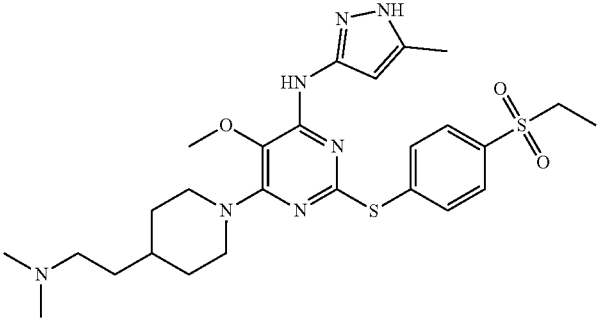 [SMILES: CCS(=O)(=O)c1ccc(Sc2nc(Nc3cc(C)[nH]n3)c(OC)c(N3CCC(CCN(C)C)CC3)n2)cc1] | XXX |
| 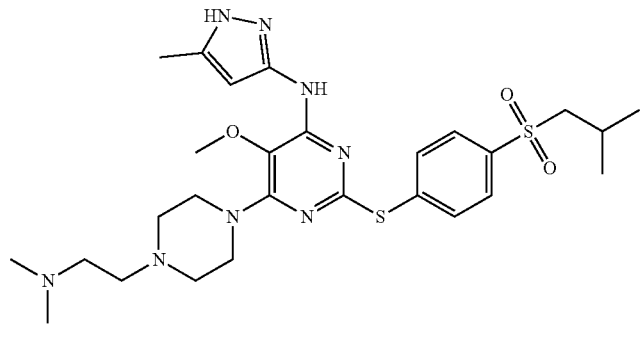 [SMILES: COc1c(Nc2cc(C)[nH]n2)nc(Sc2ccc(S(=O)(=O)CC(C)C)cc2)nc1N1CCN(CCN(C)C)CC1] | XXX |
| 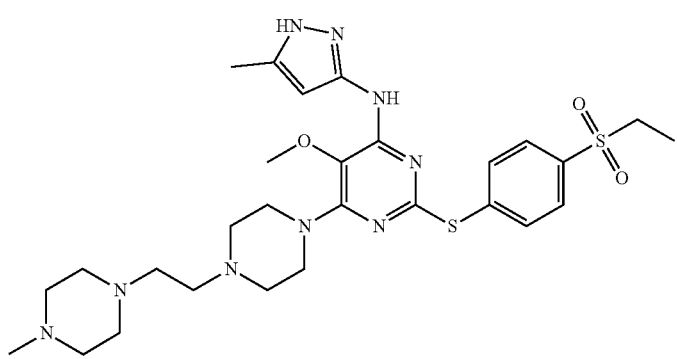 [SMILES: CCS(=O)(=O)c1ccc(Sc2nc(Nc3cc(C)[nH]n3)c(OC)c(N3CCN(CCN4CCN(C)CC4)CC3)n2)cc1] | XXX |
| 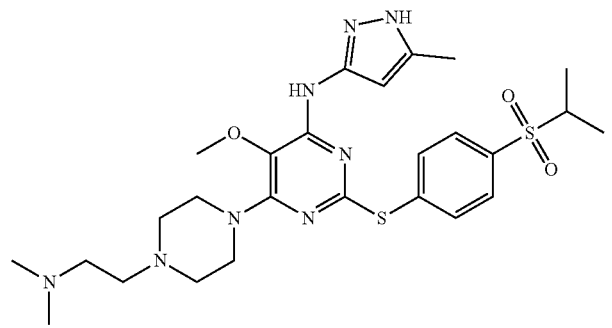 [SMILES: COc1c(Nc2cc(C)[nH]n2)nc(Sc2ccc(S(=O)(=O)C(C)C)cc2)nc1N1CCN(CCN(C)C)CC1] | XXX |

TABLE 1-continued

| Structure | Activity |
|---|---|
| (pyrazole-NH, methoxy, pyrimidine with piperazine-CH2CH2-N(CH3)2, S-phenyl-sulfonyl-CH2-(4-fluorophenyl)) | XXX |
| (pyrazole-NH, methoxy, pyrimidine with piperazine-CH2CH2-N(CH3)2, S-phenyl-sulfonyl-CH2-(4-methoxyphenyl)) | XXX |
| (pyrazole-NH, methoxy, pyrimidine with piperazine-CH2CH2-N(CH3)2, S-phenyl-sulfonyl-CH2-(2-chlorophenyl)) | XXX |
| (pyrazole-NH, methoxy, pyrimidine with piperazine-CH2CH2-N(CH3)2, S-phenyl-sulfonyl-CH2-(3-chlorophenyl)) | XXX |

TABLE 1-continued

| | Activity |
|---|---|
| (structure) | XXX |
| (structure) | XXX |
| (structure) | XXX |
| (structure) | XXX |
| (structure) | XXX |

TABLE 1-continued
| | Activity |
|---|---|
| 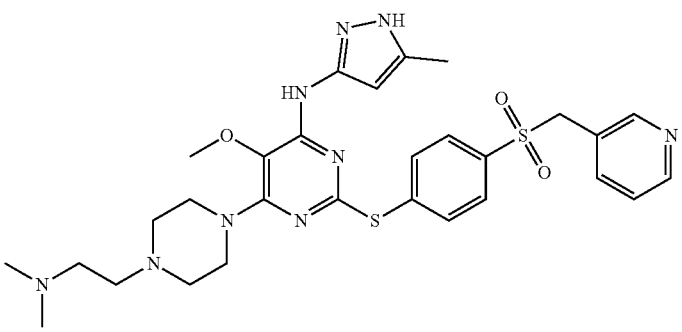 [SMILES: COc1c(Nc2cc(C)[nH]n2)nc(Sc2ccc(S(=O)(=O)Cc3cccnc3)cc2)nc1N1CCN(CCN(C)C)CC1] | XXX |
| 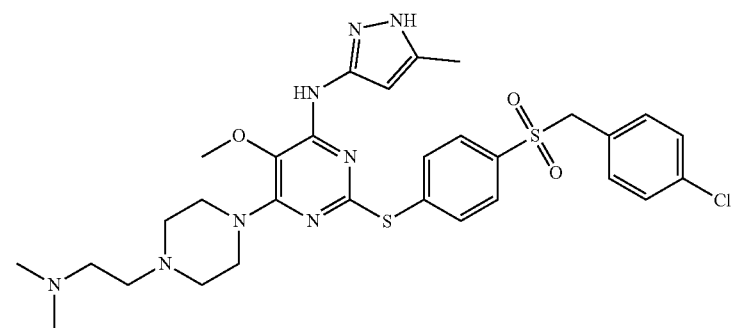 [SMILES: COc1c(Nc2cc(C)[nH]n2)nc(Sc2ccc(S(=O)(=O)Cc3ccc(Cl)cc3)cc2)nc1N1CCN(CCN(C)C)CC1] | XXX |
| 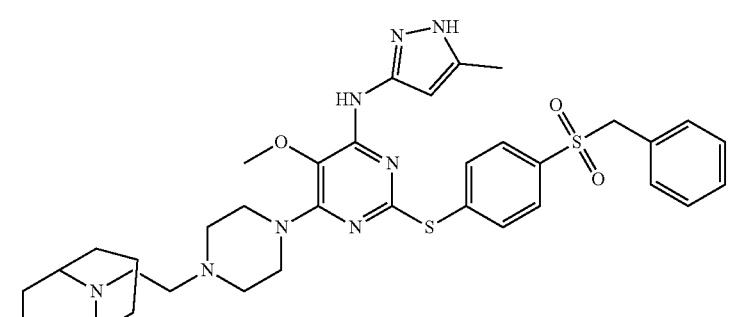 | XXX |
| 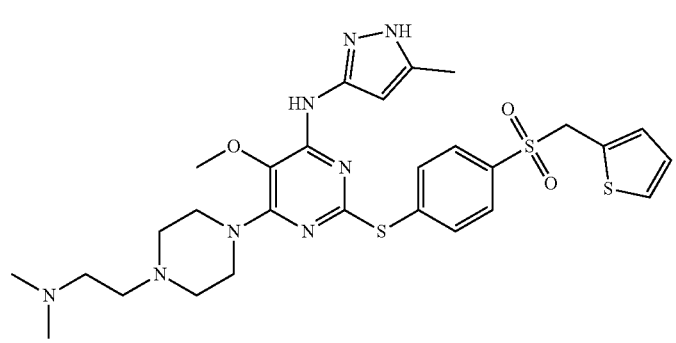 [SMILES: COc1c(Nc2cc(C)[nH]n2)nc(Sc2ccc(S(=O)(=O)Cc3cccs3)cc2)nc1N1CCN(CCN(C)C)CC1] | XXX |

TABLE 1-continued
| | Activity |
|---|---|
| 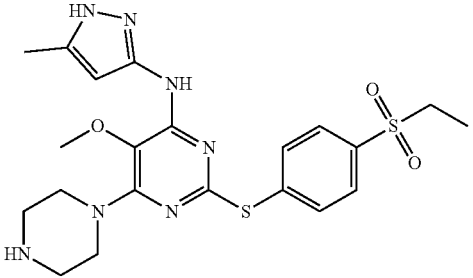 [SMILES: CCS(=O)(=O)c1ccc(Sc2nc(Nc3cc(C)[nH]n3)c(OC)c(N3CCNCC3)n2)cc1] | XXX |
| 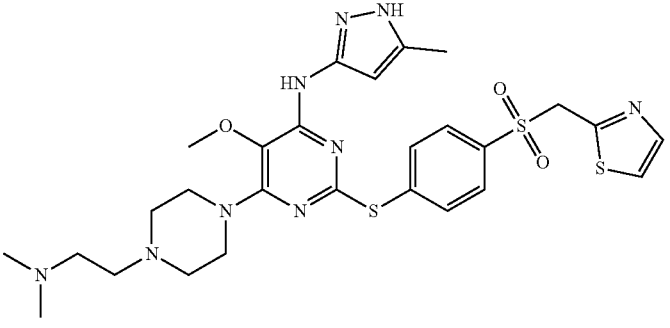 [SMILES: COc1c(Nc2cc(C)[nH]n2)nc(Sc2ccc(S(=O)(=O)Cc3nccs3)cc2)nc1N1CCN(CCN(C)C)CC1] | XXX |
| 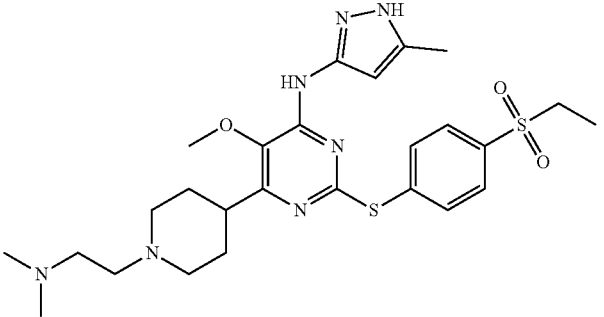 [SMILES: CCS(=O)(=O)c1ccc(Sc2nc(Nc3cc(C)[nH]n3)c(OC)c(C3CCN(CCN(C)C)CC3)n2)cc1] | XXX |
| 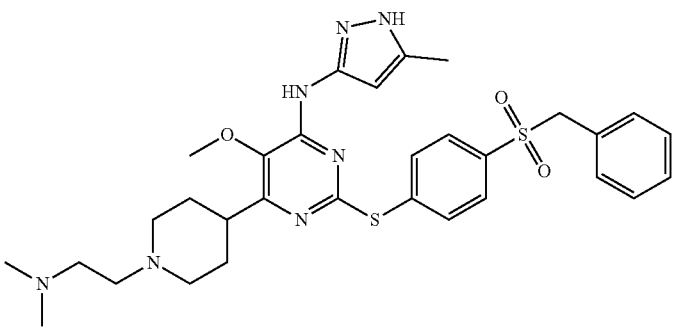 | XXX |

TABLE 1-continued
| | Activity |
|---|---|
| 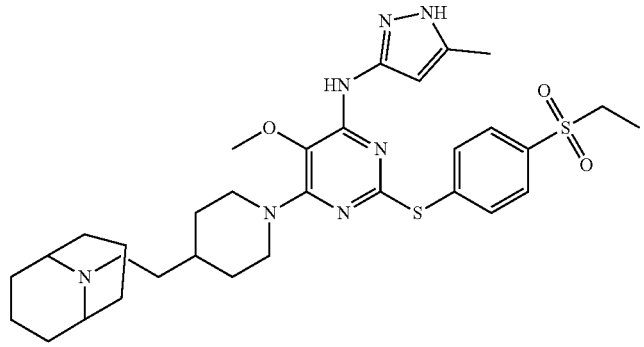 [SMILES: CCS(=O)(=O)c1ccc(Sc2nc(Nc3cc(C)[nH]n3)c(OC)c(N3CCC(CCN4C5CCCC4CCC5)CC3)n2)cc1] | XXX |
| 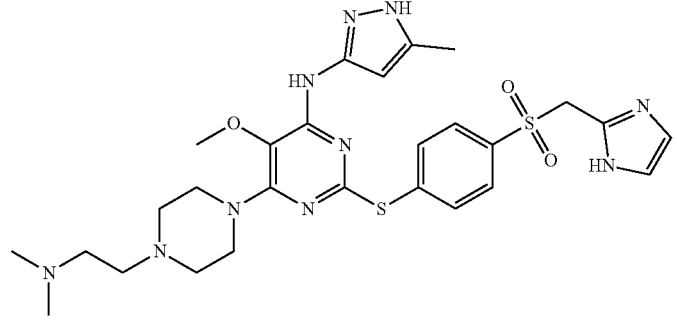 [SMILES: COc1c(Nc2cc(C)[nH]n2)nc(Sc2ccc(S(=O)(=O)Cc3ncc[nH]3)cc2)nc1N1CCN(CCN(C)C)CC1] | XXX |
| 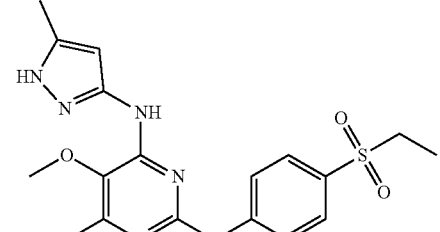 | XXX |
| 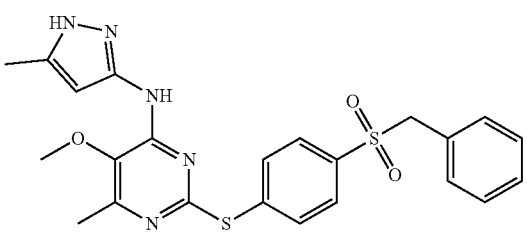 [SMILES: COc1c(C)nc(Sc2ccc(S(=O)(=O)Cc3ccccc3)cc2)nc1Nc1cc(C)[nH]n1] | XXX |
| 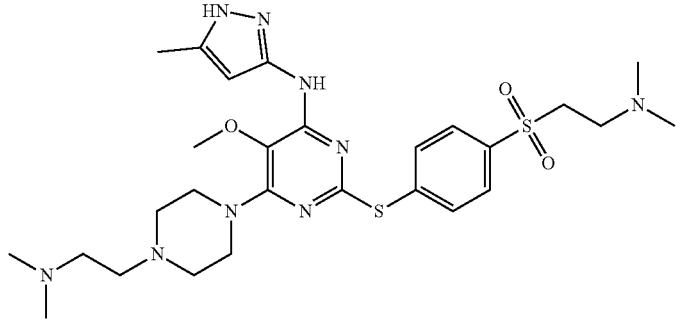 | XXX |

TABLE 1-continued
| | Activity |
|---|---|
| 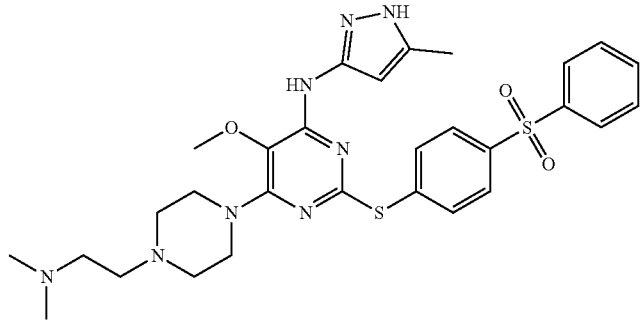 [SMILES: COc1c(Nc2cc(C)[nH]n2)nc(Sc2ccc(S(=O)(=O)c3ccccc3)cc2)nc1N1CCN(CCN(C)C)CC1] | XXX |
| 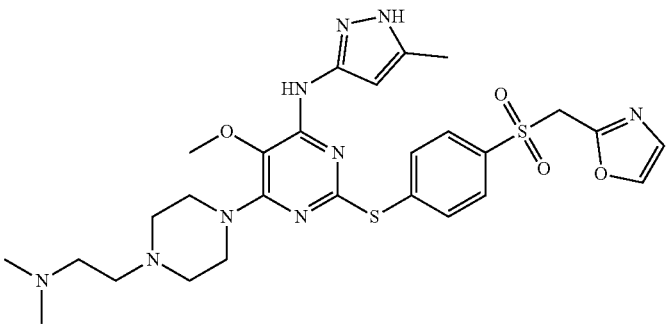 | XXX |
| 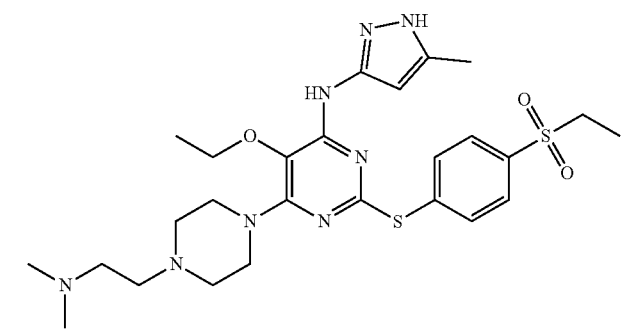 | XXX |
| 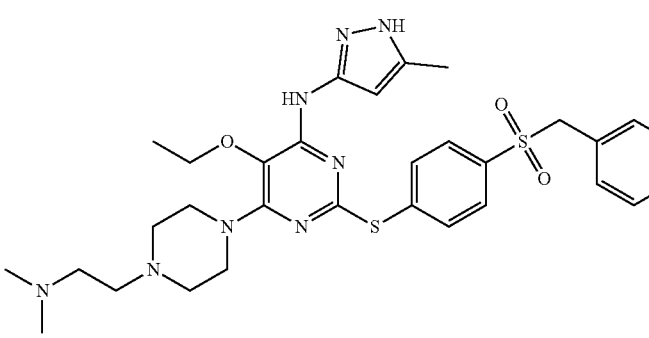 | XXX |
| 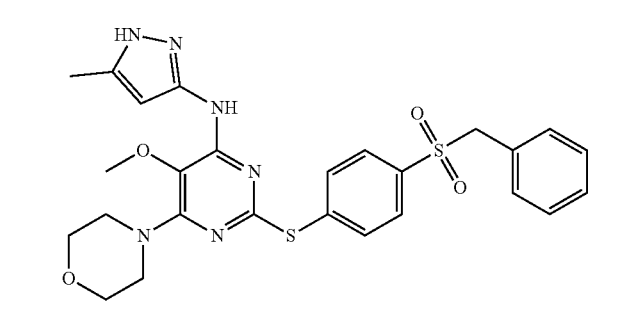 [SMILES: COc1c(Nc2cc(C)[nH]n2)nc(Sc2ccc(S(=O)(=O)Cc3ccccc3)cc2)nc1N1CCOCC1] | XXX |

TABLE 1-continued

| Structure | Activity |
|---|---|
| (chemical structure) | XXX |
| (chemical structure) | XXX |
| (chemical structure) | XXX |
| (chemical structure) | XXX |

TABLE 1-continued
| | Activity |
|---|---|
| 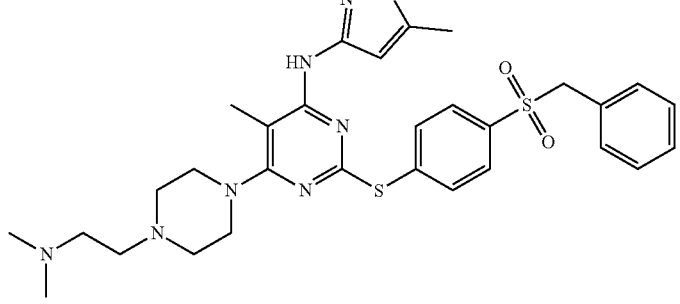 | XXX |
| 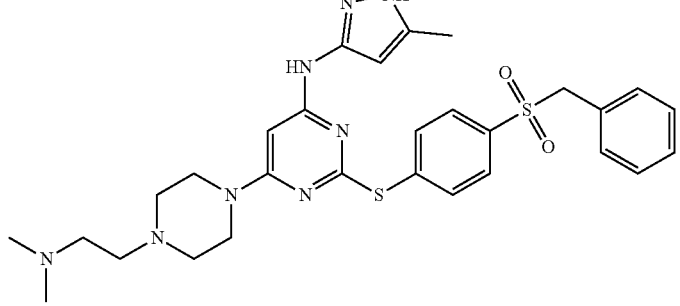 | XXX |
| 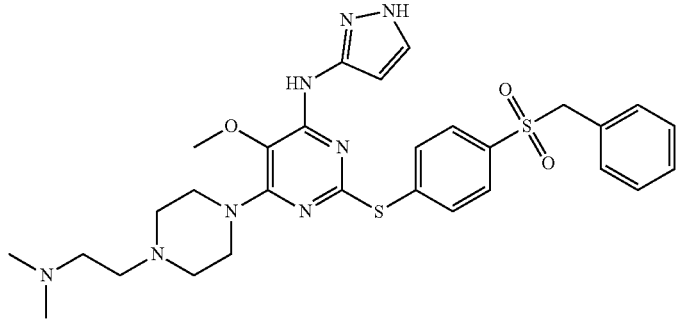 [SMILES: COc1c(Nc2cc[nH]n2)nc(Sc2ccc(S(=O)(=O)Cc3ccccc3)cc2)nc1N1CCN(CCN(C)C)CC1] | XXX |
| 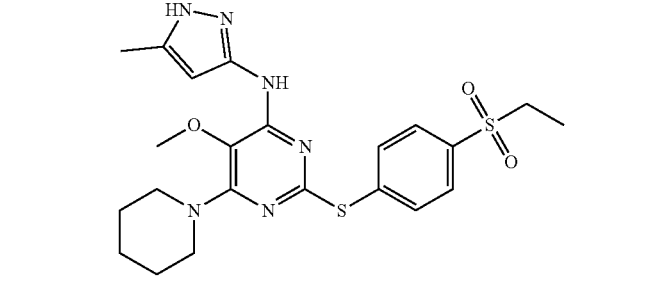 [SMILES: CCS(=O)(=O)c1ccc(Sc2nc(Nc3cc(C)[nH]n3)c(OC)c(N3CCCCC3)n2)cc1] | XXX |
| 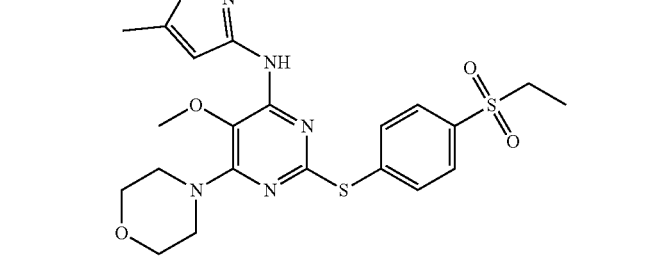 | XXX |

TABLE 1-continued

| Structure | Activity |
|---|---|
| (pyrimidine with 5-methyl-1H-pyrazol-3-ylamino, methoxy, 4-(2-(dimethylamino)ethyl)piperazin-1-yl, and 2-[(4-((3-nitrobenzyl)sulfonyl)phenyl)thio] substituents) | XXX |
| (pyrimidine with 5-methyl-1H-pyrazol-3-ylamino, methoxy, 4-(2-(dimethylamino)ethyl)piperazin-1-yl, and 2-[(4-((4-nitrobenzyl)sulfonyl)phenyl)thio] substituents) | XXX |
| (pyrimidine with 5-methyl-1H-pyrazol-3-ylamino, methoxy, diethylamino, and 2-[(4-(benzylsulfonyl)phenyl)thio] substituents) | XXX |
| (pyrimidine with 5-methyl-1H-pyrazol-3-ylamino, methoxy, diethylamino, and 2-[(4-(ethylsulfonyl)phenyl)thio] substituents) | XXX |
| (pyrimidine with 5-methyl-1H-pyrazol-3-ylamino, ethoxy, piperazin-1-yl, and 2-[(4-(benzylsulfonyl)phenyl)thio] substituents) | XXX |

TABLE 1-continued
| | Activity |
|---|---|
| 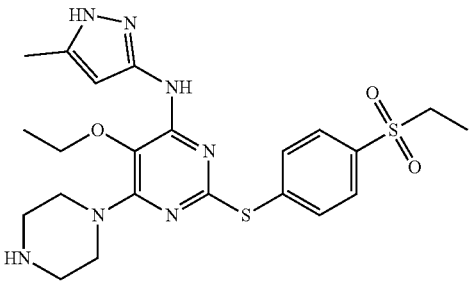 [SMILES: CCOc1c(Nc2cc(C)[nH]n2)nc(Sc2ccc(S(=O)(=O)CC)cc2)nc1N1CCNCC1] | XXX |
| 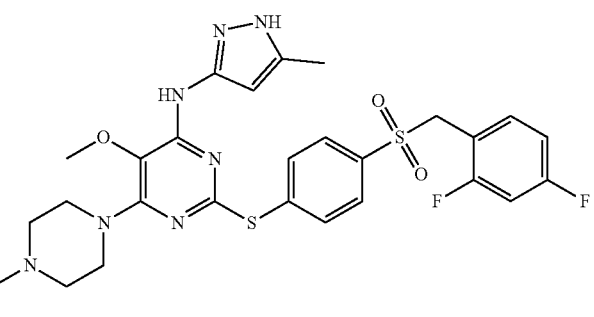 | XXX |
| 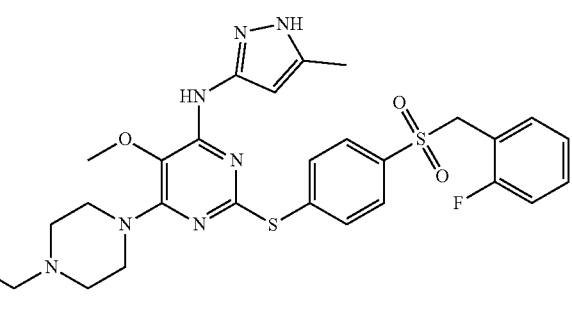 | XXX |
| 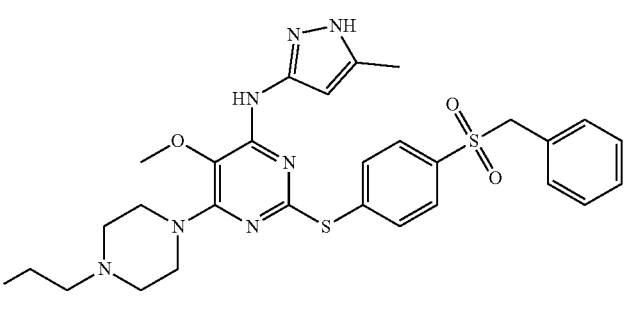 | XXX |
| 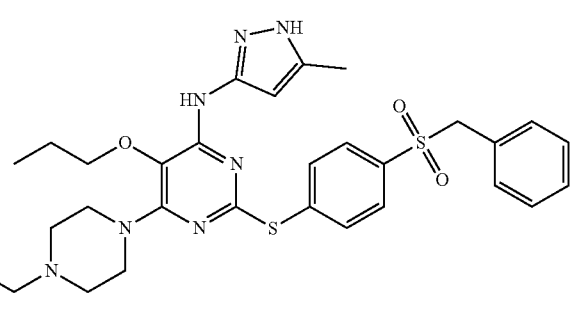 | XXX |

TABLE 1-continued
| | Activity |
|---|---|
| 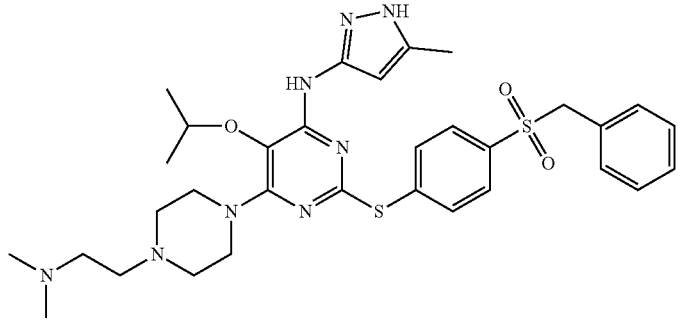 [SMILES: Cc1cc(Nc2nc(Sc3ccc(S(=O)(=O)Cc4ccccc4)cc3)nc(N3CCN(CCN(C)C)CC3)c2OC(C)C)n[nH]1] | XXX |
| 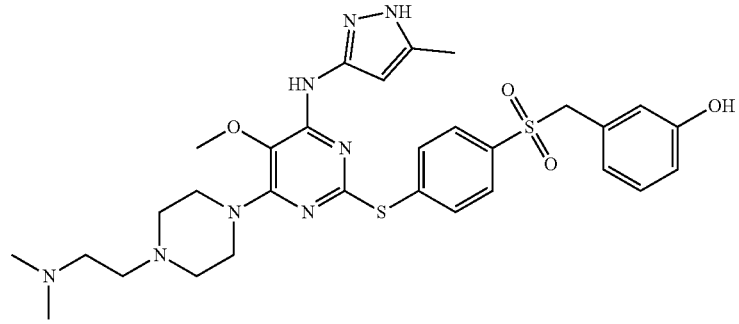 [SMILES: COc1c(Nc2cc(C)[nH]n2)nc(Sc2ccc(S(=O)(=O)Cc3cccc(O)c3)cc2)nc1N1CCN(CCN(C)C)CC1] | XXX |
| 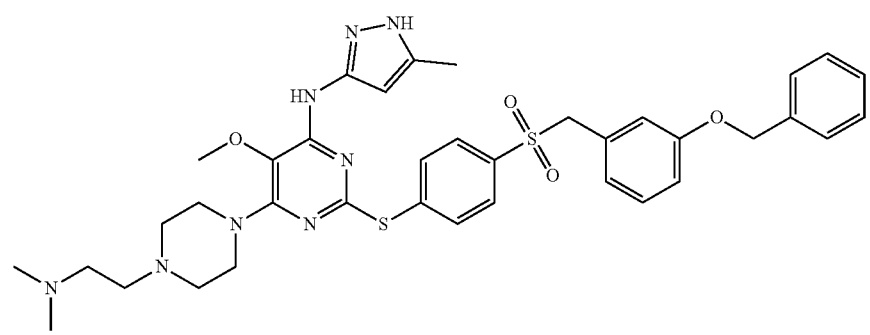 [SMILES: COc1c(Nc2cc(C)[nH]n2)nc(Sc2ccc(S(=O)(=O)Cc3cccc(OCc4ccccc4)c3)cc2)nc1N1CCN(CCN(C)C)CC1] | XXX |
| 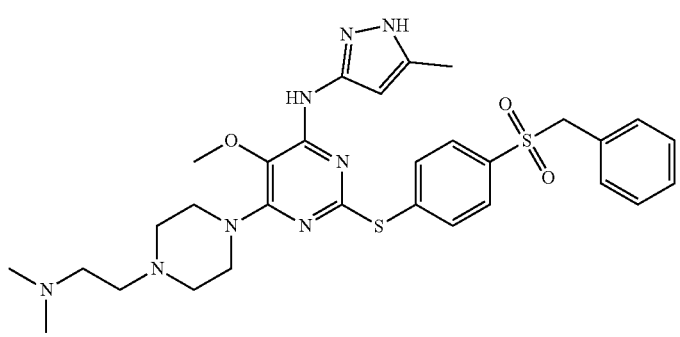 | XXX |

TABLE 1-continued
| | Activity |
|---|---|
| 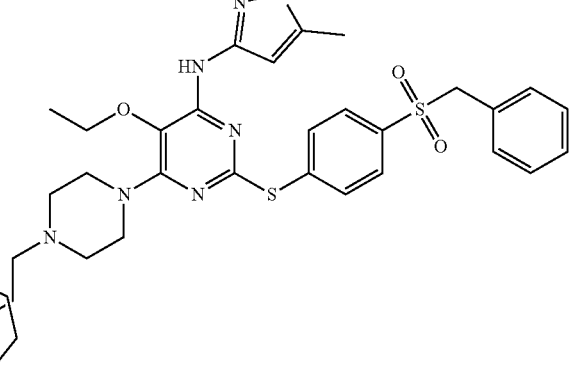 | XXX |
| 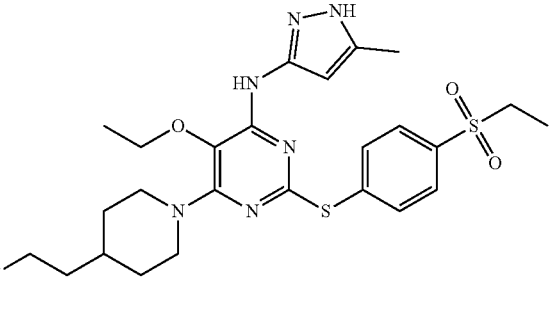 | XXX |
| 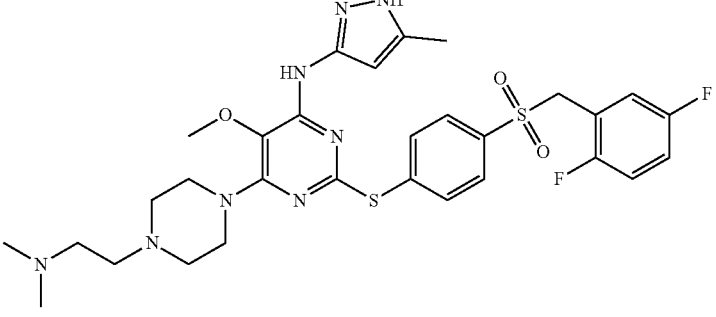 | XXX |
| 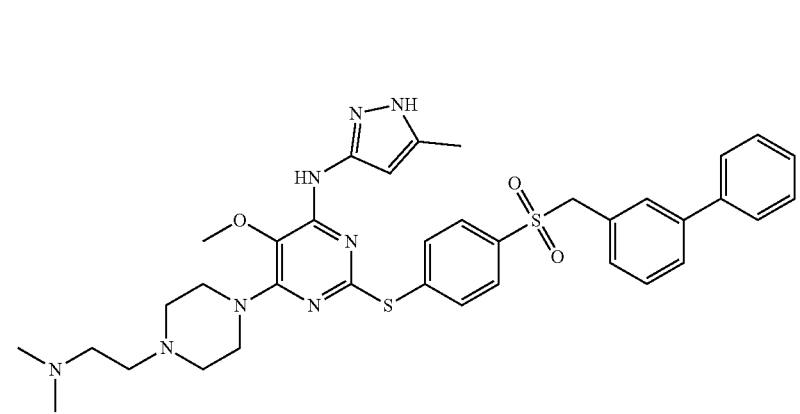 [SMILES: COc1c(Nc2cc(C)[nH]n2)nc(Sc2ccc(S(=O)(=O)Cc3cccc(-c4ccccc4)c3)cc2)nc1N1CCN(CCN(C)C)CC1] | XXX |

TABLE 1-continued

| | Activity |
|---|---|
| 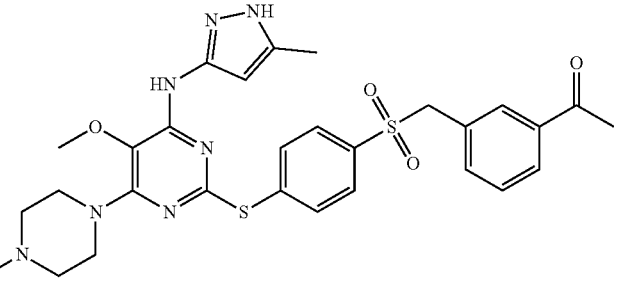 | XXX |
| 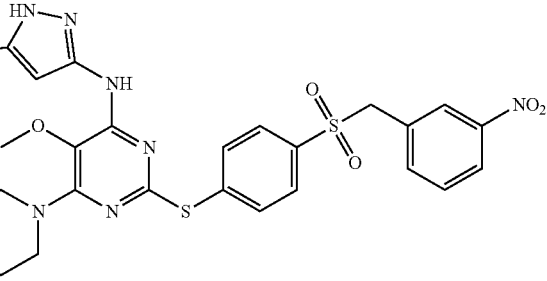 | XXX |
| 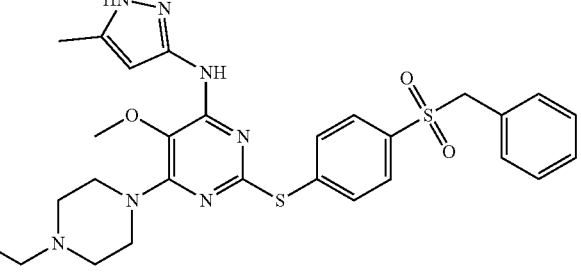 | XXX |
| 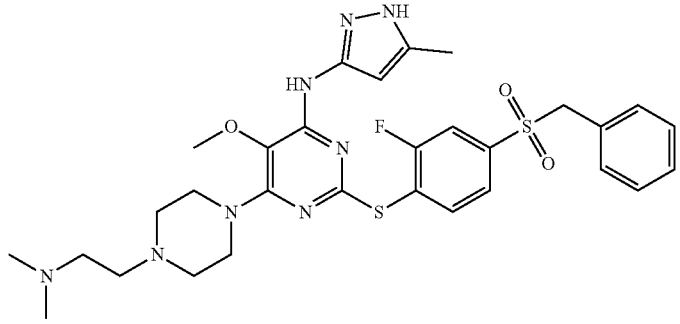 [SMILES: COc1c(Nc2cc(C)[nH]n2)nc(Sc2ccc(S(=O)(=O)Cc3ccccc3)cc2F)nc1N1CCN(CCN(C)C)CC1] | XXX |

TABLE 2

Compound Names for exemplified compounds of formula(I), (II), and (III).
All compounds were confirmed by mass spectro scopy and by $^1$H and $^{13}$C NMR.

No. Chemical Name

1  N-(4-((4,5-dimethyl-6-((5-methyl-1H-pyrazol-3-yl)amino)pyrimidin-2-yl)thio)phenyl)cyclopropanecarboxamide
2  N-(4-((4-((5-methyl-1H-pyrazol-3-yl)amino)-6,7-dihydro-5H-cyclopenta[d]pyrimidin-2-yl)thio)phenyl)cyclopropanecarboxamide
3  N-(4-((4-methyl-6-((5-methyl-1H-pyrazol-3-yl)amino)pyrimidin-2-yl)thio)phenyl)cyclopropanecarboxamide
4  N-(4-((5-(hydroxymethyl)-4-((5-methyl-1H-pyrazol-3-yl)amino)-6-(4-methylpiperazin-1-yl)pyrimidin-2-yl)thio)phenyl)cyclopropanecarboxamide TABLE 2-continued Compound Names for exemplified compounds of formula(I), (II), and (III).
All compounds were confirmed by mass spectro scopy and by $^1$H and $^{13}$C NMR.

| No. | Chemical Name |
|---|---|
| 5 | N-(4-((5-ethyl-4-((5-methyl-1H-pyrazol-3-yl)amino)-6-(4-methylpiperazin-1-yl)pyrimidin-2-yl)thio)phenyl)cyclopropanecarboxamide |
| 6 | N-(4-((5-ethyl-4-methyl-6-((5-methyl-1H-pyrazol-3-yl)amino)pyrimidin-2-yl)thio)phenyl)cyclopropanecarboxamide |
| 7 | N-(4-((5-methoxy-4-((5-methyl-1H-pyrazol-3-yl)amino)-6-(4-methylpiperazin-1-yl)pyrimidin-2-yl)thio)phenyl)cyclopropanecarboxamide |
| 8 | N-(4-((5-methyl-4-((5-methyl-1H-pyrazol-3-yl)amino)-6-(4-methylpiperazin-1-yl)pyrimidin-2-yl)thio)phenyl)cyclopropanecarboxamide |
| 9 | N-(4-((5-methyl-4-((5-methyl-1H-pyrazol-3-yl)amino)-6-morpholinopyrimidin-2-yl)thio)phenyl)cyclopropanecarboxamide |
| 10 | N-(4-((4-(3,4-dimethylpiperazin-1-yl)-5-methyl-6-((5-methyl-1H-pyrazol-3-yl)amino)pyrimidin-2-yl)thio)phenyl)cyclopropanecarboxamide |
| 11 | N-(4-((4-(4-(2-(dimethylamino)ethyl)piperazin-1-yl)-5-methyl-6-((5-methyl-1H-pyrazol-3-yl)amino)pyrimidin-2-yl)thio)phenyl)cyclopropanecarboxamide |
| 12 | N-(4-((4-(4-(2-methoxyethyl)piperazin-1-yl)-5-methyl-6-((5-methyl-1H-pyrazol-3-yl)amino)pyrimidin-2-yl)thio)phenyl)cyclopropanecarboxamide |
| 13 | N-(4-((4-(4-acetylpiperazin-1-yl)-5-methyl-6-((5-methyl-1H-pyrazol-3-yl)amino)pyrimidin-2-yl)thio)phenyl)cyclopropanecarboxamide |
| 14 | N-(4-((4-(4-isopropylpiperazin-1-yl)-5-methyl-6-((5-methyl-1H-pyrazol-3-yl)amino)pyrimidin-2-yl)thio)phenyl)cyclopropanecarboxamide |
| 15 | N-(4-((4-(dimethylamino)-5-methyl-6-((5-methyl-1H-pyrazol-3-yl)amino)pyrimidin-2-yl)thio)phenyl)cyclopropanecarboxamide |
| 16 | N-(4-((4-(ethyl(methyl)amino)-5-methyl-6-((5-methyl-1H-pyrazol-3-yl)amino)pyrimidin-2-yl)thio)phenyl)cyclopropanecarboxamide |
| 17 | N-(4-((5-methoxy-4-methyl-6-((5-methyl-1H-pyrazol-3-yl)amino)pyrimidin-2-yl)thio)phenyl)cyclopropanecarboxamide |
| 18 | N-(4-((5-methyl-4-((5-methyl-1H-pyrazol-3-yl)amino)-6,7-dihydro-5H-cyclopenta[d]pyrimidin-2-yl)thio)phenyl)cyclopropanecarboxamide |
| 19 | N-(4-((4-((2-(dimethylamino)ethyl)(methyl)amino)-5-methyl-6-((5-methyl-1H-pyrazol-3-yl)amino)pyrimidin-2-yl)thio)phenyl)cyclopropanecarboxamide |
| 20 | N-(4-((4-((2-(dimethylamino)ethyl)amino)-5-methyl-6-((5-methyl-1H-pyrazol-3-yl)amino)pyrimidin-2-yl)thio)phenyl)cyclopropanecarboxamide |
| 21 | N-(4-((4-((2-methoxyethyl)(methyl)amino)-5-methyl-6-((5-methyl-1H-pyrazol-3-yl)amino)pyrimidin-2-yl)thio)phenyl)cyclopropanecarboxamide |
| 22 | N-(4-((4-((5-ethyl-1H-pyrazol-3-yl)amino)-5-methyl-6-(4-methylpiperazin-1-yl)pyrimidin-2-yl)thio)phenyl)cyclopropanecarboxamide |
| 23 | N-(4-((4-(1H-imidazol-1-yl)-5-methyl-6-((5-methyl-1H-pyrazol-3-yl)amino)pyrimidin-2-yl)thio)phenyl)cyclopropanecarboxamide |
| 24 | N-(4-((4-(diethylamino)-5-methyl-6-((5-methyl-1H-pyrazol-3-yl)amino)pyrimidin-2-yl)thio)phenyl)cyclopropanecarboxamide |
| 25 | N-(4-((4-chloro-5-methyl-6-((5-methyl-1H-pyrazol-3-yl)amino)pyrimidin-2-yl)thio)phenyl)cyclopropanecarboxamide |
| 26 | N-(4-((5-methoxy-4-((5-methyl-1H-pyrazol-3-yl)amino)-6-(piperazin-1-yl)pyrimidin-2-yl)thio)phenyl)cyclopropanecarboxamide |
| 27 | N-(4-((5-methoxy-4-((5-methyl-1H-pyrazol-3-yl)amino)-6-morpholinopyrimidin-2-yl)thio)phenyl)cyclopropanecarboxamide |
| 28 | N-(4-((5-methyl-4-((5-methyl-1H-pyrazol-3-yl)amino)-6-(piperazin-1-yl)pyrimidin-2-yl)thio)phenyl)cyclopropanecarboxamide |
| 29 | N-(4-((5-methyl-4-(methyl(2-(methylamino)ethyl)amino)-6-((5-methyl-1H-pyrazol-3-yl)amino)pyrimidin-2-yl)thio)phenyl)cyclopropanecarboxamide |
| 30 | N-(4-((4-((1H-pyrazol-3-yl)amino)-5-methyl-6-(4-methylpiperazin-1-yl)pyrimidin-2-yl)thio)phenyl)cyclopropanecarboxamide |
| 31 | N-(4-((4-((5-methyl-1H-pyrazol-3-yl)amino)-6-(4-methylpiperazin-1-yl)-5-propoxypyrimidin-2-yl)thio)phenyl)cyclopropanecarboxamide |
| 32 | N-(4-((4-(diethylamino)-5-methoxy-6-((5-methyl-1H-pyrazol-3-yl)amino)pyrimidin-2-yl)thio)phenyl)cyclopropanecarboxamide |
| 33 | N-(4-((4-(dimethylamino)-5-methoxy-6-((5-methyl-1H-pyrazol-3-yl)amino)pyrimidin-2-yl)thio)phenyl)cyclopropanecarboxamide |
| 34 | N-(4-((4-(ethyl(methyl)amino)-5-methoxy-6-((5-methyl-1H-pyrazol-3-yl)amino)pyrimidin-2-yl)thio)phenyl)cyclopropanecarboxamide |
| 35 | N-(4-((5-(2-methoxyethoxy)-4-((5-methyl-1H-pyrazol-3-yl)amino)-6-(4-methylpiperazin-1-yl)pyrimidin-2-yl)thio)phenyl)cyclopropanecarboxamide |
| 36 | N-(4-((5-ethoxy-4-((5-methyl-1H-pyrazol-3-yl)amino)-6-(4-methylpiperazin-1-yl)pyrimidin-2-yl)thio)phenyl)cyclopropanecarboxamide |
| 37 | N-(4-((5-methoxy-4-((2-methoxyethyl)(methyl)amino)-6-((5-methyl-1H-pyrazol-3-yl)amino)pyrimidin-2-yl)thio)phenyl)cyclopropanecarboxamide |
| 38 | N-(4-((5-methyl-4-((5-methyl-1H-pyrazol-3-yl)amino)-6-(4-methylpiperazin-1-yl)pyrimidin-2-yl)thio)phenyl)cyclopentanecarboxamide |
| 39 | N-(4-((4-((2-(dimethylamino)ethyl)(methyl)amino)-5-methoxy-6-((5-methyl-1H-pyrazol-3-yl)amino)pyrimidin-2-yl)thio)phenyl)cyclopropanecarboxamide |
| 40 | N-(4-((4-((2-(dimethylamino)ethyl)amino)-5-methoxy-6-((5-methyl-1H-pyrazol-3-yl)amino)pyrimidin-2-yl)thio)phenyl)cyclopropanecarboxamide |
| 41 | N-(4-((4-(diethylamino)-6-((5-methyl-1H-pyrazol-3-yl)amino)-5-propoxypyrimidin-2-yl)thio)phenyl)cyclopropanecarboxamide |

TABLE 2-continued

Compound Names for exemplified compounds of formula(I), (II), and (III).
All compounds were confirmed by mass spectro scopy and by $^1$H and $^{13}$C NMR.

No. Chemical Name

42 N-(4-((4-(isopropyl(methyl)amino)-5-methoxy-6-((5-methyl-1H-pyrazol-3-yl)amino)pyrimidin-2-yl)thio)phenyl)cyclopropanecarboxamide
43 N-(4-((4-(isopropylamino)-5-methoxy-6-((5-methyl-1H-pyrazol-3-yl)amino)pyrimidin-2-yl)thio)phenyl)cyclopropanecarboxamide
44 N-(4-((5-methoxy-4-((2-methoxyethyl)amino)-6-((5-methyl-1H-pyrazol-3-yl)amino)pyrimidin-2-yl)thio)phenyl)cyclopropanecarboxamide
45 N-(4-((5-methoxy-4-((5-methyl-1H-pyrazol-3-yl)amino)-6-(methylamino)pyrimidin-2-yl)thio)phenyl)cyclopropanecarboxamide
46 N-(4-((5-methoxy-4-((5-methyl-1H-pyrazol-3-yl)amino)-6-(piperidin-1-yl)pyrimidin-2-yl)thio)phenyl)cyclopropanecarboxamide
47 N-(4-((5-methoxy-4-(methyl(2-(methylamino)ethyl)amino)-6-((5-methyl-1H-pyrazol-3-yl)amino)pyrimidin-2-yl)thio)phenyl)cyclopropanecarboxamide
48 N-(4-((4-((2-methoxyethyl)amino)-5-methyl-6-((5-methyl-1H-pyrazol-3-yl)amino)pyrimidin-2-yl)thio)phenyl)cyclopropanecarboxamide
49 N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)cyclopropanecarboxamide
50 N-(4-((4-(4-acetylpiperazin-1-yl)-5-methoxy-6-((5-methyl-1H-pyrazol-3-yl)amino)pyrimidin-2-yl)thio)phenyl)cyclopropanecarboxamide
51 N-(4-((4-(4-ethylpiperazin-1-yl)-5-methoxy-6-((5-methyl-1H-pyrazol-3-yl)amino)pyrimidin-2-yl)thio)phenyl)cyclopropanecarboxamide
52 N-(4-((4-(4-isopropylpiperazin-1-yl)-5-methoxy-6-((5-methyl-1H-pyrazol-3-yl)amino)pyrimidin-2-yl)thio)phenyl)cyclopropanecarboxamide
53 N-(4-((4-(ethylamino)-5-methoxy-6-((5-methyl-1H-pyrazol-3-yl)amino)pyrimidin-2-yl)thio)phenyl)cyclopropanecarboxamide
54 N-(4-((4-(isopropyl(methyl)amino)-5-methyl-6-((5-methyl-1H-pyrazol-3-yl)amino)pyrimidin-2-yl)thio)phenyl)cyclopropanecarboxamide
55 N-(4-((5-methoxy-4-(4-(2-methoxyethyl)piperazin-1-yl)-6-((5-methyl-1H-pyrazol-3-yl)amino)pyrimidin-2-yl)thio)phenyl)cyclopropanecarboxamide
56 N-(4-((5-methyl-4-((5-methyl-1H-pyrazol-3-yl)amino)-6,7-dihydro-5H-cyclopenta[d]pyrimidin-2-yl)thio)phenyl)acetamide
57 N-(4-((5-methyl-4-((5-methyl-1H-pyrazol-3-yl)amino)-6,7-dihydro-5H-cyclopenta[d]pyrimidin-2-yl)thio)phenyl)cyclopentanecarboxamide
58 N-(4-((5-methyl-4-((5-methyl-1H-pyrazol-3-yl)amino)-6-(methylamino)pyrimidin-2-yl)thio)phenyl)cyclopropanecarboxamide
59 N-(4-((5-methyl-4-((5-methyl-1H-pyrazol-3-yl)amino)-6-(piperidin-1-yl)pyrimidin-2-yl)thio)phenyl)cyclopropanecarboxamide
60 N-(4-((4-((2-methoxyethyl)(methyl)amino)-5-methyl-6-((5-methyl-1H-pyrazol-3-yl)amino)pyrimidin-2-yl)thio)phenyl)acetamide
61 N-(4-((4-((2-methoxyethyl)amino)-5-methyl-6-((5-methyl-1H-pyrazol-3-yl)amino)pyrimidin-2-yl)thio)phenyl)acetamide
62 N-(4-((4-(4-(tert-butyl)piperazin-1-yl)-5-methoxy-6-((5-methyl-1H-pyrazol-3-yl)amino)pyrimidin-2-yl)thio)phenyl)cyclopropanecarboxamide
63 N-(4-((4-(dimethylamino)-5-methyl-6-((5-methyl-1H-pyrazol-3-yl)amino)pyrimidin-2-yl)thio)phenyl)acetamide
64 N-(4-((4-(ethyl(methyl)amino)-5-methyl-6-((5-methyl-1H-pyrazol-3-yl)amino)pyrimidin-2-yl)thio)phenyl)acetamide
65 N-(4-((4-(ethylamino)-5-methyl-6-((5-methyl-1H-pyrazol-3-yl)amino)pyrimidin-2-yl)thio)phenyl)cyclopropanecarboxamide
66 N-(4-((4-(isopropylamino)-5-methyl-6-((5-methyl-1H-pyrazol-3-yl)amino)pyrimidin-2-yl)thio)phenyl)cyclopropanecarboxamide
67 N-(4-((5-methyl-4-((5-methyl-1H-pyrazol-3-yl)amino)-6-(4-methylpiperazin-1-yl)pyrimidin-2-yl)thio)phenyl)butyramide
68 N-(4-((5-methyl-4-((5-methyl-1H-pyrazol-3-yl)amino)-6-(piperidin-1-yl)pyrimidin-2-yl)thio)phenyl)acetamide
69 N-(4-((4-(4-acetylpiperazin-1-yl)-5-methoxy-6-((5-methyl-1H-pyrazol-3-yl)amino)pyrimidin-2-yl)thio)phenyl)cyclopentanecarboxamide
70 N-(4-((4-(diethylamino)-5-methoxy-6-((5-methyl-1H-pyrazol-3-yl)amino)pyrimidin-2-yl)thio)phenyl)cyclopentanecarboxamide
71 N-(4-((4-(dimethylamino)-5-methoxy-6-((5-methyl-1H-pyrazol-3-yl)amino)pyrimidin-2-yl)thio)phenyl)cyclopentanecarboxamide
72 N-(4-((4-(ethyl(methyl)amino)-5-methoxy-6-((5-methyl-1H-pyrazol-3-yl)amino)pyrimidin-2-yl)thio)phenyl)cyclopentanecarboxamide
73 N-(4-((5-methoxy-4-((2-methoxyethyl)(methyl)amino)-6-((5-methyl-1H-pyrazol-3-yl)amino)pyrimidin-2-yl)thio)phenyl)cyclopentanecarboxamide
74 N-(4-((5-methoxy-4-((2-methoxyethyl)amino)-6-((5-methyl-1H-pyrazol-3-yl)amino)pyrimidin-2-yl)thio)phenyl)cyclopentanecarboxamide
75 N-(4-((5-methoxy-4-((5-methyl-1H-pyrazol-3-yl)amino)-6-(piperidin-1-yl)pyrimidin-2-yl)thio)phenyl)cyclopentanecarboxamide
76 N-(4-((5-methoxy-4-((5-methyl-1H-pyrazol-3-yl)amino)-6-morpholinopyrimidin-2-yl)thio)phenyl)cyclopentanecarboxamide
77 N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)cyclopentanecarboxamide N-(4-((4-(diethylamino)-5-ethoxy-6-((5-methyl-1H-pyrazol-3-yl)amino)pyrimidin-2-yl)thio)phenyl)cyclopropanecarboxamide TABLE 2-continued Compound Names for exemplified compounds of formula(I), (II), and (III).
All compounds were confirmed by mass spectro scopy and by $^1$H and $^{13}$C NMR.

| No. | Chemical Name |
|---|---|
| 78 | N-(4-((4-(dimethylamino)-5-ethoxy-6-((5-methyl-1H-pyrazol-3-yl)amino)pyrimidin-2-yl)thio)phenyl)cyclopropanecarboxamide |
| 79 | N-(4-((5-ethoxy-4-((5-methyl-1H-pyrazol-3-yl)amino)-6-(piperazin-1-yl)pyrimidin-2-yl)thio)phenyl)cyclopropanecarboxamide |
| 80 | N-(4-((5-ethoxy-4-((5-methyl-1H-pyrazol-3-yl)amino)-6-(piperidin-1-yl)pyrimidin-2-yl)thio)phenyl)cyclopropanecarboxamide |
| 81 | N-(4-((5-ethoxy-4-((5-methyl-1H-pyrazol-3-yl)amino)-6-morpholinopyrimidin-2-yl)thio)phenyl)cyclopropanecarboxamide |
| 82 | N-(4-((5-ethoxy-4-(ethyl(methyl)amino)-6-((5-methyl-1H-pyrazol-3-yl)amino)pyrimidin-2-yl)thio)phenyl)cyclopropanecarboxamide |
| 83 | N-(4-((5-methoxy-4-((5-methyl-1H-pyrazol-3-yl)amino)-6-(4-methylpiperazin-1-yl)pyrimidin-2-yl)thio)phenyl)cyclopentanecarboxamide |
| 84 | N-(4-((5-methoxy-4-((5-methyl-1H-pyrazol-3-yl)amino)-6-(piperazin-1-yl)pyrimidin-2-yl)thio)phenyl)cyclopentanecarboxamide |
| 85 | N-(4-((5-methoxy-4-(4-(2-methoxyethyl)piperazin-1-yl)-6-((5-methyl-1H-pyrazol-3-yl)amino)pyrimidin-2-yl)thio)phenyl)cyclopentanecarboxamide |
| 86 | N-(4-((4-(4-(2-(dimethylamino)ethyl)piperazin-1-yl)-5-ethoxy-6-((5-methyl-1H-pyrazol-3-yl)amino)pyrimidin-2-yl)thio)phenyl)cyclopropanecarboxamide |
| 87 | N-(4-((4-(4-acetylpiperazin-1-yl)-5-ethoxy-6-((5-methyl-1H-pyrazol-3-yl)amino)pyrimidin-2-yl)thio)phenyl)cyclopropanecarboxamide |
| 88 | N-(4-((4-(diethylamino)-5-ethoxy-6-((5-methyl-1H-pyrazol-3-yl)amino)pyrimidin-2-yl)thio)phenyl)cyclopropanecarboxamide |
| 89 | N-(4-((4-(dimethylamino)-5-ethoxy-6-((5-methyl-1H-pyrazol-3-yl)amino)pyrimidin-2-yl)thio)phenyl)cyclopropanecarboxamide |
| 90 | N-(4-((5-ethoxy-4-((2-methoxyethyl)(methyl)amino)-6-((5-methyl-1H-pyrazol-3-yl)amino)pyrimidin-2-yl)thio)phenyl)cyclopropanecarboxamide |
| 91 | N-(4-((5-ethoxy-4-((2-methoxyethyl)amino)-6-((5-methyl-1H-pyrazol-3-yl)amino)pyrimidin-2-yl)thio)phenyl)cyclopropanecarboxamide |
| 92 | N-(4-((5-ethoxy-4-((5-methyl-1H-pyrazol-3-yl)amino)-6-(piperazin-1-yl)pyrimidin-2-yl)thio)phenyl)cyclopropanecarboxamide |
| 93 | N-(4-((5-ethoxy-4-(4-(2-methoxyethyl)piperazin-1-yl)-6-((5-methyl-1H-pyrazol-3-yl)amino)pyrimidin-2-yl)thio)phenyl)cyclopropanecarboxamide |
| 94 | N-(4-((5-ethoxy-4-(ethyl(methyl)amino)-6-((5-methyl-1H-pyrazol-3-yl)amino)pyrimidin-2-yl)thio)phenyl)cyclopropanecarboxamide |
| 95 | 3-(5-fluoro-2-methylpyridin-4-yl)-6-(4-(2-(piperidin-1-yl)ethoxy)phenyl)pyrazolo[1,5-α]pyrimidine |
| 96 | N-(4-((4-(4-(3-(dimethylamino)propanoyl)piperazin-1-yl)-5-methoxy-6-((5-methyl-1H-pyrazol-3-yl)amino)pyrimidin-2-yl)thio)phenyl)cyclopropanecarboxamide |
| 97 | N-(4-((4-(4-(cyclopropylmethyl)piperazin-1-yl)-5-methoxy-6-((5-methyl-1H-pyrazol-3-yl)amino)pyrimidin-2-yl)thio)phenyl)cyclopropanecarboxamide |
| 98 | N-(4-((4-(4-(dimethylglycyl)piperazin-1-yl)-5-methoxy-6-((5-methyl-1H-pyrazol-3-yl)amino)pyrimidin-2-yl)thio)phenyl)cyclopropanecarboxamide |
| 99 | N-(4-((5-ethoxy-4-((5-methyl-1H-pyrazol-3-yl)amino)-6-(piperazin-1-yl)pyrimidin-2-yl)thio)phenyl)acetamide |
| 100 | N-(4-((5-ethoxy-4-((5-methyl-1H-pyrazol-3-yl)amino)-6-(piperidin-1-yl)pyrimidin-2-yl)thio)phenyl)acetamide |
| 101 | N-(4-((5-methoxy-4-((5-methyl-1H-pyrazol-3-yl)amino)-6-(4-(1-methylpiperidin-4-yl)piperazin-1-yl)pyrimidin-2-yl)thio)phenyl)cyclopropanecarboxamide |
| 102 | N-(4-((5-methoxy-4-((5-methyl-1H-pyrazol-3-yl)amino)-6-(4-(2-(methylamino)ethyl)piperazin-1-yl)pyrimidin-2-yl)thio)phenyl)cyclopropanecarboxamide |
| 103 | N-(4-((5-methoxy-4-((5-methyl-1H-pyrazol-3-yl)amino)-6-(4-phenylpiperazin-1-yl)pyrimidin-2-yl)thio)phenyl)cyclopropanecarboxamide |
| 104 | N-(4-((5-methoxy-4-(4-(2-methoxyacetyl)piperazin-1-yl)-6-((5-methyl-1H-pyrazol-3-yl)amino)pyrimidin-2-yl)thio)phenyl)cyclopropanecarboxamide |
| 105 | N-(4-((5-methoxy-4-(4-(3-methoxyl)ropanoyl)piperazin-1-yl)-6-((5-methyl-1H-pyrazol-3-yl)amino)pyrimidin-2-yl)thio)phenyl)cyclopropanecarboxamide(1:1:1:1:1:1:1:1:1:1) |
| 106 | N-(4-((4-(4-(2-(dimethylamino)ethyl)piperazin-1-yl)-5-ethoxy-6-((5-methyl-1H-pyrazol-3-yl)amino)pyrimidin-2-yl)thio)phenyl)acetamide |
| 107 | N-(4-((4-(4-acetylpiperazin-1-yl)-5-ethoxy-6-((5-methyl-1H-pyrazol-3-yl)amino)pyrimidin-2-yl)thio)phenyl)acetamide |
| 108 | N-(4-((4-(diethylamino)-5-ethoxy-6-((5-methyl-1H-pyrazol-3-yl)amino)pyrimidin-2-yl)thio)phenyl)acetamide |
| 109 | N-(4-((4-(diethylamino)-5-ethoxy-6-((5-methyl-1H-pyrazol-3-yl)amino)pyrimidin-2-yl)thio)phenyl)cyclopentanecarboxamide |
| 110 | N-(4-((5-ethoxy-4-((5-methyl-1H-pyrazol-3-yl)amino)-6-(piperazin-1-yl)pyrimidin-2-yl)thio)phenyl)cyclopentanecarboxamide |
| 111 | N-(4-((5-ethoxy-4-((5-methyl-1H-pyrazol-3-yl)amino)-6-(piperidin-1-yl)pyrimidin-2-yl)thio)phenyl)cyclopentanecarboxamide |
| 112 | N-(4-((5-ethoxy-4-((5-methyl-1H-pyrazol-3-yl)amino)-6-morpholinopyrimidin-2-yl)thio)phenyl)acetamide |
| 113 | N-(4-((5-ethoxy-4-((5-methyl-1H-pyrazol-3-yl)amino)-6-morpholinopyrimidin-2-yl)thio)phenyl)cyclopentanecarboxamide |
| 114 | N-(4-((5-ethoxy-4-(4-(2-methoxyethyl)piperazin-1-yl)-6-((5-methyl-1H-pyrazol-3-yl)amino)pyrimidin-2-yl)thio)phenyl)acetamide |

TABLE 2-continued

Compound Names for exemplified compounds of formula(I), (II), and (III).
All compounds were confirmed by mass spectro scopy and by $^1$H and $^{13}$C NMR.

| No. | Chemical Name |
|---|---|
| 115 | N-(4-((5-ethoxy-4-(ethyl(methyl)amino)-6-((5-methyl-1H-pyrazol-3-yl)amino)pyrimidin-2-yl)thio)phenyl)acetamide |
| 116 | N-(4-((4-(4-(2-(dimethylamino)ethyl)piperazin-1-yl)-5-ethoxy-6-((5-methyl-1H-pyrazol-3-yl)amino)pyrimidin-2-yl)thio)phenyl)cyclopentanecarboxamide |
| 117 | N-(4-((4-(4-(3-(dimethylamino)propanoyl)piperazin-1-yl)-5-ethoxy-6-((5-methyl-1H-pyrazol-3-yl)amino)pyrimidin-2-yl)thio)phenyl)cyclopropanecarboxamide |
| 118 | N-(4-((4-(4-acetylpiperazin-1-yl)-5-ethoxy-6-((5-methyl-1H-pyrazol-3-yl)amino)pyrimidin-2-yl)thio)phenyl)cyclopentanecarboxamide |
| 119 | N-(4-((5-ethoxy-4-(4-(2-methoxyacetyl)piperazin-1-yl)-6-((5-methyl-1H-pyrazol-3-yl)amino)pyrimidin-2-yl)thio)phenyl)cyclopropanecarboxamide |
| 120 | N-(4-((5-ethoxy-4-(4-(2-methoxyethyl)piperazin-1-yl)-6-((5-methyl-1H-pyrazol-3-yl)amino)pyrimidin-2-yl)thio)phenyl)cyclopentanecarboxamide |
| 121 | N-(4-((5-ethoxy-4-(4-(3-methoxyl)ropanoyl)piperazin-1-yl)-6-((5-methyl-1H-pyrazol-3-yl)amino)pyrimidin-2-yl)thio)phenyl)cyclopropanecarboxamide |
| 122 | N-(4-((5-ethoxy-4-(ethyl(methyl)amino)-6-((5-methyl-1H-pyrazol-3-yl)amino)pyrimidin-2-yl)thio)phenyl)cyclopentanecarboxamide |
| 123 | N-(4-((5-ethyl-4-((5-methyl-1H-pyrazol-3-yl)amino)-6,7-dihydro-5H-cyclopenta[d]pyrimidin-2-yl)thio)phenyl)cyclopropanecarboxamide |
| 124 | N-(4-((5-methoxy-4-((5-methyl-1H-pyrazol-3-yl)amino)-6-(piperidin-4-ylamino)pyrimidin-2-yl)thio)phenyl)cyclopropanecarboxamide |
| 125 | N-(4-((5-methyl-4-((5-methyl-1H-pyrazol-3-yl)amino)-6-(4-methylpiperazin-1-yl)pyrimidin-2-yl)thio)phenyl)acetamide |
| 126 | N-(4-((5-methyl-4-((5-methyl-1H-pyrazol-3-yl)amino)-6-(4-methylpiperazin-1-yl)pyrimidin-2-yl)thio)phenyl)cyclobutanecarboxamide |
| 127 | N-(4-((4-(4-(cyclopropylmethyl)piperazin-1-yl)-5-ethoxy-6-((5-methyl-1H-pyrazol-3-yl)amino)pyrimidin-2-yl)thio)phenyl)cyclopentanecarboxamide |
| 128 | N-(4-((4-(4-(cyclopropylmethyl)piperazin-1-yl)-5-ethoxy-6-((5-methyl-1H-pyrazol-3-yl)amino)pyrimidin-2-yl)thio)phenyl)cyclopropanecarboxamide |
| 129 | N-(4-((4-(4-(dimethylglycyl)piperazin-1-yl)-5-ethoxy-6-((5-methyl-1H-pyrazol-3-yl)amino)pyrimidin-2-yl)thio)phenyl)cyclopentanecarboxamide |
| 130 | N-(4-((4-(4-(dimethylglycyl)piperazin-1-yl)-5-ethoxy-6-((5-methyl-1H-pyrazol-3-yl)amino)pyrimidin-2-yl)thio)phenyl)cyclopropanecarboxamide |
| 131 | N-(4-((5-ethoxy-4-((5-methyl-1H-pyrazol-3-yl)amino)-6-(4-(1-methylpiperidin-4-yl)piperazin-1-yl)pyrimidin-2-yl)thio)phenyl)cyclopentanecarboxamide |
| 132 | N-(4-((5-ethoxy-4-((5-methyl-1H-pyrazol-3-yl)amino)-6-(4-(1-methylpiperidin-4-yl)piperazin-1-yl)pyrimidin-2-yl)thio)phenyl)cyclopropanecarboxamide |
| 133 | N-(4-((5-ethoxy-4-((5-methyl-1H-pyrazol-3-yl)amino)-6-(4-(piperidin-4-yl)piperazin-1-yl)pyrimidin-2-yl)thio)phenyl)cyclopropanecarboxamide |
| 134 | N-(4-((5-ethoxy-4-((5-methyl-1H-pyrazol-3-yl)amino)-6-(4-methylpiperazin-1-yl)pyrimidin-2-yl)thio)phenyl)acetamide |
| 135 | N-(4-((5-ethoxy-4-(4-(2-methoxyacetyl)piperazin-1-yl)-6-((5-methyl-1H-pyrazol-3-yl)amino)pyrimidin-2-yl)thio)phenyl)cyclopentanecarboxamide |
| 136 | N-(4-((5-ethoxy-4-(4-(3-methoxyl)ropanoyl)piperazin-1-yl)-6-((5-methyl-1H-pyrazol-3-yl)amino)pyrimidin-2-yl)thio)phenyl)cyclopentanecarboxamide |
| 137 | N-(4-((5-methoxy-4-((5-methyl-1H-pyrazol-3-yl)amino)-6-((1-methylpiperidin-4-yl)amino)pyrimidin-2-yl)thio)phenyl)cyclopropanecarboxamide |
| 138 | N-(4-((4-(4-(2-(dimethylamino)ethyl)piperazin-1-yl)-5-methyl-6-((5-methyl-1H-pyrazol-3-yl)amino)pyrimidin-2-yl)thio)phenyl)acetamide |
| 139 | N-(4-((4-(4-(2-(dimethylamino)ethyl)piperazin-1-yl)-5-methyl-6-((5-methyl-1H-pyrazol-3-yl)amino)pyrimidin-2-yl)thio)phenyl)cyclopentanecarboxamide |
| 140 | N-(4-((4-(4-(2-methoxyethyl)piperazin-1-yl)-5-methyl-6-((5-methyl-1H-pyrazol-3-yl)amino)pyrimidin-2-yl)thio)phenyl)acetamide |
| 141 | N-(4-((4-(4-acetylpiperazin-1-yl)-5-methyl-6-((5-methyl-1H-pyrazol-3-yl)amino)pyrimidin-2-yl)thio)phenyl)acetamide |
| 142 | N-(4-((4-(dimethylamino)-5-ethoxy-6-((5-methyl-1H-pyrazol-3-yl)amino)pyrimidin-2-yl)thio)phenyl)acetamide |
| 143 | N-(4-((4-(dimethylamino)-5-ethoxy-6-((5-methyl-1H-pyrazol-3-yl)amino)pyrimidin-2-yl)thio)phenyl)cyclopentanecarboxamide |
| 144 | N-(4-((5-ethoxy-4-((5-methyl-1H-pyrazol-3-yl)amino)-6-(4-(piperidin-4-yl)piperazin-1-yl)pyrimidin-2-yl)thio)phenyl)cyclopentanecarboxamide |
| 145 | N-(4-((5-ethoxy-4-((5-methyl-1H-pyrazol-3-yl)amino)-6-(4-methylpiperazin-1-yl)pyrimidin-2-yl)thio)phenyl)cyclopentanecarboxamide |
| 146 | N-(4-((5-methyl-4-((5-methyl-1H-pyrazol-3-yl)amino)-6-(4-(1-methylpiperidin-4-yl)piperazin-1-yl)pyrimidin-2-yl)thio)phenyl)acetamide |
| 147 | N-(4-((5-methyl-4-((5-methyl-1H-pyrazol-3-yl)amino)-6-(piperazin-1-yl)pyrimidin-2-yl)thio)phenyl)acetamide |
| 148 | N-(4-((5-methyl-4-((5-methyl-1H-pyrazol-3-yl)amino)-6-morpholinopyrimidin-2-yl)thio)phenyl)acetamide |
| 149 | N-(4-((4-(4-(2-methoxyacetyl)piperazin-1-yl)-5-methyl-6-((5-methyl-1H-pyrazol-3-yl)amino)pyrimidin-2-yl)thio)phenyl)acetamide |
| 150 | N-(4-((4-(4-(2-methoxyethyl)piperazin-1-yl)-5-methyl-6-((5-methyl-1H-pyrazol-3-yl)amino)pyrimidin-2-yl)thio)phenyl)cyclopentanecarboxamide |

TABLE 2-continued

Compound Names for exemplified compounds of formula(I), (II), and (III).
All compounds were confirmed by mass spectro scopy and by $^1$H and $^{13}$C NMR.

| No. | Chemical Name |
|---|---|
| 151 | N-(4-((4-(4-(3-(dimethylamino)propanoyl)piperazin-1-yl)-5-ethoxy-6-((5-methyl-1H-pyrazol-3-yl)amino)pyrimidin-2-yl)thio)phenyl)cyclopentanecarboxamide |
| 152 | N-(4-((4-(4-(3-(dimethylamino)propanoyl)piperazin-1-yl)-5-methyl-6-((5-methyl-1H-pyrazol-3-yl)amino)pyrimidin-2-yl)thio)phenyl)acetamide |
| 153 | N-(4-((4-(4-acetylpiperazin-1-yl)-5-methyl-6-((5-methyl-1H-pyrazol-3-yl)amino)pyrimidin-2-yl)thio)phenyl)cyclopentanecarboxamide |
| 154 | N-(4-((4-(isopropyl(methyl)amino)-5-methyl-6-((5-methyl-1H-pyrazol-3-yl)amino)pyrimidin-2-yl)thio)phenyl)acetamide |
| 155 | N-(4-((5-(ethylthio)-4-((5-methyl-1H-pyrazol-3-yl)amino)-6-(4-methylpiperazin-1-yl)pyrimidin-2-yl)thio)phenyl)cyclopropanecarboxamide |
| 156 | N-(4-((5-methoxy-4-((5-methyl-1H-pyrazol-3-yl)amino)-6-(piperidin-1-yl)pyrimidin-2-yl)thio)phenyl)acetamide |
| 157 | N-(4-((5-methyl-4-((5-methyl-1H-pyrazol-3-yl)amino)-6-(4-(1-methylpiperidin-4-yl)piperazin-1-yl)pyrimidin-2-yl)thio)phenyl)cyclopentanecarboxamide |
| 158 | N-(4-((5-methyl-4-((5-methyl-1H-pyrazol-3-yl)amino)-6-(piperazin-1-yl)pyrimidin-2-yl)thio)phenyl)cyclopentanecarboxamide |
| 159 | N-(4-((5-methyl-4-((5-methyl-1H-pyrazol-3-yl)amino)-6-morpholinopyrimidin-2-yl)thio)phenyl)cyclopentanecarboxamide |
| 160 | N-(4-((4-((5-methyl-1H-pyrazol-3-yl)amino)-6-(4-methylpiperazin-1-yl)-5-(methylthio)pyrimidin-2-yl)thio)phenyl)cyclopropanecarboxamide |
| 161 | N-(4-((4-(4-(2-methoxyacetyl)piperazin-1-yl)-5-methyl-6-((5-methyl-1H-pyrazol-3-yl)amino)pyrimidin-2-yl)thio)phenyl)cyclopentanecarboxamide |
| 162 | N-(4-((4-(4-hydroxypiperidin-1-yl)-5-methyl-6-((5-methyl-1H-pyrazol-3-yl)amino)pyrimidin-2-yl)thio)phenyl)acetamide |
| 163 | N-(4-((4-(diethylamino)-5-methyl-6-((5-methyl-1H-pyrazol-3-yl)amino)pyrimidin-2-yl)thio)phenyl)cyclopentanecarboxamide |
| 164 | N-(4-((4-(dimethylamino)-5-methyl-6-((5-methyl-1H-pyrazol-3-yl)amino)pyrimidin-2-yl)thio)phenyl)cyclopentanecarboxamide |
| 165 | N-(4-((4-(ethyl(methyl)amino)-5-methyl-6-((5-methyl-1H-pyrazol-3-yl)amino)pyrimidin-2-yl)thio)phenyl)cyclopentanecarboxamide |
| 166 | N-(4-((4-(isopropyl(methyl)amino)-5-methyl-6-((5-methyl-1H-pyrazol-3-yl)amino)pyrimidin-2-yl)thio)phenyl)cyclopentanecarboxamide |
| 167 | N-(4-((5-methyl-4-((5-methyl-1H-pyrazol-3-yl)amino)-6-(piperidin-1-yl)pyrimidin-2-yl)thio)phenyl)cyclopentanecarboxamide |
| 168 | N-(4-((5-methyl-4-((5-methyl-1H-pyrazol-3-yl)amino)-6-(pyrrolidin-1-yl)pyrimidin-2-yl)thio)phenyl)acetamide |
| 169 | methyl(4-((5-methyl-4-((5-methyl-1H-pyrazol-3-yl)amino)-6-(piperidin-1-yl)pyrimidin-2-yl)thio)phenyl)carbamate |
| 170 | N-(4-((4-(azepan-1-yl)-5-methyl-6-((5-methyl-1H-pyrazol-3-yl)amino)pyrimidin-2-yl)thio)phenyl)acetamide |
| 171 | N-(4-((5-chloro-4-((5-methyl-1H-pyrazol-3-yl)amino)-6-(4-methylpiperazin-1-yl)pyrimidin-2-yl)thio)phenyl)acetamide |
| 172 | N-(4-((5-chloro-4-((5-methyl-1H-pyrazol-3-yl)amino)-6-(4-methylpiperazin-1-yl)pyrimidin-2-yl)thio)phenyl)cyclopropanecarboxamide |
| 173 | 1-methyl-3-(4-((5-methyl-4-((5-methyl-1H-pyrazol-3-yl)amino)-6-(piperidin-1-yl)pyrimidin-2-yl)thio)phenyl)urea |
| 174 | 2-((4-aminophenyl)thio)-5-methyl-N-(5-methyl-1H-pyrazol-3-yl)-6-(piperidin-1-yl)pyrimidin-4-amine |
| 175 | 5-methyl-N-(5-methyl-1H-pyrazol-3-yl)-2-(methylthio)-6-(piperidin-1-yl)pyrimidin-4-amine |
| 176 | 5-methyl-N-(5-methyl-1H-pyrazol-3-yl)-2-(phenylthio)-6-(piperidin-1-yl)pyrimidin-4-amine |
| 177 | 5-methyl-N-(5-methyl-1H-pyrazol-3-yl)-6-(piperidin-1-yl)-2-(p-tolylthio)pyrimidin-4-amine |
| 178 | N-(4-((4-(3,6-dihydropyridin-1(2H)-yl)-5-methyl-6-((5-methyl-1H-pyrazol-3-yl)amino)pyrimidin-2-yl)thio)phenyl)acetamide |
| 179 | N-(4-((4-(4,4-difluoropiperidin-1-yl)-5-methyl-6-((5-methyl-1H-pyrazol-3-yl)amino)pyrimidin-2-yl)thio)phenyl)acetamide |
| 180 | N-(4-((4-(4-fluoro-3,6-dihydropyridin-1(2H)-yl)-5-methyl-6-((5-methyl-1H-pyrazol-3-yl)amino)pyrimidin-2-yl)thio)phenyl)acetamide |
| 181 | N-(4-((4-(4-fluoropiperidin-1-yl)-5-methyl-6-((5-methyl-1H-pyrazol-3-yl)amino)pyrimidin-2-yl)thio)phenyl)acetamide |
| 182 | N-(4-((5-chloro-4-((5-methyl-1H-pyrazol-3-yl)amino)-6-(piperidin-1-yl)pyrimidin-2-yl)thio)phenyl)acetamide |
| 183 | N-(4-((5-ethoxy-4-((5-methyl-1H-pyrazol-3-yl)amino)-6-(4-(1-methylpiperidin-4-yl)piperazin-1-yl)pyrimidin-2-yl)thio)phenyl)acetamide |
| 184 | N-(4-((5-methoxy-4-((5-methyl-1H-pyrazol-3-yl)amino)-6-(4-(1-methylpiperidin-4-yl)piperazin-1-yl)pyrimidin-2-yl)thio)phenyl)acetamide |
| 185 | N-(4-((5-methoxy-4-((5-methyl-1H-pyrazol-3-yl)amino)-6-(4-methylpiperazin-1-yl)pyrimidin-2-yl)thio)phenyl)acetamide |
| 186 | N-(4-((5-methyl-4-((5-methyl-1H-pyrazol-3-yl)amino)-6-(4-methylpiperidin-1-yl)pyrimidin-2-yl)thio)phenyl)acetamide |

TABLE 2-continued

Compound Names for exemplified compounds of formula(I), (II), and (III).
All compounds were confirmed by mass spectro scopy and by $^1$H and $^{13}$C NMR.

| No. | Chemical Name |
|---|---|
| 187 | 2-((4-(dimethylamino)phenyl)thio)-5-methyl-N-(5-methyl-1H-pyrazol-3-yl)-6-(piperidin-1-yl)pyrimidin-4-amine |
| 188 | 5-methyl-N-(5-methyl-1H-pyrazol-3-yl)-2-((4-(methylamino)phenyl)thio)-6-(piperidin-1-yl)pyrimidin-4-amine |
| 189 | N-(4-((4-(((5-methyl-1H-pyrazol-3-yl)amino)-6-(piperidin-1-yl)pyrimidin-2-yl)thio)phenyl)acetamide |
| 190 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)acetamide |
| 191 | N-(4-((4-(4-acetylpiperazin-1-yl)-5-methoxy-6-((5-methyl-1H-pyrazol-3-yl)amino)pyrimidin-2-yl)thio)phenyl)acetamide |
| 192 | N-(4-((4-(azepan-1-yl)-5-methoxy-6-((5-methyl-1H-pyrazol-3-yl)amino)pyrimidin-2-yl)thio)phenyl)acetamide |
| 193 | N-(4-((4-(diethylamino)-5-methoxy-6-((5-methyl-1H-pyrazol-3-yl)amino)pyrimidin-2-yl)thio)phenyl)acetamide |
| 194 | N-(4-((4-(dimethylamino)-5-methoxy-6-((5-methyl-1H-pyrazol-3-yl)amino)pyrimidin-2-yl)thio)phenyl)acetamide |
| 195 | N-(4-((4-(ethyl(methyl)amino)-5-methoxy-6-((5-methyl-1H-pyrazol-3-yl)amino)pyrimidin-2-yl)thio)phenyl)acetamide |
| 196 | N-(4-((5-methoxy-4-((5-methyl-1H-pyrazol-3-yl)amino)-6-(4-methylpiperidin-1-yl)pyrimidin-2-yl)thio)phenyl)acetamide |
| 197 | N-(4-((5-methoxy-4-((5-methyl-1H-pyrazol-3-yl)amino)-6-(piperazin-1-yl)pyrimidin-2-yl)thio)phenyl)acetamide |
| 198 | N-(4-((5-methoxy-4-((5-methyl-1H-pyrazol-3-yl)amino)-6-(pyrrolidin-1-yl)pyrimidin-2-yl)thio)phenyl)acetamide |
| 199 | N-(4-((5-methoxy-4-((5-methyl-1H-pyrazol-3-yl)amino)-6-morpholinopyrimidin-2-yl)thio)phenyl)acetamide |
| 200 | N-(4-((5-methoxy-4-(4-(2-methoxyethyl)piperazin-1-yl)-6-((5-methyl-1H-pyrazol-3-yl)amino)pyrimidin-2-yl)thio)phenyl)acetamide |
| 201 | N-(4-((4-(3,6-dihydropyridin-1(2H)-yl)-5-methoxy-6-((5-methyl-1H-pyrazol-3-yl)amino)pyrimidin-2-yl)thio)phenyl)acetamide |
| 202 | N-(4-((4-(4,4-difluoropiperidin-1-yl)-5-methoxy-6-((5-methyl-1H-pyrazol-3-yl)amino)pyrimidin-2-yl)thio)phenyl)acetamide |
| 203 | N-(4-((4-(4-acetylpiperidin-1-yl)-5-methoxy-6-((5-methyl-1H-pyrazol-3-yl)amino)pyrimidin-2-yl)thio)phenyl)acetamide |
| 204 | N-(4-((4-(4-aminopiperidin-1-yl)-5-methoxy-6-((5-methyl-1H-pyrazol-3-yl)amino)pyrimidin-2-yl)thio)phenyl)acetamide |
| 205 | N-(4-((4-(4-ethylpiperazin-1-yl)-5-methyl-6-((5-methyl-1H-pyrazol-3-yl)amino)pyrimidin-2-yl)thio)phenyl)acetamide |
| 206 | N-(4-((4-(4-fluoro-3,6-dihydropyridin-1(21/)-yl)-5-methoxy-6-((5-methyl-1H-pyrazol-3-yl)amino)pyrimidin-2-yl)thio)phenyl)acetamide |
| 207 | N-(4-((4-(4-fluoropiperidin-1-yl)-5-methoxy-6-((5-methyl-1H-pyrazol-3-yl)amino)pyrimidin-2-yl)thio)phenyl)acetamide |
| 208 | N-(4-((4-(4-hydroxypiperidin-1-yl)-5-methoxy-6-((5-methyl-1H-pyrazol-3-yl)amino)pyrimidin-2-yl)thio)phenyl)acetamide |
| 209 | N-(4-((4-(isopropyl(methyl)amino)-5-methoxy-6-((5-methyl-1H-pyrazol-3-yl)amino)pyrimidin-2-yl)thio)phenyl)acetamide |
| 210 | 6-(4-(2-(dimethylamino)ethyl)piperazin-1-yl)-5-methoxy-N-(5-methyl-1H-pyrazol-3-yl)-2-((4-((2-(thiazol-2-yl)propan-2-yl)sulfonyl)phenyl)thio)pyrimidin-4-amine |
| 211 | N-(4-((5-methoxy-4-(4-(2-methoxyacetyl)piperazin-1-yl)-6-((5-methyl-1H-pyrazol-3-yl)amino)pyrimidin-2-yl)thio)phenyl)acetamide |
| 212 | N-(4-((5-methyl-4-((5-methyl-1H-pyrazol-3-yl)amino)-6-(2-methylpiperidin-1-yl)pyrimidin-2-yl)thio)phenyl)acetamide |
| 213 | N-(4-((4-(4-(2-(dimethylamino)ethyl)piperidin-1-yl)-5-methyl-6-((5-methyl-1H-pyrazol-3-yl)amino)pyrimidin-2-yl)thio)phenyl)acetamide |
| 214 | N-(4-((4-(4-(dimethylamino)piperidin-1-yl)-5-methoxy-6-((5-methyl-1H-pyrazol-3-yl)amino)pyrimidin-2-yl)thio)phenyl)acetamide |
| 215 | N-(4-((4-(4-ethylpiperazin-1-yl)-5-methoxy-6-((5-methyl-1H-pyrazol-3-yl)amino)pyrimidin-2-yl)thio)phenyl)acetamide |
| 216 | N-(4-((4-(4-isobutyrylpiperazin-1-yl)-5-methoxy-6-((5-methyl-1H-pyrazol-3-yl)amino)pyrimidin-2-yl)thio)phenyl)acetamide |
| 217 | N-(4-((5-methoxy-4-((5-methyl-1H-pyrazol-3-yl)amino)-6-(2-methylpiperidin-1-yl)pyrimidin-2-yl)thio)phenyl)acetamide |
| 218 | N-(4-((5-methoxy-4-((5-methyl-1H-pyrazol-3-yl)amino)-6-(4-propionylpiperazin-1-yl)pyrimidin-2-yl)thio)phenyl)acetamide |
| 219 | 1-(5-methyl-6-((5-methyl-1H-pyrazol-3-yl)amino)-2-(methylthio)pyrimidin-4-yl)piperidin-4-ol |
| 220 | 5-methyl-N-(5-methyl-1H-pyrazol-3-yl)-2-(methylthio)-6-morpholinopyrimidin-4-amine |
| 221 | N-(4-((4-(4-(dimethylglycyl)piperazin-1-yl)-5-methoxy-6-((5-methyl-1H-pyrazol-3-yl)amino)pyrimidin-2-yl)thio)phenyl)acetamide |
| 222 | N-(4-((4-(4-(dimethylglycyl)piperazin-1-yl)-5-methyl-6-((5-methyl-1H-pyrazol-3-yl)amino)pyrimidin-2-yl)thio)phenyl)acetamide |
| 223 | N-(4-((4-(4-acetylpiperidin-1-yl)-5-methyl-6-((5-methyl-1H-pyrazol-3-yl)amino)pyrimidin-2-yl)thio)phenyl)acetamide |

TABLE 2-continued

Compound Names for exemplified compounds of formula(I), (II), and (III).
All compounds were confirmed by mass spectro scopy and by $^1$H and $^{13}$C NMR.

| No. | Chemical Name |
|---|---|
| 224 | N-(4-((4-(4-isobutyrylpiperazin-1-yl)-5-methyl-6-((5-methyl-1H-pyrazol-3-yl)amino)pyrimidin-2-yl)thio)phenyl)acetamide |
| 225 | N-(4-((4-(4-isopropylpiperazin-1-yl)-5-methoxy-6-((5-methyl-1H-pyrazol-3-yl)amino)pyrimidin-2-yl)thio)phenyl)acetamide |
| 226 | N-(4-((4-(4-isopropylpiperazin-1-yl)-5-methyl-6-((5-methyl-1H-pyrazol-3-yl)amino)pyrimidin-2-yl)thio)phenyl)acetamide |
| 227 | N-(4-((5-methoxy-4-((5-methyl-1H-pyrazol-3-yl)amino)-6-(4-(methylglycyl)piperazin-1-yl)pyrimidin-2-yl)thio)phenyl)acetamide |
| 228 | N-(4-((5-methyl-4-((5-methyl-1H-pyrazol-3-yl)amino)-6-(4-(methylamino)piperidin-1-yl)pyrimidin-2-yl)thio)phenyl)acetamide |
| 229 | N-(4-((5-methyl-4-((5-methyl-1H-pyrazol-3-yl)amino)-6-(4-(methylglycyl)piperazin-1-yl)pyrimidin-2-yl)thio)phenyl)acetamide |
| 230 | N-(4-((5-methyl-4-((5-methyl-1H-pyrazol-3-yl)amino)-6-(4-propionylpiperazin-1-yl)pyrimidin-2-yl)thio)phenyl)acetamide |
| 231 | N-(4-((4-(4-(dimethylamino)piperidin-1-yl)-5-methyl-6-((5-methyl-1H-pyrazol-3-yl)amino)pyrimidin-2-yl)thio)phenyl)acetamide |
| 232 | N-(4-((4-(4-aminopiperidin-1-yl)-5-methyl-6-((5-methyl-1H-pyrazol-3-yl)amino)pyrimidin-2-yl)thio)phenyl)acetamide |
| 233 | N-(4-((4-(4-hydroxy-4-methylpiperidin-1-yl)-5-methyl-6-((5-methyl-1H-pyrazol-3-yl)amino)pyrimidin-2-yl)thio)phenyl)acetamide |
| 234 | N-(4-((4-(diethylamino)-5-methyl-6-((5-methyl-1H-pyrazol-3-yl)amino)pyrimidin-2-yl)thio)phenyl)acetamide |
| 235 | 1-(4-((4-(4-hydroxypiperidin-1-yl)-5-methyl-6-((5-methyl-1H-pyrazol-3-yl)amino)pyrimidin-2-yl)thio)phenyl)-3-methylurea |
| 236 | 1-methyl-3-(4-((5-methyl-4-((5-methyl-1H-pyrazol-3-yl)amino)-6-morpholinopyrimidin-2-yl)thio)phenyl)urea |
| 237 | 1-(5-methyl-6-((5-methyl-1H-pyrazol-3-yl)amino)-2-(phenylthio)pyrimidin-4-yl)piperidin-4-ol |
| 238 | 5-methyl-N-(5-methyl-1H-pyrazol-3-yl)-6-(piperidin-1-yl)-2-(p-tolyloxy)pyrimidin-4-amine |
| 239 | 5-methyl-N-(5-methyl-1H-pyrazol-3-yl)-6-morpholino-2-(phenylthio)pyrimidin-4-amine |
| 240 | N$^4$-isopropyl-N$^4$,5-dimethyl-N$^6$-(5-methyl-1H-pyrazol-3-yl)-2-(phenylthio)pyrimidine-4,6-diamine |
| 241 | N-(4-((4-(4-(2-(dimethylamino)ethyl)piperidin-1-yl)-5-methoxy-6-((5-methyl-1H-pyrazol-3-yl)amino)pyrimidin-2-yl)thio)phenyl)acetamide |
| 242 | 1-(4-((4-(4-(2-methoxyacetyl)piperazin-1-yl)-5-methyl-6-((5-methyl-1H-pyrazol-3-yl)amino)pyrimidin-2-yl)thio)phenyl)-3-methylurea |
| 243 | 1-(4-((4-(isopropyl(methyl)amino)-5-methyl-6-((5-methyl-1H-pyrazol-3-yl)amino)pyrimidin-2-yl)thio)phenyl)-3-methylurea |
| 244 | 1-(4-(2((4-aminophenyl)thio)-5-methyl-6-((5-methyl-1H-pyrazol-3-yl)amino)pyrimidin-4-yl)piperazin-1-yl)-2-methoxyethan-1-one |
| 245 | 2-methoxy-1-(4-(5-methyl-6-((5-methyl-1H-pyrazol-3-yl)amino)-2-(phenylthio)pyrimidin-4-yl)piperazin-1-yl)ethan-1-one |
| 246 | 1-(2-((4-aminophenyl)thio)-5-methyl-6-((5-methyl-1H-pyrazol-3-yl)amino)pyrimidin-4-yl)piperidin-4-ol |
| 247 | 6-(1-(2-(dimethylamino)ethyl)piperidin-4-yl)-2-((4-(ethylsulfonyl)phenyl)thio)-5-methoxy-N-(5-methyl-1H-pyrazol-3-yl)pyrimidin-4-amine |
| 248 | 6-(4-(2-(8-azabicyclo[3.2.1]octan-8-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 249 | 6-(4-(2-(9-azabicyclo[3.2.1]nonan-9-yl)ethyl)piperidin-1-yl)-2-((4-(ethylsulfonyl)phenyl)thio)-5-methoxy-N-(5-methyl-1H-pyrazol-3-yl)pyrimidin-4-amine |
| 250 | 6-(4-(2-(dimethylamino)ethyl)piperazin-1-yl)-5-methoxy-N-(5-methyl-1H-pyrazol-3-yl)-2-((4-((2-(pyrimidin-4-yl)propan-2-yl)sulfonyl)phenyl)thio)pyrimidin-4-amine |
| 251 | 6-(4-(2-(dimethylamino)ethyl)piperazin-1-yl)-2-((4-((2-(dimethylamino)ethyl)sulfonyl)phenyl)thio)-5-methoxy-N-(5-methyl-1H-pyrazol-3-yl)pyrimidin-4-amine |
| 252 | 6-(4-(2-(dimethylamino)ethyl)piperazin-1-yl)-5-ethoxy-2-((4-(ethylsulfonyl)phenyl)thio)-N-(5-methyl-1H-pyrazol-3-yl)pyrimidin-4-amine |
| 253 | 6-(4-(2-(dimethylamino)ethyl)piperazin-1-yl)-5-methoxy-N-(5-methyl-1H-pyrazol-3-yl)-2-((4-((oxazol-2-ylmethyl)sulfonyl)phenyl)thio)pyrimidin-4-amine |
| 254 | 6-(4-(2-(dimethylamino)ethyl)piperazin-1-yl)-5-methoxy-N-(5-methyl-1H-pyrazol-3-yl)-2-((4-((thiazol-2-ylmethyl)sulfonyl)phenyl)thio)pyrimidin-4-amine |
| 255 | 6-(4-(2-(dimethylamino)ethyl)piperazin-1-yl)-5-methoxy-N-(5-methyl-1H-pyrazol-3-yl)-2-((4-(phenylsulfonyl)phenyl)thio)pyrimidin-4-amine |
| 256 | 2-((4-((2,4-difluorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 257 | 2-((4-(benzylsulfonyl)phenyl)thio)-5-ethoxy-N-(5-methyl-1H-pyrazol-3-yl)-6-(piperazin-1-yl)pyrimidin-4-amine |
| 258 | 2-((4-(benzylsulfonyl)phenyl)thio)-5-methoxy-6-(4-(2-(methyl(phenyl)amino)ethyl)piperazin-1-yl)-N-(5-methyl-1H-pyrazol-3-yl)pyrimidin-4-amine |

TABLE 2-continued

Compound Names for exemplified compounds of formula(I), (II), and (III). All compounds were confirmed by mass spectro scopy and by $^1$H and $^{13}$C NMR.

No. Chemical Name 259 2-((4-(benzylsulfonyl)phenyl)thio)-6-(4-(2-(dimethylamino)ethyl)piperazin-1-yl)-5-isopropoxy-N-(5-methyl-1H-pyrazol-3-yl)pyrimidin-4-amine
260 2-((4-(benzylsulfonyl)phenyl)thio)-6-(4-(2-(dimethylamino)ethyl)piperazin-1-yl)-5-methoxy-N-(1H-pyrazol-3-yl)pyrimidin-4-amine
261 2-((4-(benzylsulfonyl)phenyl)thio)-6-(4-(2-(dimethylamino)ethyl)piperazin-1-yl)-5-methyl-N-(5-methyl-1H-pyrazol-3-yl)pyrimidin-4-amine
262 2-((4-(benzylsulfonyl)phenyl)thio)-6-(4-(2-(dimethylamino)ethyl)piperazin-1-yl)-N-(5-methyl-1H-pyrazol-3-yl)-5-propoxypyrimidin-4-amine
263 2-((4-(benzylsulfonyl)phenyl)thio)-6-(4-(2-(dimethylamino)ethyl)piperazin-1-yl)-N-(5-methyl-1H-pyrazol-3-yl)pyrimidin-4-amine
264 2-((4-(benzylsulfonyl)phenyl)thio)-$N^4$,$N^4$-diethyl-5-methoxy-$N^6$-(5-methyl-1H-pyrazol-3-yl)pyrimidine-4,6-diamine
265 2-((4-(ethylsulfonyl)phenyl)thio)-5-methoxy-N-(5-methyl-1H-pyrazol-3-yl)-6-(piperidin-1-yl)pyrimidin-4-amine
266 2-((4-(ethylsulfonyl)phenyl)thio)-5-methoxy-N-(5-methyl-1H-pyrazol-3-yl)-6-morpholinopyrimidin-4-amine
267 5-ethoxy-2-((4-(ethylsulfonyl)phenyl)thio)-N-(5-methyl-1H-pyrazol-3-yl)-6-(piperazin-1-yl)pyrimidin-4-amine
268 6-(4-(2-(dimethylamino)ethyl)piperazin-1-yl)-2-((4-((2-fluorobenzyl)sulfonyl)phenyl)thio)-5-methoxy-N-(5-methyl-1H-pyrazol-3-yl)pyrimidin-4-amine
269 6-(4-(2-(dimethylamino)ethyl)piperazin-1-yl)-5-methoxy-N-(5-methyl-1H-pyrazol-3-yl)-2-((4-((3-nitrobenzyl)sulfonyl)phenyl)thio)pyrimidin-4-amine
270 6-(4-(2-(dimethylamino)ethyl)piperazin-1-yl)-5-methoxy-N-(5-methyl-1H-pyrazol-3-yl)-2-((4-((4-nitrobenzyl)sulfonyl)phenyl)thio)pyrimidin-4-amine
271 $N^4$,$N^4$-diethyl-2-((4-(ethylsulfonyl)phenyl)thio)-5-methoxy-$N^6$-(5-methyl-1H-pyrazol-3-yl)pyrimidine-4,6-diamine
272 1-(3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenyl)ethan-1-one
273 1-(2-(4-(2-((4-(benzylsulfonyl)phenyl)thio)-5-methoxy-6-((5-methyl-1H-pyrazol-3-yl)amino)pyrimidin-4-yl)piperazin-1-yl)ethyl)piperidin-4-ol
274 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenol
275 2-((4-((2,3-difluorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine
276 2-((4-((2,5-difluorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine
277 2((4-((2-fluorobenzyl)sulfonyl)phenyl)thio)-5-methoxy-N-(5-methyl-1H-pyrazol-3-yl)-6-morpholinopyrimidin-4-amine
278 2-((4-((3-(benzyloxy)benzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine
279 2-((4-(([1,1'-biphenyl]-3-ylmethyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine
280 2-((4-(benzylsulfonyl)phenyl)thio)-5-methoxy-N-(5-methyl-1H-pyrazol-3-yl)-6-(4-(2-(piperidin-1-yl)ethyl)piperazin-1-yl)pyrimidin-4-amine
281 2-((4-(benzylsulfonyl)phenyl)thio)-6-(4-(2-(2,6-dimethylpiperidin-1-yl)ethyl)piperazin-1-yl)-5-methoxy-N-(5-methyl-1H-pyrazol-3-yl)pyrimidin-4-amine
282 5-methoxy-N-(5-methyl-1H-pyrazol-3-yl)-6-morpholino-2-((4-((3-nitrobenzyl)sulfonyl)phenyl)thio)pyrimidin-4-amine
283 6-(4-(2-(8-azabicyclo[3.2.1]octan-8-yl)ethyl)piperazin-1-yl)-2-((4-(benzylsulfonyl)phenyl)thio)-5-ethoxy-N-(5-methyl-1H-pyrazol-3-yl)pyrimidin-4-amine
284 6-(4-(2-(dimethylamino)ethyl)piperazin-1-yl)-5-methoxy-N-(5-methyl-1H-pyrazol-3-yl)-2-((4-((2-nitrobenzyl)sulfonyl)phenyl)thio)pyrimidin-4-amine
285 6-(4-(2-(dimethylamino)ethyl)piperazin-1-yl)-5-methoxy-N-(5-methyl-1H-pyrazol-3-yl)-2-((4-((3-(trifluoromethyl)benzyl)sulfonyl)phenyl)thio)pyrimidin-4-amine
286 6-(4-(2-(dimethylamino)ethyl)piperidin-1-yl)-5-ethoxy-2-((4-(ethylsulfonyl)phenyl)thio)-N-(5-methyl-1H-pyrazol-3-yl)pyrimidin-4-amine
287 $N^2$-(4-(benzylsulfonyl)phenyl)-6-(4-(2-(dimethylamino)ethyl)piperazin-1-yl)-5-methoxy-$N^4$-(5-methyl-1H-pyrazol-3-yl)pyrimidine-2,4-diamine
288 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzonitrile
289 (R)-2-((4-(benzylsulfonyl)phenyl)thio)-5-methoxy-N-(5-methyl-1H-pyrazol-3-yl)-6-(2-methylmorpholino)pyrimidin-4-amine
290 2-((4-(benzylsulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine
291 2-((4-(benzylsulfonyl)phenyl)thio)-5-methoxy-N-(5-methyl-1H-pyrazol-3-yl)-6-(4-(1-methylpiperidin-4-yl)piperazin-1-yl)pyrimidin-4-amine
292 2-((4-(benzylsulfonyl)phenyl)thio)-5-methoxy-N-(5-methyl-1H-pyrazol-3-yl)-6-(4-(2-(4-methylpiperazin-1-yl)ethyl)piperidin-1-yl)pyrimidin-4-amine

TABLE 2-continued

Compound Names for exemplified compounds of formula(I), (II), and (III).
All compounds were confirmed by mass spectro scopy and by $^1$H and $^{13}$C NMR.

| No. | Chemical Name |
|---|---|
| 293 | 2-((4-(benzylsulfonyl)phenyl)thio)-5-methoxy-N-(5-methyl-1H-pyrazol-3-yl)-6-(4-(2-(pyrrolidin-1-yl)ethyl)piperazin-1-yl)pyrimidin-4-amine |
| 294 | 2-((4-(benzylsulfonyl)phenyl)thio)-5-methoxy-N-(5-methyl-1H-pyrazol-3-yl)-6-(4-(4-methylpiperazin-1-yl)piperidin-1-yl)pyrimidin-4-amine |
| 295 | 2-((4-(benzylsulfonyl)phenyl)thio)-5-methoxy-N-(5-methyl-1H-pyrazol-3-yl)-6-(4-(pyridin-4-ylmethyl)piperazin-1-yl)pyrimidin-4-amine |
| 296 | 6-(4-(1-benzylpiperidin-4-yl)piperazin-1-yl)-2-((4-(benzylsulfonyl)phenyl)thio)-5-methoxy-N-(5-methyl-1H-pyrazol-3-yl)pyrimidin-4-amine |
| 297 | 6-(4-(2-(azepan-1-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 298 | 6-(4-(2-(dimethylamino)ethyl)piperazin-1-yl)-5-methoxy-2-((4-((2-methoxybenzyl)sulfonyl)phenyl)thio)-N-(5-methyl-1H-pyrazol-3-yl)pyrimidin-4-amine |
| 299 | 6-(4-(2-(dimethylamino)ethyl)piperazin-1-yl)-5-methoxy-2-((4-((3-methoxybenzyl)sulfonyl)phenyl)thio)-N-(5-methyl-1H-pyrazol-3-yl)pyrimidin-4-amine |
| 300 | 6-(4-(2-(dimethylamino)ethyl)piperazin-1-yl)-5-methoxy-N-(5-methyl-1H-pyrazol-3-yl)-2-((4-((3-methylbenzyl)sulfonyl)phenyl)thio)pyrimidin-4-amine |
| 301 | 6-(4-benzylpiperazin-1-yl)-2-((4-(benzylsulfonyl)phenyl)thio)-5-methoxy-N-(5-methyl-1H-pyrazol-3-yl)pyrimidin-4-amine |
| 302 | methyl 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoate |
| 303 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzamide |
| 304 | N-(2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenyl)acetamide |
| 305 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzonitrile |
| 306 | (R)-2-((4-(benzylsulfonyl)phenyl)thio)-5-methoxy-N-(5-methyl-1H-pyrazol-3-yl)-6-(3-methylmorpholino)pyrimidin-4-amine |
| 307 | (S)-2-((4-(benzylsulfonyl)phenyl)thio)-5-methoxy-N-(5-methyl-1H-pyrazol-3-yl)-6-(2-methylmorpholino)pyrimidin-4-amine |
| 308 | (S)-2-((4-(benzylsulfonyl)phenyl)thio)-5-methoxy-N-(5-methyl-1H-pyrazol-3-yl)-6-(3-methylmorpholino)pyrimidin-4-amine |
| 309 | 2-((4-((2-(dimethylamino)benzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 310 | 2-((4-(([1,1'-biphenyl]-2-ylmethyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 311 | 2-((4-(benzylsulfonyl)phenyl)thio)-6-(8-oxa-3-azabicyclo[3.2.1]octan-3-yl)-5-methoxy-N-(5-methyl-1H-pyrazol-3-yl)pyrimidin-4-amine |
| 312 | 6-(4-(2-(azetidin-1-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 313 | 6-(4-(2-(benzyl(methyl)amino)ethyl)piperazin-1-yl)-5-methoxy-2-((4-((3-methoxybenzyl)sulfonyl)phenyl)thio)-N-(5-methyl-1H-pyrazol-3-yl)pyrimidin-4-amine |
| 314 | 6-(4-(2-(dimethylamino)ethyl)piperazin-1-yl)-2-((4-((2-fluoro-3-nitrobenzyl)sulfonyl)phenyl)thio)-5-methoxy-N-(5-methyl-1H-pyrazol-3-yl)pyrimidin-4-amine |
| 315 | 6-(4-(2-(dimethylamino)ethyl)piperazin-1-yl)-2-((4-((3-fluorobenzyl)sulfonyl)phenyl)thio)-5-methoxy-N-(5-methyl-1H-pyrazol-3-yl)pyrimidin-4-amine |
| 316 | 6-(4-(2-(dimethylamino)ethyl)piperazin-1-yl)-5-methoxy-N-(5-methyl-1H-pyrazol-3-yl)-2-((4-((2-(trifluoromethyl)benzyl)sulfonyl)phenyl)thio)pyrimidin-4-amine |
| 317 | 6-(4-(2-(dimethylamino)ethyl)piperazin-1-yl)-5-methoxy-N-(5-methyl-1H-pyrazol-3-yl)-2-((4-((2-methylbenzyl)sulfonyl)phenyl)thio)pyrimidin-4-amine |
| 318 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoic acid |
| 319 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoic acid |
| 320 | methyl 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzoate |
| 321 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-N,N-dimethylbenzamide |
| 322 | 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)benzamide |
| 323 | 3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-N,N-dimethylbenzamide |
| 324 | N-(3-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)phenyl)acetamide |
| 325 | (R)-5-methoxy-N-(5-methyl-1H-pyrazol-3-yl)-6-(2-methylmorpholino)-2-((4-((3-nitrobenzyl)sulfonyl)phenyl)thio)pyrimidin-4-amine |

TABLE 2-continued

Compound Names for exemplified compounds of formula(I), (II), and (III).
All compounds were confirmed by mass spectro scopy and by $^1$H and $^{13}$C NMR.

No. Chemical Name 326 (R)-5-methoxy-N-(5-methyl-1H-pyrazol-3-yl)-6-(3-methylmorpholino)-2-((4-((3-nitrobenzyl)sulfonyl)phenyl)thio)pyrimidin-4-amine
327 (S)-5-methoxy-N-(5-methyl-1H-pyrazol-3-yl)-6-(2-methylmorpholino)-2-((4-((3-nitrobenzyl)sulfonyl)phenyl)thio)pyrimidin-4-amine
328 (S)-5-methoxy-N-(5-methyl-1H-pyrazol-3-yl)-6-(3-methylmorpholino)-2-((4-((3-nitrobenzyl)sulfonyl)phenyl)thio)pyrimidin-4-amine
329 2-((4-((3-(dimethylamino)benzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine
330 2-((4-(benzylsulfonyl)-2-chlorophenyl)thio)-6-(4-(2-(dimethylamino)ethyl)piperazin-1-yl)-5-methoxy-N-(5-methyl-1H-pyrazol-3-yl)pyrimidin-4-amine
331 2-((4-(benzylsulfonyl)phenyl)thio)-5-methoxy-N-(5-methyl-1H-pyrazol-3-yl)-6-(4-(piperidin-4-yl)piperazin-1-yl)pyrimidin-4-amine
332 6-(4-(2-(8-azabicyclo[3.2.1]octan-8-yl)ethyl)piperidin-1-yl)-2-((4-(benzylsulfonyl)phenyl)thio)-5-methoxy-N-(5-methyl-1H-pyrazol-3-yl)pyrimidin-4-amine
333 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-6-nitrobenzonitrile
334 1-(2-((4-((2-fluoro-3-nitrobenzyl)sulfonyl)phenyl)thio)-5-methoxy-6-((5-methyl-1H-pyrazol-3-yl)amino)pyrimidin-4-yl)piperidin-4-ol
335 (5)-2-((2-fluoro-4-((3-nitrobenzyl)sulfonyl)phenyl)thio)-5-methoxy-N-(5-methyl-1H-pyrazol-3-yl)-6-(3-methylmorpholino)pyrimidin-4-amine
336 2-((2-fluoro-4-((2-fluoro-3-nitrobenzyl)sulfonyl)phenyl)thio)-5-methoxy-N-(5-methyl-1H-pyrazol-3-yl)-6-morpholinopyrimidin-4-amine
337 2-((2-fluoro-4-((3-nitrobenzyl)sulfonyl)phenyl)thio)-5-methoxy-N-(5-methyl-1H-pyrazol-3-yl)-6-morpholinopyrimidin-4-amine
338 2-((4-((2-chloro-3-nitrobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine
339 2-((4-((2-fluoro-3-nitrobenzyl)sulfonyl)phenyl)thio)-5-methoxy-N-(5-methyl-1H-pyrazol-3-yl)-6-(piperidin-1-yl)pyrimidin-4-amine
340 2-((4-((2-fluoro-3-nitrobenzyl)sulfonyl)phenyl)thio)-5-methoxy-N-(5-methyl-1H-pyrazol-3-yl)-6-morpholinopyrimidin-4-amine
341 6-(4-(2-(dimethylamino)ethyl)piperazin-1-yl)-2-((2-fluoro-4-((2-fluoro-3-nitrobenzyl)sulfonyl)phenyl)thio)-5-methoxy-N-(5-methyl-1H-pyrazol-3-yl)pyrimidin-4-amine
342 6-(4-(2-(dimethylamino)ethyl)piperazin-1-yl)-2-((2-fluoro-4-((3-nitrobenzyl)sulfonyl)phenyl)thio)-5-methoxy-N-(5-methyl-1H-pyrazol-3-yl)pyrimidin-4-amine
343 6-(4-(2-(dimethylamino)ethyl)piperazin-1-yl)-2-((4-((2-fluoro-5-nitrobenzyl)sulfonyl)phenyl)thio)-5-methoxy-N-(5-methyl-1H-pyrazol-3-yl)pyrimidin-4-amine
344 6-(4-(2-(dimethylamino)ethyl)piperazin-1-yl)-2-((4-((3-fluoro-5-nitrobenzyl)sulfonyl)phenyl)thio)-5-methoxy-N-(5-methyl-1H-pyrazol-3-yl)pyrimidin-4-amine
345 6-(4-(2-(dimethylamino)ethyl)piperazin-1-yl)-5-methoxy-2-((4-((2-methoxy-3-nitrobenzyl)sulfonyl)phenyl)thio)-N-(5-methyl-1H-pyrazol-3-yl)pyrimidin-4-amine
346 6-(4-(2-(dimethylamino)ethyl)piperazin-1-yl)-5-methoxy-2-((4-((2-methoxy-5-nitrobenzyl)sulfonyl)phenyl)thio)-N-(5-methyl-1H-pyrazol-3-yl)pyrimidin-4-amine
347 2-(((4-((4-(4-(2-(dimethylamino)ethyl)piperazin-1-yl)-5-methoxy-6-((5-methyl-1H-pyrazol-3-yl)amino)pyrimidin-2-yl)thio)phenyl)sulfonyl)methyl)-6-nitrophenol
348 (R)-2-((2-fluoro-4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine
349 (R)-2-((2-fluoro-4-((3-nitrobenzyl)sulfonyl)phenyl)thio)-5-methoxy-N-(5-methyl-1H-pyrazol-3-yl)-6-(3-methylmorpholino)pyrimidin-4-amine
350 (S)-2-((2-chloro-4-(ethylsulfonyl)phenyl)thio)-5-methoxy-N-(5-methyl-1H-pyrazol-3-yl)-6-(3-methylmorpholino)pyrimidin-4-amine
351 2-((2-chloro-4-(ethylsulfonyl)phenyl)thio)-5-methoxy-N-(5-methyl-1H-pyrazol-3-yl)-6-(4-methylpiperazin-1-yl)pyrimidin-4-amine
352 2-((2-chloro-4-(ethylsulfonyl)phenyl)thio)-5-methoxy-N-(5-methyl-1H-pyrazol-3-yl)-6-morpholinopyrimidin-4-amine
353 2-((2-chloro-4-(ethylsulfonyl)phenyl)thio)-6-(4-(2-(dimethylamino)ethyl)piperazin-1-yl)-5-methoxy-N-(5-methyl-1H-pyrazol-3-yl)pyrimidin-4-amine
354 2-((2-chloro-4-(ethylsulfonyl)phenyl)thio)-6-(4-(2-(dimethylamino)ethyl)piperidin-1-yl)-5-methoxy-N-(5-methyl-1H-pyrazol-3-yl)pyrimidin-4-amine
355 2-((2-chloro-4-(methylsulfonyl)phenyl)thio)-6-(4-(2-(dimethylamino)ethyl)piperazin-1-yl)-5-methoxy-N-(5-methyl-1H-pyrazol-3-yl)pyrimidin-4-amine
356 2-((2-chloro-4-(methylsulfonyl)phenyl)thio)-6-(4-(2-(dimethylamino)ethyl)piperidin-1-yl)-5-methoxy-N-(5-methyl-1H-pyrazol-3-yl)pyrimidin-4-amine
357 6-(3-oxa-8-azabicyclo[3.2.1]octan-8-yl)-5-methoxy-N-(5-methyl-1H-pyrazol-3-yl)-2-((4-((3-nitrobenzyl)sulfonyl)phenyl)thio)pyrimidin-4-amine
358 6-(4-(2-(dimethylamino)ethyl)piperazin-1-yl)-2-((2-fluoro-4-(methylsulfonyl)phenyl)thio)-5-methoxy-N-(5-methyl-1H-pyrazol-3-yl)pyrimidin-4-amine TABLE 2-continued Compound Names for exemplified compounds of formula(I), (II), and (III).
All compounds were confirmed by mass spectro scopy and by $^1$H and $^{13}$C NMR.

No. Chemical Name 359 6-(4-(2-(dimethylamino)ethyl)piperazin-1-yl)-2-((4-(ethylsulfonyl)-2-fluorophenyl)thio)-5-methoxy-N-(5-methyl-1H-pyrazol-3-yl)pyrimidin-4-amine
360 6-(4-(2-(dimethylamino)ethyl)piperidin-1-yl)-2-((2-fluoro-4-(methylsulfonyl)phenyl)thio)-5-methoxy-N-(5-methyl-1H-pyrazol-3-yl)pyrimidin-4-amine
361 6-(4-(2-(dimethylamino)ethyl)piperidin-1-yl)-2-((4-(ethylsulfonyl)-2-fluorophenyl)thio)-5-methoxy-N-(5-methyl-1H-pyrazol-3-yl)pyrimidin-4-amine
362 6-(4-(2-(dimethylamino)ethyl)piperazin-1-yl)-5-methoxy-N-(5-methyl-1H-pyrazol-3-yl)-2-((4-((2-(pyrazin-2-yl)propan-2-yl)sulfonyl)phenyl)thio)pyrimidin-4-amine
363 (R)-(4-(5-methoxy-6-((5-methyl-1H-pyrazol-3-yl)amino)-2-((4-((3-nitrobenzyl)sulfonyl)phenyl)thio)pyrimidin-4-yl)morpholin-3-yl)methanol
364 (R)-2-((2-chloro-4-(ethylsulfonyl)phenyl)thio)-5-methoxy-N-(5-methyl-1H-pyrazol-3-yl)-6-(3-methylmorpholino)pyrimidin-4-amine
365 (R)-2-((4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine
366 (R)-6-(3-ethylmorpholino)-5-methoxy-N-(5-methyl-1H-pyrazol-3-yl)-2-((4-((3-nitrobenzyl)sulfonyl)phenyl)thio)pyrimidin-4-amine
367 (S)-2-((4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine
368 (S)-2-((4-(ethylsulfonyl)-2-fluorophenyl)thio)-5-methoxy-N-(5-methyl-1H-pyrazol-3-yl)-6-(3-methylmorpholino)pyrimidin-4-amine
369 2-((2-chloro-4-(ethylsulfonyl)phenyl)thio)-5-methoxy-N-(5-methyl-1H-pyrazol-3-yl)-6-(piperidin-1-yl)pyrimidin-4-amine
370 2-((2-fluoro-4-(methylsulfonyl)phenyl)thio)-5-methoxy-N-(5-methyl-1H-pyrazol-3-yl)-6-(piperidin-1-yl)pyrimidin-4-amine
371 2-((2-fluoro-4-(methylsulfonyl)phenyl)thio)-5-methoxy-N-(5-methyl-1H-pyrazol-3-yl)-6-morpholinopyrimidin-4-amine
372 2-((4-((2,3-difluorobenzyl)sulfonyl)phenyl)thio)-5-methoxy-N-(5-methyl-1H-pyrazol-3-yl)-6-(piperidin-1-yl)pyrimidin-4-amine
373 2-((4-(ethylsulfonyl)-2-fluorophenyl)thio)-5-methoxy-N-(5-methyl-1H-pyrazol-3-yl)-6-(piperidin-1-yl)pyrimidin-4-amine
374 2-((4-(ethylsulfonyl)-2-fluorophenyl)thio)-5-methoxy-N-(5-methyl-1H-pyrazol-3-yl)-6-morpholinopyrimidin-4-amine
375 5-methoxy-N-(5-methyl-1H-pyrazol-3-yl)-2-((4-(methylsulfonyl)phenyl)thio)-6-(piperidin-1-yl)pyrimidin-4-amine
376 6-(3-ethylmorpholino)-5-methoxy-N-(5-methyl-1H-pyrazol-3-yl)-2-((4-((3-nitrobenzyl)sulfonyl)phenyl)thio)pyrimidin-4-amine
377 1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)-N,N-dimethylpiperidine-4-carboxamide compound
378 1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)-N,N-dimethylpiperidine-4-carboxamide
379 1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidine-4-carboxamide
380 2,2,2-trifluoro-N-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)acetamide
381 2,2,2-trifluoro-N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetamide
382 2,2,2-trifluoro-N-(2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)ethyl)acetamide
383 2-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)acetamide
384 2-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)acetamide
385 2-(1-(2-((2-fluoro-4 (2-fluoro-3-nitrobenzyl)sulfonyl)phenyl)thio)-5-methoxy-6-((5-methyl-1H-pyrazol-3-yl)amino)pyrimidin-4-yl)piperidin-4-yl)acetamide
386 N-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)acetamide
387 N-(1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-4-yl)acetamide
388 N-(2-(1-(2-((2-fluoro-4-((1-(2-fluoro-3-nitrophenyl)cyclopropyl)sulfonyl)phenyl)thio)-5-methoxy-6-((5-methyl-1H-pyrazol-3-yl)amino)pyrimidin-4-yl)piperidin-4-yl)ethyl)acetamide
389 N-(2-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)ethyl)acetamide
390 N-(2-(1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-4-yl)ethyl)acetamide TABLE 2-continued Compound Names for exemplified compounds of formula(I), (II), and (III).
All compounds were confirmed by mass spectro scopy and by $^1$H and $^{13}$C NMR.

| No. | Chemical Name |
|---|---|
| 391 | 1-(4-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperazin-1-yl)ethan-1-one |
| 392 | 1-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperazin-1-yl)ethan-1-one |
| 393 | 2-((2-fluoro-4-((1-(2,3,5,6-tetrafluorophenyl)cyclopropyl)sulfonyl)phenyl)thio)-5-methoxy-N-(5-methyl-1H-pyrazol-3-yl)-6-morpholinopyrimidin-4-amine |
| 394 | 2-((2-fluoro-4-((1-(2-fluoro-3-nitrophenyl)cyclopropyl)sulfonyl)phenyl)thio)-5-methoxy-N-(5-methyl-1H-pyrazol-3-yl)-6-(piperazin-1-yl)pyrimidin-4-amine |
| 395 | 2-((2-fluoro-4-((1-(2-fluoro-3-nitrophenyl)cyclopropyl)sulfonyl)phenyl)thio)-5-methoxy-N-(5-methyl-1H-pyrazol-3-yl)-6-morpholinopyrimidin-4-amine |
| 396 | 2-((2-fluoro-4-((2-(2,3,5,6-tetrafluorophenyl)propan-2-yl)sulfonyl)phenyl)thio)-5-methoxy-N-(5-methyl-1H-pyrazol-3-yl)-6-(piperazin-1-yl)pyrimidin-4-amine |
| 397 | 2-((4-((2-(1H-imidazol-2-yl)propan-2-yl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 398 | 6-(3-aminopyrrolidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 399 | 6-(3-aminopyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 400 | 6-(4-(2-(dimethylamino)ethyl)piperazin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 401 | 6-(4-(2-(dimethylamino)ethyl)piperidin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 402 | 6-(4-(2-aminoethyl)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 403 | 6-(4-(aminomethyl)piperidin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 404 | 6-(4-(aminomethyl)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 405 | 6-(4-(aminomethyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 406 | 6-(4-aminopiperidin-1-yl)-2-((2-fluoro-4-((1-(2-fluoro-3-nitrophenyl)cyclopropyl)sulfonyl)phenyl)thio)-5-methoxy-N-(5-methyl-1H-pyrazol-3-yl)pyrimidin-4-amine |
| 407 | 6-(4-aminopiperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 408 | 6-(4-aminopiperidin-1-yl)-2-((2-fluoro-4-((2-fluoro-3-nitrobenzyl)sulfonyl)phenyl)thio)-5-methoxy-N-(5-methyl-1H-pyrazol-3-yl)pyrimidin-4-amine |
| 409 | 6-(4-(2-(dimethylamino)ethyl)piperazin-1-yl)-5-methoxy-N-(5-methyl-1H-pyrazol-3-yl)-2-((4-((2,3,6-trifluorobenzyl)sulfonyl)phenyl)thio)pyrimidin-4-amine |
| 410 | 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)benzonitrile |
| 411 | (S)-(4-(5-methoxy-6-((5-methyl-1H-pyrazol-3-yl)amino)-2-((4-((3-nitrobenzyl)sulfonyl)phenyl)thio)pyrimidin-4-yl)morpholin-3-yl)methanol |
| 412 | (S)-2-((2-fluoro-4-((2-fluoro-3-nitrobenzyl)sulfonyl)phenyl)thio)-5-methoxy-N-(5-methyl-1H-pyrazol-3-yl)-6-(3-methylmorpholino)pyrimidin-4-amine |
| 413 | (S)-2-((2-fluoro-4-(methylsulfonyl)phenyl)thio)-5-methoxy-N-(5-methyl-1H-pyrazol-3-yl)-6-(3-methylmorpholino)pyrimidin-4-amine |
| 414 | (S)-2-((4-((2,3-difluorobenzyl)sulfonyl)-2-fluorophenyl)thio)-5-methoxy-N-(5-methyl-1H-pyrazol-3-yl)-6-(3-methylmorpholino)pyrimidin-4-amine |
| 415 | 2-((2-fluoro-4-((2,3,5,6-tetrafluorobenzyl)sulfonyl)phenyl)thio)-5-methoxy-N-(5-methyl-1H-pyrazol-3-yl)-6-morpholinopyrimidin-4-amine |
| 416 | 2-((2-fluoro-4-((2-fluoro-3-(trifluoromethyl)benzyl)sulfonyl)phenyl)thio)-5-methoxy-N-(5-methyl-1H-pyrazol-3-yl)-6-morpholinopyrimidin-4-amine |
| 417 | 2-((2-fluoro-4-((2-fluoro-3-nitrobenzyl)sulfonyl)phenyl)thio)-5-methoxy-N-(5-methyl-1H-pyrazol-3-yl)-6-(piperidin-1-yl)pyrimidin-4-amine |
| 418 | 2-((4-((2,3-difluorobenzyl)sulfonyl)-2-fluorophenyl)thio)-5-methoxy-N-(5-methyl-1H-pyrazol-3-yl)-6-(piperidin-1-yl)pyrimidin-4-amine |
| 419 | 2-((4-((2,3-difluorobenzyl)sulfonyl)-2-fluorophenyl)thio)-5-methoxy-N-(5-methyl-1H-pyrazol-3-yl)-6-morpholinopyrimidin-4-amine |
| 420 | 2-((4-((2,3-difluorobenzyl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 421 | 2-((4-((3-bromo-2-fluorobenzyl)sulfonyl)-2-fluorophenyl)thio)-5-methoxy-N-(5-methyl-1H-pyrazol-3-yl)-6-morpholinopyrimidin-4-amine |
| 422 | 2-((4-((3-chloro-2-fluorobenzyl)sulfonyl)-2-fluorophenyl)thio)-5-methoxy-N-(5-methyl-1H-pyrazol-3-yl)-6-morpholinopyrimidin-4-amine |

TABLE 2-continued

Compound Names for exemplified compounds of formula(I), (II), and (III).
All compounds were confirmed by mass spectro scopy and by $^1$H and $^{13}$C NMR.

No. Chemical Name 423 6-(4-(2-(dimethylamino)ethyl)piperazin-1-yl)-2-((2-fluoro-4-((2,3,6-trifluorobenzyl)sulfonyl)phenyl)thio)-5-methoxy-N-(5-methyl-1H-pyrazol-3-yl)pyrimidin-4-amine
424 methyl 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)benzoate
425 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)-N,N-dimethylbenzamide
426 2-fluoro-3-(((3-fluoro-4-((5-methoxy-4-((5-methyl-1H-pyrazol-3-yl)amino)-6-morpholinopyrimidin-2-yl)thio)phenyl)sulfonyl)methyl)benz amide
427 3-fluoro-N-(2-fluoro-3-nitrophenyl)-4-((5-methoxy-4-((5-methyl-1H-pyrazol-3-yl)amino)-6-morpholinopyrimidin-2-yl)thio)benzamide
428 (S)-(4-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)morpholin-3-yl)methanol
429 (E)-2-((2-fluoro-4-(2-fluoro-3-nitrostyryl)phenyl)thio)-5-methoxy-N-(5-methyl-1H-pyrazol-3-yl)-6-morpholinopyrimidin-4-amine
430 2-((2-fluoro-4-((2-fluoro-3-iodobenzyl)sulfonyl)phenyl)thio)-5-methoxy-N-(5-methyl-1H-pyrazol-3-yl)-6-morpholinopyrimidin-4-amine
431 2-((2-fluoro-4-((2-fluoro-3-nitrophenyl)ethynyl)phenyl)thio)-5-methoxy-N-(5-methyl-1H-pyrazol-3-yl)-6-morpholinopyrimidin-4-amine
432 2-((2-fluoro-4-((3-nitrophenyl)sulfonyl)phenyl)thio)-5-methoxy-N-(5-methyl-1H-pyrazol-3-yl)-6-morpholinopyrimidin-4-amine
433 2-((2-fluoro-4-((fluoro(2-fluoro-3-nitrophenyl)methyl)sulfonyl)phenyl)thio)-5-methoxy-N-(5-methyl-1H-pyrazol-3-yl)-6-morpholinopyrimidin-4-amine
434 2-((2-fluoro-4-(2-fluoro-3-nitrophenethyl)phenyl)thio)-5-methoxy-N-(5-methyl-1H-pyrazol-3-yl)-6-morpholinopyrimidin-4-amine
435 2-((4-((3-amino-2-fluorobenzyl)sulfonyl)-2-fluorophenyl)thio)-5-methoxy-N-(5-methyl-1H-pyrazol-3-yl)-6-morpholinopyrimidin-4-amine
436 2-((4-((3-brom o-2-fluorobenzyl)sulfonyl)-2-fluorophenyl)thio)-5-methoxy-N-(5-methyl-1H-pyrazol-3-yl)-6-(piperidin-1-yl)pyrimidin-4-amine
437 6-(4-(2-(dimethylamino)ethyl)piperazin-1-yl)-2-((2-fluoro-4-((fluoro(2-fluoro-3-nitrophenyl)methyl)sulfonyl)phenyl)thio)-5-methoxy-N-(5-methyl-1H-pyrazol-3-yl)pyrimidin-4-amine
438 2-fluoro-3-nitrophenyl 3-fluoro-4-((5-methoxy-4-((5-methyl-1H-pyrazol-3-yl)amino)-6-morpholinopyrimidin-2-yl)thio)benzoate
439 2-(2-fluoro-3-nitrophenyl)-N-(3-fluoro-4-((5-methoxy-4-((5-methyl-1H-pyrazol-3-yl)amino)-6-morpholinopyrimidin-2-yl)thio)phenyl)acetamide
440 2-fluoro-N-(3-fluoro-4-((5-methoxy-4-((5-methyl-1H-pyrazol-3-yl)amino)-6-morpholinopyrimidin-2-yl)thio)phenyl)-3-nitrobenzamide
441 3-fluoro-4-((5-methoxy-4-((5-methyl-1H-pyrazol-3-yl)amino)-6-morpholinopyrimidin-2-yl)thio)-N-(3-nitrophenyl)benzenesulfonamide
442 2-fluoro-3-(((3-fluoro-4-((5-methoxy-4-((5-methyl-1H-pyrazol-3-yl)amino)-6-(piperidin-1-yl)pyrimidin-2-yl)thio)phenyl)sulfonyl)methyl)benzonitrile
443 2-fluoro-3-(fluoro((3-fluoro-4-((5-methoxy-4-((5-methyl-1H-pyrazol-3-yl)amino)-6-morpholinopyrimidin-2-yl)thio)phenyl)sulfonyl)methyl)benzonitrile
444 3-(((4-((4-(4-(2-(dimethylamino)ethyl)piperazin-1-yl)-5-methoxy-6-((5-methyl-1H-pyrazol-3-yl)amino)pyrimidin-2-yl)thio)-3-fluorophenyl)sulfonyl)methyl)-2-fluorobenzonitrile
445 2-(2-fluoro-3-nitrophenyl)-1-(3-fluoro-4-((5-methoxy-4-((5-methyl-1H-pyrazol-3-yl)amino)-6-morpholinopyrimidin-2-yl)thio)phenyl)ethan-1-one
446 ((3S)-4-(2-((2-fluoro-4-((fluoro(2-fluoro-3-nitrophenyl)methyl)sulfonyl)phenyl)thio)-5-methoxy-6-((5-methyl-1H-pyrazol-3-yl)amino)pyrimidin-4-yl)morpholin-3-yl)methanol
447 (R)-( 1-(2-((2-fluoro-4-((2-fluoro-3-nitrobenzyl)sulfonyl)phenyl)thio)-5-methoxy-6-((5-methyl-1H-pyrazol-3-yl)amino)pyrimidin-4-yl)piperidin-2-yl)methanol
448 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(piperidin-1-yl)pyrimidin-4-amine
449 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-morpholinopyrimidin-4-amine
450 2-((2-fluoro-4-(7-nitrobenzofuran-2-yl)phenyl)thio)-5-methoxy-N-(5-methyl-1 H-pyrazol-3-yl)-6-morpholinopyrimidin-4-amine
451 6-(4-(2-(dimethylamino)ethyl)piperazin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine
452 6-(4-(2-(dimethylamino)ethyl)piperidin-1-yl)-2-((2-fluoro-4-((2-fluoro-3-nitrobenzyl)sulfonyl)phenyl)thio)-5-methoxy-N-(5-methyl-1H-pyrazol-3-yl)pyrimidin-4-amine
453 6-(4-(2-(dimethylamino)ethyl)piperidin-1-yl)-2-((2-fluoro-4-((fluoro(2-fluoro-3-nitrophenyl)methyl)sulfonyl)phenyl)thio)-5-methoxy-N-(5-methyl-1H-pyrazol-3-yl)pyrimidin-4-amine
454 (S)-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)morpholin-3-yl)methanol
455 2-((2-fluoro-4-((2-(2,3,5,6-tetrafluoro-4-methylphenyl)propan-2-yl)sulfonyl)phenyl)thio)-5-methoxy-N-(5-methyl-1H-pyrazol-3-yl)-6-morpholinopyrimidin-4-amine
456 2-((2-fluoro-4-((2-(2,3,5,6-tetrafluorophenyl)propan-2-yl)sulfonyl)phenyl)thio)-5-methoxy-N-(5-methyl-1H-pyrazol-3-yl)-6-morpholinopyrimidin-4-amine TABLE 2-continued Compound Names for exemplified compounds of formula(I), (II), and (III).
All compounds were confirmed by mass spectro scopy and by $^1$H and $^{13}$C NMR.

| No. | Chemical Name |
|---|---|
| 457 | 2-((2-fluoro-4-((2-fluoro-3-nitrophenethyl)sulfonyl)phenyl)thio)-5-methoxy-N-(5-methyl-1H-pyrazol-3-yl)-6-morpholinopyrimidin-4-amine |
| 458 | 2-((2-fluoro-4-((fluoro(2,3,5,6-tetrafluorophenyl)methyl)sulfonyl)phenyl)thio)-5-methoxy-N-(5-methyl-1H-pyrazol-3-yl)-6-morpholinopyrimidin-4-amine |
| 459 | 2-((4-((2-(2,5-difluoro-3-nitrophenyl)propan-2-yl)sulfonyl)-2-fluorophenyl)thio)-5-methoxy-N-(5-methyl-1H-pyrazol-3-yl)-6-morpholinopyrimidin-4-amine |
| 460 | 2-((4-((2-(3-bromo-2-fluorophenyl)propan-2-yl)sulfonyl)-2-fluorophenyl)thio)-5-methoxy-N-(5-methyl-1H-pyrazol-3-yl)-6-morpholinopyrimidin-4-amine |
| 461 | 2-((4-((2-(3-bromo-2-fluorophenyl)propan-2-yl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 462 | 2-((4-((2-(3-chloro-2,5-difluorophenyl)propan-2-yl)sulfonyl)-2-fluorophenyl)thio)-5-methoxy-N-(5-methyl-1H-pyrazol-3-yl)-6-morpholinopyrimidin-4-amine |
| 463 | 2-((4-((2-(3-chloro-2-fluorophenyl)propan-2-yl)sulfonyl)-2-fluorophenyl)thio)-5-methoxy-N-(5-methyl-1H-pyrazol-3-yl)-6-morpholinopyrimidin-4-amine |
| 464 | 2-((4-((2-(3-chloro-2-fluorophenyl)propan-2-yl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine |
| 465 | 2-((4-((difluoro(2,3,5,6-tetrafluorophenyl)methyl)sulfonyl)-2-fluorophenyl)thio)-5-methoxy-N-(5-methyl-1H-pyrazol-3-yl)-6-morpholinopyrimidin-4-amine |
| 466 | 6-(4-(2-(dimethylamino)ethyl)piperazin-1-yl)-2-((2-fluoro-4-((2-(2,3,5,6-tetrafluoro-4-methylphenyl)propan-2-yl)sulfonyl)phenyl)thio)-5-methoxy-N-(5-methyl-1H-pyrazol-3-yl)pyrimidin-4-amine |
| 467 | 6-(4-(2-(dimethylamino)ethyl)piperazin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 468 | 6-(4-(2-(dimethylamino)ethyl)piperazin-1-yl)-2-((2-fluoro-4-((fluoro(2,3,5,6-tetrafluorophenyl)methyl)sulfonyl)phenyl)thio)-5-methoxy-N-(5-methyl-1H-pyrazol-3-yl)pyrimidin-4-amine |
| 469 | 6-(4-(2-(dimethylamino)ethyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 470 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)-N,N-dimethyl acetamide |
| 471 | N-(2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)ethyl)acetamide |
| 472 | 2-((2-fluoro-4-((2-(2-fluoro-3-nitrophenyl)propan-2-yl)sulfonyl)phenyl)thio)-5-methoxy-6-(4-(2-((4-methoxybenzyl)(methyl)amino)ethyl)piperidin-1-yl)-N-(5-methyl-1H-pyrazol-3-yl)pyrimidin-4-amine |
| 473 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-methylpiperazin-1-yl)pyrimidin-4-amine |
| 474 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(piperazin-1-yl)pyrimidin-4-amine |
| 475 | 2-((2-fluoro-4-((2-(2-fluoro-3-nitrophenyl)propan-2-yl)sulfonyl)phenyl)thio)-5-methoxy-$N^4$,$N^4$-dimethyl-$N^6$-(5-methyl-1H-pyrazol-3-yl)pyrimidine-4,6-diamine |
| 476 | 2-((4-((2-(2,5-difluoro-3-nitrophenyl)propan-2-yl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 477 | 2-((4-((2-(3-chloro-2,5-difluorophenyl)propan-2-yl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 478 | 2-((4-((2-(3-chloro-2-fluorophenyl)propan-2-yl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine |
| 479 | 2-((4-((3-chloro-2,5,6-trifluorobenzyl)sulfonyl)-2-fluorophenyl)thio)-5-methoxy-N-(5-methyl-1H-pyrazol-3-yl)-6-morpholinopyrimidin-4-amine |
| 480 | 6-(3-(dimethylamino)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 481 | 6-(4-((dimethylamino)methyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 482 | 6-(4-(2-(dimethylamino)ethyl)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 483 | 6-(4-(3-(dimethylamino)propyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 484 | 6-(4-(dimethylamino)piperidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine |
| 485 | 6-(4-(dimethylamino)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |

TABLE 2-continued

Compound Names for exemplified compounds of formula(I), (II), and (III).
All compounds were confirmed by mass spectro scopy and by $^1$H and $^{13}$C NMR.

No. Chemical Name 486 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetic acid
487 methyl 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetate
488 2-(dimethylamino)-1-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperazin-1-yl)ethan-1-one
489 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)ethan-1-ol
490 2-((2-fluoro-4-(((perfluorophenyl)methyl)sulfonyl)phenyl)thio)-5-methoxy-N-(5-methyl-1H-pyrazol-3-yl)-6-morpholinopyrimidin-4-amine
491 2-((2-fluoro-4-((2-(2-fluoro-3-nitrophenyl)propan-2-yl)sulfonyl)phenyl)thio)-5-methoxy-6-(3-methoxypyrrolidin-1-yl)-N-(5-methyl-1H-pyrazol-3-yl)pyrimidin-4-amine
492 2-((2-fluoro-4-((2-(2-fluoro-3-nitrophenyl)propan-2-yl)sulfonyl)phenyl)thio)-5-methoxy-6-(4-(2-methoxyethyl)piperidin-1-yl)-N-(5-methyl-1H-pyrazol-3-yl)pyrimidin-4-amine
493 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-(2-(methylamino)ethyl)piperidin-1-yl)pyrimidin-4-amine
494 2-((2-fluoro-4-((2-(perfluorophenyl)propan-2-yl)sulfonyl)phenyl)thio)-5-methoxy-N-(5-methyl-1H-pyrazol-3-yl)-6-morpholinopyrimidin-4-amine
495 2-((4-((2-(3-chloro-2,5,6-trifluorophenyl)propan-2-yl)sulfonyl)-2-fluorophenyl)thio)-5-methoxy-N-(5-methyl-1H-pyrazol-3-yl)-6-morpholinopyrimidin-4-amine
496 2-((4-((3-chloro-2,5,6-trifluorobenzyl)sulfonyl)-2-fluorophenyl)thio)-6-(4-(2-(dimethylamino)ethyl)piperazin-1-yl)-5-methoxy-N-(5-methyl-1H-pyrazol-3-yl)pyrimidin-4-amine
497 2-((4-((3-chloro-2,5,6-trifluorobenzyl)sulfonyl)-2-fluorophenyl)thio)-6-(4-(2-(dimethylamino)ethyl)piperidin-1-yl)-5-methoxy-N-(5-methyl-1H-pyrazol-3-yl)pyrimidin-4-amine
498 6-(3-(dimethylamino)pyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine
499 6-(4-(2-aminoethyl)piperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine
500 (S)-N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)pyrrolidin-3-yl)acetamide
501 2-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)-N,N-dimethylacetamide
502 2-(4-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperazin-1-yl)-N,N-dimethylacetamide
503 N-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)acetamide
504 N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetamide
505 1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)pyrrolidin-3-ol
506 (R)-6-(3-(dimethylamino)pyrrolidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine
507 (R)-6-(3-(dimethylamino)pyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine
508 (S)-6-(3-(dimethylamino)pyrrolidin-1-yl)-2-((2-fluoro-4-((2-(2,3,5,6-tetrafluorophenyl)propan-2-yl)sulfonyl)phenyl)thio)-5-methoxy-N-(5-methyl-1H-pyrazol-3-yl)pyrimidin-4-amine
509 (S)-6-(3-(dimethylamino)pyrrolidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine
510 2-((4-(tert-butylsulfonyl)phenyl)thio)-6-(4-(2-(dimethylamino)ethyl)piperazin-1-yl)-5-methoxy-N-(5-methyl-1H-pyrazol-3-yl)pyrimidin-4-amine
511 6-(4-(2-(dimethylamino)ethyl)piperazin-1-yl)-2-((2-fluoro-4-((2-(perfluorophenyl)propan-2-yl)sulfonyl)phenyl)thio)-5-methoxy-N-(5-methyl-1H-pyrazol-3-yl)pyrimidin-4-amine
512 6-(4-(2-(dimethylamino)ethyl)piperidin-1-yl)-2-((2-fluoro-4-((2-(perfluorophenyl)propan-2-yl)sulfonyl)phenyl)thio)-5-methoxy-N-(5-methyl-1H-pyrazol-3-yl)pyrimidin-4-amine
513 6-(4-(dimethylamino)piperidin-1-yl)-2-((2-fluoro-4-((2-(perfluorophenyl)propan-2-yl)sulfonyl)phenyl)thio)-5-methoxy-N-(5-methyl-1H-pyrazol-3-yl)pyrimidin-4-amine
514 1-(2-((2-fluoro-4-((2-(2,3,5,6-tetrafluorophenyl)propan-2-yl)sulfonyl)phenyl)thio)-5-methoxy-6((5-methyl-1H-pyrazol-3-yl)amino)pyrimidin-4-yl)piperidin-4-yl acetate TABLE 2-continued Compound Names for exemplified compounds of formula(I), (II), and (III).
All compounds were confirmed by mass spectro scopy and by $^1$H and $^{13}$C NMR.

| No. | Chemical Name |
|---|---|
| 515 | 1-(2-((2-fluoro-4-((2-(2,3,5,6-tetrafluorophenyl)propan-2-yl)sulfonyl)phenyl)thio)-5-methoxy-6((5-methyl-1H-pyrazol-3-yl)amino)pyrimidin-4-yl)pyrrolidin-3-yl acetate |
| 516 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)-N,N-dimethylpiperidine-4-carboxamide |
| 517 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidine-4-carboxamide |
| 518 | N-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)piperidin-4-yl)-N-methyl acetamide |
| 519 | N-(1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)pyrrolidin-3-yl)acetamide |
| 520 | N-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)-N-methylacetamide |
| 521 | 1-(2-((2-fluoro-4-((2-(2,3,5,6-tetrafluorophenyl)propan-2-yl)sulfonyl)phenyl)thio)-5-methoxy-6((5-methyl-1H-pyrazol-3-yl)amino)pyrimidin-4-yl)piperidin-4-ol |
| 522 | 1-(2-((2-fluoro-4-((2-(2,3,5,6-tetrafluorophenyl)propan-2-yl)sulfonyl)phenyl)thio)-5-methoxy-6-((5-methyl-1H-pyrazol-3-yl)amino)pyrimidin-4-yl)pyrrolidin-3-ol |
| 523 | 2-((2-fluoro-4-((2-(2,3,5,6-tetrafluorophenyl)propan-2-yl)sulfonyl)phenyl)thio)-5-methoxy-6-(4-methoxyl)iperidin-1-yl)-N-(5-methyl-1H-pyrazol-3-yl)pyrimidin-4-amine |
| 524 | 2-((2-fluoro-4-((4-methoxybenzyl)sulfonyl)phenyl)thio)-5-methoxy-N-(5-methyl-1H-pyrazol-3-yl)-6-(piperidin-1-yl)pyrimidin-4-amine |
| 525 | 2-((2-fluoro-4-((4-methoxybenzyl)sulfonyl)phenyl)thio)-5-methoxy-N-(5-methyl-1H-pyrazol-3-yl)-6-morpholinopyrimidin-4-amine |
| 526 | 5-methoxy-2-((4-((4-methoxybenzyl)sulfonyl)phenyl)thio)-N-(5-methyl-1H-pyrazol-3-yl)-6-(piperidin-1-yl)pyrimidin-4-amine |
| 527 | 5-methoxy-2-((4-((4-methoxybenzyl)sulfonyl)phenyl)thio)-N-(5-methyl-1H-pyrazol-3-yl)-6-morpholinopyrimidin-4-amine |
| 528 | 6-(4-(2-(dimethylamino)ethyl)piperazin-1-yl)-2-((2-fluoro-4-((2-(2,3,6-trifluoro-5-nitrophenyl)propan-2-yl)sulfonyl)phenyl)thio)-5-methoxy-N-(5-methyl-1H-pyrazol-3-yl)pyrimidin-4-amine |
| 529 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)-N-methyl acetamide |
| 530 | 2-(1-(2-((2-fluoro-4-((2-(2-fluoro-3-nitrophenyl)propan-2-yl)sulfonyl)phenyl)thio)-5-methoxy-6-((5-methyl-1H-pyrazol-3-yl)amino)pyrimidin-4-yl)piperidin-4-yl)acetamide |
| 531 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-(2-((1,1,1-trifluoropropan-2-yl)amino)ethyl)piperidin-1-yl)pyrimidin-4-amine |
| 532 | 2-((2-fluoro-4-((2-(2-fluoro-3-nitrophenyl)propan-2-yl)sulfonyl)phenyl)thio)-5-methoxy-N-(5-methyl-1H-pyrazol-3-yl)-6-(4-(methylamino)piperidin-1-yl)pyrimidin-4-amine |
| 533 | 2-((2-fluoro-4-((2-fluoro-3-nitrobenzyl)sulfonyl)phenyl)thio)-5-methoxy-6-(piperidin-1-yl)-N-(1H-pyrazol-3-yl)pyrimidin-4-amine |
| 534 | 2-((2-fluoro-4-((2-fluoro-3-nitrobenzyl)sulfonyl)phenyl)thio)-5-methoxy-6-morpholino-N-(1H-pyrazol-3-yl)pyrimidin-4-amine |
| 535 | 2-((2-fluoro-4-((2-fluoro-3-nitrobenzyl)sulfonyl)phenyl)thio)-5-methoxy-N-(5-methyl-1H-pyrazol-3-yl)-6-(4-methylpiperazin-1-yl)pyrimidin-4-amine |
| 536 | 2-((2-fluoro-4-((2-fluoro-3-nitrobenzyl)sulfonyl)phenyl)thio)-5-methoxy-N-(5-methyl-1H-pyrazol-3-yl)-6-(piperazin-1-yl)pyrimidin-4-amine |
| 537 | 2-((4-((2-cyclopropylpropan-2-yl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 538 | 6-(4-(2-(dimethylamino)ethyl)piperazin-1-yl)-5-methoxy-N-(5-methyl-1H-pyrazol-3-yl)-2-((4-((2-(pyridin-3-yl)propan-2-yl)sulfonyl)phenyl)thio)pyrimidin-4-amine |
| 539 | 6-(4-(2-(dimethylamino)ethyl)piperazin-1-yl)-5-methoxy-N-(5-methyl-1H-pyrazol-3-yl)-2-4-((42-(thiophen-2-yl)propan-2-yl)sulfonyl)phenyl)thio)pyrimidin-4-amine |
| 540 | 6-(4-aminopiperidin-1-yl)-2-((2-fluoro-4-((2-(2-fluoro-3-nitrophenyl)propan-2-yl)sulfonyl)phenyl)thio)-5-methoxy-N-(5-methyl-1H-pyrazol-3-yl)pyrimidin-4-amine |
| 541 | 1-(5-methyl-6-((5-methyl-1H-pyrazol-3-yl)amino)-2-(p-tolylthio)pyrimidin-4-yl)piperidin-4-ol |
| 542 | 2-((4-aminophenyl)thio)-5-methyl-N-(5-methyl-1H-pyrazol-3-yl)-6-morpholinopyrimidin-4-amine |
| 543 | 2((4-aminophenyl)thio)-$N^4$-isopropyl-$N^4$,5-dimethyl-$N^6$-(5-methyl-1H-pyrazol-3-yl)pyrimidine-4,6-diamine |
| 544 | $N^4$-isopropyl-$N^4$,5-dimethyl-$N^6$-(5-methyl-1H-pyrazol-3-yl)-2-(methylthio)pyrimidine-4,6-diamine |
| 545 | N-(4-((4-((2-hydroxyethyl)(isopropyl)amino)-5-methyl-6-((5-methyl-1H-pyrazol-3-yl)amino)pyrimidin-2-yl)thio)phenyl)acetamide |
| 546 | N-(4-((4-(ethyl(isopropyl)amino)-5-methyl-6-((5-methyl-1H-pyrazol-3-yl)amino)pyrimidin-2-yl)thio)phenyl)acetamide |

TABLE 2-continued

Compound Names for exemplified compounds of formula(I), (II), and (III).
All compounds were confirmed by mass spectro scopy and by $^1$H and $^{13}$C NMR.

| No. | Chemical Name |
|---|---|
| 547 | N-(4-((4-(isopropyl(2-methoxyethyl)amino)-5-methyl-6-((5-methyl-1H-pyrazol-3-yl)amino)pyrimidin-2-yl)thio)phenyl)acetamide |
| 548 | N-(4-((5-chloro-2-(4-hydroxypiperidin-1-yl)-6-((5-methyl-1H-pyrazol-3-yl)amino)pyrimidin-4-yl)thio)phenyl)acetamide |
| 549 | N-(4-((5-chloro-4-(4-hydroxypiperidin-1-yl)-6-((5-methyl-1H-pyrazol-3-yl)amino)pyrimidin-2-yl)thio)phenyl)acetamide |
| 550 | 2-methoxy-1-(4-(5-methyl-6-((5-methyl-1H-pyrazol-3-yl)amino)-2-(p-tolylthio)pyrimidin-4-yl)piperazin-1-yl)ethan-1-one |
| 551 | 5-methyl-N-(5-methyl-1H-pyrazol-3-yl)-6-morpholino-2-(p-tolylthio)pyrimidin-4-amine |
| 552 | N-(4-((4-(4-hydroxypiperidin-1-yl)-5-methoxy-6-((5-methyl-1H-pyrazol-3-yl)amino)pyrimidin-2-yl)thio)phenyl)cyclopropanecarboxamide |
| 553 | N-(4-((4-(4-hydroxypiperidin-1-yl)-5-methyl-6-((5-methyl-1H-pyrazol-3-yl)amino)pyrimidin-2-yl)thio)phenyl)cyclopropanecarboxamide |
| 554 | N-(4-((5-ethoxy-4-(4-hydroxypiperidin-1-yl)-6-((5-methyl-1H-pyrazol-3-yl)amino)pyrimidin-2-yl)thio)phenyl)acetamide |
| 555 | N-(4-((5-methyl-4-((5-methyl-1H-pyrazol-3-yl)amino)-6-(4-(2-morpholinoethyl)piperazin-1-yl)pyrimidin-2-yl)thio)phenyl)acetamide |
| 556 | 2-methoxy-1-(4-(5-methyl-6-((5-methyl-1H-pyrazol-3-yl)amino)-2-(methylthio)pyrimidin-4-yl)piperazin-1-yl)ethan-1-one |
| 557 | 1-(5-ethoxy-6-((5-methyl-1H-pyrazol-3-yl)amino)-2-(methylthio)pyrimidin-4-yl)piperidin-4-ol |
| 558 | 5-ethoxy-N-(5-methyl-1H-pyrazol-3-yl)-2-(methylthio)-6-(piperidin-1-yl)pyrimidin-4-amine |
| 559 | 5-ethoxy-N-(5-methyl-1H-pyrazol-3-yl)-6-(4-methylpiperazin-1-yl)-2-(methylthio)pyrimidin-4-amine |
| 560 | 6-(4-(2-(dimethylamino)ethyl)piperazin-1-yl)-5-ethoxy-N-(5-methyl-1H-pyrazol-3-yl)-2-(methylthio)pyrimidin-4-amine |
| 561 | $N^4$-isopropyl-$N^4$,5-dimethyl-$N^6$-(5-methyl-1H-pyrazol-3-yl)-2-(p-tolylthio)pyrimidine-4,6-diamine |
| 562 | (S)-N-(4-((5-methyl-4-((5-methyl-1H-pyrazol-3-yl)amino)-6-(3-methylmorpholino)pyrimidin-2-yl)thio)phenyl)acetamide |
| 563 | N-(4-((4-(3-hydroxy-8-azabicyclo[3.2.1]octan-8-yl)-5-methoxy-6-((5-methyl-1H-pyrazol-3-yl)amino)pyrimidin-2-yl)thio)phenyl)acetamide |
| 564 | N-(4-((4-(3-hydroxy-8-azabicyclo[3.2.1]octan-8-yl)-5-methyl-6-((5-methyl-1H-pyrazol-3-yl)amino)pyrimidin-2-yl)thio)phenyl)acetamide |
| 565 | N-(4-((4-(4-(2-(dimethylamino)ethoxy)piperidin-1-yl)-5-methyl-6-((5-methyl-1H-pyrazol-3-yl)amino)pyrimidin-2-yl)thio)phenyl)acetamide |
| 566 | N-(4-((4-(4-hydroxy-2-methylpiperidin-1-yl)-5-methyl-6-((5-methyl-1H-pyrazol-3-yl)amino)pyrimidin-2-yl)thio)phenyl)acetamide |
| 567 | N-(4-((5-ethoxy-4-(4-hydroxypiperidin-1-yl)-6-((5-methyl-1H-pyrazol-3-yl)amino)pyrimidin-2-yl)thio)phenyl)cyclopropanecarboxamide |
| 568 | N-(4-((5-methoxy-4-((5-methyl-1H-pyrazol-3-yl)amino)-6-(4-(2-morpholinoethyl)piperazin-1-yl)pyrimidin-2-yl)thio)phenyl)acetamide |
| 569 | N-(4-((5-methyl-4-((5-methyl-1H-pyrazol-3-yl)amino)-6-(4-(2-(piperidin-1-yl)ethyl)piperazin-1-yl)pyrimidin-2-yl)thio)phenyl)acetamide |
| 570 | 2-((4-aminophenyl)thio)-6-(4-(2-(dimethylamino)ethyl)piperazin-1-yl)-5-methoxy-N-(5-methyl-1H-pyrazol-3-yl)pyrimidin-4-amine |
| 571 | 6-(4-(2-(dimethylamino)ethyl)piperazin-1-yl)-5-methoxy-N-(5-methyl-1H-pyrazol-3-yl)-2-(methylthio)pyrimidin-4-amine |
| 572 | 6-(4-(2-(dimethylamino)ethyl)piperazin-1-yl)-5-methoxy-N-(5-methyl-1H-pyrazol-3-yl)-2-(phenylthio)pyrimidin-4-amine |
| 573 | (R)-N-(4-((5-methyl-4-((5-methyl-1H-pyrazol-3-yl)amino)-6-(3-methylmorpholino)pyrimidin-2-yl)thio)phenyl)acetamide |
| 574 | N-(4-((4-(3-hydroxyl)yrrolidin-1-yl)-5-methoxy-6-((5-methyl-1H-pyrazol-3-yl)amino)pyrimidin-2-yl)thio)phenyl)acetamide |
| 575 | N-(4-((4-(4-(2-(dimethylamino)ethoxy)piperidin-1-yl)-5-methoxy-6-((5-methyl-1H-pyrazol-3-yl)amino)pyrimidin-2-yl)thio)phenyl)acetamide |
| 576 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)-2,2,2-trifluoroacetamide |
| 577 | N-(4-((4-(4-(2-acetamidoethyl)piperazin-1-yl)-5-methoxy-6-((5-methyl-1H-pyrazol-3-yl)amino)pyrimidin-2-yl)thio)phenyl)acetamide |
| 578 | N-(4-((4-(4-(3-(dimethylamino)propyl)piperazin-1-yl)-5-methoxy-6-((5-methyl-1H-pyrazol-3-yl)amino)pyrimidin-2-yl)thio)phenyl)acetamide |
| 579 | N-(4-((5-methoxy-4-((5-methyl-1H-pyrazol-3-yl)amino)-6-(4-(2-(methylamino)ethyl)piperazin-1-yl)pyrimidin-2-yl)thio)phenyl)acetamide |
| 580 | N-(4-((5-methoxy-4-((5-methyl-1H-pyrazol-3-yl)amino)-6-(4-(2-(piperidin-1-yl)ethyl)piperazin-1-yl)pyrimidin-2-yl)thio)phenyl)acetamide |
| 581 | 1-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)-3-methylurea |
| 582 | 6-(4-(2-(dimethylamino)ethyl)piperazin-1-yl)-5-methyl-N-(5-methyl-1H-pyrazol-3-yl)-2-(methylthio)pyrimidin-4-amine |
| 583 | (R)-N-(4-((5-methoxy-4-((5-methyl-1H-pyrazol-3-yl)amino)-6-(3-methylmorpholino)pyrimidin-2-yl)thio)phenyl)acetamide |

TABLE 2-continued

Compound Names for exemplified compounds of formula(I), (II), and (III).
All compounds were confirmed by mass spectro scopy and by $^1$H and $^{13}$C NMR.

No. Chemical Name 584 (S)-N-(4-((5-methoxy-4-((5-methyl-1H-pyrazol-3-yl)amino)-6-(3-methylmorpholino)pyrimidin-2-yl)thio)phenyl)acetamide
585 2-(4-(2-((4-ac etamidophenyl)thio)-5-methoxy-6-((5-methyl-1H-pyrazol-3-yl)amino)pyrimidin-4-yl)piperazin-1-yl)-N,N-dimethylacetamide
586 4-(2-((4-acetamidophenyl)thio)-5-methoxy-6-((5-methyl-1H-pyrazol-3-yl)amino)pyrimidin-4-yl)-N,N-dimethylpiperazine-1-carboxamide
587 N-(4-((5-methoxy-4-((5-methyl-1H-pyrazol-3-yl)amino)-6-((1-methylpiperidin-4-yl)amino)pyrimidin-2-yl)thio)phenyl)acetamide
588 N-(4-((5-methoxy-4-((5-methyl-1H-pyrazol-3-yl)amino)-6-(4-(2-morpholinoethyl)piperidin-1-yl)pyrimidin-2-yl)thio)phenyl)acetamide
589 N-(4-((5-methyl-4-((5-methyl-1H-pyrazol-3-yl)amino)-6-((1-methylpiperidin-4-yl)amino)pyrimidin-2-yl)thio)phenyl)acetamide
590 N-(4-((5-methyl-4-((5-methyl-1H-pyrazol-3-yl)amino)-6-(piperidin-4-ylamino)pyrimidin-2-yl)thio)phenyl)acetamide
591 1-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)urea
592 N-(3-((4-(4-(2-(dimethylamino)ethyl)piperazin-1-yl)-5-methoxy-6-((5-methyl-1H-pyrazol-3-yl)amino)pyrimidin-2-yl)thio)phenyl)acetamide
593 N-(3-((5-methoxy-4-((5-methyl-1H-pyrazol-3-yl)amino)-6-morpholinopyrimidin-2-yl)thio)phenyl)acetamide
594 N-(4-((4-((5-methyl-1H-pyrazol-3-yl)amino)-1'-pivaloyl-5,6-dihydrospiro[cyclopenta[d]pyrimidine-7,4'-piperidin]-2-yl)thio)phenyl)acetamide
595 N-(4-((5-methoxy-4-((5-methyl-1H-pyrazol-3-yl)amino)-6-(1,2,3,6-tetrahydropyridin-4-yl)pyrimidin-2-yl)thio)phenyl)acetamide
596 N-(4-((5-methoxy-4-((5-methyl-1H-pyrazol-3-yl)amino)-6-(4-(2-morpholino-2-oxoethyl)piperazin-1-yl)pyrimidin-2-yl)thio)phenyl)acetamide
597 N-(4-((5-methoxy-4-((5-methyl-1H-pyrazol-3-yl)amino)-6-(4-(2-oxo-2-(piperidin-1-yl)ethyl)piperazin-1-yl)pyrimidin-2-yl)thio)phenyl)acetamide
598 N-(4-((5-methoxy-4-((5-methyl-1H-pyrazol-3-yl)amino)-6-(piperidin-4-ylamino)pyrimidin-2-yl)thio)phenyl)acetamide
599 N-(545-methoxy-4-((5-methyl-1H-pyrazol-3-yl)amino)-6-morpholinopyrimidin-2-yl)thio)pyridin-2-yl)acetamide
600 2,2-dimethyl-1-(4-(((5-methyl-1H-pyrazol-3-yl)amino)-2-((4-nitrophenyl)thio)-5,6-dihydrospiro[cyclopenta[d]pyrimidine-7,4'-piperidin]-1'-yl)propan-1-one
601 6-(4-(2-(dimethylamino)ethyl)piperazin-1-yl)-5-methoxy-N-(5-methyl-1H-pyrazol-3-yl)-2-((4-nitrophenyl)thio)pyrimidin-4-amine
602 6-(4-(2-(dimethylamino)ethyl)piperazin-1-yl)-N-(5-ethyl-1H-pyrazol-3-yl)-5-methoxy-2-(methylthio)pyrimidin-4-amine
603 6-(4-(2-(dimethylamino)ethyl)piperazin-1-yl)-N-(5-ethyl-1H-pyrazol-3-yl)-5-methyl-2-(methylthio)pyrimidin-4-amine
604 N-(5-methyl-1H-pyrazol-3-yl)-2-((4-nitrophenyl)thio)-5,6-dihydrospiro[cyclopenta[d]pyrimidine-7,4'-piperidin]-4-amine
605 2-(4-(2-((4-acetamidophenyl)thio)-5-methoxy-6-((5-methyl-1H-pyrazol-3-yl)amino)pyrimidin-4-yl)-3,6-dihydropyridin-1(2H)-yl)-N,N-dimethylacetamide
606 N-(4-((1'-(2-(dimethylamino)ethyl)-4-((5-methyl-1H-pyrazol-3-yl)amino)-5,6-dihydrospiro[cyclopenta[d]pyrimidine-7,4'-piperidin]-2-yl)thio)phenyl)acetamide
607 N-(4-((4-(1-(2-(dimethylamino)ethyl)-1,2,3,6-tetrahydropyridin-4-yl)-5-methoxy-6-((5-methyl-1H-pyrazol-3-yl)amino)pyrimidin-2-yl)thio)phenyl)acetamide
608 N-(4-((4-(4-(2-(diethylamino)ethyl)piperazin-1-yl)-5-methoxy-6-((5-methyl-1H-pyrazol-3-yl)amino)pyrimidin-2-yl)thio)phenyl)acetamide
609 N-(4-((4-(4-(2-(dimethylamino)ethyl)-2-methylpiperazin-1-yl)-6-((5-methyl-1H-pyrazol-3-yl)amino)pyrimidin-2-yl)thio)phenyl)acetamide
610 N-(4-((4-(4-(2-(dimethylamino)ethyl)-3-methylpiperazin-1-yl)-5-methoxy-6-((5-methyl-1H-pyrazol-3-yl)amino)pyrimidin-2-yl)thio)phenyl)acetamide
611 N-(4-((4-(4-(2-(ethyl(methyl)amino)ethyl)piperazin-1-yl)-5-methoxy-6-((5-methyl-1H-pyrazol-3-yl)amino)pyrimidin-2-yl)thio)phenyl)acetamide
612 N-(4-((4-(4-(2-aminoethyl)piperazin-1-yl)-5-methoxy-6-((5-methyl-1H-pyrazol-3-yl)amino)pyrimidin-2-yl)thio)phenyl)acetamide
613 N-(4-((5-methoxy-4-((5-methyl-1H-pyrazol-3-yl)amino)-6-(4-(2-(piperazin-1-yl)ethyl)piperazin-1-yl)pyrimidin-2-yl)thio)phenyl)acetamide
614 N-(4-((5-methoxy-4-((5-methyl-1H-pyrazol-3-yl)amino)-6-(4-(2-(pyrrolidin-1-yl)ethyl)piperazin-1-yl)pyrimidin-2-yl)thio)phenyl)acetamide
615 N-(4-((5-methoxy-4-(1-methyl-1,2,3,6-tetrahydropyridin-4-yl)-6-((5-methyl-1H-pyrazol-3-yl)amino)pyrimidin-2-yl)thio)phenyl)acetamide
616 1'-(2-(dimethylamino)ethyl)-N-(5-methyl-1H-pyrazol-3-yl)-2-((4-nitrophenyl)thio)-5,6-dihydrospiro[cyclopenta[d]pyrimidine-7,4'-piperidin]-4-amine
617 2-((4-aminophenyl)thio)-1'-(2-(dimethylamino)ethyl)-N-(5-methyl-1H-pyrazol-3-yl)-5,6-dihydrospiro[cyclopenta[d]pyrimidine-7,4'-piperidin]-4-amine 2-(1-(2-((4-acetamidophenyl)thio)-5-methoxy-6-((5-methyl-1H-pyrazol-3-yl)amino)pyrimidin-4-yl)piperidin-4-yl)acetic acid
618 2-(3-((6-(4-(2-(dimethylamino)ethyl)piperazin-1-yl)-5-methoxy-2-(methylthio)pyrimidin-4-yl)amino)-1H-pyrazol-5-yl)acetic acid
619 2-(4-(2-((4-acetamidophenyl)thio)-5-methoxy-6-((5-methyl-1H-pyrazol-3-yl)amino)pyrimidin-4-yl)piperazin-1-yl)acetic acid TABLE 2-continued Compound Names for exemplified compounds of formula(I), (II), and (III).
All compounds were confirmed by mass spectro scopy and by $^1$H and $^{13}$C NMR.

No. Chemical Name 620 methyl 2-(1-(2-((4-acetamidophenyl)thio)-5-methoxy-6-((5-methyl-1H-pyrazol-3-yl)amino)pyrimidin-4-yl)piperidin-4-yl)acetate
621 methyl 2-(3-((6-(4-(2-(dimethylamino)ethyl)piperazin-1-yl)-5-methoxy-2-(methylthio)pyrimidin-4-yl)amino)-1H-pyrazol-5-yl)acetate
622 2-(1-(2-((4-acetamidophenyl)thio)-5-methoxy-6-((5-methyl-1H-pyrazol-3-yl)amino)pyrimidin-4-yl)piperidin-4-yl)acetamide
623 2-(3-((6-(4-(2-(dimethylamino)ethyl)piperazin-1-yl)-5-methoxy-2-(methylthio)pyrimidin-4-yl)amino)-1H-pyrazol-5-yl)-N-methylacetamide
624 2-(4-(2-((4-acetamidophenyl)thio)-5-methoxy-6-((5-methyl-1H-pyrazol-3-yl)amino)pyrimidin-4-yl)piperazin-1-yl)acetamide
625 4-(2-((4-acetamidophenyl)thio)-5-methoxy-6-((5-methyl-1H-pyrazol-3-yl)amino)pyrimidin-4-yl)piperazine-1-carboxamide
626 N-(4-((4-(4-(2-(4-hydroxypiperidin-1-yl)ethyl)piperazin-1-yl)-5-methoxy-6-((5-methyl-1H-pyrazol-3-yl)amino)pyrimidin-2-yl)thio)phenyl)acetamide
627 N-(4-((4-(4-( N-hydroxycarbamimidoyl)piperazin-1-yl)-5-methoxy-6-((5-methyl-1H-pyrazol-3-yl)amino)pyrimidin-2-yl)thio)phenyl)acetamide
628 N-(4-((4-(8-(2-(dimethylamino)ethyl)-3,8-diazabicyclo[3.2.1]octan-3-yl)-5-methoxy-6-((5-methyl-1H-pyrazol-3-yl)amino)pyrimidin-2-yl)thio)phenyl)acetamide
629 N-(4-((5-methoxy-4-((5-methyl-1H-pyrazol-3-yl)amino)-6-(4-(2-(4-methylpiperazin-1-yl)ethyl)piperazin-1-yl)pyrimidin-2-yl)thio)phenyl)acetamide
630 N-(4-((5-methoxy-4-((5-methyl-1H-pyrazol-3-yl)amino)-6-(4-(2-(piperidin-1-yl)ethyl)piperidin-1-yl)pyrimidin-2-yl)thio)phenyl)acetamide
631 methyl 2-(4-(2-((4-acetamidophenyl)thio)-5-methoxy-6-((5-methyl-1H-pyrazol-3-yl)amino)pyrimidin-4-yl)piperazin-1-yl)acetate
632 methyl 4-((4-(4-(2-(dimethylamino)ethyl)piperazin-1-yl)-5-methoxy-6-((5-methyl-1H-pyrazol-3-yl)amino)pyrimidin-2-yl)thio)benzoate
633 2-(1-(2-((4-acetamidophenyl)thio)-5-methoxy-6-((5-methyl-1H-pyrazol-3-yl)amino)pyrimidin-4-yl)piperidin-4-yl)-N,N-dimethylacetamide
634 4-((4-(4-(2-(dimethylamino)ethyl)piperazin-1-yl)-5-methoxy-6-((5-methyl-1H-pyrazol-3-yl)amino)pyrimidin-2-yl)thio)-N,N-dimethylbenzamide
635 N-(4-((4-(1-(2-(dimethylamino)ethyl)piperidin-4-yl)-5-methoxy-6-((5-methyl-1H-pyrazol-3-yl)amino)pyrimidin-2-yl)thio)phenyl)acetamide
636 N-(4-((4-(4-(2-(azepan-1-yl)ethyl)piperazin-1-yl)-5-methoxy-6-((5-methyl-1H-pyrazol-3-yl)amino)pyrimidin-2-yl)thio)phenyl)acetamide
637 N-(4-((4-(4-(2-(azocan-1-yl)ethyl)piperazin-1-yl)-5-methoxy-6-((5-methyl-1H-pyrazol-3-yl)amino)pyrimidin-2-yl)thio)phenyl)acetamide
638 N-(4-((4-(4-(2-(dimethylamino)ethyl)-3,5-dimethylpiperazin-1-yl)-5-methoxy-6-((5-methyl-1H-pyrazol-3-yl)amino)pyrimidin-2-yl)thio)phenyl)acetamide
639 N-(4-((4-(4-(2-guanidinoethyl)piperazin-1-yl)-5-methoxy-6-((5-methyl-1H-pyrazol-3-yl)amino)pyrimidin-2-yl)thio)phenyl)acetamide
640 N-(4-((4-(4-carbamimidoylpiperazin-1-yl)-5-methoxy-6-((5-methyl-1H-pyrazol-3-yl)amino)pyrimidin-2-yl)thio)phenyl)acetamide
641 N-(4-((5-methoxy-4-((5-methyl-1H-pyrazol-3-yl)amino)-6-(4-(2-oxo-2-(piperidin-1-yl)ethyl)piperidin-1-yl)pyrimidin-2-yl)thio)phenyl)acetamide
642 N-(4-((5-methoxy-4-((5-methyl-1H-pyrazol-3-yl)amino)-6-(4-(2-ureidoethyl)piperazin-1-yl)pyrimidin-2-yl)thio)phenyl)acetamide
643 N-(4-((5-methoxy-4-((5-methyl-1H-pyrazol-3-yl)amino)-6-(8-(2-(4-methylpiperazin-1-yl)ethyl)-3,8-diazabicyclo[3.2.1]octan-3-yl)-pyrimidin-2-yl)thio)phenyl)acetamide
644 N-(4-((5-methoxy-4-(4-(2-(methoxy(methyl)amino)ethyl)piperazin-1-yl)-6-((5-methyl-1H-pyrazol-3-yl)amino)pyrimidin-2-yl)thio)phenyl)acetamide
645 1-(4-((4-(4-(2-(dimethylamino)ethyl)piperazin-1-yl)-5-methoxy-6-((5-methyl-1H-6-((5 pyrazol-3-yl)amino)pyrimidin-2-yl)thio)phenyl)ethan-1-one
646 2-(3-((6-(4-(2-(dimethylamino)ethyl)piperazin-1-yl)-5-methoxy-2-(methylthio)pyrimidin-4-yl)amino)-1H-pyrazol-5-yl)-N-(3-fluorophenyl)acetamide
647 4-((4-(4-(2-(dimethylamino)ethyl)piperazin-1-yl)-5-methoxy-6-((5-methyl-1H-pyrazol-3-yl)amino)pyrimidin-2-yl)thio)-N-methylbenzamide
648 N-(4-((4-(1-(2-(dimethylamino)ethyl)piperidin-4-yl)-5-methyl-6-((5-methyl-1H-pyrazol-3-yl)amino)pyrimidin-2-yl)thio)phenyl)acetamide
649 N-(4-((4-(4-(2-((1R,5S)-8-azabicyclo[3.2.1]octan-8-yl)ethyl)piperazin-1-yl)-5-methoxy-6-((5-methyl-1H-pyrazol-3-yl)amino)pyrimidin-2-yl)thio)phenyl)acetamide
650 N-(4-((4-(4-(2-(9-azabicyclo[3.3.1]nonan-9-yl)ethyl)piperazin-1-yl)-5-methoxy-6-((5-methyl-1H-pyrazol-3-yl)amino)pyrimidin-2-yl)thio)phenyl)acetamide
651 N-(4-((4-(4-(2-(benzyl(methyl)amino)ethyl)piperazin-1-yl)-5-methoxy-6-((5-methyl-1H-pyrazol-3-yl)amino)pyrimidin-2-yl)thio)phenyl)acetamide
652 N-(4-((4-(4-(2-(dimethylamino)ethyl)-2-methylpiperazin-1-yl)-5-methoxy-6-((5-methyl-1H-pyrazol-3-yl)amino)pyrimidin-2-yl)thio)phenyl)acetamide
653 N-(4-((4-(4-(2-(dimethylamino)ethyl)piperazin-1-yl)-5-methoxy-6-((5-methylthiazol-2-yl)amino)pyrimidin-2-yl)thio)phenyl)acetamide
654 N-(4-((4-(8-(2-(azocan-1-yl)ethyl)-3,8-diazabicyclo[3.2.1]octan-3-yl)-5-methoxy-6-((5-methyl-1H-pyrazol-3-yl)amino)pyrimidin-2-yl)thio)phenyl)acetamide
655 N-(4-((5-methoxy-4-((5-methyl-1H-pyrazol-3-yl)amino)-6-(4-(2-(methylsulfonyl)ethyl)piperazin-1-yl)pyrimidin-2-yl)thio)phenyl)acetamide
656 N-(4-((5-methoxy-4-(4-(2-(methyl(phenyl)amino)ethyl)piperazin-1-yl)-6-((5-methyl-1H-pyrazol-3-yl)amino)pyrimidin-2-yl)thio)phenyl)acetamide TABLE 2-continued Compound Names for exemplified compounds of formula(I), (II), and (III).
All compounds were confirmed by mass spectro scopy and by $^1$H and $^{13}$C NMR.

| No. | Chemical Name |
|---|---|
| 657 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)methanesulfonamide |
| 658 | 5-methoxy-N-(5-methyl-1H-pyrazol-3-yl)-6-(4-(2-(4-methylpiperazin-1-yl)ethyl)piperazin-1-yl)-2-((4-(methylsulfonyl)phenyl)thio)pyrimidin-4-amine |
| 659 | 6-(4-(2-(dimethylamino)ethyl)piperazin-1-yl)-5-methoxy-N-(5-methyl-1H-pyrazol-3-yl)-2-((4-(methylsulfinyl)phenyl)thio)pyrimidin-4-amine |
| 660 | 6-(4-(2-(dimethylamino)ethyl)piperazin-1-yl)-5-methoxy-N-(5-methyl-1H-pyrazol-3-yl)-2-((4-(methylsulfonyl)phenyl)thio)pyrimidin-4-amine |
| 661 | 2-(3-((6-(4-(2-(dimethylamino)ethyl)piperazin-1-yl)-5-methoxy-2-(methylthio)pyrimidin-4-yl)amino)-1H-pyrazol-5-yl)-N-(3-fluorophenyl)acetamide |
| 662 | 4-((4-(4-(2-(dimethylamino)ethyl)piperazin-1-yl)-5-methoxy-6-((5-methyl-1H-pyrazol-3-yl)amino)pyrimidin-2-yl)thio)-N-methylbenzamide |
| 663 | N-(4-((4-(1-(2-(dimethylamino)ethyl)piperidin-4-yl)-5-methyl-6-((5-methyl-1H-pyrazol-3-yl)amino)pyrimidin-2-yl)thio)phenyl)acetamide |
| 664 | N-(4-((4-(4-(2-((1R,5S)-8-azabicyclo[3.2.1]octan-8-yl)ethyl)piperazin-1-yl)-5-methoxy-6-((5-methyl-1H-pyrazol-3-yl)amino)pyrimidin-2-yl)thio)phenyl)acetamide |
| 665 | N-(4-((4-(4-(2-(9-azabicyclo[3.3.1]nonan-9-yl)ethyl)piperazin-1-yl)-5-methoxy-6-((5-methyl-1H-pyrazol-3-yl)amino)pyrimidin-2-yl)thio)phenyl)acetamide |
| 666 | N-(4-((4-(4-(2-(benzyl(methyl)amino)ethyl)piperazin-1-yl)-5-methoxy-6-((5-methyl-1H-pyrazol-3-yl)amino)pyrimidin-2-yl)thio)phenyl)acetamide |
| 667 | N-(4-((4-(4-(2-(dimethylamino)ethyl)-2-methylpiperazin-1-yl)-5-methoxy-6-((5-methyl-1H-pyrazol-3-yl)amino)pyrimidin-2-yl)thio)phenyl)acetamide |
| 668 | N-(4-((4-(4-(2-(dimethylamino)ethyl)piperazin-1-yl)-5-methoxy-6-((5-methylthiazol-2-yl)amino)pyrimidin-2-yl)thio)phenyl)acetamide |
| 669 | N-(4-((4-(8-(2-(azocan-1-yl)ethyl)-3,8-diazabicyclo[3.2.1]octan-3-yl)-5-methoxy-6-((5-methyl-1H-pyrazol-3-yl)amino)pyrimidin-2-yl)thio)phenyl)acetamide |
| 670 | N-(4-((5-methoxy-4-((5-methyl-1H-pyrazol-3-yl)amino)-6-(4-(2-(methylsulfonyl)ethyl)piperazin-1-yl)pyrimidin-2-yl)thio)phenyl)acetamide |
| 671 | N-(4-((5-methoxy-4-(4-(2-(methyl(phenyl)amino)ethyl)piperazin-1-yl)-6-((5-methyl-1H-pyrazol-3-yl)amino)pyrimidin-2-yl)thio)phenyl)acetamide |
| 672 | N-(4-((4-(4-(2-(dimethylamino)ethyl)piperazin-1-yl)-5-methoxy-6-((5-methyl-1H-pyrazol-3-yl)amino)pyrimidin-2-yl)thio)phenyl)methanesulfonamide |
| 673 | 5-methoxy-N-(5-methyl-1H-pyrazol-3-yl)-6-(4-(2-(4-methylpiperazin-1-yl)ethyl)piperazin-1-yl)-2-((4-(methylsulfonyl)phenyl)thio)pyrimidin-4-amine |
| 674 | 6-(4-(2-(dimethylamino)ethyl)piperazin-1-yl)-5-methoxy-N-(5-methyl-1H-pyrazol-3-yl)-2-((4-(methylsulfinyl)phenyl)thio)pyrimidin-4-amine |
| 675 | 6-(4-(2-(dimethylamino)ethyl)piperazin-1-yl)-5-methoxy-N-(5-methyl-1H-pyrazol-3-yl)-2-((4-(methylsulfonyl)phenyl)thio)pyrimidin-4-amine |
| 676 | 2-((4-((2-chlorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 677 | 2-((4-((3-chlorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 678 | 2-((4-((4-chlorobenzyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |
| 679 | 2-((4-(benzylsulfonyl)phenyl)thio)-5-methoxy-N-(5-methyl-1H-pyrazol-3-yl)-6-(4-methylpiperazin-1-yl)pyrimidin-4-amine |
| 680 | 2-((4-(benzylsulfonyl)phenyl)thio)-6-(4-(2-(dimethylamino)ethyl)piperidin-1-yl)-5-methoxy-N-(5-methyl-1H-pyrazol-3-yl)pyrimidin-4-amine |
| 681 | 2-((4-(ethylsulfonyl)phenyl)thio)-5-methoxy-N-(5-methyl-1H-pyrazol-3-yl)-6-(4-(2-(4-methylpiperazin-1-yl)ethyl)piperazin-1-yl)pyrimidin-4-amine |
| 682 | 2-((4-(ethylsulfonyl)phenyl)thio)-5-methoxy-N-(5-methyl-1H-pyrazol-3-yl)-6-(4-methylpiperazin-1-yl)pyrimidin-4-amine |
| 683 | 2-((4-(ethylsulfonyl)phenyl)thio)-5-methoxy-N-(5-methyl-1H-pyrazol-3-yl)-6-(piperazin-1-yl)pyrimidin-4-amine |
| 684 | 6-(4-(2-(9-azabicyclo[3.3.1]nonan-9-yl)ethyl)piperazin-1-yl)-2-((4-(benzylsulfonyl)phenyl)thio)-5-methoxy-N-(5-methyl-1H-pyrazol-3-yl)pyrimidin-4-amine |
| 685 | 6-(4-(2-(dimethylamino)ethyl)piperazin-1-yl)-2-((4-((4-fluorobenzyl)sulfonyl)phenyl)thio)-5-methoxy-N-(5-methyl-1H-pyrazol-3-yl)pyrimidin-4-amine |
| 686 | 6-(4-(2-(dimethylamino)ethyl)piperazin-1-yl)-2-((4-(isopropylsulfonyl)phenyl)thio)-5-methoxy-N-(5-methyl-1H-pyrazol-3-yl)pyrimidin-4-amine |
| 687 | 6-(4-(2-(dimethylamino)ethyl)piperazin-1-yl)-5-methoxy-2-((4-((4-methoxybenzyl)sulfonyl)phenyl)thio)-N-(5-methyl-1H-pyrazol-3-yl)pyrimidin-4-amine |
| 688 | 6-(4-(2-(dimethylamino)ethyl)piperazin-1-yl)-5-methoxy-N-(5-methyl-1H-pyrazol-3-yl)-2-((4-((pyridin-3-ylmethyl)sulfonyl)phenyl)thio)pyrimidin-4-amine |
| 689 | 6-(4-(2-(dimethylamino)ethyl)piperazin-1-yl)-5-methoxy-N-(5-methyl-1H-pyrazol-3-yl)-2-((4-((pyridin-4-ylmethyl)sulfonyl)phenyl)thio)pyrimidin-4-amine |
| 690 | 6-(4-(2-(dimethylamino)ethyl)piperazin-1-yl)-5-methoxy-N-(5-methyl-1H-pyrazol-3-yl)-2-((4-((thiophen-2-ylmethyl)sulfonyl)phenyl)thio)pyrimidin-4-amine |
| 691 | 6-(4-(2-(dimethylamino)ethyl)piperidin-1-yl)-5-methoxy-N-(5-methyl-1H-pyrazol-3-yl)-2-((4-(methylsulfonyl)phenyl)thio)pyrimidin-4-amine |
| 692 | 2-((4-(((1H-imidazol-2-yl)methyl)sulfonyl)phenyl)thio)-6-(4-(2-(dimethylamino)ethyl)piperazin-1-yl)-5-methoxy-N-(5-methyl-1H-pyrazol-3-yl)pyrimidin-4-amine |

TABLE 2-continued

Compound Names for exemplified compounds of formula(I), (II), and (III).
All compounds were confirmed by mass spectro scopy and by $^1$H and $^{13}$C NMR.

No. Chemical Name 693 2-((4-(benzylsulfonyl)phenyl)thio)-5-methoxy-6-methyl-N-(5-methyl-1H-pyrazol-3-yl)pyrimidin-4-amine
694 2-((4-(benzylsulfonyl)phenyl)thio)-5-methoxy-N-(5-methyl-1H-pyrazol-3-yl)-6-(4-(2-(4-methylpiperazin-1-yl)ethyl)piperazin-1-yl)pyrimidin-4-amine
695 2-((4-(benzylsulfonyl)phenyl)thio)-5-methoxy-N-(5-methyl-1H-pyrazol-3-yl)-6-(piperidin-1-yl)pyrimidin-4-amine
696 2-((4-(benzylsulfonyl)phenyl)thio)-5-methoxy-N-(5-methyl-1H-pyrazol-3-yl)-6-morpholinopyrimidin-4-amine
697 2-((4-(benzylsulfonyl)phenyl)thio)-5-methoxy-$N^4$,$N^4$-dimethyl-$N^6$-(5-methyl-1H-pyrazol-3-yl)pyrimidine-4,6-diamine
698 2-((4-(benzylsulfonyl)phenyl)thio)-6-(1-(2-(dimethylamino)ethyl)piperidin-4-yl)-5-methoxy-N-(5-methyl-1H-pyrazol-3-yl)pyrimidin-4-amine
699 2-((4-(benzylsulfonyl)phenyl)thio)-6-(4-(2-(dimethylamino)ethyl)piperazin-1-yl)-5-ethoxy-N-(5-methyl-1H-pyrazol-3-yl)pyrimidin-4-amine
700 2-((4-(ethylsulfonyl)phenyl)thio)-5-methoxy-6-methyl-N-(5-methyl-1H-pyrazol-3-yl)pyrimidin-4-amine The compounds described herein, including the compounds in Table 1 and Table 2, may be synthesized by methods known in the art. In embodiments, the compounds described herein, including the compounds in Table 1 and Table 2, are synthesized by the methods set forth in WO 2016/166604 published on 20 Oct. 2016, the disclosure of which is incorporated by reference herein in its entirety.

Pharmaceutical Compositions

Provided herein are pharmaceutical compositions of the compounds described herein. In one aspect is a pharmaceutical composition that includes a pharmaceutically acceptable excipient and a compound (e.g. formula (I), (II) (including the first or second aspect), (III), or a compound of Table 1 or Table 2) as described herein. The compound may be a compound having the formula (I) as described herein. The compound may be a compound having the formula (II) (including the first or second aspect) as described herein. The compound may be a compound having the formula (III) as described herein. The compound may be a compound set forth in Table 1. The compound may be a compound set forth in Table 2.

The pharmaceutical composition may include a second agent in a therapeutically effective amount. The pharmaceutical composition may include a second agent where the second agent treats cancer. The second agent may be an anti-cancer agent as described herein.

Formulations

The pharmaceutical composition may be prepared and administered in a wide variety of dosage formulations. Compounds described herein (e.g. formula (I), (II) (including the first or second aspect), (III) or a compound of Table 1 or Table 2) may be administered orally, rectally, or by injection (e.g. intravenously, intramuscularly, intracutaneously, subcutaneously, intraduodenally, or intraperitoneally).

For preparing pharmaceutical compositions from compounds having formula (I), (II) (including the first or second aspect), (III) or a compound of Table 1 or Table 2, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired. The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Methods of Treating Cancer

The disclosure provides methods of treating cancer in a subject in need thereof, the method comprising administering to the subject an effective amount of a PLK4 inhibitor to treat the cancer; wherein the subject has an elevated level of TRIM37, Chromogranin A, and/or Synaptophysin. In embodiments, the subject has an elevated level of TRIM37. In embodiments, the subject has an elevated level of Chromogranin A. In embodiments, the subject has an elevated level of Synaptophysin. In embodiments, the subject has an elevated level of TRIM37 and an elevated level of Chromogranin A. In embodiments, the subject has an elevated level of TRIM37 and an elevated level of Synaptophysin. In embodiments, the subject has an elevated level of Chromogranin A and an elevated level of Synaptophysin. In embodiments, the subject has an elevated level of TRIM37, an elevated level of Chromogranin A, and an elevated level of Synaptophysin level. In embodiments, the subject has an elevated level of TRIM37, Chromogranin A, and/or Synaptophysin, when compared to a control. In embodiments, the subject has an elevated level of TRIM37 when compared to a control. In embodiments, the subject has an elevated level of Chromogranin A when compared to a control. In embodiments, the subject has an elevated level of Synaptophysin when compared to a control. In embodiments, the subject has an elevated level of TRIM37 and an elevated level of Chromogranin A when compared to a control. In embodiments, the subject has an elevated level of TRIM37 and an elevated level of Synaptophysin when compared to a control. In embodiments, the subject has an elevated level of Chromogranin A and an elevated level of Synaptophysin when compared to a control. In embodiments, the subject has an elevated level of TRIM37, an elevated level of Chromogranin A, and an elevated level of Synaptophysin level when compared to a control. In embodiments, the methods are for treating a cancer tumor. In embodiments, the PLK4 inhibitor is compound of Formula (Ia), a compound of Formula (Ib), a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the cancer is a cancer tumor, such as a primary tumor or a metastatic cancer tumor. In embodiments, the cancer is a pediatric cancer. In embodiments, the pediatric cancer is a rhabdoid tumor, a neuroblastoma, an acute lymphoblastic leukemia tumor, or a brain and central nervous system tumor. In embodiments, the cancer is a neural crest-derived cancer. In embodiments, the neural crest-derived tumor is a small cell lung cancer, a melanoma, or a breast cancer. In embodiments, the cancer is neuroblastoma. In embodiments, the cancer is acute myeloid leukemia, prostate cancer, glioma, mesothelioma, osteosarcoma, breast cancer, Ewing's sarcoma, soft tissue cancer, or T cell lymphoma. In embodiments, the T cell lymphoma is extranodal T cell lymphoma, cutaneous T cell lymphoma, anaplastic large cell lymphoma, or angioimmunoblastic T cell lymphoma. In embodiments, the cancer is a rhabdoid tumor, basal cell carcinoma, small cell lung cancer, endometrial cancer, non-small cell lung cancer, ovarian cancer, thyroid cancer, kidney cancer, Hodgkin's lymphoma, stomach cancer, liver cancer, Burkitt lymphoma, giant cell tumor of bone, medulloblastoma, a urinary tract cancer, meningioma, bile duct cancer, melanoma, esophageal cancer, upper aerodigestive cancer, colorectal cancer, chondrosarcoma, multiple myeloma, B cell lymphoma, leukemia, diffuse large B cell lymphoma, or chronic myeloid leukemia. In embodiments, the cancer is a p53 positive cancer, including a wild type p53 positive cancer or a mutant p53 positive cancer. In embodiments, the methods further comprising administering a chemotherapeutic agent, radiation therapy, or a combination thereof. In aspects, the chemotherapeutic agent comprises a tubule polymerization inhibitor, such as vincristine, vinblastine, vinorelbine, vinfluine, a dolastatin, a halichondrin, a hemiasterline, cryptophysin 52, or a combination of two or more thereof. In aspects the chemotherapeutic agent comprises cyclophosphamide, ifosfamide, cisplatin, carboplatin, vincristine, doxorubicin, etoposide, topotecan, busulfan, melphalan, or a combination of two or more thereof. In aspects, the chemotherapeutic agent comprises differentiation therapy, wherein the chemotherapeutic agent is retinoic acid (e.g., all-trans-retinoic acid, 13-cis-retinoic acid), arsenic trioxide, or a combination thereof.

The disclosure provides methods of treating a p53 positive cancer in a subject in need thereof, the method comprising administering to the subject an effective amount of a PLK4 inhibitor to treat the p53 positive cancer. In embodiments, the methods comprise treating a wild type p53 positive cancer in a subject in need thereof comprising administering to the subject an effective amount of a PLK4 inhibitor to treat the wild type p53 positive cancer. In embodiments, the methods comprise treating a mutant p53 positive cancer in a subject in need thereof comprising administering to the subject an effective amount of a PLK4 inhibitor to treat the mutant p53 positive cancer. In embodiments, the subject has an elevated level of TRIM37, Chromogranin A, and/or Synaptophysin, when compared to a control. In embodiments, the subject has an elevated level of TRIM37 when compared to a control. In embodiments, the subject has an elevated level of Chromogranin A when compared to a control. In embodiments, the subject has an elevated level of Synaptophysin when compared to a control. In embodiments, the subject has an elevated level of TRIM37 and an elevated level of Chromogranin A when compared to a control. In embodiments, the subject has an elevated level of TRIM37 and an elevated level of Synaptophysin when compared to a control. In embodiments, the subject has an elevated level of Chromogranin A and an elevated level of Synaptophysin when compared to a control. In embodiments, the subject has an elevated level of TRIM37, an elevated level of Chromogranin A, and an elevated level of Synaptophysin level when compared to a control. In embodiments, the methods are for treating a cancer tumor. In embodiments, the PLK4 inhibitor is compound of Formula (Ia), a compound of Formula (Ib), a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the cancer is a cancer tumor, such as a primary tumor or a metastatic cancer tumor. In embodiments, the cancer is a pediatric cancer. In embodiments, the pediatric cancer is a rhabdoid tumor, a neuroblastoma, an acute lymphoblastic leukemia tumor, or a brain and central nervous system tumor. In embodiments, the cancer is a neural crest-derived cancer. In embodiments, the neural crest-derived tumor is a small cell lung cancer, a melanoma, or a breast cancer. In embodiments, the cancer is neuroblastoma. In embodiments, the cancer is acute myeloid leukemia, prostate cancer, glioma, mesothelioma, osteosarcoma, breast cancer, Ewing's sarcoma, soft tissue cancer, or T cell lymphoma. In embodiments, the T cell lymphoma is extranodal T cell lymphoma, cutaneous T cell lymphoma, anaplastic large cell lymphoma, or angioimmunoblastic T cell lymphoma. In embodiments, the cancer is a rhabdoid tumor, basal cell carcinoma, small cell lung cancer, endometrial cancer, non-small cell lung cancer, ovarian cancer, thyroid cancer, kidney cancer, Hodgkin's lymphoma, stomach cancer, liver cancer, Burkitt lymphoma, giant cell tumor of bone, medulloblastoma, a urinary tract cancer, meningioma, bile duct cancer, melanoma, esophageal cancer, upper aerodigestive cancer, colorectal cancer, chondrosarcoma, multiple myeloma, B cell lymphoma, leukemia, diffuse large B cell lymphoma, or chronic myeloid leukemia. In embodiments, the methods further comprising administering a chemotherapeutic agent, radiation therapy, or a combination thereof. In aspects, the chemotherapeutic agent comprises a tubule polymerization inhibitor, such as vincristine, vinblastine, vinorelbine, vinfluine, a dolastatin, a halichondrin, a hemiasterline, cryptophysin 52, or a combination of two or more thereof. In aspects the chemotherapeutic agent comprises cyclophosphamide, ifosfamide, cisplatin, carboplatin, vincristine, doxorubicin, etoposide, topotecan, busulfan, melphalan, or a combination of two or more thereof. In aspects, the chemotherapeutic agent comprises differentiation therapy, wherein the chemotherapeutic agent is retinoic acid (e.g., all-trans-retinoic acid, 13-cis-retinoic acid), arsenic trioxide, or a combination thereof.

The disclosure provides methods of treating neuroblastoma in a subject in need thereof, the method comprising administering to the subject an effective amount of a PLK4 inhibitor to treat the neuroblastoma; wherein the subject has an elevated level of TRIM37, Chromogranin A, and/or Synaptophysin. The disclosure provides methods of treating a wild type or mutant p53 positive neuroblastoma in a subject in need thereof, the method comprising administering to the subject an effective amount of a PLK4 inhibitor to treat the wild type or mutant p53 positive neuroblastoma. The disclosure provides methods of treating a wild type or mutant p53 positive neuroblastoma in a subject in need thereof, the method comprising administering to the subject an effective amount of a PLK4 inhibitor to treat the wild type or mutant p53 positive neuroblastoma; wherein the subject has an elevated level of TRIM37, Chromogranin A, and/or Synaptophysin. In embodiments, the subject has an elevated level of TRIM37. In embodiments, the subject has an elevated level of Chromogranin A. In embodiments, the subject has an elevated level of Synaptophysin. In embodiments, the subject has an elevated level of TRIM37 and an elevated level of Chromogranin A. In embodiments, the subject has an elevated level of TRIM37 and an elevated level of Synaptophysin. In embodiments, the subject has an elevated level of Chromogranin A and an elevated level of Synaptophysin. In embodiments, the subject has an elevated level of TRIM37, an elevated level of Chromogranin A, and an elevated level of Synaptophysin level. In embodiments, the subject has an elevated level of TRIM37, Chromogranin A, and/or Synaptophysin when compared to a control. In embodiments, the subject has an elevated level of TRIM37 when compared to a control. In embodiments, the subject has an elevated level of Chromogranin A when compared to a control. In embodiments, the subject has an elevated level of Synaptophysin when compared to a control. In embodiments, the subject has an elevated level of TRIM37 and an elevated level of Chromogranin A when compared to a control. In embodiments, the subject has an elevated level of TRIM37 and an elevated level of Synaptophysin when compared to a control. In embodiments, the subject has an elevated level of Chromogranin A and an elevated level of Synaptophysin when compared to a control. In embodiments, the subject has an elevated level of TRIM37, an elevated level of Chromogranin A, and an elevated level of Synaptophysin level when compared to a control. In embodiments, the PLK4 inhibitor is compound of Formula (Ia), a compound of Formula (Ib), a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the subject is a human. In embodiments, the methods further comprising administering a chemotherapeutic agent, radiation therapy, or a combination thereof. In aspects, the chemotherapeutic agent comprises a tubule polymerization inhibitor, such as vincristine, vinblastine, vinorelbine, vinfluine, a dolastatin, a halichondrin, a hemiasterline, cryptophysin 52, or a combination of two or more thereof. In aspects the chemotherapeutic agent comprises cyclophosphamide, ifosfamide, cisplatin, carboplatin, vincristine, doxorubicin, etoposide, topotecan, busulfan, melphalan, or a combination of two or more thereof. In aspects, the chemotherapeutic agent comprises differentiation therapy, wherein the chemotherapeutic agent is retinoic acid (e.g., all-trans-retinoic acid, 13-cis-retinoic acid), arsenic trioxide, or a combination thereof.

The disclosure provides methods of treating small cell lung cancer, neuroblastoma, prostate cancer, glioma, mesothelioma, osteosarcoma, breast cancer, Ewing's sarcoma, soft tissue cancer, or T-Cell lymphoma in a subject in need thereof comprising administering to the subject an effective amount of a PLK4 inhibitor; wherein the subject has an elevated level of TRIM37, Chromogranin A, and/or Synaptophysin. The disclosure provides methods of treating a wild type or mutant p53 positive small cell lung cancer, a wild type or mutant p53 positive neuroblastoma, a wild type or mutant p53 positive prostate cancer, a wild type or mutant p53 positive glioma, a wild type or mutant p53 positive mesothelioma, a wild type or mutant p53 positive osteosarcoma, a wild type or mutant p53 positive breast cancer, a wild type or mutant p53 positive Ewing's sarcoma, a wild type or mutant p53 positive soft tissue cancer, or a wild type or mutant p53 positive T-Cell lymphoma in a subject in need thereof comprising administering to the subject an effective amount of a PLK4 inhibitor. The disclosure provides methods of treating a wild type or mutant p53 positive small cell lung cancer, a wild type or mutant p53 positive neuroblastoma, a wild type or mutant p53 positive prostate cancer, a wild type or mutant p53 positive glioma, a wild type or mutant p53 positive mesothelioma, a wild type or mutant p53 positive osteosarcoma, a wild type or mutant p53 positive breast cancer, a wild type or mutant p53 positive Ewing's sarcoma, a wild type or mutant p53 positive soft tissue cancer, or a wild type or mutant p53 positive T-Cell lymphoma in a subject in need thereof comprising administering to the subject an effective amount of a PLK4 inhibitor; wherein the subject has an elevated level of TRIM37, Chromogranin A, and/or Synaptophysin. In embodiments, the subject has an elevated level of TRIM37. In embodiments, the subject has an elevated level of Chromogranin A. In embodiments, the subject has an elevated level of Synaptophysin. In embodiments, the subject has an elevated level of TRIM37 and an elevated level of Chromogranin A. In embodiments, the subject has an elevated level of TRIM37 and an elevated level of Synaptophysin. In embodiments, the subject has an elevated level of Chromogranin A and an elevated level of Synaptophysin. In embodiments, the subject has an elevated level of TRIM37, an elevated level of Chromogranin A, and an elevated level of Synaptophysin level. In embodiments, the subject has an elevated level of TRIM37, Chromogranin A, and/or Synaptophysin, when compared to a control. In embodiments, the subject has an elevated level of TRIM37 when compared to a control. In embodiments, the subject has an elevated level of Chromogranin A when compared to a control. In embodiments, the subject has an elevated level of Synaptophysin when compared to a control. In embodiments, the subject has an elevated level of TRIM37 and an elevated level of Chromogranin A when compared to a control. In embodiments, the subject has an elevated level of TRIM37 and an elevated level of Synaptophysin when compared to a control. In embodiments, the subject has an elevated level of Chromogranin A and an elevated level of Synaptophysin when compared to a control. In embodiments, the subject has an elevated level of TRIM37, an elevated level of Chromogranin A, and an elevated level of Synaptophysin level when compared to a control. In embodiments, the PLK4 inhibitor is compound of Formula (Ia), a compound of Formula (Ib), a 5 compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the cancer is a primary cancer. In embodiments, the cancer is metastatic cancer. In aspects, the methods comprise treating small cell lung cancer, a wild type p53 positive small cell lung cancer, or a mutant p53 positive small cell lung cancer. In aspects, the methods comprise treating neuroblastoma, a wild type p53 positive neuroblastoma, or a mutant p53 positive neuroblastoma. In aspects, the methods comprise treating prostate cancer, a wild type p53 positive prostate cancer, or a mutant p53 positive prostate cancer. In aspects, the methods comprise treating glioma, a wild type p53 positive glioma, or a mutant p53 positive glioma. In aspects, the methods comprise treating mesothelioma, a wild type p53 positive mesothelioma, or a mutant p53 positive mesothelioma. In aspects, the methods comprise treating osteosarcoma, a wild type p53 positive osteosarcoma, or a mutant p53 positive osteosarcoma. In aspects, the methods comprise treating breast cancer, a wild type p53 positive breast cancer, or a mutant p53 positive breast cancer. In aspects, the methods comprise treating Ewing's sarcoma, a wild type p53 positive Ewing's sarcoma, or a mutant p53 positive Ewing's sarcoma. In aspects, the methods comprise treating soft tissue cancer, a wild type p53 positive soft tissue cancer, or a mutant p53 positive soft tissue cancer. In aspects, the methods comprise treating T cell lymphoma, a wild type p53 positive T cell lymphoma, or a mutant p53 positive T cell lymphoma. In aspects, the T cell lymphoma is extranodal T cell lymphoma. In aspects, the T cell lymphoma is cutaneous T cell lymphoma. In aspects, the T cell lymphoma is anaplastic large cell lymphoma. In aspects, the T cell lymphoma is angioimmunoblastic T cell lymphoma. In embodiments, the methods further comprising administering a chemotherapeutic agent, radiation therapy, or a combination thereof. In aspects, the chemotherapeutic agent comprises a tubule polymerization inhibitor, such as vincristine, vinblastine, vinorelbine, vinfluine, a dolastatin, a halichondrin, a hemiasterline, cryptophysin 52, or a combination of two or more thereof. In aspects the chemotherapeutic agent comprises cyclophosphamide, ifosfamide, cisplatin, carboplatin, vincristine, doxorubicin, etoposide, topotecan, busulfan, melphalan, or a combination of two or more thereof. In aspects, the chemotherapeutic agent comprises differentiation therapy, wherein the chemotherapeutic agent is retinoic acid (e.g., all-trans-retinoic acid, 13-cis-retinoic acid), arsenic trioxide, or a combination thereof.

The disclosure provides methods of treating a pediatric cancer or a neural crest-derived caner in a subject in need thereof comprising administering to the subject an effective amount of a PLK4 inhibitor; wherein the subject has an elevated level of TRIM37, Chromogranin A, and/or Synaptophysin. The disclosure provides methods of treating a wild type or mutant a pediatric cancer or a wild-type or mutant neural crest-derived caner in a subject in need thereof comprising administering to the subject an effective amount of a PLK4 inhibitor. The disclosure provides methods of treating a wild type or mutant a pediatric cancer or a wild-type or mutant neural crest-derived caner in a subject in need thereof comprising administering to the subject an effective amount of a PLK4 inhibitor; wherein the subject has an elevated level of TRIM37, Chromogranin A, and/or Synaptophysin. In embodiments, the subject has an elevated level of TRIM37. In embodiments, the subject has an elevated level of Chromogranin A. In embodiments, the subject has an elevated level of Synaptophysin. In embodiments, the subject has an elevated level of TRIM37 and an elevated level of Chromogranin A. In embodiments, the subject has an elevated level of TRIM37 and an elevated level of Synaptophysin. In embodiments, the subject has an elevated level of Chromogranin A and an elevated level of Synaptophysin. In embodiments, the subject has an elevated level of TRIM37, an elevated level of Chromogranin A, and an elevated level of Synaptophysin level. In embodiments, the subject has an elevated level of TRIM37, Chromogranin A, and/or Synaptophysin, when compared to a control. In embodiments, the subject has an elevated level of TRIM37 when compared to a control. In embodiments, the subject has an elevated level of Chromogranin A when compared to a control. In embodiments, the subject has an elevated level of Synaptophysin when compared to a control. In embodiments, the subject has an elevated level of TRIM37 and an elevated level of Chromogranin A when compared to a control. In embodiments, the subject has an elevated level of TRIM37 and an elevated level of Synaptophysin when compared to a control. In embodiments, the subject has an elevated level of Chromogranin A and an elevated level of Synaptophysin when compared to a control. In embodiments, the subject has an elevated level of TRIM37, an elevated level of Chromogranin A, and an elevated level of Synaptophysin level when compared to a control. In embodiments, the PLK4 inhibitor is compound of Formula (Ia), a compound of Formula (Ib), a compound of Formula (Ia1), a compound of Formula (Ia2), a 5 compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the cancer is a primary cancer. In embodiments, the cancer is metastatic cancer. In aspects, the methods comprise treating pediatric cancer, a wild type p53 positive pediatric cancer, or a mutant p53 positive pediatric cancer. In embodiments, the pediatric cancer is a rhabdoid tumor, a neuroblastoma, an acute lymphoblastic leukemia tumor, or a brain and central nervous system tumor. In aspects, the methods comprise treating neural crest-derived cancer, a wild type p53 positive neural crest-derived cancer, or a mutant p53 positive neural crest-derived cancer. In embodiments, the neural crest-derived tumor is a small cell lung cancer, a melanoma, or a breast cancer. In embodiments, the methods further comprising administering a chemotherapeutic agent, radiation therapy, or a combination thereof. In aspects, the chemotherapeutic agent comprises a tubule polymerization inhibitor, such as vincristine, vinblastine, vinorelbine, vinfluine, a dolastatin, a halichondrin, a hemiasterline, cryptophysin 52, or a combination of two or more thereof. In aspects, the chemotherapeutic agent comprises cyclophosphamide, ifosfamide, cisplatin, carboplatin, vincristine, doxorubicin, etoposide, topotecan, busulfan, melphalan, or a combination of two or more thereof. In aspects, the chemotherapeutic agent comprises differentiation therapy, wherein the chemotherapeutic agent is retinoic acid (e.g., all-trans-retinoic acid, 13-cis-retinoic acid), arsenic trioxide, or a combination thereof.

The disclosure provides methods of treating cancer in a subject in need thereof, the method comprising: (i) measuring a TRIM37 level, Chromogranin A level and/or Synaptophysin level in a biological sample obtained from the subject; and (ii) administering an effective amount of a PLK4 inhibitor to the subject to treat the cancer. In embodiments, the methods comprise measuring: (i) the gene level, (ii) the mRNA level, (iii) the protein level, or (iv) a combination of two or more of the gene, mRNA, and protein levels of: (a) TRIM37, (b) Chromogranin A, (c) Synaptophysin, or (d) a combination of two or more of TRIM37, Chromogranin A, and Synaptophysin. In embodiments, the methods comprise measuring a TRIM37 gene level in the biological sample. In embodiments, the methods comprise measuring a TRIM37 mRNA level in the biological sample. In embodiments, the methods comprise measuring a TRIM37 protein level in the biological sample. In embodiments, the methods comprise measuring a Chromogranin A gene level in the biological sample. In embodiments, the methods comprise measuring a Chromogranin A mRNA level in the biological sample. In embodiments, the methods comprise measuring a Chromogranin A protein level in the biological sample. In embodiments, the methods comprise measuring a Synaptophysin gene level in the biological sample. In embodiments, the methods comprise measuring a Synaptophysin mRNA level in the biological sample. In embodiments, the methods comprise measuring a Synaptophysin protein level in the biological sample. In embodiments, the subject has an elevated TRIM37 level. In embodiments, the subject has an elevated Chromogranin A level. In embodiments, the subject has an elevated Synaptophysin level. In embodiments, the subject has an elevated TRIM37 level and an elevated Chromogranin A level. In embodiments, the subject has an elevated TRIM37 level and an elevated Synaptophysin level. In embodiments, the subject has an elevated Chromogranin A level and an elevated Synaptophysin level. In embodiments, the subject has an elevated TRIM37 level, an elevated Chromogranin A level, and an elevated Synaptophysin level. In embodiments, the subject has an elevated TRIM37 level when compared to a control. In embodiments, the subject has an elevated Chromogranin A level when compared to a control. In embodiments, the subject has an elevated Synaptophysin level when compared to a control. In embodiments, the subject has an elevated TRIM37 level and an elevated Chromogranin A level when compared to a control. In embodiments, the subject has an elevated TRIM37 level and an elevated Synaptophysin level when compared to a control. In embodiments, the subject has an elevated Chromogranin A level and an elevated Synaptophysin level when compared to a control. In embodiments, the subject has an elevated TRIM37 level, an elevated Chromogranin A level, and an elevated Synaptophysin level when compared to a control. In embodiments, the subject has a wild type or mutant p53 positive cancer. In embodiments, the biological sample is a plasma sample. In embodiments, the biological sample is a serum sample. In embodiments, the biological sample is a tissue sample. In embodiments, the biological sample is a cell sample. In embodiments, the biological sample is a blood sample. In embodiments, the biological sample is a peripheral blood sample. In embodiments, the biological sample is a tumor sample. In embodiments, the biological sample is a primary tumor sample. In embodiments, the biological sample is a metastatic tumor sample. In embodiments, the biological sample is a resected tumor sample. In embodiments, the biological sample is a tumor biopsy sample. In embodiments, the biological sample is a resected primary tumor sample. In embodiments, the biological sample is a resected metastatic tumor sample. In embodiments, the biological sample is a primary tumor biopsy sample. In embodiments, the biological sample is a metastatic tumor biopsy sample. In embodiments, the PLK4 inhibitor is compound of Formula (Ia), a compound of Formula (Ib), a compound of Formula (Ia1), a compound of Formula (Ia2), a compound of 10 Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the cancer is a cancer tumor. In embodiments, the cancer tumor is a primary cancer tumor. In embodiments, the cancer tumor is a metastatic cancer tumor.

Methods to Identify and Select Subjects

The disclosure provides methods to identify a subject responsive to a PLK4 inhibitor, the method comprising: (i) obtaining a biological sample from the subject; and (ii) measuring a TRIM37 level, a Chromogranin A level, and/or a Synaptophysin level in the biological sample; wherein if the TRIM37 level, the Chromogranin A level, and/or the Synaptophysin level is elevated the subject is identified as responsive to the PLK4 inhibitor. The disclosure provides methods to identify a subject responsive to a PLK4 inhibitor, the method comprising: (i) obtaining a biological sample from the subject; (ii) measuring a TRIM37 level, a Chromogranin A level, and/or a Synaptophysin level in the biological sample; (iii) analyzing the biological sample for p53; wherein if the subject has an elevated TRIM37 level a Chromogranin A level, and/or a Synaptophysin level and is p53 positive, the subject is identified as responsive to the PLK4 inhibitor. In embodiments, the methods comprise measuring: (i) the gene level, (ii) the mRNA level, (iii) the protein level, or (iv) a combination of two or more of the gene, mRNA, and protein levels of: (a) TRIM37, (b) Chromogranin A, (c) Synaptophysin, or (d) a combination of two or more of TRIM37, Chromogranin A, and Synaptophysin. In embodiments, the methods comprise measuring a TRIM37 gene level in the biological sample. In embodiments, the methods comprise measuring a TRIM37 mRNA level in the biological sample. In embodiments, the methods comprise measuring a TRIM37 protein level in the biological sample. In embodiments, the methods comprise measuring a Chromogranin A gene level in the biological sample. In embodiments, the methods comprise measuring a Chromogranin A mRNA level in the biological sample. In embodiments, the methods comprise measuring a Chromogranin A protein level in the biological sample. In embodiments, the methods comprise measuring a Synaptophysin gene level in the biological sample. In embodiments, the methods comprise measuring a Synaptophysin mRNA level in the biological sample. In embodiments, the methods comprise measuring a Synaptophysin protein level in the biological sample. In embodiments, the TRIM37 level is elevated. In embodiments, the Chromogranin A level is elevated. In embodiments, the Synaptophysin level is elevated. In embodiments, the TRIM37 level is elevated and the Chromogranin A level is elevated. In embodiments, the TRIM37 level is elevated and the Synaptophysin level is elevated. In embodiments, the Chromogranin A level is elevated and the Synaptophysin level is elevated. In embodiments, the TRIM37 level is elevated, the Chromogranin A level is elevated, and the Synaptophysin level is elevated. In embodiments, the TRIM37 level is elevated when compared to a control. In embodiments, the Chromogranin A level is elevated when compared to a control. In embodiments, the Synaptophysin level is elevated when compared to a control. In embodiments, the TRIM37 level is elevated and the Chromogranin A level is elevated when compared to a control. In embodiments, the TRIM37 level is elevated and the Synaptophysin level is elevated when compared to a control. In embodiments, the Chromogranin A level is elevated and the Synaptophysin level is elevated when compared to a control. In embodiments, the TRIM37 level is elevated, the Chromogranin A level is elevated, and the Synaptophysin level is elevated when compared to a control. The disclosure provides methods to identify a subject responsive to a PLK4 inhibitor, the method comprising: (i) obtaining a biological sample from the subject; (ii) analyzing the biological sample for mutant or wild type p53; wherein if the subject is p53 positive, the subject is identified as responsive to the PLK4 inhibitor. In embodiments, the methods further comprising administering an effective amount of a PLK4 inhibitor to the subject. In embodiments, the biological sample is a plasma sample. In embodiments, the biological sample is a serum sample. In embodiments, the biological sample is a tissue sample. In embodiments, the biological sample is a cell sample. In embodiments, the biological sample is a blood sample. In embodiments, the biological sample is a peripheral blood sample. In embodiments, the biological sample is a tumor sample. In embodiments, the biological sample is a primary tumor sample. In embodiments, the biological sample is a metastatic tumor sample. In embodiments, the biological sample is a resected tumor sample. In embodiments, the biological sample is a tumor biopsy sample. In embodiments, the biological sample is a resected primary tumor sample. In embodiments, the biological sample is a resected metastatic tumor sample. In embodiments, the biological sample is a primary tumor biopsy sample. In embodiments, the biological sample is a metastatic tumor biopsy sample. In embodiments, the PLK4 inhibitor is compound of Formula (Ia), a compound of Formula (Ib), a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the subject has cancer. In embodiments, the cancer is a cancer tumor. In embodiments, the cancer tumor is a primary cancer tumor. In embodiments, the cancer tumor is a metastatic cancer tumor.

The disclosure provides methods of selecting a subject for treatment with a PLK4 inhibitor, the method comprising: (i) obtaining a biological sample from the subject; and (ii) measuring a TRIM37 level, a Chromogranin A level, and/or a Synaptophysin level in the biological sample; wherein if the TRIM37 level, the Chromogranin A level, and/or the Synaptophysin level is elevated, the subject is selected for treatment with the PLK4 inhibitor. The disclosure provides methods of selecting a subject for treatment with a PLK4 inhibitor, the method comprising: (i) obtaining a biological sample from the subject; (ii) measuring a TRIM37 level, a Chromogranin A level, and/or a Synaptophysin level in the biological sample; and (iii) analyzing the biological sample for p53; wherein if the subject has an elevated TRIM37 level, a Chromogranin A level, and/or a Synaptophysin level and is p53 positive, the subject is identified as responsive to the PLK4 inhibitor. In embodiments, the methods comprise measuring: (i) the gene level, (ii) the mRNA level, (iii) the protein level, or (iv) a combination of two or more of the gene, mRNA, and protein levels of: (a) TRIM37, (b) Chromogranin A, (c) Synaptophysin, or (d) a combination of two or more of TRIM37, Chromogranin A, and Synaptophysin. In embodiments, the methods comprise measuring a TRIM37 gene level in the biological sample. In embodiments, the methods comprise measuring a TRIM37 mRNA level in the biological sample. In embodiments, the methods comprise measuring a TRIM37 protein level in the biological sample. In embodiments, the methods comprise measuring a Chromogranin A gene level in the biological sample. In embodiments, the methods comprise measuring a Chromogranin A mRNA level in the biological sample. In embodiments, the methods comprise measuring a Chromogranin A protein level in the biological sample. In embodiments, the methods comprise measuring a Synaptophysin gene level in the biological sample. In embodiments, the methods comprise measuring a Synaptophysin mRNA level in the biological sample. In embodiments, the methods comprise measuring a Synaptophysin protein level in the biological sample. In embodiments, the TRIM37 level is elevated. In embodiments, the Chromogranin A level is elevated. In embodiments, the Synaptophysin level is elevated. In embodiments, the TRIM37 level is elevated and the Chromogranin A level is elevated. In embodiments, the TRIM37 level is elevated and the Synaptophysin level is elevated. In embodiments, the Chromogranin A level is elevated and the Synaptophysin level is elevated. In embodiments, the TRIM37 level is elevated, the Chromogranin A level is elevated, and the Synaptophysin level is elevated. In embodiments, the TRIM37 level is elevated when compared to a control. In embodiments, the Chromogranin A level is elevated when compared to a control. In embodiments, the Synaptophysin level is elevated when compared to a control. In embodiments, the TRIM37 level is elevated and the Chromogranin A level is elevated when compared to a control. In embodiments, the TRIM37 level is elevated and the Synaptophysin level is elevated when compared to a control. In embodiments, the Chromogranin A level is elevated and the Synaptophysin level is elevated when compared to a control. In embodiments, the TRIM37 level is elevated, the Chromogranin A level is elevated, and the Synaptophysin level is elevated when compared to a control. The disclosure provides methods of selecting a subject for treatment with a PLK4 inhibitor, the method comprising: (i) obtaining a biological sample from the subject; (ii) analyzing the biological sample for wild type or mutant p53; wherein if the subject is p53 positive, the subject is identified as responsive to the PLK4 inhibitor. In embodiments, the methods further comprising administering an effective amount of a PLK4 inhibitor to the subject. In embodiments, the biological sample is a plasma sample. In embodiments, the biological sample is a serum sample. In embodiments, the biological sample is a tissue sample. In embodiments, the biological sample is a cell sample. In embodiments, the biological sample is a blood sample. In embodiments, the biological sample is a peripheral blood sample. In embodiments, the biological sample is a tumor sample. In embodiments, the biological sample is a primary tumor sample. In embodiments, the biological sample is a metastatic tumor sample. In embodiments, the biological sample is a resected tumor sample. In embodiments, the biological sample is a tumor biopsy sample. In embodiments, the biological sample is a resected primary tumor sample. In embodiments, the biological sample is a resected metastatic tumor sample. In embodiments, the biological sample is a primary tumor biopsy sample. In embodiments, the biological sample is a metastatic tumor biopsy sample. In embodiments, the PLK4 inhibitor is compound of Formula (Ia), a compound of Formula (Ib), a compound of Formula (Ia1), a compound of Formula (Ia2), a compound of Formula (Ia3), a compound of Formula (Ia4), a compound of Formula (Ia5), a compound of Formula (Ia6), a compound of Formula (Ia7), a compound of Formula (Ia8), a compound of Formula (Ia9a), a compound of Formula (Ia9b), a compound of Formula (Ia9c), a compound of Formula (Ia9d), a compound of Formula (Ia9f), a compound of Formula (Ib1), a compound of Formula (Ib2), a compound of Formula (Ib3), a compound of Formula (Ib4), a compound of Formula (Ib5), a compound of Formula (Ib6), a compound of Formula (Ib7), a compound of Formula (IC), a compound of Formula (II), a compound of Formula (III), or a pharmaceutically acceptable salt of any one of the foregoing. In embodiments, the PLK4 inhibitor is compound set forth in Table 1. In embodiments, the PLK4 inhibitor is compound set forth in Table 2. In embodiments, the PLK4 inhibitor is centrinone. In embodiments, the PLK4 inhibitor is centrinone B. In embodiments, the subject has cancer. In embodiments, the cancer is a cancer tumor. In embodiments, the cancer tumor is a primary cancer tumor. In embodiments, the cancer tumor is a metastatic cancer tumor.

EMBODIMENTS

Embodiment 1

A method of treating cancer in a subject in need thereof, the method comprising administering to the subject an effective amount of a PLK4 inhibitor to treat the cancer; wherein the subject has an elevated level of TRIM37 when compared to a control.

Embodiment 2

The method of Embodiment 1, wherein the subject has an elevated level of Chromogranin A; an elevated level of Synaptophysin; or an elevated level of Chromogranin A and an elevated level of Synaptophysin.

Embodiment 3

A method of treating cancer in a subject in need thereof, the method comprising: (i) measuring a TRIM37 level in a biological sample obtained from the subject; and (ii) administering an effective amount of a PLK4 inhibitor to the subject to treat the cancer.

Embodiment 4

The method of Embodiment 3, comprising measuring copies of the TRIM37 gene, measuring the level of the TRIM37 mRNA, measuring the level of the TRIM37 protein, or a combination of two or more thereof.

Embodiment 5

The method of Embodiment 3 or 4, wherein the biological sample obtained from the subject has an elevated level of TRIM37 when compared to a control.

Embodiment 6

The method of any one of Embodiments 3 to 5, further comprising measuring a Chromogranin A level; a Synaptophysin level; or a Chromogranin A level and a Synaptophysin level.

Embodiment 7

The method of any one of Embodiments 3 to 6, wherein the biological sample is a tumor sample.

Embodiment 8

The method of Embodiment 7, wherein the tumor sample is a resected tumor sample.

Embodiment 9

The method of Embodiment 7, wherein the tumor sample is a tumor biopsy sample.

Embodiment 10

The method of anyone of Embodiments 7 to 9, wherein the tumor sample is a primary tumor sample.

Embodiment 11

The method of any one of Embodiments 7 to 9, wherein the tumor sample is a metastisic tumor sample.

Embodiment 12

The method of any one of Embodiments 3 to 6, wherein the biological sample is a blood sample.

Embodiment 13

The method of Embodiment 12, wherein the blood sample is a peripheral blood sample.

Embodiment 14

The method of any one of Embodiments 1 to 13, wherein the cancer is a pediatric cancer.

Embodiment 15

The method of any one of Embodiments 1 to 14, wherein the cancer is a rhabdoid tumor.

Embodiment 16

The method of any one of Embodiments 1 to 14, wherein the cancer is a neuroblastoma.

Embodiment 17

The method of any one of Embodiments 1 to 14, wherein the cancer is an acute lymphoblastic leukemia tumor.

Embodiment 18

The method of any one of Embodiments 1 to 14, wherein the cancer is a brain and central nervous system tumor.

Embodiment 19

The method of any one of Embodiments 1 to 14, wherein the cancer is a neural crest-derived cancer.

Embodiment 20

The method of Embodiment 19, wherein the neural crest-derived cancer is small cell lung cancer.

Embodiment 21

The method of Embodiment 19, wherein the neural crest-derived cancer is melanoma.

Embodiment 22

The method of Embodiment 19, wherein the neural crest-derived cancer is breast cancer.

Embodiment 23

The method of any one of Embodiments 1 to 14, wherein the cancer is acute myeloid leukemia.

Embodiment 24

The method of any one of Embodiments 1 to 14, wherein the cancer is Ewing's sarcoma.

Embodiment 25

The method of any one of Embodiments 1 to 14, wherein the cancer is prostate cancer.

Embodiment 26

The method of any one of Embodiments 1 to 14, wherein the cancer is basal cell carcinoma.

Embodiment 27

The method of any one of Embodiments 1 to 14, wherein the cancer is medulloblastoma.

Embodiment 28

The method of any one of Embodiments 1 to 14, wherein the cancer is glioma.

Embodiment 29

The method of any one of Embodiments 1 to 14, wherein the cancer is small cell lung cancer.

Embodiment 30

The method of any one of Embodiments 1 to 14, wherein the cancer is a non small cell lung cancer.

Embodiment 31

The method of any one of Embodiments 1 to 14, wherein the cancer is breast cancer.

Embodiment 32

The method of any one of Embodiments 1 to 14, wherein the cancer is mesothelioma.

Embodiment 33

The method of any one of Embodiments 1 to 14, wherein the cancer is osteosarcoma.

Embodiment 34

The method of any one of Embodiments 1 to 14, wherein the cancer is soft tissue sarcoma.

Embodiment 35

The method of anyone of Embodiments 1 to 14, wherein the cancer is T cell lymphoma.

Embodiment 36

The method of Embodiment 35, wherein the T cell lymphoma is extranodal T cell lymphoma, cutaneous T cell lymphoma, anaplastic large cell lymphoma, or angioimmunoblastic T cell lymphoma.

Embodiment 37

The method of any one of Embodiments 1 to 36, wherein the cancer is a p53 positive cancer.

Embodiment 38

The method of Embodiment 37, wherein the cancer is a wild-type p53 positive cancer.

Embodiment 39

The method of Embodiment 37, wherein the cancer is a mutant p53 positive cancer.

Embodiment 40

A method of treating a p53 positive cancer in a subject in need thereof, the method comprising administering to the subject an effective amount of a PLK4 inhibitor to treat the p53 positive cancer.

Embodiment 41

The method of Embodiment 40, wherein the p53 positive cancer is a wild type p53 positive cancer.

Embodiment 42

The method of Embodiment 40, wherein the p53 positive cancer is a mutant p53 positive cancer.

Embodiment 43

A method of treating a wild type p53 positive pediatric cancer in a subject in need thereof, the method comprising administering to the subject an effective amount of a PLK4 inhibitor to treat the wild type p53 positive pediatric cancer.

Embodiment 44

A method of treating a mutant p53 positive pediatric cancer in a subject in need thereof, the method comprising administering to the subject an effective amount of a PLK4 inhibitor to treat the mutant p53 positive pediatric cancer.

Embodiment 45

A method of treating a wild-type p53 positive pediatric cancer in a subject in need thereof, the method comprising administering to the subject an effective amount of a PLK4 inhibitor to treat the wild-type p53 positive pediatric cancer; wherein the subject has an elevated level of TRIM37 when compared to a control.

Embodiment 46

The method of Embodiment 45, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 47

A method of treating a mutant p53 positive pediatric cancer in a subject in need thereof, the method comprising administering to the subject an effective amount of a PLK4 inhibitor to treat the mutant p53 positive pediatric cancer; wherein the subject has an elevated level of TRIM37 when compared to a control.

Embodiment 48

The method of Embodiment 47, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 49

A method of treating a pediatric cancer in a subject in need thereof, the method comprising administering to the subject an effective amount of a PLK4 inhibitor to treat the pediatric cancer; wherein the subject has an elevated level of TRIM37 when compared to a control.

Embodiment 50

The method of Embodiment 49, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 51

The method of anyone of Embodiments 43 to 50, wherein the pediatric cancer is acute lymphoblastic leukemia, neuroblastoma, a rhabdoid tumor, or tumor of the brain and central nervous system.

Embodiment 52

A method of treating a wild type p53 positive, neural crest-derived cancer in a subject in need thereof, the method comprising administering to the subject an effective amount of a PLK4 inhibitor to treat the wild type p53 positive, neural crest-derived cancer.

Embodiment 53

A method of treating a mutant type p53 positive, neural crest-derived cancer in a subject in need thereof, the method comprising administering to the subject an effective amount of a PLK4 inhibitor to treat the mutant p53 positive, neural crest-derived cancer.

Embodiment 54

A method of treating a wild type p53 positive, neural crest-derived cancer in a subject in need thereof, the method comprising administering to the subject an effective amount of a PLK4 inhibitor to treat the wild type p53 positive, neural crest-derived cancer; wherein the subject has an elevated level of TRIM37 when compared to a control.

Embodiment 55

The method of Embodiment 54, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 56

A method of treating a mutant p53 positive, neural crest-derived cancer in a subject in need thereof, the method comprising administering to the subject an effective amount of a PLK4 inhibitor to treat the mutant p53 positive, neural crest-derived cancer; wherein the subject has an elevated level of TRIM37 when compared to a control.

Embodiment 57

The method of Embodiment 56, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 58

A method of treating a neural crest-derived cancer in a subject in need thereof, the method comprising administering to the subject an effective amount of a PLK4 inhibitor to treat the neural crest-derived cancer; wherein the subject has an elevated level of TRIM37 when compared to a control.

Embodiment 59

The method of Embodiment 58, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 60

The method of any one of Embodiments 52 to 59, wherein the neural crest-derived cancer is small cell lung cancer, breast cancer, or melanoma.

Embodiment 61

A method of treating a wild-type p53 positive cancer in a subject in need thereof, the method comprising administering to the subject an effective amount of a PLK4 inhibitor to treat the wild-type p53 positive cancer; wherein the subject has an elevated level of TRIM37 when compared to a control.

Embodiment 62

The method of Embodiment 61, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 63

A method of treating a mutant p53 positive cancer in a subject in need thereof, the method comprising administering to the subject an effective amount of a PLK4 inhibitor to treat the mutant p53 positive cancer; wherein the subject has an elevated level of TRIM37 when compared to a control.

Embodiment 64

The method of Embodiment 63, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 65

A method of treating a wild type p53 positive neuroblastoma in a subject in need thereof, the method comprising administering to the subject an effective amount of a PLK4 inhibitor to treat the wild type p53 positive neuroblastoma; wherein the subject has an elevated level of TRIM37 when compared to a control.

Embodiment 66

The method of Embodiment 65, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 67

A method of treating a mutant p53 positive neuroblastoma in a subject in need thereof, the method comprising administering to the subject an effective amount of a PLK4 inhibitor to treat the mutant p53 positive neuroblastoma; wherein the subject has an elevated level of TRIM37 when compared to a control.

Embodiment 68

The method of Embodiment 67, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 69

A method of treating a wild type or mutant p53 positive neuroblastoma in a subject in need thereof, the method comprising administering to the subject an effective amount of a PLK4 inhibitor to treat the wild type or mutant p53 positive neuroblastoma.

Embodiment 70

A method of treating a wild type p53 positive small cell lung cancer in a subject in need thereof, the method comprising administering to the subject an effective amount of a PLK4 inhibitor to treat the wild type p53 positive small cell lung cancer; wherein the subject has an elevated level of TRIM37 when compared to a control.

Embodiment 71

The method of Embodiment 70, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 72

A method of treating a mutant p53 positive small cell lung cancer in a subject in need thereof, the method comprising administering to the subject an effective amount of a PLK4 inhibitor to treat the mutant p53 positive small cell lung cancer; wherein the subject has an elevated level of TRIM37 when compared to a control.

Embodiment 73

The method of Embodiment 72, wherein the subject has an elevated level of Chromogranin A when compared to a control; an elevated level of Synaptophysin when compared to a control; or an elevated level of Chromogranin A and an elevated level of Synaptophysin when compared to a control.

Embodiment 74

A method of treating a wild type or mutant p53 positive small cell lung cancer in a subject in need thereof, the method comprising administering to the subject an effective amount of a PLK4 inhibitor to treat the wild type or mutant p53 positive small cell lung cancer.

Embodiment 75

The method of any one of Embodiments 1 to 74, further comprising administering an effective amount of a chemotherapeutic agent to the subject.

Embodiment 76

The method of Embodiment 75, wherein the chemotherapeutic agent is a tubule polymerization inhibitor.

Embodiment 77

The method of Embodiment 76, wherein the tubule polymerization inhibitor is vincristine, vinblastine, vinorelbine, vinfluine, a dolastatin, a halichondrin, a hemiasterline, cryptophysin 52, or a combination of two or more thereof.

Embodiment 78

The method of Embodiment 75, wherein the chemotherapeutic agent comprises cyclophosphamide, ifosfamide, cisplatin, carboplatin, vincristine, doxorubicin, etoposide, topotecan, busulfan, melphalan, or a combination of two or more thereof.

Embodiment 79

The method of any one of Embodiments 1 to 78, further comprising administering differentiation therapy to the subject.

Embodiment 80

The method of Embodiment 79, wherein the differentiation therapy comprises retinoic acid, arsenic trioxide, or a combination thereof.

Embodiment 81

The method of Embodiment 80, wherein the retinoic acid is all-trans-retinoic acid, 13-cis-retinoic acid, or a combination thereof.

Embodiment 82

The method of anyone of Embodiments 1 to 81, further comprising administering radiation therapy to the subject.

Embodiment 83

A method to identify a subject responsive to a PLK4 inhibitor, the method comprising: (i) obtaining a biological sample from the subject; and (ii) measuring a TRIM37 level in the biological sample; wherein if the TRIM37 level is elevated when compared to a control, the subject is identified as responsive to the PLK4 inhibitor.

Embodiment 84

The method of Embodiment 83, further comprising measuring a Chromogranin A level; measuring a Synaptophysin level; or measuring a Chromogranin A and a Synaptophysin level.

Embodiment 85

A method of selecting a subject for treatment with a PLK4 inhibitor, the method comprising: (i) obtaining a biological sample from the subject; and (ii) measuring a TRIM37 level in the biological sample; wherein if the TRIM37 level is elevated when compared to a control, the subject is selected for treatment with the PLK4 inhibitor.

Embodiment 86

The method of Embodiment 85, further comprising measuring a Chromogranin A level; measuring a Synaptophysin level; or measuring a Chromogranin A and a Synaptophysin level.

Embodiment 87

The method of any one of Embodiments 83 to 86, further comprising determining if the biological sample is p53 positive.

Embodiment 88

The method of anyone of Embodiments 83 to 87, wherein the subject has cancer.

Embodiment 89

The method of any one of Embodiments 83 to 88, wherein the biological sample is a tumor sample.

Embodiment 90

The method of Embodiment 89, wherein the tumor sample is a resected tumor or a tumor biopsy sample.

Embodiment 91

The method of Embodiment 89 or 90, wherein the tumor sample is a primary tumor sample or a metastisic tumor sample.

Embodiment 92

The method of any one of Embodiments 83 to 88, wherein the biological sample is a blood sample.

Embodiment 93

The method of any one of Embodiments 1 to 92, wherein the PLK4 inhibitor is a compound of Formula (Ia) or a pharmaceutically acceptable salt thereof:

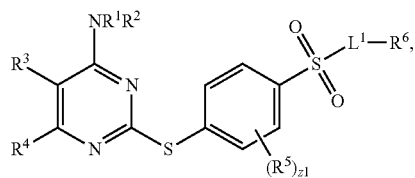

(Ia)

wherein the substituents are as defined in the specification.

Embodiment 94

The method of Embodiment 93, wherein the compound of Formula (Ia)

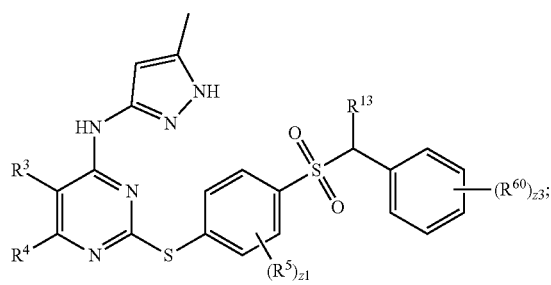

wherein $R^3$, $R^4$, $R^5$, z1, $R^{13}$, and $R^{60}$ areas defined in the specification.

Embodiment 95

The method of Embodiment 93, wherein the compound of Formula (Ia) is:

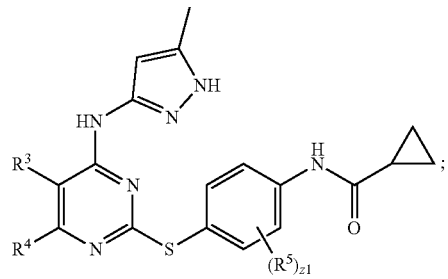

wherein $R^3$, $R^4$, $R^5$, z1, z3, and $R^{60}$ are as defined in the specification.

Embodiment 96

The method of Embodiment 93, wherein the compound of Formula (Ia) is

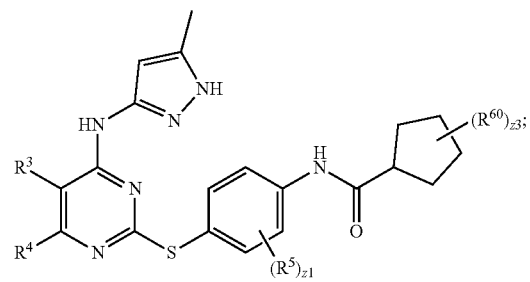

wherein $R^3$, $R^4$, $R^5$, z1, z3, and $R^{60}$ are as defined in the specification.

Embodiment 97

The method of any one of Embodiments 1 to 92, wherein the PLK4 inhibitor is a compound of Formula (Ia1) or a pharmaceutically acceptable salt thereof:

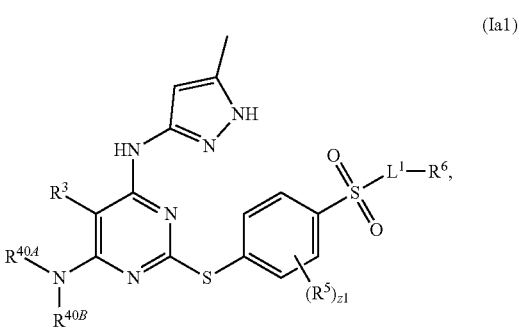

(Ia1)

wherein the substituents are as defined in the specification.

Embodiment 98

The method of any one of Embodiments 1 to 92, wherein the PLK4 inhibitor is a compound of Formula (Ia2) or a pharmaceutically acceptable salt thereof:

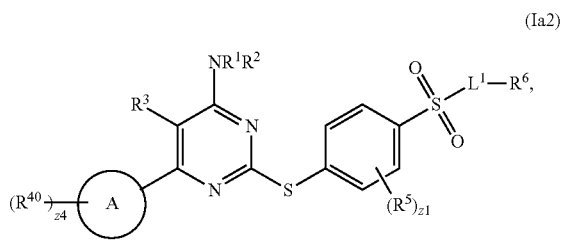

(Ia2)

wherein $L^1$, z1, $R^1$, $R^2$, $R^5$, $R^6$, and $R^{40}$ are as defined in the specification.

Embodiment 99

The method of any one of Embodiments 1 to 92, wherein the PLK4 inhibitor is a compound of Formula (Ia3) or a pharmaceutically acceptable salt thereof:

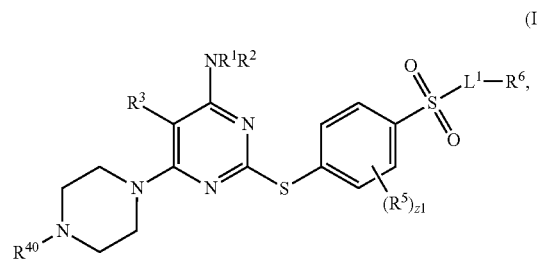

(Ia3)

where $L^1$, z1, $R^1$, $R^2$, $R^5$, $R^6$, and $R^{40}$ are as defined in the specification.

Embodiment 100

The method of Embodiment 99, wherein the compound of Formula (Ia3) is:

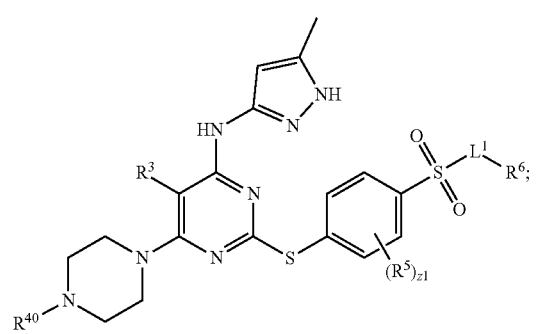

wherein the substituents are as defined in the specification.

Embodiment 101

The method of any one of Embodiments 1 to 92, wherein the PLK4 inhibitor is a compound of Formula (Ia4) or a pharmaceutically acceptable salt thereof:

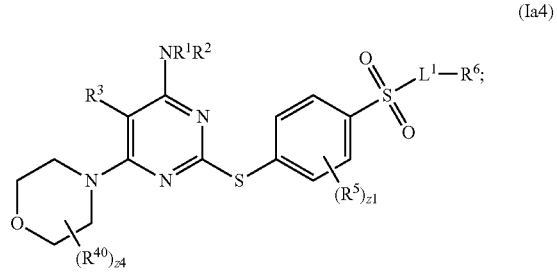

(Ia4)

wherein $L^1$, z1, $R^1$, $R^2$, $R^5$, $R^6$, and $R^{40}$ are as defined in the specification.

Embodiment 102

The method of Embodiment 101, wherein the compound of Formula (Ia4) is:

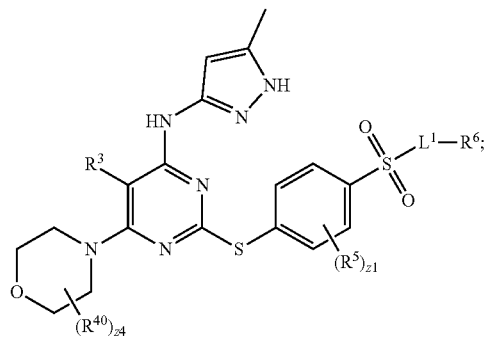

wherein the substituents are as defined in the specification.

Embodiment 103

The method of any one of Embodiments 1 to 92, wherein the PLK4 inhibitor is a compound of Formula (Ia5) or a pharmaceutically acceptable salt thereof:

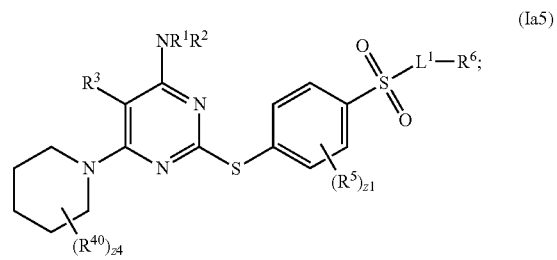

(Ia5)

wherein $L^1$, z1, z4, $R^1$, $R^2$, $R^5$, $R^6$ and $R^{40}$ areas defined in the specification.

Embodiment 104

The method of Embodiment 103, wherein the compound of Formula (Ia5) is:

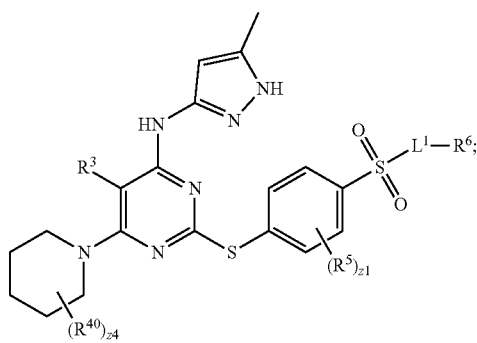

wherein the substituents are as defined in the specification.

Embodiment 105

The method of any one of Embodiments 1 to 92, wherein the PLK4 inhibitor is a compound of Formula (Ia6) or a pharmaceutically acceptable salt thereof:

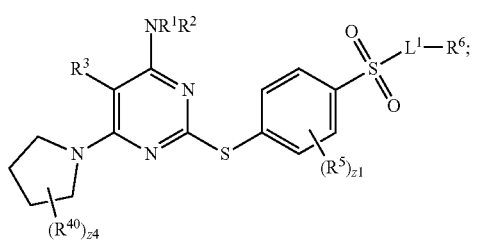

(Ia6)

wherein $L^1$, z1, $R^1$, $R^2$, $R^5$, $R^6$, and $R^{40}$ are as defined in the specification.

Embodiment 106

The method of Embodiment 105, wherein the compound of Formula (Ia6) is:

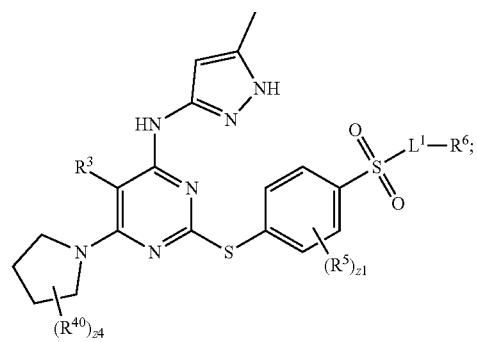

wherein the substituents are as defined herein.

Embodiment 107

The method of any one of Embodiments 1 to 92, wherein the PLK4 inhibitor is a compound of Formula (Ia7) or a pharmaceutically acceptable salt thereof:

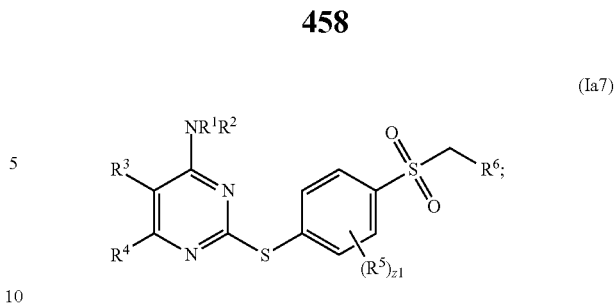

(Ia7)

wherein z1, $R^1$, $R^2$, $R^3$, $R^4$, $R^5$, and $R^6$ are as defined in the specification.

Embodiment 108

The method of Embodiment 107, wherein the compound of Formula (Ia7) is:

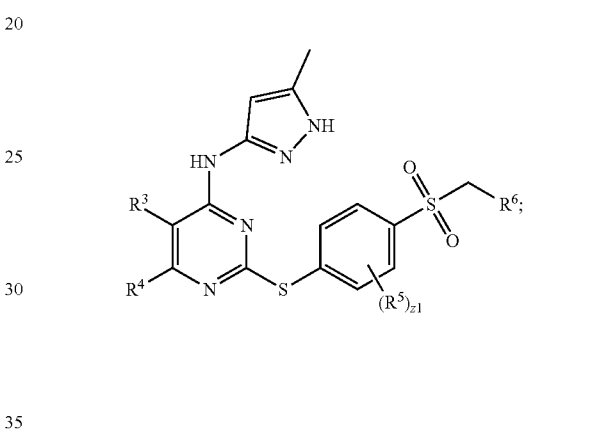

wherein the substituents are as defined in the specification.

Embodiment 109

The method of any one of Embodiments 1 to 92, wherein the PLK4 inhibitor is a compound of Formula (Ia8) or a pharmaceutically acceptable salt thereof:

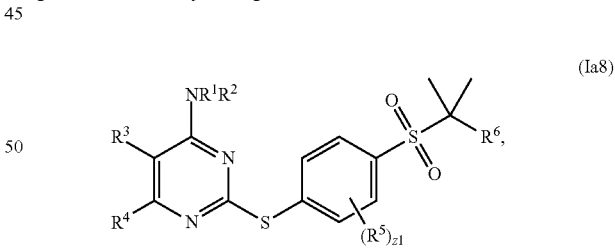

(Ia8)

wherein z1, $R^1$, $R^2$, $R^3$, $R^4$, R, and $R^6$ are as defined in the specification.

Embodiment 110

The method of Embodiment 109, wherein the compound of Formula (Ia8) is:

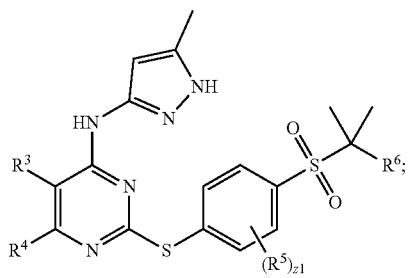

(Ia9a)

wherein the substituents are as defined in the specification.

Embodiment 111

The method of any one of Embodiments 1 to 92, wherein the PLK4 inhibitor is a compound of Formula (Ia9a) or a pharmaceutically acceptable salt thereof:

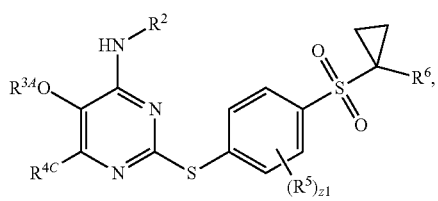

(Ia9a)

wherein $R^{3A}$ is substituted or unsubstituted alkyl, and $R^{4C}$ is substituted or unsubstituted heterocycloalkyl, and the remaining substituents are as defined in the specification.

Embodiment 112

The method of any one of Embodiments 1 to 92, wherein the PLK4 inhibitor is a compound of Formula (Ia9b) or a pharmaceutically acceptable salt thereof:

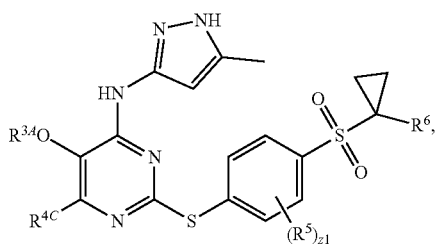

(Ia9b)

wherein the substituents are as defined in the specification.

Embodiment 113

The method of anyone of Embodiments 1 to 92, wherein the PLK4 inhibitor is a compound of Formula (Ia9c) or a pharmaceutically acceptable salt thereof:

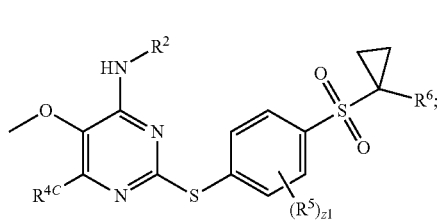

(Ia9c)

wherein the substituents are as defined in the specification.

Embodiment 114

The method of any one of Embodiments 1 to 92, wherein the PLK4 inhibitor is a compound of Formula (a9d) or a pharmaceutically acceptable salt thereof:

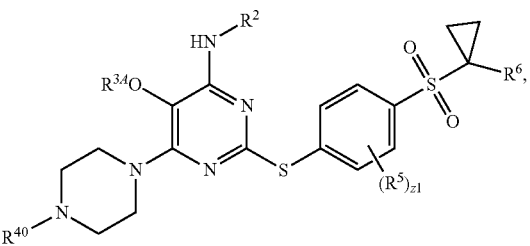

(Ia9d)

wherein the substituents are as defined in the specification.

Embodiment 115

The method of anyone of Embodiments 1 to 92, wherein the PLK4 inhibitor is a compound of Formula (Ia9f) or a pharmaceutically acceptable salt thereof:

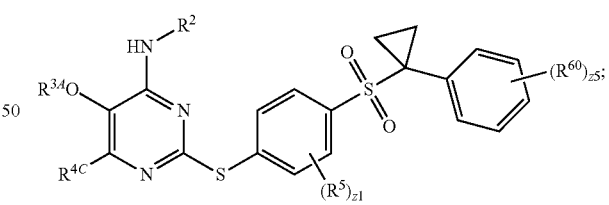

(Ia9f)

wherein the substituents are as defined in the specification.

Embodiment 116

The method of anyone of Embodiments 1 to 92, wherein the PLK4 inhibitor is a compound of Formula (Ib) or a pharmaceutically acceptable salt thereof:

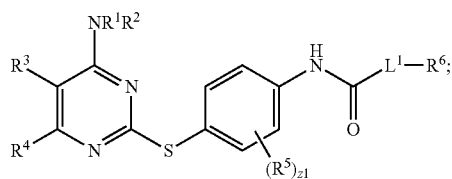

wherein $L^1$, $z1$, $R^3$, $R^5$, $R^6$, $R^{4A}$, and $R^{40B}$ are as defined in the specification.

Embodiment 117

The method of anyone of Embodiments 1 to 92, wherein the PLK4 inhibitor is a compound of Formula (Ib1) or a pharmaceutically acceptable salt thereof:

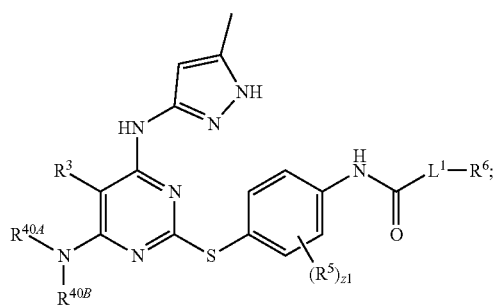

where $L^1$, $z1$, $R^3$, $R^5$, $R^6$, $R^{40A}$, and $R^{40B}$ areas defined in the specification.

Embodiment 118

The method of any one of Embodiments 1 to 92, wherein the PLK4 inhibitor is a compound of Formula (Ib2) or a pharmaceutically acceptable salt thereof:

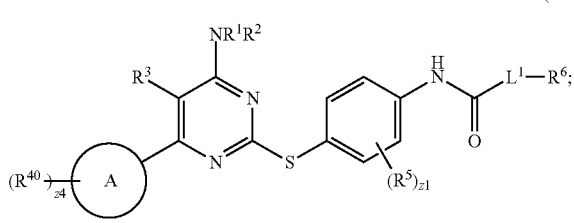

wherein $L^1$, $z1$, $z4$, $R^1$, $R^2$, $R^5$, $R^6$, and $R^{40}$ are as defined in the specification.

Embodiment 119

The method of any one of Embodiments 1 to 92, wherein the PLK4 inhibitor is a compound of Formula (Ib3) or a pharmaceutically acceptable salt thereof:

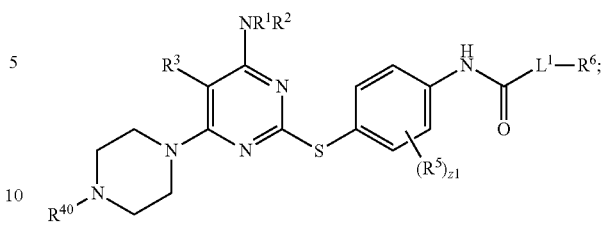

wherein $L^1$, $z1$, $R$, $R^2$, $R^5$, $R^6$, and $R^{40}$ are as defined in the specification.

Embodiment 120

The method of Embodiment 119, wherein the compound of Formula (Ib3) is:

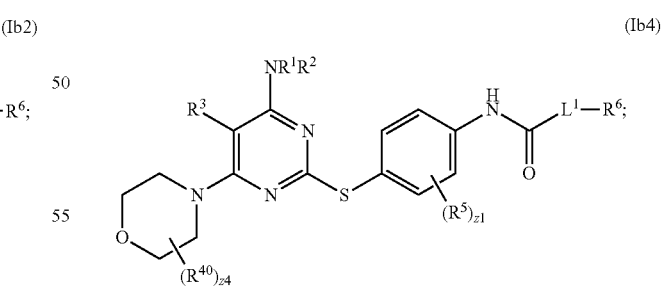

wherein the substituents are as defined in the specification.

Embodiment 121

The method of any one of Embodiments 1 to 92, wherein the PLK4 inhibitor is a compound of Formula (Ib4) or a pharmaceutically acceptable salt thereof:

(Ib4)

wherein $L^1$, $z1$, $R$, $R^2$, $R^5$, $R^6$, and $R^{40}$ are as defined in the specification.

Embodiment 122

The method of Embodiment 121, wherein the compound of Formula (Ib4) is:

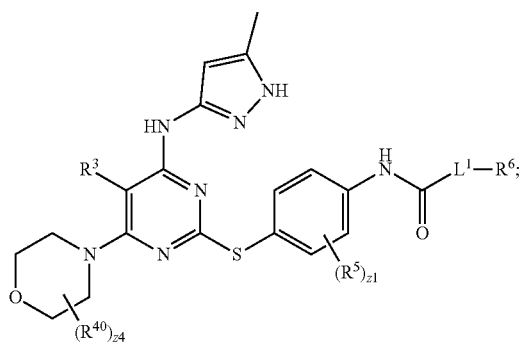

wherein the substituents are as defined in the specification.

Embodiment 123

The method of any one of Embodiments 1 to 92, wherein the PLK4 inhibitor is a compound of Formula (Ib) or a pharmaceutically acceptable salt thereof:

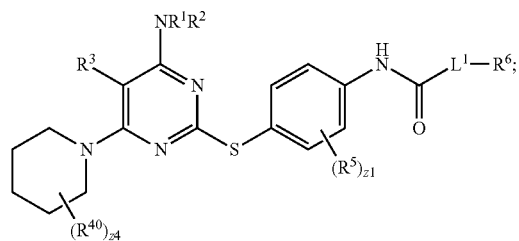
(Ib5)

wherein $L^1$, z1, $R^1$, $R^2$, $R^5$, $R^6$, and $R^{40}$ are as defined in the specification.

Embodiment 124

The method of Embodiment 123, wherein the compound of Formula (Ib5) is:

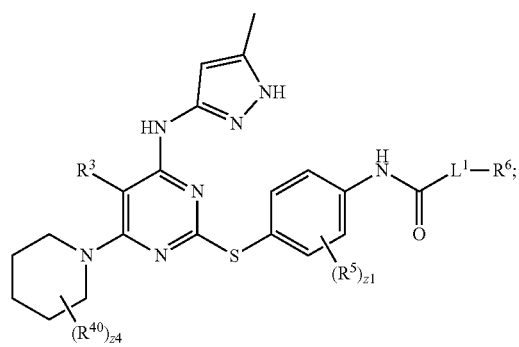

wherein the substituents are as defined in the specification.

Embodiment 125

The method of any one of Embodiments 1 to 92, wherein the PLK4 inhibitor is a compound of Formula (Ib6) or a pharmaceutically acceptable salt thereof:

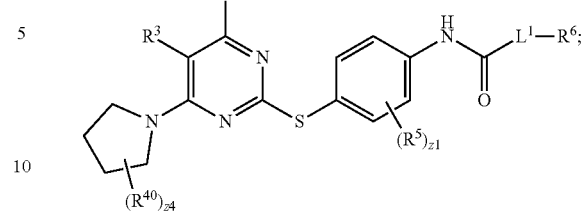
(Ib6)

wherein $L^1$, z1, $R^1$, $R^2$, $R^5$, $R^6$, and $R^{40}$ are as defined in the specification.

Embodiment 126

The method of Embodiment 125, wherein the compound of Formula (Ib6) is:

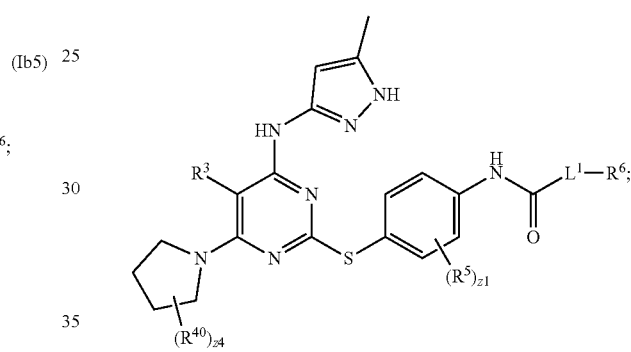

wherein the substituents are as defined in the specification.

Embodiment 127

The method of any one of Embodiments 1 to 92, wherein the PLK4 inhibitor is a compound of Formula (Ib7) or a pharmaceutically acceptable salt thereof:

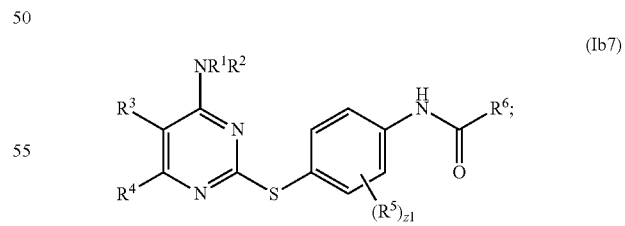
(Ib7)

wherein z1, $R^1$, $R^2$, $R^3$, $R^4$, $R^5$, and $R^6$ are as defined in the specification.

Embodiment 128

The method of Embodiment 127, wherein the compound of Formula (Ib7) is:

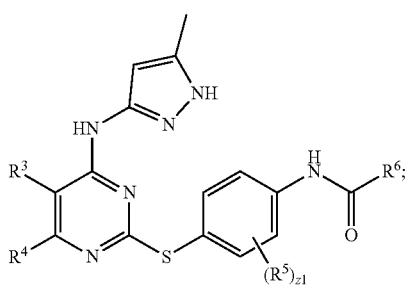

wherein the substituents are as defined in the specification.

Embodiment 129

The method of any one of Embodiments 1 to 92, wherein the PLK4 inhibitor is a compound of Formula (IC) or a pharmaceutically acceptable salt thereof:

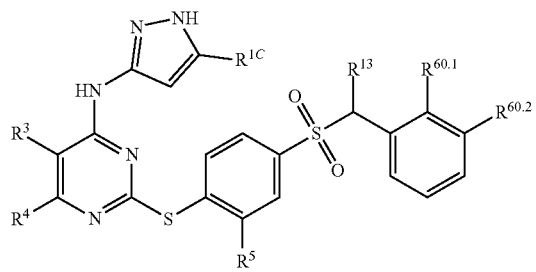

wherein the substituents are as defined in the specification.

Embodiment 130

The method of any one of Embodiments 1 to 92, wherein the PLK4 inhibitor is a compound of Formula (II) or a pharmaceutically acceptable salt thereof:

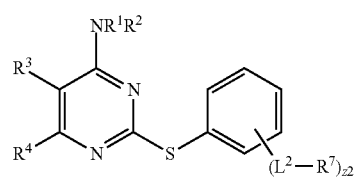
(II)

wherein the substituents are as defined in the specification.

Embodiment 131

The method of Embodiment 130, wherein the compound of Formula (II) is:

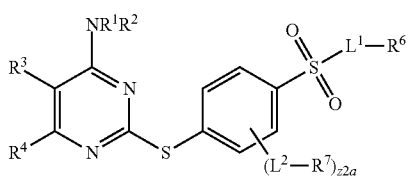

wherein the substituents are as defined in the specification.

Embodiment 132

The method of Embodiment 130, wherein the compound of Formula (II) is:

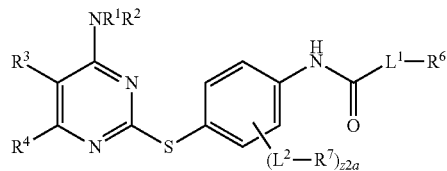

wherein the substituents are as defined in the specification.

Embodiment 133

The method of any one of Embodiments 1 to 92, wherein the PLK4 inhibitor is a compound of Formula (III) or a pharmaceutically acceptable salt thereof:

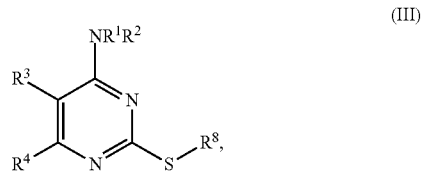
(III)

wherein the substituents are as defined in the specification.

Embodiment 134

The method of any one of Embodiments 1 to 92, wherein the PLK4 inhibitor is a compound set forth in Table 1 or a pharmaceutically acceptable salt thereof.

Embodiment 135

The method of Embodiment 134, wherein the compound set forth in Table 1 has an activity identified as X.

Embodiment 136

The method of Embodiment 134, wherein the compound set forth in Table 1 has an activity identified as XX.

Embodiment 137

The method of Embodiment 134, wherein the compound set forth in Table 1 has an activity identified as XXX.

Embodiment 138

The method of anyone of Embodiments 1 to 92, wherein the PLK4 inhibitor is a compound set forth in Table 2 or a pharmaceutically acceptable salt thereof.

Embodiment 139

The method of any one of Embodiments 1 to 92, wherein the PLK4 inhibitor is a compound described in the specification or a pharmaceutically acceptable salt thereof.

Embodiment 140

The method of any one of Embodiments 1 to 92, wherein the PLK4 inhibitor is not tozasertib.

Embodiment 141

The method of anyone of Embodiments 1 to 92, wherein the PLK4 inhibitor is tozasertib or a pharmaceutically acceptable salt thereof.

Embodiment 142

The method of any one of Embodiments 1 to 92, wherein the PLK4 inhibitor is centrinone or a pharmaceutically acceptable salt thereof.

Embodiment 143

The method of any one of Embodiments 1 to 92, wherein the PLK4 inhibitor is centrinone B or a pharmaceutically acceptable salt thereof.

EXAMPLES

The following example is for purposes of illustration and are not intended to limit the spirit or scope of the disclosure or claims.

Example 1

Experiments described herein tested the idea that cancer cell types that express high levels of TRIM37 might be more susceptible to death due to centrosome removal, either due to mitotic failure or to p53 stabilization resulting from exceeding the mitotic duration sensor time limit.

It was theorized that centrosome removal would trigger the mitotic duration sensor in these cell lines, enhancing the effect of centrosome removal on proliferation. To confirm, six neuroblastoma cells lines were collected (SH—SY5Y, CHP134, IMR32, CHP212, SK-N—SH, and SK-N-F1) along with 5 other control cell lines derived from tumors from children or adolescents (1 hepatocellular carcinoma, HepG2; 2 Rhabdoid Tumor (ATRT), BT-12 and BT-16; and 2 Ewing Sarcoma SK-ES-1 and A673).

Figure 1B:
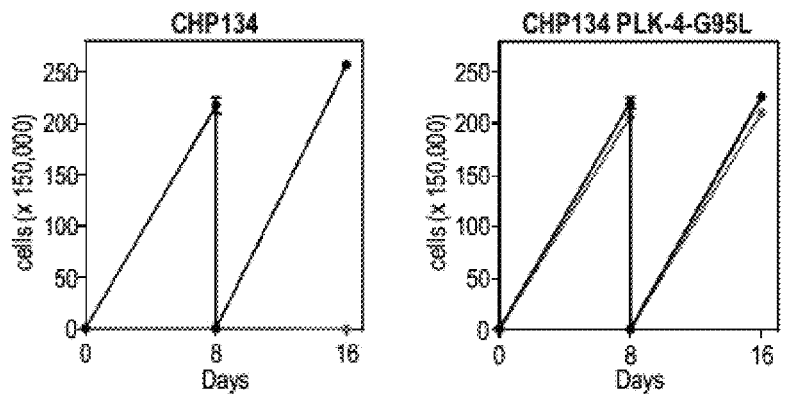
Figure 1C:
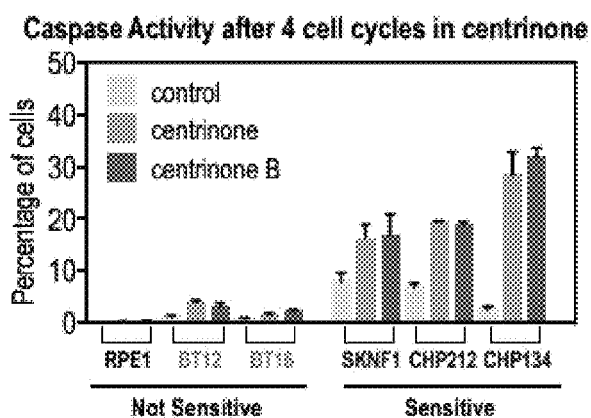

All 6 of the neuroblastoma cell lines grew robustly in the presence of DMSO in 12-day passaging assays. In contrast, following centrinone addition, cell number rapidly declined to zero (FIG. 1A, designated PLK4 inhibition 'Sensitive' cell lines). In contrast, the five control cell lines continued to proliferate in the presence of centrinone, albeit at a reduced rate compared to the cultures treated with the DMSO vehicle (FIG. 1A, designated PLK4 inhibition 'Not Sensitive' cell lines). Caspase assays comparing RPE1 cells, which senesce but do not die in the presence of centrinone, and two other 'Not Sensitive' cell lines (BT-12 and BT-16), to three of the 'Sensitive' neuroblastoma cell lines, revealed high levels of caspase activity in the 'Sensitive' cell lines compared to relatively low levels in the cell lines that were 'Not Sensitive' (FIG. 1C). Comparable levels of caspase activity were also detected in cells treated with centrinone B, a related PLK4 inhibitor, suggesting that the effect the result of inhibiting PLK4, rather than an off target effect. To confirm that cell death was due to inhibition of PLK4 and not an off target effect of centrinone and/or centrinone B, both PLK4 alleles in one of the neuroblastoma lines, CHP134, was engineered to express a G95L mutant PLK4 protein. The CHP134 cells harboring the G95L mutant PLK4 proliferated in centrinone at a rate comparable to non-mutant cells in DMSO (FIG. 1B) demonstrating that the cell death in the presence of centrinone is due to PLK4 inhibition.

Figure 2A:
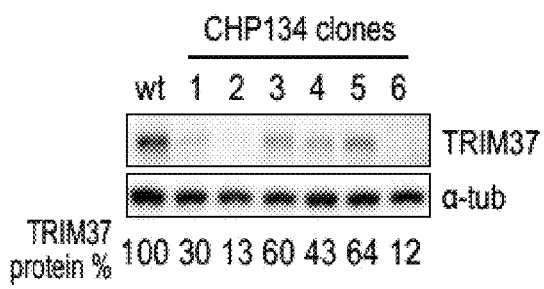
FIGS. 2A-D show mitotic duration and anaphase failure rates following centrosome removal correlate with TRIM37 protein levels.
Figure 2B:
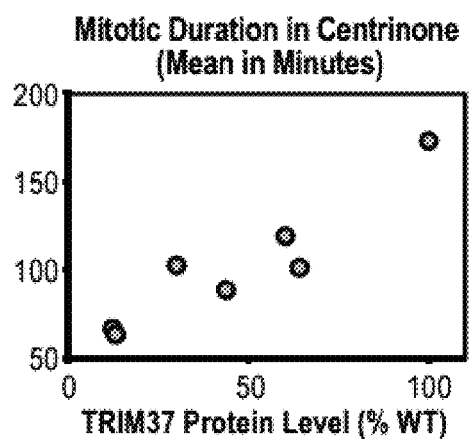
Figure 2C:
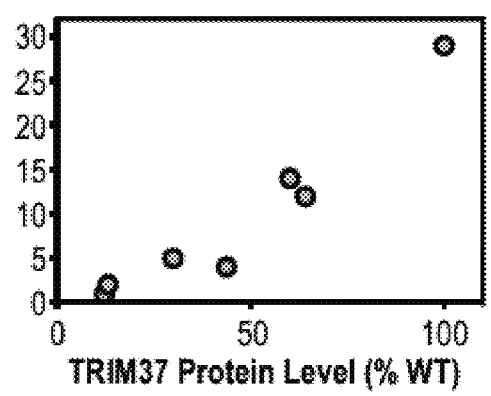
Figure 2D:
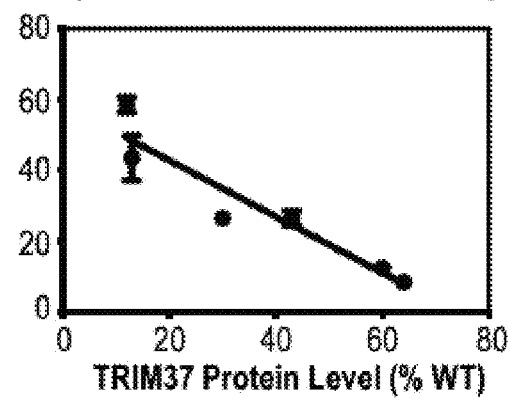

Mitotic duration and anaphase failure rates following centrosome removal were shown to correlate with TRIM37 protein levels. FIG. 2A shows the CHP134 neuroblastoma cell line has four (4) copies of the TRIM37 gene. After CRISPR targeting, CHP134 clones with varying TRIM37 copy numbers were isolated and the levels of TRIM37 protein were measured by quantitative western blotting. Alpha-tubulin was used as a blotting control. Clones with TRIM37 levels between 12 and 64% of the levels in the WT cell line were isolated. FIGS. 2B and 2C show analysis of mitosis by live cell filming in the CHP134 clones after 3 cell cycles in 150 nM centrinone and the duration of mitosis and rate of anaphase failure were measured for each clone. Graphs plot mean mitotic duration (FIG. 2B) and the percentage of cells exhibiting anaphase failure (FIG. 2C) versus measured TRIM37 protein level. FIG. 2D presents data in which cellular proliferation was assessed for each of the CHP134 clones by performing an ATPlite assay after 5 days in 125 nM centrinone. Results are expressed as the percent of the value for the equivalent DMSO-treated control and are plotted versus measured TRIM37 protein level. Note that WT CHP134 cells exhibited a loss in proliferation comparable to that of the two highest mutant clones. Thus, for centrinone-treated CHP134 cells, mitotic success and cell viability both decreased as TRIM37 levels increased.

Figure 3A:
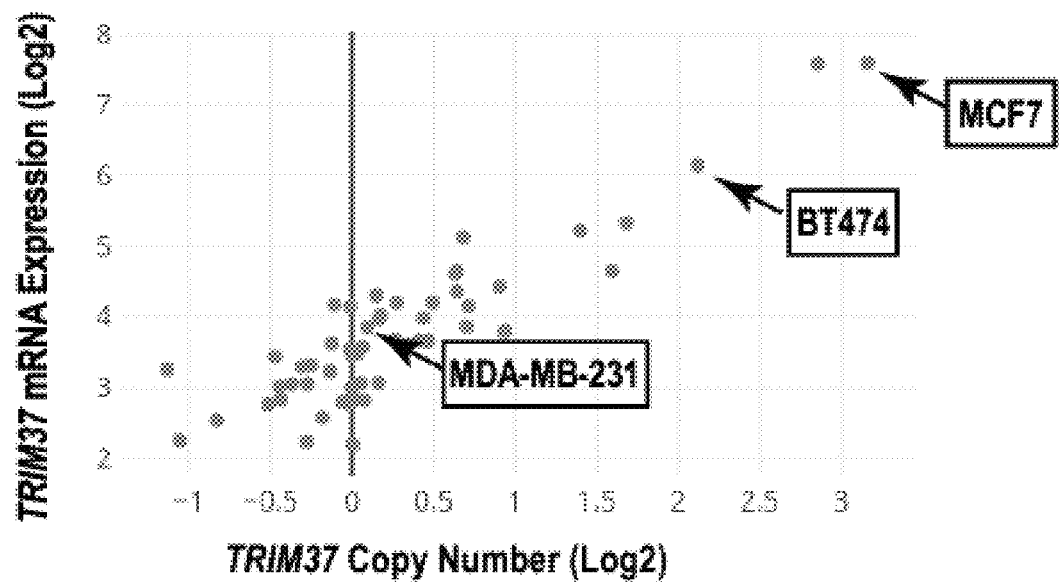
FIGS. 3A-B show sensitivity to centrosome removal correlates with TRIM37 copy number in breast cancer.
Figure 3B:
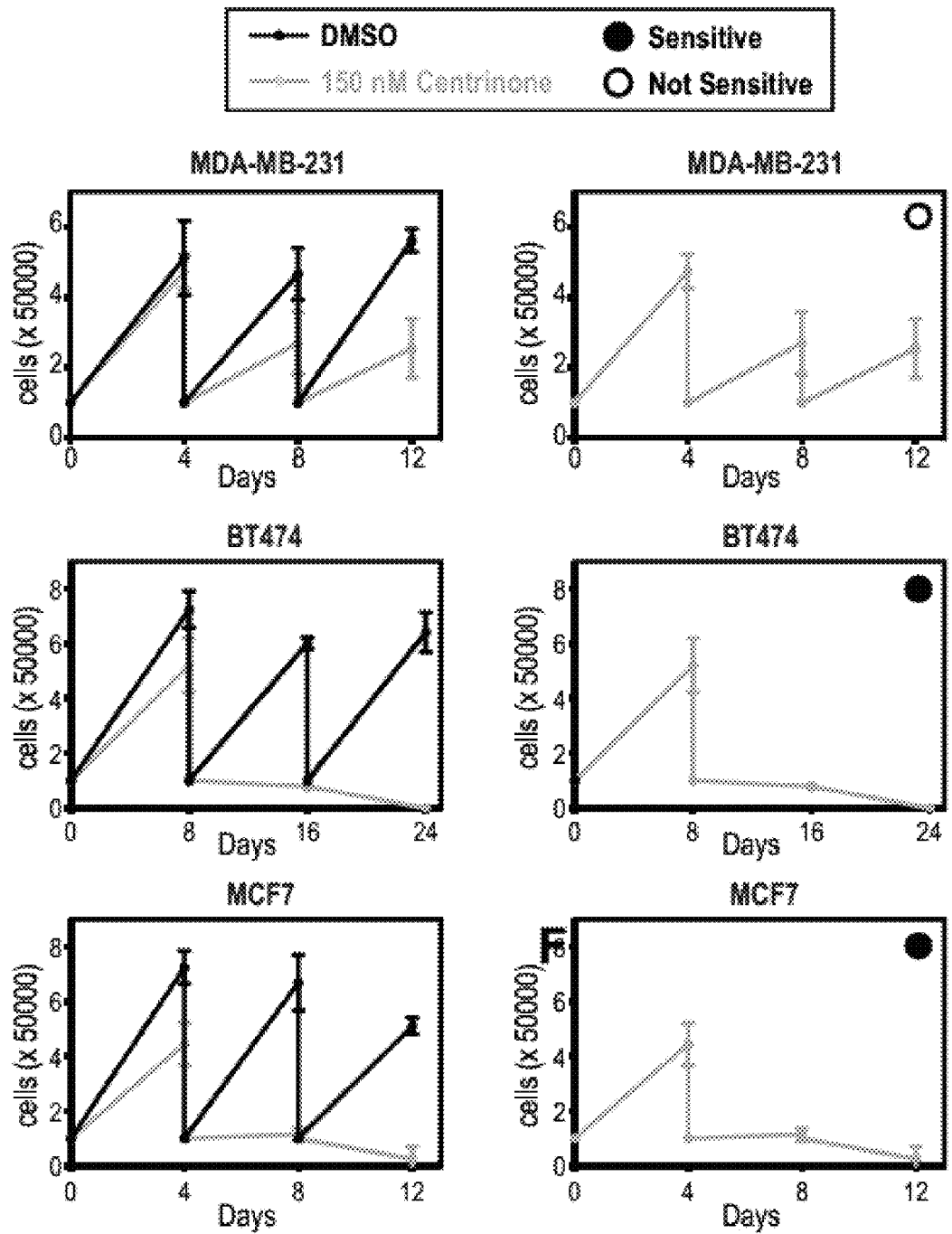

Sensitivity to centrosome removal correlated with TRIM37 copy number in breast cancer as well. FIG. 3A is a graph plotting TRIM37 copy number versus expression level for breast cancer cell lines (data from the CCLE database; (Barretina et al., 2012)). FIG. 3B are graphs showing the results of passaging assays for the indicated cancer cell lines that monitor cell proliferation after the addition of DMSO (vehicle; black) or 150 nM centrinone (grey) at day 0. The right graph in each pair shows the centrinone-treated curve without the control. Cell lines in which the number of cells decreased to zero following centrinone addition were considered 'Sensitive' to PLK4 inhibition (marked with the filled circles in the upper right hand corner, whereas cell lines that continued to proliferate were considered 'Not Sensitive' (marked with the empty circles in the upper right hand corner). The two cell lines with amplification of the TRIM37 locus (BT474 and MCF7) were highly sensitive to centrosome removal, whereas MDA-MB-231, which has not amplified the TRIM37 locus was not.

Figure 4A:
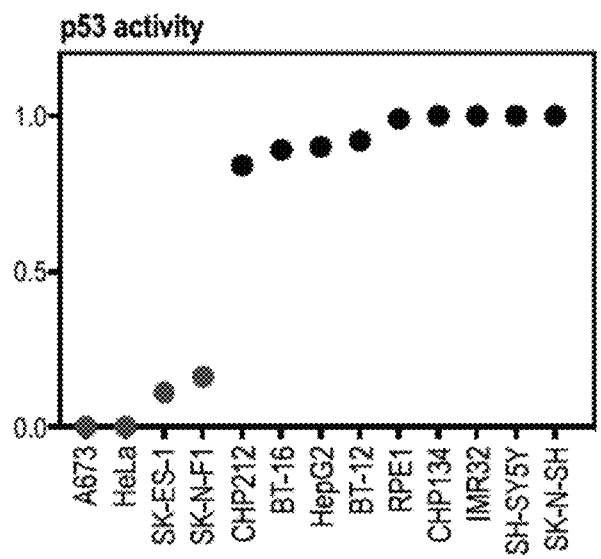
FIGS. 4A-4C show the quantification of p53 activity and TRIM37 protein levels.
Figure 4B:
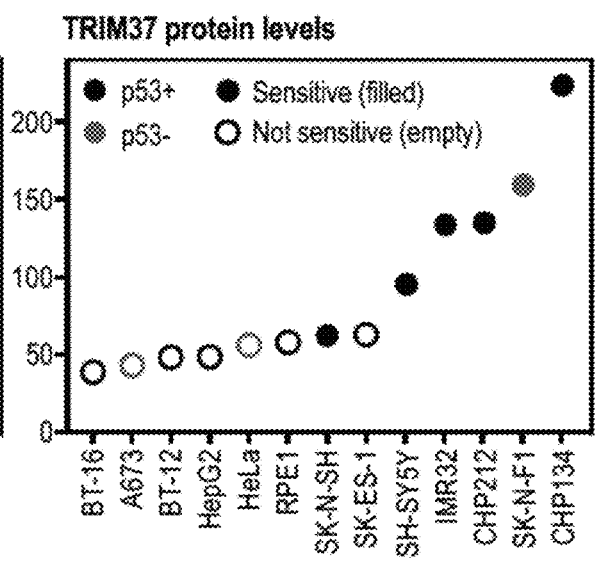
Figure 4C:
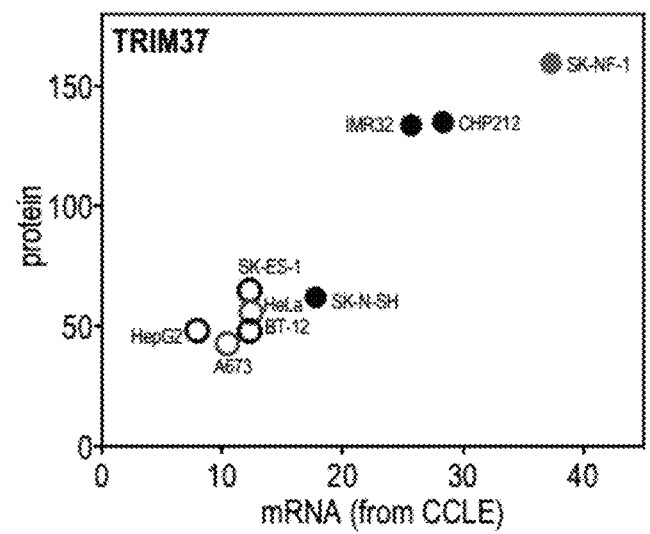

Next, p53 activity and TRIM37 protein levels across the same panel of cell lines as in FIG. 1 was examined. To measure p53 activity, cells were challenged by incubation with an inhibitor of Mdm2, an ubiquitin ligase that continuously targets p53 for proteasomal degradation. After incubation with Mdm2 inhibitor for 4 days, cells were counted and p53 activity was assessed quantified using the equation $A_{p53}=1-(C_{MDM2}-C_0)/(C_{CNTR}-C_0)$, where $C_{MDM2}$ was the cell count after 4 days in Mdm2 inhibitor; C0 was the number of cells seeded at the beginning of the experiment, and $C_{CNTR}$ was the cell count in the after 4 days growth without inhibitor. A value of 1 means that there was no cell proliferation after addition of Mdm2 inhibitor indicating fully functional p53, and a value of 0 means that proliferation was comparable in the presence and absence of Mdm2 inhibitor, indicating lack of functional p53. This analysis revealed that p53 was functional in RPE1 cells as well as 5 of the neuroblastoma cell lines (SH—SY5Y, CHP134, MR32, CHP212 and SK-N—SH) and 3 of the control cell lines (HepG2, BT-12, and BT-16) and was inactive in HeLa cells as well as 1 of the neuroblastoma cell lines (SK-N-F1) and two of the control cell lines (A673 and SK-ES-1) (FIG. 4A). TRIM37 protein levels were measured across the same panel of cell lines by quantitative western blotting (FIG. 4B). Among the p53+ cell lines (black in FIG. 4B), the five p53+ neuroblastoma cell lines all expressed more TRIM37 than the four p53+ control cell lines. Among the four p53− cell lines (FIG. 4B), the one p53-neuroblastoma cell line that we analyzed (SK-N-F1) expressed substantially more TRIM37 than the three p53− control cell lines. A comparison of this TRIM37 protein expression data with TRIM37 gene expression data from the Cancer Cell Line Encyclopedia also (Barretina et al., 2012) revealed a linear relationship, indicating that TRIM37 transcript levels are a good predictor of protein levels.

Thus, among the nine p53+ cell lines that were analyzed, the five with the highest TRIM37 protein levels were sensitive to centrinone, whereas the four with the lowest levels were not. Among the p53− cell lines, the one that expressed the highest levels of TRIM37 (SK-N-F1) was sensitive to centrinone and the other three cell lines, which had substantially lower TRIM37 protein levels, were not.

To examine the effects of centrosome removal, progression through mitosis after centrosome depletion was analyzed in three control cell lines with low TRIM37 levels (RPE1, BT-12 and BT-16), and in the three cell lines with the highest TRIM37 levels (CHP212, CHP134 and SK-N-F1). All of the tested cell lines, with the exception of SK-N-F1, were p53+. For control cultures grown in the absence of centrinone, no anaphase failure or cell death during mitosis was observed, with the exception of SK-N-F1 where a very low rate of cell death during mitosis was observed (3%, FIG. 5A). After three cell cycles in centrinone (when the majority of cells have lost their centrosomes), rates of anaphase failure and/or cell death during mitosis remained relatively low in the three cell lines with low TRIM37 levels (Range 3-14%), but were much higher in the cell lines with high TRIM37 levels (Range 31-74%, FIG. 5A). Thus, in contrast to the relatively low percentage of cells that failed mitosis when centrosomes were removed in the low TRIM37 cell lines, one third to three quarters of cells in the high TRIM37 cell lines failed to complete mitosis following centrosome removal.

For cells that completed mitosis, the inventors measured mitotic duration to determine if they would be likely to die due to tripping the mitotic duration sensor. For control cultures grown in the absence of centrinone, the mean duration of mitosis was similar for the five p53+ cell lines (Range 32.1 to 41.8 minutes, black bars in FIG. 5B). The mean duration of mitosis in control SK-N-F1 cells, a p53− neuroblastoma cell line, was longer (104.7 minutes). After three cell cycles in centrinone (when the majority of cells have lost their centrosomes), the mean duration of mitosis increased substantially (Range 69.4 to 490.3 minutes, FIG. 5B). The three cell lines with the low TRIM37 levels exhibited the lowest mean mitotic durations after centrinone treatment (Range 69.4 to 152.8) and the three cell lines with high TRIM37 levels exhibited the highest mean mitotic durations (Range 221.1 to 490.3 minutes).

Figure 5A:
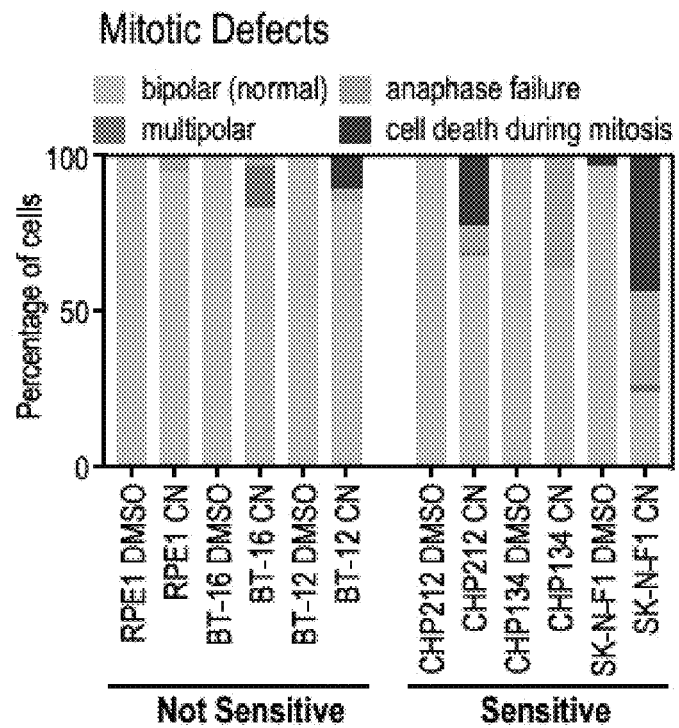
FIGS. 5A-5C shows PLK4 inhibition leads to mitotic failure and cell death due to activation of the mitotic duration sensor in cell lines expressing high levels of TRIM37.
Figure 5B:
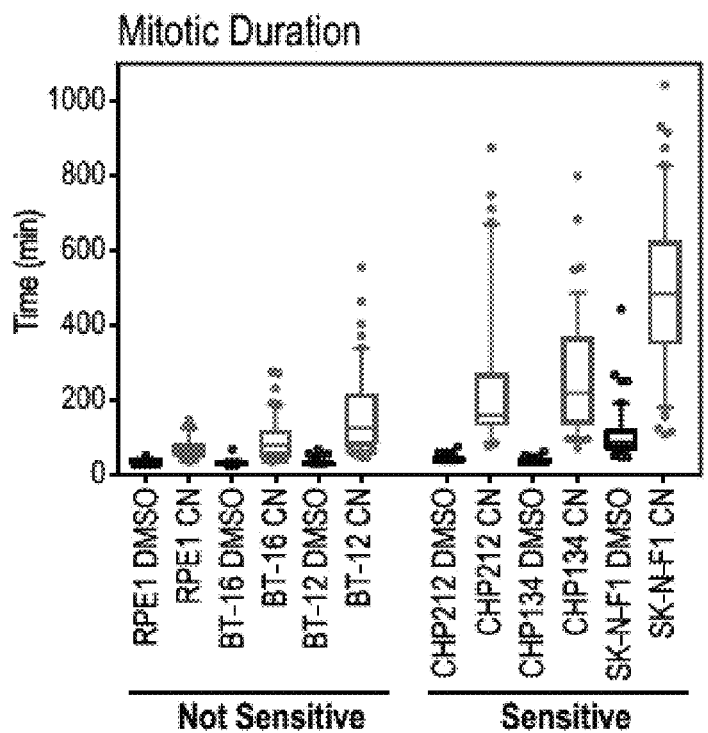
Figure 5C:
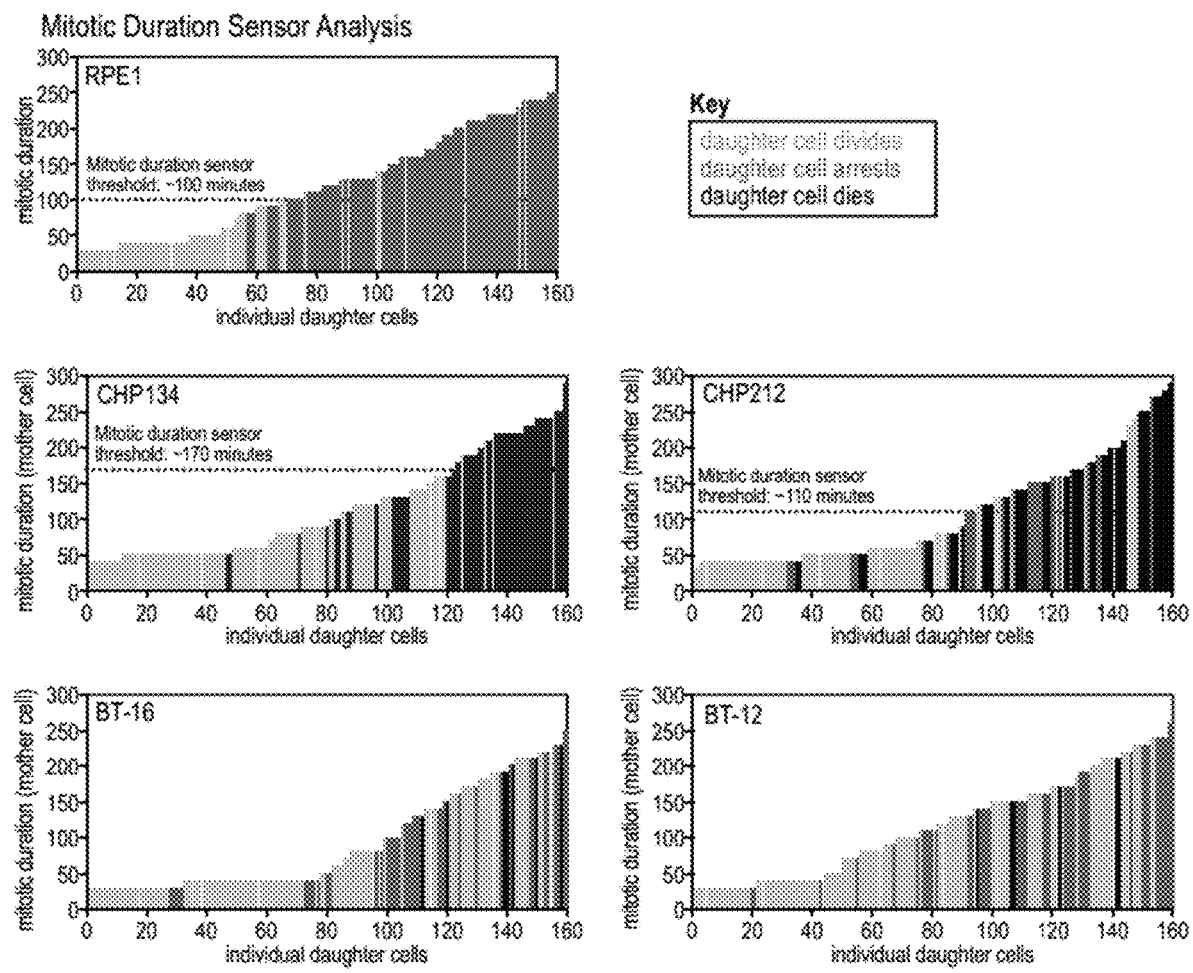

To determine whether the long times spent in mitosis in the p53+ cell lines would trigger p53 stabilization and death due to activation of the mitotic duration sensor, the procedure described in Meitinger et al., 2016 and Uetake et al., 2010 was used to assess the state of the mitotic duration sensor in each of the five p53+ cell lines (FIG. 5C). In this procedure, an inhibitor of the kinesin Eg5 (monastrol) was used to prolong mitosis for varying amounts of time, and daughter cells were followed for 48 hours after drug washout to determine whether they arrested, died (black bars) or divided (grey bars). In RPE1 cells mitotic durations greater than 100 minutes led to penetrant arrest, but no cell death, (Mitotic duration sensor threshold: about 100 minutes, FIG. 5C). In CIP134 cells, mitotic durations longer than a 170 minute threshold led to penetrant cell death (FIG. 5C). In CIP212 cells, mitotic durations longer than a 110 minute threshold led to a penetrant mixture of cell death and arrest (about 60% of cells died and about 30% arrested, FIG. 5C). Interestingly, despite the fact that BT-12 and BT-16 cells were p53+ they exhibited only a weak mitotic duration response, with very few daughter cells dying for mitotic durations up to 250 minutes in both cases (FIG. 5C). The results indicate that in the low TRIM37 cell lines the majority of the daughter cells resulting from successful mitosis would not die due to activation of the mitotic duration sensor. In contrast, for the two high TRIM37 cell lines that are p53+, the mean duration of mitosis after centrosome removal (221 and 257 minutes, respectively, for CHP212 and CHP134) is substantially higher than the mitotic duration thresholds for these cell lines (110 and 170 minutes, respectively, for CHP212 and CHP134), indicating that a large percentage of the daughter cells arising from the cells that managed to complete mitosis in the high TRIM37 cell lines would die to activation of the mitotic duration sensor. It was concluded that the rapid death of the high TRIM37 cell lines following centrosome removal due to PLK4 inhibition results from a combination of mitotic failure (FIG. 5A) and cell death due to activation of the mitotic duration sensor (FIG. 5B).

To determine whether the observed effects on mitosis were related to the high TRIM37 levels in the sensitive cell lines, a more detailed analysis in the CHP134 cell line was performed. The analysis described above suggested that about one third of CHP134 cells that enter the absence of centrioles would fail to segregate their chromosomes (FIG. 5A, about 36%). In addition, of the daughter cells generated by the cells that completed mitosis, the majority would die due to p53 stabilization resulting from activation of the mitotic duration sensor. If this was true, the inventors would expect that knockdown of p53 would substantially rescue the phenotype by eliminating the mitotic duration sensor. Similarly, if the high levels of TRIM37 were rendered the cells more sensitive to centrosome removal, the inventors would expect TRIM37 deletion to reduce mitotic duration, suppress mitotic failure, and enable proliferation in the presence of centrinone.

Figure 6A:
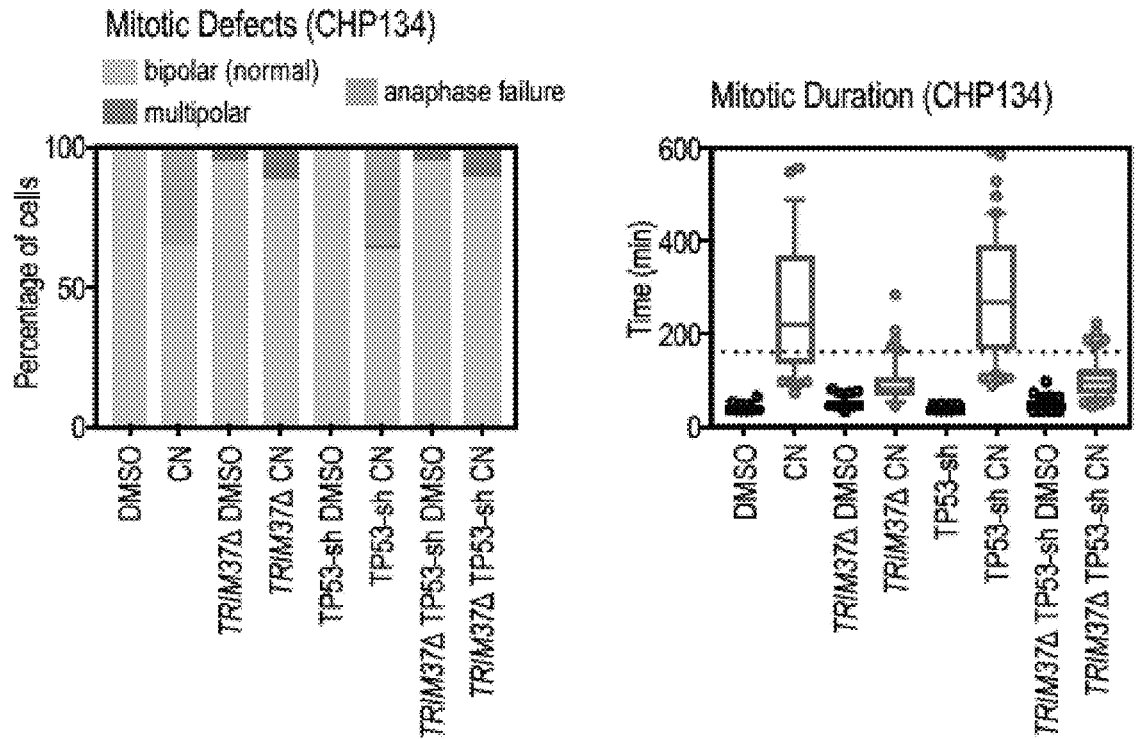
FIGS. 6A-6B show that TRIM37 deletion suppresses the mitotic defects resulting from PLK4 inhibition in CHP134 cells and restores their ability to proliferate.
Figure 6B:
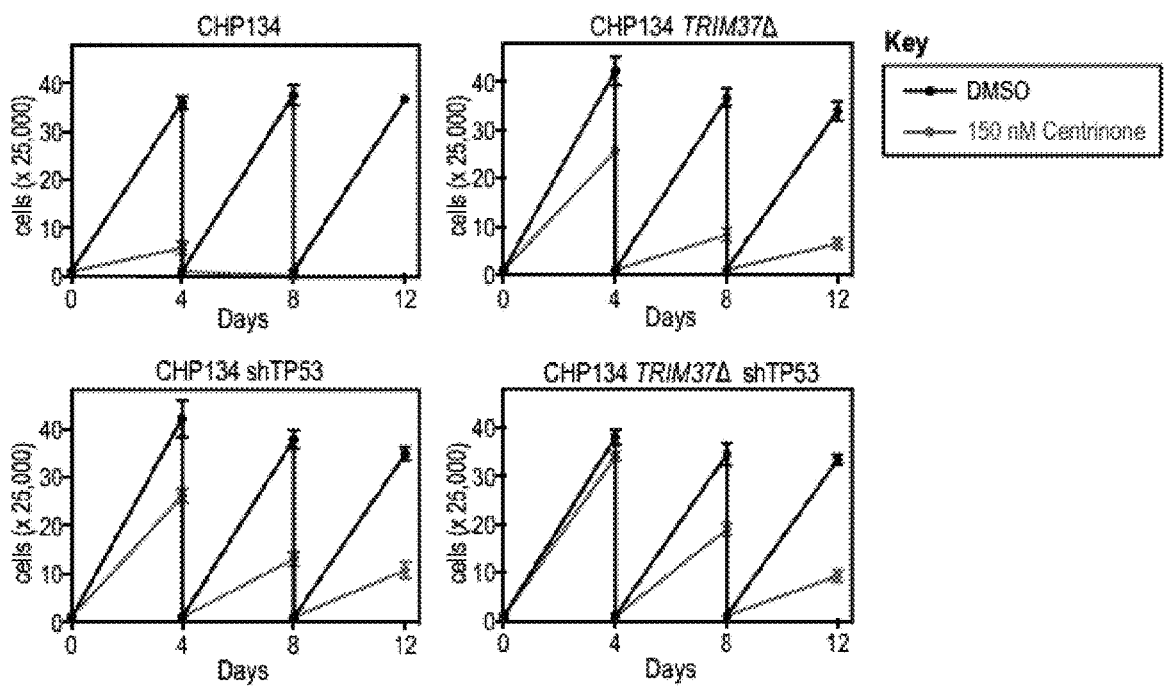

Consistent with these' expectations, TRIM37 deletion completely suppressed the anaphase failure and indicated the increase in mitotic duration observed in centrinone-treated CHP134 cells (FIG. 6A), and enabled their proliferation in a 12-day passaging assay (FIG. 6B). shRNA-mediated knockdown of p53, which abrogates the mitotic duration sensor, did not prevent the anaphase failure or increase in mitotic duration resulting from centrinone-mediated centrosome loss. However, it allowed CHP134 cells to proliferate in the 12-day passaging assay, presumably because it enabled daughter cells born after prolonged mitosis to continue to divide. As expected, CHP134 cells in which TRIM37 was deleted and p53 was knocked down also exhibited robust proliferation in centrinone (FIG. 6A, B).

Figure 7A:
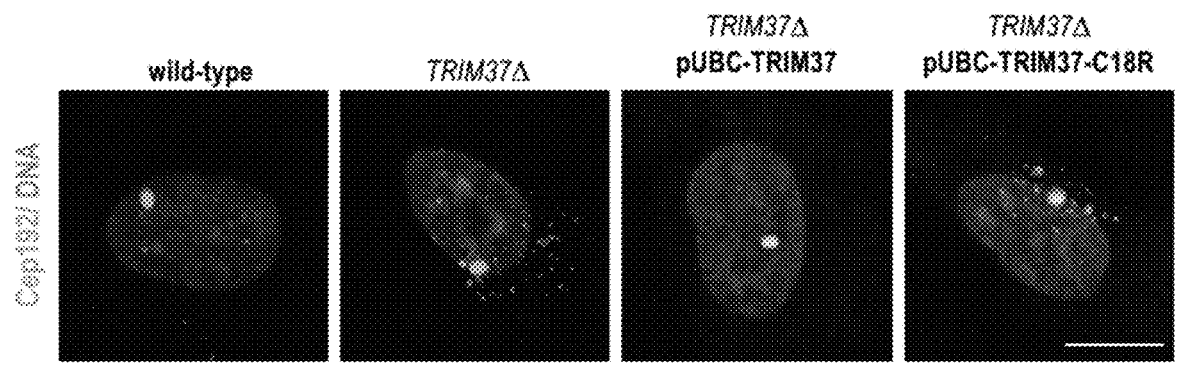
FIGS. 7A-7D show that ligase activity of TRIM37 prevents the assembly of ectopic foci containing centrosomal proteins.
Figure 7B:
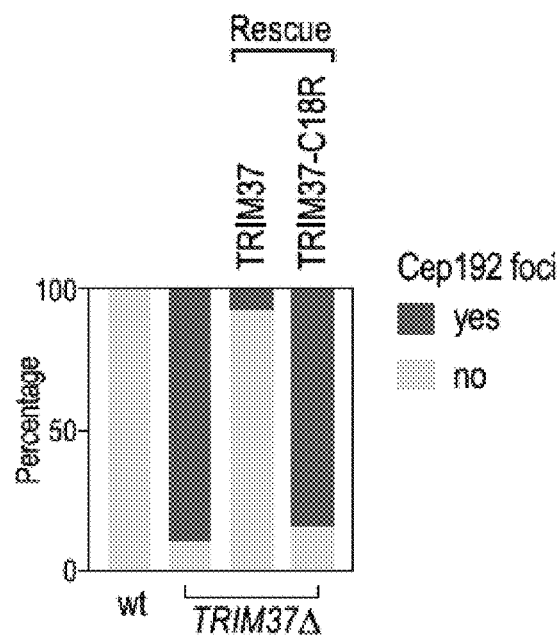
Figure 7C:
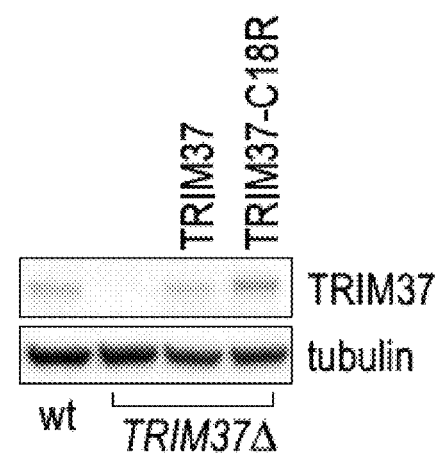
Figure 7D:
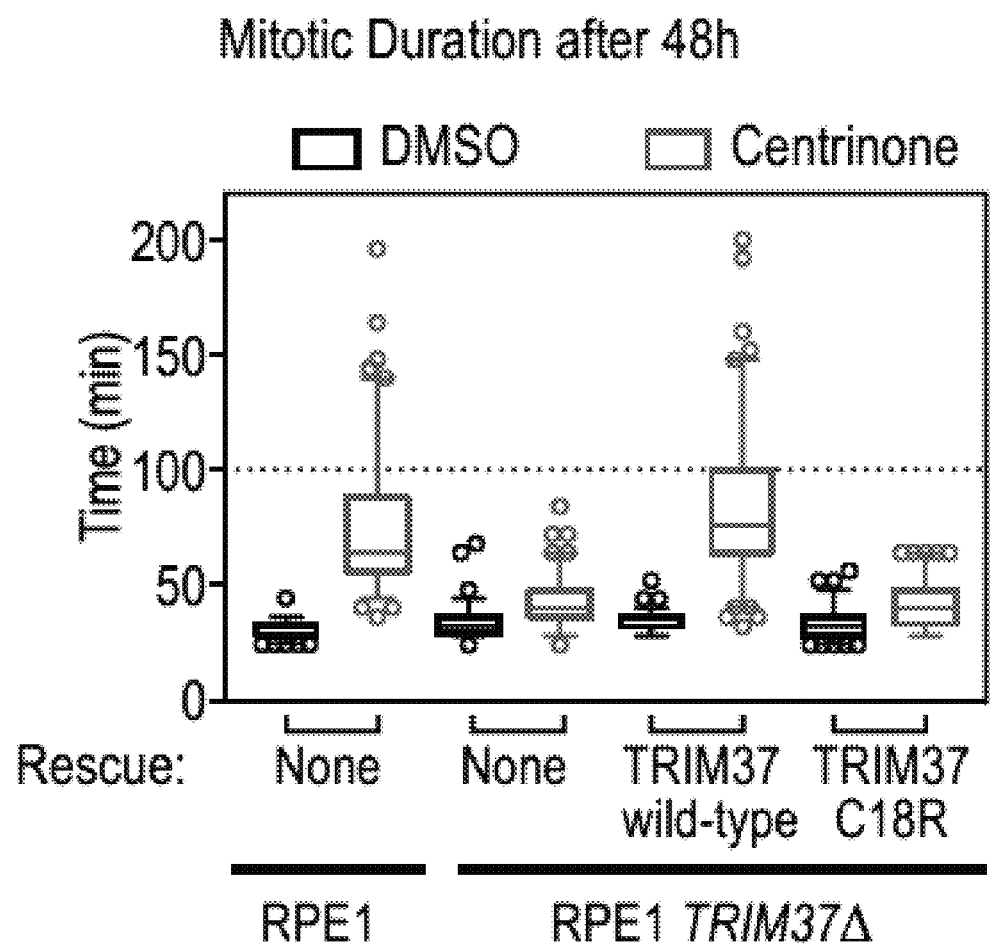

The normal activity of TRIM37 is to suppress the formation of ectopic centrosome-like foci. Cep192 is an E3 ubiquitin ligase of the TRIpartite Motif (TRIM) protein family. To determine if its ligase activity is important for its activity in antagonizing the formation of centrosome-like foci, the formation of foci containing the centrosomal protein Cep192 was examined in control RPE1 cells, RPE1 TRIM37Δ cells, along with RPE1 TRIM37Δ cells in which expression of wild-type TRIM37 or a TRIM37 mutant with a residue change previously shown to its ubiquitin ligase activity (TRIM37-C18R; (Bhatnagaar et al., 2014)) was reconstituted at levels comparable to those in unperturbed cells by expression under the UBC promoter (FIG. 7A-C). As expected this analysis revealed that the majority of TRIM37Δ cells exhibit a cluster of ectopic Cep192 foci that surround the centrosome. Expression of wild-type TRIM37, but not TRIM37-C18R, prevented formation of the ectopic Cep192 foci (FIG. 7A-C). Control RPE1 cells and RPE1 TRIM37Δ reconstituted with wild-type TRIM37 showed a substantial increase in mitotic duration after treatment with centrinone, likely due to difficulties in spindle assembly, whereas mitotic duration was only modestly increased following centrosome removal in RPE1 TRIM37Δ cells and in RPE1 TRIM37Δ cells reconstituted with the ligase dead $C_{18}R$ TRIM37 mutant, which have the ectopic Cep192-containing foci (FIG. 7D).

Example 2: Identifying PLK4 Inhibitor—Sensitive Lines

As shown in FIG. 8, plotting both TRIM 37 and CHGA mRNA—Seq values helps identify PLK4i-sensitive lines. PLK4i sensitivity was measured similarly to experiments described in FIG. 3B above.

Figure 9:
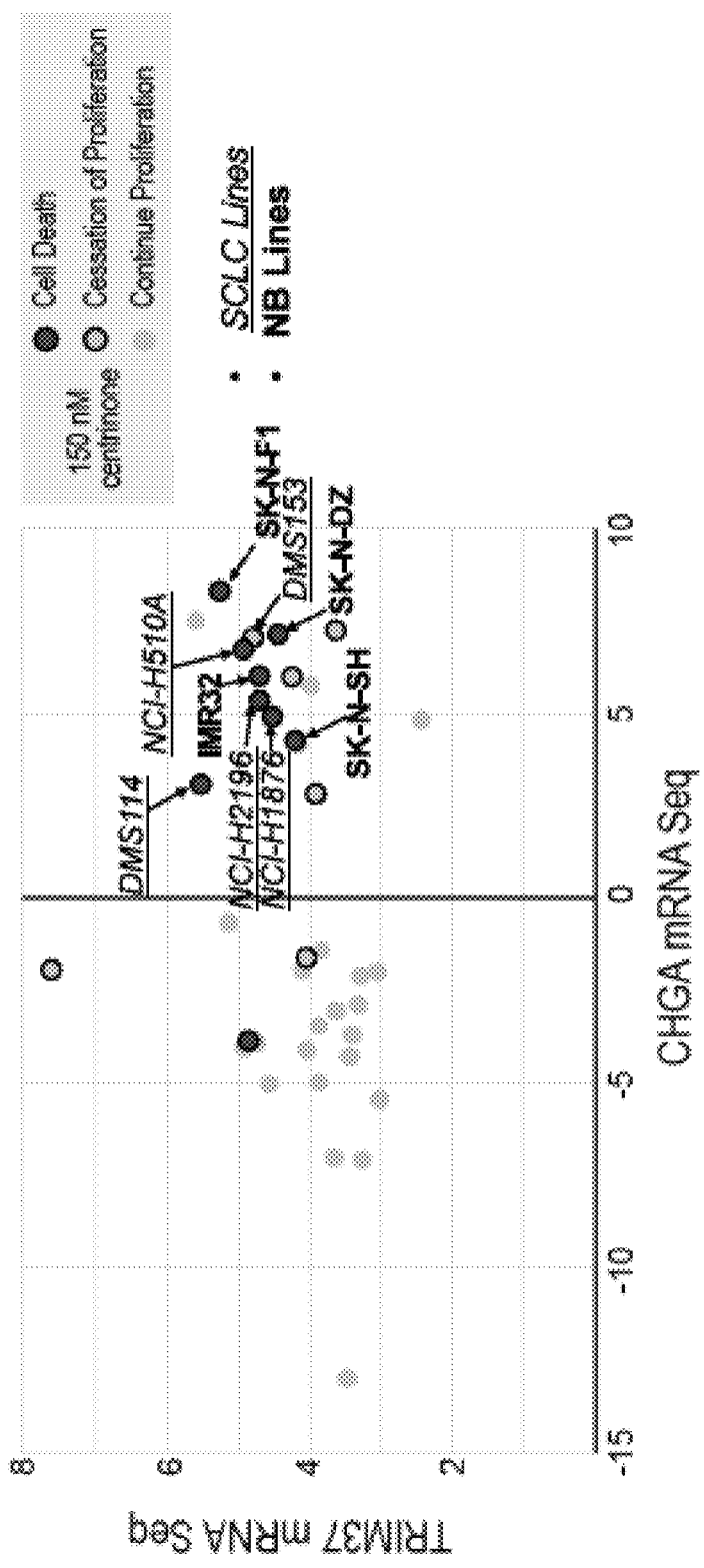
FIG. 9 shows a plot of CHGA versus TRIM37 mRNA—Seq values for a number of cell lines. The majority of PLK4i-sensitive lines express CHGA and high TRIM37. Small cell lung carcinoma cell lines are underlined and neuroblastoma (NB) cell lines are bolded. PLK4i sensitivity was measured similarly to experiments in FIG. 3B above.

As shown in FIG. 9, the majority of PLK4i-sensitive lines express CHGA and high TRIM37. PLK4i sensitivity was measured similarly to experiments described in FIG. 3B above.

Example 3: Experimental Methods

Cell lines: Cells were maintained in ATCC-recommended complete growth media with 100 U/mL penicillin and 100 μg/mL streptomycin at 37° C. and 5% CO2. The RPE-1 TRIM37Δ knockout cell line was previously described (Meitinger et al., 2016). The CHP134 and HCT116 TRIM37Δ knockout cell lines were generated by transfection and nucleofection, respectively, of preassembled RNPs using a TRIM37 specific gRNA (CTCCC-CAAAGTGCACACTGA). The CHP134 G95L cell line was generated as previously described (Wong et al., 2015). For generation of H2B-mRFP expressing cell lines, cells were infected with a H2B-mRFP expressing lentiviral construct (Meitinger et al., 2016). Populations of each cell line expressing H2B-mRFP were enriched by FACS. To knock down TP53 (p53), cells were infected with a lentivirus containing sh-p53 made using the plasmid shp53 pLKO.1 puro (Godar et al., Cell. 134:62-73 (2008)). Positive selection of sh-p53 expressing cells was performed 2 days after infection with 10 μg/ml puromycin.

Proliferation assays: Cells were seeded in triplicates for each condition into 6-well plates at 25,000-150,000 cells/well and treated with DMSO (control) or 150 nM centrinone. Plated cell numbers were adjusted to the cell line characteristics (doubling time and cell size). At 96-hour intervals, plates were harvested, counted and re-plated at 25,000-150,000 cells/plate. Cell counting was performed using a TC20 automated cell counter (Bio-Rad).

Immunoblot and quantification of TRIM37 protein level: Cells were grown in 10 cm plates, harvested at 70-80% confluence and lysed by sonication in RIPA buffer+protease and phosphatase inhibitor cocktail (Thermo Scientific). Cell extracts were stored at −80° C. until use. Before use, extract concentrations were normalized based on a Bio-Rad Protein Assay (Bio-Rad). For each sample, 30 g protein/lane was run on Mini-PROTEAN gels (Bio-Rad), and transferred to PVDF membranes using a TransBlot Turbo system (Bio-Rad). Blocking and antibody incubations (DM1A, anti-α-tubulin, 1:5000, Sigma-Aldrich; anti-GAPDH, 1:1000, Cell Signaling, 14C10; anti-Trim37, 1:2000, Bethyl Laboratories, A301-174A) were performed in TBS-T+5% non-fat dry milk. Detection was performed using HRP-conjugated secondary antibodies (GE Healthcare) with SuperSignal West Femto (Thermo Scientific) substrates. Membranes were imaged on a ChemiDoc MP system (Bio-Rad). Ponceau S staining and antibodies against α-tubulin or GAPDH served as loading controls.

Standard for TRIM37 protein levels: Lysates from wild-type and TRIM37Δ HCT116 cells were mixed in different ratios (100/0; 50/50; 25/75; 12.5/87.5 and 0/100) and loaded onto each gel together with lysates from other cell lines. A standard curve was generated for each immunoblot. TRIM37 levels were measured using Image Lab software. Relative TRIM37 levels for each cell line was determined from the corresponding standard curve relative to TRIM37 levels in HCT116 lysates.

Assessing mitotic phenotypes: First, the cell cycle duration of the indicated cell lines was determined for each cell line by imaging cells expressing H2B-mRFP for 48-72 hours. The mean time from the beginning the first mitosis (nuclear envelope breakdown) until the beginning of the second mitosis in each daughter cell was the cell line specific cell cycle duration. To measure the mitotic characteristics for centrinone treated and untreated conditions, cells were grown for three cell cycle durations in 150 nM centrinone or DMSO prior to imaging. Cells were seeded into 96-well polystyrene plates at 10,000 cells/well, 14-16 hours before imaging. Images were acquired on a CQ1 spinning disk confocal systems (Yokogawa Electric Corporation) with an Olympus UPLSAPO40 X 40×0.95 objective and 2560×2160 sCMOS camera (Andor) at 37° C. and 5% CO2 at 2×2 binning. Image acquisition and data analysis were performed using CellVoyager software and ImageJ, respectively. 12-24 fields/well were imaged. 5×2 μm z-sections in RFP (25% power, 150 ms) channels were captured in each field at 4-minute intervals for 24 hours. Mitotic duration was measured as the interval between nuclear envelope breakdown and chromosome decondensation. Mitotic phenotypes were categorized into 'bipolar', 'multipolar', 'cell death during mitosis' and 'anaphase failure'.

Characterization of the mitotic duration sensor: The correlation between mother cell mitotic duration and daughter cell fate was analyzed in stable cell lines expressing H2B-mRFP. Cells were seeded into 96-well polystyrene plates at 1000-2000 cells/well, 12-14 hours before imaging. Cells were treated with 100 μM monastrol and immediately imaged on the CQ1 spinning disk confocal system (Yokogawa Electric Corporation) with an Olympus UPLSAPO20 X 20×0.75 NA U-PlanApo objective and 2560× 2160 sCMOS camera (Andor) at 37° C. and 5% CO2 at 2×2 binning. Image acquisition and data analysis were performed using CellVoyager software and ImageJ, respectively. 30 fields/well were imaged. 5×2 μm z-sections in RFP (25% power, 150 ms) were acquired in each field at 10-minute intervals for 190 minutes. The plate was then removed from the microscope, and wells were washed twice with warm medium. The plate was returned to the microscope and imaging was resumed for additional 48-72 hours at 10 minutes intervals. The fate of daughter cells was analyzed and categorized into 'arrest', 'cell death' or 'dividing'.

Caspase activation assay: To measure activation of the apoptosis pathway, 250-1000 cells/well were seeded into 96 well plates and treated for four cell cycle durations with DMSO, 150 nM centrinone or 500 nM centrinone B. Cells were then treated with 6.5 µM Hoechst 33342 (Invitrogen) and 25 µl/ml CellEvent™ Caspase-3/7 Green (Invitrogen) for 20 min. The entire wells with labeled cells were imaged on the CQ1 spinning disk confocal system (Yokogawa Electric Corporation) with an Olympus UPLSAPO10X2 10×0.4 NA U-PanApo objective and 2560×2160 sCMOS camera (Andor) at 37° C. and 5% CO2 and at 2×2 binning. Image acquisition and data analysis were performed using CellVoyager software and CV7000 analysis software, respectively.

p53 activity assay: To measure p53 activity in the different cell lines, 25,000-100,000 cells were plated in triplicates into 6-well plates and treated for four days with 1 µM MDM2 inhibitor ((2-(4-(tert-butyl)-2-ethoxyphenyl)-4,5-bis (4-chlorophenyl)-4,5-dimethyl-4,5-dihydro-1H-imidazol-1-yl)(4-(3-(methylsulfonyl)propyl)piperazin-1-yl)methanone). After 4 days, cells were counted. The equation $A_{p53}=1-(C_{MDM2}-C_0)/(C_{CNTR}-C_0)$ was used to calculate the activity of p53 ($A_{p53}$, p53 activity; $C_{MDM2}$, cell count after 4 days MDM2 inhibitor treatment; C0, cells seeded at the beginning of the experiment; $C_{CNTR}$, cell count in the after 4 days growth without inhibitor; negative values for ($C_{MDM2}-C_0$) were set to 0).

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. It should be understood that various alternatives to the embodiments described herein may be employed.

What is claimed is:

1. A method of treating cancer in a subject in need thereof, the method comprising;
   (i) measuring a TRIM37 level in a biological sample obtained from the subject; and
   (ii) administering to the subject an effective amount of a PLK4 inhibitor to treat the cancer;
   wherein the subject has an elevated level of TRIM37 when compared to a control.

2. The method of claim 1, wherein the cancer is a pediatric cancer.

3. The method of claim 1, wherein the cancer is a rhabdoid tumor, a neuroblastoma, an acute lymphoblastic leukemia tumor, a brain and central nervous system tumor, small cell lung cancer, melanoma, breast cancer, acute myeloid leukemia, Ewing's sarcoma, prostate cancer, basal cell carcinoma, medulloblastoma, glioma, a non small cell lung cancer, mesothelioma, osteosarcoma, soft tissue sarcoma, or -T cell lymphoma.

4. The method of claim 1, wherein the cancer is a p53 positive cancer is a wild-type p53 positive cancer or a mutant p53 positive cancer.

5. The method of claim 1, further comprising administering an effective amount of a chemotherapeutic agent to the subject, radiation therapy, or a combination thereof.

6. The method of claim 5, wherein the chemotherapeutic agent is a tubule polymerization inhibitor, cyclophosphamide, ifosfamide, cisplatin, carboplatin, doxorubicin, etoposide, topotecan, busulfan, melphalan, or a combination of two or more thereof.

7. The method of claim 6, wherein the tubule polymerization inhibitor is vincristine, vinblastine, vinorelbine, vinflunine, a dolastatin, a halichondrin, a hemiasterlin, cryptophycin 2, or a combination of two or more thereof.

8. The method of claim 1, further comprising administering differentiation therapy to the subject; wherein the differentiation therapy comprises retinoic acid, arsenic trioxide, or a combination thereof.

9. The method of claim 1, wherein the PLK4 inhibitor is a compound having the structure:

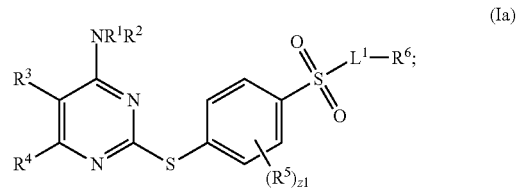

(Ia)

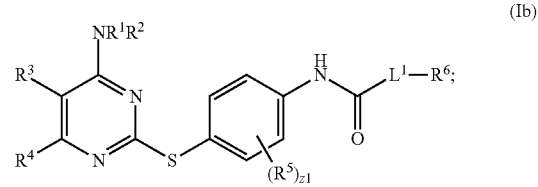

(Ib)

or a pharmaceutically acceptable salt of one of the foregoing;
wherein:
$L^1$ is a bond, —C(O)—, —C(O)O—, —O—, —S—, —$NR^{13}$—, —C(O)$NR^{13}$—, —$NR^{13}$C(O)—, —S(O)$_2$—, —S(O)$NR^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{13}$ is hydrogen, oxo, halogen, —CN, —OH, —COOH, —CONH$_2$, —NO$_2$, —SH, —S(O)$_2$Cl, —S(O)$_3$H, —S(O)$_4$H, —S(O)$_2$NH$_2$, —NHNH$_2$, —NHC(O)NHNH$_2$, —NHC(O)NH$_2$, —NHS(O)$_2$H, —NHC(O)H, —NHC(O)—OH, —NHOH, —OCHF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_n$R$^{1A}$, —S(O)$_n$OR$^{1A}$, —S(O)$_n$NR$^{1A}$R$^{1B}$, —HNR$^{1A}$R$^{1B}$—ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$N_3$, —$CF_3$, —$CCl_3$, —$CBr_3$, —$CI_3$, —CN, —$COR^{2A}$, —$OR^{2A}$, 13 $NR^{2A}R^{2B}$, C(O) $OR^{2A}$, —C(O)$NR^{2A}R^{2B}$, $NO_2$, $SR^{2A}$, —S(O)$_{n2}R^{2A}$, —S(O)$_{n2}OR^{2A}$, —S(O)$_{n2}NR^{2A}R^{2B}$, —$NHNR^{2A}R^{2B}$, —$ONR^{2A}R^{2B}$, —NHC(O)$NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$N_3$, —$CF_3$, —$CCl_3$, —$CBr_3$, —$CI_3$, —CN, —$COR^{3A}$, —$OR^{3A}$, —$NR^{3A}R^{3B}$, —C(O)$OR^{3A}$, —C(C)$NR^{3A}R^{3B}$, —$NO_2$, —$SR^{3A}$, —S(O)$_{n3}R^{3A}$, —S(O)$_{n3}OR^{3A}$, —S(O)$_{n3}NR^{3A}R^{3B}$, —$NHNR^{3A}R^{3B}$, —$ONR^{3A}R^{3B}$, (O)$NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$N_3$, —$CF_3$, —$CCl_3$, —$CBr_3$, —$CI_3$, —CN, —$COR^{4A}$, —$NR^{4A}R^{4B}$, —C(O)$OR^{4A}$, —C(O)$NR^{4A}R^{4B}$, $NO_2$, —$SR^{4A}$, —S(O)$_{n4}R^{4A}$, —S(O)$_{n4}OR^{4A}$, —S(O)$_{n4}NR^{4A}R^{4B}$, —$NHNR^{4A}R^{4B}$, —$ONR^{4A}R^{4B}$,—NHC(O)$NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein $R^3$ and $R^4$ are optionally combined to form a substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, —$N_3$, —$CF_3$, —$CCl_3$, —$CBr_3$, —$CI_3$, —CN, —$COR^{5A}$, —$OR^{5A}$, —$NR^{5A}R^{5B}$, —C(O)$OR^{5A}$, —C(O)$NR^{5A}R^{5B}$, —$NO_2$, —$SR^{5A}$, —S(O)$_{n5}R^{5A}$, —S(O)$_{n5}OR^{5A}$, —S(O)$_{n5}NR^{5A}R^{5B}$, —$NHNR^{5A}R^{5B}$, —$ONR^{5A}R^{5B}$, —NHC(O)$NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, oxo, halogen, —$N_3$, —$CF_3$, —$CCl_3$, —$CBr_3$, —$CI_3$, —CN, —CHO, —$OR^{6A}$, —$NR^{6A}R^{6B}$, —C(O)$OR^{6A}$, —C(O)$NR^{6A}R^{6B}$, —$NO_2$, —$SR^{6A}$, —S(O)$_{n6}R^{6A}$, —S(O)$_{n6}OR^{6A}$, —S(O)$_{n6}NR^{6A}R^{6B}$, —$NHNR^{6A}R^{6B}$, —$ONR^{6A}R^{6B}$, —NHC(O)$NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n1, n2, n3, n4, n5, and n6 are independently 1 or 2;

z1 is 1, 2, 3, or 4; and $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, and $R^{6B}$ are independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —$NHS(O)_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

10. The method of claim 9, wherein the PLK4 inhibitor is a compound having the structure:

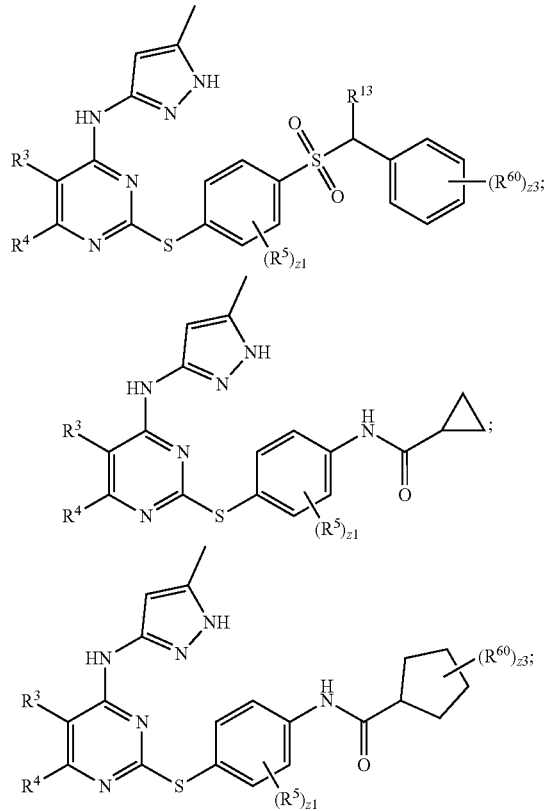

or a pharmaceutically acceptable salt of one of the foregoing;

wherein:

z3 is an integer of 0, 1, 2, 3, 4, or 5;

$R^{13}$ is hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —$NHS(O)_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{60}$ is hydrogen, halogen, —$N_3$, —$CF_3$, —$CCl_3$, —$CBr_3$, —$CI_3$, —CN, —$COR^{61}$, —$OR^{60A}$, —$NR^{60A}R^{60B}$, —C(O)$OR^{60A}$, —C(O)$NR^{60A}R^{60B}$, —$NO_2$, —$SR^{60A}$, —S(O)$_2$H, —S(O)$_2$OH, —S(O)$_2NH_2$, —$NHNH_2$, —$ONH_2$, —NHC(O)$NHNR^{60A}R^{60B}$, $R^{61}$ substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl;

$R^{60A}$ and $R^{60B}$ are each independently hydrogen, oxo, halogen, —$N_3$, —$CF_3$, —$CCl_3$, —$CBr_3$, —$CI_3$, —CN, —OH, —NH₂, —COOH, —CONH₂, —COH, —COCH₃, —NO₂, —SH, —S(O)₂Cl, —S(O)₃H, —S(O)₄H, —S(O)₂NH₂, —NHNH₂, —ONH₂, —NHC(O)NHNH₂, —NHC(O)NH₂, —NHS(O)₂H, —NHC(O)H, —NHC(O)—OH, —NHOH, —OCHF₂, unsubstituted alkyl, unsubstituted heteroalkyl, unsubstituted cycloalkyl, unsubstituted heterocycloalkyl, unsubstituted aryl, or unsubstituted heteroaryl; and R⁶¹ is hydrogen, oxo, halogen, —N₃, —CF₃, —CCl₃, —CBr₃, —CI₃, —CN, —OH, —NH₂, —COOH, —CONH₂, —COH, —COCH₃, —NO₂, —SH, —S(O)₂Cl, —S(O)₃H, —S(O)₄H, —S(O)₂NH₂, —NHNH₂, —ONH₂, —NHC(O)NHNH₂, —NHC(O)NH₂, —NHS(O)₂H, —NHC(O)H, —NHC(O)-OH, —NHOH, —OCHF₂, unsubstituted alkyl, unsubstituted heteroalkyl, unsubstituted cycloalkyl, unsubstituted heterocycloalkyl, unsubstituted aryl, or unsubstituted heteroaryl.

11. The method of claim 9, wherein the PLK4 inhibitor is a compound having the structure:

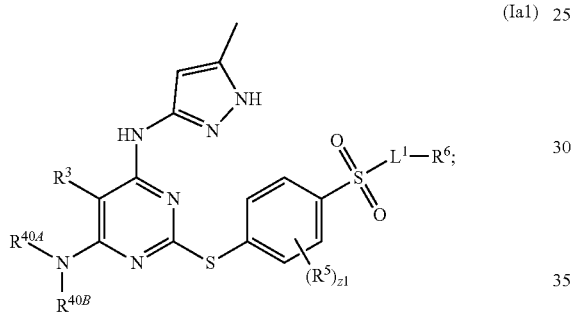
(Ia1)

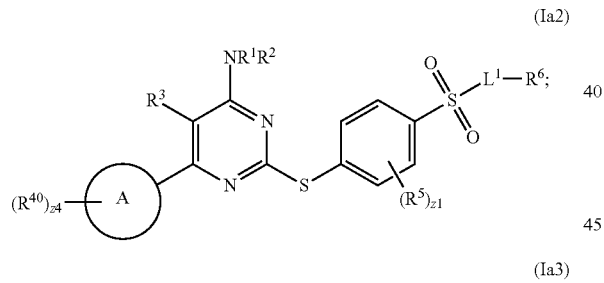
(Ia2)

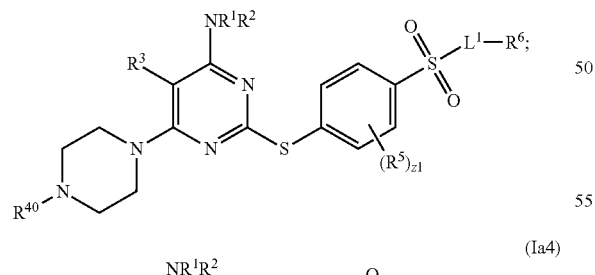
(Ia3)

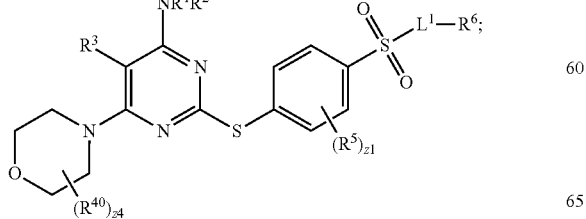
(Ia4)

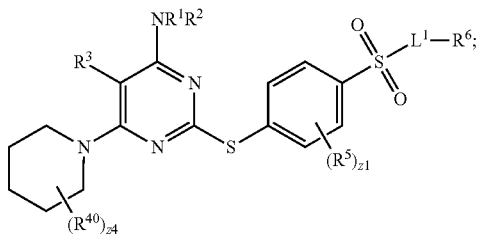
(Ia5)

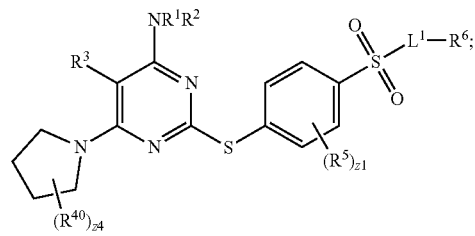
(Ia6)

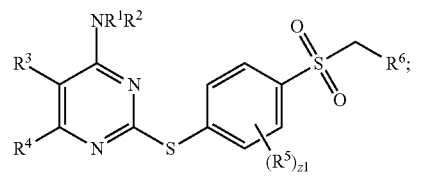
(Ia7)

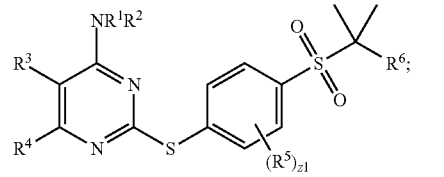
(Ia8)

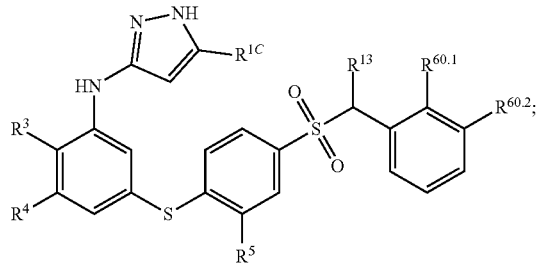
(IC)

or a pharmaceutically acceptable salt of one of the foregoing;
wherein:
Ring A is cycloalkyl or heterocycloalkyl;
z4 is an integer of 0, 1, 2, 3, 4, 5, 6, or 7 in Formula (Ia2);
z4 is an integer of 0, 1, 2, 3, or 4 in Formula (Ia4) and Formula (Ia6)₁
z4 is an integer of 0, 1, 2, 3, 4, or 5 in Formula (Ia5);
R⁴⁰ is independently oxo, halogen, —N₃, —CF₃, —CCl₃, —CBr₃, —CN, —COR⁴⁰ᴬ, —OR⁴⁰ᴬ, —NR⁴⁰ᴬR⁴⁰ᴮ, —C(O)OR⁴⁰ᴬ, —C(O)NR⁴⁰ᴬR⁴⁰ᴮ, —NO₂, —SR⁴⁰ᴬ, —S(O)₂R⁴⁰ᴬ, —S(O)₂OR⁴⁰ᴬ, —S(O)₂NR⁴⁰ᴬR⁴⁰ᴮ, —NHNR⁴⁰ᴬR⁴⁰ᴮ, —ONR⁴⁰ᴬR⁴⁰ᴮ, —NHC(O)NHNR⁴⁰ᴬN⁴⁰ᴮ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{40A}$ and R$^{40B}$ are each independently hydrogen, oxo, halogen, —N$_3$, —CF$_3$, —CCl$_3$, —CBr$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl;

R$^{1C}$ is independently halogen, oxo, N$_3$, —CF$_3$, —CCl$_3$, —CBr$_3$, —CI$_3$, —CN, —OH, —COR$^{1D}$, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)-OH, —NHOH, —OCHF$_2$, unsubstituted alkyl, unsubstituted heteroalkyl, unsubstituted cycloalkyl, unsubstituted heterocycloalkyl, unsubstituted aryl, or unsubstituted heteroaryl;

R$^{1D}$ is hydrogen, halogen, oxo, N$_3$, —CF$_3$, —CCl$_3$, —CBr$_3$, —CN, —OH, —NH$_2$, —COOH, —CONH$_2$, —COH, —COCH$_3$—NO$_2$, —SH, —S(O)$_2$Cl, —S(O)$_3$H, —S(O)$_4$H, —S(O)$_2$NH, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted heteroalkyl, unsubstituted cycloalkyl, unsubstituted heterocycloalkyl, unsubstituted aryl, or unsubstituted heteroaryl;

R$^{60.1}$ and R$^{60.2}$ are independently hydrogen, halogen, —N$_3$, —CF$_3$, —CCl$_3$, —CBr$_3$, —CI$_3$, —CN, —COR$^{61}$, —OR$^{60A}$, —NR$^{60A}$R$^{60B}$, —C(O)OR$^{60A}$, —C(O)NR6$^{0A}$R$^{60B}$, —NO2, SR$^{60A}$, —S(O)$_2$H, —S(O)$_{20}$H, —S(O)$_2$NH$_2$, —NHNH$_2$, —ONH$_2$, —NHC(O)NHNR$^{60A}$R$^{60B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{60A}$ and R$^{60B}$ are each independently hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCHF$_2$, unsubstituted alkyl, unsubstituted heteroalkyl, unsubstituted cycloalkyl, unsubstituted heterocycloalkyl, unsubstituted aryl, or unsubstituted heteroaryl; and R$^{61}$ is hydrogen, oxo, halogen, —N$_3$, —CF$_3$, —CCl$_3$, —CBr$_3$, —CI$_3$, —CN, —OH, —NH$_2$, —COOH, —CONH$_2$, —COH, —COCH$_3$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O) NH$_2$, —NHS(O)$_2$H, —NHC(O)H, —NHC(O)—OH, —NHOH, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

12. The method of claim 11, wherein the wherein the compound of Formula (Ia3) is:

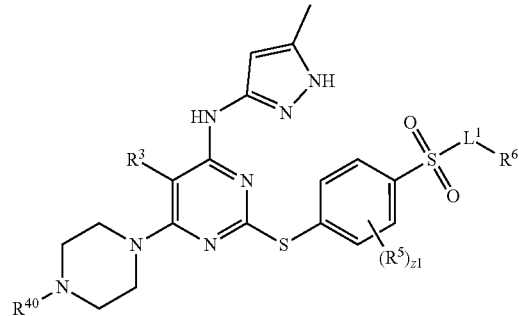

or a pharmaceutically acceptable salt thereof; wherein the compound of Formula (Ia4) is:

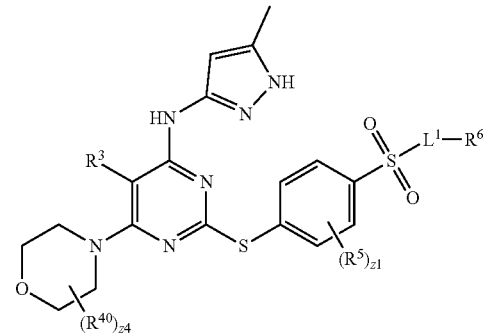

or a pharmaceutically acceptable salt thereof; wherein the compound of Formula (Ia5) is:

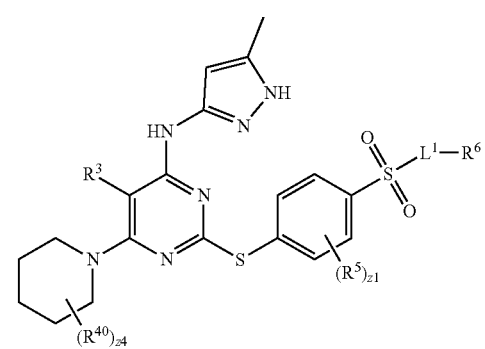

or a pharmaceutically acceptable salt thereof; wherein the compound of Formula (Ia6) is:

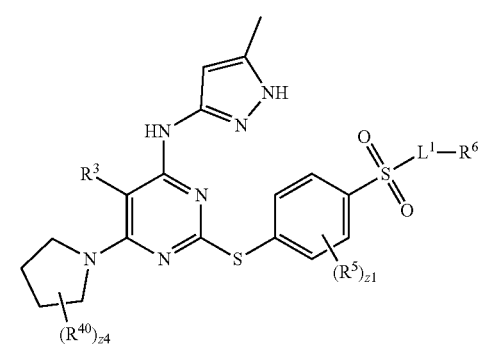

or a pharmaceutically acceptable salt thereof;
wherein the compound of Formula (Ia7) is:

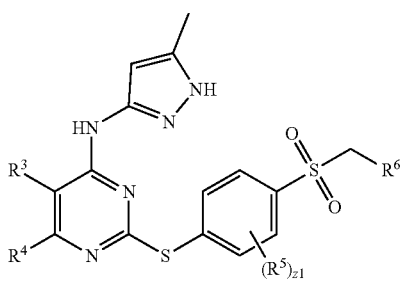

or a pharmaceutically acceptable salt thereof; and
wherein the compound of Formula (Ia8) is:

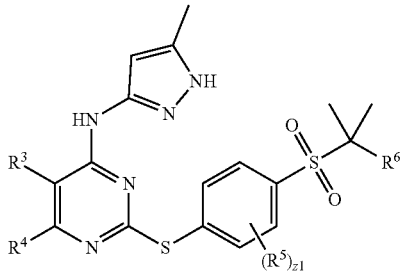

or a pharmaceutically acceptable salt thereof.

13. The method of claim 9, wherein the compound of Formula (Ia) is:

(Ia9a)

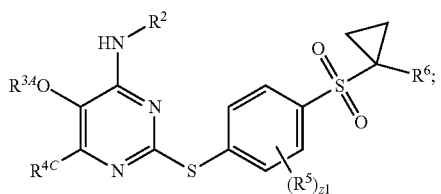

(Ia9b)

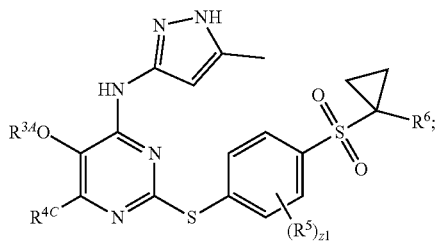

(Ia9c)

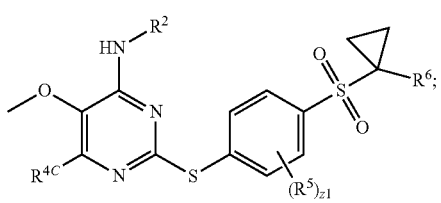

-continued (Ia9d)

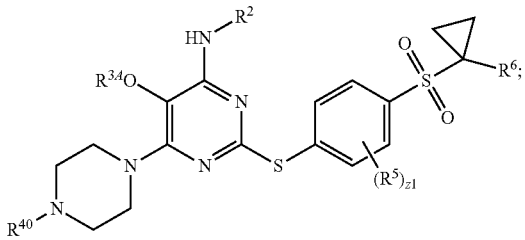

(Ia9f)

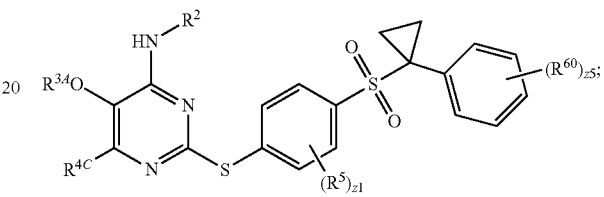

or a pharmaceutically acceptable salt of one of the foregoing;
wherein:
$R^2$ is substituted or unsubstituted heteroaryl;
$R^{3A}$ is substituted or unsubstituted alkyl;
$R^{4C}$ is substituted or unsubstituted heterocycloalkyl;
$R^5$ is halogen;
$R^6$ is substituted or unsubstituted aryl;
$R^{40}$ is substituted or unsubstituted alkyl or substituted or unsubstituted heteroalkyl;
$R^{60}$ is halogen or —$NO_2$;
z1 is 1;
z5 is 1 or 2.

14. The method of claim 9, wherein the compound of Formula (Ib) is:

(Ib1)

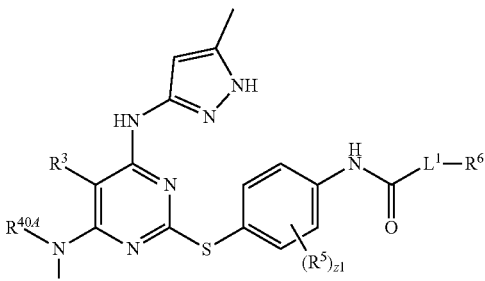

(Ib2)

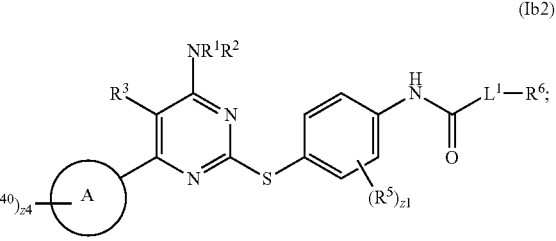

-continued (Ib3)
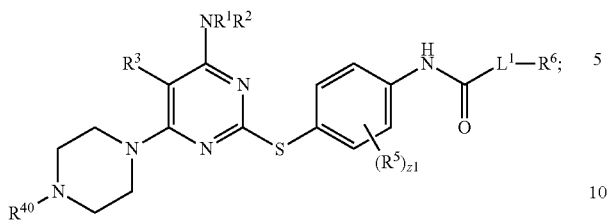

(Ib4)
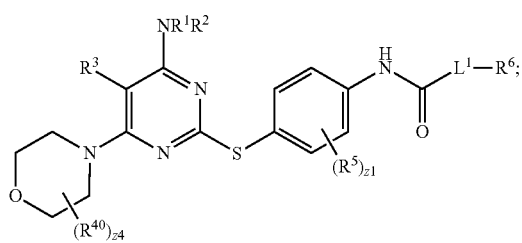

(Ib5)
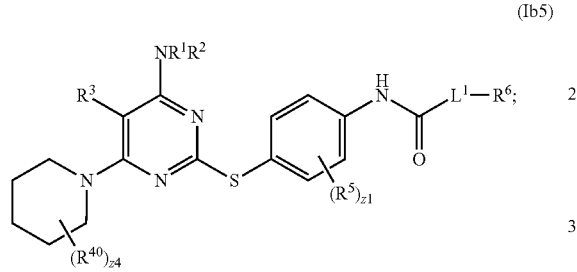

(Ib6)
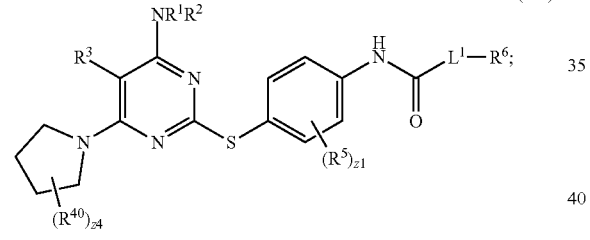

(Ib7)
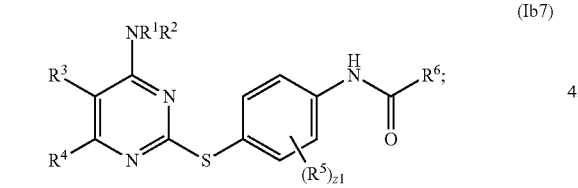

or a pharmaceutically acceptable salt of one of the foregoing;

wherein:

Ring A is cycloalkyl or heterocycloalkyl;

z4 is an integer of 0, 1, 2, 3, 4, 5, 6, or 7 in Formula (Ib2);

z4 is an integer of 0, 1, 2, 3, or 4 in Formula (Ib4) and Formula (Ib6);

z4 is an integer of 0, 1, 2, 3, 4, or 5 in Formula (Ib5);

$R^{40}$ is independently oxo, halogen, —$N_3$, —$CF_3$, —$CCl_3$, —$CBr_3$, —$CI_3$, —CN, —$COR^{40A}$, —$OR^{40A}$, $NR^{40A}R^{40B}$ —$C(O)OR^{40A}$, —$C(O)NR^{40A}R^{40B}$, —$NO_2$, $SR^{40A}$, $S(O)_2R^{40A}$, —$S(O)_2OR^{40A}$, —$S(O)_2NR^{40A}R^{40B}$, —$NHNR^{40A}R^{40B}$—$ONR^{40A}R^{40B}$—$NHC(O)$ $NHNR^{40A}N^{40B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{40A}$ and $R^{40B}$ are each independently hydrogen, oxo, halogen, —$N_3$, —$CF_3$, —$CCl_3$, —$CBr_3$, —$CI_3$, —CN, —OH, —$NH_2$, —COOH, —$CONH_2$, —COH, —$COCH_3$, —$NO_2$, —SH, —$S(O)_2Cl$, —$S(O)_3H$, —$S(O)_4H$,—$S(O)_2NH_2$, —$NHNH_2$, —$ONH_2$, —NHC(O)NHNH$_2$, —NHC(O)NH$_2$, —NHS(O)$_2$H, —NHC(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

15. The method of claim 14, wherein the compound of Formula (Ib3) is:

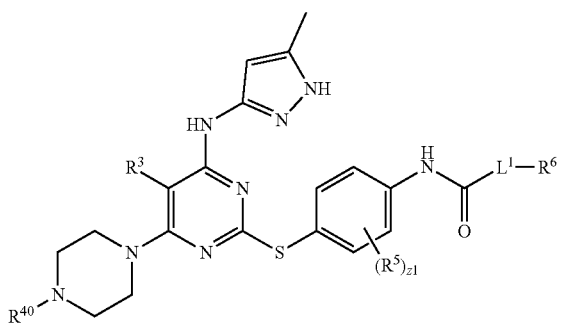

or a pharmaceutically acceptable salt thereof;

wherein the compound of Formula (Ib4) is:

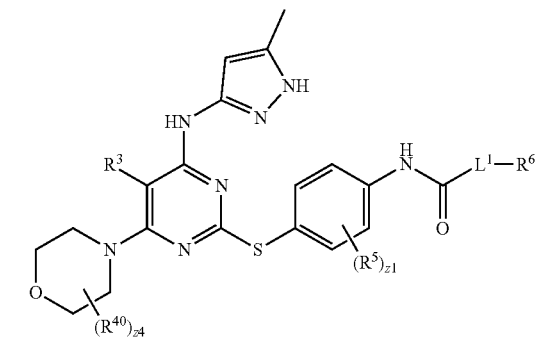

or a pharmaceutically acceptable salt thereof;

wherein the compound of Formula (Ib5) is:

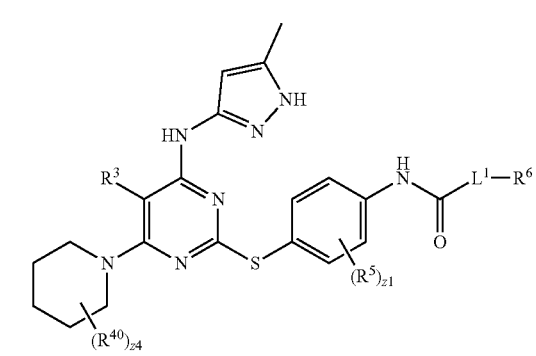

or a pharmaceutically acceptable salt thereof;

wherein the compound of Formula (Ib6) is:

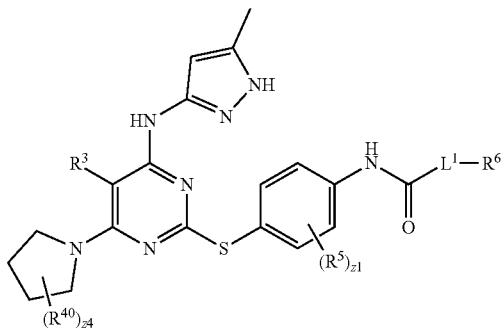

or a pharmaceutically acceptable salt thereof; and
wherein the compound of Formula (Ib7) is:

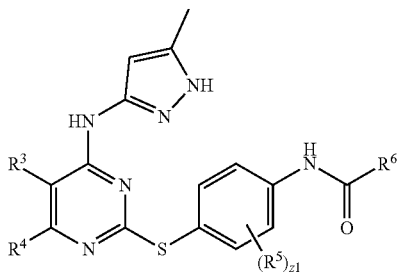

or a pharmaceutically acceptable salt thereof.

16. The method of claim 1, wherein the PLK4 inhibitor is:

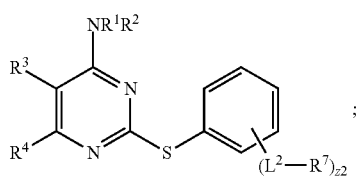

(II)

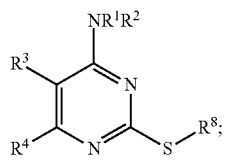

(III)

or a pharmaceutically acceptable salt of one of the foregoing;
wherein:
L$^2$ is independently a bond, —C(O)—, —C(O)O—, —O—, —S—, —NR$^{14}$—, —C(O)NR$^{14}$—NR$^{14}$C(O)—, —S(O)—, —S(O)$_2$—, —S(O)NR$^{14}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
R$^7$ is independently hydrogen, oxo, halogen, —N$_3$, —CF$_3$, —CCl$_3$, —CBr$_3$, —CI$_3$, —CN, —COR$^{7A}$, —OR$^{7A}$, —NR$^{7A}$R$^{7B}$, —C(O)OR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$ONR$^{7A}$R$^{7B}$, —NHNR$^{7A}$R$^{7B}$, —ONR$^{7A}$R$^{7B}$, —NHC(O)NHNR$^{7A}$R$^{7B}$, -L$^1$-R$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
L$^1$ is a bond, —C(O)—, —C(O)O—, —O—, —S—, —NR$^{13}$—, —C(O)NR$^{13}$—, —NR$^{13}$C(O)—, —S(O)$_2$—, —S(O)NR$^{13}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
n7 is independently 1 or 2;
z2 is 1, 2, 3, 4, or 5;
n1, n2, n3, n4, and n6 are independently 1 or 2;
R$^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, C(O)OR$^{2A}$, —C(O)NR$^{2A}$R$^{2B}$, NO$_2$, SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, (O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^4$ is halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein R$^3$ and R$^4$ are optionally combined to form a substituted or unsubstituted cycloalkyl, substituted or unsubstituted heterocycloalkyl, substituted or unsubstituted aryl, or substituted or unsubstituted heteroaryl;
R$^6$ is hydrogen, oxo, halogen, —N$_3$, —CF$_3$, —CCl$_3$, —CBr$_3$, —CI$_3$, —CN, —CHO, —OR$^{6A}$, —NR$^{6A}$R$^{6B}$, C(O)OR$^{6A}$, —C(O)NR$^{6A}$R$^{6B}$, —NO$_2$, —SR$^{6A}$, —S(O)$_{n6}$R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently hydrogen, halogen, —$N_3$, —$CF_3$, —$CCl_3$, —$CBr_3$, —$CI_3$, —CN, —$COR^{7A}$, —$OR^{7A}$, —$NR^{7A}R^{7B}$, —C(O)$OR^{7A}$, —C(O)$NR^{7A}R^{7B}$, —$NO_2$, —$SR^{7A}$, —S(O)$_{n7}R^{7A}$, —S(O)$_{n7}OR^{7A}$, —S(O)$_{n7}NR^{7A}R^{7B}$, —$NHNR^{7A}R^{7B}$, —$ONR^{7A}R^{7B}$, —NHC(O)$NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{2A}$, $R^{2B}$, $R^{3A}$, $R^{3B}$, $R^{4A}$, $R^{4B}$, $R^{6A}$, $R^{6B}$, $R^{7A}$, and $R_{7B}$ are independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^{13}$ and $R^{14}$ are each independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)-OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^8$ is unsubstituted $C_1$-$C_5$ alkyl.

17. The method of claim 16, wherein the compound of Formula

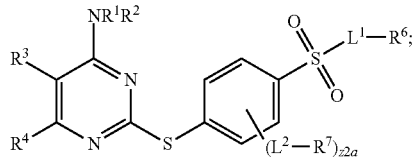

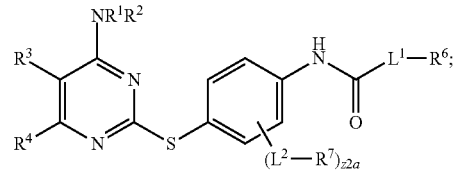

or a pharmaceutically acceptable salt of one of the foregoing;

wherein z2a is 0, 1, or 2.

18. The method of claim 1, wherein the PLK4 inhibitor is tozasertib or a pharmaceutically acceptable salt thereof; centrinone or a pharmaceutically acceptable salt thereof or centrinone B or a pharmaceutically acceptable salt thereof.

19. The method of claim 1, wherein measuring the TRIM37 level comprises measuring copies of the TRIM37 gene, measuring the level of the TRIM37 mRNA, measuring the level of the TRIM37 protein, or a combination of two or more thereof.

20. The method of claim 1, wherein the biological sample is a tumor sample or a blood sample.

* * * * *